(12) United States Patent
Hao et al.

(10) Patent No.: US 12,305,167 B2
(45) Date of Patent: May 20, 2025

(54) SYSTEMS AND METHODS FOR BIOMOLECULE RETENTION

(71) Applicant: Nautilus Subsidiary, Inc., Seattle, WA (US)

(72) Inventors: Pengyu Hao, Belmont, CA (US); Elvis Ikwa, San Leandro, CA (US); Pierre Indermuhle, Berkeley, CA (US); Christina Inman, San Mateo, CA (US); Parag Mallick, San Mateo, CA (US); Torri Elise Rinker, San Francisco, CA (US); Steven Tan, San Mateo, CA (US); Tural Aksel, Redwood City, CA (US); Stephen Hendricks, Los Gatos, CA (US); Sadie Ingle, Suttons Bay, MI (US)

(73) Assignee: Nautilus Subsidiary, Inc., Seattle, WA (US)

( * ) Notice: Subject to any disclaimer, the term of this patent is extended or adjusted under 35 U.S.C. 154(b) by 0 days.

(21) Appl. No.: 18/770,462

(22) Filed: Jul. 11, 2024

(65) Prior Publication Data

US 2024/0368585 A1    Nov. 7, 2024

Related U.S. Application Data

(63) Continuation of application No. 18/416,639, filed on Jan. 18, 2024, now Pat. No. 12,071,618, which is a continuation of application No. 18/361,731, filed on Jul. 28, 2023, now Pat. No. 11,912,990, which is a continuation of application No. 18/050,732, filed on Oct. 28, 2022, now Pat. No. 11,760,997, which is a continuation of application No. 17/692,035, filed on Mar. 10, 2022, now Pat. No. 11,505,796.

(60) Provisional application No. 63/256,761, filed on Oct. 18, 2021, provisional application No. 63/159,500, filed on Mar. 11, 2021.

(51) Int. Cl.
| | |
|---|---|
| *C12N 15/10* | (2006.01) |
| *B01J 19/00* | (2006.01) |
| *B82Y 5/00* | (2011.01) |
| *C12Q 1/6804* | (2018.01) |
| *C12Q 1/6837* | (2018.01) |

(52) U.S. Cl.
CPC ...... *C12N 15/1093* (2013.01); *B01J 19/0046* (2013.01); *B82Y 5/00* (2013.01); *C12Q 1/6804* (2013.01); *C12Q 1/6837* (2013.01); *B01J 2219/0061* (2013.01)

(58) Field of Classification Search
None
See application file for complete search history.

(56) References Cited

U.S. PATENT DOCUMENTS

| | | |
|---|---|---|
| 5,324,633 A | 6/1994 | Fodor et al. |
| 5,919,626 A | 7/1999 | Shi et al. |
| 6,255,469 B1 | 7/2001 | Seeman et al. |
| 6,391,625 B1 | 5/2002 | Park et al. |
| 6,589,726 B1 | 7/2003 | Butler et al. |
| 6,610,482 B1 | 8/2003 | Fodor et al. |
| 6,737,236 B1 | 5/2004 | Pieken et al. |
| 6,806,361 B1 | 10/2004 | Kajisa et al. |
| 6,824,866 B1 | 11/2004 | Glazer et al. |
| 7,148,058 B2 | 12/2006 | Charych et al. |
| 7,158,224 B2 | 1/2007 | Montagu |
| 7,183,054 B2 | 2/2007 | Myers et al. |
| 7,259,258 B2 | 8/2007 | Kozlov et al. |
| 7,351,528 B2 | 4/2008 | Landegren |
| 7,375,234 B2 | 5/2008 | Sharpless et al. |
| 7,427,678 B2 | 9/2008 | Pieken et al. |
| 7,598,363 B2 | 10/2009 | Seeman et al. |
| 7,635,562 B2 | 12/2009 | Harris et al. |
| 7,763,736 B2 | 7/2010 | Sharpless et al. |
| 7,794,799 B1 | 9/2010 | Kim et al. |
| 7,842,793 B2 | 11/2010 | Rothemund |
| 7,855,054 B2 | 12/2010 | Schneider et al. |
| 7,955,837 B2 | 6/2011 | Pawlak et al. |
| 7,964,356 B2 | 6/2011 | Zichi et al. |
| 8,013,134 B2 | 9/2011 | Fredriksson |
| 8,133,719 B2 | 3/2012 | Drmanac et al. |
| 8,222,047 B2 | 7/2012 | Duffy et al. |
| 8,236,574 B2 | 8/2012 | Duffy et al. |
| 8,268,554 B2 | 9/2012 | Schallmeiner |
| 8,404,830 B2 | 3/2013 | Zichi et al. |
| 8,415,171 B2 | 4/2013 | Rissin et al. |

(Continued)

FOREIGN PATENT DOCUMENTS

| | | |
|---|---|---|
| EP | 1 105 529 B2 | 5/2013 |
| EP | 3 699 142 A1 | 8/2020 |

(Continued)

OTHER PUBLICATIONS

Angelin et al., "Multiscale Origami Structures as Interface for Cells," Angew. Chem. Int. Ed. 2015, 54:15813-15817, with 29 pages of Supporting Information. (Year: 2015).*
Cutler et al., "Spheric Nucleic Acids," Journal of the American Chemical Society, 2012, vol. 134, pp. 1376-1391.
Derr et al., "Tug of War in Motor Protein Ensembles Revealed with a Programmable DNA Origami Scaffold," Science, Nov. 2, 2012, vol. 338, No. 6107, pp. 662-665.

(Continued)

*Primary Examiner* — Kaijiang Zhang
(74) *Attorney, Agent, or Firm* — Orrick, Herrington & Sutcliffe, LLP

(57) ABSTRACT

Compositions, systems, and methods for the display of analytes such as biomolecules are described. Display of analytes is achieved by coupling of the analytes to displaying molecules that are configured to associate with surfaces or interfaces. Arrays of analytes may be formed from the described systems for utilization in assays and other methods.

29 Claims, 105 Drawing Sheets

Specification includes a Sequence Listing.

(56) References Cited

U.S. PATENT DOCUMENTS

| | | |
|---|---|---|
| 8,445,194 B2 | 5/2013 | Drmanac et al. |
| 8,501,923 B2 | 8/2013 | Rothemund |
| 8,685,894 B2 | 4/2014 | Chaput et al. |
| 8,877,516 B2 | 11/2014 | Lin et al. |
| 8,945,811 B2 | 2/2015 | True |
| 8,945,830 B2 | 2/2015 | Heil et al. |
| 8,975,026 B2 | 3/2015 | Zichi et al. |
| 8,975,388 B2 | 3/2015 | Zichi et al. |
| 9,163,056 B2 | 10/2015 | Rohloff et al. |
| 9,275,871 B2 | 3/2016 | Sandhu |
| 9,330,932 B1 | 5/2016 | Sills et al. |
| 9,340,416 B2 | 5/2016 | Maune et al. |
| 9,395,359 B2 | 7/2016 | Walt et al. |
| 9,399,795 B2 | 7/2016 | Chee et al. |
| 9,404,919 B2 | 8/2016 | Schneider et al. |
| 9,466,504 B1 | 10/2016 | Sills et al. |
| 9,551,663 B2 | 1/2017 | Rissin et al. |
| 9,556,360 B2 | 1/2017 | Mcgall et al. |
| 9,625,469 B2 | 4/2017 | Marcotte et al. |
| 9,678,068 B2 | 6/2017 | Duffy et al. |
| 9,717,685 B2 | 8/2017 | Shih et al. |
| 9,777,315 B2 | 10/2017 | Fredriksson et al. |
| 9,796,749 B2 | 10/2017 | Yin et al. |
| 9,881,786 B2 | 1/2018 | Sills et al. |
| 9,926,566 B2 | 3/2018 | Ochsner et al. |
| 9,938,314 B2 | 4/2018 | Rohloff et al. |
| 9,975,916 B2 | 5/2018 | Yin et al. |
| 10,099,920 B2 | 10/2018 | Shen et al. |
| 10,221,207 B2 | 3/2019 | Rohloff et al. |
| 10,221,421 B2 | 3/2019 | Jarvis et al. |
| 10,239,908 B2 | 3/2019 | Rohloff et al. |
| 10,316,321 B2 | 6/2019 | Zichi et al. |
| 10,392,621 B2 | 8/2019 | Ochsner et al. |
| 10,473,654 B1 | 11/2019 | Mallick |
| 10,513,535 B2 | 12/2019 | He et al. |
| 10,545,153 B2 | 1/2020 | Marcotte et al. |
| 10,550,145 B2 | 2/2020 | Han et al. |
| 10,604,543 B2 | 3/2020 | Yin et al. |
| 10,646,505 B2 | 5/2020 | Schulz et al. |
| 10,741,382 B2 | 8/2020 | Sills et al. |
| 11,001,606 B2 | 5/2021 | Tikhomirov et al. |
| 11,060,135 B2 | 7/2021 | Bowen et al. |
| 11,125,748 B2 | 9/2021 | Gopinath et al. |
| 11,162,192 B2 | 11/2021 | Gopinath et al. |
| 11,192,083 B2 | 12/2021 | Kraft et al. |
| 11,203,612 B2 | 12/2021 | Gremyachinskiy et al. |
| 11,235,972 B2 | 2/2022 | Gopalkrishnan et al. |
| 11,760,997 B2 | 9/2023 | Aksel et al. |
| 2004/0209383 A1 | 10/2004 | Yin et al. |
| 2005/0054118 A1 | 3/2005 | Lebrun |
| 2005/0095577 A1 | 5/2005 | Yang et al. |
| 2005/0287523 A1 | 12/2005 | Letant et al. |
| 2006/0035220 A1 | 2/2006 | Tashiro et al. |
| 2009/0018028 A1 | 1/2009 | Lindsay et al. |
| 2010/0069621 A1 | 3/2010 | Maune et al. |
| 2015/0004193 A1 | 1/2015 | Chang et al. |
| 2016/0060687 A1 | 3/2016 | Zhu et al. |
| 2016/0102344 A1* | 4/2016 | Niemeyer et al. ... C12Q 1/6837 536/23.1 |
| 2017/0327888 A1 | 11/2017 | Ong et al. |
| 2018/0044663 A1 | 2/2018 | Yan |
| 2018/0148514 A1 | 5/2018 | Williams |
| 2019/0145982 A1 | 5/2019 | Chee et al. |
| 2019/0195869 A1 | 6/2019 | Fan et al. |
| 2019/0323002 A1 | 10/2019 | Gopinath et al. |
| 2020/0082914 A1 | 3/2020 | Patel et al. |
| 2020/0090785 A1 | 3/2020 | Patel et al. |
| 2020/0286584 A9 | 9/2020 | Patel et al. |
| 2020/0289658 A1 | 9/2020 | Stephanopoulos et al. |
| 2020/0318101 A1 | 10/2020 | Mallick |
| 2020/0348307 A1 | 11/2020 | Beierle et al. |
| 2020/0348308 A1 | 11/2020 | Chee et al. |
| 2021/0032775 A1 | 2/2021 | Gopinath et al. |
| 2021/0101930 A1 | 4/2021 | Gremyachinskiy et al. |
| 2021/0239705 A1 | 8/2021 | Mallick |

FOREIGN PATENT DOCUMENTS

| | | |
|---|---|---|
| EP | 3 498 865 B1 | 10/2020 |
| WO | 2005/065814 A1 | 7/2005 |
| WO | 2019/211631 A1 | 11/2019 |
| WO | 2019/236749 A2 | 12/2019 |
| WO | 2020/106889 A1 | 5/2020 |
| WO | 2020/223368 A1 | 11/2020 |
| WO | 2020/254684 A1 | 12/2020 |
| WO | 2021/087402 A1 | 5/2021 |

OTHER PUBLICATIONS

Drmanac et al., "Human Genome Sequencing Using Unchained Base Reads on Self-Assembling DNA Nanoarrays," Science, Jan. 1, 2010, vol. 327, pp. 78-81.

Gopinath et al., "Optimized Assembly and Covalent Coupling of Single-Molecule DNA Origami Nanoarrays," ACS Nano, 2014, vol. 8, No. 12, pp. 12030-12040.

Hookway et al., "Aggregate formation and suspension culture of human pluripotent stem cells and differentiated progeny," Methods, 2016, vol. 101, 28 pages.

International Search Report and Written Opinion in PCT/US2022/019831, mailed Jul. 6, 2022, 15 pages.

Jaekel et al., "Manipulating Enzymes Properties with DNA Nanostructures," Molecules, 2019, vol. 24 No. 3694, 1-24.

Jensen et al., "Nanoengineered Bioplatforms Based on DNA Origami," Proceedings of the IEEE, Jul. 2014, vol. 102, No. 7, pp. 1046-1049.

Kolb et al., "Click Chemistry: Diverse Chemical Function from a Few Good Reactions," Angewandte Chemie International Edition, 2001, vol. 40, pp. 2004-2021.

Rissin et al., "Single-Molecule enzyme-linked immunosorbent assay detects serum proteins at subfemtomolar concentrations," Nature Biotechnology, Jun. 2010, vol. 28, No. 6, pp. 595-599.

Rothemund, P., "Folding DNA to create nanoscale shapes and patterns," Nature, Mar. 16, 2006, vol. 440, pp. 297-300.

Spicer et al., "Achieving Controlled Biomolecule-Biomaterial Conjugation," Chemical Reviews, 2018, vol. 118, pp. 7702-7743.

Stawicki et al., "Modular fluorescent nanoparticle DNA probes for detection of peptides and proteins," Scientific Reports, 2021, vol. 11, No. 19921, 15 pages.

Swaminathan et al., "Highly parallel single-molecule identification of proteins in zeptomole-scale mixtures," Nature Biotechnology, Apr. 25, 2019, pp. 1-29.

Vauquelin et al., "Exploring avidity: understanding the potential gains in functional affinity and target residence time of bivalent and heterobivalent ligands," British Journal of Pharmacology, 2013, vol. 168, pp. 1771-1785.

Weinrich et al., "Applications of Protein Biochips in Biomedical and Biotechnological Research", Angewandte Chemie International Edition, 2009, vol. 48, pp. 7744-7751.

Xin et al., "Self-assembly of highly ordered DNA origami lattices at solid-liquid interfaces by controlling cation binding and exchange," Nano Research, 2020. vol. 13, No. 11, pp. 3142-3150.

Xu et al., "Super-resolution Geometric Barcoding for Multiplexed miRNA Profiling," Angewandte Chemie International Edition, Oct. 22, 2018, vol. 57, No. 43, pp. 14075-14079.

Xu et al., "Supporting Information—Super-resolution Geometric Barcoding for Multiplexed miRNA Profiling," Angewandte Chemie, Oct. 22, 2018, vol. 57, No. 43, 34 pages.

Yang et al., "Programmable Site-Specific Functionalization of DNA Origami with Polynucleotide Brushes," Angewandte Chemie International Edition, 2021, vol. 60, pp. 2-9.

Zakeri et al., "Peptide tag forming a rapid covalent bond to a protein, through engineering a bacterial adhesin," PNAS, Mar. 20, 2012, vol. 109, No. 12, pp. E690-E697.

Zhang et al., "Capturing transient antibody conformations with DNA origami epitopes," Nature Communications, 2020, vol. 11, No. 3114, pp. 1-9.

(56) References Cited

OTHER PUBLICATIONS

Zhao et al., "Organizing DNA Origami Tiles Into Larger Structures Using Pre-formed Scaffold Frames," NanoLetters, Jul. 13, 2011, vol. 11, No. 7, pp. 2997-3002.

* cited by examiner

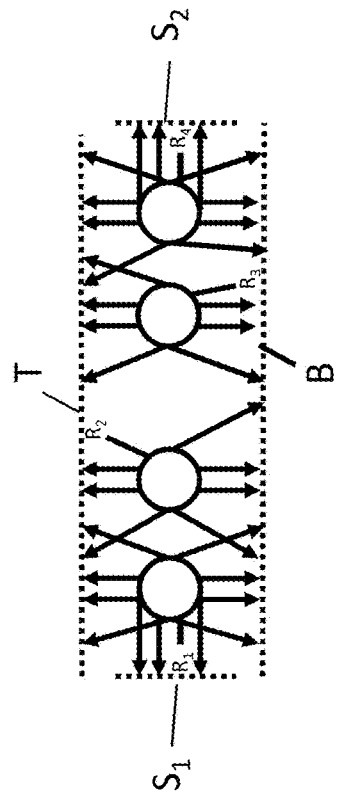
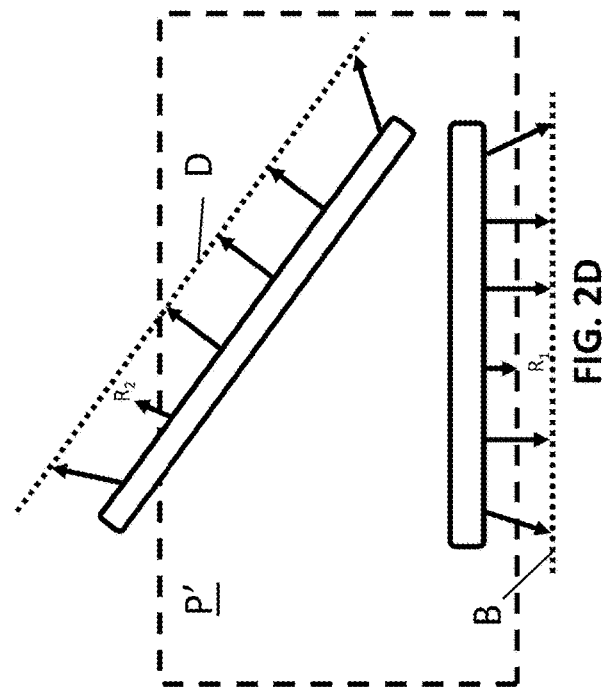
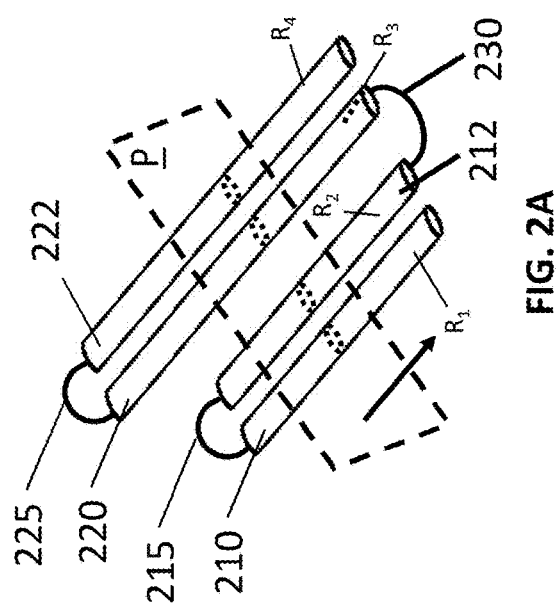
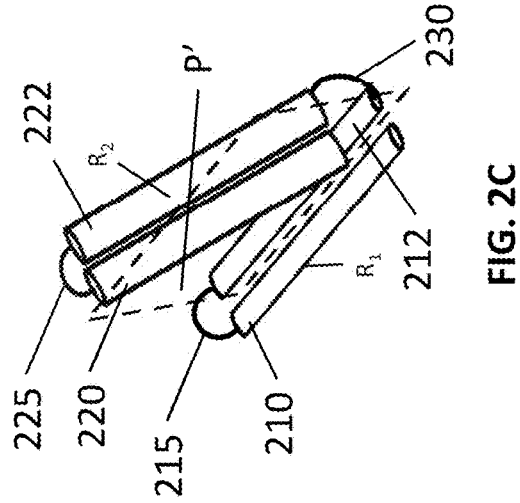

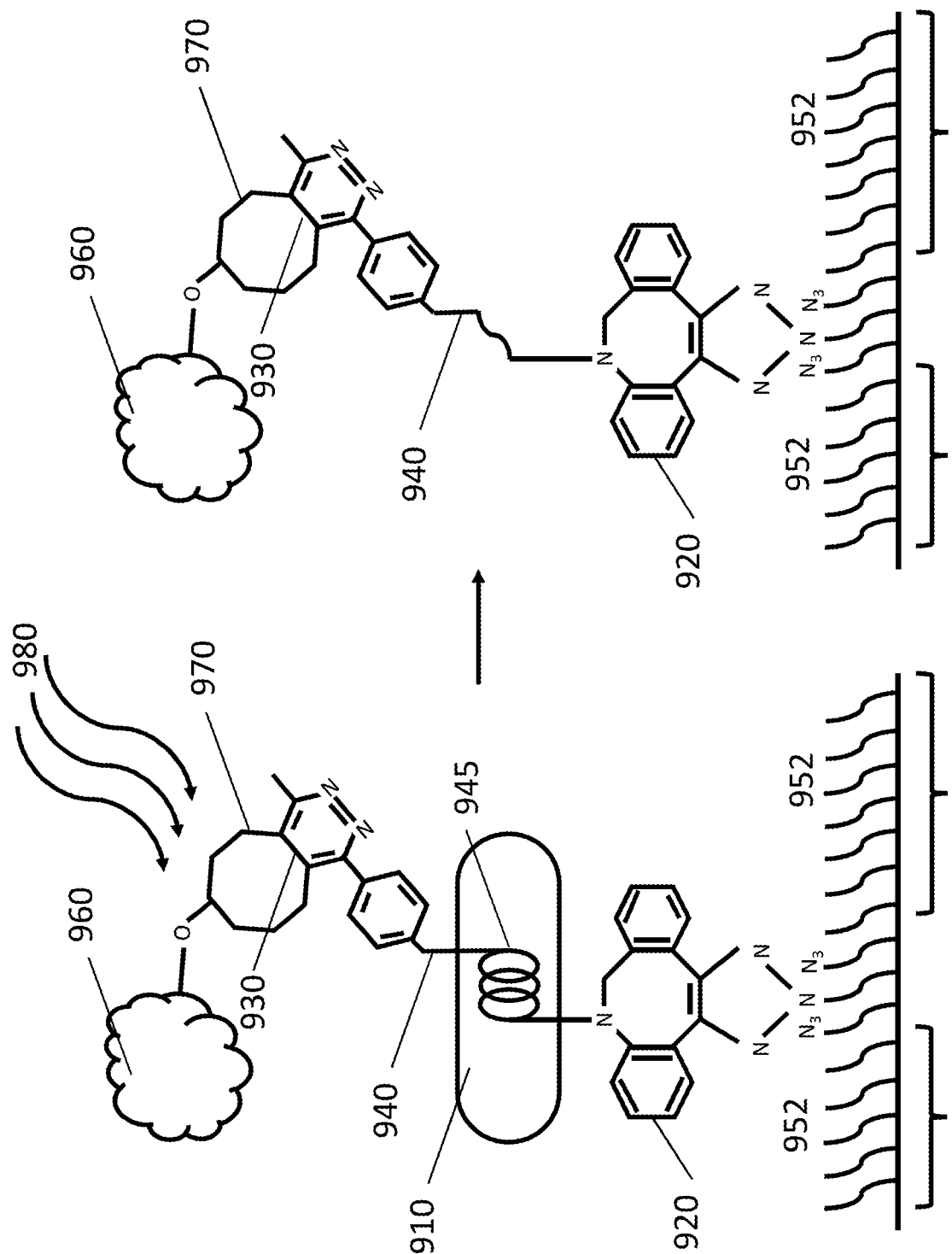

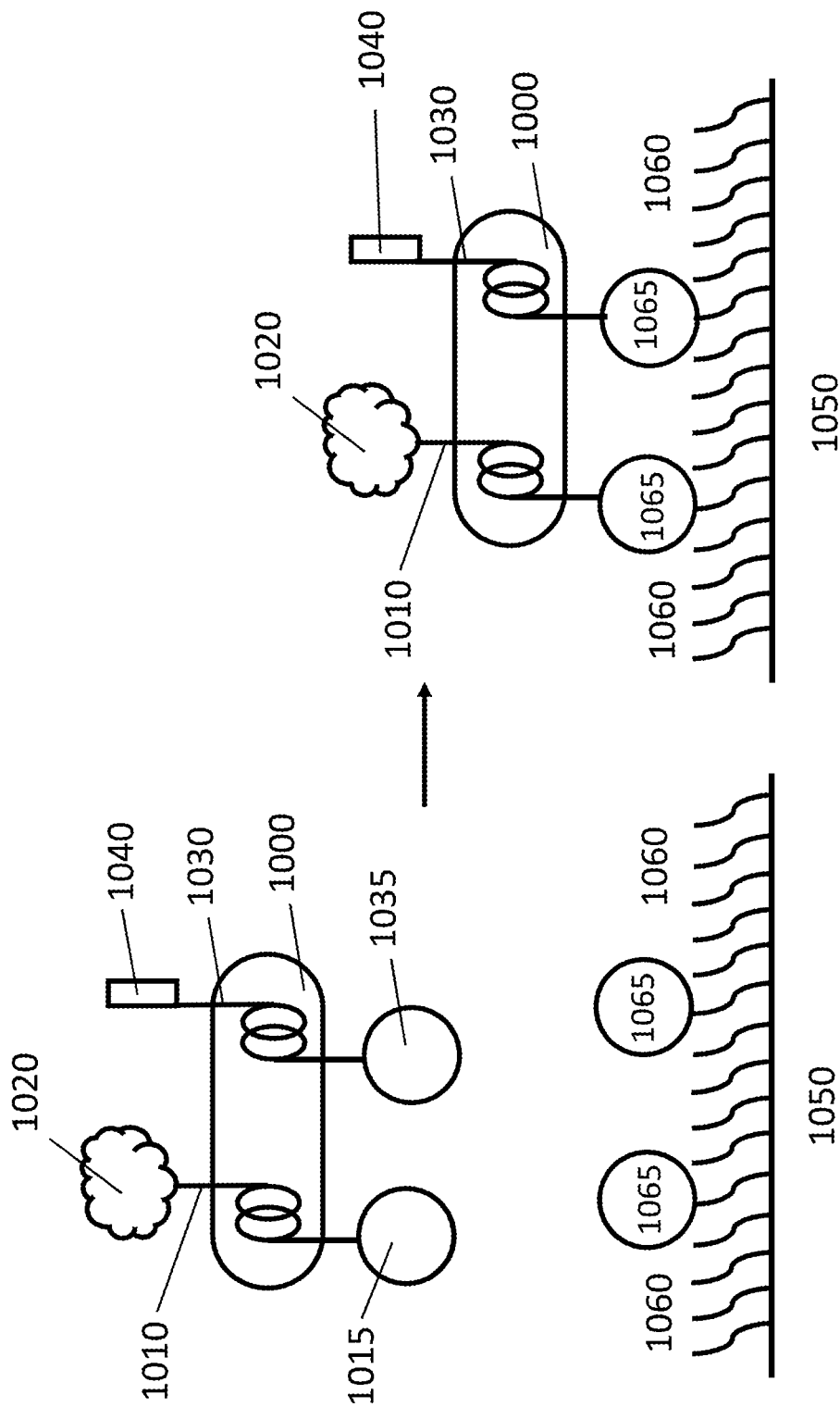

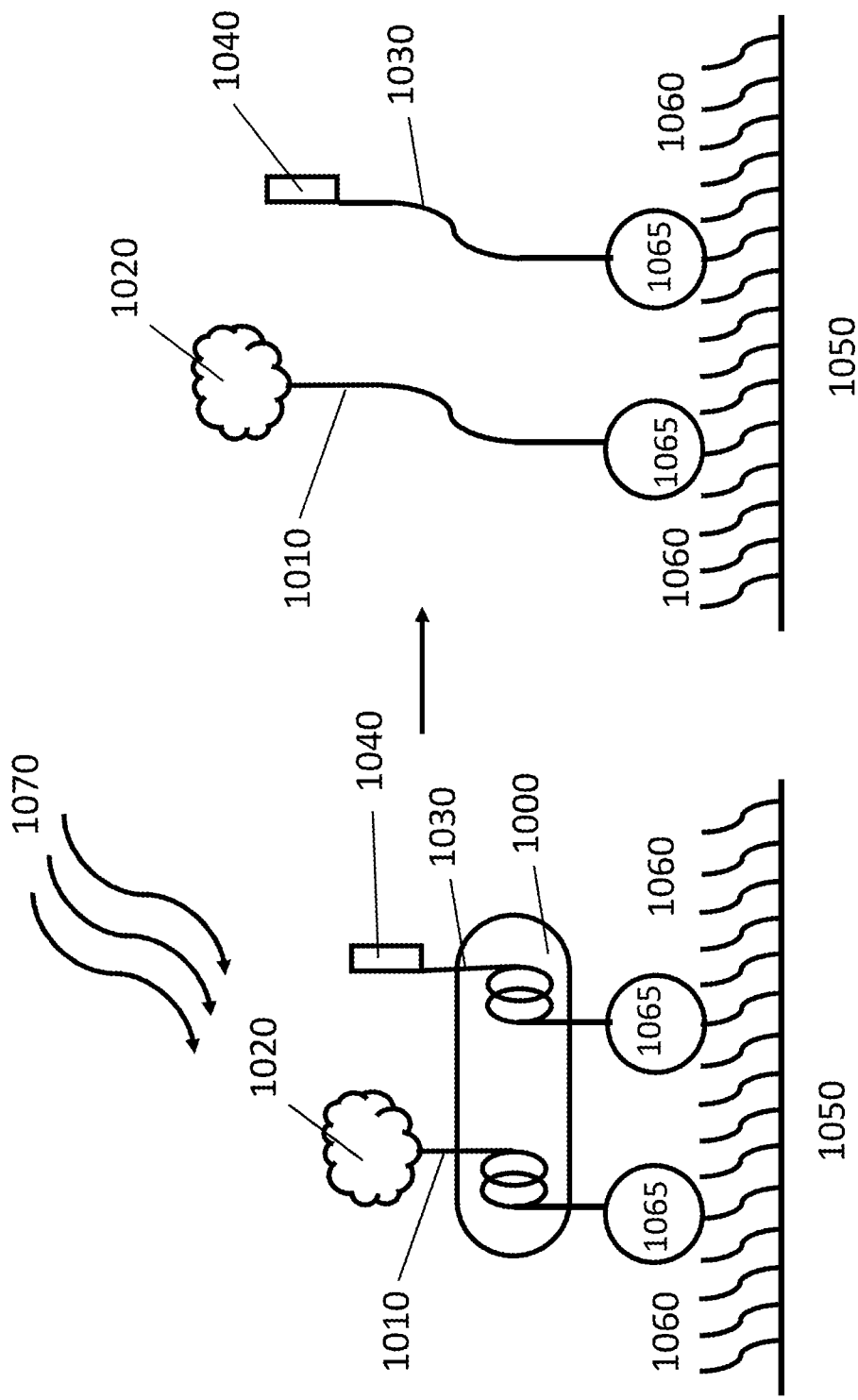

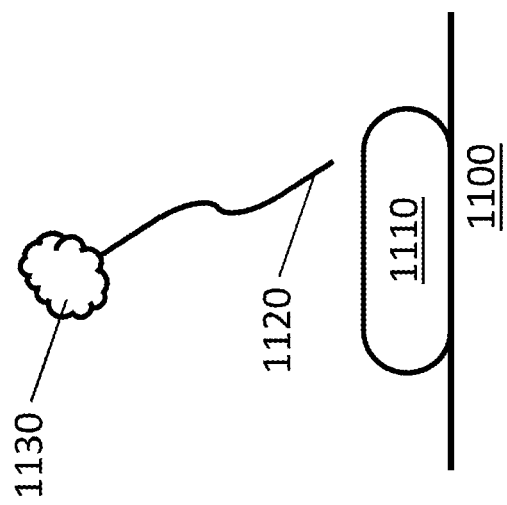
FIG. 11A
FIG. 11B
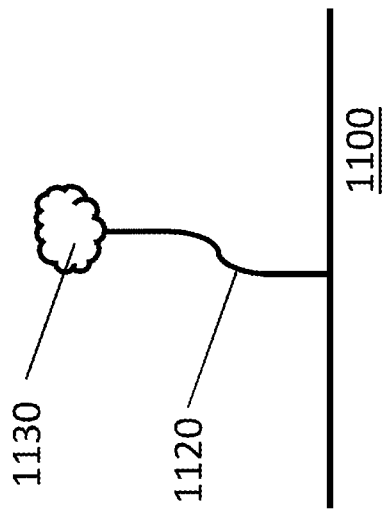
FIG. 11D
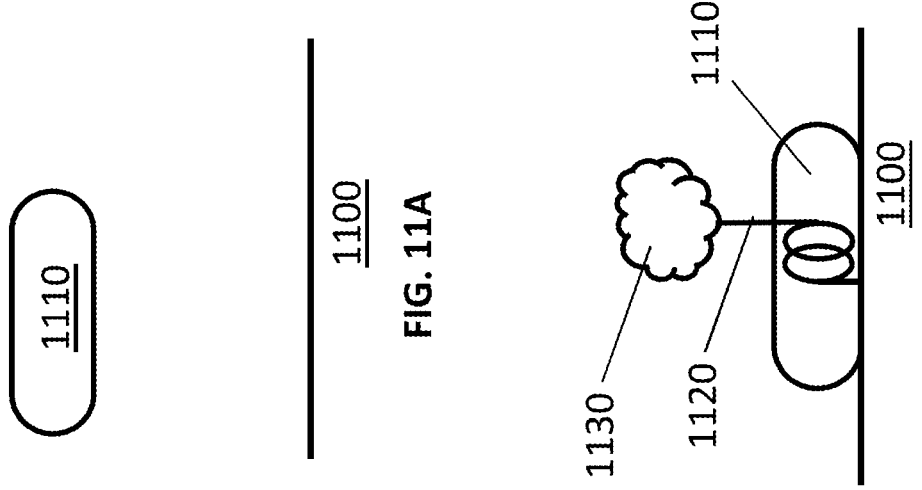
FIG. 11C

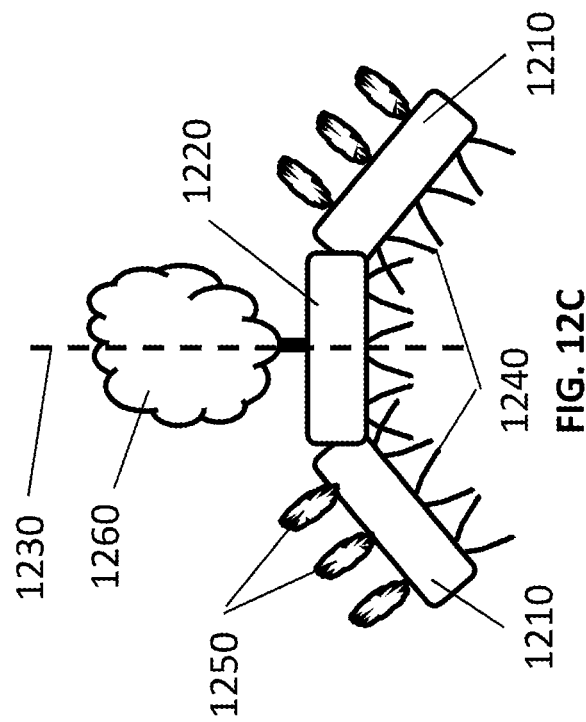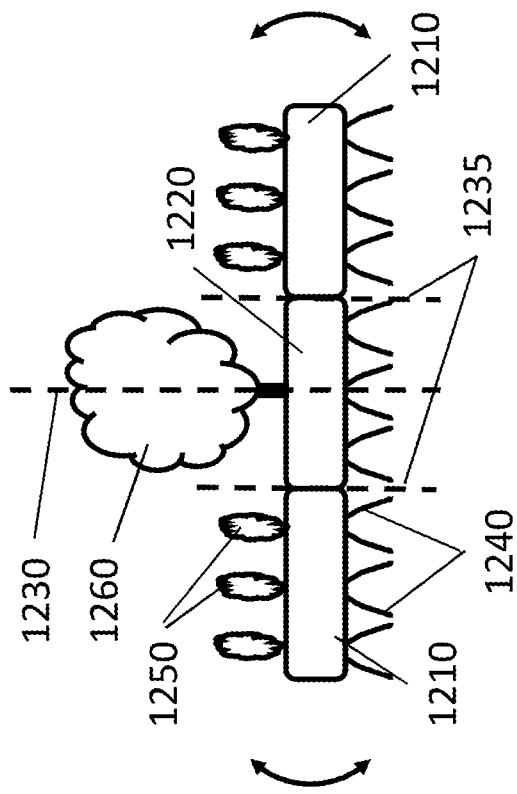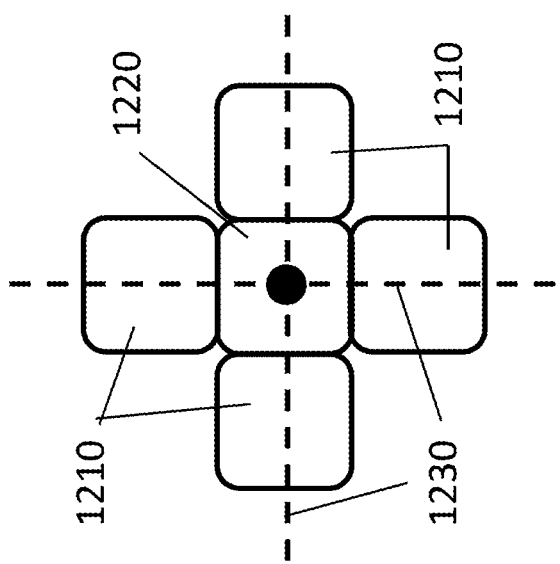
FIG. 12A
FIG. 12B
FIG. 12C

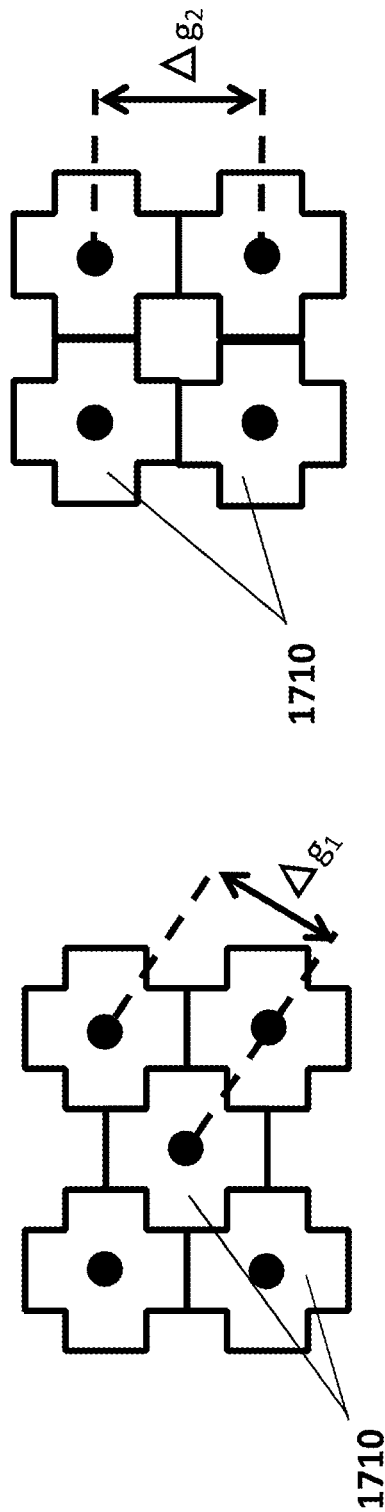
FIG. 17B
FIG. 17A
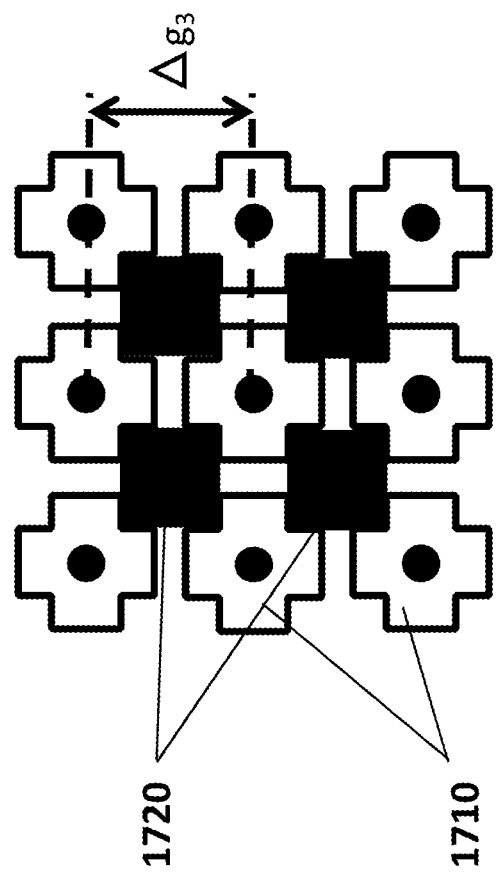
FIG. 17C

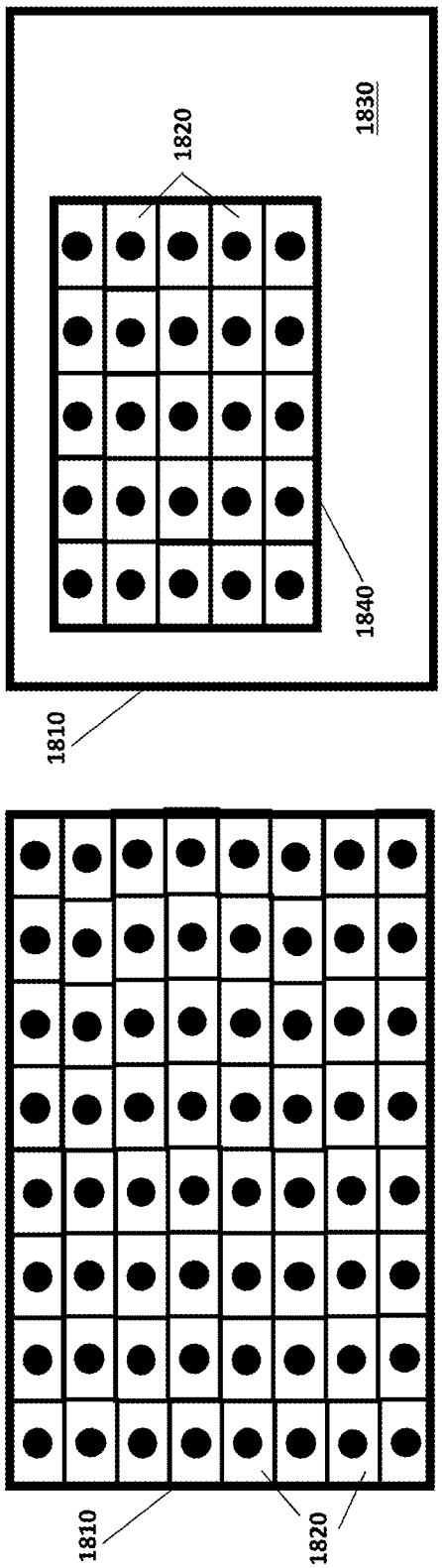
FIG. 18A
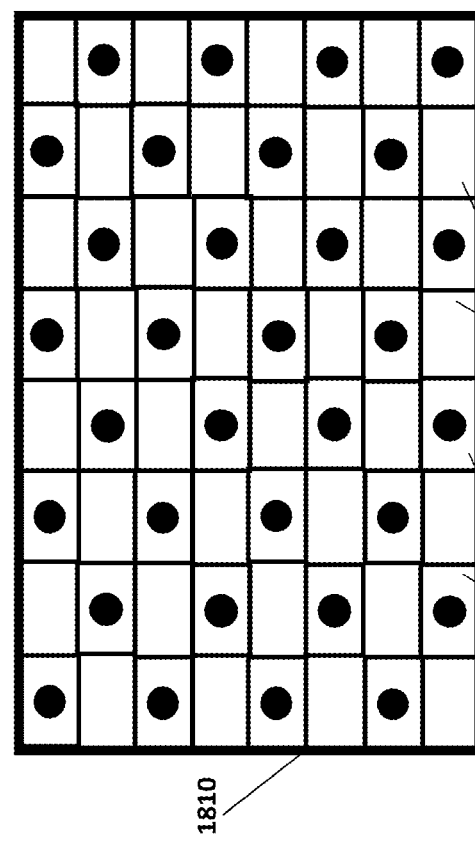
FIG. 18B
FIG. 18C

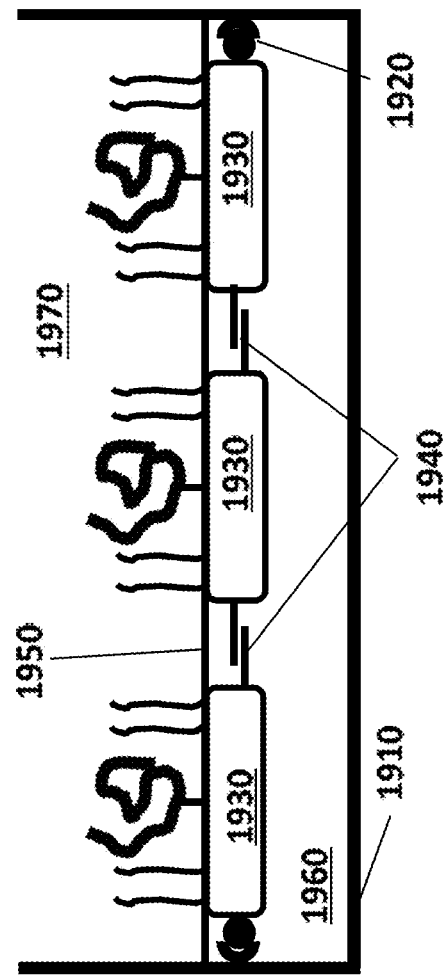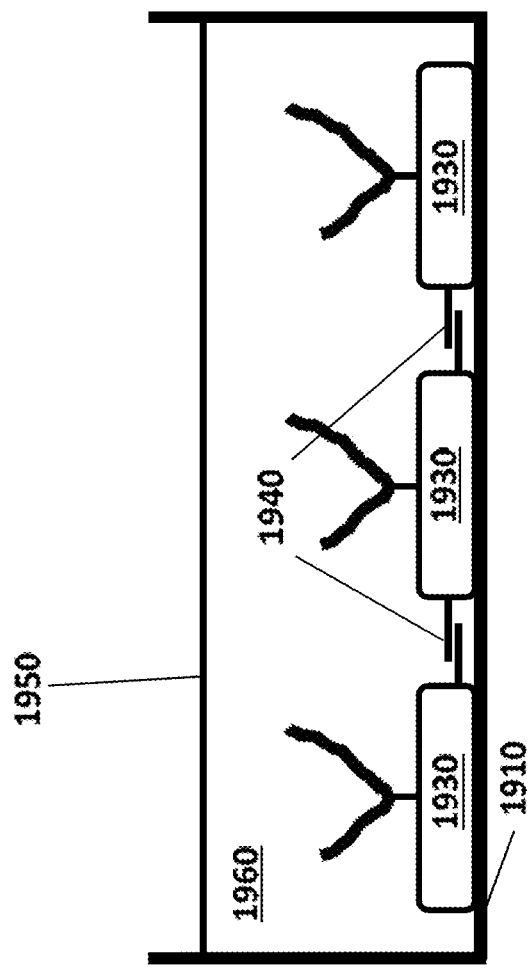

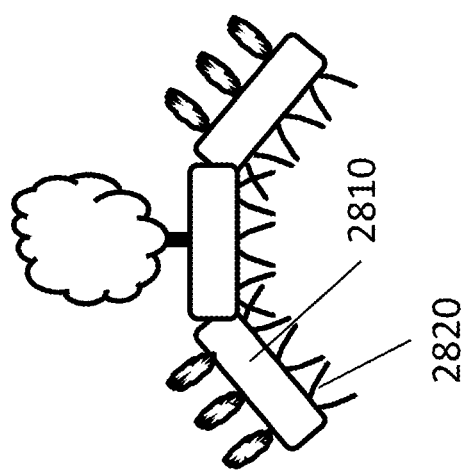
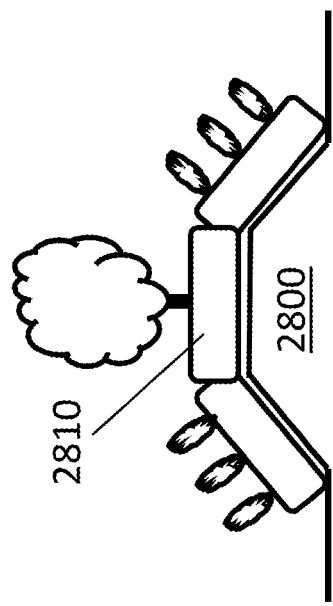
FIG. 28A
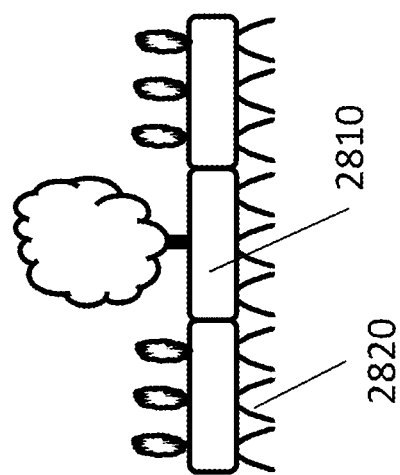
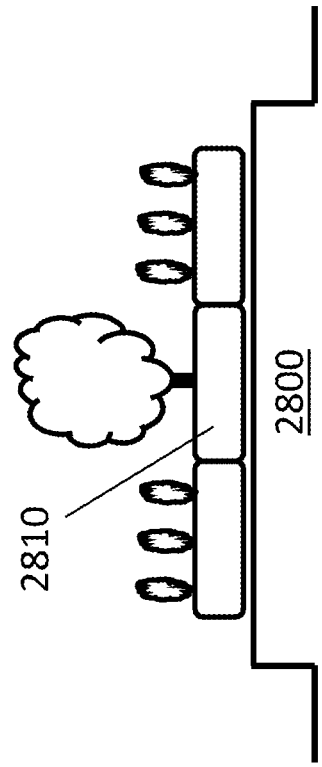
FIG. 28B

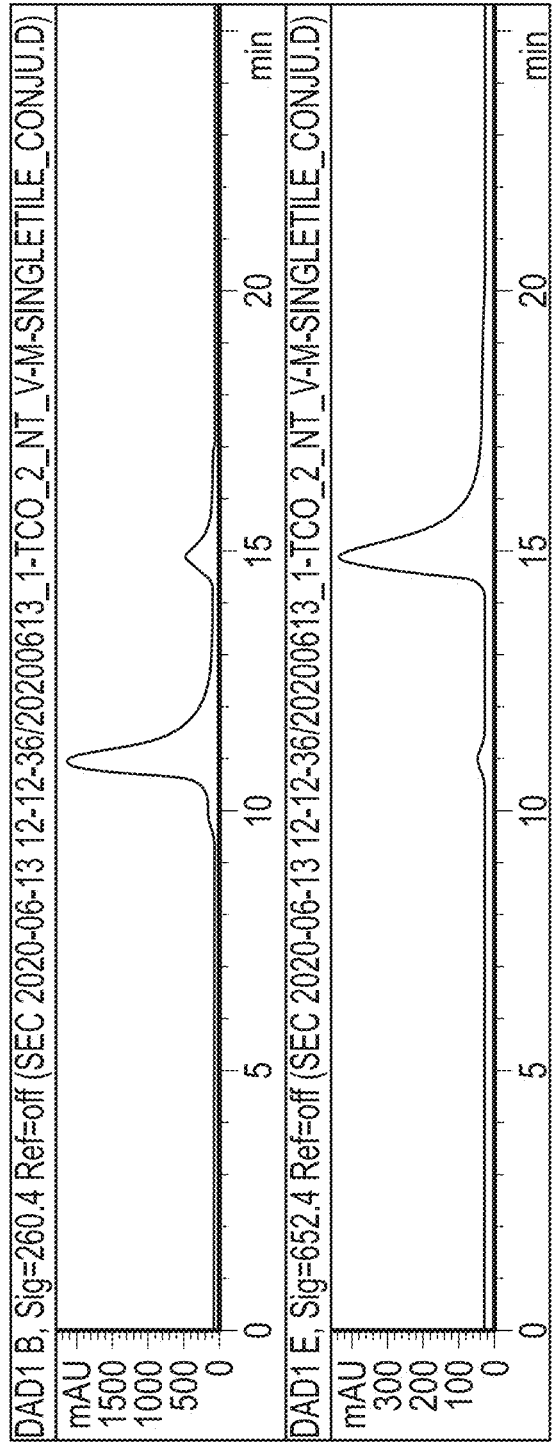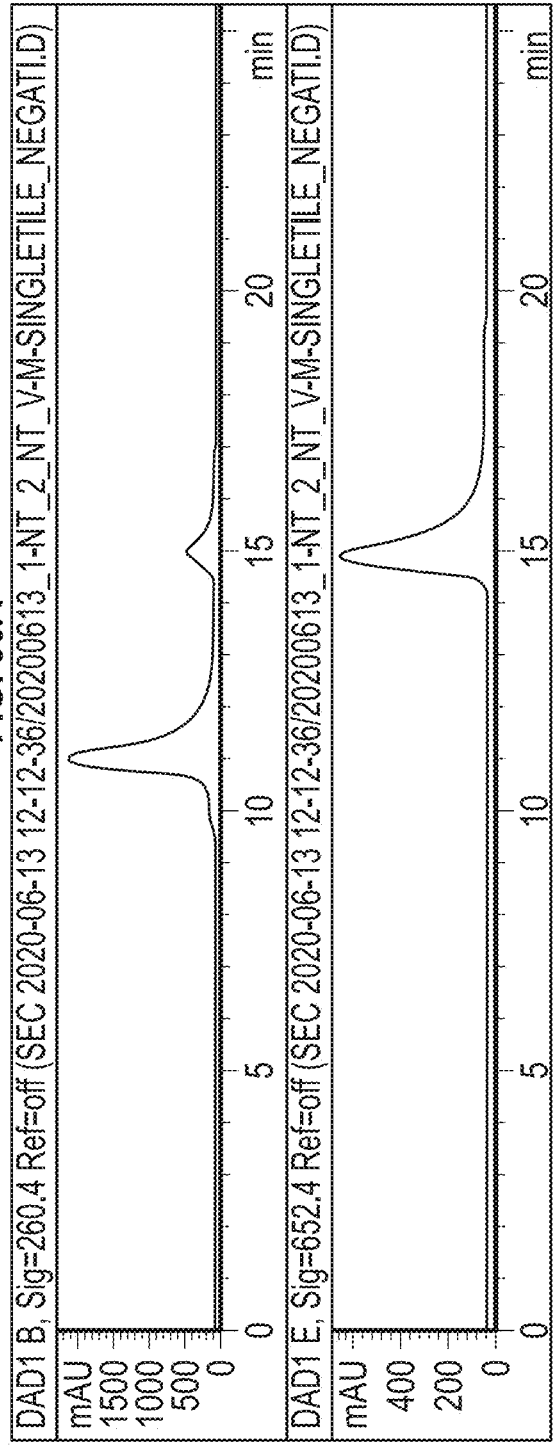

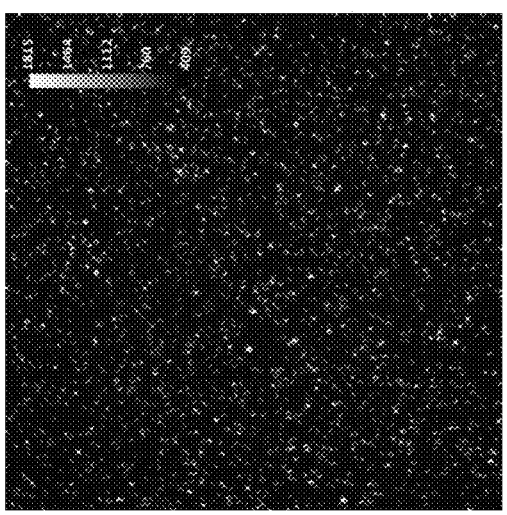
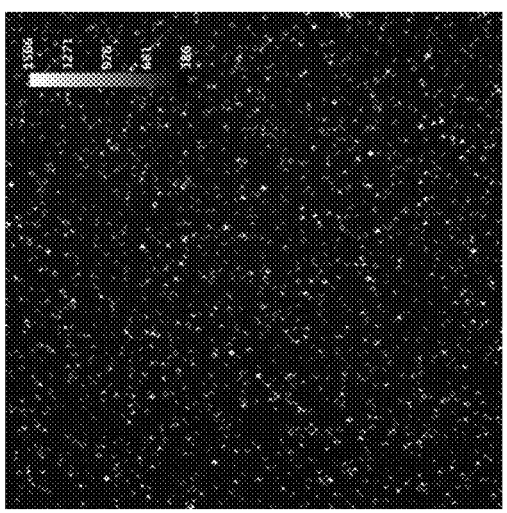
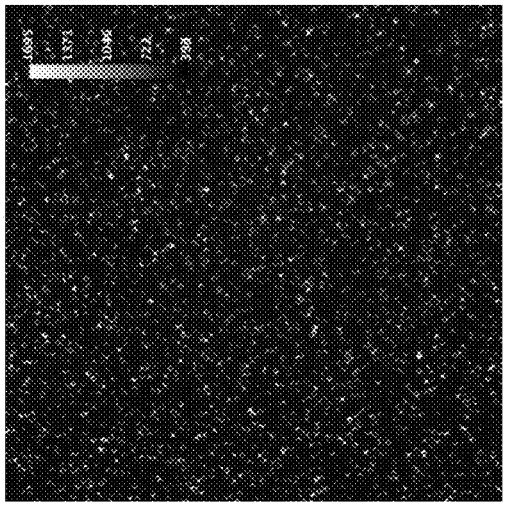
FIG. 34A
FIG. 34B
FIG. 34C

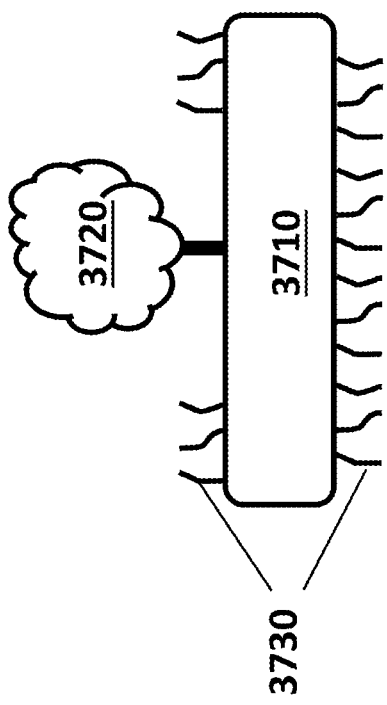
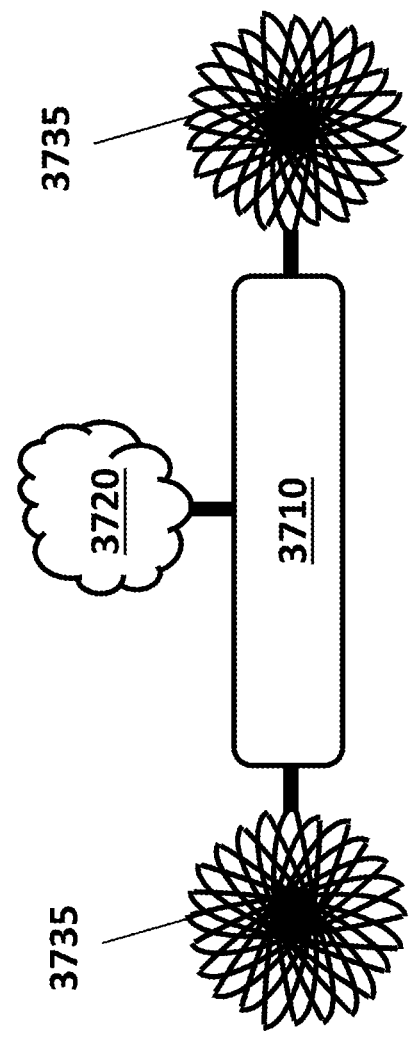
FIG. 37A
FIG. 37B

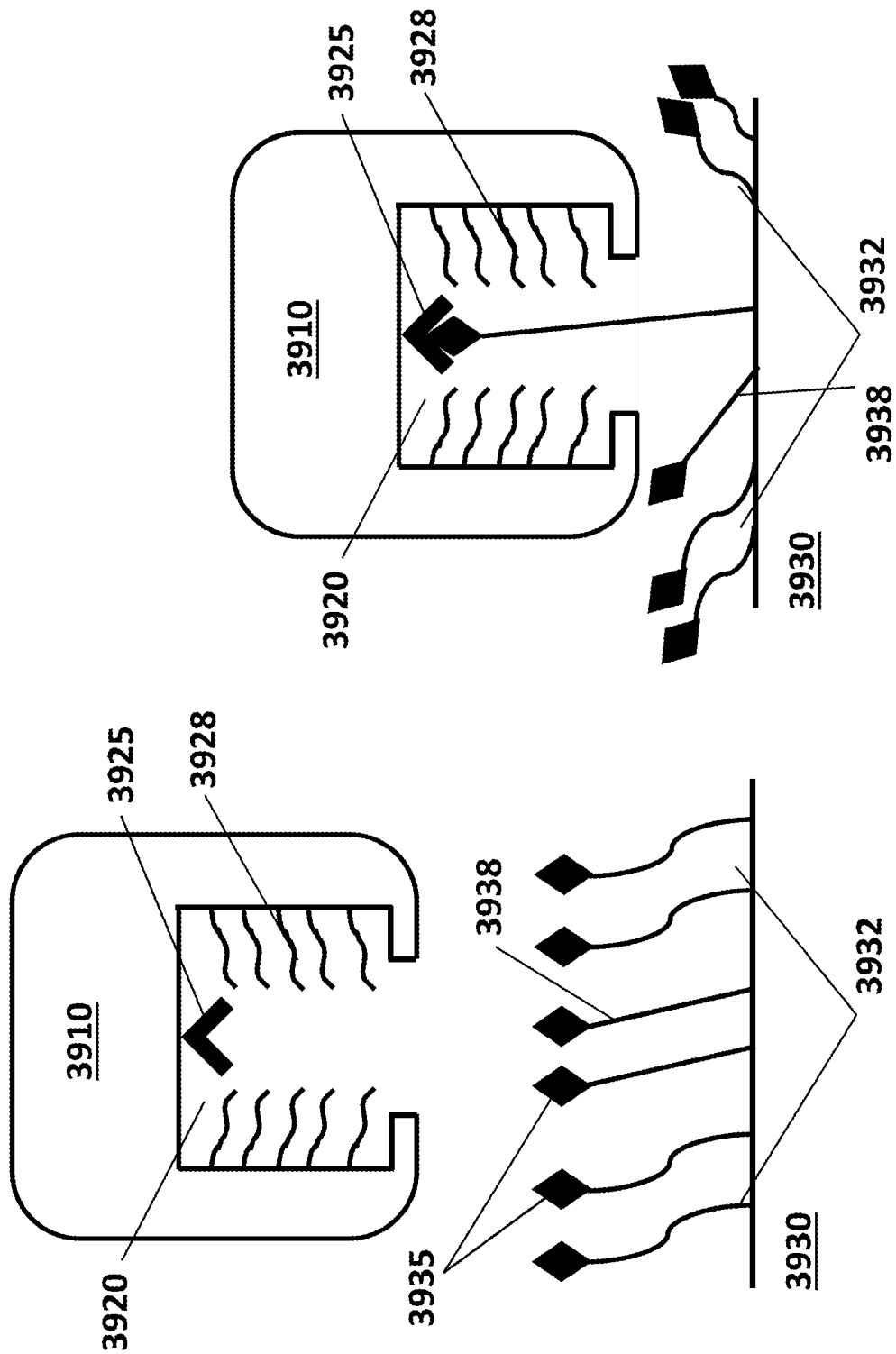

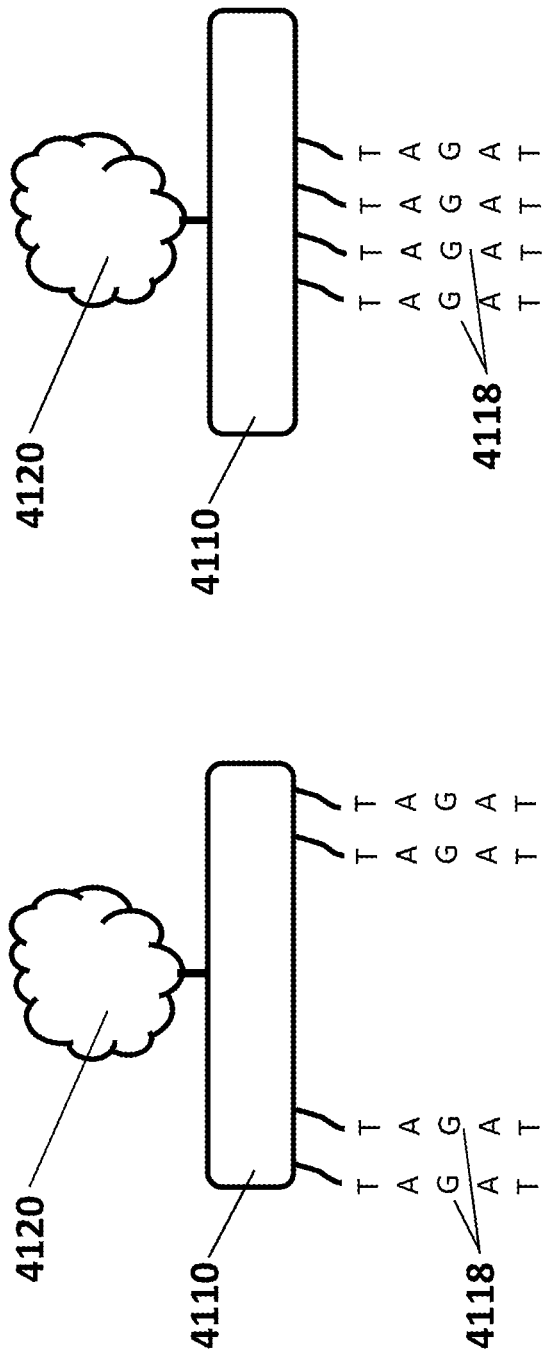

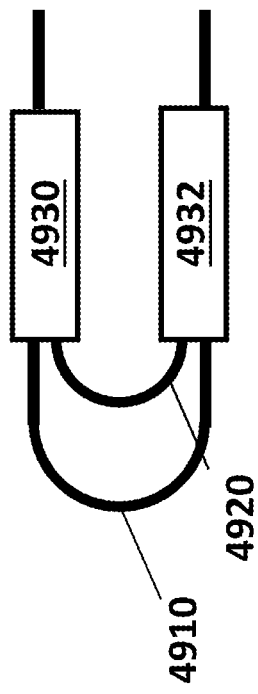
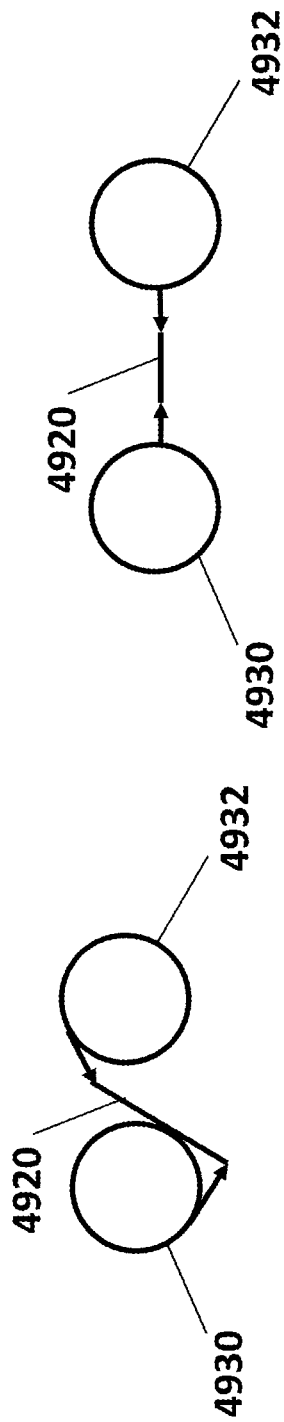
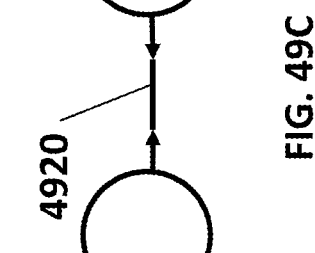
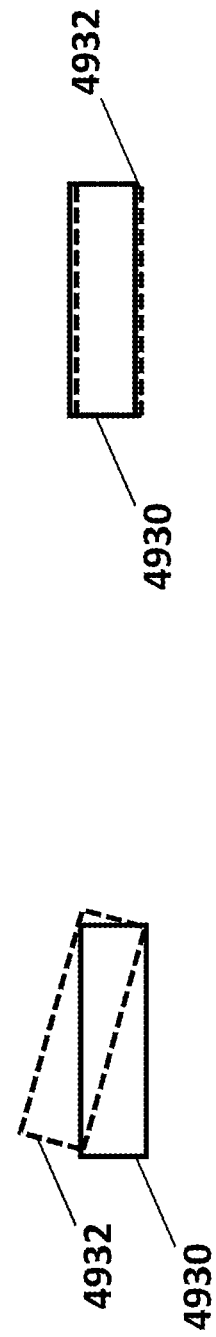

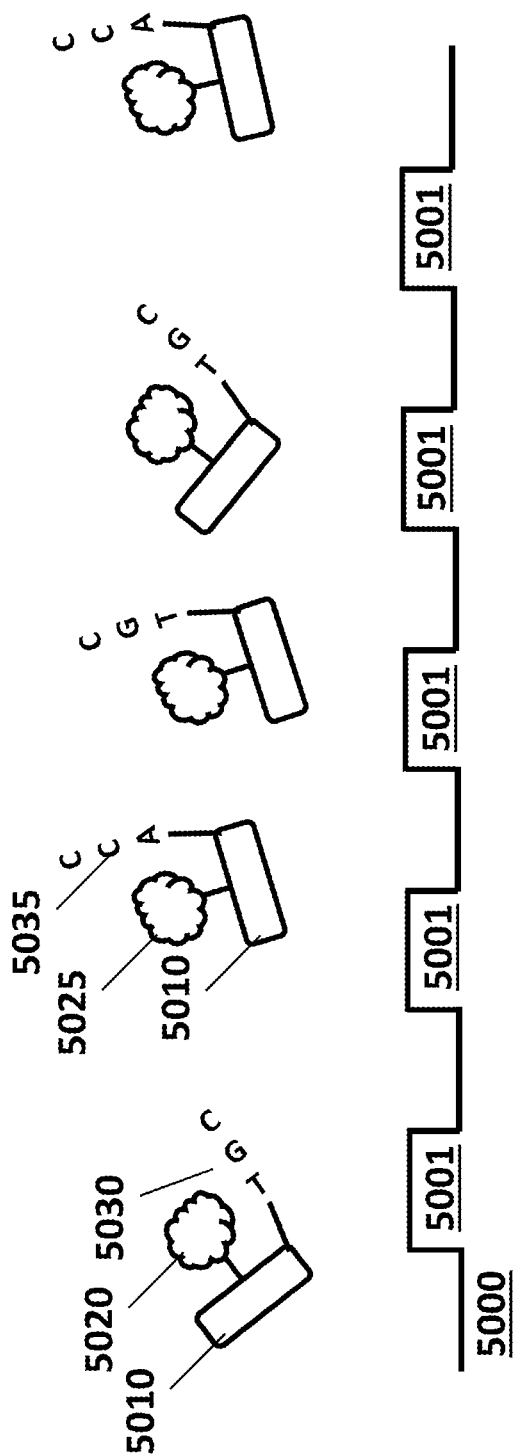
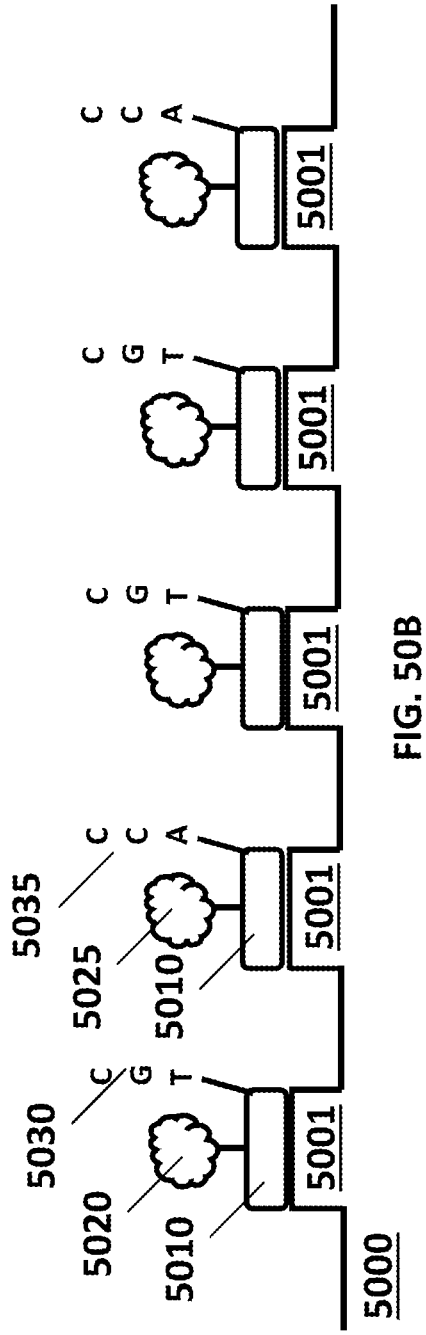
FIG. 50A
FIG. 50B

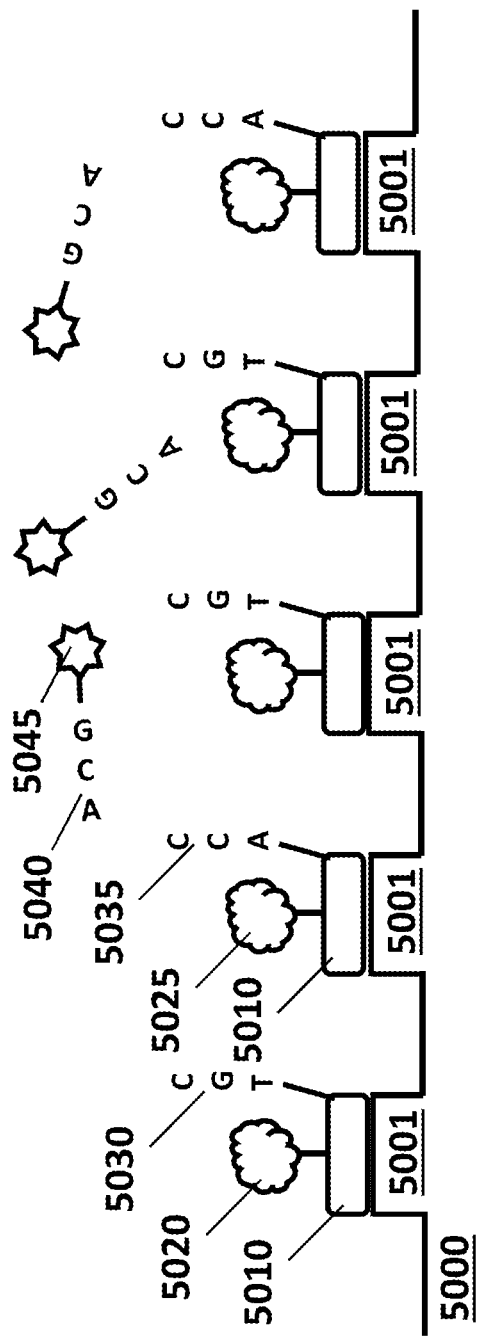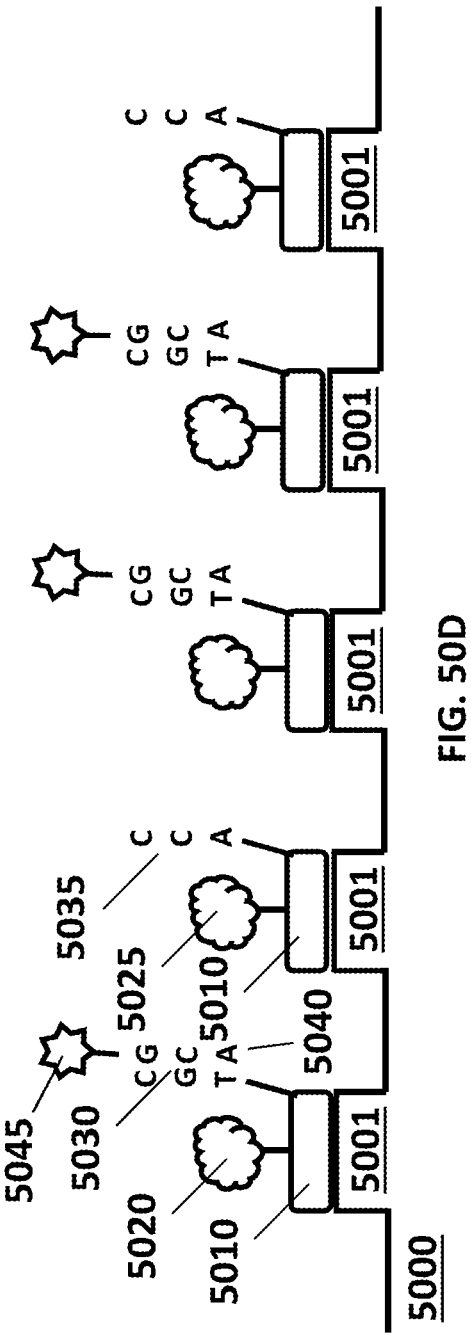
FIG. 50C
FIG. 50D

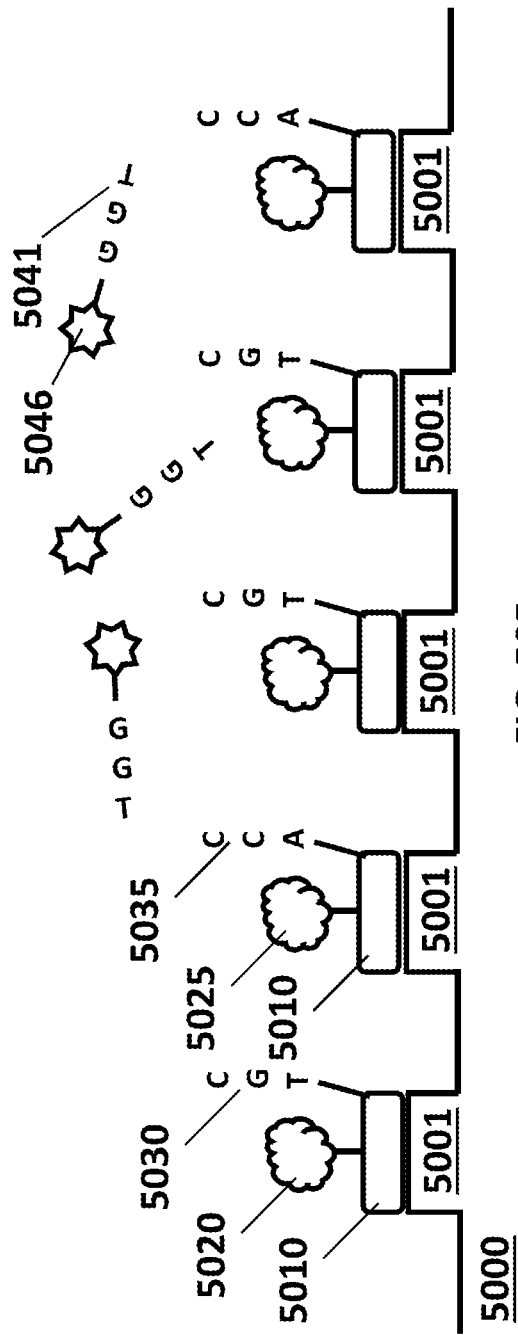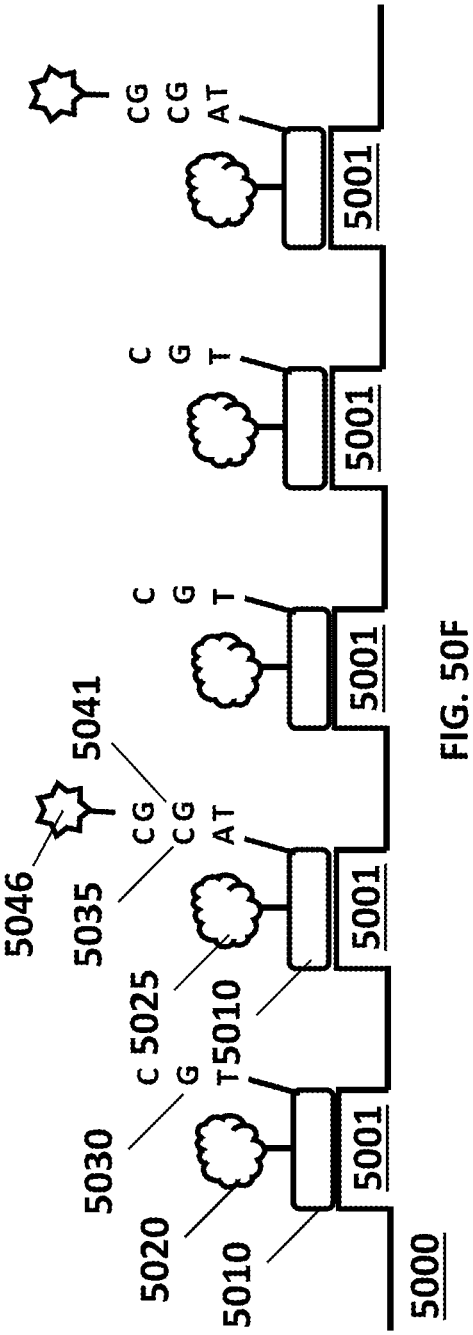
FIG. 50E
FIG. 50F

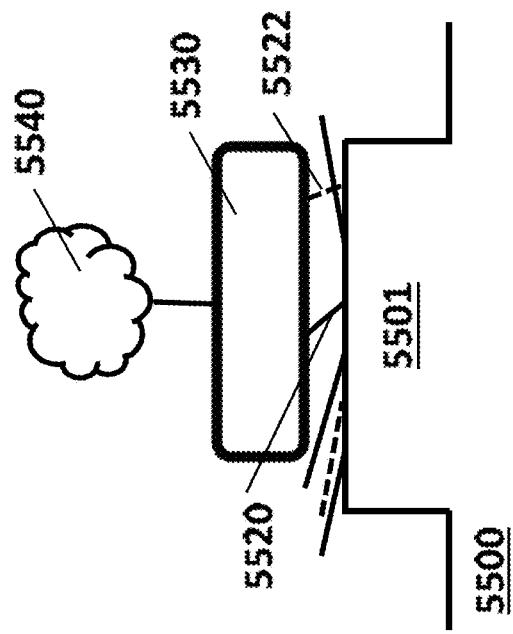
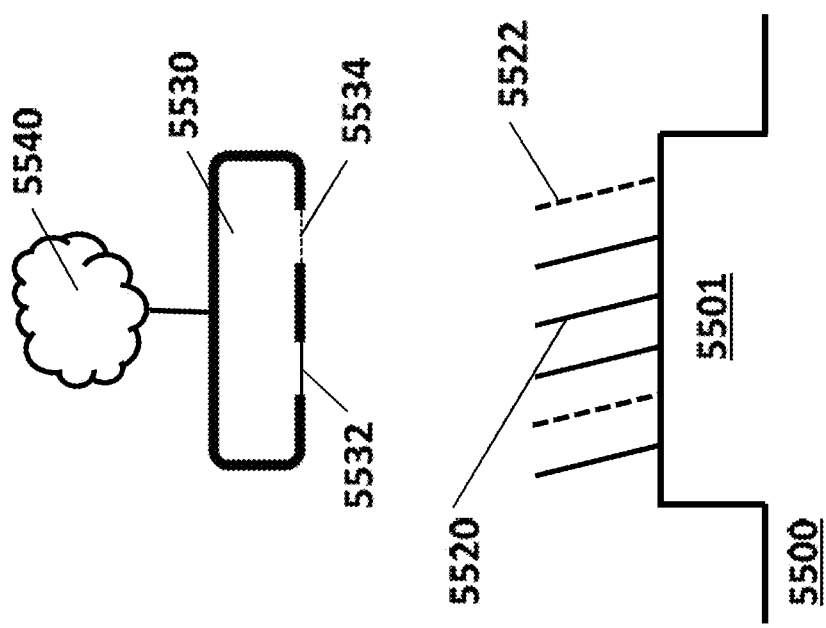

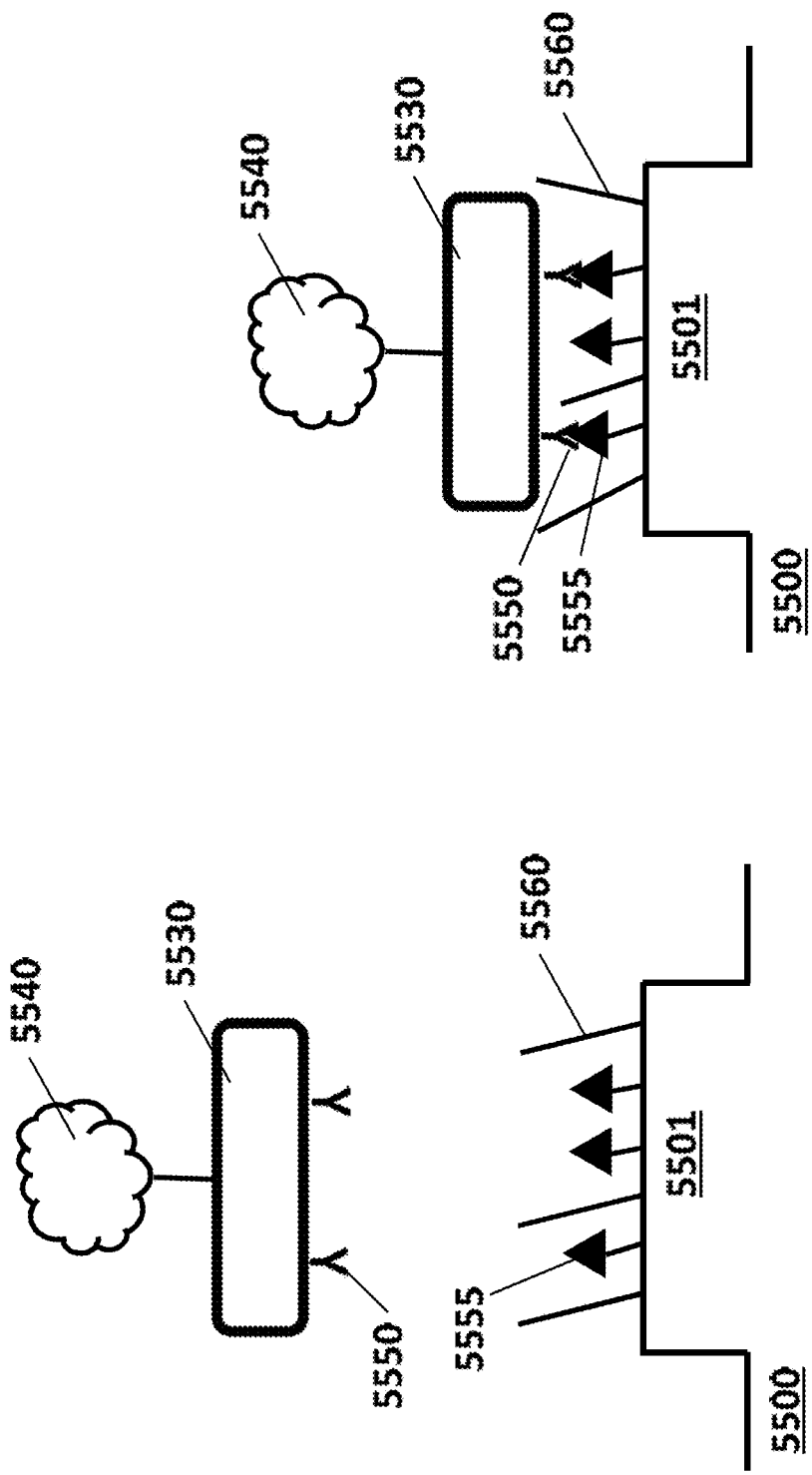

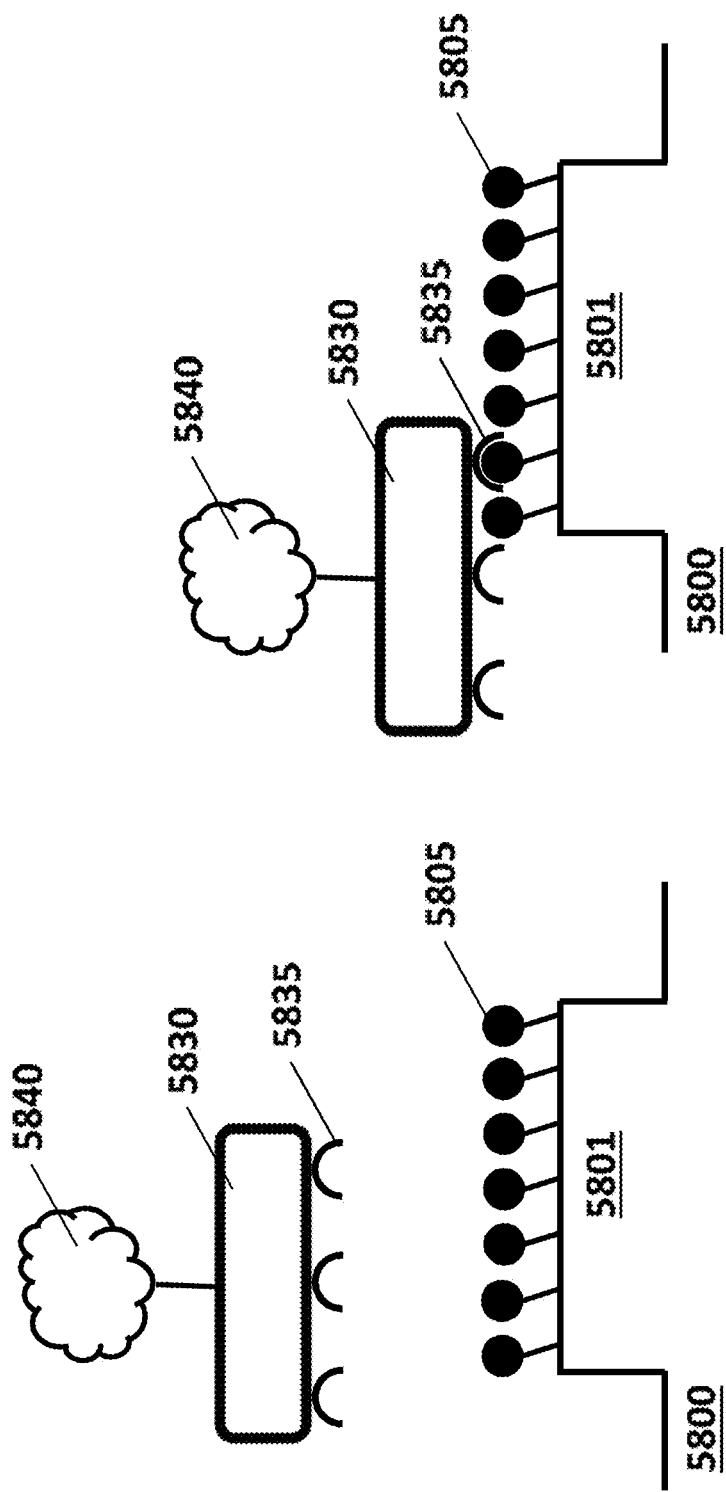

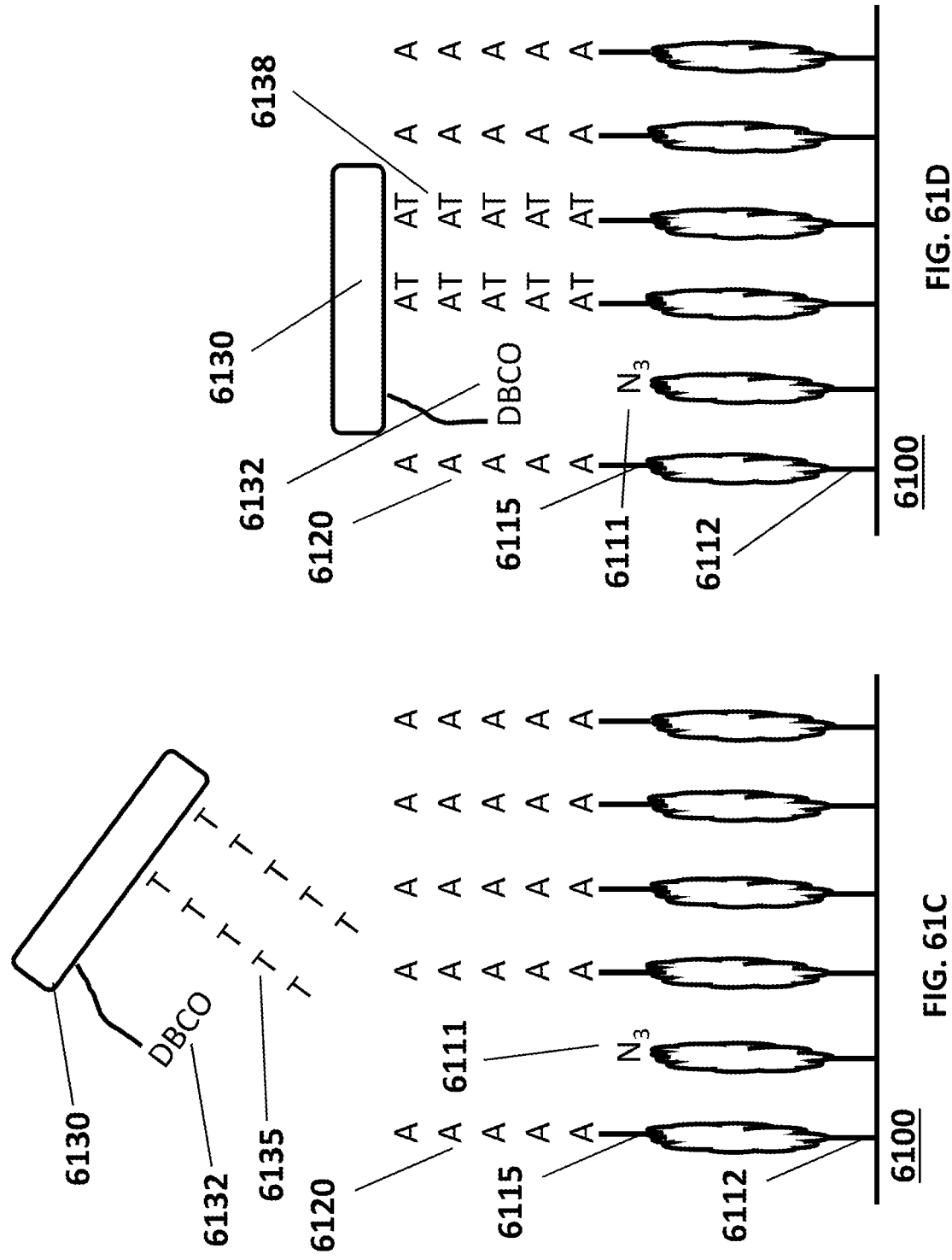

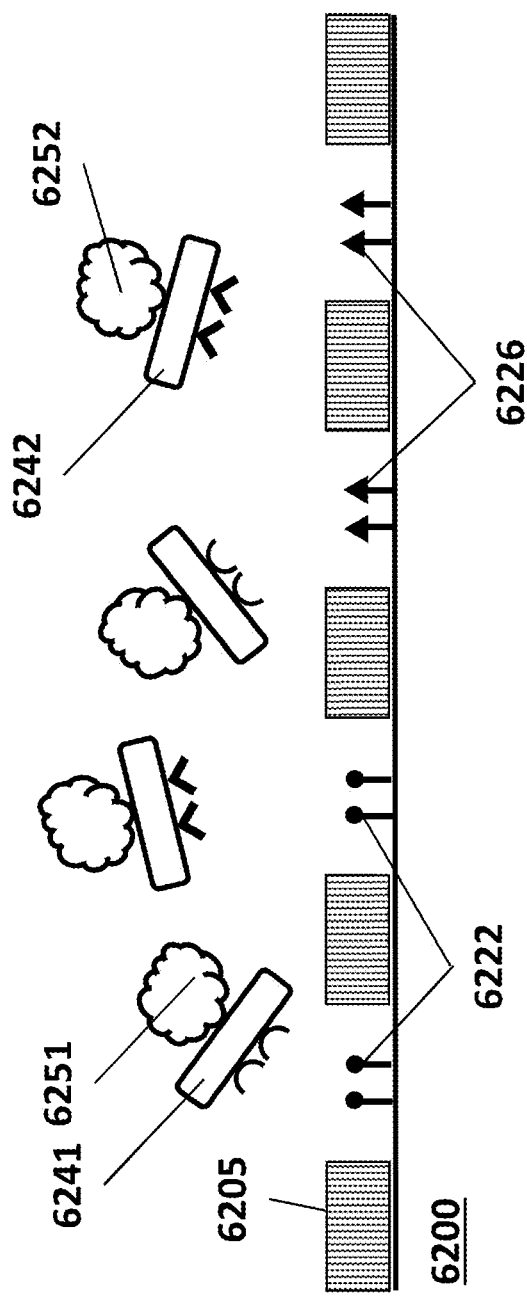
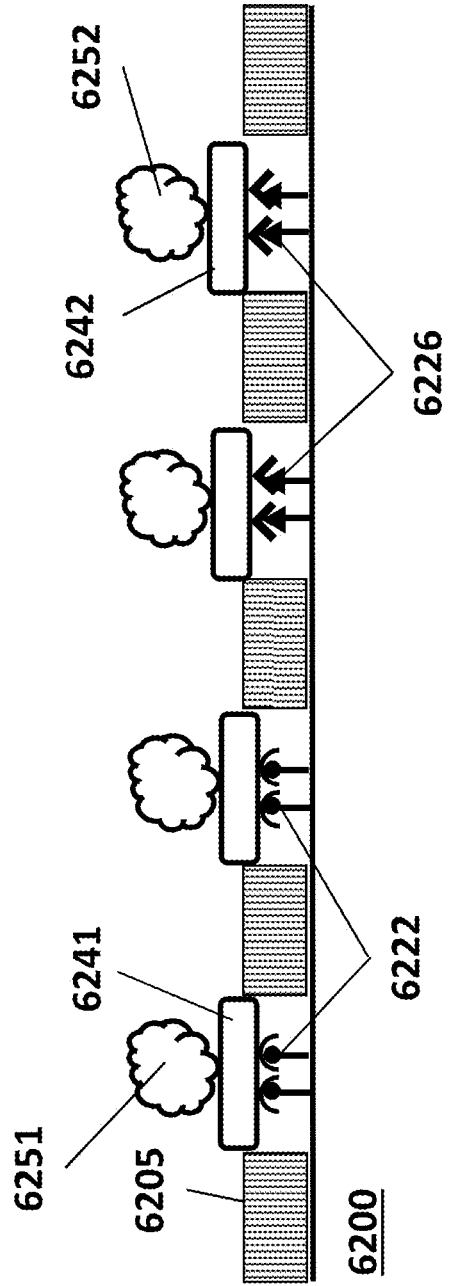

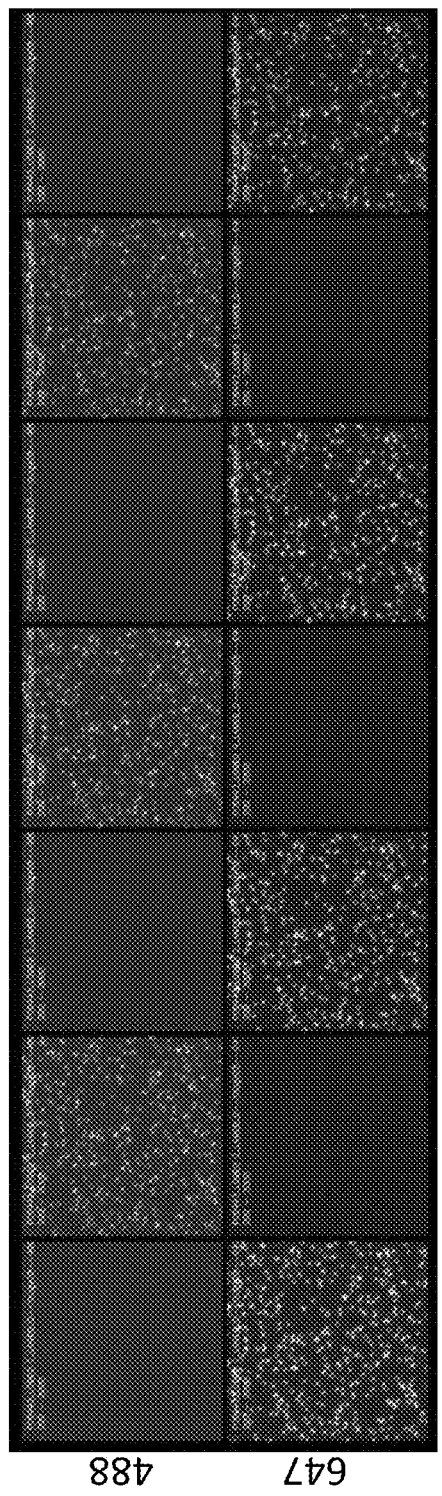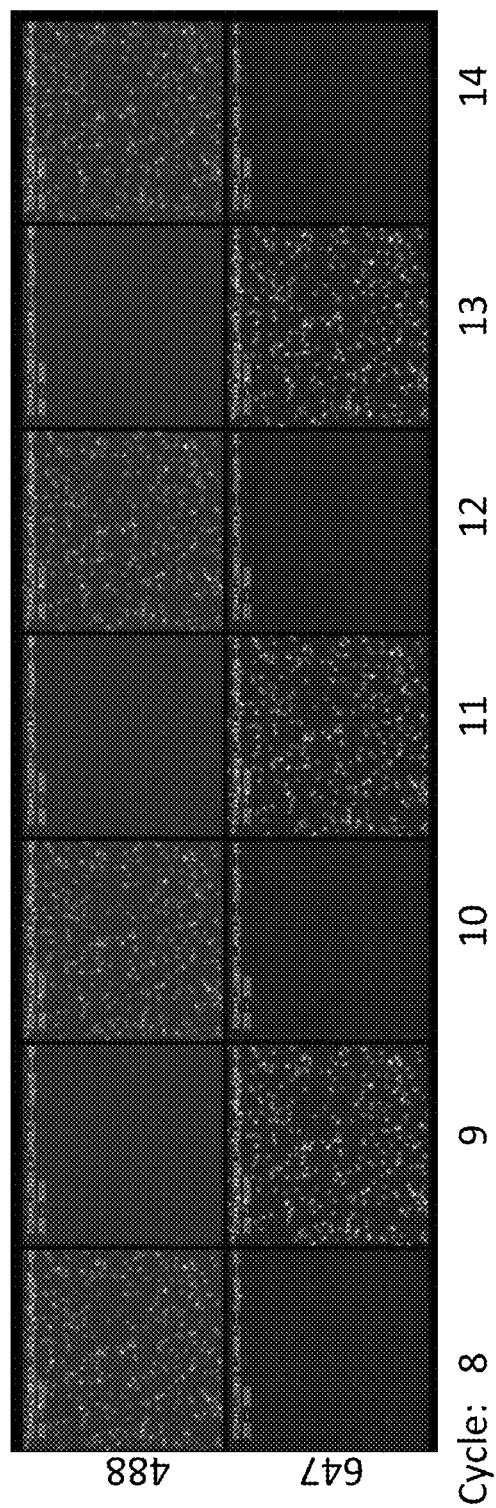
FIG. 68

SYSTEMS AND METHODS FOR BIOMOLECULE RETENTION

CROSS-REFERENCE TO RELATED APPLICATIONS

This application is a continuation of U.S. application Ser. No. 18/416,639, filed Jan. 18, 2024, which is a continuation of U.S. application Ser. No. 18/361,731, filed Jul. 28, 2023, which is a continuation of U.S. application Ser. No. 18/050,732, filed Oct. 28, 2022, which is a continuation of U.S. application Ser. No. 17/692,035, filed Mar. 10, 2022, which claims priority to U.S. Provisional Application No. 63/159,500, filed on Mar. 11, 2021, and U.S. Provisional Application No. 63/256,761, filed on Oct. 18, 2021, each of which is incorporated herein by reference in its entirety.

SEQUENCE LISTING

This application contains a Sequence Listing which has been submitted electronically in XML format and is hereby incorporated by reference in its entirety. Said XML copy, created on Jul. 8, 2024, is named SL_50109_4005US06.xml and is 574,343 bytes in size.

BACKGROUND OF THE INVENTION

Analytes and other molecules may be formed into structured or ordered arrays for various purposes, including for analytical techniques and other chemical purposes. For example, biomolecules may be patterned into single-molecule arrays for purposes such as sequencing or molecule identification. High efficiency of analyte deposition on single-molecule arrays may benefit from methods of preparing analytes and preparing surfaces or interfaces where the analytes are to be deposited.

SUMMARY OF THE INVENTION

In an aspect, provided herein is a composition, comprising: a structured nucleic acid particle (SNAP) comprising (i) a display moiety that is configured to couple to an analyte, (ii) a capture moiety that is configured to couple with a surface, and (iii) a multifunctional moiety comprising a first functional group and a second functional group, wherein the multifunctional moiety is coupled to the structured nucleic acid particle, and wherein the first functional group is coupled to the display moiety, and wherein the second functional group is coupled to the capture moiety.

In another aspect, provided herein is a composition, comprising: a structured nucleic acid particle, and a multifunctional moiety, wherein the multifunctional moiety is coupled to the SNAP, and wherein the multifunctional moiety is configured to form a continuous linker from a surface to an analyte.

In another aspect, provided herein is a structured nucleic acid particle (SNAP) complex, comprising two or more SNAPs, wherein each SNAP of the two or more SNAPs is selected independently from the group consisting of a display SNAP, a utility SNAP, or a combination thereof, wherein the display SNAP comprises a display moiety that is configured to couple to an analyte, wherein the utility SNAP comprises a capture moiety that is configured to couple with a surface, and wherein the two or more SNAPs are coupled to form the SNAP complex.

In another aspect, provided herein is a structured nucleic acid particle (SNAP) composition, comprising: a material comprising a surface, and two or more SNAPs, wherein each SNAP of the two or more SNAPs is selected independently from the group consisting of a display SNAP, a utility SNAP, or a combination thereof, wherein the display SNAP comprises a display moiety that is configured to couple to an analyte, wherein the two or more SNAPs are coupled to the surface, and wherein a first SNAP of the two or more SNAPs is coupled to a second SNAP of the two or more SNAPs, thereby forming a SNAP complex.

In another aspect, provided herein is a composition, comprising: a) an analyte, b) a display SNAP, and c) one or more SNAPs selected from the group consisting of a display SNAP, a utility SNAP, and combinations thereof, wherein the display SNAP comprises a display moiety that is configured to couple to the analyte, wherein the display SNAP is coupled to the analyte, and wherein the display SNAP is coupled to the one or more SNAPs, thereby forming a SNAP complex.

In another aspect, provided herein is a structured nucleic acid particle composition, comprising: a) a material comprising a surface, b) an analyte, c) a display SNAP, and one or more SNAPs selected from the group consisting of a display SNAP, a utility SNAP, and combinations thereof, wherein the display SNAP comprises a display moiety that is configured to couple to the analyte, wherein the display SNAP is coupled to the analyte, wherein the display SNAP is coupled to the one or more SNAPs, thereby forming a SNAP complex, and wherein the SNAP complex is coupled to the surface.

In another aspect, provided herein is an array, comprising: a) a plurality of SNAP complexes, and b) a material comprising a surface, wherein each of the SNAP complexes is coupled to the surface, wherein each SNAP complex of the plurality of SNAP complexes is coupled to one or more other SNAP complexes of the plurality of SNAP complexes, and wherein each SNAP complex of the plurality of SNAP complexes comprises two or more SNAPs selected independently from the group consisting of a display SNAP, a utility SNAP, and combinations thereof.

In another aspect, provided herein is a method of forming an array, comprising: a) providing a plurality of SNAP complexes, b) coupling each SNAP complex of the plurality of SNAP complexes to one or more additional SNAP complexes from the plurality of SNAP complexes, and c) coupling each SNAP complex of the plurality of SNAP complexes with a surface, wherein each SNAP complex comprises a display SNAP and one or more utility SNAPs, and wherein each SNAP complex comprises a coupling moiety that couples with the surface, thereby forming an array.

In another aspect, provided herein is a composition, comprising: a) a structured nucleic acid particle, wherein the structured nucleic acid particle comprises: i) a retaining component; ii) a display moiety comprising a coupling group that is configured to couple an analyte, wherein the display moiety is coupled to the retaining component, and iii) a capture moiety that is configured to couple with a surface, wherein the capture moiety comprises a plurality of first surface-interacting oligonucleotides, and wherein each first surface-interacting oligonucleotide of the plurality of first surface-interacting oligonucleotides comprises a first nucleic acid strand that is coupled to the retaining component and a first surface-interacting moiety, wherein the first surface-interacting moiety is configured to form a coupling interaction with a surface-linked moiety, wherein the capture moiety is restrained from contacting the display moiety by the retaining component, and b) an analyte comprising a complementary coupling group that is configured to couple to the display moiety of the structured nucleic acid particle.

In another aspect, provided herein is a composition, comprising: a) a structured nucleic acid particle, wherein the structured nucleic acid particle comprises: i) a retaining component; ii) a display moiety that is coupled to the retaining component; and iii) a capture moiety that is coupled to the retaining component, wherein the capture moiety comprises a plurality of oligonucleotides, and wherein each oligonucleotide of the plurality of oligonucleotides comprises a surface-interacting moiety, and b) a solid support comprising a coupling surface, wherein the surface comprises a surface-linked moiety, and wherein a surface-interacting moiety of the plurality of surface-interacting moieties is coupled to the surface-linked, wherein the display moiety is restrained from contacting the surface by the retaining component.

In another aspect, provided herein is a method of identifying a polypeptide, the method comprising: a) providing a SNAP composition as set forth herein, wherein the polypeptide is coupled to the display moiety, b) contacting the solid support with a plurality of detectable affinity reagents, c) detecting presence or absence of binding of the detectable affinity reagent of the plurality of detectable affinity agents to the polypeptide, d) optionally repeating steps b)-c) with a second plurality of detectable affinity reagents, and e) based upon the presence or absences of binding of one or more of the affinity reagents, identifying the polypeptide.

In another aspect, provided herein is a method of sequencing a polypeptide, the method comprising: a) providing a SNAP composition as set forth herein, wherein the polypeptide is coupled to the display moiety, b) removing a terminal amino acid residue of the polypeptide by an Edman-type degradation reaction, c) identifying the terminal amino acid residue, and d) repeating steps b-c) until a sequence of amino acid residues has been identified for the polypeptide.

In another aspect, provided herein is a single-analyte array, comprising: a) a solid support comprising a plurality of addresses, wherein each address of the plurality of addresses is resolvable at single-analyte resolution, wherein each address comprises a coupling surface, and wherein each coupling surface comprises one or more surface-linked moieties, b0 a plurality of structured nucleic acid particles, wherein each structured nucleic acid particle comprises a coupling moiety, wherein the coupling moiety comprises a plurality of oligonucleotides, wherein each oligonucleotide of the plurality of oligonucleotides comprises a surface-interacting moiety, wherein each structured nucleic acid particle of the plurality of structured nucleic acid particles is coupled to an address of the plurality of addresses by a binding of the surface-interacting moiety of the plurality of oligonucleotides to a surface-linked moiety of the one or more complementary oligonucleotides, and wherein a structured nucleic acid particle of the plurality of structured nucleic acid particles comprises a display moiety comprising a coupling site that is coupled to an analyte.

In another aspect, provided herein is a single-analyte array, comprising: a) a solid support comprising a plurality of addresses, wherein each address of the plurality of addresses is resolvable from each other address at single-analyte resolution, and wherein each address is separated from each adjacent address by one or more interstitial regions, and b) a plurality of analytes, wherein a single analyte of the plurality of analytes is coupled to an address of the plurality of addresses, wherein each address of the plurality of addresses comprises no more than one single analyte, wherein each single analyte is coupled to a coupling surface of the address by a nucleic acid structure, and wherein the nucleic acid structure occludes the single analyte from contacting the coupling surface.

In another aspect, provided herein is a nucleic acid nanostructure, comprising at least 10 coupled nucleic acids, wherein the nucleic acid nanostructure comprises: a) a compacted region comprising a high internal complementarity, wherein the high internal complementarity comprises at least 50% double-stranded nucleic acids and at least 1% single-stranded nucleic acids, and wherein the compacted region comprises a display moiety, wherein the display moiety is coupled to, or configured to couple to, an analyte of interest; and b) a pervious region comprising a low internal complementarity, wherein the low internal complementarity comprises at least about 50% single-stranded nucleic acids, and wherein the pervious region comprises a coupling moiety, wherein the coupling moiety forms, or is configured to form, a coupling interaction with a solid support.

In another aspect, provided herein is a nucleic acid nanostructure, comprising: a) a compacted structure, wherein the compacted structure comprises a scaffold strand and a first plurality of staple oligonucleotides, wherein at least 80% of nucleotides of the scaffold strand are hybridized to nucleotides of the first plurality of staple oligonucleotides, wherein the first plurality of staple oligonucleotides hybridizes to the scaffold strand to form a plurality of tertiary structures, wherein the plurality of tertiary structures includes adjacent tertiary structures linked by a single-stranded nucleic acid region of the scaffold, and wherein a relative position of an adjacent tertiary structure of the adjacent tertiary structures is positionally constrained; and b) a pervious structure, wherein the pervious structure comprises a second plurality of staple oligonucleotides, wherein the staple oligonucleotides are coupled to the scaffold strand of the compacted structure, wherein the pervious structure comprises at least 50% single-stranded nucleic acid, and wherein the pervious structure has an anisotropic three-dimensional distribution around at least a portion of the compacted structure.

In another aspect, provided herein is a nucleic acid nanostructure, comprising: a) a compacted structure, wherein the compacted structure comprises a scaffold strand and a first plurality of staple oligonucleotides, wherein at least 80% of nucleotides of the scaffold strand are hybridized to nucleotides of the first plurality of staple oligonucleotides, wherein the first plurality of staple oligonucleotides hybridizes to the scaffold strand to form a plurality of tertiary structures, wherein the plurality of tertiary structures includes adjacent tertiary structures linked by a single-stranded region of the scaffold strand, wherein the relative positions of the adjacent tertiary structures are positionally constrained, and wherein the compacted structure comprises an effective surface area; and b) a pervious structure, wherein the pervious structure comprises a second plurality of staple oligonucleotides, wherein the staple oligonucleotides are coupled to the scaffold strand of the compacted structure, and wherein the pervious structure comprises at least 50% single-stranded nucleic acid; and wherein (i) an effective surface area of the nucleic acid nanostructure is larger than the effective surface area of the compacted structure, or ii) the ratio of effective surface area to volume of the nucleic acid nanostructure is larger than the ratio of effective surface area to volume of the compacted structure.

In another aspect, provided herein is a nucleic acid nanostructure, comprising a plurality of nucleic acid strands, wherein each nucleic acid strand of the plurality of nucleic acid strands is hybridized to another nucleic acid strand of the plurality of nucleic acid strands to form a plurality of tertiary structures, and wherein a nucleic acid strand of the plurality of nucleic acid strands comprises a first nucleotide sequence that is hybridized to a second nucleic acid strand of the plurality of nucleic acid strands, wherein the nucleic acid strand of the plurality of nucleic acid strands further comprises a second nucleotide sequence of at least 100 consecutive nucleotides, and wherein at least 50 nucleotides of the second nucleotide sequence is single-stranded.

In another aspect, provided herein is a composition, comprising: a) a solid support comprising a plurality of sites; and b) a plurality of structured nucleic acid particles (SNAPs), in which each SNAP is coupled to, or is configured to couple to, an analyte, and in which each SNAP of the plurality of SNAPs is coupled to a site of the plurality of sites, wherein the plurality of sites comprises a first subset comprising a first quantity of sites and a second subset comprising a second quantity of sites, in which each site of the first subset comprises two or more coupled SNAPs, in which each site of the second subset comprises one and only one coupled SNAP, and in which a ratio of the quantity of sites of the first subset to the quantity of sites of the second subset is less than a ratio predicted by a Poisson distribution.

In another aspect, provided herein is an analyte array, comprising: a) a solid support comprising a plurality of sites; and b) a plurality of nucleic acid nanostructures, wherein each nucleic acid nanostructure is coupled to an analyte of interest, and wherein each nucleic acid nanostructure of the plurality of nucleic acid nanostructures is coupled to a site of the plurality of sites, wherein at least 40% of sites of the plurality of sites comprise one and only one analyte of interest.

In another aspect, provided herein is a composition comprising: a) a solid support comprising a site that is configured to couple a nucleic acid nanostructure; and b) the nucleic acid nanostructure, wherein the nucleic acid nanostructure is coupled to the site, wherein the nucleic acid nanostructure is coupled to an analyte of interest; and wherein the nucleic acid nanostructure is configured to prevent contact between the analyte of interest and the solid support.

In another aspect, provided herein is a composition, comprising: a) a solid support comprising a site that is configured to couple a nucleic acid nanostructure, wherein the site comprises a surface area; and b) the nucleic acid nanostructure, wherein the nucleic acid nanostructure is coupled to the site, wherein the nucleic acid nanostructure is coupled to, or is configured to couple to, an analyte of interest; wherein the nucleic acid nanostructure comprises a total effective surface area in an unbound configuration, wherein the nucleic acid nanostructure comprises a compact structure with an effective surface area, wherein the effective surface area of the compacted structure in the unbound configuration is less than 50% of the surface area of the site, and wherein the unbound configuration comprises the nucleic acid nanostructure being uncoupled from the site.

In another aspect, provided herein is a method of coupling a nucleic acid nanostructure to an array site, comprising: a) contacting an array comprising a site with a nucleic acid nanostructure, wherein the site comprises a plurality of surface-linked moieties, and wherein the nucleic acid nanostructure comprises a plurality of capture moieties; b) coupling the nucleic acid nanostructure to the site in an initial configuration, wherein the initial configuration does not comprise a stable configuration, and wherein the nucleic acid nanostructure is coupled by a coupling of a capture moiety of the plurality of capture moieties to a surface-linked moiety of the plurality of surface-linked moieties; c) uncoupling the coupling of the capture moiety of the plurality of capture moieties to the surface-linked moiety of the plurality of surface-linked moieties; and d) altering the nucleic acid nanostructure from the initial configuration to the stable configuration, wherein each capture moiety of the plurality of capture moieties is coupled to a surface-linked moiety of the plurality of surface-linked moieties.

In another aspect provided herein is a method of forming a multiplex array of analytes, comprising: a) contacting an array comprising a plurality of sites with a first plurality of nucleic acid nanostructures, wherein each nucleic acid nanostructure of the first plurality of nucleic acid nanostructures is coupled to an analyte of interest of a first plurality of analytes of interest; b) contacting the array comprising the plurality of sites with a second plurality of nucleic acid nanostructures, wherein each nucleic acid nanostructure of the second plurality of nucleic acid nanostructures is coupled to an analyte of interest of a second plurality of analytes of interest; c) depositing the first plurality of nucleic acid nanostructures at a first subset of sites of the plurality of sites; and d) depositing the second plurality of nucleic acid nanostructures at a second subset of sites of the plurality of sites, wherein the first subset of sites and the second subset of sites comprise a random spatial distribution.

In another aspect, provided herein is a nanostructure, comprising: a) a compacted nucleic acid structure comprising a scaffold strand hybridized to a first plurality of staple oligonucleotides, wherein the first plurality of staple oligonucleotides hybridizes to the scaffold strand to form a plurality of tertiary structures, wherein the plurality of tertiary structures comprises adjacent tertiary structures linked by a single-stranded region of the scaffold strand, and wherein relative positions of the adjacent tertiary structures are positionally constrained; b) a pervious structure, wherein the pervious structure comprises a second plurality of staple oligonucleotides hybridized to the scaffold strand; and c) a solid support comprising surface-linked oligonucleotides, wherein the surface-linked oligonucleotides are attached to a surface of the solid support, and wherein the surface-linked oligonucleotides are hybridized to staple oligonucleotides of the pervious structure.

In another aspect, provided herein is a method of coupling a nucleic acid nanostructure to an array, comprising: a) contacting a solid support with a nucleic acid nanostructure, wherein the solid support comprises surface-linked oligonucleotides attached to the solid support, and wherein the nucleic acid nanostructure comprises: i) a compacted nucleic acid structure comprising a scaffold strand hybridized to a first plurality of staple oligonucleotides, wherein the first plurality of staple oligonucleotides hybridizes to the scaffold strand to form a plurality of tertiary structures, wherein the plurality of tertiary structures comprises adjacent tertiary structures linked by a single-stranded region of the scaffold strand, and wherein relative positions of the adjacent tertiary structures are positionally constrained; and ii) a pervious structure, wherein the pervious structure comprises a second plurality of staple oligonucleotides hybridized to the scaffold strand; and b) hybridizing a surface-linked oligonucleotide to a staple oligonucleotide of the second plurality of staple oligonucleotides.

In another aspect, provided herein is a method of preparing an array of analytes, comprising: a) providing an array comprising a plurality of sites, wherein each site comprises surface-linked oligonucleotides; b) contacting the array with a plurality of analytes, wherein each analyte is coupled to a nucleic acid nanostructure, wherein each nucleic acid nanostructure comprises a plurality of surface-coupling oligonucleotides; and c) coupling one and only one nucleic acid nanostructure to a site of the plurality of sites, wherein coupling the nucleic acid nanostructure comprises hybridizing a surface-linked oligonucleotide of the site to the surface-coupling oligonucleotide of the nucleic acid nanostructure.

In another aspect, provided herein is an array of analytes of interest, comprising: a) a solid support comprising a plurality of sites, wherein each site comprises surface-linked oligonucleotides; b) a plurality of nucleic acid nanostructures, wherein each nucleic acid nanostructure is configured to couple an analyte, wherein each nucleic acid nanostructure comprises a plurality of surface-coupling oligonucleotides, wherein each surface-coupling oligonucleotide comprises no self-complementarity, and wherein each nucleic acid nanostructure of the plurality of nucleic acid nanostructures is coupled to a site of the plurality of sites by a hybridizing of a surface-coupling oligonucleotide to a surface-linked oligonucleotide; and c) a plurality of analytes of interest, in which each analyte of interest is coupled to a nucleic acid nanostructure of the plurality of nucleic acid nanostructures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A illustrates angular offset for two faces of a structured nucleic acid particle (SNAP), in accordance with some embodiments. FIG. 1B illustrates angular offset for two faces of a SNAP, in accordance with some embodiments.

FIGS. 2A-2D show a SNAP with tertiary structures. FIG. 2A depicts two sets of tertiary structures in a SNAP, in accordance with some embodiments. FIG. 2B shows a cross-section of a SNAP with multiple faces, in accordance with some embodiments. FIG. 2C depicts two sets of tertiary structures in a SNAP, in accordance with some embodiments. FIG. 2D shows a cross-section of a SNAP with multiple faces, in accordance with some embodiments.

FIG. 3A shows a SNAP comprising a multifunctional moiety, in accordance with some embodiments. FIG. 3B shows a linking moiety of a multifunctional moiety, in accordance with some embodiments. FIG. 3C shows a SNAP comprising a multifunctional moiety coupled to a solid support, in accordance with some embodiments. FIG. 3D shows an analyte coupled to a solid support by a multifunctional moiety, in accordance with some embodiments.

FIG. 7A shows a multifunctional moiety comprising an alkyl group, in accordance with some embodiments. FIG. 7B shows a multifunctional moiety comprising modified oligonucleotides, in accordance with some embodiments.

FIGS. 9A, 9B, 9C, 9D, 9E, and 9F illustrate a method of coupling an analyte to a surface, in accordance with some embodiments.

FIGS. 10A, 10B, 10C, and 10D depict a SNAP comprising two multifunctional moieties, in accordance with some embodiments.

FIGS. 11A, 11B, 11C, and 11D illustrate a SNAP comprising a multifunctional moiety, in accordance with some embodiments.

FIGS. 12A, 12B, and 12C show a SNAP complex comprising tile-shaped SNAPs, in accordance with some embodiments.

FIGS. 17A, 17B, and 17C show an array formed from SNAP complexes, in accordance with some embodiments.

FIGS. 18A, 18B, and 18C show an array formed from SNAP complexes, in accordance with some embodiments.

FIGS. 19A and 19B depict a complex of SNAPs formed at an interface, in accordance with some embodiments.

FIGS. 28A and 28B illustrate a SNAP complex coupling to a patterned surface, in accordance with some embodiments.

FIGS. 30A, 30B, 30C, and 30D show HPLC data for SNAP-protein conjugate purification.

FIGS. 34A, 34B, and 34C show fluorescent confocal scanning microscopy image data for SNAP deposition.

FIGS. 37A and 37B depict a SNAP comprising regions of full structuring and partial structuring, in accordance with some embodiments.

FIGS. 39A and 39B depict a SNAP comprising a chemically-modified internal volume region, in accordance with some embodiments.

FIGS. 41A and 41B show differing distributions of surface-interacting moieties on a capture moiety of a SNAP, in accordance with some embodiments.

FIGS. 49A, 49B, 49C, 49D, and 49E illustrate aspects of nucleic acid structure and conformation, in accordance with some embodiments.

FIGS. 50A, 50B, 50C, 50D, 50E, and 50F show steps of a method for forming a multiplexed single-analyte array, in accordance with some embodiments.

FIGS. 55A, 55B, 55C, and 55D display methods for forming multi-valent binding interactions between a nucleic acid nanostructure and a solid support, in accordance with some embodiments.

FIGS. 58A, 58B, and 58C show a method of reconfiguring a binding configuration of a nucleic acid nanostructure coupled to an array site, in accordance with some embodiments.

FIGS. 59A and 59B display atomic force microscopy images of nucleic acid nanostructures. FIGS. 59C and 59D plot various measurements of nucleic acid nanostructure yield and size.

FIGS. 61A, 61B, 61C, 61D, and 61E display steps of a method of coupling a nucleic acid nanostructure to a solid support utilizing unreacted functional groups, in accordance with some embodiments.

FIGS. 62A-62E show methods of forming arrays and depositing analytes to form multiplexed arrays. FIGS. 62A, 62B, and 62C illustrate methods of forming arrays that are configured to produce multiplexed arrays of analytes, in accordance with some embodiments.

FIGS. 62D and 62E illustrate a method of depositing two or more types of analytes to form a multiplexed array, in accordance with some embodiments.

FIG. 67A illustrates a schematic of a functionalized array site, in accordance with some embodiments. FIG. 67B displays fluorescence microscopy characterization of an array formed by lithographic patterning. FIG. 67C displays atomic force microscopy data of surface roughness of an array site formed by lithographic patterning. FIGS. 67D and 67E plot data for average array site diameter and site pitch for arrays formed by lithographic patterning.

FIG. 68 displays fluorescence microscopy images for cycles of binding and stripping fluorescently-labeled oligonucleotides from functional nucleic acids.

DETAILED DESCRIPTION OF THE INVENTION

Figure 1B:
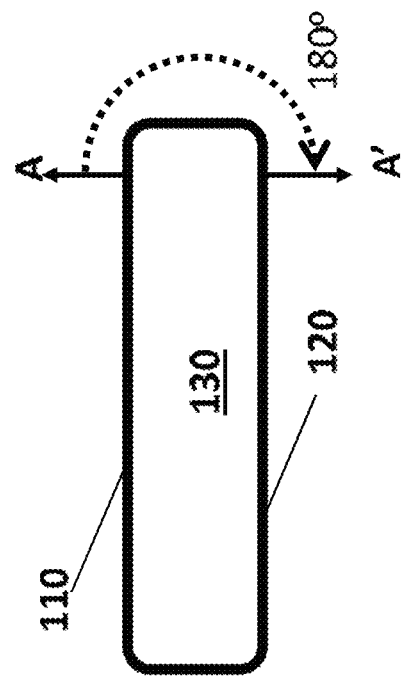
FIGS. 1A and 1B show a structured nucleic acid particle (SNAP) with two faces.

The ordering of molecules at the nanoscale is a critical problem for numerous technologies, including analytical and bioanalytical methods, catalysis and biocatalysis, micro- and nanofluidics, and micro- and nano-electronics. Of particular interest are methods of arranging molecules at surfaces or interfaces where the length scales of surface features or surface irregularities often approach the length scale of molecules that are to be arranged at the surface or interface. For example, single-molecule analytical techniques are of interest for numerous biological applications, including genomics, transcriptomics, and proteomics. The formation of single-analyte biomolecule arrays can be limited by nanoscale and/or single-molecule effects that can alternately cause limited biomolecule deposition or excess biomolecule deposition at binding sites on a single-analyte array. For example, defects in the nanoscale fabrication of solid surfaces can produce sites that have anomalous binding properties, thereby producing localized defects in array patterning. Likewise, thermodynamic effects (e.g., entropy) and/or kinetic effects (e.g., slow dissociation) can cause unintended phenomena (e.g., molecule co-localization) at array sites given a large enough sample of molecules. Consequently, in forming single-analyte arrays, methods of preparing consistent surfaces or interfaces and carefully controlling the deposition of molecules on the surfaces or interfaces is important.

It is preferable for many single-analyte, array-based techniques to form arrays that are substantially uniform, both in terms of having a single analyte be present at substantially all array sites of a single-analyte array (i.e., an array site occupancy value >0 analytes), and in terms of having no more than one single-analyte at each array site of the single-analyte array (i.e., an array site occupancy value=1 analyte). The uniformity of a single-analyte array may increase as a Poisson-like probability distribution narrows around an array site occupancy value of 1 analyte. Accordingly, array formation methods that facilitate such a narrowing of a probability mass function around an array site occupancy value of 1 analyte are preferable for the formation of single-analyte arrays.

Intermediary particles offer a potential approach to controlling the deposition of molecules on surfaces or interfaces. Particularly useful intermediary particles have tunable characteristics that allow the intermediary particle to selectively interact with surfaces or interfaces while displaying analytes and other molecules favorably on a surface or interface. Surfaces can be readily patterned using nanofabrication techniques to create sites or addresses that are uniquely configured to capture particles set forth herein. As such, a surface can be patterned with an array of sites configured to capture a plurality of particles. By using a plurality of particles, in which each particle is attached to a different analyte, an array of different analytes can be formed on the surface and in a predetermined pattern that is suited to a desired analytical assay method, such as an analytical method set forth herein. Exemplary intermediary particles are structured nucleic acid particles (SNAPs), such as nucleic acid origami. The tunability of such particles arises from the helical nature of nucleic acid tertiary structures. Over the course of a single helical revolution, a nucleic acid helix can orient a coupled ligand in virtually any direction over a full 360° of aspect. Consequently, structured nucleic acid particles can be engineered to display attached molecules at specific locations and orientations on the particle, permitting multiple attached molecules to be optimally separated and positioned for best effect. Other nucleic acid nanostructures can be similarly deployed as intermediate particles for displaying analytes on a surface.

Described herein are structured nucleic acid particles and systems thereof that can be used to facilitate the formation of single-molecule arrays of analytes and other molecules. In particular configurations, the structured nucleic acid particles comprise several structural features that increase the specificity of coupling interactions on surfaces or interfaces, or decrease the sensitivity of the particles to defects or irregularities on surfaces or interfaces, thereby permitting the formation of more uniform single-molecule arrays. In particular, provided herein are systems comprising structured nucleic acid particles and solid supports whose complementary chemistries encourage the controlled deposition of single-analyte arrays. Each structured nucleic acid particle may be coupled to one or multiple analytes of interest, permitting the formation of uniform arrays of analytes on a surface or interface. For example, analytes of interest may be nucleic acids, proteins, metabolites or other targets of interest for analytical characterization. In another example, the analytes can be reagents used for synthetic methods such as synthesis of nucleic acids, proteins, small molecules, candidate therapeutics, non-biological polymers, or the like.

Also described herein are complexes that may be formed by the coupling of multiple structured nucleic acid particles. The complexes may increase the efficiency and control of analyte or molecule display at a surface or interface by increasing binding interactions with surface binding sites and/or reducing the likelihood of unwanted analyte or molecule co-deposition at a single location on a surface or array. In some configurations, structured nucleic acid complexes may be configured to form a self-assembling or self-patterning arrays for the display or analytes or other molecules.

Definitions

As used herein, the terms "nucleic acid nanostructure" or "nucleic acid nanoparticle," refer synonymously to a single- or multi-chain polynucleotide molecule comprising a compacted three-dimensional structure. The compacted three-dimensional structure can optionally have a characteristic tertiary structure. An exemplary nucleic acid nanostructure is a structured nucleic acid particle (SNAP). A SNAP can be configured to have an increased number of interactions between regions of a polynucleotide strand, less distance between the regions, increased number of bends in the strand, and/or more acute bends in the strand, as compared to the same nucleic acid molecule in a random coil or other non-structured state. Alternatively or additionally, the compacted three-dimensional structure of a nucleic acid nanostructure can optionally have a characteristic quaternary structure. For example, a nucleic acid nanostructure can be configured to have an increased number of interactions between polynucleotide strands or less distance between the strands, as compared to the same nucleic acid molecule in a random coil or other non-structured state. In some configurations, the tertiary structure (i.e. the helical twist or direction of the polynucleotide strand) of a nucleic acid nanostructure can be configured to be more dense than the same nucleic acid molecule in a random coil or other non-structured state. Nucleic acid nanostructures may include deoxyribonucleic acid (DNA), ribonucleic acid (RNA), peptide nucleic acid (PNA), other nucleic acid analogs, and combinations thereof. Nucleic acid nanostructures may have naturally-arising or engineered secondary, tertiary, or quaternary structures. A structured nucleic acid particle can contain at least one of: i) a moiety that is configured to couple an analyte to the nucleic acid nanostructure, ii) a moiety that is configured to couple the nucleic acid nanostructure to another object such as another SNAP, a solid support or a surface thereof, iii) a moiety that is configured to provide a chemical or physical property or characteristic to a nucleic acid nanostructure, or iv) a combination thereof. Exemplary SNAPs may include nucleic acid nanoballs (e.g. DNA nanoballs), nucleic acid nanotubes (e.g. DNA nanotubes), and nucleic acid origami (e.g. DNA origami). A SNAP may be functionalized to include one or more reactive handles or other moieties. A SNAP may comprise one or more incorporated residues that contain reactive handles or other moieties (e.g., modified nucleotides).

As used herein, the term "primary structure," when used in reference to a nucleic acid, refers to a residue sequence of a single-stranded nucleic acid. As used herein, the term "secondary structure," when used in reference to a nucleic acid, refers to the base-pairing interactions within a single nucleic acid polymer or between two polymers. Secondary structure may include multi-stranded nucleic acids formed by self-complementarity of a single oligonucleotide, such as stems, loops, bulges, and junctions. As used herein, the term "tertiary structure," when used in reference to a nucleic acid, refers to the three-dimensional conformation of a nucleic acid, such as the overall three-dimensional shape of a single-stranded nucleic acid or multi-stranded nucleic acid.

As used herein, the term "pervious," when used in reference to a structure of a nucleic acid, refers to the structure containing two or more structural elements (e.g., single-stranded nucleic acids, double-stranded nucleic acids, a nucleic acid strand containing double-stranded and single-stranded nucleic acids, non-nucleic acid moieties, etc.) having a spatial degree of freedom (e.g., translational, rotational, vibrational, bending, etc.) to facilitate contact of the two or more structural elements with another molecule. The other molecule can be, for example, a molecule having a molecular weight greater than 0.5, 1, 5, 10 or more kilo-Daltons. Optionally, each structural element of the two or more structural elements can move in concert with the movement of the nucleic acid. Optionally, for an unbound nucleic acid comprising a pervious structure containing a plurality of pendant, non-interacting moieties, each pendant moiety will rotate if the nucleic acid rotates, but a free terminus of each pendant moiety is capable of moving independently of the motion of the other free termini of the other pendant moieties. A spatial degree of freedom may be assessed for a structural element of a nucleic acid with respect to a natural and/or stochastic spatial variation in the structure of the nucleic acid (e.g., a spatial degree of freedom comprising motion beyond the natural thermal or Brownian motion of the nucleic acid structure). A first structural element of a pervious structure may have a spatial degree of freedom with respect to a second structural element in one spatial dimension, two spatial dimensions, or three spatial dimensions. A pervious structure may be characterized as comprising a differing chemical characteristic from a compacted structure of a nucleic acid, as set forth herein, such as greater or lesser mass diffusivity for small molecules or macromolecules, a greater or lesser hydrophobicity, a greater or lesser hydrophilicity, a greater or lesser binding strength or specificity for another nucleic acid, a greater or lesser likelihood of binding another nucleic acid, a greater or lesser likelihood of binding a solid support, a greater or lesser binding strength or specificity for a solid support, or a combination thereof. A pervious structure may comprise a differing characteristic or configuration when bound to another entity (e.g., a solid support, a second nucleic acid). In some configurations, when bound to a second entity, a pervious structure may satisfy one or more of i) each structural element of the two or more structural elements moving in concert with a movement of the nucleic acid, ii) each structural element of the two or more structural elements having a reduced spatial degree of freedom relative to an unbound configuration, and iii) each structural element of the two or more structural elements containing at least one spatial degree of freedom (e.g., translational, rotational, vibrational, bending, etc.) with respect to each other structural element of the two or more structural elements. For example, for a nucleic acid coupled to a solid support by a pervious structure containing a plurality of pendant, non-interacting moieties, each pendant moiety may be coupled to a complementary moiety on the solid support, thereby co-locating the nucleic acid and its pervious structure on the solid support, but each pendant moiety may possess an independent ability to disrupt an existing interaction with a complementary surface moiety and form a new interaction with a differing complementary surface moiety.

As used herein, the term "residue," when used in reference to a polymer, refers to a monomeric unit of a polymer structure. When used in reference to a nucleic acid, a residue may refer to a nucleotide, nucleoside, or a synthetic, modified, or non-natural analogue thereof. When used in reference to a polypeptide, a residue may refer to an amino acid or a synthetic, modified, or non-natural analogue thereof.

As used herein, the terms "type" or "species," when used in reference to a molecule, refer to a molecule with a unique, distinguishable chemical structure. As used herein, the term "type of SNAP" refers to a SNAP with a unique, distinguishable primary structure, for example, compared to other SNAPs. Two SNAPs are of the same species if they possess the same primary, secondary or tertiary structure. SNAP variants are different species from each other. For example, members of a "type of SNAP" can have a unique, distinguishable structure that is common to the members compared to other SNAPs that lack the unique, distinguishable structure. SNAP types may be identified, for example, by common shape and/or conformation, number of coupling sites, or type of coupling sites.

As used herein, the terms "click reaction," "click-type reaction," or "bioorthogonal reaction" refer to single-step, thermodynamically-favorable conjugation reaction utilizing biocompatible reagents. A click reaction may be configured to not utilize toxic or biologically incompatible reagents (e.g., acids, bases, heavy metals) or to not generate toxic or biologically incompatible byproducts. A click reaction may utilize an aqueous solvent or buffer (e.g., phosphate buffer solution, Tris buffer, saline buffer, MOPS, etc.). A click reaction may be thermodynamically favorable if it has a negative Gibbs free energy of reaction, for example a Gibbs free energy of reaction of less than about −5 kiloJoules/mole (kJ/mol), −10 kJ/mol, −25 kJ/mol, −50 kJ/mol, −100 kJ/mol, −200 kJ/mol, −300 kJ/mol, −400 kJ/mol, or less than −500 kJ/mol. Exemplary bioorthogonal and click reactions are described in detail in WO 2019/195633A1, which is herein incorporated by reference in its entirety. Exemplary click reactions may include metal-catalyzed azide-alkyne cycloaddition, strain-promoted azide-alkyne cycloaddition, strain-promoted azide-nitrone cycloaddition, strained alkene reactions, thiol-ene reaction, Diels-Alder reaction, inverse electron demand Diels-Alder reaction, [3+2]cycloaddition, [4+1] cycloaddition, nucleophilic substitution, dihydroxylation, thiol-yne reaction, photoclick, nitrone dipole cycloaddition, norbornene cycloaddition, oxanobomadiene cycloaddition, tetrazine ligation, and tetrazole photoclick reactions. Exemplary functional groups or reactive handles utilized to perform click reactions may include alkenes, alkynes, azides, epoxides, amines, thiols, nitrones, isonitriles, isocyanides, aziridines, activated esters, and tetrazines. Other well-known click conjugation reactions may be used having complementary bioorthogonal reaction species, for example, where a first click component comprises a hydrazine moiety and a second click component comprises an aldehyde or ketone group, and where the product of such a reaction comprises a hydrazone functional group or equivalent.

As used herein, the term "array" refers to a population of molecules or analytes that are attached to unique identifiers such that the analytes can be distinguished from each other. As used herein, the term "unique identifier" refers to a solid support (e.g., particle or bead), spatial address in an array, tag, label (e.g., luminophore), or barcode (e.g., nucleic acid barcode) that is attached to an analyte and that is distinct from other identifiers, throughout one or more steps of a process. The process can be an analytical process such as a method for detecting, identifying, characterizing or quantifying an analyte. Attachment to a unique identifier can be covalent or non-covalent (e.g., ionic bond, hydrogen bond, van der Waals forces etc.). A unique identifier can be exogenous to the analyte, for example, being synthetically attached to the analyte. Alternatively, a unique identifier can be endogenous to the analyte, for example, being attached or associated with the analyte in the native milieu of the analyte. An array can include different analytes that are each attached to different unique identifiers. For example, an array can include different molecules or analytes that are each located at different addresses on a solid support. Alternatively, an array can include separate solid supports each functioning as an address that bears a different molecule or analyte, where the different molecules or analytes can be identified according to the locations of the solid supports on a surface to which the solid supports are attached, or according to the locations of the solid supports in a liquid such as a fluid stream. The molecules or analytes of the array can be, for example, nucleic acids such as SNAPs, polypeptides, proteins, peptides, oligopeptides, enzymes, ligands, or receptors such as antibodies, functional fragments of antibodies or aptamers. The addresses of an array can optionally be optically observable and, in some configurations, adjacent addresses can be optically distinguishable when detected using a method or apparatus set forth herein. As used herein, the terms "address," "binding site," and "site," when used in reference to an array, means a location in an array where a particular molecule or analyte is present. An address can contain only a single molecule or analyte, or it can contain a population of several molecules or analytes of the same species (i.e. an ensemble of the molecules). Alternatively, an address can include a population of molecules or analytes that are different species. Addresses of an array are typically discrete. The discrete addresses can be contiguous, or they can have interstitial spaces between each other. An array useful herein can have, for example, addresses that are separated by less than 100 microns, 10 microns, 1 micron, 500 nm, 100 nm, 10 nm or less. Alternatively or additionally, an array can have addresses that are separated by at least 10 nm, 100 nm, 500 nm, 1 micron, 5 microns, 10 microns, 50 microns, 100 microns or more. The addresses can each have an area of less than 1 square millimeter, 500 square microns, 100 square microns, 25 square microns, 1 square micron or less. An array can include at least about $1 \times 10^4$, $1 \times 10^5$, $1 \times 10^6$, $1 \times 10^8$, $1 \times 10^{10}$, $1 \times 10^{12}$, or more addresses.

As used herein, the term "solid support" refers to a substrate that is insoluble in aqueous liquid. Optionally, the substrate can be rigid. The substrate can be non-porous or porous. The substrate can optionally be capable of taking up a liquid (e.g., due to porosity) but will typically, but not necessarily, be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor™, silica or silica-based materials including silicon and modified silicon, carbon, metals, metal oxides (e.g., zirconia, titania, alumina, etc.), inorganic glasses, optical fiber bundles, gels, and polymers.

As used herein, the terms "group" and "moiety" are intended to be synonymous when used in reference to the structure of a molecule. The terms refer to a component or part of the molecule. The terms do not necessarily denote the relative size of the component or part compared to the rest of the molecule, unless indicated otherwise. A group or moiety can contain one or more atom. As used herein, the term "display moiety" refers to a component or part of a molecule that is configured to couple the molecule to an analyte or that couples the molecule to the analyte. As used herein, the term "capture moiety" refers to a component or part of a molecule that is configured to couple the molecule to a solid support, surface or interface, or that couples the molecule to the solid support, surface or interface. As used herein, the term "coupling moiety" refers to a component or part of a molecule that is configured to couple the molecule to a second molecule, or that couples the molecule to the second molecule. As used herein, the term "utility moiety" refers to a component or part of a molecule that is configured to provide a functionality or structure to the molecule, or that provides the functionality or structure to the molecule. The functionality or structure can be a new function or structure that is not provided by a display moiety, capture moiety, or coupling moiety of the molecule; or it can be a modification (e.g., inhibition or activation) of a structure or function that is provided by a display moiety, capture moiety, or coupling moiety of the molecule.

As used herein, the term "face" refers to a portion of a molecule, particle, or complex (e.g., a SNAP or a SNAP complex) that contains one or more moieties with substantially similar orientation and/or function. For example, a substantially rectangular or square SNAP may have a coupling face that comprises one or more coupling moieties, with each coupling moiety having a substantially similar orientation to each other coupling moiety (e.g., oriented about 180° from a display moiety that is configured to be coupled to an analyte). In another example, a spherical nanoparticle may have a coupling face comprising a coupled plurality of coupling moieties confined to a hemisphere of the particle (i.e., a plurality of coupling moieties having similar function but differing orientations). In some cases, a face may be defined by an imaginary plane relative to which a moiety or a portion thereof may have a spatial proximity or angular orientation when the plane is contacted with a point or portion of a molecule, particle, or complex. A moiety or a portion thereof may have a spatial separation from an imaginary plane defining a face of a molecule, particle, or complex of no more than about 100 nanometers (nm), 90 nm, 80 nm, 70 nm, 60 nm, 50 nm, 40 nm, 30 nm, 25 nm 20 nm, 15 nm, 10 nm, 9 nm, 8 nm, 7 nm, 6 nm, 5 nm, 4 nm, 3 nm, 2 nm, 1 nm, 0.5 nm, 0.1 nm, or less than 0.1 nm. A moiety or a portion thereof may have an angular orientation relative to a normal vector of an imaginary plane of no more than about 90°, 85°, 80°, 75°, 70°, 65°, 60°, 55°, 50°, 45°, 40°, 35°, 30°, 25°, 20°, 15°, 10°, 5°, 1°, or less than 1°.

As used herein, the term "analyte" and "analyte of interest," when used in reference to a structured nucleic acid particle, refer to a molecule, particle, or complex of molecules or particles that is coupled to a display moiety of a structured nucleic acid particle. An analyte may comprise a target for an analytical method (e.g., sequencing, identification, quantification, etc.) or may comprise a functional element such as a binding ligand or a catalyst. An analyte may comprise a biomolecule, such as a polypeptide, polysaccharide, nucleic acid, lipid, metabolite, enzyme cofactor or a combination thereof. An analyte may comprise a non-biological molecule, such as a polymer, metal, metal oxide, ceramic, semiconductor, mineral, or a combination thereof. As used herein, the terms "sample analyte" refers to an analyte derived from a sample collected from a biological or non-biological system. A sample analyte may be purified or unpurified. As used herein, the term "control analyte" refers to an analyte that is provided as a positive or negative control for comparison to a sample analyte. A control analyte may be derived from the same source as a sample analyte, or derived from a differing source from the sample analyte. As used herein, the term "standard analyte" refers to a known or characterized analyte that is provided as a physical or chemical reference to a process. A standard analyte may comprise the same type of analyte as a sample analyte, or may differ from a sample analyte. For example, a polypeptide analyte process may utilize a polypeptide standard analyte with known characteristics. In another example, a polypeptide analyte process may utilize a non-polypeptide standard analyte with known characteristics. As used herein, the term "inert analyte" refers to an analyte with no expected function in a process or system.

As used herein, the terms "linker," "linking group," or "linking moiety" refer to a molecule or molecular chain that is configured to attach a first molecule to a second molecule. A linker, linking group, or linking moiety may be configured to provide a chemical or mechanical property to a region separating a first molecule from a second molecule, such as hydrophobicity, hydrophilicity, electrical charge, polarity, rigidity, or flexibility. A linker, linking group, or linking moiety may comprise two or more functional groups that facilitate the coupling of the linker, linking group, or linking moiety to the first and second molecule. A linker, linking group, or linking moiety may include polyfunctional linkers such as homobifunctional linkers, heterobifunctional linkers, homopolyfunctional linkers, and heteropolyfunctional linkers. The molecular chain may be characterized by a minimum size such as, for example, at least about 100 Daltons (Da), 200 Da, 300 Da, 400 Da, 500 Da, 600 Da, 700 Da, 800 Da, 900 Da, 1 kiloDalton (kDa), 2 kDa, 3 kDa, 4 kDa, 5 kDa, 10 kDa, 15 kDa, 20 kDa or more than 20 kDa. Alternatively or additionally, a molecular chain may be characterized by a maximum size such as, for example, no more than about 20 kDa, 15 kDa, 10 kDa, 5 kDa, 4 kDa, 3 kDa, 2 kDa, 1 kDa, 900 Da, 800 Da, 700 Da, 600 Da, 500 Da, 400 Da, 300 Da, 200 Da, 100 Da, or less than 100 Da. Exemplary molecular chains may comprise polyethylene glycol (PEG), polyethylene oxide (PEO), alkane chains, fluorinated alkane chains, dextrans, and polynucleotides.

As used herein, the terms "reversible" and "reversibility" are used in reference to a chemical or physical coupling of two entities (e.g., molecules, analytes, functional groups, or moieties) that has a substantial likelihood of uncoupling under one or more conditions of use. Reversibility may consist of thermodynamic reversibility, kinetic reversibility, or a combination thereof. Reversible coupling of a first entity to a second entity may be characterized by a temporary change to the structure or function of the first and/or second entity when coupled to each other. Reversing the coupling can optionally revert the structure or function of the first and/or second entity to the same state as it was prior to the temporary change. The context for determining reversibility may comprise the likelihood of detecting a reversed coupling given the specific spatial, temporal, and physical environment in which two coupled molecules are located. For example, in a population of one million streptavidin-biotin coupled pairs, a detectable number of reversed couplings may be predicted thermodynamically, however the slow kinetic reversal of the binding reaction may make such decouplings not detectable above detection noise if the detection time scale is on the order of seconds or minutes. In this context, the streptavidin-biotin coupling would be described as irreversible. The context of reversibility may be process-dependent for a system that undergoes multiple processes. For example, measurable de-coupling of coupled molecules may occur during months of storage but a subsequent process utilizing the coupled molecules may occur in minutes. In this context, the coupled molecules may be reversibly coupled with respect to storage but irreversibly coupled with respect to utilization. Measures of reversibility may include use of quantitative measures such as equilibrium constants or kinetic on-rates and/or off-rates. Reversibility may be directly measured by an equilibrium assay. Reversibility may vary with changes in a chemical system, such as changes in temperature or solvent composition. A reversible coupling may include meta-stable couplings that remain coupled until a change in physical environment. For example, complementary nucleic acids may remain stably coupled at 20° C. but may rapidly decouple above 75° C. A reversible coupling may remain coupled for a time period of at least about 1 second (s), 1 minute (min), 5 min, 10 min, 15 min, 30 min, 1 hour (hr), 2 hr, 3 hr, 4 hr, 5 hr, 6 hr, 12 hr, 18 hr, 1 day, 1 week, 1 month, 6 months, 1 year, or more than 1 year. Alternatively or additionally, a reversible coupling may become decoupled in a time period of no more than about 1 year, 6 months, 1 month, 1 week, 1 day, 18 hrs, 12 hrs, 6 hrs, 5 hrs, 4 hrs, 3 hrs, 2 hrs, 1 hr, 30 min, 15 min, 10 min, 5 min, 1 min, 1 s, or less than 1 s.

As used herein, terms "irreversible" and "irreversibility" are used in reference to a chemical or physical coupling of two entities (e.g., molecules, analytes, functional groups, or moieties) that has a likelihood of remaining coupled under one or more conditions of use. A system that is determined to not be reversible as described above may be described as irreversible. For example, irreversible coupling of a first entity to a second entity may be characterized by a permanent change to the structure or function of the first and/or second entity after being coupled to each other. Uncoupling can cause substantial change to the structure or function of one or both of the entities compared to the structure or function of the respective entity or entities prior to the coupling. An irreversible coupling may remain coupled for a time period of at least about 1 second (s), 1 minute (min), 5 min, 10 min, 15 min, 30 min, 1 hour (hr), 2 hr, 3 hr, 4 hr, 5 hr, 6 hr, 12 hr, 18 hr, 1 day, 1 week, 1 month, 6 months, 1 year, or more than 1 year.

As used herein, the term "affinity reagent" refers to a molecule or other substance that is capable of specifically or reproducibly binding to a binding partner or other substance. Binding can optionally be used to identify, track, capture, alter, or influence the binding partner. The binding partner can optionally be larger than, smaller than or the same size as the affinity reagent. An affinity reagent may form a reversible or irreversible interaction with a binding partner. An affinity reagent may bind with a binding partner in a covalent or non-covalent manner. An affinity reagent may be configured to perform a chemical modification (e.g., ligation, cleavage, concatenation, etc.) that produces a detectable change in the larger molecule, thereby permitting observation of the interaction that occurred. Affinity reagents may include chemically reactive affinity reagents (e.g., kinases, ligases, proteases, nucleases, etc.) and chemically non-reactive affinity reagents (e.g., antibodies, antibody fragments, aptamers, DARPins, peptamers, etc.). An affinity reagent may comprise one or more known and/or characterized binding components or binding sites (e.g., complementarity-defining regions) that mediate or facilitate binding with a binding partner. Accordingly, an affinity reagent can be monovalent or multivalent (e.g. bivalent, trivalent, tetravalent, etc.). An affinity reagent is typically non-reactive and non-catalytic, thereby not permanently altering the chemical structure of a substance it binds in a method set forth herein.

As used herein, the terms "protein" and "polypeptide" are used interchangeably to refer to a molecule or analyte comprising two or more amino acids joined by a peptide bond. A polypeptide may refer to a peptide (e.g., a polypeptide with less than about 200, 150, 100, 75, 50, 40, 30, 20, 15, 10, or less than about 10 linked amino acids). A polypeptide may refer to a naturally-occurring molecule, or an artificial or synthetic molecule. A polypeptide may include one or more non-natural, modified amino acids, or non-amino acid linkers. A polypeptide may contain D-amino acid enantiomers, L-amino acid enantiomers or both. A polypeptide may be modified naturally or synthetically, such as by post-translational modifications.

As used herein, the term "detectable label" refers to a moiety of an affinity reagent or other substance that provides a detectable characteristic. The detectable characteristic can be, for example, an optical signal such as absorbance of radiation, luminescence or fluorescence emission, luminescence or fluorescence lifetime, luminescence or fluorescence polarization, or the like; Rayleigh and/or Mie scattering; binding affinity for a ligand or receptor; magnetic properties; electrical properties; charge; mass; radioactivity or the like. A label component can be a detectable chemical entity that is conjugated to or capable of being conjugated to another molecule or substance. Exemplary molecules that can be conjugated to a label component include an affinity reagent or a binding partner. A label component may produce a signal that is detected in real-time (e.g., fluorescence, luminescence, radioactivity). A label component may produce a signal that is detected off-line (e.g., a nucleic acid barcode) or in a time-resolved manner (e.g., time-resolved fluorescence). A label component may produce a signal with a characteristic frequency, intensity, polarity, duration, wavelength, sequence, or fingerprint. Exemplary labels include, without limitation, a fluorophore, luminophore, chromophore, nanoparticle (e.g., gold, silver, carbon nanotubes), heavy atom, radioactive isotope, mass label, charge label, spin label, receptor, ligand, nucleic acid barcode, polypeptide barcode, polysaccharide barcode, or the like.

As used herein, the term "nucleic acid origami" refers to a nucleic acid construct comprising an engineered secondary, tertiary or quaternary structure. A nucleic acid origami may include DNA, RNA, PNA, LNAs, other nucleic acid analog, modified or non-natural nucleic acids, or combinations thereof. A nucleic acid origami may comprise a plurality of oligonucleotides that hybridize via sequence complementarity to produce the engineered structuring of the origami particle. A nucleic acid origami may comprise sections of single-stranded or double-stranded nucleic acid, or combinations thereof. A nucleic acid origami may comprise one or more tertiary structures of a nucleic acid, such as A-DNA, B-DNA, C-DNA, L-DNA, M-DNA, Z-DNA, etc. A nucleic acid origami may comprise single-stranded nucleic acid, double-stranded nucleic acid, multi-stranded nucleic acid, or combinations thereof. Exemplary nucleic acid origami structures may include nanotubes, nanowires, cages, tiles, nanospheres, blocks, and combinations thereof.

As used herein, the term "nucleic acid nanoball" refers to a globular or spherical nucleic acid structure. A nucleic acid nanoball may comprise a concatemer of oligonucleotides that arranges in a globular structure. A nucleic acid nanoball may comprise one or more oligonucleotides, including oligonucleotides comprising self-complementary nucleic acid sequences. A nucleic acid nanoball may comprise a palindromic nucleic acid sequence. A nucleic acid nanoball may include DNA, RNA, PNA, LNAs, other nucleic acid analog, modified or non-natural nucleic acids, or combinations thereof.

As used herein, the term "oligonucleotide" refers to a molecule comprising two or more nucleotides joined by a phosphodiester bond or analog thereof. An oligonucleotide may comprise DNA, RNA, PNA, LNAs, other nucleic acid analog, modified nucleotides, non-natural nucleotides, or combinations thereof. An oligonucleotide may include a limited number of bonded nucleotides, such as, for example, less than about 200, 190, 180, 170, 160, 150, 140, 130, 120, 110, 100, 90, 80, 70, 60, 50, 40, 30, 25, 20, 15, 10, or less than 5 nucleotides. An oligonucleotide may include a linking group or linking moiety at a terminal or intermediate position. For example, an oligonucleotide may comprise two nucleic acid strands that are joined by an intermediate PEG molecule. In another example, an oligonucleotide may comprise a cleavable linker (e.g., a photocleavable linker, an enzymatically-cleavable linker, a restriction site, etc.) that joins two portions of the oligonucleotide. The terms "polynucleotide" and "nucleic acid" are used herein synonymously with the term "oligonucleotide."

As used herein, the term "scaffold" refers to a molecule or complex of molecules having a structure that couples two or more entities to each other. A scaffold can form a structural basis for coupling binding components and/or labeling components to a detectable probe. A scaffold may comprise a plurality of attachment sites that permit the coupling or conjugation of detectable probe components to the scaffold. Scaffold attachment sites may include functional groups, active sites, binding ligands, binding receptors, nucleic acid sequences, or any other entity capable of forming a covalent or non-covalent attachment to a binding component, label component, or other detectable probe component. A scaffold may comprise an oligonucleotide molecule that serves as the primary structural unit for a nucleic acid origami. A scaffold may comprise single-stranded nucleic acids, double-stranded nucleic acids, or combinations thereof. A scaffold may be a circular oligonucleotide or a linear (i.e. non-circular) oligonucleotide. A scaffold may be derived from a natural source, such as a bacterial or viral genome (e.g., plasmid DNA or a phage genome). A circular scaffold may be formed by the ligation of a non-circular nucleic acid. A scaffold may comprise a particular number of nucleotides, for example, at least about 500, 1000, 1500, 2000, 2500, 3000, 3500, 4000, 4500, 5000, 5500, 6000, 6500, 7000, 7500, 8000, 8500, 9000, 9500, 10000, or more than 10000 oligonucleotides. A scaffold may comprise an organic or inorganic particle or nanoparticle. A scaffold may comprise a coating or layer applied to a particle or nanoparticle that permits attachment of detectable label components.

As used herein, the term "two-dimensional projection" refers to the area or shape that would be occupied by the projection of a three-dimensional structure onto a planar two-dimensional surface without substantial geometric or spatial distortion. For example, the two-dimensional projection of a sphere onto a planar two-dimensional surface would produce a circular area on the surface with a diameter equivalent to the diameter of the sphere. A two-dimensional projection may be formed from any frame of reference, including a frame of reference that is orthogonal to any surface of the three-dimensional structure. Many three-dimensional structures are capable of producing projections of different size or shape depending upon the frame of reference. Accordingly, the largest two-dimensional projection for a three-dimensional structure refers to the largest area or shape that is produced from all frames of reference for the three-dimensional structure; the smallest two-dimensional projection for a three-dimensional structure refers to the smallest area or shape that is produced from all frames of reference for the three-dimensional structure; and the average two-dimensional projection for a three-dimensional structure refers to the average area or shape that is produced from all frames of reference for the three-dimensional structure.

Figure 48:
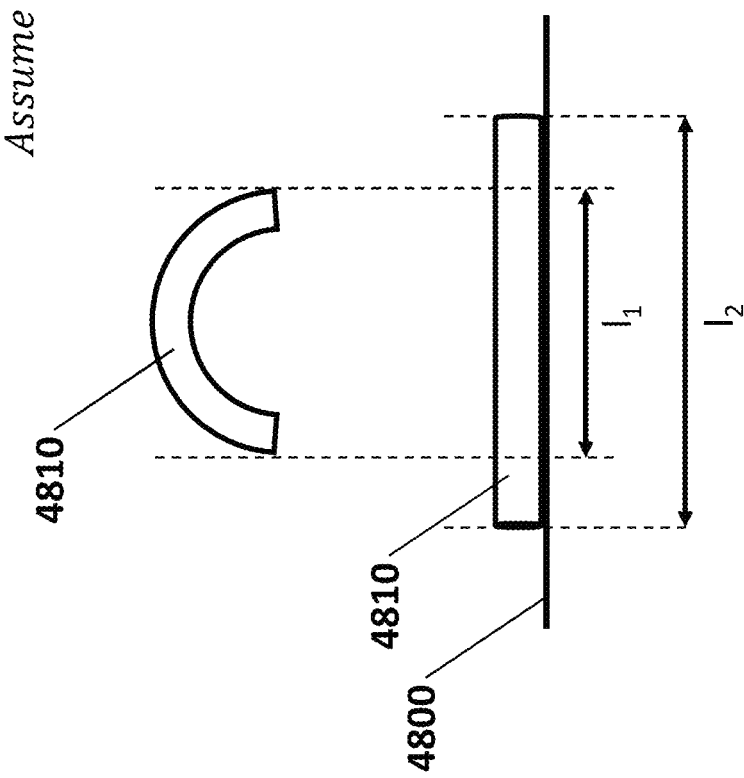
FIG. 48 depicts a difference between an effective surface area and a footprint of a nucleic acid, in accordance with some embodiments.

As used herein, the term "effective surface area," when used in reference to a nucleic acid, refers to a surface area of a two-dimensional projection of the nucleic acid or a portion thereof when the nucleic acid is not bound to a surface (e.g., solvated or suspended in a fluidic medium). As used herein, the term "footprint," when used in reference to a nucleic acid, refers to a surface area of a two-dimensional projection of the nucleic acid or a portion thereof when the nucleic acid is bound to a surface (e.g., coupled to a solid support). FIG. 48 depicts a difference between an effective surface area and a footprint of a nucleic acid. In an unbound configuration, a two-dimensional projection of the nucleic acid 4810 onto a surface 4800 would have a surface area that is proportional to a length, $l_1$, that is substantially the same as a distance between the two ends of the unbound nucleic acid 4810. In a bound configuration, the coupling of the nucleic acid 4810 to the surface 4800 increases the distance between the ends of the nucleic acid, thereby increasing the surface area of the two-dimensional projection of the nucleic acid onto the surface 4800. Accordingly, the nucleic acid has a larger footprint than its effective surface area.

Figure 1A:
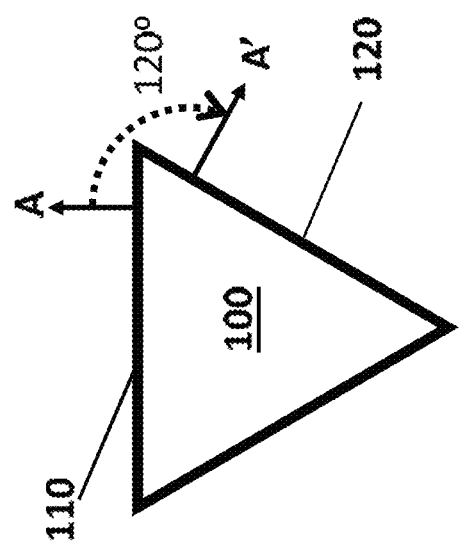

As used herein, the term "offset" refers to the spatial difference in orientation between two lines (2-dimensional) or surfaces (3-dimensional). An offset may include a distance offset and/or an angular offset. FIGS. 1A and 1B depict examples of angular offset for differing two-dimensional shapes (which could be two-dimensional projections of three-dimensional structures). The isosceles triangle 100 of FIG. 1A has an angular offset of 120° between the first face 110 and the second face 120 whose relative orientations are depicted by orthogonal vectors A and A'. The rectangle 130 of FIG. 1B has an angular offset of 180° between the first face 110 and the second face 120, whose relative orientations are depicted by orthogonal vectors A and A'.

As used herein, the term "binding specificity" refers to the tendency of an affinity reagent to preferentially interact with a binding partner, affinity target, or target moiety relative to other binding partners, affinity targets, or target moieties. An affinity reagent may have a calculated, observed, known, or predicted binding specificity for any possible binding partner, affinity target, or target moiety. Binding specificity may refer to selectivity for a single binding partner, affinity target, or target moiety in a sample over at least one other analyte in the sample. Moreover, binding specificity may refer to selectivity for a subset of binding partners, affinity targets, or target moieties in a sample over at least one other analyte in the sample.

As used herein, the term "binding affinity" or "affinity" refers to the strength or extent of binding between an affinity reagent and a binding partner, affinity target or target moiety. In some cases, the binding affinity of an affinity reagent for a binding partner, affinity target, or target moiety may be vanishingly small or effectively zero. A binding affinity of an affinity reagent for a binding partner, affinity target, or target moiety may be qualified as being a "high affinity," "medium affinity," or "low affinity." A binding affinity-of an affinity reagent for a binding partner, affinity target, or target moiety may be quantified as being "high affinity" if the interaction has a dissociation constant of less than about 100 nM, "medium affinity" if the interaction has a dissociation constant between about 100 nM and 1 mM, and "low affinity" if the interaction has a dissociation constant of greater than about 1 mM. Binding affinity—can be described in terms known in the art of biochemistry such as equilibrium dissociation constant ($K_D$), equilibrium association constant ($K_A$), association rate constant ($k_{on}$), dissociation rate constant ($k_{off}$) and the like. See, for example, Segel, Enzyme Kinetics John Wiley and Sons, New York (1975), which is incorporated herein by reference in its entirety.

As used herein, the term "promiscuity," when used in reference to binding, may refer to affinity reagent properties of 1) binding to a plurality of binding partners due to the presence of a particular affinity target or target moiety, regardless of the binding context of the affinity target or target moiety; or 2) binding to a plurality of affinity targets or target moieties within the same or differing binding partners; or 3) a combination of both properties. With regard to the first form of binding promiscuity, "binding context" may refer to the local chemical environment surrounding an affinity target or target moiety, such as flanking, adjacent, or neighboring chemical entities (e.g., for a polypeptide epitope, flanking amino acid sequences, or adjacent or neighboring non-contiguous amino acid sequences relative to the epitope). With regard to the second form of binding promiscuity, the definition may refer to an affinity reagent or probe binding to structurally- or chemically-related affinity targets or target moieties despite differences between the affinity targets or target moieties. For example, an affinity reagent may be considered promiscuous if it possesses a binding affinity for trimer peptide sequences having the form WXK, where W is tryptophan, K is lysine and X is any possible amino acid. Additional concepts pertaining to binding promiscuity are discussed in WO 2020106889A1, which is incorporated herein by reference in its entirety.

As used herein, the term "binding probability" refers to the probability that an affinity reagent may be observed to interact with a binding partner and/or an affinity target within a particular binding context. A binding probability may be expressed as a discrete number such as a value N in the range $0 \leq N \leq 1$ (e.g. 0.4) or a percent value (e.g., 40%), a matrix of discrete numbers. or as mathematical model (e.g., a theoretical or empirical model). A binding probability ma, include one or more factors, including the binding specificity, the likelihood of locating the affinity target, and the likelihood of binding for a sufficient amount of time for the binding interaction to be detected. An overall binding probability may include binding probability when all factors have been weighted relative to the binding context.

As used herein, the term "binding context" may refer to the environmental conditions in which an affinity reagent-binding partner interaction is observed. The binding context may be a constant condition or a condition that changes within a range. Environmental conditions may include any factors that may influence an interaction between an affinity reagent and a binding partner, such as temperature, fluid properties (e.g., ionic strength, polarity, pH), relative concentrations, absolute concentrations, fluid composition, binding partner conformation, affinity reagent conformation, and combinations thereof.

As used herein the term "tunable", when used in reference to a structured nucleic acid particle, refers to the specific, precise, and/or rational location of components or attachment sites for components with an assembly or structure. Tunable retaining components may refer to the ability to couple or conjugate probe components at specific sites or within specific regions of the retaining component structure, or to generate attachment sites for the coupling or conjugation of probe components at specific sites or specific regions of the retaining component structure. As used herein, "tunability" refers to the property of a probe or retaining component having a tunable structure or architecture.

As used herein, the term "functional group" refers to a group of atoms in a molecule that confer a chemical property, such as reactivity, polarity, hydrophobicity, hydrophilicity, solubility, etc., on the molecule. Functional groups may comprise organic moieties or may comprise inorganic atoms. Exemplary functional groups may include alkyl, alkenyl, alkynyl, phenyl, halide, hydroxyl, carbonyl, aldehyde, acyl halide, ester, carboxylate, carboxyl, carboalkoxy, methoxy, 3lydroperoxyl, ether, hemiacetal, hemiketal, acetal, ketal, orthoester, epoxide, carboxylic anhydride, carboxamide, amine, ketimine, aldimine, imide, azide, azo, cyanate, isocyanate, nitrate, nitrile, isonitrile, nitrosoxy, nitro, nitroso, oxime, pyridyl, carbamate, sulfhydryl, sulfide, disulfide, sulfinyl, sulfonyl, sulfinom, sulfo, thiocyanate, isothiocyanate, carbonothioyl, thioester, thionoester, phosphino, phosphono, phosphonate, phosphate, borono, boronate, and borinate functional groups.

As used herein, the term "functionalized" refers to any material or substance that has been modified to include a functional group. A functionalized material or substance may be naturally or synthetically functionalized. For example, a polypeptide can be naturally functionalized with a phosphate, oligosaccharide (e.g., glycosyl, glycosylphosphatidylinositol or phosphoglycosyl), nitrosyl, methyl, acetyl, lipid (e.g., glycosyl phosphatidylinositol, myristoyl or prenyl), ubiquitin or other naturally occurring post-translational modification. A functionalized material or substance may be functionalized for any given purpose, including altering chemical properties (e.g., altering hydrophobicity or changing surface charge density) or altering reactivity (e.g., capable of reacting with a moiety or reagent to form a covalent bond to the moiety or reagent).

Other than in the operating examples, or where otherwise indicated, all numbers expressing quantities of ingredients or reaction conditions used herein should be understood as modified in all instances by the term "about." As used herein, the term "about," when used in connection with percentages, may mean a variance of at most ±5% of the value being referred to. For example, about 90% may mean from 5% to 95%. In some cases, "about" may mean a variance of at most ±4%, ±3%, ±2%, ±1%, ±0.5% or less of the value being referred to. As used herein, the term "substantially," when used in reference to a measurable quantity or property, refers to the quantity or property having a value within ±10% of a reference value. For example, a first value may be substantially the same as a second value if the first value is within ±10% of the second value. In another example, a shape may be substantially square if a ratio of side lengths of a rectangle is within a range between 0.90 and 1.10, inclusive. In some cases, "substantially" may mean a quantity or property having a value within at most±9%, +8%, +7%±6%, ±5%, 4%, ±3%, 2%, 1%, 0.5% or less of a reference value.

As used herein, the terms "attached" or "coupled" refer to the state of two things being joined, fastened, adhered, connected or bound to each other. Attachment can be covalent or non-covalent. For example, a particle can be attached or coupled to a protein by a covalent or non-covalent bond. Similarly, a first nucleic acid can be attached or coupled to a second nucleic acid via hybridization or Watson-Crick base pairing. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions, adhesion, adsorption, and hydrophobic interactions.

The term "comprising" is intended herein to be open-ended, including not only the recited elements, but further encompassing any additional elements.

As used herein, the term "each," when used in reference to a collection of items, is intended to identify an individual item in the collection but does not necessarily refer to every item in the collection. Exceptions can occur if explicit disclosure or context clearly dictates otherwise.

Nucleic Acid Structures

Provided herein are nucleic acids that are useful for the formation of arrays of analytes that permit the interrogation of the analytes of the array at single-analyte resolution. The nucleic acids set forth herein can be characterized as possessing tunable two-dimensional or three-dimensional structures that facilitate one or more characteristics selected from: i) displaying an analyte in an orientation that facilitates interrogation of the analyte at single-analyte resolution; ii) maximizing likelihood of coupling to a solid support or a surface thereof at a site that is configured to bind the nucleic acid; iii) maximizing likelihood of coupling to a site on a solid support or surface thereof in a controllable and/or non-random fashion; iv) minimizing a likelihood of coupling to a solid support or a surface thereof at a site that is already occupied by another nucleic acid; and v) minimizing a likelihood of coupling to a solid support or a surface thereof at an address that is not configured to bind the nucleic acid. In some configurations, a nucleic acid, as set forth herein, may possess all of the aforementioned characteristics. In other configurations, two or more nucleic acids may be complexed, in which the nucleic acid complex possesses all of the aforementioned characteristics.

Described herein are nucleic acids that are useful for the organization of individual moieties in single-analyte systems. A nucleic acid, as set forth herein, may be characterized by one or more characteristics of: i) comprising a display moiety that is configured to couple an analyte to the nucleic acid, or that couples the analyte to the nucleic acid; ii) comprising a capture moiety that is configured to couple the nucleic acid to a solid support or a surface thereof, or that couples the nucleic acid to the solid support or surface thereof; iii) comprising a coupling moiety that is configured to couple a second molecule to the nucleic acid, or that couples the second molecule to the nucleic acid; and iv) comprising a utility moiety that modifies a physical and/or chemical property of the nucleic acid. In some cases, the nucleic acid is a nucleic acid nanostructure or structured nucleic acid particle (SNAP).

A nucleic acid, as set forth herein, may comprise a naturally-occurring nucleic acid structure, such as a naturally-occurring primary structure (e.g., a naturally-occurring single-stranded nucleotide sequence, a single strand of a plasmid, etc.), a naturally-occurring secondary structure (e.g., a naturally-occurring A-DNA, B-DNA, Z-DNA or double-stranded helical structure), a naturally-occurring tertiary structure (e.g., a nucleic acid comprising an origami structure nucleosome, chromatin, etc.). A nucleic acid, as set forth herein, may comprise a synthetic, artificial, or engineered nucleic acid structure. In some configurations, a nucleic acid may comprise a nucleic acid nanostructure, in which the nucleic acid nanostructure comprises a compacted three-dimensional structure. A nucleic acid nanostructure may comprise one or more structures that are not known to occur in a naturally-occurring nucleic acid. A nucleic acid nanostructure may comprise one or more structures with a characterizable property that differs from the same characterizable property of a naturally-occurring nucleic acid (e.g., a higher or lower average persistence length over a nucleic acid strand comprising N nucleotides, a higher or lower radius of curvature of a nucleic acid strand comprising at least 75% double-stranded nucleic acid, a shorter or longer distance between two non-contiguous regions of a nucleic acid strand, a temporal variation in any aforementioned property, etc.).

The compositions and methods set forth herein will generally be exemplified with reference to a nucleic acid nanostructure or SNAP; however, it will be understood that the methods and compositions exemplified can be extended to other nucleic acids, such as those set forth herein.

It will also be understood that the nucleic acid structures are described with respect to an average spatial and/or temporal configuration. A nucleic acid structure, as set forth herein, can be in a dynamic state with respect to common physical phenomena (e.g., thermal motion, intermolecular collisions, externally-applied forces, intramolecular vibration, intramolecular bending, intramolecular rotation, etc.) that cause spatial and/or temporal variations in the configuration of the nucleic acid. Quantitative descriptions of nucleic acid structure can include spatial and/or temporal variations in accordance with the dynamic nature of molecular structure understood in the art.

Aspects of Nucleic Acid Structure: A nucleic acid nanostructure, such as a SNAP, may comprise various structures or structural motifs that give rise to higher ordered structures or geometries. For example, a concatemerized rolling-circle amplification (RCA) product may produce a globular nanoball structure with spike-like structures at the outer boundary where the single-stranded, concatemerized nucleic acid forms nearly 180° turns (i.e., a nanoscale urchin-like structure). In another example, a SNAP may comprise a DNA origami particle comprising a scaffold single-stranded nucleic acid hybridized with a plurality of oligonucleotides that shape the scaffold strand into an overall tertiary structure. Regions of the tertiary structure may be connected by certain oligonucleotides of the plurality of oligonucleotides to pattern the scaffold into a regular or irregular shapes such as a tile, disc, triangle, torus, cube, pyramid, cylinder, tube, and other more complex two-dimensional or three-dimensional structures.

A nucleic acid nanostructure, such as a SNAP, may comprise one or more faces that provide a structural feature and/or perform a function for the nucleic acid nanostructure. A nucleic acid nanostructure, such as a SNAP, may comprise one or more of 1) a display face; 2) a capture face; 3) a coupling face; and 4) a utility face. A display face may comprise a capture moiety that couples, or is configured to couple, a nucleic acid nanostructure to an analyte. A capture face may comprise a capture moiety that couples, or is configured to couple, a nucleic acid nanostructure to a surface or interface. A coupling face may comprise a coupling moiety that couples, or is configured to couple, a first nucleic acid nanostructure to a second nucleic acid nanostructure. A utility face may comprise a utility moiety that provides an additional utility to a nucleic acid nanostructure (e.g., a SNAP), such as providing structure, providing stability, altering an interaction (e.g., attraction or repulsion, steric hindrance, etc.) between a nucleic acid nanostructure and another entity (e.g., a second nucleic acid nanostructure, a surface, etc.), or altering a physical property of a nucleic acid nanostructure (e.g., a utility moiety may comprise an electrical, magnetic, or optical material, etc.). A nucleic acid nanostructure, such as a SNAP, may comprise a face with more than one function. For example, a coupling face may also comprise a utility face. In another example, a display face may also comprise a utility face or a capture face. A nucleic acid nanostructure, such as a SNAP, may comprise a face that is comprised of one or more other types of faces. For example, a display face may comprise portions or regions that are utility faces comprising steric blocking groups (e.g., PEG, PEO, dextrans, etc.). In some configurations, a multi-function face may be counted as a single face. For example, a cube-like SNAP may comprise about six distinct faces, with each of the six faces comprising one or more functions, e.g., a display face and a utility face on one of the six sides.

A nucleic acid nanostructure, such as a SNAP, may comprise one or more faces that provide functionality to the nucleic acid nanostructure. A face may comprise a side or portion of a nucleic acid nanostructure with a similar orientation or two-dimensional projection onto an imaginary planar surface. FIG. 2A-2D depict examples of faces for simplified structures similar to those that might be encountered on nanostructures such as SNAPs. FIG. 2A shows two shorter tertiary structures 210 and 212 (e.g., DNA double helices) linked by a first turning linker 215. The two shorter tertiary structures 210 and 212 are linked to longer tertiary structures 220 and 222, which are linked by a third turning linker 225. The two shorter tertiary structures 210 and 212 are linked to the two longer tertiary structures 220 and 222 by a second turning linker 230. The two shorter tertiary structures 210 and 212 and the two longer tertiary structures 220 and 222 are oriented to be coplanar. Functional groups $R_1$, $R_2$, $R_3$, and $R_4$ extend outward from the tertiary structures in particular orientations that extend out from the plane in which the tertiary structures are oriented. An imaginary plane P is placed orthogonal to, and is intersected by, the four tertiary structures. FIG. 2B depicts a cross-sectional view of the tertiary structures taken at plane P. The relative positions of functional groups $R_1$, $R_2$, $R_3$, and $R_4$ are shown with respect to the tertiary structures from which the functional groups are displayed. The structures depicted in FIG. 2A can be defined by four faces, $S_1$, $S_2$, T, and B, as shown in FIG. 2B. The faces represent a projection of the tertiary structures onto the imaginary planes defined by faces $S_1$, $S_2$, B, and T. Due to some degrees of freedom in the position of functional groups and/or moieties that may extend from the tertiary structures, as well as the size and length of the functional groups or moieties, the faces may extend beyond a simple orthogonal projection of the tertiary structures onto faces $S_1$, $S_2$, B, or T. In some cases, a functional group or moiety extending from a nucleic acid nanostructure may be considered to be located in two or more faces of the nucleic acid nanostructure. In other cases, a functional group or moiety extending from a nucleic acid nanostructure may be considered to be located within a single face of the nucleic acid nanostructure. The face to which a functional group or moiety is assigned may be defined by the utility or purpose of the functional group or moiety. For example, a moiety with a rigid chain that is located near two differing faces may be assigned to a single face because the orientation caused by the rigid chain makes the moiety functionally inaccessible to the other face. Due to the aligned and coplanar geometry of the tertiary structures, the faces $S_1$ and $S_2$ would orthogonally meet faces B and T if extended. In some cases (e.g., a cylindrical or tube structure), a face may comprise up to 360° of total aspect or orientation.

FIGS. 2C-2D depict the location of nucleic acid nanostructure faces for a plurality of tertiary structures that are not coplanar. FIG. 2C shows two shorter tertiary structures 210 and 212 (e.g., DNA double helices) linked by a first turning linker 215. The two shorter tertiary structures 210 and 212 are linked to longer tertiary structures 220 and 222, which are linked by a third turning linker 225. The two shorter tertiary structures 210 and 212 are linked to the two longer tertiary structures 220 and 222 by a second turning linker 230. The two shorter tertiary structures 210 and 212 are positioned beneath the longer tertiary structures 220 and 222. Imaginary, reference plane P' defines roughly a plane of mirror symmetry with respect to the tertiary structures. FIG. 2D depicts a projection of the tertiary structures on the plane P'. Two faces, D and B can be defined for the nucleic acid nanostructure depicted in FIG. 2C. The faces, if extended, would intersect, although due to the relative geometry, the intersection would not occur orthogonally.

A nucleic acid nanostructure, such as a SNAP, may have a particular number of faces. A nucleic acid nanostructure may have at least about 1, 2, 3, 4, 5, 6, 7, 8, 9, 10, 11, 12, 13, 14, 15, 16, 17, 18, 19, 20, or more than 20 faces. Additionally or alternatively, a nucleic acid nanostructure may have no more than about 20, 19, 18, 17, 16, 15, 14, 13, 12, 11, 10, 9, 8, 7, 6, 5, 4, 3, 2 or less than 2 faces. The number of faces of a nucleic acid nanostructure may be chosen to match a functionality for the nucleic acid nanostructure. For example, a SNAP that is configured to couple an analyte to a solid support may necessitate at least 2 faces (a display face and a coupling face), with additional faces added based upon other design considerations (e.g., utility faces).

A nucleic acid nanostructure, such as a SNAP, may comprise two or more faces where each face has a differing utility. A nucleic acid nanostructure may comprise one or more utilities selected from the group consisting of: 1) a display face that couples, or is configured to couple, an analyte; 2) a capture face that couples, or is configured to couple, to a surface; 3) a coupling face that couples, or is configured to couple, a first nucleic acid nanostructure to a second nucleic acid nanostructure; and 4) a utility face that provides any additional utility (e.g., steric blocking). In some configurations, a nucleic acid nanostructure may comprise a first utility (e.g., a display face comprising a display moiety) and a second face may comprise a second utility (e.g., a capture face comprising a capture moiety). In other configurations, two or more faces may have the same utility (e.g., two or more display faces) but one face of the two or more faces may comprise a differing utility (e.g., a capture face). In some configurations, a nucleic acid nanostructure may comprise the same two or more utilities on two or more faces (e.g., two opposed faces that function as display faces and capture faces).

A nucleic acid nanostructure, such as a SNAP, may comprise structural symmetry, for example, according to an axis of symmetry (i.e., rotational symmetry) or a plane of symmetry (i.e., reflection symmetry). A tertiary structure of a nucleic acid nanostructure may comprise structural symmetry, for example, according to an axis of symmetry (e.g., aligned with a centerline of a helical structure). A plurality of tertiary structures taken as a whole may comprise structural symmetry, for example, according to an axis of symmetry or a plane of symmetry. A face of a nucleic acid nanostructure may be oriented with respect to an axis or plane of symmetry for the nucleic acid nanostructure or a tertiary structure of a plurality of tertiary structures that form the nucleic acid nanostructure. For example, for the cross-section shown in FIG. 2B, the top Face T may be oriented at 0° relative to an axis of symmetry that is coaxial to any of the four tertiary structures, while faces $S_1$, B, and $S_2$, may be oriented at 90°, 180°, and 270°, respectively. For a nucleic acid nanostructure (e.g., a SNAP) comprising a first tertiary structure and a second tertiary structure, an orientation of a first face (e.g., a display face, a capture face, a coupling face, or a utility face) or an orientation of a second face (e.g., a display face, a capture face, a coupling face, or a utility face) can be defined relative to an axis of symmetry for the first tertiary structure or an axis of symmetry for the second tertiary structure. In some configurations, an orientation of a first face may be the same as an orientation of a second face (e.g., a face that has display and capture utility). An orientation of a first face may be determined with respect to an orientation of a second face based upon an angular offset between a first vector that is normal to a plane defining an average spatial location of the first face and a second vector that is normal to a plane defining an average spatial location of the second face. In other configurations, an orientation of a first face may be offset from an orientation of a second face by at least about 90°. In other configurations, an orientation of a first face may be offset from an orientation of a second face by about 180°. A nucleic acid nanostructure may comprise a first face and a second face with an angular offset of at least about 10°, 20°, 30°, 40°, 50°, 60°, 70°, 80°, 90°, 100°, 110°, 120°, 130°, 140°, 150°, 160°, 170°, 180°, 190°, 200°, 210°, 220°, 230°, 240°, 250°, 260°, 270°, 280°, 290°, 300°, 310°, 320°, 330°, 340°, 350°, or more than 350°. Alternatively or additionally, a nucleic acid nanostructure may comprise a first face and a second face with an angular offset of no more than about 360°, 350°, 340°, 330°, 320°, 310°, 300°, 290°, 280°, 270°, 260°, 250°, 240°, 230°, 220°, 210°, 200°, 190°, 180°, 170°, 160°, 150°, 140°, 130°, 120°, 110°, 100°, 90°, 80°, 70°, 60°, 50°, 40°, 30°, 20°, 10°, or less than 10°.

A nucleic acid nanostructure, such as a SNAP, may comprise a plurality of tertiary or quaternary structures that at least partially surrounds or substantially encloses an internal volume region. A nucleic acid nanostructure may have a three-dimensional structure such as a pyramid, shell, cylinder, disk, sphere, cuboid (e.g., square cube or rectangular cuboid), or block, that comprises an internal volume region. An internal volume region may be a three-dimensional volume within a nucleic acid nanostructure that is large enough to accommodate an analyte or other molecule set forth herein. A nucleic acid nanostructure may be configured to comprise an internal volume region, where the internal volume region comprises a utility face, such as a display face or a capture face. A utility moiety may be displayed within the internal volume region. For example, a display moiety may be displayed within an internal volume region of a SNAP such that an analyte is at least partially coupled within the internal volume region. In another example, a capture moiety may be displayed within an internal volume region of a SNAP such that a complementary moiety of a surface must at least partially enter the internal volume region to couple with the capture moiety (see FIGS. 38A and 38B).

In some configurations, an internal volume region may be created in a nucleic acid nanostructure (e.g., a SNAP) to control the interactions between the nucleic acid nanostructure and other entities. An internal volume region may comprise one or more moieties that alter the chemical properties (e.g., hydrophobicity, hydrophilicity, reactivity, polarity, solubility, etc.) of the internal volume region to differ from the chemical properties of the surrounding nucleic acid nanostructure. FIG. 39A depicts a SNAP 3910 comprising an internal volume region 3920 containing a capture moiety comprising a reactive group 3925 and a plurality of hydrophobic molecules 3928 surrounding the reactive group 3925. The SNAP may be contacted with a surface 3930 comprising a plurality of hydrophilic groups 3932 terminated with complementary reactive groups 3935 and a plurality of hydrophobic groups 3938 terminated with complementary reactive groups 3935. As shown in FIG. 39B, the hydrophobic property of the internal volume region 3920 may increase the likelihood that the SNAP 3910 will deposit and couple to the surface 3930 at a region comprising the plurality of hydrophobic groups 3938.

Figure 38B:
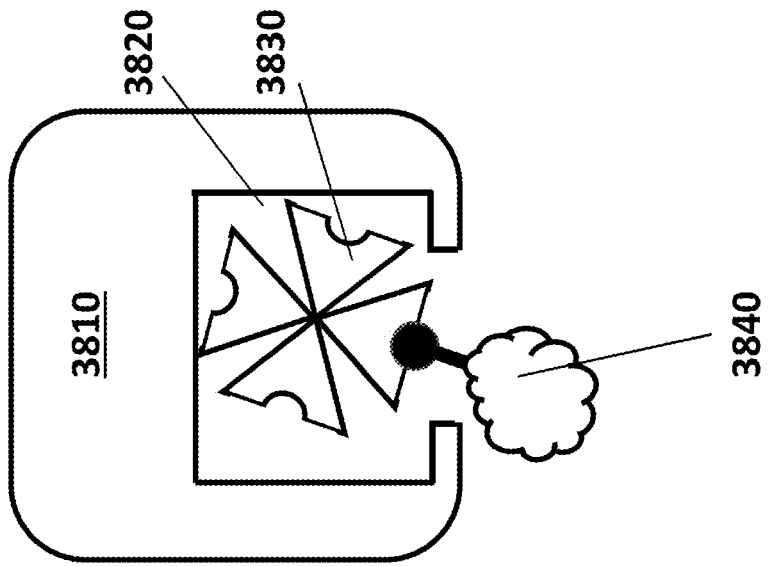
FIGS. 38A and 38B depict a SNAP comprising a multi-valent moiety in an internal volume region, in accordance with some embodiments.
Figure 38A:
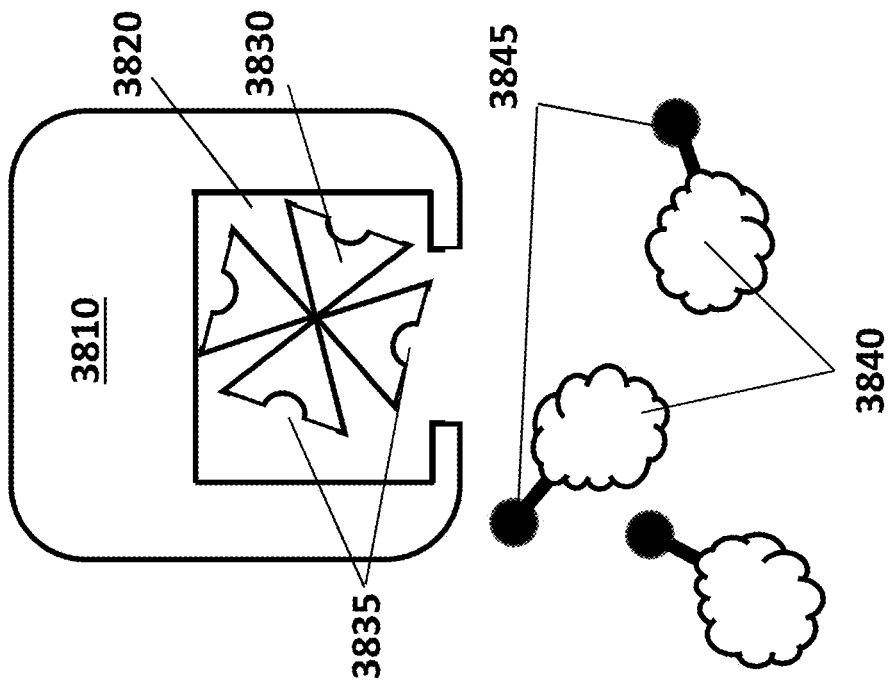

In some configurations, an internal volume region may be created in a nucleic acid nanostructure (e.g., a SNAP) to control the interactions in which a moiety within the internal volume region may participate. The orientation of a moiety within the internal volume region may be controlled to increase, decrease, or otherwise control the orientation with which an interaction may occur. A moiety may be displayed within an internal volume region in a manner that limits or controls the size of entities that may interact with the moiety. FIG. 38A depicts a SNAP 3810 comprising an internal volume region 3820 containing a coupled multivalent binding moiety (e.g., streptavidin, avidin) 3830. The coupled multivalent binding moiety 3830 is oriented within the internal volume region 3820 such that only one binding site 3835 is available to participate in a binding interaction with an entity 3840 comprising a complementary binding group (e.g., biotin) 3845 that is configured to couple to the binding site 3835. As shown in FIG. 38B, the coupled multivalent binding moiety 3830 has been made substantially monovalent due to its orientation within the internal volume region 3820, thereby forming only one binding interaction with an entity 3840.

A nucleic acid nanostructure may comprise a first tertiary structure domain and a second tertiary structure domain that are oriented with respect to each other by one or more nucleic acid strands that form linking strands (e.g., staple oligonucleotides) between the first tertiary structure domain and the second tertiary structure domain. A linking strand may comprise a single-stranded, double-stranded, partially double-stranded or multi-stranded nucleic acid. In some configurations, a nucleic acid nanostructure may comprise a first oligonucleotide with a first nucleic acid sequence and a second nucleic acid sequence that hybridize to complementary sequences of a second oligonucleotide to form a first tertiary structure domain and a second tertiary structure domain, in which the first nucleic acid sequence and the second nucleic acid sequence of the first oligonucleotide are separated by a linking nucleic acid sequence that comprises a single-stranded linking strand between the first tertiary structure domain and the second tertiary structure domain. For example, the first oligonucleotide can be a staple that hybridizes to a scaffold nucleic acid to form the first tertiary structure domain and the second tertiary structure domain in a nucleic acid origami structure.

A nucleic acid nanostructure may comprise a first tertiary structure domain and a second tertiary structure domain, in which a relative angular orientation or spatial separation of the two domains is controlled by one or more linking strands. Angular orientation and/or spatial separation of a first tertiary structure domain and a second tertiary structure domain may be tunable based upon the spatial locations of nucleotides within the helical structure of the domains. Each complete revolution of a double-stranded nucleic acid helix typically contains 10 to 11 nucleotide base pairs. Accordingly, the initial angle of projection of a linking strand may be tuned by the nucleotide position within a helical structure. Tunability of structure of a nucleic acid nanostructure can also be obtained by varying a length of a linking strand and varying a separation distance between consecutive linking strands. FIGS. 49A-49E depict aspects of controlling orientation of tertiary structures in a nucleic acid nanostructure. FIG. 49A depicts a top-down view of a portion of a nucleic acid nanostructure comprising a first oligonucleotide 4910 (e.g., a scaffold strand) and a second oligonucleotide 4920 (e.g., a staple oligonucleotide), in which the second oligonucleotide 4920 hybridizes to the first oligonucleotide 4910 to form a first tertiary structure domain 4930 and a second tertiary structure domain 4932 that are connected by a linking strand comprising a single-stranded nucleic acid sequence of the second oligonucleotide 4920. FIGS. 49B-49C depict differences in initial orientation of the linking strand, as determined by nucleotide position within a revolution of a helical structure, of the second oligonucleotide 4920 as seen relative to the helical axes of the first tertiary structure domain 4930 and the second tertiary structure domain 4932. FIG. 49B depicts a configuration in which the initial orientation of linking strands is not coplanar, while FIG. 49C depicts a configuration in which the initial orientation of linking strands is coplanar. Further, for a fixed length of a linking strand, the difference in initial orientation of the linking strand may affect the separation distance or amount of variation in separation distance between two neighboring tertiary structure domains, for example, as shown in FIGS. 49B and 49C. FIGS. 49D-49E illustrate possible relative positions of the tertiary structure domains based upon the linking strand orientations, as shown in FIGS. 49B-49C, respectively. FIG. 49D depicts a skewed orientation between the first tertiary structure domain 4930 and the secondary tertiary structure domain 4932, while FIG. 49E depicts a coplanar orientation between the first tertiary structure domain 4930 and the second tertiary structure domain 4932, with each orientation of the two tertiary structure domains arising from the positioning of the nucleotide at which the second oligonucleotide 4920 transitions from a component of a double-stranded nucleic acid to a single-stranded nucleic acid of the linking strand.

Location of linking strands may affect the conformation of a first tertiary structure domain relative to a second tertiary structure domain in a nucleic acid nanostructure. For example, to configure a first tertiary structure domain and a second tertiary structure domain in a substantially coplanar orientation (i.e., a minimal angular offset between the two tertiary structure domains), consecutive linking strands may be placed at about an odd number of helical half revolutions apart (e.g., about 1, 3, 5, 7, 9, etc. half turns or about 6, 16, 27, 37, 48, etc. nucleotides apart). Alternatively, to configure a first tertiary structure domain and a second tertiary structure domain in a skewed orientation (i.e., a measurable angular offset between the two tertiary structures), consecutive linking strands may be placed at positions other than helical half revolutions, or may be placed at random or varying positions including helical half revolutions and positions other than helical half-revolutions. For example, consecutive linking strands may be placed at about an even number of helical half revolutions apart (e.g., about 2, 4, 6, 8, 10, etc. half turns or about 11, 21, 31, 41, 52, etc. nucleotides apart) or fractional numbers of helical half revolutions other than half revolutions (e.g., ¾ revolution, 1¾ revolutions, 2¼ revolutions, etc.). In some configurations, it may be preferable to produce a nucleic acid nanostructure that comprises a substantially planar structure, in which the planar structure comprises a plurality of coplanar tertiary structures. For example, a nucleic acid nanostructure may comprise a capture face that is substantially planar to increase an electrostatic interaction between the capture face and a planar surface of a solid support. In other configurations, it may be preferable to produce a nucleic acid nanostructure that comprises a non-planar structure comprising a plurality of tertiary structures, such as a curved surface or a corrugated surface. For example, a nucleic acid nanostructure may comprise a capture face that comprises a corrugated texture to increase an electrostatic interaction between the capture face and a rough surface of a solid support.

A nucleic acid nanostructure may comprise one or more characteristics or configurations that deviate from characteristics or configurations of naturally-occurring nucleic acids. A nucleic acid nanostructure, as set forth herein, may comprise one or more non-natural nucleic acid structures that increase the tunability of the nanostructure for one or more purposes, such as the coupling and/or display of analytes, and the coupling of the nanostructure to a solid support or a surface thereof. A nucleic acid nanostructure may be characterized by presence of one or more non-natural nucleic acid structures, including but not limited to: i) a larger number of oligonucleotides hybridized to a given nucleic acid strand compared to the number of oligonucleotides hybridized to a natural nucleic acid strand of the same length and sequence, ii) increased volumetric and/or areal density of nucleotide packing within a nanostructure or a component structure thereof compared to a natural nucleic acid having the same or similar sequence content, iii) increased sharpness of bending of a nucleic acid strand relative to a naturally-occurring nucleic acid having the same sequence or length, iv) decreased separation distance between non-contiguous regions of a nucleic acid strand within a nanostructure compared to a naturally-occurring nucleic acid having the same sequence or length, v) low degree of sequence complementarity within a nanostructure relative to the degree of sequence complementarity in a naturally-occurring nucleic acid that occupies a similar volume in solution, vi) greater mechanical rigidity of a nucleic acid strand in a nanostructure compared to the mechanical rigidity of a naturally-occurring nucleic acid having the same sequence or length, and vii) combinations thereof.

A nucleic acid nanostructure, as set forth herein, may comprise more complexed oligonucleotides or nucleic acid strands than is known to occur in a natural nucleic acid system such as a natural nucleic acid system having the same mass as the nucleic acid nanostructure. Naturally-occurring nucleic acids are predominantly nucleic acid strands (e.g., chromosomal DNA, plasmid strands) with partial or complete complementary strands. Naturally-occurring nucleic acids may be distinguished by complete or nearly-complete complementarity of hybridized nucleic acid strands. Naturally-occurring nucleic acids may be further distinguished by a relative small number of nucleic acid strands complexed simultaneously by hybridization between each nucleic acid strand within the nucleic acid complex. For example, a naturally-occurring Holliday junction structure will typically involve the hybridization of four nucleic acid strands, with each strand of the junction complex having a high degree of sequence complementarity to two other strands of the complex. Naturally-occurring nucleic acids often require additional proteins to complex multiple nucleic acid strands (e.g., chromosomal kinetochores, 3 nucleic acid complex during gene transcription formed by RNA polymerase, the RNA strand, and the two complementary DNA strands, etc.). In contrast, a nucleic acid nanostructure, as set forth herein, may comprise a larger quantity of complex nucleic acid oligonucleotides or nucleic acid strands than is known to occur in a natural nucleic acid system. For example, a nucleic acid nanostructure may comprise at least 10, 25, 50, 100, 150, 200, or more than 200 complexed oligonucleotides or nucleic acid strands, in which each oligonucleotide or nucleic acid strand is hybridized to at least one other oligonucleotide or nucleic acid strand of the nucleic acid nanostructure. In some configurations, a nucleic acid nanostructure may be further characterized by an absence of a non-nucleic acid structural element (e.g., a polypeptide, a protein, a polymer, a nanoparticle) that is configured to join a first oligonucleotide or nucleic acid strand to a second oligonucleotide or nucleic acid strand.

A nucleic acid nanostructure, as set forth herein, may comprise increased volumetric and/or areal density of nucleotide packing within a nanostructure or a component structure thereof relative to a naturally-occurring nucleic acid such as a naturally-occurring nucleic acid having the same mass, nucleotide sequence or sequence length as the nucleic acid nanostructure. Naturally-occurring nucleic acids typically achieve volumetric nucleotide density through helical coiling of double-stranded nucleic acids and supercoiling of helical nucleic acids into compacted structures. However, to achieve packing of double-stranded nucleic acids with strand curvatures that exceed the persistence length of double-stranded nucleic acids, naturally-occurring nucleic acids are typically complexed with proteins (e.g., histones) that condense helical nucleic acids into supercoiled structures. In contrast, a nucleic acid nanostructure may comprise a volumetric density of nucleotides that exceeds a volumetric nucleotide density of a naturally-occurring nucleic acid. A nucleic acid nanostructure may achieve a greater volumetric nucleotide density than a naturally-occurring nucleic acid through increased bending and/or curvature of nucleic acid structures and/or closer proximity of helical structures within the nucleic acid nanostructure. In some configurations, a nucleic acid nanostructure may achieve a greater volumetric nucleotide density than a naturally-occurring nucleic acid in the absence of a non-nucleic acid structural element (e.g., a polypeptide, a protein, a polymer, a nanoparticle) that is configured to condense a nucleic acid structure.

A nucleic acid nanostructure, as set forth herein, may comprise increased sharpness of bending of a nucleic acid relative to sequence length and/or degree of secondary structuring relative to a naturally-occurring nucleic acid such as a naturally-occurring nucleic acid having the same nucleotide sequence or mass as the nucleic acid nanostructure. Naturally-occurring double-stranded nucleic acids have a large persistence length that makes it unlikely that any portion of the double-stranded nucleic acid can approach within, for example, about 10 nanometers of any other portion in the absence of a structure-altering group (e.g., a histone). Even if single-stranded nucleic acid is present within a naturally-occurring nucleic acid, two portions of tertiary structure are unlikely to approach within, for example, about 10 nanometers of each other due to electrostatic repulsion by negatively charged polynucleotide backbones. Moreover, in the absence of a unifying element (e.g., a histone, a linking nucleic acid), two tertiary structures are unlikely to remain stably oriented in a close configuration in a naturally-occurring nucleic acid. In contrast, a nucleic acid nanostructure, as set forth herein, may comprise sharply bent nucleic acid structures that increase the proximity of helical structures through the segmentation of double-stranded nucleic acids with sequences of single-stranded nucleic acids. Neighboring helical structures may be held in close proximity by linking nucleic acid strands that spatially and/or temporally stabilize the proximity and orientation of the neighboring helical structures relative to each other. A nucleic acid nanostructure, as set forth herein, may be further distinguished from naturally-occurring nucleic acids due to a presence of a stable (i.e., spatially and/or temporally invariant) bend in a nucleic acid strand that comprises two segmented regions of helical structure, for example a bend of at least 90° to 180°), relative to a length of a segment of single-stranded nucleic acid (e.g., no more than 50, 40, 30, 25, 20, 15, or 10 nucleotides) of the nucleic acid strand that separates the two segmented regions of helical structure. Alternatively or additionally, a nucleic acid nanostructure, as set forth herein, may be further distinguished from naturally-occurring nucleic acids due to a presence of a stable (i.e., spatially and/or temporally invariant) bend in a nucleic acid strand that comprises two segmented regions of helical structure, for example a bend of at least 90° to 180°), relative to a degree of secondary structuring of the nucleic acid nanostructure (e.g., comprising at least about 80%, 85%, 90%, or 95% of base-paired nucleotides relative to total nucleotide content).

A nucleic acid nanostructure, as set forth herein, may comprise decreased separation distance between neighboring nucleic acid structures within a nanostructure relative to a naturally-occurring nucleic acid such as a naturally-occurring nucleic acid having the same mass, nucleotide sequence or sequence length as the nucleic acid nanostructure. Adjacent helical (e.g., tertiary) structures may be held in a temporally and/or spatially stable configuration at a distance of, for example, less than about 10, 9, 8, 7, 6, 5, 4, 3, or 2 nanometers. The close proximity of adjacent helical structures in nucleic acid nanostructures are unlikely to occur due to structural strain introduced by electrostatic repulsion of adjacent polynucleotide chains. Nucleic acid nanostructures may be capable of achieving close spatial proximities of helical structures and sharp bending angles of nucleic acid strands due to a presence of one or more linking nucleic acid strands that stabilize the nucleic acid structure.

A nucleic acid nanostructure, as set forth herein, may comprise a low degree of sequence complementarity relative to total amount of nucleic acid present relative to a naturally-occurring nucleic acid such as a naturally-occurring nucleic acid having the same mass or sequence length as the nucleic acid nanostructure. A naturally-occurring nucleic acid strand will typically be hybridized to a complementary nucleic acid strand with an identical sequence length. Aside from replication or proofreading errors, the co-hybridized strands can be expected to have near complete sequence complementarity, leading to an almost fully hybridized structure in a stable configuration. In contrast, a nucleic acid nanostructure, as set forth herein, may comprise a plurality of single-stranded nucleic acids within the nanostructure. The single-stranded nucleic acids within a nucleic acid nanostructure may be characterized as spatially and/or temporally stable, in contrast to naturally-occurring nucleic acids, in which single-stranded nucleic acids are often formed and unformed transiently throughout the structure of the nucleic acid due to various biological processes. A nucleic acid nanostructure, as set forth herein, may comprise a stable fraction of single-stranded nucleic acid as measured by percentage of unpaired nucleotides within a nanostructure. In some configurations, a nucleic acid nanostructure may comprise a compacted region of predominantly double-stranded nucleic acids and a pervious region of predominantly single-stranded nucleic acids. In particular configurations, a nucleic acid nanostructure may comprise a compacted region of predominantly double-stranded nucleic acids and a pervious region of predominantly single-stranded nucleic acids, in which the pervious region comprises a larger total quantity of nucleotides than the compacted region. A nucleic acid nanostructure may comprise a spatially and/or temporally stable fraction of single-stranded nucleic acids as measured by unpaired nucleotides, such as at least about 5%, 10%, 20%, 30%, 40%, 50%, 60%, or more than 60% single-stranded nucleic acids.

A nucleic acid nanostructure, as set forth herein, may comprise greater mechanical rigidity relative to amount of single-stranded nucleic acid within a nanostructure when compared to naturally-occurring nucleic acids such as a naturally-occurring nucleic acids having the same mass, nucleotide sequence or sequence length as the nucleic acid nanostructure. For example, a strand of single-stranded nucleic acid within a linear double-stranded nucleic acid would typically create decreased rigidity within the double-stranded nucleic acid as evidenced by increased relative motion between ends of the nucleic acid. Increased amount of single-stranded nucleic acid within a linear double-stranded nucleic acid would be expected to further decrease the amount of rigidity of the nucleic acid. In contrast, a nucleic acid nanostructure, as set forth herein may comprise greater rigidity on a spatial and/or temporal basis relative to total single-stranded nucleic acid content relative to a naturally-occurring nucleic acid with a same single-stranded nucleic acid content. The increased rigidity may arise due to linking strands that stabilize nucleic acid structures relative to each other within the nucleic acid nanostructure.

Nucleic Acid Configurations: Described herein are nucleic acid nanostructures such as SNAPs. The nucleic acid nanostructures may be utilized for multiple purposes, including the display of molecules or analytes at a surface or interface, such as a solid support or a phase boundary. The described nucleic acid nanostructures, such as SNAPs, may comprise various primary, secondary, tertiary, or quaternary structures that give rise to compacted nucleic acid particles with various geometries that add utility to the nanostructures. Any given nucleic acid nanostructure may serve one or more functions, including displaying a molecule or an analyte (a display SNAP), or performing other nanostructure-related utilities (a utility SNAP). A nucleic acid nanostructure, such as a utility SNAP, may perform such functions as coupling a molecule or an analyte to a surface or interface (a capture SNAP), coupling a nucleic acid nanostructure to another nucleic acid nanostructure (a coupling SNAP), providing other structural utilities to a nucleic acid nanostructure or a complex thereof (a structural SNAP), or a combination thereof. In some configurations, a nucleic acid nanostructure may comprise a display SNAP, a utility SNAP, or a combination thereof. For example, a nucleic acid nanostructure (e.g., a SNAP) may be configured to couple to an analyte and a solid support, thereby making the nucleic acid nanostructure both a display nanostructure and a utility nanostructure.

A nucleic acid nanostructure, such as a SNAP, may comprise a display face that contains a display moiety. A display moiety may be configured to couple an analyte by a suitable interaction, such as a covalent bond, a non-covalent interaction, an electrostatic interaction, or a magnetic interaction. A display moiety may comprise one or more functional groups, ligands, or other moieties that are configured to couple an analyte. A display moiety may comprise a residue of a nucleic acid, or may comprise a functional group, ligand, or moiety coupled thereto. A display moiety may further comprise one or more secondary, tertiary, or quaternary structures that are positioned within a display face. A nucleic acid nanostructure, such as a SNAP, may comprise a capture face that contains a capture moiety. The capture moiety may be configured to couple to a surface by a suitable interaction, such as a covalent bond, a non-covalent interaction, an electrostatic interaction, or a magnetic interaction. A capture moiety may comprise one or more functional groups, ligands, or other moieties that are configured to couple to a surface. A capture moiety may further comprise one or more secondary, tertiary, or quaternary structures that are positioned within a capture face.

A display moiety may include two or more display tertiary structures of a plurality of tertiary structures. A capture moiety may include two or more capture tertiary structures of a plurality of tertiary structures. In some configurations, a display tertiary structure of the two or more display tertiary structures may comprise a capture tertiary structure of the two or more capture tertiary structures. For example, in FIG. 2B, face T may comprise the display moiety and face B may comprise the capture moiety, with the four tertiary structures belonging to both moieties. In other configurations, the two or more display tertiary structures do not comprise any capture tertiary structure of the two or more capture tertiary structures. For example, in FIG. 2D, the display moiety may comprise the two tertiary structures associated with face D and the capture moiety may comprise the two tertiary structures associated with face B. In some configurations, the two or more capture tertiary structures do not comprise any display tertiary structure of the two or more display tertiary structures.

A nucleic acid nanostructure, such as a SNAP, may comprise a plurality of nucleic acid strands, the strands being molecules that are separable one from another without breaking covalent bonds. For example, a SNAP may comprise a nucleic acid molecule that forms a scaffold strand and a plurality of staple oligonucleotide molecules hybridized to the scaffold strand. In some configurations, a scaffold strand may comprise an oligonucleotide of a plurality of oligonucleotides, in which the oligonucleotide is coupled to a greater quantity of oligonucleotides of the plurality of oligonucleotides than any other oligonucleotide of the plurality of oligonucleotides. A scaffold strand may comprise a linear, branched, or circular polynucleotide. In some configurations, a nucleic acid nanostructure may comprise two or more scaffold strands, such as about 2, 3, 4, 5, 6, 7, 8, 9, 10, 15, 20 or more scaffold strands, where each strand is optionally a molecule that is separable from the other strand(s) of the nucleic acid nanostructure. A nucleic acid nanostructure with two or more scaffold strands may comprise a first scaffold strand that is linked to a second scaffold strand by one or more oligonucleotides of the plurality of oligonucleotides that are hybridized to the first scaffold strand and the second scaffold strand. A first scaffold strand may be linked to a second scaffold strand by a certain number of the plurality of oligonucleotides, such as, for example, at least about 1%, 2%, 3%, 4%, 50%, 6%, 7%, 80%, 9%, 10%, 110%, 12%, 130%, 14%, 150%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or more than 50% of oligonucleotides in the plurality of oligonucleotides. Alternatively or additionally, a first scaffold strand may be linked to a second scaffold strand by no more than about 50%, 49%, 48%, 47%, 46%, 45%, 44%, 43%, 42%, 41% 40%, 39%, 38%, 37%, 36%, 35%, 34%, 33%, 32%, 31% 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or less than 1% of oligonucleotides in the plurality of oligonucleotides.

A nucleic acid scaffold may comprise a continuous strand of nucleic acids that, with or without complementary oligonucleotides, is a circular or joined strand (i.e., the scaffold strand having no 5' or 3' termini). In some configurations, a scaffold strand is derived from a natural source, such as a viral genome or a bacterial plasmid. In other configurations, a scaffold strand may be engineered, rationally designed, or synthetic, in whole or in part. A scaffold strand may comprise one or more modified nucleotides. Modified nucleotides may provide conjugation sites for attaching additional components, such as affinity reagents or detectable labels. A modified nucleotide may be utilized as a conjugation site for an additional component (e.g. binding component or label component) before, during, or after assembly of a nucleic acid nanostructure, such as a SNAP. A modified nucleotide may include a linking group or a reactive handle (e.g., a functional group configured to perform a click reaction). In some configurations, a nucleic acid scaffold may comprise a single strand of an M13 viral genome. The size of a scaffold strand may vary depending upon the desired size of a nucleic acid nanostructure. A scaffold strand may comprise a length of at least about 1000, 1500, 2000, 2500, 3000, 3500, 4000, 4500, 5000, 5200, 5400, 5600, 5800, 6000, 6200, 6400, 6600, 6800, 7000, 7200, 7400, 7600, 7800, 8000, 8200, 8400, 8600, 8800, 9000, 9500, 10000, or more than 10000 nucleotides. Alternatively or additionally, a scaffold strand may comprise a length of at most about 10000, 9500, 9000, 8800, 8600, 8400, 8200, 7800, 7600, 7400, 7200, 7000, 6800, 6600, 6400, 6200, 6000, 5800, 5600, 5400, 5200, 5000, 4500, 4000, 3500, 3000, 2500, 3000, 2500, 2000, 1500, 1000 or less than 1000 nucleotides.

A nucleic acid nanostructure, such as a SNAP, may comprise a plurality of staple oligonucleotides. A staple oligonucleotide may comprise any oligonucleotide that is hybridized with, or configured to hybridize with, a nucleic acid scaffold, other staples, or a combination thereof. A staple oligonucleotide may be modified to include additional chemical entities, such as binding components, label components, chemically-reactive groups or handles, or other groups (e.g., polyethylene glycol (PEG) moieties). A staple oligonucleotide may comprise linear or circular nucleic acids. A staple oligonucleotide may comprise one or more single-stranded regions, double-stranded regions, or combinations thereof. A staple oligonucleotide may be hybridized with, or configured to hybridize with, a scaffold strand or one or more other staples, for example, via complementary base pair hybridization (e.g., Watson-Crick hybridization). A staple oligonucleotide may be hybridized with other nucleic acids by complementary base pair hybridization or ligation. A staple oligonucleotide may be configured to act as a primer for a complementary nucleic acid strand and the primer staple may be extended by an enzyme (e.g., a polymerase) to form lengthened regions of double-stranded nucleic acid, for example, using a scaffold, staple or other strand as a template. In some cases the primer need not be hybridized to a template when extended. For example, a primer can be extended by template-free addition of one or more nucleotides by a terminal transferase enzyme, by template-free addition of one or more oligonucleotides by a ligase enzyme or template-free addition of nucleotide(s) or oligonucleotide(s) by non-enzymatic chemical reaction. A staple oligonucleotide may include one or more modified nucleotides. A modified nucleotide may include a linking group or a reactive handle (e.g., a functional group configured to perform a click-type reaction).

A staple oligonucleotide may be any length depending upon the design of the SNAP. A staple oligonucleotide may be designed by a software package, such as caDNAno$^2$, ATHENA, OR DAEDALUS. A staple oligonucleotide may have a length of at least about 10, 25, 50, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2500, 3000, 3500, 4000, 4500, 5000, or more than 5000 nucleotides. Alternatively or additionally, a staple may have a length of no more than about 5000, 4500, 4000, 3500, 3000, 2500, 2000, 1900, 1800, 1700, 1600, 1500, 1400, 1300, 1200, 1100, 1000, 950, 900, 850, 800, 750, 700, 650, 600, 550, 500, 450, 400, 350, 300, 250, 200, 150, 100, 50, 25, 10, or less than 10 nucleotides.

A staple may comprise a first nucleotide sequence and a second nucleotide sequence, in which the first nucleotide sequence hybridized to a first complementary sequence, and in which the second nucleotide sequence is hybridized to a second complementary sequence. In some configurations, a staple may comprise a first nucleotide sequence and a second nucleotide sequence, in which the first nucleotide sequence is hybridized to a first complementary sequence, in which the second nucleotide sequence is hybridized to a second complementary sequence, and in which the first nucleotide sequence is linked to the second nucleotide sequence by a linking moiety (e.g., a linker as set forth herein, an intermediate single-stranded nucleotide sequence, an intermediate double-stranded nucleotide sequence, an intermediate nucleotide sequence that is not configured to couple to a complementary nucleotide sequence, etc.). In some configurations, a staple may comprise a first nucleotide sequence and a second nucleotide sequence, in which the first nucleotide sequence is hybridized to a first complementary sequence of a scaffold strand, and in which the second nucleotide sequence hybridized to a second complementary sequence of the scaffold strand. In particular configurations, a first complementary sequence and a second complementary sequence of a scaffold strand may be non-consecutive, such that the two complementary sequence regions are separated by a third region of the scaffold strand. A staple may comprise a first nucleotide sequence and a second nucleotide sequence, in which the first nucleotide sequence is hybridized to a first complementary sequence, and in which the second nucleotide sequence is not hybridized to a second complementary sequence (e.g., a pendant moiety). A first nucleotide sequence or a second nucleotide sequence of a staple oligonucleotide may comprise a sequence length of at least about 3, 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides. Alternatively or additionally, a first nucleotide sequence or a second nucleotide sequence of a staple oligonucleotide may comprise a sequence length of no more than about 30, 29, 28 27, 26, 25, 24, 23, 22, 21, 20, 19, 18, 17, 16, 15, 14, 13, 12, 11, 10, 9, 8, 7, 6, 5, 4, 3, or less than 3 nucleotides. A sequence length of a nucleotide sequence of a staple oligonucleotide may be chosen to provide a hybridized nucleic acid containing the staple oligonucleotide a particular melting temperature, as set forth herein.

A staple oligonucleotide may include one or more modified nucleotides. Modified nucleotides may provide conjugation sites for attaching additional components, such as binding components or label components. A modified nucleotide may increase the stability of an oligonucleotide to chemical degradation, e.g., a locked nucleic acid (LNA). A modified nucleotide may be utilized as a conjugation site for an additional component before, during, or after assembly of a nucleic acid nanostructure, such as a SNAP. A staple oligonucleotide may include at least about 0, 1, 2, 3, 4, 5, 6, 7, 8, 9, 10, 11, 12, 13, 14, 15, 16, 17, 18, 19, 20, 25, 30, 35, 40, 45, 50, 75, 100 or more than 100 modified nucleotides. Alternatively or additionally, A staple oligonucleotide may include no more than about 100, 75, 50, 45, 40, 35, 30, 25, 20, 19, 18, 17, 16, 15, 14, 13, 12, 11, 10, 9, 8, 7, 6, 5, 4, 3, 2, or less than 2 modified nucleotides.

A nucleic acid nanostructure, as set forth herein, may comprise a plurality of nucleic acids, in which each nucleic acid of the plurality of nucleic acids is hybridized to one or more other nucleic acid of the plurality of nucleic acids. In some configurations, a nucleic acid nanostructure may comprise at least 5 nucleic acids, in which each nucleic acid of the at least 5 nucleic acids is coupled to one or more other nucleic acids of the at least 5 nucleic acids. A plurality of nucleic acids of a nucleic acid nanostructure may comprise a scaffold strand, in which the scaffold strand is characterized by one or more characteristics of: i) comprising a longest nucleotide sequence of the plurality of nucleic acids, and ii) being configured to hybridize with a greater quantity of other nucleic acids of the plurality of nucleic acids. A plurality of nucleic acids of a nucleic acid nanostructure may further comprise one or more staple oligonucleotides, in which a staple oligonucleotide is characterized by one or more characteristics of: i) comprising two or more non-consecutive nucleotide sequences that are configured to hybridize to one or more other nucleic acids (e.g., one or more regions of a scaffold strand, a scaffold strand and a second staple oligonucleotide, a second staple oligonucleotide and a third staple oligonucleotide, etc.), ii) comprising two or more non-consecutive nucleotide sequences that are configured to form two or more secondary and/or tertiary structures when hybridized with one or more other nucleic acids, ii) comprising one or more nucleotide sequences that are not configured to hybridize to other nucleic acids, and iii) comprising one or more nucleotide sequences that are configured to constrain a position, orientation, and/or motion of a first secondary and/or tertiary nucleic acid structure relative to a second secondary and/or tertiary nucleic acid structure.

Figure 51:
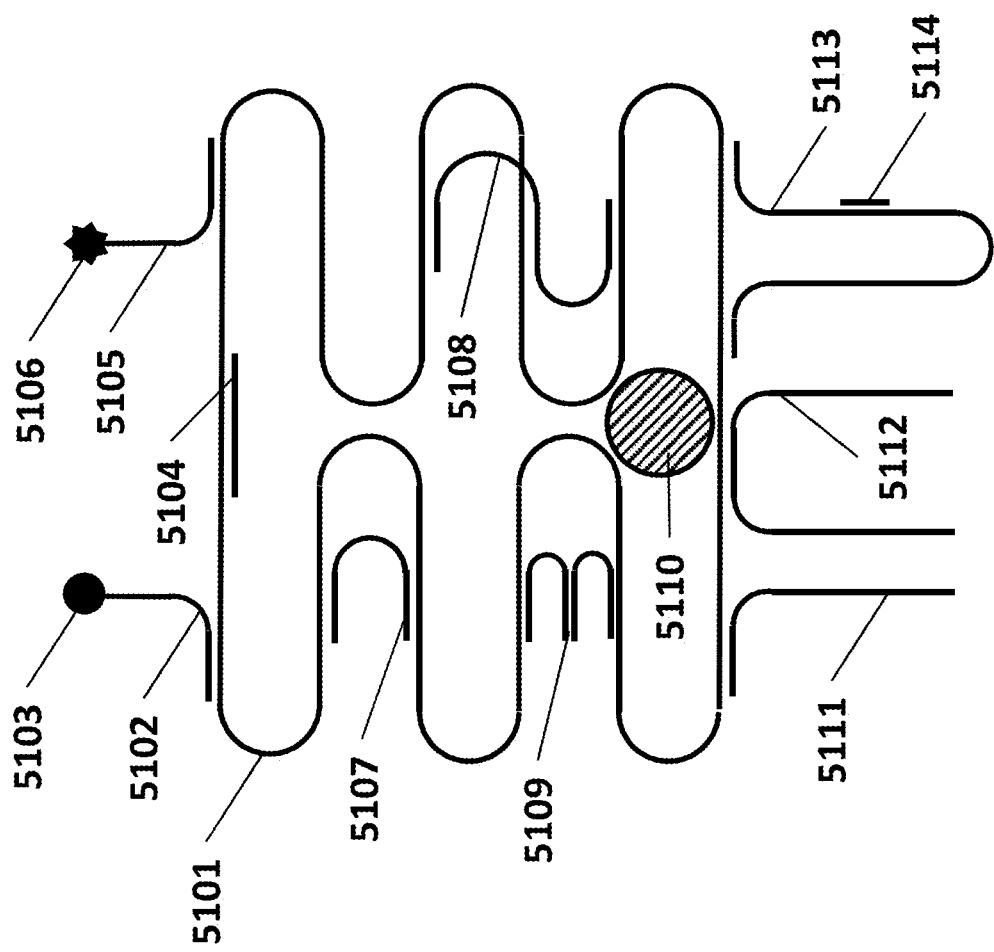
FIG. 51 displays a nucleic acid nanostructure comprising a scaffold strand and a plurality of staple oligonucleotides, in accordance with some embodiments.

FIG. 51 illustrates a schematic of a nucleic acid nanostructure comprising a scaffold strand 5101 and a plurality of staple oligonucleotides, in which the staple oligonucleotides have a variety of structural and/or functional roles. The nucleic acid nanostructure comprises a plurality of structural staple oligonucleotides that each have one or more properties of i) binding with the scaffold strand 5101 to form one or more tertiary structures, and ii) forming linking single-stranded nucleic acids that position and orient two or more tertiary structures of the nucleic acid nanostructure with respect to each other. Structural staple oligonucleotides include: 1) nucleic acid 5104, which binds to the scaffold strand 5101 to form a region of tertiary structure, 2) nucleic acid 5107, which binds to the scaffold strand 5101 at two nucleotide sequences to form a substantially 180° bend in the nucleic acid nanostructure and links the two tertiary structures formed by the binding of the nucleic acid 5107 to the scaffold strand 5101 by a linking strand comprising a single-stranded nucleotide sequence of nucleic acid 5107, 3) nucleic acid 5108, which binds to the scaffold strand 5101 at three non-consecutive nucleotide sequences to form at least 3 tertiary structures and 2 substantially 180° bends in the nucleic acid nanostructure, and 4) nucleic acids 5109, which each comprise a first sequence that is complementary to the scaffold strand 5101 and a second sequence that is complementary to the other nucleic acid 5109 to form a 3 tertiary structures and 1 substantially 180° bend in the nucleic acid nanostructure. A nucleic acid nanostructure may also comprise a non-nucleic acid structural element 5110, such as a nucleic-acid binding protein (e.g., a histone) or a nanoparticle, in which the non-nucleic acid structural element 5110 forms or stabilizes a portion of the two-dimensional and/or three-dimensional structure of the nucleic acid nanostructure. The nucleic acid nanostructure further comprises a plurality of functional staple oligonucleotides that each have one or more properties of: i) binding with the scaffold strand 5101 to form one or more tertiary structures, and ii) modifying the nucleic acid nanostructure to provide additional chemical and/or physical properties to the nucleic acid nanostructure. Functional staple oligonucleotides include: 1) nucleic acid 5102, which binds to the scaffold strand 5101 to form a tertiary structure and comprises a moiety 5103 (e.g., a terminal ligand, a non-terminal ligand, a terminal functional group, a non-terminal functional group, a modified nucleotide, a non-nucleic acid polymer, etc.), 2) nucleic acid 5105, which binds to the scaffold strand 5101 to form a tertiary structure and comprises a detectable label 5106 (e.g., a fluorophore, a nucleic acid barcode, a peptide barcode, etc.), 3) pendant nucleic acid 5111, which binds to the scaffold strand 5101 to form a tertiary structure and comprises an uncoupled terminal residue or nucleotide sequence, 4) pendant nucleic acid 5112, which comprises two uncoupled terminal residues or nucleotide sequences and an intermediate nucleotide sequence that binds to the scaffold strand 5101 to form a tertiary structure, and 5) pendant nucleic acid 5113, which comprise two terminal nucleotide sequences that bind to the scaffold strand 5101 to form tertiary structures and an intermediate single-stranded nucleotide sequence that is pendant from the nucleic acid nanostructure (including one or more coupled oligonucleotides 5114 that provide tertiary structuring to the pendant portion of nucleic acid 5113.

A nucleic acid nanostructure, such as a SNAP can include a nucleic acid origami. Accordingly, a nucleic acid nanostructure can include one or more nucleic acids having tertiary or quaternary structures such as spheres, cages, tubules, boxes, tiles, blocks, trees, pyramids, wheels, combinations thereof, and any other possible structure. Examples of such structures formed with DNA origami are set forth in Zhao et al. *Nano Lett.* 11, 2997-3002 (2011), which is incorporated herein by reference. In some configurations, a nucleic acid nanostructure, such as a SNAP, may comprise a scaffold strand and a plurality of staple oligonucleotides, where the scaffold strand is a single, continuous strand of nucleic acid, and the staple oligonucleotides are configured to bind, in whole or in part, with the scaffold strand. Examples of DNA origami structures formed using a continuous scaffold strand and several staple strands are set forth in Rothemund *Nature* 440:297-302 (2006) and U.S. Pat. Nos. 8,501,923 and 9,340,416, each of which is incorporated herein by reference. A nucleic acid nanostructure comprising one or more nucleic acids (e.g., as found in origami or nanoball structures) may comprise regions of single-stranded nucleic acid, regions of double-stranded nucleic acid, or combinations thereof. In some configurations, a nucleic acid nanostructure may comprise a nucleic acid origami and a nucleic acid structure other than a nucleic acid origami. For example, a nucleic acid origami may be coupled to one or more single-stranded nucleic acids, in which the one or more single-stranded nucleic acids do not form any secondary and/or tertiary structures. In an advantageous configuration, a nucleic acid origami may comprise a tile structure. A tile structure of a nucleic acid origami may refer to a structure with an average thickness that is substantially smaller than a characteristic dimension (e.g., side length, side width, maximum diameter, average diameter, etc.). For example, a tile structure of a nucleic acid origami may have an aspect ratio between a characteristic dimension and an average thickness of at least about 2:1, 3:1, 4:1, 5:1, 10:1, 20:1, or more than 20:1. Alternatively or additionally, a tile structure may have an aspect ratio between a characteristic dimension and an average thickness of no more than about 20:1, 10:1, 5:1, 4:1, 3:1, 2:1, or less than 2:1. A tile structure may have a shape, such as a substantially rectangular tile, a substantially square tile, a substantially triangular tile, a substantially circular tile, a substantially oval tile, or a substantially polygonal tile. A tile may comprise one or more faces that are substantially planar. A tile may comprise one or more faces that are substantially non-planar (e.g., curved, corrugated, etc.).

A nucleic acid nanostructure, such as a SNAP, may comprise two or more utility faces that are formed by the scaffold strand hybridizing to the plurality of staple oligonucleotides. The hybridizing of the plurality of staple oligonucleotides to the scaffold strand may form a plurality of tertiary nucleic acid structures in a nucleic acid nanostructure. In some configurations, a plurality of tertiary structures may comprise a first tertiary structure belonging to a first utility face (e.g., a display face) and a secondary tertiary structure belonging to a second utility face (e.g., a capture face). Two tertiary structures in a nucleic acid nanostructure (e.g., a SNAP) may be oriented with respect to each other relative to an axis or plane of symmetry. Two tertiary structures in a nucleic acid nanostructure may be oriented with respect to each other relative to an axis or plane of symmetry of one or both of the tertiary structures, such as the coaxial axis of symmetry for a nucleic acid double helix. In some configurations with a first and second tertiary structure belonging to differing utility faces, the axis of symmetry of the first tertiary structure and the axis of symmetry of the second tertiary structure are coplanar. For configurations in which a first and second tertiary structure belong to differing utility faces, the axis of symmetry of the first tertiary structure and the axis of symmetry of the second tertiary structure can be non-coplanar. In some configurations in which a first and second tertiary structure belong to differing utility faces, the axis of symmetry of the first tertiary structure and the axis of symmetry of the second tertiary structure can be intersecting. In some configurations in which a first and second tertiary structure belong to differing utility faces, the axis of symmetry of the first tertiary structure and the axis of symmetry of the second tertiary structure can be non-intersecting. A symmetry characteristic of a nucleic acid nanostructure (e.g., a SNAP) may be determined with respect to an average dimension, shape, or configuration of the nucleic acid nanostructure. Slight variations in positioning of features, for example, due to the helical structure and tertiary structures of a nucleic acid nanostructure or temporal variations due to environmental conditions (e.g., Brownian motion, fluidic shear, electromagnetic forces, etc.), may cause small differences between two opposed sides of a nucleic acid nanostructure that is designed to have a symmetrical structure. A nucleic acid nanostructure may be considered symmetric if two symmetric features lie within about 10% of the expected position with respect to an axis or plane of symmetry.

A nucleic acid nanostructure composition (e.g., a SNAP composition) may further comprise a molecule or an analyte. Optionally, the molecule or analyte is a non-nucleic acid molecule or analyte, respectively. In some configurations, a display moiety of a nucleic acid nanostructure may be coupled to the molecule or analyte. For example, a plurality of SNAPs may be deposited on an array after each SNAP of the plurality of SNAPs has been coupled to the molecule or analyte. In other configurations, a display moiety of a nucleic acid nanostructure need not be coupled to a molecule or an analyte. For example, a plurality of SNAPs may be deposited on an array before each SNAP of the plurality of SNAPs has been coupled to a molecule or an analyte. In some configurations, a molecule or an analyte may comprise a biomolecule selected from the group consisting of polypeptide, polysaccharide, nucleic acid, lipid, metabolite, enzyme cofactor, and a combination thereof. In some configurations, a molecule or an analyte may comprise a non-biological particle selected from the group consisting of polymer, metal, metal oxide, ceramic, semiconductor, mineral, and a combination thereof.

A nucleic acid nanostructure composition (e.g., a SNAP composition) may comprise a linker that is configured to couple an entity (e.g., a SNAP, an analyte, a coupling surface, etc.) to a moiety (e.g., a surface-interacting moiety, a display moiety, a capture moiety, a surface-linked moiety, etc.). A linker may have a size of at least about 100 Da, 500 Da, 1 kDa, 5 kDa, 10 kDa, 20 kDa, 25 kDa, 50 kDa, 100 kDa, 250 kDa, 500 kDa, or more than 500 kDa. Alternatively or additionally, a linker may have a size of no more than about 500 kDa, 250 kDa, 100 kDa, 50 kDa, 25 kDa, 20 kDa, 10 kDa, 5 kDa, 1 kDa, 500 Da, 100 Da, or less than about 100 Da. A linker may comprise a chemical physical property (e.g., hydrophobicity, hydrophilicity, polarity, steric size, net electrical charge, etc.) that mediates an interaction between an entity and a moiety that are joined by the linker. For example, a SNAP may comprise a rigid linker that separates an analyte of interest from a surface by a separation distance and/or prevents contact between the analyte of interest and a face of the SNAP.

A nucleic acid nanostructure (e.g., a SNAP) may comprise a functional nucleic acid. A functional nucleic acid may bring an additional utility to a nucleic acid nanostructure. A functional nucleic acid may comprise a nucleic acid barcode that may provide a tagging or information encoding function, for example, in the form of an identifying sequence for an analyte that is colocalized with the functional nucleic acid. As shown in FIGS. 10A-10D, the utility moiety 1040 may comprise a nucleic acid barcode sequence that may be transcribed onto a molecule that interacts with the analyte 1020, or vice versa. A barcode sequence contained on a utility moiety 1040 or an interacting molecule may be sequenced to determine a characteristic or prior use of analyte 1020, such as any interactions that may have occurred with the analyte 1020. A functional nucleic acid may comprise a retaining moiety, in which the retaining moiety comprises a hybridizing nucleic acid sequence that is configured to form a short-term or weak interaction that temporarily co-locates an interacting molecule in the vicinity of the analyte to increase the likelihood of an interaction being observed or to decrease the rate at which the interacting molecule dissociates from the analyte. A hybridizing nucleic acid sequence may comprise a short region of complementarity with another oligonucleotide (e.g., less than about 20, 19, 18, 17, 16, 15, 14, 13, 12, 11, 10, 9, 8, 7, 6, or 5 nucleotides), a nucleic acid sequence with imperfect complementarity to another nucleic acid, a toehold sequence, or any other configuration that promotes an easily reversible nucleic acid hybridization interaction. A functional nucleic acid may comprise a nucleic acid sequence that is configured to bind a labeled nucleic acid (e.g., a fluorescently-labeled oligonucleotide) for a purpose such as detecting a spatial address of a nucleic acid nanostructure (e.g., on a site of a solid support).

In another aspect, provided herein is a method of forming a multiplex array of analytes, comprising: a) contacting an array comprising a plurality of sites with a first plurality of nucleic acid nanostructures, as set forth herein, in which each nucleic acid nanostructure of the first plurality of nucleic acid nanostructures is coupled to an analyte of interest of a first plurality of analytes of interest, b) contacting the array comprising the plurality of sites with a second plurality of nucleic acid nanostructures, as set forth herein, in which each nucleic acid nanostructure of the second plurality of nucleic acid nanostructures is coupled to an analyte of interest of a second plurality of analytes of interest, c) depositing the first plurality of nucleic acid nanostructures at a first subset of sites of the plurality of sites, and d) depositing the second plurality of nucleic acid nanostructures at a second subset of sites of the plurality of sites, in which the first subset of sites and the second subset of sites comprise a random spatial distribution. In some configurations, each nucleic acid nanostructure of the first plurality of nucleic acid nanostructures may comprise a first functional nucleic acid, in which the first functional nucleic acid comprises a first nucleotide sequence, in which each nucleic acid nanostructure of the second plurality of nucleic acid nanostructures may comprise a second functional nucleic acid, in which the second functional nucleic acid comprises a second nucleotide sequence, and in which the first nucleotide sequence differs from the second nucleotide sequence. In some configurations, a method of forming a multiplex array may comprise simultaneously contacting the array with the first plurality of nucleic acid nanostructure and the second plurality of nucleic acid nanostructures. For example, an array may be contacted with a fluidic medium containing a mixture of the first plurality of nucleic acid nanostructures and the second plurality of nucleic acid nanostructures. In other configurations, a method of forming a multiplex array may comprise sequentially contacting the array with the first plurality of nucleic acid nanostructure and the second plurality of nucleic acid nanostructures. In some configurations, a method of forming a multiplex array may comprise simultaneously depositing on the array the first plurality of nucleic acid nanostructure and the second plurality of nucleic acid nanostructures. For example, an array may be contacted with a fluidic medium containing a mixture of the first plurality of nucleic acid nanostructures and the second plurality of nucleic acid nanostructures, then contacted with a second fluidic medium that facilitates the deposition of the nucleic acid nanostructures onto sites of the array. In other configurations, a method of forming a multiplex array may comprise sequentially depositing on the array the first plurality of nucleic acid nanostructure and the second plurality of nucleic acid nanostructures.

A method of forming a multiplex array of analytes may further comprise a step of contacting the array with a first plurality of detectable nucleic acids, in which each first detectable nucleic acid of the first plurality of detectable nucleic acids comprises a first complementary nucleotide sequence and a detectable label, in which the first complementary nucleotide sequence is complementary to a first nucleotide sequence of a first functional nucleic acid of a nucleic acid nanostructure of the first plurality of nucleic acid nanostructures. After contacting the array with the first plurality of detectable nucleic acids, a method of forming a multiplex array of analytes may further comprise coupling a first detectable nucleic acid to each first functional nucleic acid. After coupling the first detectable nucleic acid to each first functional nucleic acid, the method may further comprise a step of detecting each address of the array comprising the first detectable nucleic acid, as set forth herein. After coupling the first detectable nucleic acid to each first functional nucleic acid, the method may further comprise a step of removing the first detectable nucleic acid from the first functional nucleic acid. In some configurations, removing the first detectable nucleic acid from the first functional nucleic acid may comprise heating a nucleic acid nanostructure of the first plurality of nucleic acid nanostructures to at least a melting temperature of the first functional nucleic acid, thereby uncoupling the first detectable nucleic acid from the first functional nucleic acid. In other configurations, removing a first detectable nucleic acid from the first functional nucleic acid may comprise contacting a solid support with a fluidic medium that is configured to separate the first detectable nucleic acid from the first functional nucleic acid (e.g., a denaturant, a chaotrope, etc.), optionally in the presence of heating.

A method of forming a multiplex array of analytes may comprise contacting the array with two or more pluralities of detectable nucleic acids. For example, a method exemplified above, may further comprise a step of contacting the array with a second plurality of detectable nucleic acids, in which each second detectable nucleic acid of the second plurality of detectable nucleic acids comprises a second complementary nucleotide sequence and a detectable label, in which the second complementary nucleotide sequence is complementary to a second nucleotide sequence of a second functional nucleic acid of a nucleic acid nanostructure of the second plurality of nucleic acid nanostructures. After contacting the array with the second plurality of detectable nucleic acids, a method of forming a multiplex array of analytes may further comprise coupling a second detectable nucleic acid to each second functional nucleic acid. After coupling the second detectable nucleic acid to each second functional nucleic acid, the method may further comprise a step of detecting each address of the array comprising the second detectable nucleic acid, as set forth herein. After coupling the second detectable nucleic acid to each second functional nucleic acid, the method may further comprise a step of removing the second detectable nucleic acid from the second functional nucleic acid. In some configurations, removing the second detectable nucleic acid from the second functional nucleic acid may comprise heating a nucleic acid nanostructure of the second plurality of nucleic acid nanostructures to at least a melting temperature of the second functional nucleic acid, thereby uncoupling the second detectable nucleic acid from the second functional nucleic acid. In other configurations, removing a second detectable nucleic acid from the second functional nucleic acid may comprise contacting a solid support with a fluidic medium that is configured to separate the second detectable nucleic acid from the second functional nucleic acid (e.g., a denaturant, a chaotrope, etc.), optionally in the presence of heating.

FIGS. 50A-50F depict a method of utilizing a functional nucleic acid for forming a multiplexed array of analytes of interest. FIG. 50A illustrates an array comprising a solid support 5000 comprising a plurality of sites 5001, with each site coupled to a SNAP 5010. The solid support 5000 is contacted with a plurality of SNAPs 5010. A first subset of the plurality of SNAPs 5010 comprise a SNAP 5010 coupled to a first analyte of interest 5020 (e.g., polypeptides from a first sample), in which each SNAP 5010 of the first subset comprises a first functional nucleic acid 5030 containing a nucleotide sequence of CGT. A second subset of the plurality of SNAPs comprise a SNAP 5010 coupled to a second analyte of interest 5025 (e.g., polypeptides from a second sample), in which each SNAP 5010 of the second subset comprises a second functional nucleic acid 5035 containing a nucleotide sequence of CCA. FIG. 50B illustrates a multiplexed array formed by deposition of the plurality of SNAPs 5010 at the plurality of sites 5001 on the solid support 5010. The first subset of SNAPs 5010 and the second subset of SNAPs 5010 comprise a random spatial distribution at the plurality of sites 5001, in which the addresses of first analytes of interest 5020 and second analytes of interest 5025 on the array are not initially known after deposition. FIG. 50C depicts contacting the solid support 5000 with a first plurality of detectable nucleic acids, in which each detectable nucleic acid comprises a detectable label 5045 and a complementary nucleic acid 5040 with a nucleotide sequence of GCA. FIG. 50D depicts the multiplexed array of SNAPs 5010, in which the first subset of SNAPs 5010 have coupled a detectable nucleic acid of the first plurality of detectable nucleic acids by base-pair bonding between the first functional nucleic acids 5030 and the complementary nucleic acids 5040. Each site 5001 comprising a first analyte of interest 5020 may be detectable at single-analyte resolution by detection of the detectable label 5045 at addresses on the array. FIG. 50E depicts contacting the solid support 5000 with a second plurality of detectable nucleic acids, in which each detectable nucleic acid comprises a detectable label 5046 and a complementary nucleic acid 5041 with a nucleotide sequence of GGT. FIG. 50F depicts the multiplexed array of SNAPs 5010, in which the second subset of SNAPs 5010 have coupled a detectable nucleic acid of the second plurality of detectable nucleic acids by base-pair bonding between the second functional nucleic acids 5035 and the complementary nucleic acids 5041. Each site 5001 comprising a first analyte of interest 5025 may be detectable at single-analyte resolution by detection of the detectable label 5046 at addresses on the array. In some configurations, the addresses of the first analytes of interest 5020 and the second analytes of interest 5025 can be simultaneously detected, for example by the use of detectable labels 5045 and 5046 (e.g., fluorophores) with differing detection characteristics (e.g., excitation wavelength, emission wavelength).

A functional nucleic acid, as set forth herein, may comprise a nucleotide sequence that is configured to hybridize with a complementary nucleotide sequence of a coupled moiety (e.g., a detectable label, a nucleic acid barcode, a retaining moiety, etc.). A functional nucleic acid may comprise a nucleotide sequence that is configured to form a double-stranded nucleic acid with a complementary nucleic acid, in which the double-stranded nucleic acid is disruptable by melting of the double-stranded nucleic acid. A double-stranded functional nucleic acid may have a melting temperature of at least about 50° C., 55° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or more than 99° C. Alternatively or additionally, a double-stranded functional nucleic acid may have a melting temperature of no more than about 99° C., 98° C., 97° C., 96° C., 95° C., 94° C., 93° C., 92° C., 91° C., 90° C., 89° C., 88° C., 87° C., 86° C., 85° C., 84° C., 83° C., 82° C., 81° C., 80° C., 79° C., 78° C., 77° C., 76° C., 75° C., 74° C., 73° C., 72° C., 71° C., 70° C., 69° C., 68° C., 67° C., 66° C., 65° C., 64° C., 63° C., 62° C., 61° C., 60° C., 55° C., 50° C., or less than 50° C. In some configurations, a melting temperature of a double-stranded functional nucleic acid of a nucleic acid nanostructure may be designed to be lower than a melting temperature of some or all other double-stranded nucleic acids of the nucleic acid nanostructure. In a particular configuration, a melting temperature of a double-stranded functional nucleic acid of a nucleic acid nanostructure may be designed to be lower than a melting temperature of at least 50%, 60%, 70%, 80%, 90%, 95%, or more than 95% of some or all of the double-stranded nucleic acids of the nucleic acid nanostructure. For example, a functional nucleic acid may be separated from a complementary nucleic acid at a melting temperature that does not cause a loss of a component oligonucleotide of a nucleic acid nanostructure containing the functional nucleic acid. In some configurations, a melting temperature of a double-stranded nucleic acid containing a functional nucleic acid may be designed to be lower than a dissociation temperature (e.g., a nucleic acid melting temperature, a ligand-receptor dissociation temperature, a covalent bond decomposition temperature, etc.) for a nucleic acid nanostructure coupled to a solid support or a coupling moiety attached to the solid support. For example, a melting temperature of a double-stranded functional nucleic acid of a nucleic acid nanostructure may be designed to be at least 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 35° C., 40° C., 45° C., 50° C., or more than 50° C. lower than a dissociation temperature of the nucleic acid nanostructure coupled to a solid support or a coupling moiety of the nucleic acid nanostructure that is attached to the solid support.

A nucleic acid nanostructure (e.g., a SNAP) may comprise a capture face or capture moiety that comprises one or more modifying groups that alter an interaction between the nucleic acid nanostructure and a surface. An altered interaction between a nucleic acid nanostructure and a surface may comprise: 1) increasing the rate or strength of coupling to a desired region of the surface; 2) decreasing the rate or strength of coupling to an undesired region of the surface; 3) enhancing the specificity of coupling to a surface; 4) diminishing non-specific couplings to a surface; 5) decreasing the strength of interactions (e.g., agglomeration, co-binding) between two or more nucleic acid nanostructures, and 6) combinations thereof. In some configurations, a capture moiety may comprise a modifying moiety, selected from the group consisting of an electrically-charged moiety (e.g. a cationic or anionic moiety), a polar moiety, a non-polar moiety, a ligand moiety that is recognized by a receptor, a receptor moiety that is recognized by a ligand, a magnetic moiety, a steric moiety, an amphipathic moiety, a hydrophobic moiety, and a hydrophilic moiety. In some configurations, the electrically-charged moiety may comprise a single-stranded nucleic acid or a charged polymer (e.g., a cationic or anionic polymer). In some configurations, a capture moiety of a nucleic acid nanostructure may comprise a plurality of single-stranded nucleic acids, where the single stranded nucleic acids are regions (e.g. tails or loops) of longer oligonucleotides that are hybridized to the nucleic acid nanostructure. In other configurations, a capture moiety of a nucleic acid nanostructure may comprise a plurality of single-stranded nucleic acids or electrically-charged polymers, where the single stranded nucleic acids are coupled to oligonucleotides that are hybridized to the nucleic acid nanostructure, for example by a covalent linker (e.g., click-type reaction product) or non-covalent linker (e.g., streptavidin-biotin complex).

Provided herein is a composition comprising: a) a nucleic acid nanostructure (e.g. a structured nucleic acid particle), wherein the nucleic acid nanostructure comprises: i) a display moiety comprising a coupling group that is coupled with, or configured to couple with, an analyte; and ii) a capture moiety that is coupled with, or configured to couple with, a surface, wherein the capture moiety comprises a plurality of first surface-interacting oligonucleotides, and wherein each first surface-interacting oligonucleotide of the plurality of first surface-interacting oligonucleotides comprises a first nucleic acid that is coupled with the structured nucleic acid particle and a first surface-interacting moiety, wherein the first surface-interacting moiety is coupled with, or configured to form a coupling interaction with, a surface-linked moiety, wherein the capture moiety and the display moiety have different orientations; and b) an analyte comprising a complementary coupling group that is coupled with, or configured to couple with the display moiety of the structured nucleic acid particle.

A nucleic acid nanostructure composition (e.g., a SNAP composition) may comprise a capture moiety with a plurality of pendant groups that mediate a coupling interaction with a surface (e.g., a coupling surface of a solid support).

A pendant group, as set forth herein, may be characterized by one or more characteristics of: i) comprising an uncoupled terminal moiety or residue, ii) comprising a moiety (e.g., a polymer strand) whose spatial degrees of freedom are not constrained by a coupling interaction with a second moiety of a nucleic acid nanostructure, and iii) comprising a moiety whose average temporal variations in position relative to a nucleic acid nanostructure exceed an average temporal variation in position of a moiety incorporated within the nucleic acid nanostructure. Without wishing to be bound by theory, the pendant groups may facilitate multiple properties of a nucleic acid nanostructure, including 1) increased specificity of surface coupling by the interactions between a capture moiety and surface-linked moieties on a solid support, 2) increased avidity of binding due to a multiplicity of binding interactions between a nucleic acid nanostructure and a coupling surface, 3) tunable binding kinetics based upon pendant groups added to a nucleic acid nanostructure, 4) tunable binding thermodynamics based upon free energy minimization between a capture moiety and a coupling surface, 5) decreased interactions between incidental nucleic acid nanostructure s due to binding incompatibility of nucleic acid nanostructure capture moieties, and 6) combinations thereof.

Figure 40A:
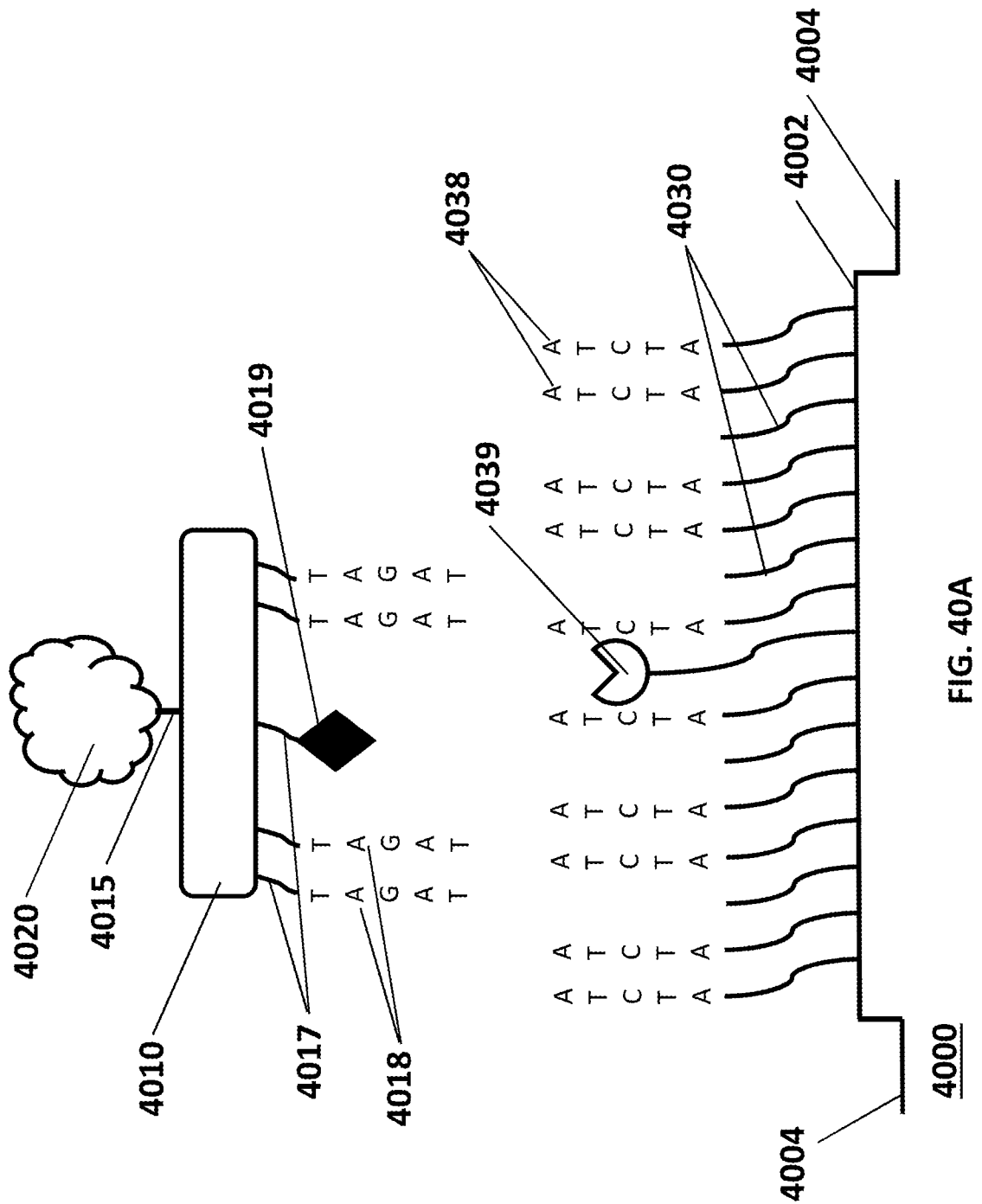
FIGS. 40A, 40B, and 40C illustrate various configurations of a SNAP containing a plurality of surface-interacting moieties in contact with a coupling surface comprising a plurality of surface-linked moieties, in accordance with some embodiments.
Figure 40B:
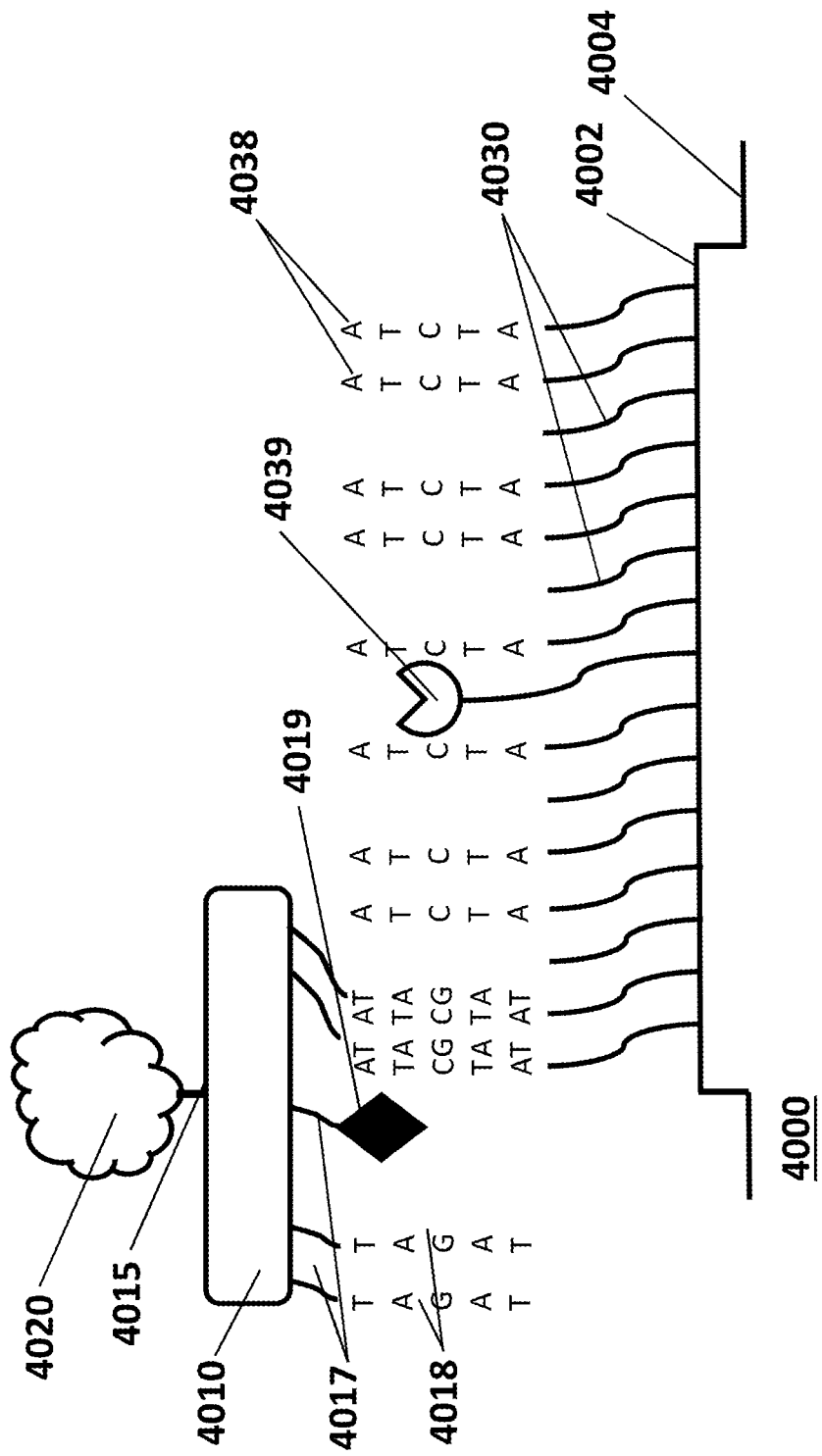
Figure 40C:
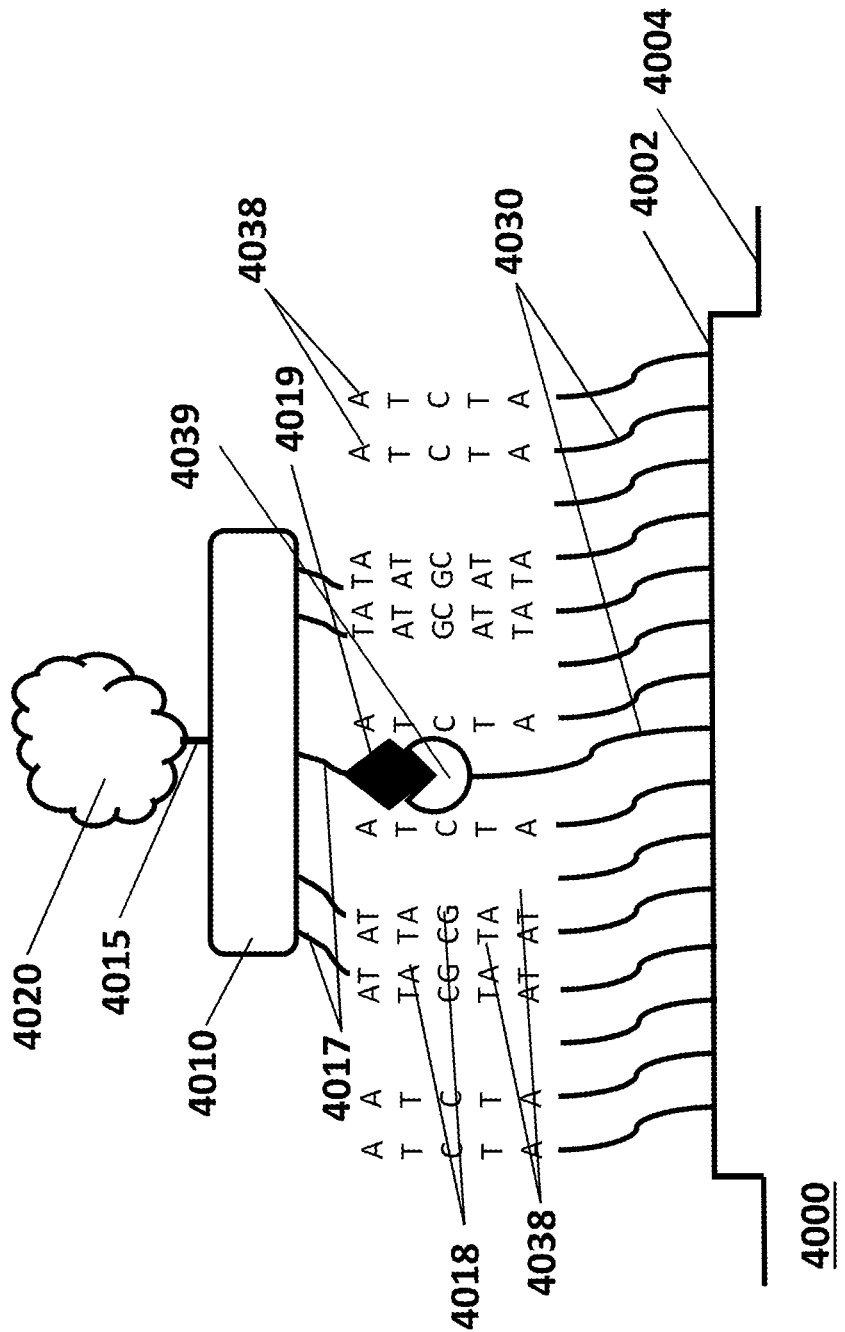

FIGS. 40A-40C illustrate SNAP compositions that include pendant groups on the capture moiety of a SNAP. FIG. 40A shows a SNAP 4010 comprising an upward-oriented display face containing a display moiety 4015 that is coupled to an analyte 4020 (e.g., a polypeptide). A downward-oriented capture face of the SNAP 4010 comprises a plurality of pendant groups. Each pendant group comprises an optional linker 4017 and a surface-interacting moiety, such as a surface-interacting oligonucleotide 4018 or a surface-interacting coupling group 4019 (e.g., a reactive group, a streptavidin, etc.). The SNAP 4010 may be contacted with a solid support 4000 comprising a coupling surface 4002 and one or more interstitial regions 4004. The coupling surface 4002 may comprise a plurality of surface-linked groups, in which each surface-linked group contains an optional linker 4030 (e.g., a passivating molecule such as PEG) and a surface-linked moiety, such as a complementary oligonucleotide 4038 or a complementary coupling group 4039 (e.g., a complementary reactive group, a biotin, etc.). Optionally, a surface may comprise a mixture of surface-linked groups, in which a first plurality of surface-linked groups comprises a passivating moiety (e.g., a PEG chain) and no coupling moiety, and a second plurality of surface-linked groups comprises a coupling moiety and a passivating moiety (e.g., an oligonucleotide coupled to a PEG chain). FIG. 40B shows a first coupling configuration of the SNAP 4010 to the solid support 4000. One or more surface-interacting oligonucleotides 4018 have hybridized to surface-linked complementary oligonucleotides 4038, but one or more other surface-interacting moieties remain unbound. This may suggest that the coupled SNAP is not in an energetically favorable binding position. FIG. 40C shows a second coupling configuration of the SNAP 4010 to the solid support 4000. Each surface-interacting moiety has formed a coupling interaction with a complementary surface-linked moiety. Such a configuration may be the most energetically and/or most stable position for the SNAP 4010 on the coupling surface 4002.

A nucleic acid nanostructure (e.g., a SNAP) may comprise a capture moiety that comprises a plurality of oligonucleotides that couple to the nucleic acid nanostructure and provide a plurality of pendant groups, in which each pendant group comprises a surface-interacting moiety. A surface-interacting moiety may form a coupling interaction with a surface-linked moiety on a solid support, thereby coupling a nucleic acid nanostructure comprising the surface-linked moiety to the solid support. A nucleic acid nanostructure may comprise a plurality of oligonucleotides, in which an oligonucleotide of the plurality of oligonucleotides comprises: a) a first nucleic acid that is configured to couple to a capture moiety of the nucleic acid nanostructure, and b) a first surface-interacting moiety. In some configurations, the first surface-interacting moiety may comprise a second nucleic acid. For example, an oligonucleotide of a plurality of oligonucleotides may comprise a first nucleic acid sequence that is configured to couple to a SNAP and a second nucleic acid sequence that is configured to bind to a complementary, surface-linked nucleic acid strand of a surface-linked moiety by base-pair hybridization. In some cases, the oligonucleotide containing the first nucleic acid sequence and the second nucleic acid sequence may further comprise a third nucleic acid sequence that is configured to not hybridize to another nucleic acid, for example to provide flexibility or rigidity to a pendant group as necessary. In some configurations, a first surface-interacting moiety may comprise, in addition to a second nucleic acid or in place of a second nucleic acid, a capture group selected from the group consisting of a reactive group, an electrically-charged group, a magnetic group, and a component of a binding pair. In some configurations, a binding pair may be selected from the group consisting of streptavidin-biotin, SpyCatcher-Spytag, SnoopCatcher-Snooptag, and SdyCatcher-Sdytag. In some configurations, a reactive group may be configured to perform a Click-type reaction with a surface-linked moiety. In some configurations, a first surface-interacting moiety may comprise a group that is configured to form a non-covalent interaction with a surface-linked moiety, in which the interaction is selected from the group consisting of an electrostatic interaction, a magnetic interaction, a hydrogen bond, an ionic bond, a van der Waals bond, a hydrophobic interaction, or a hydrophilic interaction. In particular configurations, a first surface-interacting moiety may comprise a nanoparticle selected from the group consisting of an inorganic nanoparticle, a carbon nanoparticle, a polymer nanoparticle, and a biopolymer. In some configurations, a first surface-interacting moiety may further comprise a linker that couples the surface-interacting moiety to a nucleic acid nanostructure. In some configurations, the linker may comprise a hydrophobic linker, a hydrophilic linker, or a cleavable linker.

An oligonucleotide comprising a surface-interacting moiety may form a portion of a nucleic acid nanostructure (e.g., a SNAP structure). A nucleic acid nanostructure may comprise a) a scaffold nucleic acid strand; and b) a plurality of staple nucleic acid strands coupled to the scaffold nucleic acid strand. In some configurations, a plurality of staple nucleic acid strands may comprise a first surface-interacting oligonucleotide of a plurality of first surface-interacting oligonucleotides, in which the first surface-interacting oligonucleotide comprises a surface-interacting moiety. A coupling of a first surface-interacting oligonucleotide may form a tertiary structure of a nucleic acid nanostructure (e.g., a SNAP). In some configurations, the capture moiety may comprise a tertiary structure formed by a coupling of a first surface-interacting oligonucleotide with a nucleic acid nanostructure (e.g., a SNAP). In other configurations, a display moiety may comprise a tertiary structure formed by a coupling of a first surface-interacting oligonucleotide with a nucleic acid nanostructure.

A nucleic acid nanostructure (e.g., a SNAP) may comprise a capture moiety containing a plurality of pendant groups, in which a pendant group of the plurality of pendant groups comprises a nucleic acid. In some configurations, a pendant group may comprise a nucleic acid with a nucleotide sequence that comprises no self-complementarity. As such, a surface-interacting oligonucleotide or other nucleic acid can be inhibited from forming a self-hybrid structure under the conditions of a composition or method set forth herein. For example, a nucleotide sequence of a pendant nucleic acid may comprise a DNA sequence with no more than 3 deoxyribonucleotide species selected from the group consisting of deoxyadenosine, deoxycytosine, deoxyguanosine, and deoxythymidine (e.g., ACTACCTACAT). In other configurations, a nucleic acid such as a surface-interacting oligonucleotide or pendant group may comprise a nucleotide sequence that comprises self-complementarity. For example, a nucleic acid sequence may form a self-hybrid structure, such as a double-helix, a stem loop, a pseudoknot, a hairpin or a G-quadruplex under some or all conditions of a composition or method set forth herein. A method set forth herein can be configured such that a nucleic acid is in a self-hybrid form in one step but not in another step. For example, in a first step of a method a first nucleic acid can be in a self-hybrid state to inhibit unwanted hybridization to a second nucleic acid strand, and in a second step the first nucleic acid can be in a single stranded state or hybridized to a second nucleic acid strand. In some configurations, a surface-interacting oligonucleotide of a plurality of surface-interacting oligonucleotides may comprise a homopolymeric nucleotide sequence selected from the group consisting of a poly-deoxyadenosine sequence, a poly-deoxycytosine sequence, a poly-deoxyguanosine sequence, or a poly-deoxythymidine sequence. A first contiguous sequence of a nucleic acid strand that is configured to form self-complementarity with a second portion of the nucleic acid strand may comprise at least about 2, 3, 4, 5, 6, 7, 8, 9, 10, 11, 12, 13, 14, 15, 16, 17, 18, 19, 20, 25, 30, 35, 40, 45, 50, or more than 50 contiguous nucleotides. Alternatively or additionally, a first contiguous sequence of a nucleic acid strand that is configured to form self-complementarity with a second portion of the nucleic acid strand may comprise no more than about 50, 45, 40, 35, 30, 25, 20, 19, 18, 17, 16, 15, 14, 13, 12, 11, 10, 9, 8, 7, 6, 5, 4, 3, or less than 3 contiguous nucleotides. A first contiguous sequence of a nucleic acid strand that is configured to form self-complementarity with a second portion of the nucleic acid strand may be separated from the second portion of the nucleic acid strand by at least about 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 750, 1000, or more than 1000 nucleotides. Alternatively or additionally, a first contiguous sequence of a nucleic acid strand that is configured to form self-complementarity with a second portion of the nucleic acid strand may be separated from the second portion of the nucleic acid strand by no more than about 1000, 750, 500, 400, 300, 200, 100, 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, or less than 3 contiguous nucleotides.

A pendant nucleic acid portion of a pendant group of a surface-interacting moiety may comprise a particular number of linked nucleotides (e.g., natural nucleotides, modified nucleotides, etc.). In some cases, a nucleic acid portion of a surface-interacting moiety may comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, or more than 100 nucleotides. Alternatively or additionally, a nucleic acid portion of a surface-interacting moiety may comprise no more than about 100, 90, 80, 70, 60, 50, 45, 40, 35, 30, 29, 28, 27, 26, 25, 24, 23, 22, 21, 20, 19, 18, 17, 16, 15, 14, 13, 12, 11, 10, 9, 8, 7, 6, 5, 4, 3, 2, or less than 2 nucleotides.

A nucleic acid nanostructure (e.g., a SNAP) may comprise a capture moiety with a plurality of pendant groups containing surface-interacting moieties. A capture moiety may comprise at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more than 100 surface-interacting moieties. Alternatively or additionally, a capture moiety may comprise no more than about 100, 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, 2, or less than 2 surface-interacting moieties. A nucleic acid nanostructure (e.g., a SNAP) may be configured to have an average surface density of pendant groups comprising surface-interacting moieties (e.g., surface-interacting oligonucleotides, surface-interacting reactive groups, etc.). An average surface density of surface-interacting moieties for a nucleic acid nanostructure may be determined by the number of surface-interacting moieties that are configured to couple to a coupling surface of a solid support relative to an effective surface area or footprint of a capture moiety of the nucleic acid nanostructure that couples to the coupling surface. An effective surface area of a capture moiety may include a two-dimensional projection of the capture moiety onto an effectively planar surface, and may optionally include additional surface area caused by the maximal extension of one or more pendant groups from the capture moiety of the nucleic acid nanostructure. A footprint of a nucleic acid nanostructure may comprise a maximum cross-sectional area of a nucleic acid nanostructure or a capture moiety thereof when the nucleic acid nanostructure is coupled to a surface. A capture moiety of a nucleic acid nanostructure (e.g., a SNAP) may have an average surface-interacting moiety density of at least 0.0001 surface-interacting moieties per square nanometer ($/nm^2$), $0.005/nm^2$, $0.001/nm^2$, $0.05/nm^2$, $0.01/nm^2$, $0.05/nm^2$, $0.1/nm^2$, $0.5/nm^2$, $1/nm^2$, $5/nm^2$, $10/nm^2$, or more than $10/nm^2$. Alternatively or additionally, a capture moiety of a nucleic acid nanostructure may have an average surface-interacting moiety density of no more than about $10/nm^2$, $5/nm^2$, $1/nm^2$, $0.5/nm^2$, $0.1/nm^2$, $0.05/nm^2$, $0.01/nm^2$, $0.005/nm^2$, $0.001/nm^2$, $0.0005/nm^2$, $0.0001/nm^2$, or less than $0.0001/nm^2$.

A plurality of surface-interacting moieties may be distributed or spaced over a capture moiety of a nucleic acid nanostructure (e.g., a SNAP). In some configurations, a surface-interacting moiety distribution or density is substantially uniform over an effective surface area or footprint of a capture moiety (e.g., nearly uniform spacing and/or orientation between adjacent surface-interacting moieties). In other configurations, a surface-interacting moiety distribution or density is not substantially uniform over an effective surface area or footprint of a capture moiety. For example, a fraction or an entirety of a plurality of surface-interacting moieties may be located near a central region of the capture moiety. In another configuration, a fraction or an entirety of a plurality of surface-interacting moieties may be located near an outer region of the capture moiety. FIGS. 41A-41B depict SNAP configurations with differing SNAP distributions. FIG. 41A depicts a SNAP 4110 that is coupled to an analyte 4120 and contains a plurality of surface-interacting moieties 4118 on a capture moiety, in which the plurality of surface-interacting moieties is distributed toward the outer edges of the capture moiety face. FIG. 41B depicts a SNAP 4110 that is coupled to an analyte 4120 and contains a plurality of surface-interacting moieties 4118 on a capture moiety, in which the plurality of surface-interacting moieties is distributed toward the central portion of the capture moiety face.

In some configurations, a nucleic acid nanostructure (e.g., a SNAP) may comprise a capture moiety comprising more than one type of surface-interacting moiety. A capture moiety may comprise more than one type of surface-interacting moiety to increase the specificity of binding location for a nucleic acid nanostructure. For example, a SNAP may comprise a plurality of surface-interacting oligonucleotides and one or more surface-interacting reactive groups. In a particular example, such a SNAP may be contacted with a coupling surface comprising a high surface density of complementary oligonucleotides and a low surface density of complementary reactive groups, in which binding interactions between surface-interacting oligonucleotides and complementary oligonucleotides keep the SNAP coupled near the coupling surface until a covalent binding interaction can form between the surface-interacting reactive group and the relatively rare, surface-linked complementary reactive group. A nucleic acid nanostructure may interact with a surface through a combination of types of interactions, such as through two differing non-covalent interactions (e.g., nucleic acid hybridization and an electrostatic interaction, etc.), two differing covalent interactions (e.g., two bioorthogonal Click-type reactions), or a combination of a covalent interaction and a non-covalent interaction (e.g., a covalent interaction and nucleic acid hybridization, a covalent interaction and an electrostatic interaction, a covalent interaction with nucleic acid hybridization and electrostatic interactions, etc.).

In another aspect, provided herein is a composition comprising: a) nucleic acid nanostructure (e.g., a SNAP), wherein the nucleic acid nanostructure comprises: i) a display moiety that is coupled with, or configured to couple with, an analyte; and ii) a capture moiety that is coupled with, or configured to couple with a coupling surface, wherein the capture moiety comprises a plurality of oligonucleotides, and wherein each oligonucleotide of the plurality of oligonucleotides comprises a surface-interacting moiety; b) an analyte coupled with the display moiety; and c) a solid support comprising the coupling surface, wherein the surface comprises one or more surface-linked moieties, and wherein a surface-interacting moiety of the plurality of surface-interacting moieties is coupled with a surface-linked moiety of the one or more surface-linked moieties.

Figure 29:
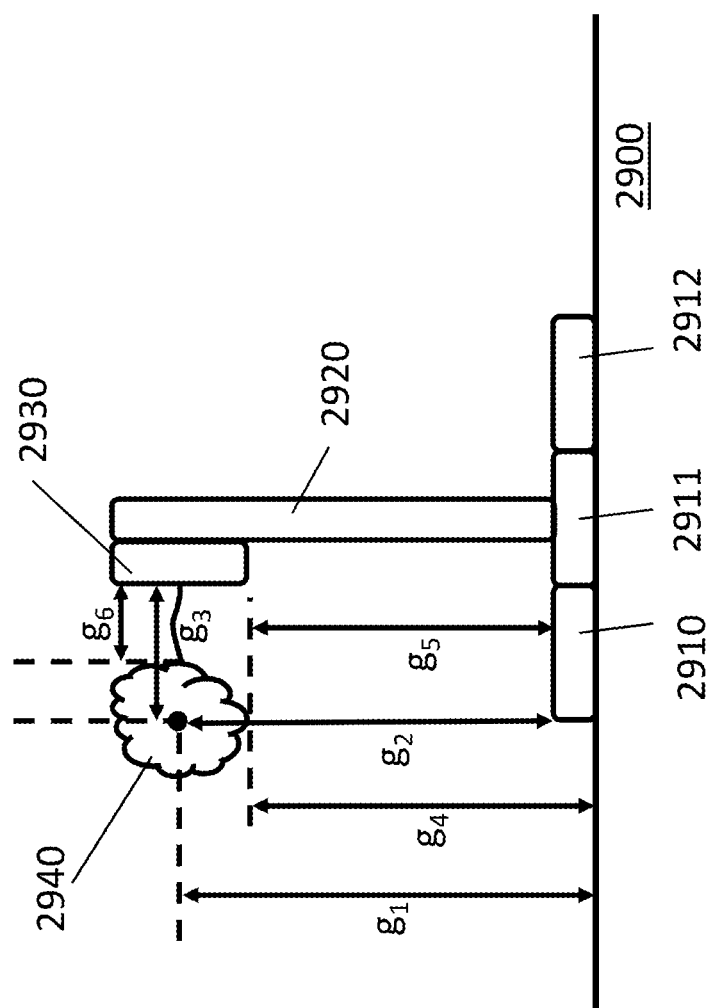
FIG. 29 depicts a three-dimensional SNAP complex, in accordance with some embodiments.

A nucleic acid nanostructure composition (e.g., a SNAP composition), as set forth herein, may further comprise a separating group. A separating group may comprise a molecule, linker, or nucleic acid nanostructure (e.g., a display SNAP or a structural SNAP) that is configured to create a separation or gap between an analyte and a surface or a portion of a nucleic acid nanostructure (e.g., a display face or moiety, a capture face or moiety). FIG. 29 illustrates a profile view of a SNAP complex comprising an analyte with various possible separation gaps labeled. The SNAP complex may comprise capture utility SNAPs 2910, 2911 and 2912 that couple the complex to a solid support 2900. A display SNAP 2930 is coupled to a structural utility SNAP 2920 that is coupled to the capture utility SNAP 2911. An analyte 2940 is coupled to the display SNAP 2930. A separation gap may be measured from the analyte to a surface or SNAP. Some possible separation gaps may include the gap from the center of analyte 2940 to the solid support 2900 ($g_1$), to the top face of the capture utility SNAPs 2910 ($g_2$) or the top face of the display SNAP 2930 ($g_3$); the gap between the external surface of analyte 2940 and the surface of solid support 2900 ($g_4$); the gap between the external surface of analyte 2940 and the face of capture utility SNAP 2910 ($g_5$); or the gap between the external surface of analyte 2940 and the face of the display SNAP 2930 ($g_6$). FIGS. 3A-3D illustrate a SNAP 300 comprising a polyvalent linker 320 that creates an average separation gap between an analyte 310 and the upper face of the SNAP 300. If the SNAP 300 is coupled to a solid support 330, the analyte 310 will also have an average separation gap with the solid support 330. In some configurations, a separating group may comprise a rigid separating group selected from the group comprising a polymer linker, a nucleic acid linker, and a nanoparticle linker. In some specific configurations, the nucleic acid linker comprises a tertiary structure (e.g., a DNA double helix). In other configurations, the separating group comprises a flexible linker. A separation gap may have a characteristic average, maximum of minimum dimension. The average, maximum or minimum dimension of a separation gap can be at least about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm, 100 nm, or more than 100 nm. Alternatively or additionally, the average, maximum or minimum dimension of a separation gap can be no more than about 100 nm, 90 nm, 80 nm, 70 nm, 60 nm, 50 nm, 45 nm, 40 nm, 35 nm, 30 nm, 25 nm, 20 nm, 19 nm, 18 nm, 17 nm, 16 nm, 15 nm, 14 nm, 13 nm, 12 nm, 11 nm, 10 nm, 9 nm, 8 nm, 7 nm, 6 nm, 5 nm, 4 nm, 3 nm, 2 nm, 1 nm, or less than 1 nm.

A nucleic acid nanostructure (e.g., a SNAP) may comprise a plurality of nucleic acids (e.g., scaffold strands, a plurality of oligonucleotides) that form stable hybridized structures through complementary base pair binding. The stability of specific hybridized structures may be characterized through routine methods, such as by degree of complementarity or estimated or measured secondary structure melting temperature. A stability (e.g., a melting temperature) may be predicted by a software package, such as CAD-NANO, ATHENA, or DAEDALUS. A hybridized nucleic acid structure may have a characterized melting temperature of at least about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or more than 90° C. Alternatively or additionally, a hybridized nucleic acid structure may have a characterized melting temperature of no more than about 90° C., 89° C., 88° C., 87° C., 86° C., 85° C., 84° C., 83° C., 82° C., 81° C., 80° C., 79° C., 78° C., 77° C., 76° C., 75° C., 74° C., 73° C., 72° C., 71° C., 70° C., 69° C., 68° C., 67° C., 66° C., 65° C., 64° C., 63° C., 62° C., 61° C., 60° C., 59° C., 58° C., 57° C., 56° C., 55° C., 54° C., 53° C., 52° C., 51° C., 50° C., or less than 50° C.

A nucleic acid nanostructure (e.g., a SNAP) or a face of a nucleic acid nanostructure (e.g., a display face, a capture face) may have a characteristic dimension (e.g., length, width, radius). A characteristic dimension may include any characterizing measure pertaining to the group or probe size, such as length, width, height, radius, circumference, etc. A nucleic acid nanostructure or a face of a nucleic acid nanostructure may have a characteristic dimension of at least about 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 120 nm, 140 nm, 160 nm, 180 nm, 200 nm, 250 nm, 300 nm, 350 nm, 400 nm, 450 nm, 500 nm, 600 nm, 700 nm, 800 nm, 900 nm, 1000 nm, or more than 1000 nm. Alternatively or additionally, a nucleic acid nanostructure or a face of a nucleic acid nanostructure may have a characteristic dimension of no more than about 1000 nm, 900 nm, 800 nm, 700 nm, 600 nm, 500 nm, 450 nm, 400 nm, 350 nm, 300 nm, 250 nm, 200 nm, 180 nm, 160 nm, 140 nm, 120 nm, 100 nm, 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, 10 nm, 5 nm, or less than 5 nm.

A nucleic acid nanostructure (e.g., a SNAP) may be coupled to, or configured to couple to, one or more analytes. A nucleic acid nanostructure may comprise one or more display faces or display moieties that are coupled to, or configured to couple to, one or more analytes. A nucleic acid nanostructure may be coupled to one or more analytes. A nucleic acid nanostructure may comprise one or more display faces or display moieties that are coupled to one or more analytes. A nucleic acid nanostructure display face or display moiety may comprise one or more functional groups or moieties that are configured to couple to an analyte. When multiple functional groups are present, the functional groups can be the same type as each other, or alternatively, different functional groups can be present. A nucleic acid nanostructure may comprise at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more than 100 functional groups or moieties that are configured to couple to an analyte. Alternatively or additionally, a nucleic acid nanostructure may comprise no more than about 100, 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, 2, or less than about 2 functional groups or moieties that are configured to couple to an analyte.

A plurality of nucleic acid nanostructures (e.g., SNAPs) and a plurality of analytes may be coupled in a fixed molecular ratio. The ratio of analyte to nucleic acid nanostructures may be calculated as an average ratio. The analyte:nanostructure ratio may follow some quantifiable distribution, such as a Poisson distribution, binomial distribution, beta-binomial distribution, hypergeometric distribution, or bimodal distribution. In some configurations, there may be, on average, more than one analyte coupled to a nucleic acid nanostructure. In some configurations, there may be, on average, more than one nucleic acid nanostructure coupled to an analyte. A plurality of analyte-coupled nucleic acid nanostructures may have an average analyte:nanostructure ratio of no more than about 100:1, 50:1, 25:1, 20:1, 15:1, 10:1, 5:1, 4:1, 3:1, 2:1, 1.5:1, 1:1, 1:1.5, 1:2, 1:3, 1:4, 1:5, 1:10, 1:15, 1:20, 1:25, 1:50, 1:100, or less than 1:100. Alternatively or additionally, a plurality of analyte-coupled nucleic acid nanostructures may have an average analyte:nanostructure ratio of at least about 1:100, 1:50, 1:25, 1:20, 1:15, 1:10, 1:5, 1:4, 1:3, 1:2, 1:1.5, 1:1, 1.5:1, 2:1, 3:1, 4:1, 5:1, 10:1, 15:1, 20:1, 25:1, 50:1, 100:1, or more than 100:1.

A plurality of nucleic acid nanostructures (e.g., SNAPs) may be characterized by an occupancy ratio. An occupancy ratio may be defined as the fraction of nucleic acid nanostructures with at least one coupled analyte. The nucleic acid nanostructure occupancy ratio may be controlled to provide a desired occupancy (such as a maximum occupancy) by increasing the relative ratio of analytes to nucleic acid nanostructures during analyte coupling. The nucleic acid nanostructure occupancy ratio may be controlled to minimize the number of nucleic acid nanostructures with more than one analyte by, for example, reducing the concentration of analyte relative to nucleic acid nanostructures during analyte coupling. For example, a composition of SNAPs with 70% of the SNAPs being coupled to one or more analytes would have an occupancy ratio of 0.7. Occupancy ratio may be determined by an appropriate analytical technique, such as fluorescent microscopy or spectroscopic analysis. A plurality of nucleic acid nanostructures may have an occupancy ratio of at least about 0.01, 0.05, 0.1, 0.15, 0.2, 0.25, 0.3, 0.35, 0.4. 0.45, 0.5, 0.55, 0.6, 0.65, 0.7, 0.75, 0.8, 0.85, 0.9, 0.95, 0.96, 0.97, 0.98, 0.99, or more than 0.99. Alternatively or additionally, a plurality of nucleic acid nanostructures may have an occupancy ratio of no more than about 0.99, 0.98, 0.97, 0.96, 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, 0.01, or less than about 0.01.

A nucleic acid nanostructure (e.g., a SNAP), as set forth herein, may further comprise a capture face. The capture face may be configured to facilitate an interaction between a surface or an interface, such as a binding interaction or a phase separation interaction. A surface may be any solid and/or rigid boundary where the nucleic acid nanostructure is substantially inhibited from, or cannot, transfer orthogonally through the solid and/or rigid boundary. An interface may refer to a non-solid or deformable boundary where the nucleic acid nanostructure can transfer orthogonally through the non-solid or deformable boundary. A surface may comprise a surface of a solid material such as a metal, metal oxide, ceramic, glass, polymer, or semiconductor. An interface may comprise an air/liquid or liquid/liquid phase boundary. Exemplary interfaces may include an air/water interface, or a water/oil interface such as an oil-in-water or water-in-oil emulsion. A capture face or capture moiety may be configured to form a reversible or irreversible interaction with a surface. For example, a capture face of a SNAP may comprise one or more single-stranded nucleic acid strands that are configured to hybridize to complementary single-stranded nucleic acids that are displayed on a surface, thereby reversibly coupling the SNAP to the surface. In another example, a capture face of a SNAP may comprise one or more click-type reaction groups that are configured to covalently bond to complementary click-type reaction groups that are displayed on a surface, thereby irreversibly coupling the SNAP to the surface. In some configurations, a nucleic acid nanostructure (e.g., a SNAP) may comprise a capture face comprising a first moiety and a second moiety, where the first moiety is configured to reversibly couple to a surface and second moiety is configured to irreversibly couple to a surface. In some cases, a nucleic acid nanostructure may be configured to provide a temporary association with a solid support. For example, a SNAP may be configured to reversibly couple an analyte (e.g., by an oligonucleotide hybridized to the SNAP structure), then bind to a surface of the solid support temporarily, thereby permitting the analyte to be transferred to an analyte-coupling moiety on the surface (e.g., a complementary oligonucleotide, a Click-type reactive group, etc.). After the analyte has been transferred to the surface, the SNAP may be dissociated and optionally reused to transfer a second analyte to the solid support.

A nucleic acid nanostructure (e.g., a SNAP) may interact with a surface or interface by an interaction that associates the nucleic acid nanostructure with the surface or interface. A nucleic acid nanostructure may associate with a surface or an interface by a binding interaction such as an electrostatic interaction, magnetic interaction, covalent bond, or non-covalent bond (e.g., hydrogen bonding, nucleic acid base pair binding). A nucleic acid nanostructure may comprise one or more faces that are configured to effect a phase separation at a phase boundary. For example, a SNAP may comprise a first face comprising a plurality of hydrophobic moieties and a second face comprising a plurality of hydrophilic moieties, where the SNAP is configured to become associated to a phase boundary by segregation of the first face into a more hydrophobic phase.

Figure 4B:
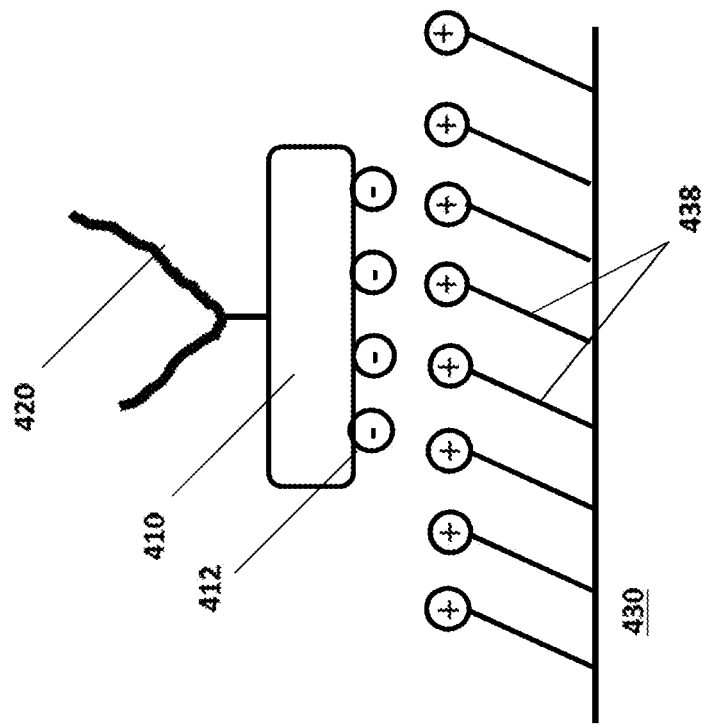
FIGS. 4A, 4B, 4C, 4D, 4E, 4F, 4G, and 4H show a SNAP coupled to a surface, in accordance with some embodiments.
Figure 4A:
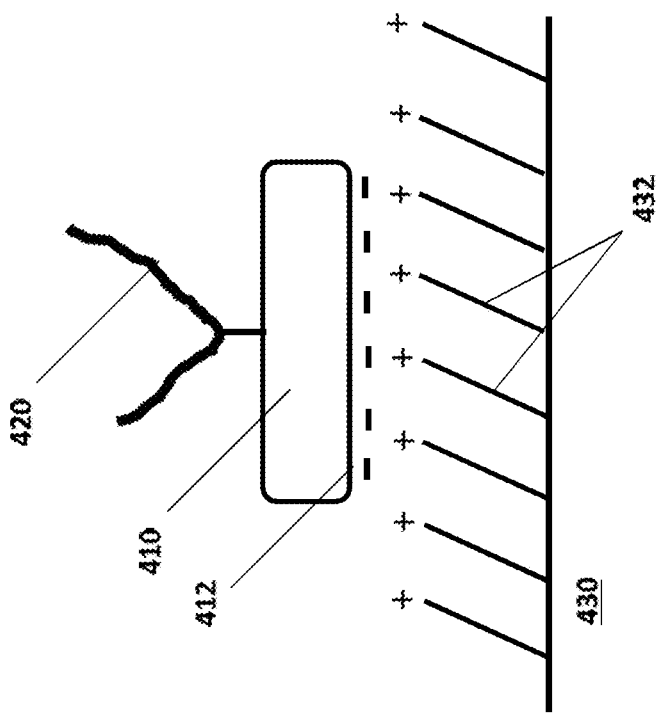
Figure 4D:
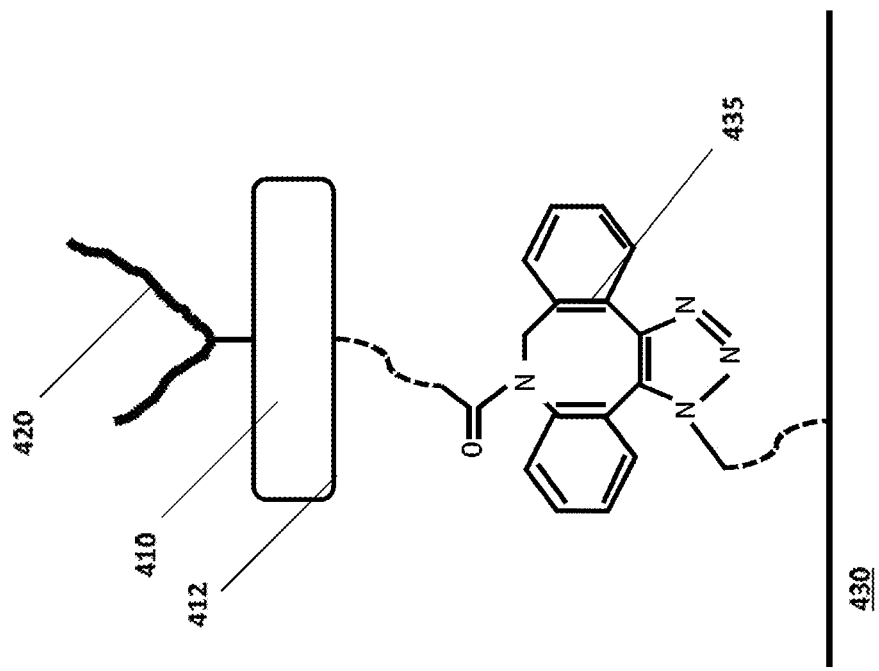
Figure 4C:
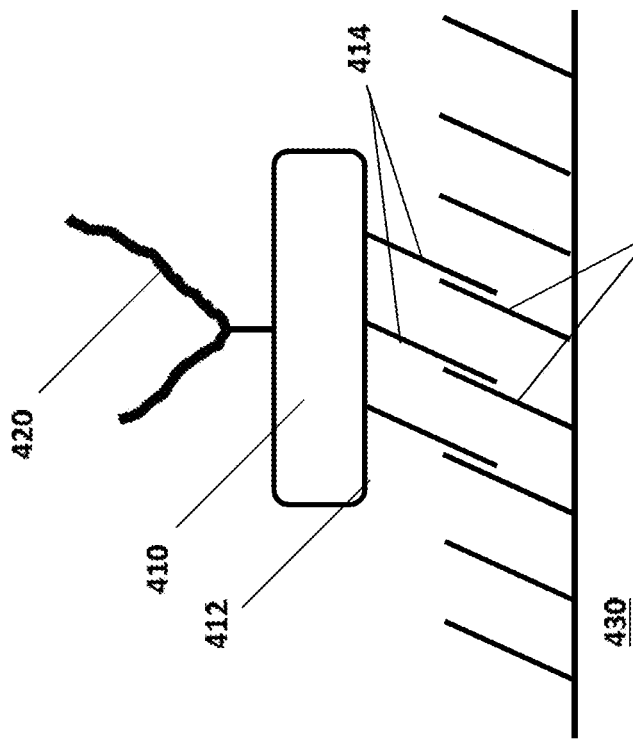

FIGS. 4A-4G show various configurations of a SNAP interacting with a surface or interface. FIG. 4A illustrates a SNAP 410 coupled to an analyte 420 interacting with a surface 430 via an electrostatic interaction. A SNAP may comprise a negatively charged capture face 412 that may be attracted to a positively-charged surface 430, for example a surface 430 functionalized with positively-charged functional groups 432. The negative charge of the SNAP may be due to one or both of the negative charges present in phosphodiester backbone of nucleic acid or negatively charged moieties conjugated to the SNAP. FIG. 4B illustrates a SNAP 410 coupled to an analyte 420 (e.g., a polypeptide) interacting with a surface 430 via a magnetic interaction. The SNAP may comprise a capture face 412 comprising a plurality of magnetic groups (e.g., paramagnetic particles conjugated to the SNAP) that may be attracted to a surface 430, for example a surface 430 comprising a plurality of oppositely-polarized magnetic groups 438. FIG. 4C illustrates a SNAP 410 coupled to an analyte 420 (e.g., a polypeptide) interacting with a surface 430 by a non-covalent binding interaction between complementary oligonucleotides. The SNAP 410 comprises a capture face 412 comprising a plurality of oligonucleotides 414 that hybridize with a plurality of complementary oligonucleotides 434 that are coupled to the surface 430. FIG. 4D illustrates a SNAP 410 coupled to an analyte 420 (e.g., a polypeptide) that is covalently conjugated to a surface 430. A covalent linkage 435 may form between complementary reactive groups on the surface 430 and the capture face 412 of the SNAP 410, such as click reaction groups (e.g., methyltetrazine-transcyclooctylene, azide-dibenzocylooctyne, etc.). In some configurations, the SNAP 410 may comprise a plurality of reactive groups on the capture face 412 that are configured to form covalent linkages 430.

Figure 4F:
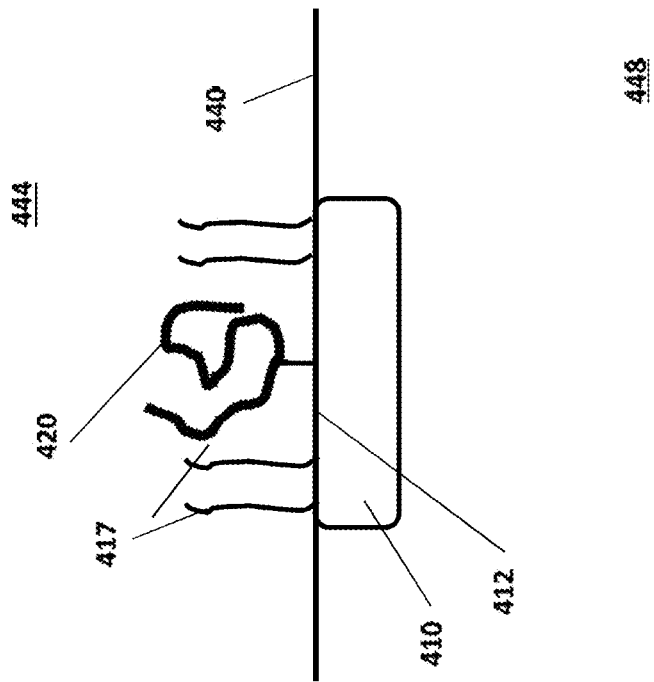
Figure 4E:
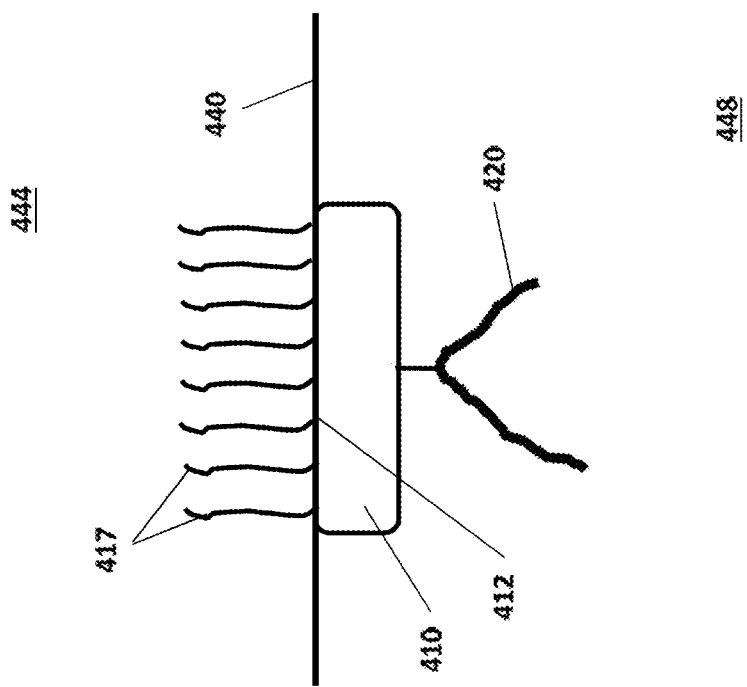

FIGS. 4E-4F depict configurations of SNAPs interacting with an interface (e.g., water/air or water/oil). A SNAP may associate with an interface by a phase separation interaction. FIG. 4E depicts a SNAP 410 coupled to an analyte 420 comprising a capture face 412 containing a plurality of hydrophobic groups 417 (e.g., lipids). The presence of the hydrophobic groups 417 associates the SNAP 410 with an interface 440 that forms between a non-aqueous phase 444 and an aqueous phase 448. The hydrophobic groups 417 may preferentially migrate into the non-aqueous phase 444 while the more hydrophilic SNAP 410 and analyte 420 may remain in the aqueous phase 448. FIG. 4F depicts an alternative configuration of an interface-associating SNAP 410. FIG. 4F depicts a SNAP 410 coupled to an analyte 420 comprising a capture face 412 containing a plurality of hydrophobic groups 417. The SNAP is further configured such that the capture face 412 is also the display face of the SNAP. The presence of the hydrophobic groups 417 associates the SNAP 410 with an interface 440 that forms between a non-aqueous phase 444 and an aqueous phase 448. The hydrophobic groups 417 and the analyte 420 may preferentially migrate into the non-aqueous phase 444 while the more hydrophilic SNAP 410 may remain in the aqueous phase 448. The configuration of FIG. 4F may be advantageous for the display of hydrophobic analytes (e.g., membrane proteins, inorganic nanoparticles).

Figure 4H:
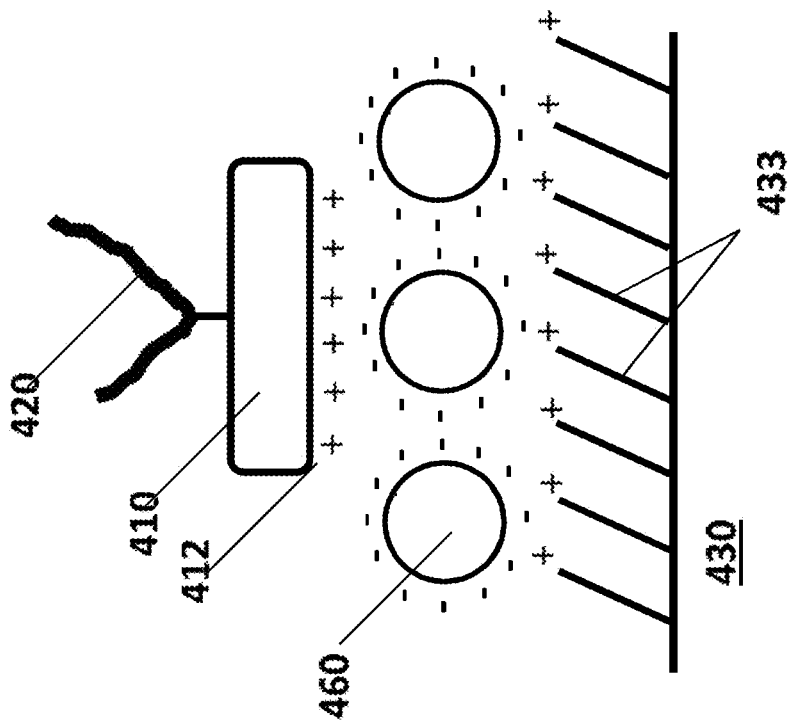
Figure 4G:
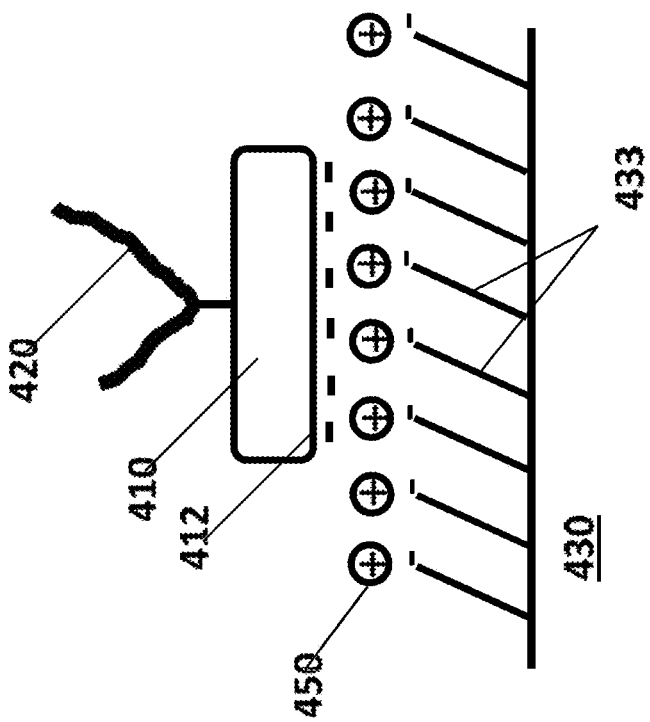

FIG. 4G depicts a configuration of a SNAP 410 coupled to an analyte 420 interacting with a surface 430 by an ion-mediated coupling interaction. A SNAP may comprise a negatively charged capture face 412 that may be attracted to a surface 430, for example a surface 430 functionalized with negatively-charged functional groups 433. In other configurations, the surface material may possess an inherent negative charge. The negative charge of the SNAP 410 may be due to the negative charges present in phosphodiester backbone of nucleic acid or due to negatively charged moieties conjugated to the SNAP. The inherent repulsion between the capture face 412 of the SNAP 410 and the negatively-charged functional groups 433 may be overcome by the complexing or layering of positively-charged ions 450 to for an ion-mediating layer between the SNAP 410 and the surface 430. The skilled person will readily recognize that ion-mediated interactions may be modified for other situations, such as mediating positive-positive charge interactions, or varying the strength of positive-negative charge interactions. Deposition of SNAPs at a surface by an ion-mediated charge interaction may occur in the presence of a particular monatomic ion, polyatomic ion, monovalent ion, polyvalent ion, metal ion, or non-metal ion, such as $H^+$, $Li^+$, $Na^+$, $K^+$, $Rb^+$, $Cs^+$, $Mg^{2+}$, $Ca^{2+}$, $Sr^{2+}$, $Ba^{2+}$, $Al^{3+}$, $Ag^+$, $Zn^{2+}$, $Fe^{2+}$, $Fe^{3+}$, $Cu^+$, $Cu^{2+}$, $H^-$, $F^-$, $Cl^-$, $Br^-$, $I^-$, $O^{2-}$, $S^{2-}$, $N^{3-}$, $P^{3-}$, $B(OH)_4^-$, $C_2H_5O^-$, $CH_3COO^-$, $C_6H_5COO^-$, $C_6H_5O_7^{3-}$, $CO_3^{2-}$, $C_2O_4^{2-}$, $CN^-$, $CrO_4^{2-}$, $Cr_2O_7^{2-}$, $HCO_3^-$, $HPO_4^{2-}$, $H_2PO_4^-$, $HSO_4^-$, $MnO_4^{2-}$, $MnO_4^-$, $NH_2^-$, $O_2^{2-}$, $OH^-$, $SH^-$, $SCN^-$, $SiO_4^{2-}$, $S_2O_3^{2-}$, $C(NH_2)^{3+}$, $NH_4^+$, $PH_4^+$, $H_3O^+$, $H_2F^+$, $C_5H_5O^+$, $Hg_2^{2+}$, and combinations thereof. FIG. 4H depicts a configuration of a SNAP 410 coupled to an analyte 420 interacting with a surface 430 by a particle-mediated coupling interaction. A SNAP may comprise a positively-charged capture face 412 (e.g., comprising one or more aminated capture moieties) that may be inherently repulsed by a surface 430, for example a surface 430 functionalized with positively-charged functional groups 433 (e.g., aminated silanes). An intermediate negatively-charged particle 460 may facilitate an interaction between the SNAP 410 and the surface 430 by passivating the surface positive charge and providing a negative charge that electrostatically couples the positively-charged capture face 412 of the SNAP 410. Negatively-charged particles 460 may include carboxylated inorganic nanoparticles (e.g., carboxylated gold nanoparticles, carboxylated silver nanoparticles, etc.) or carboxylated organic nanoparticles (e.g., carboxylated dextran nanoparticles, carboxylated polystyrene particles, etc.).

In some configurations, a nucleic acid nanostructure (e.g., a SNAP) may be structured to inhibit or avoid forming a charge-mediated interaction. Nucleic acid nanostructures may be non-specifically attracted to areas of a surface where deposition is not supposed to occur due to charge-mediated interactions, for example, by ionic components of a deposition buffer. A nucleic acid nanostructure may be configured to display ligands or other groups on a capture face or capture moiety that disrupt unwanted interactions. For example, a SNAP may comprise one or more single-stranded nucleic acids (e.g., pendant tails of oligonucleotides that partially hybridize to the SNAP structure) that disrupt the formation of charge-mediated interactions. In another example, a SNAP may comprise a capture moiety containing one or more oligonucleotides, where each oligonucleotide comprises a modified nucleotide that is configured to disrupt the formation of a charge-mediated interaction. The modified nucleotides may be chemically homogeneous (e.g., same charge, same structure, same polarity, etc.) or may be chemically heterogeneous.

A capture face of a nucleic acid nanostructure (e.g., a SNAP) may be configured to mediate the association between the nucleic acid nanostructure and a surface or interface. The configuration of a nucleic acid nanostructure may determine the strength of an association between the nucleic acid nanostructure and a surface or interface. A nucleic acid nanostructure may have a reversible or irreversible association with a surface or interface. An irreversible association between a nucleic acid nanostructure and a surface or interface may be formed by covalent bonding or very strong non-covalent interaction(s) (e.g., streptavidin-biotin). A reversible association between a nucleic acid nanostructure and a surface or interface may be formed by a weaker interaction such as an electrostatic interaction, magnetic interaction, or hydrogen bonding. A reversible association may be stable until it is disrupted, for example by the introduction of a denaturant or salt, or the cleavage of a photolinker.

Figure 5B:
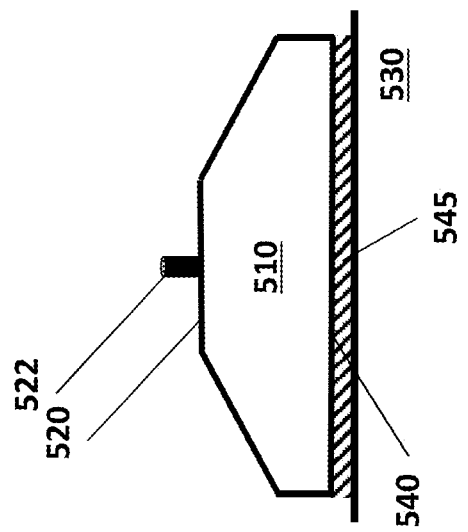
FIGS. 5A, 5B, 5C, and 5D illustrate a SNAP with different capture face conformations, in accordance with some embodiments.
Figure 5D:
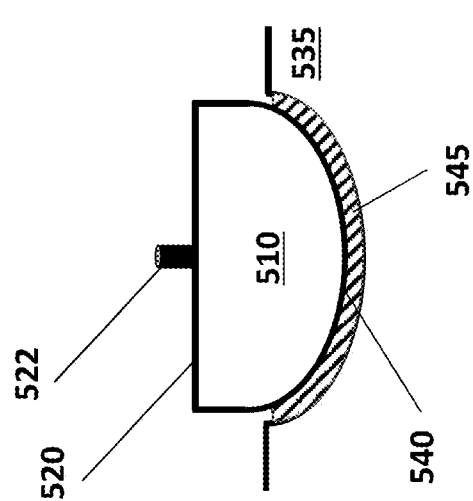
Figure 5A:
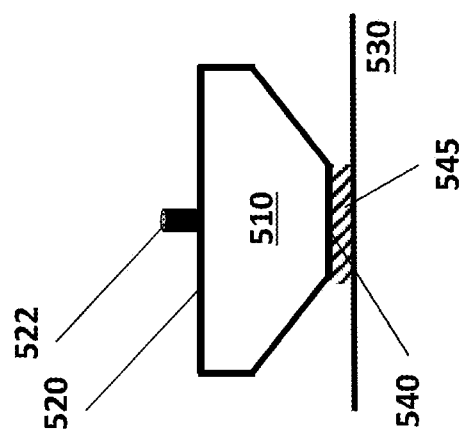
Figure 5C:
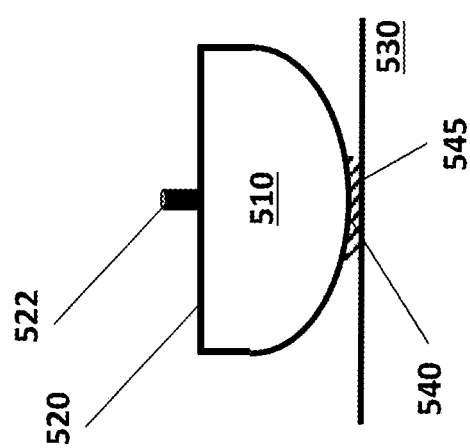

The size and or conformation of a nucleic acid nanostructure capture face may affect the strength of an association between a nucleic acid nanostructure and a surface or interface. A smaller interaction region between a capture face and a surface or interface may facilitate a weaker interaction between a nucleic acid nanostructure and the surface or interface. A capture face or capture moiety may comprise one or more tertiary nucleic acid structures that form interactions with a surface, such as an electrostatic interaction. Increased size or number of tertiary structures in a capture face or capture moiety may increase the strength of an interaction with a surface. For example, increased size, increased quantity, or increased local density of nucleic acid tertiary structures in a capture moiety may increase the strength of an electrostatic interaction between the capture moiety and a surface due to an increased number of negatively-charged phosphodiester groups in the nucleic acid backbones of each tertiary structure. FIGS. 5A-5D depict various configurations of SNAPs with differing capture face sizes and/or conformations. FIGS. 5A and 5B depict tapered SNAP structures with differing two-dimensional projections between the display face and the capture face. FIG. 5A depicts a SNAP 510 that is bound to a surface 530. The SNAP comprises a larger display face 520 comprising a display moiety 522. The SNAP also comprises a capture face 540 whose area is smaller than the area of the display face 520. The capture face 540 forms a small interaction region 545 with the surface 530, possibly leading to a weaker association between the SNAP 510 and the surface 530. FIG. 5B depicts a SNAP 510 that is bound to a surface 530. The SNAP comprises a smaller display face 520 comprising an analyte conjugation site 522. The SNAP also comprises a capture face 540 whose area is larger than the area of the display face 520. The capture face 540 forms a large interaction region 545 with the surface 530, optionally leading to a stronger association between the SNAP 510 and the surface 530. FIG. 5C depicts a SNAP 510 comprising a non-planar capture face 540 that associates the SNAP 510 with a surface 530. The SNAP comprises a larger display face 520 containing a display moiety 522. Due to the non-planar capture face, the SNAP forms a smaller interaction region 545 with the surface 530, optionally leading to a weaker association between the SNAP 510 and the surface 530. FIG. 5D depicts a SNAP 510 comprising a non-planar capture face 540 that associates the SNAP 510 with a non-planar surface 535. The SNAP comprises a display face 520 containing a capture moiety 522. Due to the shape complementarity between the capture face 540 and the non-planar surface 535, the SNAP forms a larger interaction region 545 with the surface 535, possibly leading to a stronger association between the SNAP 510 and the surface 535. Accordingly, the size and/or shape of a nucleic acid nanostructure (e.g., a SNAP) capture face can be useful for orienting the nucleic acid nanostructure on a surface. The surface can be patterned with interaction regions to provide further control over location and/or orientation of nucleic acid nanostructures on the surface. For example, a hexagonal array of nucleic acid nanostructures can be formed by attachment of the nanostructures to a surface having a hexagonal pattern of interaction regions, wherein the interaction regions are separated by interstitial regions that are inert to binding the nanostructures. Moreover, engineering the size and/or shape for one or both of a surface and a plurality of nucleic acid nanostructures can provide for control over the arrangement of the nucleic acid nanostructures into an array. Accordingly, a user can achieve a desired density of nucleic acid nanostructures in the array, average spacing of nucleic acid nanostructures in the array, minimal separation between adjacent nucleic acid nanostructures in the array or maximum separation between adjacent nucleic acid nanostructures in the array. As such, analytes that are conjugated to nucleic acid nanostructures will also be arranged accordingly.

Figure 6:
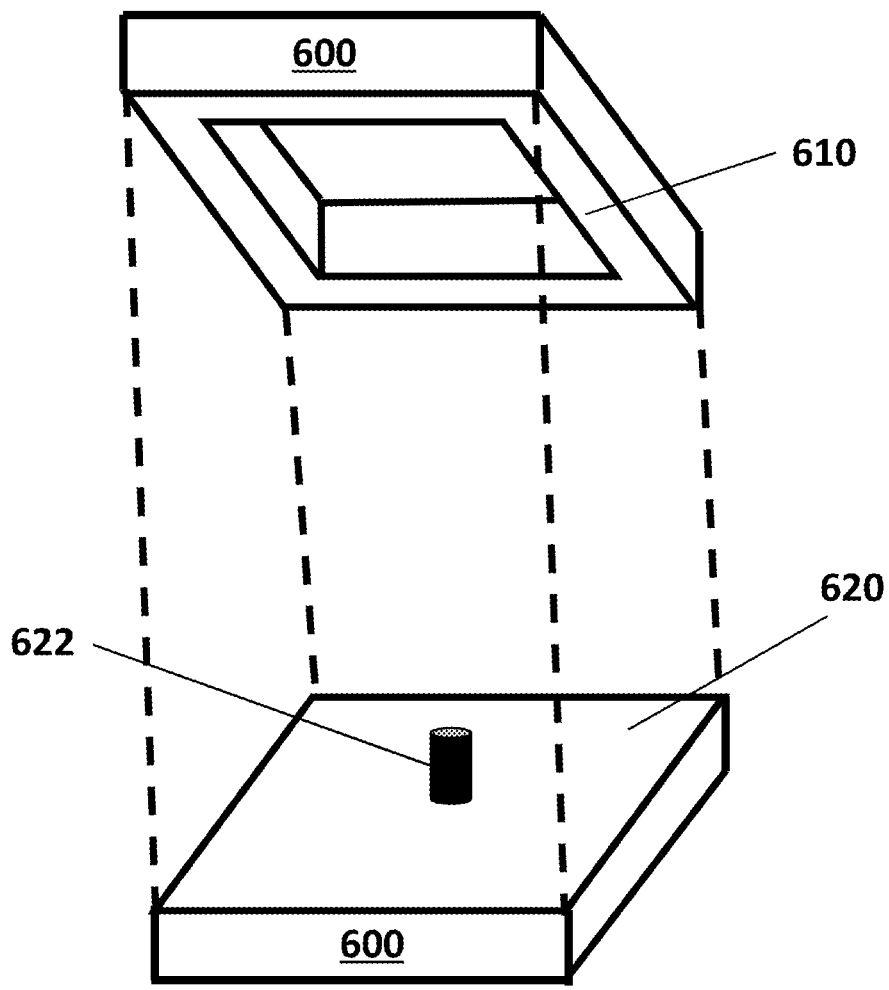
FIG. 6 depicts a square-shaped SNAP, in accordance with some embodiments.

A nucleic acid nanostructure (e.g., a SNAP) may comprise a capture face that forms a smaller interaction region than its two-dimensional projection. FIG. 6 depicts views of the bottom surface and top surface of a rectangular-shaped SNAP 600. The correspondence of edges between the top view and bottom view are indicated by the dashed lines. The SNAP 600 comprises a capture face 610 that is configured to only contact a surface or interface (not shown) around the perimeter of the SNAP 600. The SNAP further comprises a display face 620 comprising a display moiety 622. The display face 620 occupies the full area of the top face of the SNAP 600. The configuration depicted in FIG. 6 would limit the size and/or strength of an association between the SNAP 600 and a surface or interface while maximizing the available area for analyte display. The skilled person will readily recognize that the configuration depicted in FIG. 6 could be reconfigured to increase or decrease the sizes of the capture faces 610 and displaying surface 620 by altering the structured nucleic acid components that constitute the SNAP 600.

A nucleic acid nanostructure (e.g., a SNAP), as set forth herein, may comprise a utility face or utility moiety comprising one or more modifying moieties. In some configurations, a utility face may comprise all or portions of another face, such as a display face or a capture face. Modifying moieties may be added to a capture face or capture moiety to alter the characteristics of the surface while mediating an association between a nucleic acid nanostructure and a surface, a nucleic acid nanostructure and an interface, a first nucleic acid nanostructure and a second nucleic acid nanostructure, or a nucleic acid nanostructure and a coincident molecule (e.g., an affinity reagent, a fluorophore, etc.). Modifying moieties may be attached covalently or non-covalently. Modifying moieties may be coupled to a nucleic acid nanostructure before, during, or after assembly of the nanostructure. Utility face modification groups may include electrically-charged moieties, magnetic moieties, steric moieties, amphipathic moieties, optical moieties (e.g., reflective materials, absorptive materials), hydrophobic moieties, and hydrophilic moieties. Electrically-charged moieties may include functional groups that may carry an intrinsic positive or negative charge, or may carry a charge under dissociating conditions (e.g., carboxylic acids, nitrates, sulfones, phosphates, phosphonates, etc.). Magnetic moieties may include paramagnetic, diamagnetic, and ferromagnetic particles such as nanoparticles (e.g., gadolinium, manganese, iron oxide, bismuth, gold, silver, cobalt nanoparticles, etc.). Steric moieties may include polymers and biopolymers (e.g., PEG, PEO, dextran, sheared nucleic acids). Amphipathic moieties may include phospholipids (e.g., phosphatidic acid, phosphatidylethanolamine, phosphatidylcholine, phosphatidylserine, phosphatidylinositol, phosphatidylinositol phosphate, phosphatidylinositol biphosphate, phosphatidylinositol triphosphate, ceramide phosphorylcholine, ceramide phophorylethanolamine, ceramide phosphoryllipid), glycolipids (e.g., glyceroglycolipids, sphingoglycolipids, rhamnolipids, etc.), and sterols (e.g., cholesterol, campesterol, sitosterol, stigmasterol, ergosterol, etc.). Hydrophobic moieties may include steroids (e.g., cholesterol), saturated fatty acids (e.g., caprylic acid, capric acid, lauric acid, myristic acid, palmitic acid, stearic acid, arachidic acid, behenic acid, lignoceric acid, cerotic acid, etc.), and unsaturated fatty acids (e.g., myristoleic acid, palmitoleic acid, sapienic acid, oleic acid, elaidic acid, vaccenic acid, linoleic acid, arachidonic acid, eicosapentaenoic acid, erucic acid, docosahexanenoic acid, etc.). Hydrophilic compounds may include charged molecules and polar molecules (e.g., glycols, cyclodextrins, cellulose, polyacrylamides, etc.).

In some configurations, a nucleic acid nanostructure (e.g., a SNAP) may comprise a utility face or utility moiety comprising one or more extendable nucleic acid (e.g., a nucleic acid primer) or extended nucleic acids (e.g. an extended nucleic acid primer). A primer or other extendable nucleic acid terminus can be hybridized to a template strand to direct polymerase-based extension. However, extension need not involve addition of nucleotides by a template-directed polymerase, for example, instead involving nucleotide addition by a terminal deoxynucleotidyl transferase or oligonucleotide addition by a ligase. Optionally, some or all nucleic acid termini in the nucleic acid nanostructure, other than a given primer that is to be extended, can be non-extendable, for example, due to the presence of a 5' or 3' extension blocking moiety. Accordingly, extension can selectively occur at the given primer instead of at the other termini. Exemplary extension blocking moieties include, but are not limited to, those used in nucleic acid sequencing-by-synthesis reactions such as reversible terminators. Reversible terminator moieties can be particularly useful since they can be present at a first nucleic acid to prevent its extension during extension of a second nucleic acid terminus, and then removed from the first terminus to render it extendable.

An extended nucleic acid may be configured to occupy a volume surrounding a nucleic acid nanostructure and/or exclude other molecules (e.g., other SNAPs, analytes, etc.) from approaching or contacting the nucleic acid nanostructure. An extended nucleic acid may comprise a single-stranded nucleic acid strand, a double-stranded nucleic acid strand, or a combination thereof. An extended nucleic acid may comprise a secondary structure (e.g., a helical structure). An extended nucleic acid may comprise a region of random or disordered structure. An extended nucleic acid strand may incorporate modified or non-natural nucleotides, or other linking moieties. An extended nucleic acid may be formed by a method such as terminal deoxynucleotidyl transferase (TdT) polymerization. Methods of forming extended nucleic acids are described in Yang, et al. *Angewandte Chemie Int. Ed.*, 10.1002/anie.202107829, (2021), which is herein incorporated by reference in its entirety. An extended nucleic acid may have a sequence comprising at least about 100, 200, 300, 400, 500, 750, 1000, 1500, 2000, 2500, 3000, 4000, 5000, 10000, 15000, 20000, or more than 20000 nucleotides. Alternatively or additionally, an extended nucleic acid may have a sequence comprising no more than about 20000, 15000, 10000, 5000, 4000, 3000, 2500, 2000, 1500, 1000, 750, 500, 400, 300, 200, 100, or less than 100 nucleotides. An extended nucleic acid may have a length, in an extended or condensed state (e.g., coiled, self-hybridized, etc.), of at least about 10 nanometers (nm), 20 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 350 nm, 400 nm, 450 nm, 500 nm, or more than 500 nm. Alternatively or additionally, an extended nucleic acid may have a length, in an extended or condensed state (e.g., coiled, self-hybridized, etc.), of no more than about 500 nm, 450 nm, 400 nm, 350 nm, 300 nm, 250 nm, 200 nm, 180 nm, 160 nm, 140 nm, 120 nm, 100 nm, 90 nm, 80. nm, 70 nm, 60 nm, 50 nm, 40 nm, 30 nm, 20 nm, 10 nm, or less than 10 nm.

A utility face or utility moiety of a nucleic acid nanostructure (e.g., a SNAP) may comprise one or more modifying moieties. A utility face of a nucleic acid nanostructure may comprise at least about 10, 50, 100, 500, 1000, 5000, 10000, 50000, 100000, 50000, 1000000, or more than 1000000 modifying groups. Alternatively or additionally, a utility face of a nucleic acid nanostructure may comprise no more than about 1000000, 500000, 100000, 50000, 10000, 5000, 1000, 500, 100, 50, 10, or less than 10 modifying groups.

A nucleic acid nanostructure (e.g., a SNAP) may comprise a utility face with a characteristic density of modifying moieties. The modifying moiety density may refer to an average or localized area density of modifying moieties on a nucleic acid nanostructure utility face. A utility face of a nucleic acid nanostructure may have a modifying moiety density of no more than about 1 group/nm$^2$, 1 group/10 nm$^2$, 1 group/100 nm$^2$, 1 group/1000 nm$^2$, 1 group/10000 nm$^2$, 1 group/100000 nm$^2$, 1 group/1000000 nm$^2$, or less than 1 group/1000000 nm$^2$. Alternatively or additionally, a utility face of a nucleic acid nanostructure may have a modifying moiety density of at least about 1 group/1000000 nm$^2$, 1 group/100000 nm$^2$, 1 group/10000 nm$^2$, 1 group/1000 nm$^2$, 1 group/100 nm$^2$, 1 group/10 nm$^2$, 1 group/nm$^2$, or more than 1 group/nm$^2$.

A nucleic acid nanostructure (e.g., a SNAP), as set forth herein, may comprise one or more detectable labels, for example, at a utility face of the nanostructure. A detectable label may comprise a group that is configured to provide or transmit a signal. A detectable label may provide or transmit a signal in real time (e.g., a fluorophore, a radiolabel) or at a later time (e.g., a barcode). A detectable label may comprise a detectable label selected from the group consisting of a fluorescent group, a luminescent group, a radiolabel, an isotope, and a barcode. Any of a wide variety of fluorescent labels known in the art may be used to label the probes. In some cases, the fluorescent label may be a small molecule. In some cases, the fluorescent label may be a protein. In some cases, the fluorescent label may be a nanoparticle (e.g., a quantum dot, a fluorescently-labeled polymer nanoparticle, etc.). Fluorescent labels may include labels that emit in the ultraviolet spectrum, visible spectrum, or infrared spectrum. In some cases, the fluorescent molecule may be selected from the group consisting of FITC, Alexa Fluor® 350, Alexa Fluor® 405, Alexa Fluor® 488, Alexa Fluor® 532, Alexa Fluor® 546, Alexa Fluor® 555, Alexa Fluor®

568, Alexa Fluor® 594, Alexa Fluor® 647, Alexa Fluor® 680, Alexa Fluor® 750, Pacific Blue, Coumarin, BODIPY FL, Pacific Green, Oregon Green, Cy3, Cy5, Pacific Orange, TRITC, Texas Red, R-Phycoerythrin, and Allophycocyanin (APC). In some cases, the label may be an Atto dye, for example Atto 390, Atto 425, Atto 430, Atto 465, Atto 488, Atto 490, Atto 495, Atto 514, Atto 520, Atto 532, Atto 540, Atto 550, Atto 565, Atto 580, Atto 590, Atto 594, Atto 610, Atto 611, Atto 612, Atto 620, Atto 633, Atto 635, Atto 647, Atto 655, Atto 680, Atto 700, Atto 725, Atto 740, Atto MB2, Atto Oxa12, Atto Rho101, Atto Rho12, Atto Rho13, Atto Rho14, Atto Rho3B, Atto Rho6G, or Atto Thio12. A wide range of effective fluorescent labeling groups may be commercially available from the Molecular Probes division of ThermoFisher Scientific and are generally described in the Molecular Probes Handbook (11th Edition) which is hereby incorporated by reference. Detectable labels may also include intercalation dyes, such as ethidium bromide, propidium bromide, crystal violet, 4',6-diamidino-2-phenylindole (DAPI), 7-aminoactinomycin D (7-AAD), Hoescht 33258, Hoescht 33342, Hoescht 34580, YOYO-1, DiYO-1, TOTO-1, DiTO-1, or combinations thereof.

A nucleic acid nanostructure (e.g., a SNAP), as set forth herein, may comprise a three-dimensional structure. A nucleic acid nanostructure may comprise a plurality of faces, including a display face, a binding face, and additional utility faces. In some configurations, utility faces may be located on the regions of a nucleic acid nanostructure that constitute a height or depth of the nucleic acid nanostructure. A utility face may be utilized for any of a variety of purposes, including coupling a nucleic acid nanostructure to other structures, or providing spacing between a nucleic acid nanostructure and other structures or molecules. A utility face may comprise one or more modifying groups. Utility face modifying groups may be attached covalently or non-covalently. Utility face modifying groups may be coupled to a nucleic acid nanostructure before, during, or after assembly of the nanostructure. Utility face modifying groups may include electrically-charged moieties, magnetic moieties, steric moieties, hydrophobic moieties, hydrophilic moieties, and coupling groups. Coupling groups may comprise any groups that are configured to couple a nucleic acid nanostructure to a solid support or to another molecule, such as another nucleic acid nanostructure. Coupling groups may include covalent coupling groups and non-covalent coupling groups. Covalent coupling groups may include chemically reactive species such as click reaction groups and cross-linking molecules. Cross-linking molecules may include chemical cross-linking molecules and photo-initiated cross-linking molecules. Non-covalent coupling groups may include binding pairs (e.g., streptavidin-biotin) and nucleic acids configured to base-pair with complementary nucleic acids on other molecules. A nucleic acid nanostructure (e.g., a SNAP), molecule that is to be conjugated to a nucleic acid nanostructure, or solid support that is to be conjugated to a nucleic acid nanostructure can include any of a variety of coupling groups such as those set forth in U.S. patent application Ser. No. 17/062,405 or WO 2019/195633 A1, each of which is incorporated herein by reference. A utility face of a nucleic acid nanostructure may comprise one or more steric groups that hinder other molecules from approaching within a proximity of the nucleic acid nanostructure, as determined by the size of the one or more steric groups.

A nucleic acid nanostructure (e.g., a SNAP) may comprise one or more coupling faces or coupling moieties. A utility face or a utility moiety may comprise one or more functional groups or moieties that are configured to couple a first nucleic acid nanostructure to a second nucleic acid nanostructure. Coupling moieties may include those set forth herein, for example in the context of utility faces. Couplings between nucleic acid nanostructures (e.g., a display SNAP and a spacer SNAP) or between nucleic acid nanostructure complexes may be formed by the reversible or irreversible binding of complementary sets of coupling moieties on each pair-forming nucleic acid nanostructure. Reversible binding of complementary nucleic acid nanostructures may occur via a non-covalent bond (e.g., nucleic acid hybridization, hydrogen bonding) or a thermodynamically-reversible covalent bond (e.g., a peroxide bond, a disulfide bond). A nucleic acid nanostructure or complex thereof may comprise one or more coupling groups that are configured to couple with one or more complementary coupling moieties on a second nucleic acid nanostructure or complex thereof. A nucleic acid nanostructure or complex thereof may comprise one or more faces containing one or more coupling moieties that are configured to couple with one or more complementary coupling moieties on a face of a second nucleic acid nanostructure or complex thereof. A nucleic acid nanostructure or complex thereof may comprise a plurality of coupling moieties that are configured to couple with a plurality of complementary coupling moieties on a second nucleic acid nanostructure or complex thereof. In some configurations, a nucleic acid nanostructure or complex thereof may comprise a plurality of coupling moieties to ensure that at least one coupling interaction, but preferably more than one coupling interaction, is formed with a complementary nucleic acid nanostructure or complex thereof.

A nucleic acid nanostructure may comprise a plurality of coupling faces or coupling moieties that are configured to couple the nucleic acid nanostructure to a plurality of nucleic acid nanostructures. For example, a square- or rectangular-shaped SNAP may comprise four coupling faces, with each coupling face configured along one of the four edges comprising the square or rectangle. A coupling face may comprise one or more functional groups or moieties that are configured to couple a first nucleic acid nanostructure to a second nucleic acid nanostructure. For example, a coupling face or coupling moiety may comprise a plurality of single-stranded nucleic acids that are configured to hybridize to a plurality of complementary single-stranded nucleic acids on a second coupling face or coupling moiety, thereby coupling the first coupling face to the second coupling face. In another example, a coupling face may comprise a single streptavidin molecule that is configured to bind to a biotin molecule on a second coupling face, thereby coupling the first coupling face to the second coupling face. In some configurations, the coupling of a first nucleic acid nanostructure to a second nucleic acid nanostructure may comprise an intermediary coupling group that mediates the coupling of the first nucleic acid nanostructure to the second nucleic acid nanostructure. For example, a plurality of SNAPs may be configured to only display streptavidin molecules on one or more coupling faces such that a first SNAP cannot directly bind to a second SNAP. An intermediary coupling group comprising only surface-displayed biotin may permit the coupling of the first SNAP to the second SNAP. An intermediary coupling group may comprise a nucleic acid nanostructure or a non-nucleic acid particle or molecule (e.g., an organic or inorganic nanoparticle). The coupling of a first nucleic acid nanostructure to a second nucleic acid nanostructure may be reversible (e.g., nucleic acid hybridization) or irreversible (e.g., a click reaction).

A nucleic acid nanostructure (e.g., a SNAP), as set forth herein, may comprise one or more sites that permit controlled degradation of the nucleic acid nanostructure. A nucleic acid nanostructure may comprise one or more photocleavable linkers. Photocleavable linkers may be located within any portion of the nucleic acid nanostructure, including the scaffold strand and any oligonucleotide of a plurality of oligonucleotides that may be coupled within a nucleic acid nanostructure. In some cases, a nucleic acid nanostructure may comprise a plurality of photocleavable linkers. Photocleavable linkers may be located within a nucleic acid nanostructure to permit controlled degradation of the nucleic acid nanostructure, for example for programmed removal of the SNAP, or programmed release of the SNAP and analyte from a surface. For nucleic acid nanostructure compositions comprising a multifunctional moiety that is hybridized to a portion of the nucleic acid nanostructure, the multifunctional moiety may comprise a photocleavable linker. In some configurations, the multifunctional moiety may comprise no photocleavable linkers. A photocleavable linker may be included in a multifunctional moiety to permit programmable release of the analyte from a nucleic acid nanostructure or a solid support to which the analyte is coupled. A photocleavable linker may include any suitable photocleavable linker, such as nitrobenzyl, carbonyl, or benzyl-based photocleavable linkers. A photocleavable linker may be configured to cleave under a particular wavelength, or within a particular frequency range, such as far infrared, near infrared, visible, near ultraviolet, far ultraviolet, or a combination thereof. A photocleavable linker may be selected because it has a peak scission wavelength that does not interfere with other biological or chemical processes, such as the absorbance or emission wavelength of a fluorophore. A nucleic acid nanostructure (e.g., a SNAP) may comprise one or more degradation sites that are substrates for enzymatic degradation, for example by restriction enzymes, proteases, kinases, or other suitable enzymes. A nucleic acid nanostructure may incorporate moieties that are substrates for enzymatic degradation, such as uracil nucleotides that are degraded by Uracil DNA glycosylase and endonuclease VIII (sold commercially as USER® Enzyme by New England Biolabs, Beverley MA), 8-oxoguanine nucleotides that are degraded by DNA glycosylase OGG1, or peptides that are degraded by proteases. For nucleic acid nanostructure compositions comprising a multifunctional moiety that is hybridized to a portion of the nucleic acid nanostructure, the multifunctional moiety may comprise a degradation site that is a target for enzymatic degradation. In some configurations, the multifunctional moiety may comprise no degradation sites that are targets for enzymatic degradation.

A nucleic acid nanostructure (e.g., a SNAP), as set forth herein, may comprise one or more sites or groups that are incorporated into a nucleic acid nanostructure to promote stability of the nucleic acid nanostructure. A nucleic acid nanostructure (e.g., a SNAP) may comprise modified or non-natural nucleotides (e.g., PNAs, locked nucleic acids, etc.) that are resistant to degradation via endonucleases or other enzymes. A nucleic acid nanostructure may comprise one or more cross-linking groups that couple nucleic acid nanostructure components to each other (e.g., an oligonucleotide to a scaffold strand) and/or one or more cross-linking groups that couple a nucleic acid nanostructure to another entity (e.g., a solid support, a second nucleic acid nanostructure, etc.).

Figure 3C:
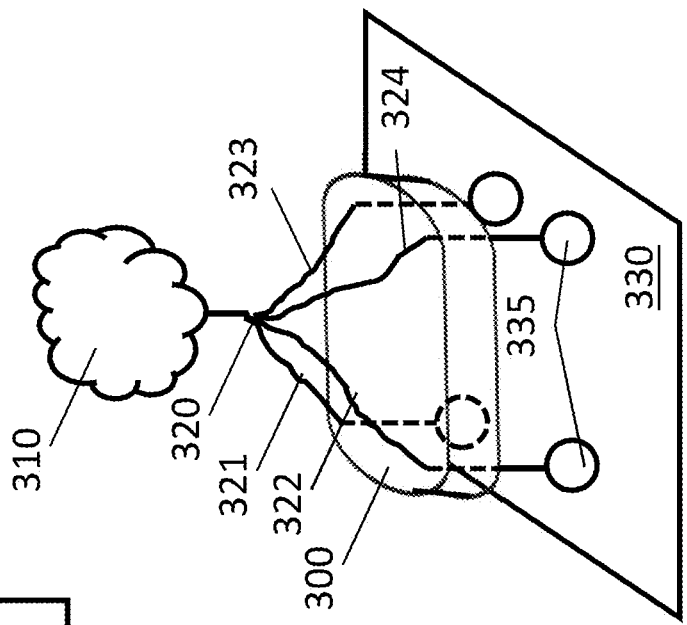
FIGS. 3A-3D show a SNAP, a multifunctional moiety, a linking moiety, a solid support, and an analyte.
Figure 3B:
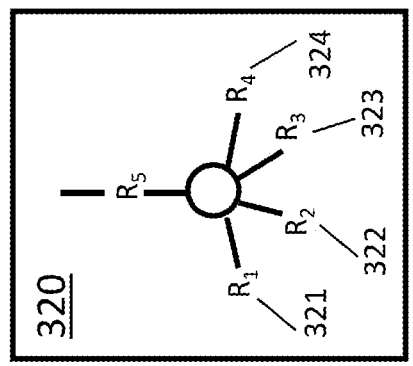
Figure 3A:
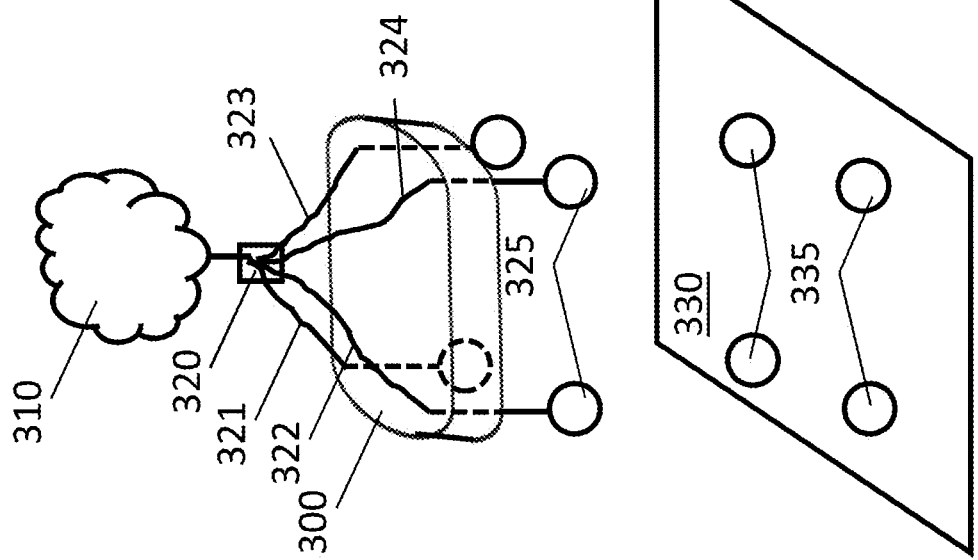
Figure 3D:
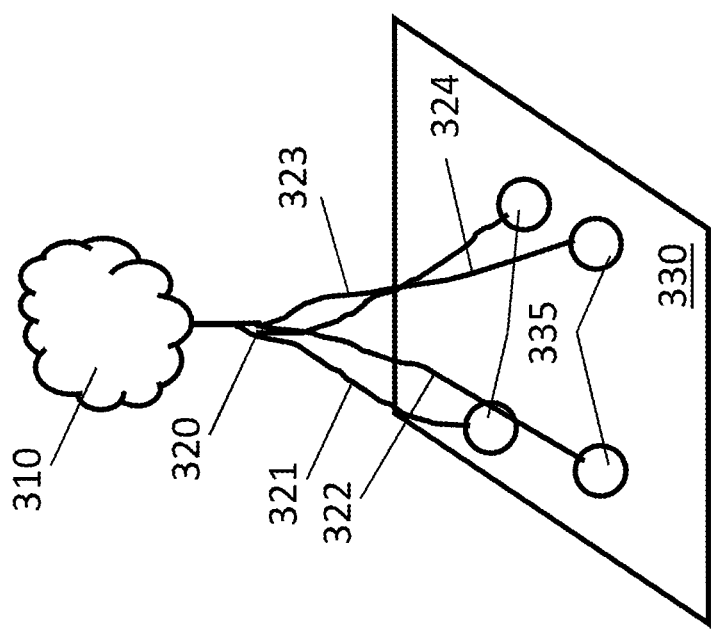

A nucleic acid nanostructure (e.g., a SNAP), as set forth herein, may comprise one or more linkers. A linker may comprise a molecular chain or moiety that links two portions of an oligonucleotide, including for example, any nucleic acid components of a nucleic acid nanostructure, such as a scaffold strand, an oligonucleotide that is hybridized to a scaffold strand, or a multifunctional oligonucleotide that is hybridized to a nucleic acid nanostructure. A linker may comprise a rigid linker or a flexible linker. A linker may comprise a polymeric moiety, such as a polyethylene glycol (PEG), a polyethylene oxide (PEO) moiety, or a polynucleotide. A linker may introduce a desired chemical property, such as hydrophobicity, hydrophilicity, polarity, or electrical charge. A linker may include a moiety that is configured to link one or more additional moieties or molecules together, such as multiple multifunctional moieties. A linker may include one or more modified nucleotides, such as PNAs, LNAs, and/or nucleotides modified with functional groups configured to perform a click-type reaction. FIG. 3A-3D depicts a method of coupling an analyte to a solid support utilizing a multifunctional moiety comprising a linking group. As shown in FIG. 3A, a SNAP 300 that is coupled to an analyte 310 by a polyvalent linker 320 is contacted with a solid support 330 comprising a plurality of surface-linked coupling moieties 335. The polyvalent linker is coupled to four arms of a multifunctional moiety (321, 322, 323, 324) that are hybridized to the SNAP and comprise functional groups 325 that are configured to couple to surface-linked coupling moieties 335. FIG. 3B depicts a close-up view of the polyvalent linker 320 comprising five functional groups, $R_1$, $R_2$, $R_3$, $R_4$, and $R_5$, respectively. Functional groups $R_1$, $R_2$, $R_3$, and $R_4$ are coupled to the four arms of the multifunctional moiety 321, 322, 323, and 324, respectively. Functional group $R_5$ is coupled to the analyte 310. FIG. 3C depicts the coupling of the SNAP 300 and analyte 310 to the solid support 330 by the coupling of the functional groups 325 to the surface-linked coupling moieties 335. FIG. 3D depicts the composition after the SNAP 300 structure has been degraded, thereby leaving the analyte 310 coupled to the solid support 330 by the four arms of the multifunctional moiety (321, 322, 323, 324). Such a configuration may have the advantage of increasing the chemical stability of the coupling of the analyte as the multiple coupling multifunctional moieties provide redundancy against decoupling of any single strand. The configuration may also be advantageous because multiple coupling multifunctional moieties may stabilize the spatial position of the analyte where only a single coupling multifunctional moiety may have more translational freedom.

A nucleic acid nanostructure (e.g., a SNAP), as set forth herein, may comprise one or more cross-linking groups. Cross-linking groups may include chemical, enzymatic, and photochemical cross-linking groups. A cross-linking group may stabilize or prevent the dissociation of one or more nucleic acid structures in a nucleic acid nanostructure. An oligonucleotide of a plurality of oligonucleotides may be cross-linked to a scaffold strand of a nucleic acid nanostructure. A first oligonucleotide of a plurality of oligonucleotides may be cross-linked to a second oligonucleotide of the plurality of oligonucleotides in a nucleic acid nanostructure. An oligonucleotide comprising an important structural feature, such as a utility moiety (e.g., a display moiety, a capture moiety) may be cross-linked to a nucleic acid nanostructure to enhance stability or prevent dissociation of the oligonucleotide. A multifunctional moiety comprising two or more utility moieties (e.g., display moiety and capture moiety) may comprise one or more cross-linking groups to a nucleic acid nanostructure.

A nucleic acid nanostructure (e.g., a SNAP) may comprise portions that are fully structured and/or portions that are partially structured. A fully structured portion of a nucleic acid nanostructure may be identified as a region of a nucleic acid nanostructure that maintains primary, secondary, and tertiary structure during the course of use. A partially-structured portion of a nucleic acid nanostructure may be identified as a region of a nucleic acid nanostructure that comprises a primary structure but does not maintain a particular secondary and/or tertiary structure during the course of use. In some configurations, a partially-structured portion of a nucleic acid nanostructure may comprise a single-stranded nucleic acid. A single-stranded nucleic acid may be located between regions of double-stranded nucleic acid, or may comprise a pendant or terminal strand of nucleic acid. A single-stranded nucleic acid may have a particular length, such as, for example, at least about 5, 10, 15, 20, 25, 30, 35, 40, 45, 50 or more than 50 nucleotides. Alternatively or additionally, a single-stranded nucleic acid may have a length of no more than about 50, 45, 40, 35, 30, 25, 20, 15, 10, 5, or less than 5 nucleotides. In some configurations, a partially-structured portion of a nucleic acid nanostructure may comprise a non-nucleic acid moiety, molecular group or chain, such as a PEG or polymer chain. In some configurations, a partially-structured portion of a nucleic acid nanostructure may comprise an amorphous structure, such as a globular structure (e.g., a nanoball, a dendrimer, etc.). FIG. 37A depicts a SNAP 3710 with partially-structured regions 3730 (e.g., single-stranded nucleic acids, polymers, dendrimers, etc.). The SNAP 3710 is coupled to an analyte 3720. The partially-structured regions 3730 may be located on multiple SNAP faces (e.g., a capture face, a display face). Partially-structured regions 3730 may provide one or more functionalities to the SNAP 3710 such as, for example, increasing binding strength to targeted binding surfaces, decreasing binding strength to non-targeted surfaces, and prevent non-specific binding of other molecules to a SNAP face or a coupled analyte.

Multifunctional Moieties: In an aspect, described herein is a composition comprising a nucleic acid nanostructure (e.g., a SNAP) and a multifunctional moiety, where the multifunctional moiety may be configured to be coupled to the nucleic acid nanostructure, and where the multifunctional moiety may be configured to form two or more additional interactions. In some configurations, the multifunctional moiety may be configured to be coupled to the nucleic acid nanostructure, and may continuously couple a surface to an analyte. A continuous coupling of the surface to the analyte may comprise a coupling where the surface is directly coupled to the analyte by the multifunctional moiety, without any other intervening groups or moieties. For example, if a SNAP was coupled to a surface by a multifunctional moiety and an analyte was coupled to the SNAP but not coupled to the multifunctional moiety, the analyte would not be continuously coupled to the surface by the multifunctional moiety. The multifunctional moiety may comprise a first functional group and a second functional group. In some configurations, the first functional group may be coupled to, or configured to couple to, the surface, and the second functional group may be coupled to, or configured to couple to, the analyte. In some configurations, the multifunctional moiety may be coupled to, or configured to be coupled to, a nucleic acid nanostructure, and may form two or more coupling interactions with a surface. A multifunctional moiety may comprise a display moiety and a surface-interacting moiety.

A multifunctional moiety, as set forth herein, may comprise a plurality of functional groups. A multifunctional moiety may comprise at least about 2, 3, 4, 5, 6, 7, 8, 9, 10, 11, 12, 13, 14, 15, 16, 17, 18, 19, 20, or more than 20 functional groups. Alternatively or additionally, a multifunctional moiety may comprise no more than about 20, 19, 18, 17, 16, 15, 14, 13, 12, 11, 10, 9, 8, 7, 6, 5, 4, 3, or less than 3 functional groups.

Figure 7A:
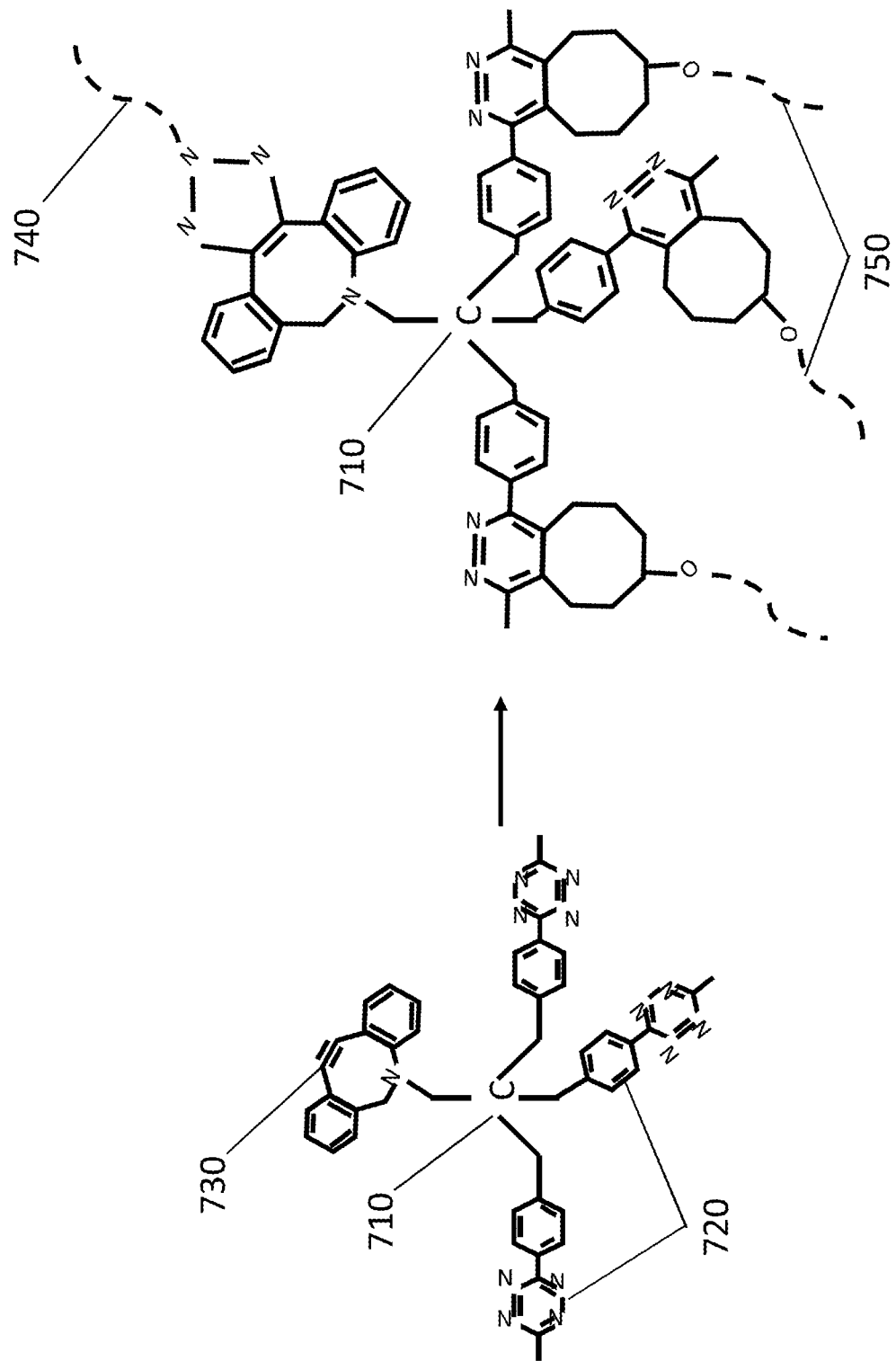
FIGS. 7A-7B show multifunctional moieties.
Figure 7B:
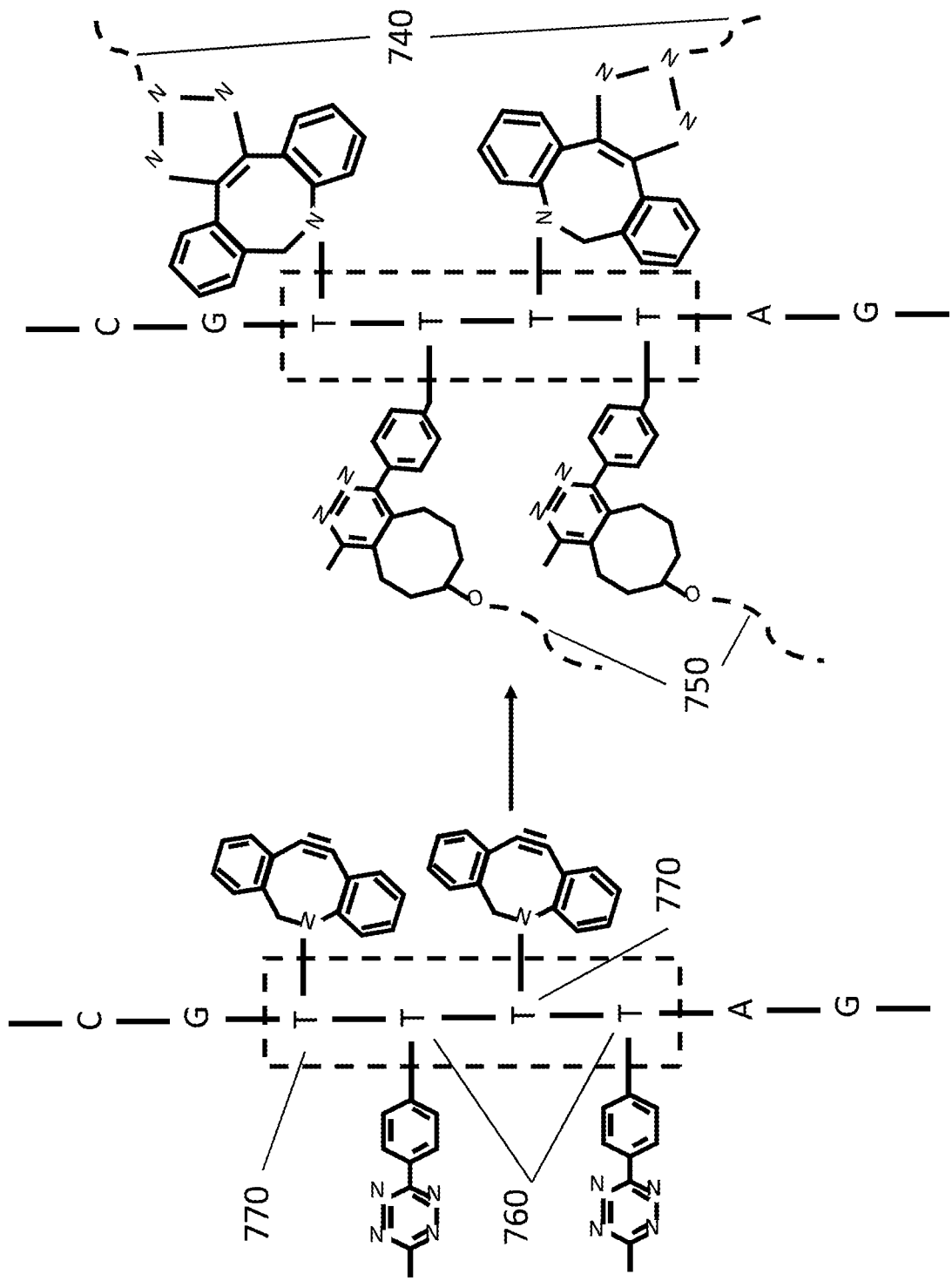

A multifunctional moiety, as set forth herein, may comprise one or more molecular chains. A molecular chain may comprise a multimeric compound such as an oligonucleotide or a polymer chain (e.g., polyethylene, polypropylene, polyethylene glycol, polyethylene oxide, etc.). In other configurations, a multifunctional moiety may comprise no nucleic acids. In some configurations a multifunctional moiety may comprise a plurality of molecular chains. A multifunctional moiety may comprise at least about 1, 2, 3, 4, 5, 6, 7, 8, 9, 10, or more than 10 molecular chains. Alternatively or additionally, a multifunctional moiety may comprise no more than about 10, 9, 8, 7, 6, 5, 4, 3, 2, or less than 2 molecular chains. Two or more molecular chains of a multifunctional moiety may be joined, coupled, or linked by a linking moiety. FIGS. 7A-7B depict exemplary configurations of linking moieties. FIG. 7A depicts the formation of a multifunctional moiety comprising an alkyl linking moiety. The linking moiety comprises an alkyl linking group 710 that comprises four reactive functional groups, including 3 methyltetrazine (mTz) groups 720 and 1 dibenzocyclooctene (DBCO) group 730. The linking moiety may be contacted with a molecular chain 740 comprising an azide functional group, thereby linking the azide-functionalized molecular chain 740 to the DBCO group 730 by an azide-DBCO click reaction. The linking moiety may also be contacted with molecular chains 750 comprising transcyclooctyne (TCO) functional groups, thereby linking the TCO-functionalized molecular chains 750 to the mTz functional groups 720 by an mTz-TCO click reaction. FIG. 7B depicts a multifunctional moiety comprising a group of modified nucleotides in a longer oligonucleotide molecular chain. The linking moiety comprising the modified nucleotides is shown in the dashed box. The linking moiety comprises four modified thymine nucleotides, including two mTz-functionalized thymines 760 and two DBCO-functionalized thymines 770. The multifunctional moiety may be contacted with azide-functionalized molecular chains 740 and/or TCO-functionalized molecular chains 750 to couple one or more molecular chains by click reactions.

Figure 8A:
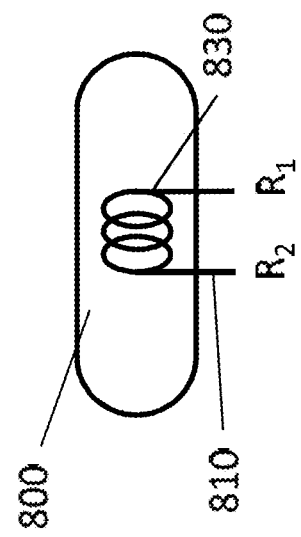
FIGS. 8A, 8B, 8C, and 8D illustrate a SNAP comprising a multifunctional moiety, in accordance with some embodiments.
Figure 8B:
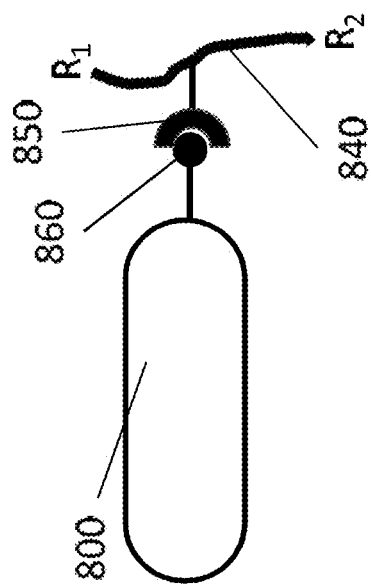
Figure 8C:
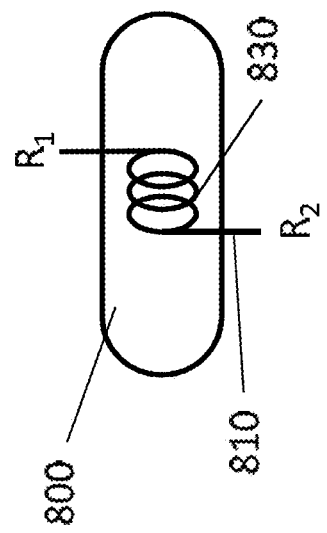
Figure 8D:
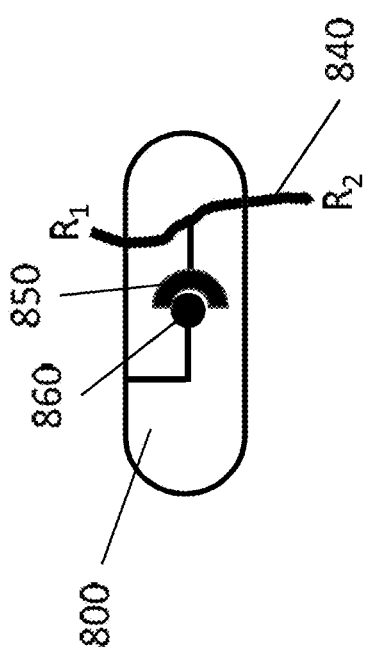

A multifunctional moiety may be configured to couple to a nucleic acid nanostructure (e.g., a SNAP). A coupling of a nucleic acid nanostructure may depend upon how the nucleic acid nanostructure is to be utilized. For example, in some configurations, a multifunctional moiety may facilitate positioning and coupling a SNAP on a surface. In other configurations, a SNAP may facilitate positioning and coupling a multifunctional moiety to the surface. FIGS. 8A-8D depict various configurations of multifunctional moieties coupled to SNAPs. FIG. 8A shows a multifunctional moiety 810 with functional groups $R_1$ and $R_2$ comprising an oligonucleotide that couples to a SNAP 800 to form a region of hybridized nucleic acids 830. The functional groups $R_1$ and $R_2$ are displayed through a top face (e.g., a display face) and a bottom face (e.g., a capture face), respectively. FIG. 8B shows a multifunctional moiety 810 with functional groups $R_1$ and $R_2$ comprising an oligonucleotide that couples to a SNAP 800 to form a region of hybridized nucleic acids 830. The functional groups $R_1$ and $R_2$ are displayed on a bottom face (e.g., a capture face). FIG. 8C depicts a multifunctional moiety 840 with functional groups $R_1$ and $R_2$ comprising a molecular chain (e.g., a polymer, an oligonucleotide) that couples to a SNAP 800 by a functional group or moiety 850 that couples to a complementary functional group or moiety 860 in the SNAP 800 (e.g., by a click reaction, by nucleic acid hybridization). The functional groups $R_1$ and $R_2$ are displayed through a top face (e.g., a display face) and a bottom face (e.g., a capture face), respectively. FIG. 8D depicts a multifunctional moiety 840 with functional groups $R_1$ and $R_2$ comprising a molecular chain (e.g., a polymer, an oligonucleotide) that couples to a SNAP 800 by a functional group or moiety 850 that couples to a complementary functional group or moiety 860 on an external face of the SNAP 800 (e.g., by a click reaction, by nucleic acid hybridization). The multifunctional moiety 810 is coupled to the SNAP 800 but is configured to be completely external to the SNAP 800 structure.

In some configurations, a nucleic acid nanostructure composition (e.g., a SNAP composition) may comprise a nucleic acid nanostructure and a multifunctional moiety that is configured to be coupled to the nucleic acid nanostructure. In other configurations, a nucleic acid nanostructure composition may comprise a multifunctional moiety that is coupled to the nucleic acid nanostructure. For example, a SNAP composition may comprise a fluidic medium that, in a first configuration, contains a plurality of partially-formed SNAPs contacted with a plurality of multifunctional moieties, and in a second configuration, a plurality of fully-formed SNAPs, in which a multifunctional moiety is coupled to each SNAP. In some configurations, a nucleic acid nanostructure composition may further comprise an analyte that is configured to be coupled to the multifunctional moiety. For example, a SNAP composition may comprise a fluidic medium comprising a plurality of SNAPs containing multifunctional moieties and a plurality of analytes that are configured to be coupled to the multifunctional moieties. In some configurations, a nucleic acid nanostructure composition may further comprise an analyte that is coupled to the multifunctional moiety. For example, a SNAP composition may comprise a plurality of partially formed SNAPs that are contacted with a plurality of multifunctional moieties, in which each multifunctional moiety is coupled to an analyte. In another example, a SNAP composition may comprise a plurality of SNAPs containing multifunctional moieties, in which each multifunctional moiety is coupled to an analyte. In some configurations, a nucleic acid nanostructure composition may further comprise a surface that is configured to be coupled to the multifunctional moiety. For example, a SNAP composition may comprise a solid support comprising a plurality of surface-linked moieties, in which the solid support is contacted with a plurality of SNAP containing multifunctional moieties, in which each multifunctional moiety comprises a surface-interacting moiety that is configured to couple to a surface-linked moiety. In some configurations, a nucleic acid nanostructure composition may further comprise a surface that is coupled to the multifunctional moiety. For example, a SNAP composition may comprise a solid support comprising a plurality of surface-linked moieties, in which one or more surface-linked moieties are coupled to surface-interacting moieties of a plurality of SNAPs containing multifunctional moieties, and in which the solid support is contacted with a fluidic medium comprising a plurality of analytes, in which each analyte is configured to couple to a display moiety of a multifunctional moiety. The skilled person will readily recognize numerous variations of nucleic acid nanostructure compositions based upon the ordering with which different components (e.g., SNAPs, multifunctional moieties, analytes, solid supports, etc.) are introduced into a system, as set forth herein.

In some configurations, provided herein are compositions comprising a nucleic acid nanostructure (e.g., a SNAP) comprising a display moiety that is configured to couple to an analyte and a capture moiety that is configured to couple with a surface, and a multifunctional moiety comprising a first functional group and a second functional group where the multifunctional moiety is hybridized to a nanostructure moiety, and where the display moiety comprises the first functional group and the capture moiety comprises the second functional group. Such nucleic acid nanostructures may be configured to utilize the first functional group to couple to an analyte and to utilize the second functional group to couple to a surface or interface. The nanostructure moiety can be configured to occupy a given area of the surface to prevent other nucleic acid nanostructures from occupying the same area. This can occur, for example, due to steric exclusion, charge repulsion or other mechanisms. Such configurations may provide surprising advantages, such as a linking connection between the analyte and the surface by the multifunctional moiety, and preventing more than one analyte from occupying the given area of the surface due to the presence of the nanostructure moiety. The nanostructure moiety can be removed (e.g. degraded), intentionally or unintentionally, such that the analyte may remain coupled to the surface. Accordingly, a nanostructure moiety can beneficially inhibit interaction of an analyte with other analytes, reagents or objects during surface deposition, and then the nanostructure moiety can be removed to facilitate interaction of the analyte with other analytes, reagents or objects that are useful for on-surface detection or on-surface manipulation of the analyte.

Figures 9A, 9B:
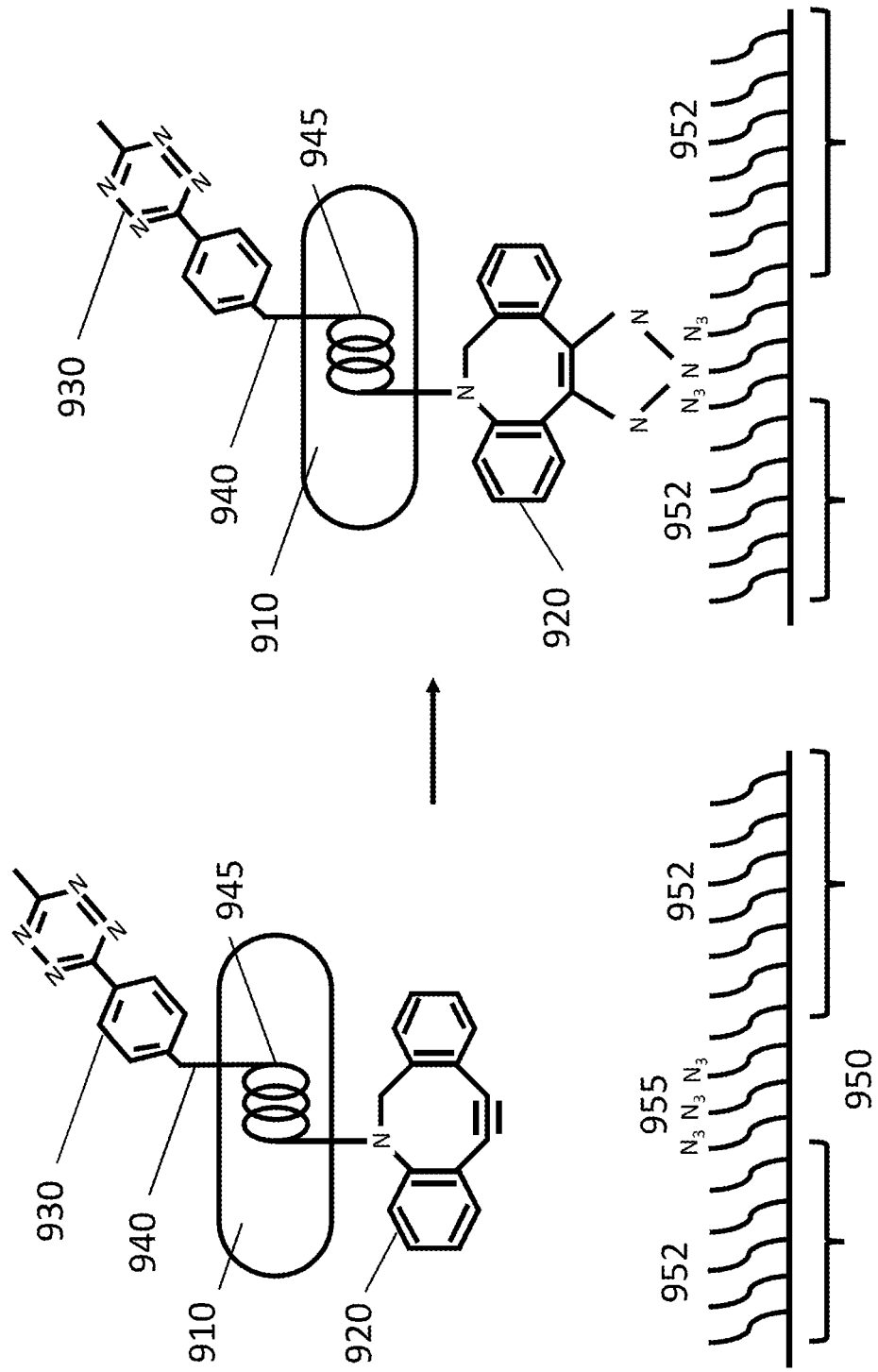
Figure 9D:
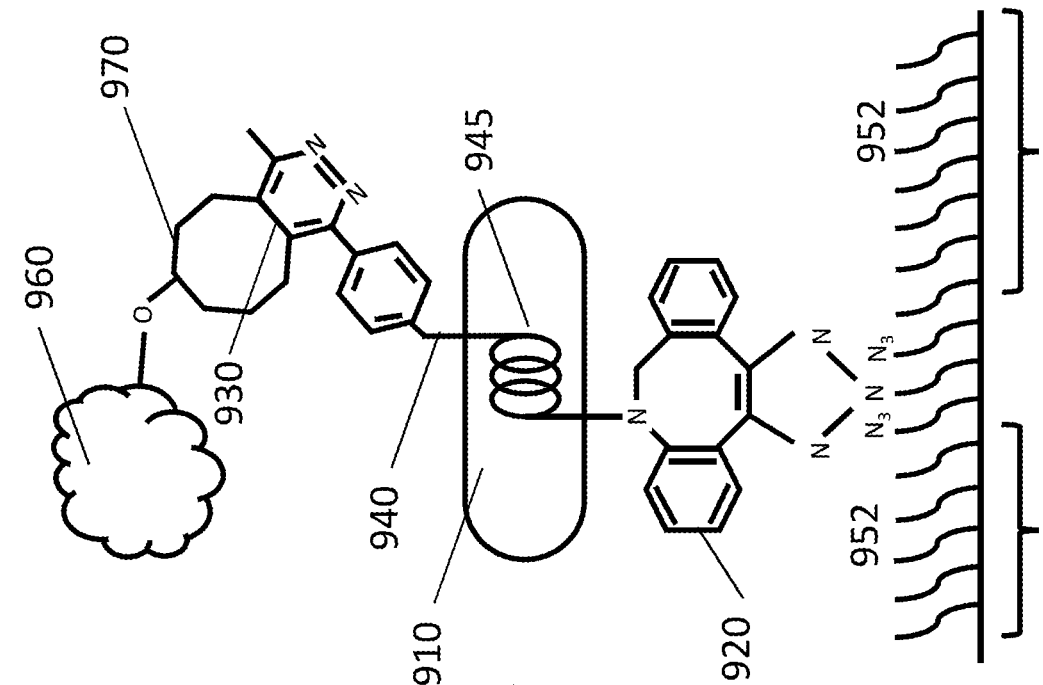
Figure 9C:
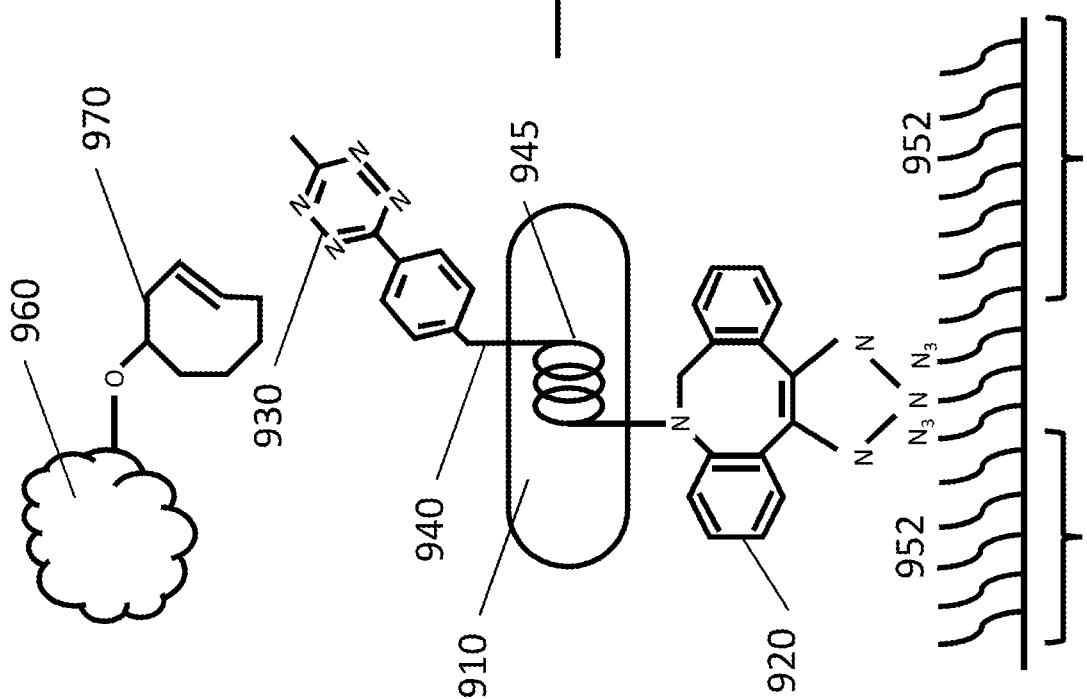

FIGS. 9A-9F depict a method of coupling an analyte to a surface utilizing a SNAP with a multifunctional oligonucleotide. FIG. 9A depicts a schematic of a SNAP 910 comprising an oligonucleotide 940 with a first terminal functional group 920 comprising dibenzocyclooctyne (DBCO) and a second terminal functional group 930 comprising methyltetrazine (mTz). The oligonucleotide 940 is configured to hybridize to a portion of the SNAP such that it forms a localized region of secondary or tertiary structure 945 (e.g., a double helix), thereby stabilizing the oligonucleotide 940 within the SNAP structure 910. The SNAP 910 is contacted with a solid support 950 comprising non-reactive regions 952, and region comprising a reactive third functional group 955 comprising an azide moiety that is configured to react with the first terminal functional group 920. As shown in FIG. 9B, the first terminal functional group 920 may react with the third functional group 955 to form a covalent bond that couples the SNAP 910 to the solid support 950 in the vicinity of where the third functional group 955 is coupled to the solid support 950. As shown in FIG. 9C, the coupled SNAP may be contacted with an analyte 960 comprising a fourth functional group 970 comprising transcyclooctene that is configured to react with the second terminal functional group 930. As shown in FIG. 9D, the second terminal functional group 930 may react with the fourth functional group 970 to form a covalent bond that couples the analyte 960 to the solid support 950. It will be understood that functional groups 920, 955, 930 and 970 are exemplary and can be replaced with other coupling moieties such as those set forth herein or known in the art. As shown in FIG. 9E, the SNAP-analyte composition may be subjected to a degrading phenomena, such as a light source 980, that disrupts the structure of the SNAP 910, thereby degrading the SNAP 910. Degradation can be carried out using other means such as endonuclease digestion of one or more nucleic acid strands in the SNAP, thermal or chemical denaturation of nucleic acid strand interaction, or chemical lysis of a scissile linkage in the SNAP. As shown in FIG. 9F, after degradation of the SNAP 910, the analyte 960 may remain coupled to the solid support 950 by the oligonucleotide 940.

A nucleic acid nanostructure (e.g., a SNAP) comprising a multifunctional moiety, such as the configurations depicted in FIGS. 9A-9F, may be configured to form a hybridization region with the multifunctional moiety consisting of a plurality of nucleic acid base pairs. In some configurations, a multifunctional moiety may form a hybridization region with a nucleic acid nanostructure comprising at least about 10, 20, 30, 40, 50, 60, 70, 80, 90, 100, 125, 150, 200, or more than 200 nucleotides. Alternatively or additionally, a multifunctional moiety may form a hybridization region with a nucleic acid nanostructure comprising no more than about 200, 150, 125, 100, 90, 80, 70, 60, 50, 40, 30, 20, 10, or less than about 10 nucleotides. A hybridization region formed between a nucleic acid nanostructure and a multifunctional moiety may be characterized by a particular number of helical revolutions formed (where a single revolution usually comprises between 10 and 11 base pairs). In some configurations, a multifunctional moiety may form a hybridization region comprising at least 1, 2, 3, 4, 5, 6, 7, 8, 9, 10, 11, 12, 13, 14, 15, 16, 17, 18, 19, 20, or more than 20 helical revolutions. Alternatively or additionally, a multifunctional moiety may form a hybridization region comprising no more than 20, 19, 18, 17, 16, 15, 14, 13, 12, 11, 10, 9, 8, 7, 6, 5, 4, 3, 2, 1 or less than 1 helical revolution.

A nucleic acid nanostructure (e.g., a SNAP) may comprise a plurality of tertiary structures that collectively form quaternary or other higher order structures in the nucleic acid nanostructure. Particular tertiary structures may comprise moieties or structures that belong to a particular face of the nucleic acid nanostructure. A nucleic acid nanostructure may comprise a plurality of tertiary structures, where a display face comprises a first tertiary structure of the plurality of tertiary structures, and a capture face comprises a second tertiary structure of the plurality of tertiary structures. In some configurations, the first tertiary structure may be the same as the second tertiary structure. In other configurations, the first tertiary structure is different from the second tertiary structure. In nucleic acid nanostructure configurations comprising a multifunctional moiety with a first functional group and a second functional group, the multifunctional moiety may be hybridized to the nucleic acid nanostructure, thereby forming a portion of the first tertiary structure or a portion of the second tertiary structure. In other configurations, the multifunctional moiety may be hybridized to a nucleic acid nanostructure, thereby forming a portion of both the first tertiary structure and a portion of the second tertiary structure.

A nucleic acid nanostructure (e.g., a SNAP) comprising a first multifunctional moiety may further comprise a second multifunctional moiety that comprises a third functional group and a fourth functional group. In some configurations, a utility moiety (e.g., a display moiety) may comprise a third functional group and a second utility moiety (e.g., a capture moiety) may comprise a fourth functional group. In some configurations, a third or fourth functional group may be configured to couple to a surface. In some specific configurations, a third or fourth functional group may be coupled to a surface. In some configurations, a third or fourth functional group may be configured to couple to a second analyte. In some specific configurations, a third or fourth functional group may be coupled to a second analyte. In some configurations, a third or fourth functional group may be configured to be coupled to an analyte to which a first multifunctional moiety is coupled. In some specific configurations, a third or fourth functional group may be coupled to an analyte to which a first multifunctional moiety is coupled.

FIG. 10A-10D illustrate a method of coupling a SNAP comprising two multifunctional moieties to a surface. FIG. 10A shows a SNAP 1000 comprising a first multifunctional moiety 1010 that is coupled to an analyte 1020 and comprises a first functional group 1015. The SNAP 1000 also comprises a second multifunctional moiety 1030 that is coupled to a utility moiety 1040 and comprises a second functional group 1035. The SNAP 1000 may comprise a capture face comprising a capture moiety containing the first functional group and the second functional group. The SNAP 1000 may be contacted with a solid support 1050 comprising a plurality of functional groups or moieties including surface linked non-coupling groups 1060 and surface-linked coupling groups 1065 that are configured to couple to a capture moiety or a plurality of capture moieties. As shown in FIG. 10B, the first functional group and/or the second functional group may couple to a surface linked coupling group 1065, thereby coupling the SNAP 1010 to the solid support 1050 by at least one of the two functional groups comprising the capture moiety. As shown in FIG. 10C, the SNAP 1000 coupled to the solid support 1050 may be exposed to a degrading phenomenon, such as a light source 1070, that causes degradation of the SNAP 1000 structure. Degradation can be carried out using other means such as endonuclease digestion of one or more nucleic acid strands in the SNAP, heat, pH change, chemical lysis of a scissile linkage in the SNAP, or any other suitable method of degradation. As shown in FIG. 10D, after degradation of the SNAP structure, the first multifunctional moiety 1010 that is coupled to the analyte 1020 and the second multifunctional moiety 1030 that is coupled to a utility moiety 1040 are co-localized on the solid support 1050.

A multifunctional moiety that is hybridized to a nucleic acid nanostructure structure (e.g., a SNAP) may be configured to couple the nucleic acid nanostructure or a moiety thereof to a surface. In some configurations, a surface may comprise a surface functional group that is configured to couple to a functional group contained on a multifunctional moiety. In some configurations, a surface functional group may comprise a functional group that is configured to form a covalent bond with a functional group contained on a multifunctional moiety. In some specific configurations, a surface functional group and a functional group contained on a multifunctional moiety may form a covalent bond, for example by a click-type reaction, a substitution reaction, an elimination reaction, or any other suitable bonding chemistry.

A nucleic acid nanostructure (e.g., a SNAP) comprising a multifunctional moiety may be formed before or after coupling the nucleic acid nanostructure with a surface. FIG. 11A-11D depict a method of hybridizing a multifunctional moiety to a SNAP after the SNAP has been coupled to a surface. FIG. 11A shows a SNAP 1110 that is contacted with a surface 1100, thereby permitting the SNAP to couple to the surface, for example by an electrostatic, magnetic, or covalent interaction. FIG. 11B shows a contacting of a multifunctional moiety 1120 that is coupled to an analyte 1130 with the SNAP 1110 coupled to the surface 1100. As shown in FIG. 11C, the multifunctional moiety 1120 hybridizes to the SNAP 1110, forming a region of tertiary structure 1150. The multifunctional moiety 1120 may further couple to the surface 1100. FIG. 11D depicts a continuous linkage of the analyte 1130 to the surface 1100 after the SNAP 1110 is optionally removed.

Partially-Compacted Nucleic Acids: A nucleic acid that is useful for the formation of an array of analytes may comprise a structure that has one or more characteristics of: i) coupling an analyte at a tunable and/or controllable location on a face of the nucleic acid, ii) inhibiting unwanted coupling of analytes or other moieties at portions of the nucleic acid not intended for coupling, iii) comprising a structure or a face that is configured to form a specific binding interaction with a solid support or a surface thereof, iv) comprising a structure or a face that is configured to form a specific binding interaction with a solid support or a surface thereof that is more likely to occur than a non-specific binding interaction between an analyte coupled to the nucleic acid and the solid support or surface thereof, v) comprising a structure or a face that is configured to inhibit contact between an analyte coupled to the nucleic acid and a solid support or a surface thereof, vi) inhibiting unwanted binding interactions (e.g., aggregation, co-localization, etc.) with other nucleic acids or analytes coupled thereto.

A useful configuration of a nucleic acid, such as a nucleic acid nanostructure, may comprise a nucleic acid comprising a compacted structure and a pervious structure. A compacted structure of a nucleic acid may provide spatial and orientational tunability for moieties coupled to or emerging from a structure of a nucleic acid. For example, a nucleic acid origami comprising a compacted structure may be designed to orient a display moiety at substantially a 180° orientation from one or more capture moieties, thereby increasing likelihood that the nucleic acid origami is coupled to a solid support by the one or more capture moieties rather and not coupled by an analyte coupled to the display moiety. Tunability of a compacted structure may arise from several aspects of a nucleic acid structure, including a plurality of tertiary structures that provide substantially 360° of rotational freedom for the orientation of moieties coupled to a nucleic acid, and one or more linking strands that couple tertiary structures within a nucleic acid structure, thereby providing a degree of rigidity to the nucleic acid structure and fixing the separation distance and orientation of tertiary structures with respect to each other in the nucleic acid structure. A pervious structure of a nucleic acid may provide additional chemical and/or physical properties to a nucleic acid that facilitate wanted interactions with other entities (e.g., analytes, unbound moieties, reagents, other nucleic acids, solid supports, fluidic media, etc.) or inhibit unwanted interactions with other entities. For example, a nucleic acid may comprise a plurality of pendant single-stranded nucleic acid moieties comprising homopolymer repeats (e.g., poly-T repeats, poly-A repeats, poly-C repeats, poly-G repeats), in which the pendant single-stranded nucleic acid moieties are configured to inhibit co-localization of two or more nucleic acids on a solid support (e.g., at the same address in an array of addresses on a solid support). By coupling a pervious structure to a tunable compacted structure of a nucleic acid, the location and orientation of the pervious structure can be controlled to produce more specific and localized interactions between the nucleic acid and other entities.

A nucleic acid nanostructure, as set forth herein, may comprise at least one compacted region or structure. A compacted region of a nucleic acid nanostructure may refer to a region or structure with an average characteristic closer to an average characteristic for a multi-stranded nucleic acid (e.g., double-stranded DNA, triple-stranded DNA, etc.) relative to a single-stranded nucleic acid. A nucleic acid nanostructure, as set forth herein, may comprise at least one pervious region or structure. A pervious region of a nucleic acid nanostructure may refer to a region or structure with an average characteristic closer to an average characteristic for a single-stranded nucleic acid relative to a multi-stranded nucleic acid. A nucleic acid nanostructure, as set forth herein, need not comprise a pervious region or structure. A compacted region or structure of a nucleic acid nanostructure may comprise one or more characteristics of i) comprising a scaffold strand, ii) comprising a plurality of nucleic acids coupled to a scaffold strand, in which at least 50%, and optionally at least 60%, 70%, 75%, 80%, 85%, 90%, or 95% of nucleotides of the scaffold strand are base-pair hybridized to nucleotides of the plurality of nucleic acids, iii) comprising a plurality of coupled nucleic acids, in which at least 50%, and optionally at least 60%, 70%, 75%, 80%, 85%, 90%, or 95% of nucleotides of the plurality of nucleic acids are base-pair hybridized to other nucleotides of the plurality of nucleic acids, iv) comprising a plurality of secondary and/or tertiary nucleic acid structures, in which a position, orientation, and/or motion of a first secondary and/or tertiary nucleic acid structure relative to a second secondary and/or tertiary nucleic acid structure is constrained, v) comprising a first helical nucleic acid structure and a second helical nucleic acid structure, in which the first helical nucleic acid structure and the second helical nucleic acid structure are linked by a single-stranded nucleic acid, in which the first helical nucleic acid structure and the second helical nucleic acid structure each comprise a helical axis of symmetry parallel oriented in a 3' to 5' direction relative to the single-stranded nucleic acid, and in which an orientation of the helical axis of symmetry of the first helical nucleic acid structure relative to the helical axis of symmetry of the second helical nucleic acid structure has an angle between about 90° and 180°, vi) comprising a single-stranded nucleic acid that constrains a position, orientation, and/or motion of a first secondary and/or tertiary nucleic acid structure relative to a second secondary and/or tertiary nucleic acid structure; vii) comprising a moiety (e.g., a polypeptide, a polysaccharide, a nanoparticle, etc.) that constrains a position, orientation, and/or motion of a first secondary and/or tertiary nucleic acid structure relative to a second secondary and/or tertiary nucleic acid structure; viii) comprising a volume that encloses each nucleotide of the compacted region or structure, in which a characteristic dimension of the volume (e.g., a length, a depth, a diameter, etc.) does not vary by more than 10%, and optionally by no more than 5% or 1% due to intermolecular or extramolecular motion (e.g., Brownian motion, fluidic shear, electromagnetic forces, etc.), or due to intramolecular motion (e.g., translation, vibration, bending, rotation, etc.), ix) comprising a first nucleotide with a first tunable location and a second nucleotide with a second tunable location, in which the first tunable location comprises a distance from and orientation relative to the second tunable location, x) comprising a first nucleotide with a first tunable location and a second nucleotide with a second tunable location, in which the first tunable location comprises a distance from or an orientation relative to the second tunable location that varies by no more than 10%, xi) comprising a volume that encloses each nucleotide of the compacted region or structure, in which a characteristic dimension of the volume (e.g., a length, a depth, a diameter, etc.) does not vary by more than 10%, and optionally no more than 5%, or 1%, when the nucleic acid nanostructure comprising the compacted region or structure forms a binding interaction with a molecule, moiety, structure, or solid support, xii) comprising a two-dimensional projection of an area of the compacted region or structure that surrounds each nucleotide of the compacted region or structure, in which the two-dimensional projection does not vary by more than 10%, and optionally no more than 5%, or 1%, when the nucleic acid nanostructure comprising the compacted region or structure forms a binding interaction with a molecule, moiety, structure, or solid support, xiii) comprising a plurality of single-stranded nucleic acids, in which each single-stranded nucleic acid is less than about 20 nucleotides in length, and optionally no more than about 15, 10, or 5 nucleotides in length, xiv) comprising a first tertiary structure and a second tertiary structure, in which the second tertiary structure is adjacent to the first tertiary structure, and in which an average separation distance between the first tertiary structure and the secondary structure is no more than about 20 nanometers (nm), and optionally no more than about 10 nm or 5 nm as measured by an average separation distance between an axis of symmetry for the first tertiary structure and an axis of symmetry for the second tertiary structure, xv) comprising a first tertiary structure and a second tertiary structure, in which the second tertiary structure is adjacent to the first tertiary structure, in which the first tertiary structure and the second tertiary structure each comprise a common nucleic acid, and optionally two common nucleic acids, and in which the common nucleic acid comprises a bend of at least about 90°, in which the bend has a radius of curvature of no more than 10 nanometers (nm), and optionally no more than 5 nm or 2.5 nm, and xvi) comprising a first tertiary structure and a second tertiary structure, in which the second tertiary structure is adjacent to the first tertiary structure, in which the first tertiary structure and the second tertiary structure each comprise a common nucleic acid, and optionally two common nucleic acids, in which the common nucleic acid comprises a bend of at least about 90°, in which the bend has a radius of curvature of no more than 10 nanometers (nm), and optionally no more than 5 nm or 2.5 nm, and in which the first tertiary structure is not positioned adjacent to the second tertiary structure by a nucleic acid-binding entity (e.g., a nucleic acid-binding protein, a nanoparticle, etc.).

A nucleic acid nanostructure, as set forth herein, may comprise at least one pervious region or structure. A pervious region or structure of a nucleic acid nanostructure may comprise one or more characteristics of: i) not comprising a scaffold strand, ii) comprising one or more nucleic acids, in which each nucleic acid of the one or more nucleic acids comprises a first nucleotide sequence that is configured to hybridize to a scaffold strand of a compacted region or structure, and a second nucleotide sequence that is not configured to hybridize to an nucleic acid of the nucleic acid nanostructure, iii) comprising one or more nucleic acids, in which each nucleic acid of the one or more nucleic acids comprises a single-stranded nucleic acid of at least about 20 nucleotides in length, and optionally at least about 25, 50, 100, 500, 1000, or more than 1000 nucleotides in length, iv) comprising one or more nucleic acids, in which each nucleic acids of the one or more nucleic acids comprises an uncoupled terminal nucleotide (e.g., a 3' terminal nucleotide, a 5' terminal nucleotide), v) comprising a plurality of pendant moieties (e.g., single-stranded nucleic acids, partially-double-stranded nucleic acids, polymer chains, etc.), in which each pendant moiety comprises a position, orientation, or motion that is not constrained by an intramolecular or intrastructure binding interaction (e.g., base-pair hybridization, hydrogen-bonding, van der Waals interactions, etc.), vi) comprising a plurality of pendant moieties, in which each pendant moiety comprises a position, orientation, or motion that is constrained by a non-binding interaction (e.g., steric occlusion, electrostatic repulsion, magnetic repulsion, hydrophobic interactions, hydrophilic interactions, vii) comprising one or more coupled nucleic acids, in which less than 50%, and optionally less than 40%, 30%, 20%, 10%, 5%, or 1% of nucleotides of the plurality of nucleic acids are base-pair hybridized to other nucleotides of the plurality of nucleic acids, ix) comprising one or more nucleic acids, in which the one or more nucleic acids comprise a first single-stranded nucleic acid and a second single-stranded nucleic acid, in which the first single-stranded nucleic acid is not configured to hybridize to the second single-stranded nucleic acid, x) comprising one or more nucleic acids, in which the one or more nucleic acids comprise a single-stranded nucleic acid comprising a polynucleotide repeat (e.g., poly-A, poly-C, poly-G, poly-T), optionally in which the polynucleotide repeat comprises at least about 10 nucleotides, or at least about 20, 30, 40, 50, 100, 200, 500, 1000, or more than 1000 nucleotides, xi) comprising a volume that encloses each nucleotide of the pervious region or structure, in which a characteristic dimension of the volume (e.g., a length, a depth, a diameter, etc.) varies by more than 10%, and optionally by more than 15% or 20% due to intermolecular or extramolecular motion (e.g., Brownian motion, fluidic shear, electromagnetic forces, etc.), or due to intramolecular motion (e.g., translation, vibration, bending, rotation, etc.), xii) comprising a volume that encloses each nucleotide of the pervious region or structure, in which a characteristic dimension of the volume (e.g., a length, a depth a diameter, etc.) varies by more than 10%, and optionally more than 15% or 20%, when the nucleic acid nanostructure comprising the compacted region or structure forms a binding interaction with a molecule, moiety, structure, or solid support, xiii) comprising a two-dimensional projection of an area of the pervious region or structure that surrounds a furthest extent of the pervious region or structure when the nucleic acid nanostructure is not coupled to a molecule, moiety, structure or location, in which the two-dimensional projection varies by more than 10%, and optionally no more than 15%, or 20%, when the nucleic acid nanostructure comprising the pervious region or structure forms a binding interaction with the molecule, moiety, structure, or solid support, and xiv) comprising an nucleic acid, in which a first nucleotide sequence of the nucleic acid is coupled to a compacted structure, in which a second nucleotide sequence of the nucleic acid is not coupled to a compacted structure, and in which a nucleotide of the second nucleotide sequence comprises a larger spatial and/or temporal variation of a standard deviation in distance to the compacted structure relative to a nucleotide of the first nucleotide sequence.

In an aspect, provided herein is a nucleic acid nanostructure, comprising at least 10 coupled nucleic acids, in which the nucleic acid nanostructure comprises: a) a compacted region comprising high internal complementarity, in which the high internal complementarity comprises at least 50% double-stranded nucleic acids and at least 1% single-stranded nucleic acids, and in which the compacted region comprises a display moiety, in which the display moiety is coupled to, or configured to couple to, an analyte of interest, and b) a pervious region comprising low internal complementarity, in which the low internal complementarity comprises at least about 50% single-stranded nucleic acids, and in which the pervious region comprises a coupling moiety, in which the coupling moiety forms, or is configured to form, a coupling interaction with a solid support.

In another aspect, provided herein is a nucleic acid nanostructure, comprising: a) a compacted structure, in which the compacted structure comprises a scaffold strand and a first plurality of staple oligonucleotides, in which at least 80% of nucleotides of the scaffold strand are hybridized to nucleotides of the first plurality of staple oligonucleotides, in which the first plurality of staple oligonucleotides hybridizes to the scaffold strand to form a plurality of tertiary structures, in which the plurality of tertiary structures includes adjacent tertiary structures linked by a single-stranded region of the scaffold strand, and in which the relative positions of the adjacent tertiary structures are positionally constrained, and b) a pervious structure, in which the pervious structure comprises a second plurality of staple oligonucleotides, in which the staple oligonucleotides are coupled to the scaffold strand of the compacted structure, in which the pervious structure comprises at least 50% single-stranded nucleic acid, and in which the pervious structure has an anisotropic three-dimensional distribution around at least a portion of the compacted structure.

In another aspect, provided herein is a nucleic acid nanostructure, comprising: a) a compacted structure, in which the compacted structure comprises a scaffold strand and a first plurality of staple oligonucleotides, in which at least 80% of nucleotides of the scaffold strand are hybridized to nucleotides of the first plurality of staple oligonucleotides, in which the first plurality of staple oligonucleotides hybridizes to the scaffold strand to form a plurality of tertiary structures, in which the plurality of tertiary structures includes adjacent tertiary structures linked by a single-stranded region of the scaffold, in which the relative positions of the adjacent tertiary structures are positionally constrained, and in which the compacted structure comprises an effective surface area; and b) a pervious structure, in which the pervious structure comprises a second plurality of staple oligonucleotides, in which the staple oligonucleotides are coupled to the scaffold strand of the compacted structure, in which the pervious structure comprises at least 50% single-stranded nucleic acid, and in which (i) the effective surface area of the nucleic acid nanostructure is larger than the effective surface area of the compacted structure or (ii) the ratio of effective surface area to volume of the nucleic acid nanostructure is larger than the ratio of effective surface area to volume of the compacted structure.

In another aspect, provided herein is a nucleic acid nanostructure, comprising a plurality of nucleic acid strands, in which each strand of the plurality of strands is hybridized to another strand of the plurality of strands to form a plurality of tertiary structures, and in which a strand of the plurality of strands comprises a first nucleotide sequence that is hybridized to a second strand of the plurality of strands, in which the strand of the plurality of strands further comprises a second nucleotide sequence of at least 100 consecutive nucleotides, and in which at least 50 nucleotides of the second nucleotide sequence is single-stranded.

Figures 52A, 52B:
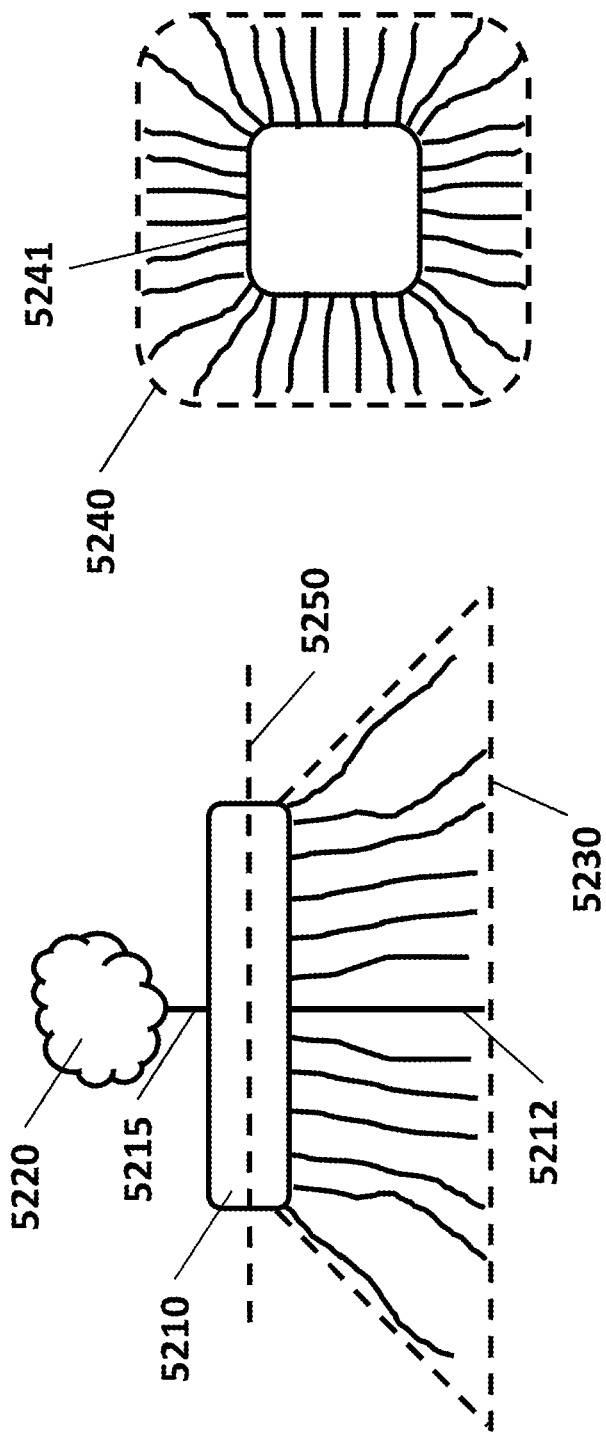
FIGS. 52A, 52B, 52C, 52D, 52E, 52F, 52G, and 52H depict various configurations of nucleic acid nanostructures comprising compacted structures and pervious structures, in accordance with some embodiments.

FIGS. 52A-52H illustrate various configurations of nucleic acid nanostructure comprising a compacted structure and a pervious structure. FIG. 52A depicts a cross-sectional view of a nucleic acid nanostructure comprising a SNAP 5210 (e.g., a nucleic acid origami) coupled to an analyte 5220 by a display moiety 5215 on a display face of the SNAP 5210. The nucleic acid nanostructure further comprises a capture face that is opposite (e.g., about 180° in orientation from) the display face of the SNAP 5210. The capture face comprises a pervious structure comprising a plurality of pendant moieties 5212 (e.g., single-stranded nucleic acids, polymer chains, etc.) that are coupled to the capture face of the SNAP 5210, in which the pendant moieties 5212 comprise unbound termini. Depending upon the density of the plurality of pendant moieties 5212 and the rigidity of the coupling points to the compacted structure of the SNAP 5210, the plurality of pendant moieties may arrange in an outwardly-fanned configuration. Volume 5230 encloses an average space occupied by the pervious structure comprising the plurality of pendant moieties. The pendant moieties 5212 within volume 5230 have an anisotropic spatial distribution with respect to the compacted structure of the SNAP 5210 due to the tunable positioning and orientation of the pendant moieties on the capture face of the SNAP 5210. FIG. 52B illustrates a top-down view of the nucleic acid nanostructure in FIG. 52A. Line 5241 outlines the effective surface area of the compacted structure of the SNAP 5210 and line 5240 outlines the effective surface area of the complete nucleic acid nanostructure (i.e. including the compacted structure and the pervious structure), which is greater than the effective surface area of the compacted structure due to the outward fanning of the pendant moieties 5212.

Figures 52C, 52D:
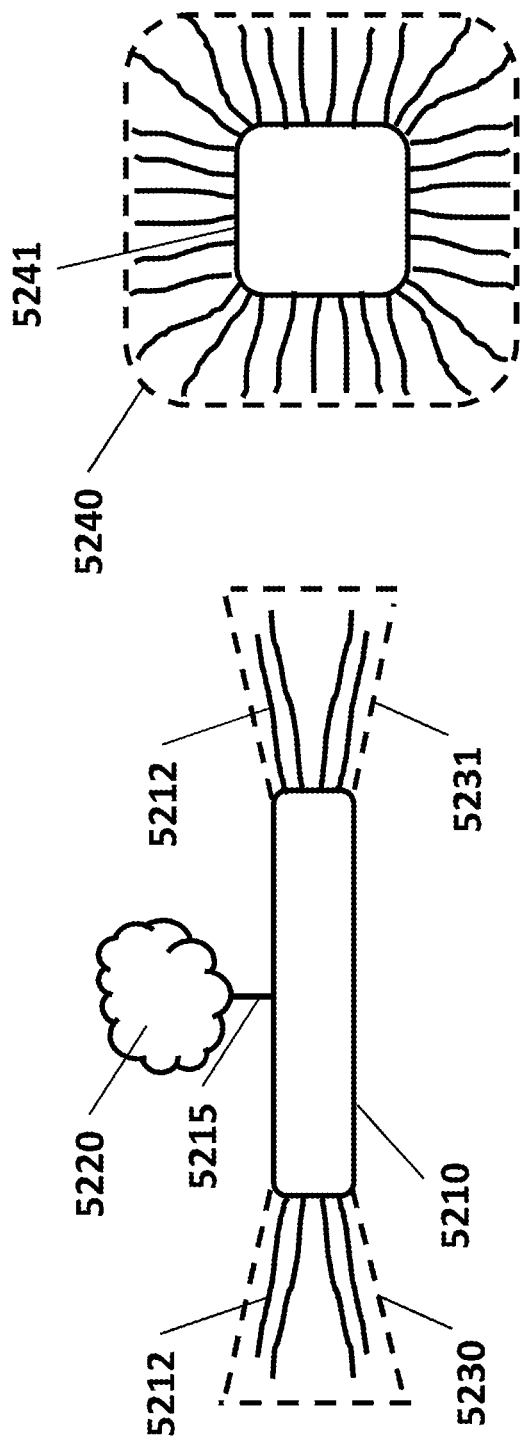

FIG. 52C depicts a cross-sectional view of a nucleic acid nanostructure comprising a SNAP 5210 (e.g., a nucleic acid origami) coupled to an analyte 5220 by a display moiety 5215 on a display face of the SNAP 5210. The nucleic acid nanostructure further comprises one or more utility faces that are adjacent and orthogonal to (e.g., about 90° in orientation from) the display face of the SNAP 5210. Each utility face comprises a pervious structure comprising a plurality of pendant moieties 5212 (e.g., single-stranded nucleic acids, polymer chains, etc.) that are coupled to the utility face of the SNAP 5210. Depending upon the density of the plurality of pendant moieties 5212, the flexibility of the pendant moieties 5212 and the rigidity of the coupling points to the compacted structure of the SNAP 5210, the plurality of pendant moieties 5212 may arrange in an outwardly-fanned configuration. lines 5230 and 5231 encloses an average cross-sectional area of the space occupied by the pervious structure comprising the plurality of pendant moieties. Pendant moieties 5212 within the space indicated by lines 5230 and 5231 comprise a substantially isotropic spatial distribution with respect to the midline of the compacted structure of the SNAP 5210 and an anisotropic spatial distribution relative to the analyte 5220 due to the tunable positioning and orientation of the pendant moieties on the capture face of the SNAP 5210. FIG. 52D illustrates a top-down view of the nucleic acid nanostructure. Line 5241 outlines the effective surface area of the compacted structure of the SNAP 5210 and line 5240 outlines the effective surface area of the complete nucleic acid nanostructure (i.e. including the compacted structure and the pervious structure), which is greater than the effective surface area of the compacted structure due to the outward direction of the pedant moieties 5212.

Figure 52F:
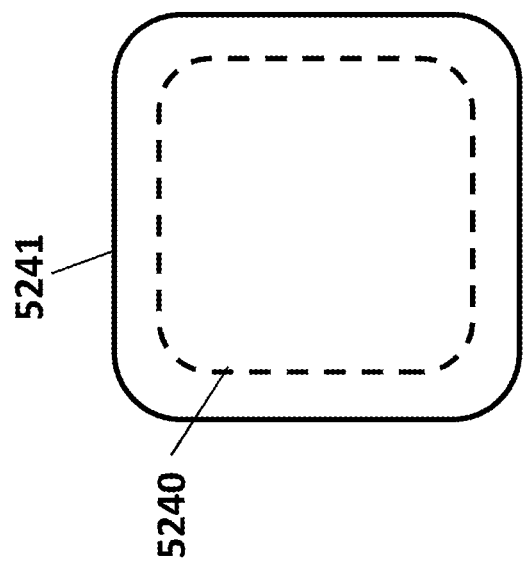
Figure 52E:
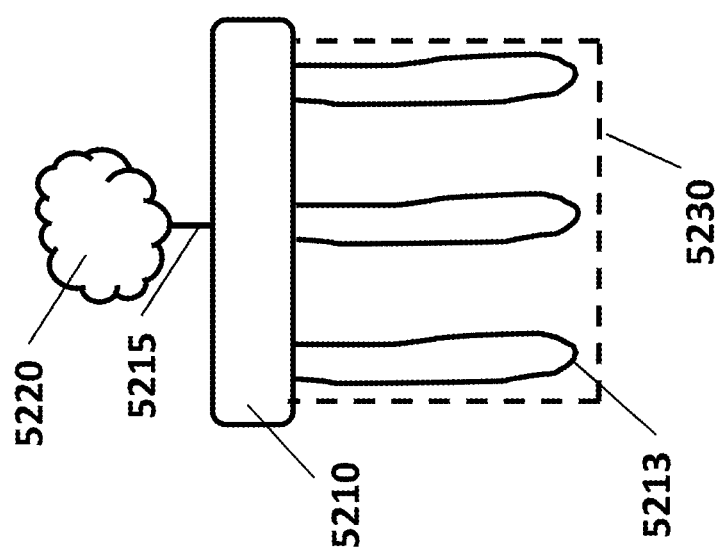

FIG. 52E depicts a cross-sectional view of a nucleic acid nanostructure comprising a SNAP 5210 (e.g., a nucleic acid origami) coupled to an analyte 5220 by a display moiety 5215 on a display face of the SNAP 5210. The nucleic acid nanostructure further comprises a capture face that is opposite (e.g., about 180° in orientation from) the display face of the SNAP 5210. The capture face comprises a pervious structure comprising a plurality of pendant moieties 5213 (e.g., single-stranded nucleic acids, polymer chains, etc.) that are coupled to the capture face of the SNAP 5210, in which the pendant moieties 5213 have both termini coupled to the compacted structure of the SNAP 5210. Depending upon the density of the plurality of pendant moieties 5213, their flexibility and the rigidness of the coupling points to the compacted structure of the SNAP 5210, the plurality of pendant moieties may occupy a volume directly below the capture face of the SNAP 5210. Line 5230 encloses an average cross-sectional area of the space occupied by the pervious structure comprising the plurality of pendant moieties 5213. Pendant moieties 5213 within the space indicated by line 5230 comprises an anisotropic spatial distribution with respect to the compacted structure of the SNAP 5210 due to the tunable positioning and orientation of the pendant moieties on the capture face of the SNAP 5210. FIG. 52F illustrates a top-down view of the nucleic acid nanostructure. Line 5241 outlines the effective surface area of the compacted structure of the SNAP 5210 and line 5240 outlines the effective surface area of the complete nucleic acid nanostructure (i.e. including the compacted structure and the pervious structure), which is smaller than the effective surface area of the compacted structure of the SNAP 5210.

Figures 52G, 52H:
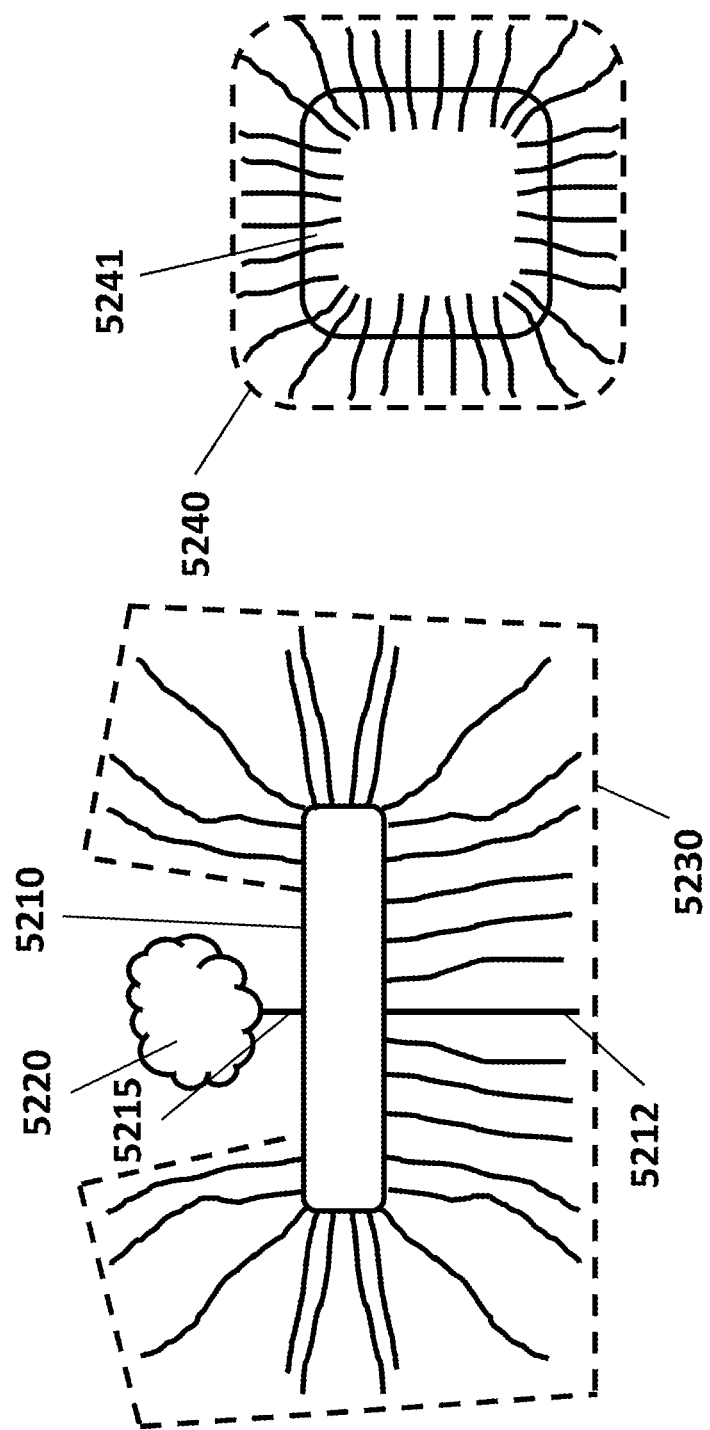

FIG. 52G depicts a cross-sectional view of a nucleic acid nanostructure comprising a SNAP 5210 (e.g., a nucleic acid origami) coupled to an analyte 5220 by a display moiety 5215 on a display face of the SNAP 5210. The nucleic acid nanostructure further comprises a plurality of pendant moieties 5212 (e.g., single-stranded nucleic acids, polymer chains, etc.) that are coupled to nearly all orientations of the SNAP 5210 excluding a volume occupied by the analyte 5220. Depending upon the density of the plurality of pendant moieties 5212, their flexibility and the rigidness of the coupling points to the compacted structure of the SNAP 5210, the plurality of pendant moieties may arrange in an outwardly-fanned configuration. Line 5230 encloses an average cross-section of the space occupied by the pervious structure comprising the plurality of pendant moieties 5212. Pendant moieties 5212 within the space indicated by line 5230 comprises an anisotropic spatial distribution with respect to the compacted structure of the SNAP 5210 although it may be an isotropic spatial distribution excluding the volume occupied by the analyte 5220. FIG. 52H illustrates a top-down view of the nucleic acid nanostructure. Line 5241 outlines the effective surface area of the compacted structure of the SNAP 5210 and line 5240 outlines the effective surface area of the complete nucleic acid nanostructure (i.e. including the compacted structure and the pervious structure), which is greater than the effective surface area of the compacted structure due to the outward fanning of the pedant moieties 5212.

Figure 53B:
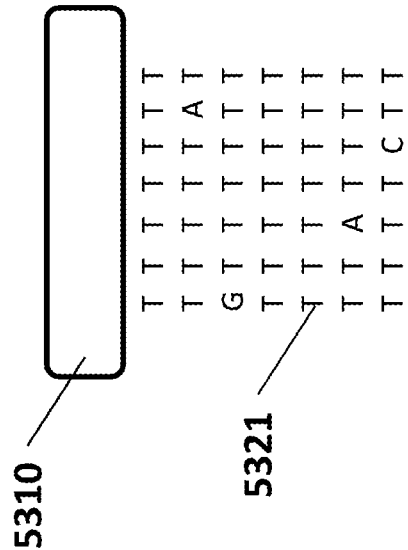
FIGS. 53A, 53B, 53C, 53D, and 53E illustrate various configurations of nucleic acid nanostructures comprising pervious structures that are configured to form multi-valent binding interactions, in accordance with some embodiments.
Figure 53A:
Figure 53E:
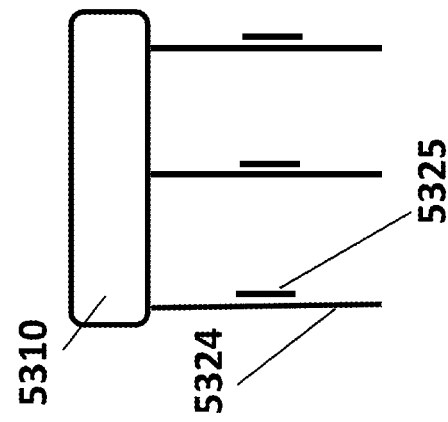
Figure 53D:
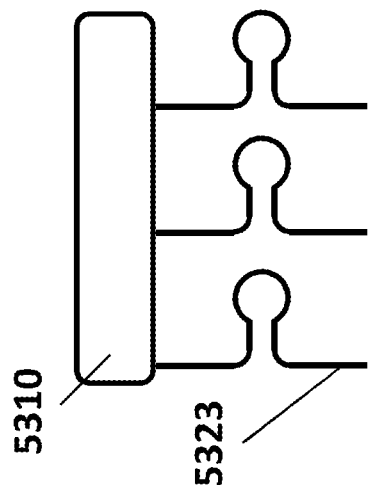
Figure 53C:
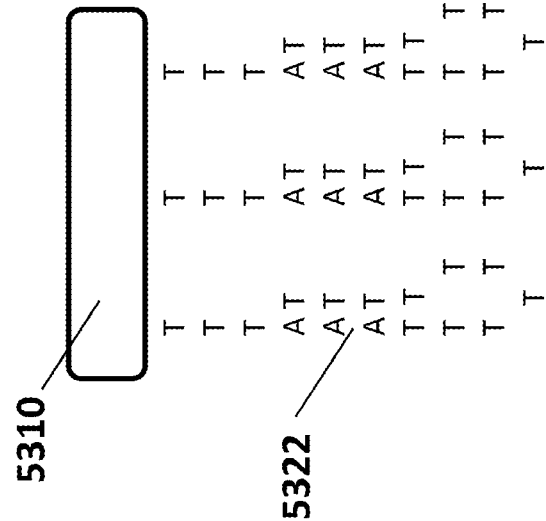

FIGS. 53A-53E depict cross-sectional views of various nucleic acid nanostructure configurations, in which each nucleic acid nanostructure comprises a pervious structure, and in which each pervious structure comprises a plurality of pendant moieties that are configured to have differing interactions with other entities (e.g., analytes, other nucleic acid nanostructures, solid supports, reagents, etc.). FIG. 53A depicts a compacted structure 5310 (e.g., a SNAP) that is coupled to a pervious structure comprising a plurality of pendant oligonucleotides 5320, in which each pendant oligonucleotide comprises a homopolymer. The homopolymer of each pendant oligonucleotide 5320 may inhibit binding interactions with other nucleic acid nanostructures having the same or similar pendant oligonucleotide sequences. FIG. 53B depicts a compacted structure 5310 (e.g., a SNAP) that is coupled to a pervious structure comprising a plurality of pendant oligonucleotides 5321, in which each pendant oligonucleotide comprises homopolymer sequences, and in which some homopolymers are interrupted by random substitutions of nucleotides other than the nucleotide of the homopolymer sequence (e.g., a poly-T sequence comprising randomly-substituted A, C, or G nucleotides). FIG. 53C depicts a compacted structure 5310 (e.g., a SNAP) that is coupled to a pervious structure comprising a plurality of pendant oligonucleotides 5320, in which each pendant oligonucleotide comprises a homopolymer sequence region, and a sequence region that complements the homopolymer sequence region. As shown the complementary regions can form a double stranded region 5322 to form a loop structure. FIG. 53D depicts a compacted structure 5310 (e.g., a SNAP) that is coupled to a pervious structure comprising a plurality of pendant oligonucleotides 5323, in which each pendant oligonucleotide comprises a nucleotide sequence with a degree of self-complementarity (e.g., forming a stem, loop, hairpin, or bulge structure). FIG. 53E depicts a compacted structure 5310 (e.g., a SNAP) that is coupled to a pervious structure comprising a plurality of pendant oligonucleotides 5324, in which each pendant oligonucleotide comprises a second oligonucleotide 5325 that hybridizes to the pendant oligonucleotide 5324. The configurations illustrated in FIGS. 53A-53E (e.g., polynucleotide repeats, random nucleotide substitutions, self-complementarity, intermittent secondary structure) may facilitate re-arrangement of orientation of the nucleic acid nanostructure on a coupling surface, thereby facilitating positioning of the nucleic acid nanostructure in a stable configuration on the coupling surface.

Figure 54A:
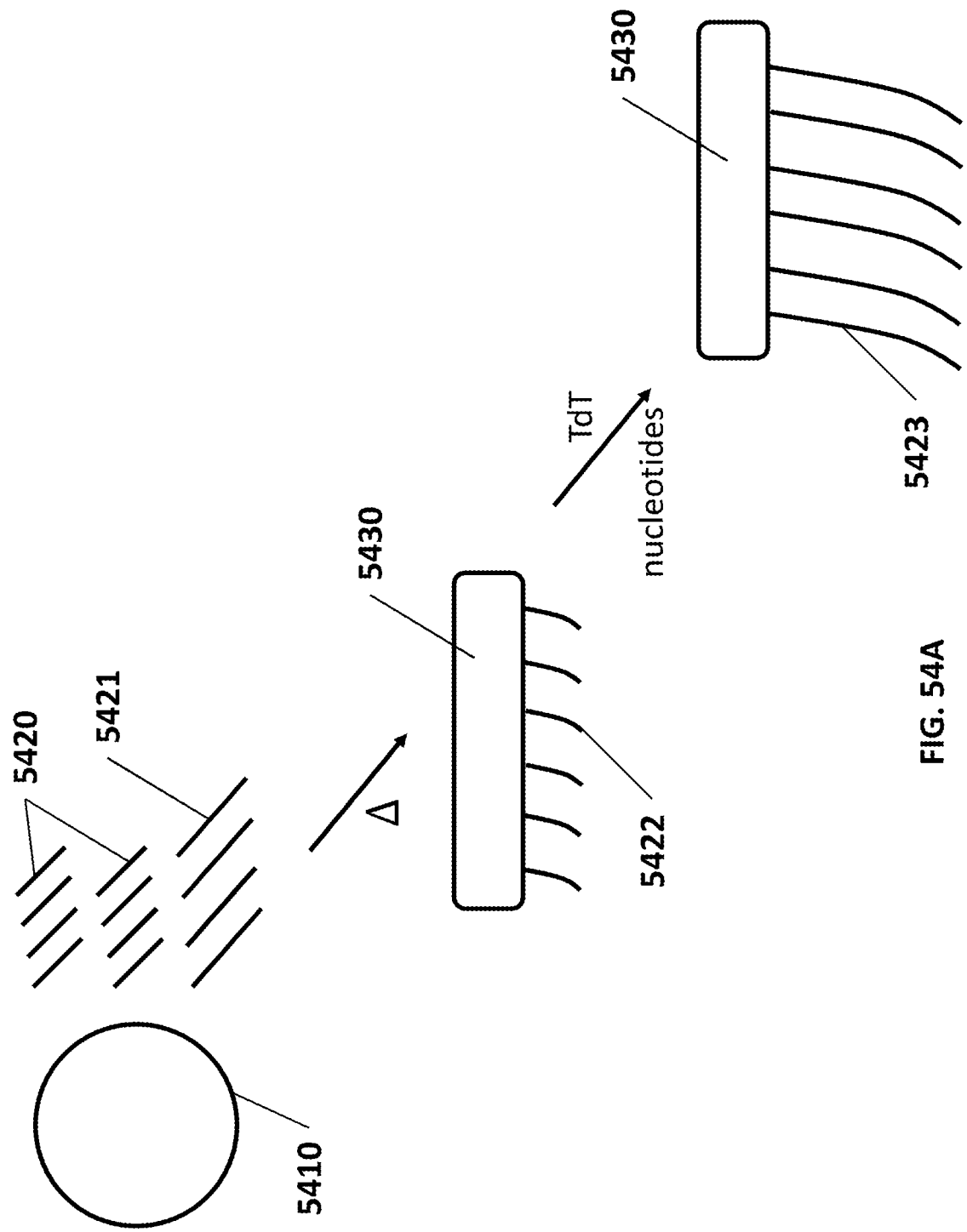
FIGS. 54A, 54B, and 54C show methods for forming nucleic acid nanostructures with pervious structures, in accordance with some embodiments.
Figure 54B:
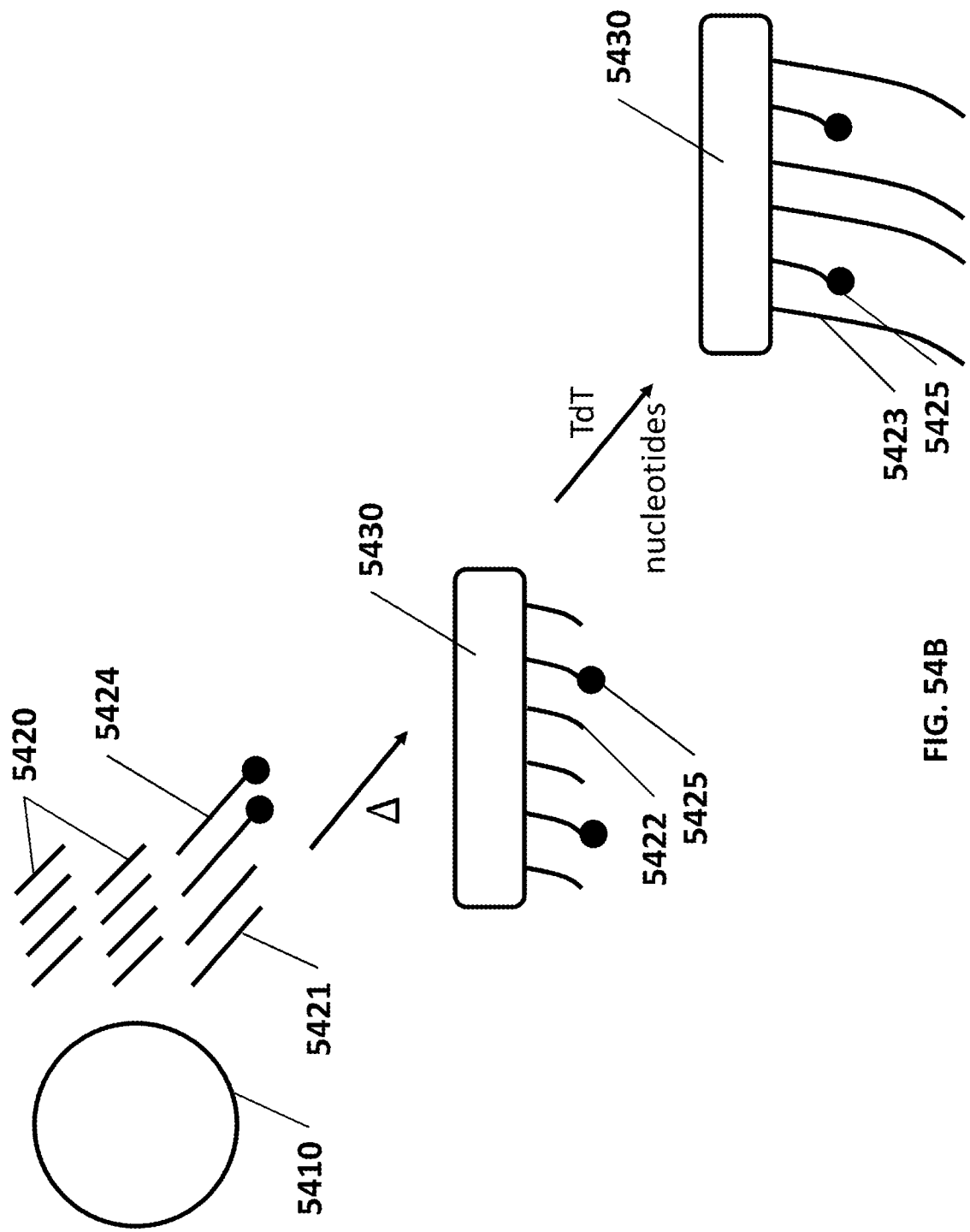
Figure 54C:
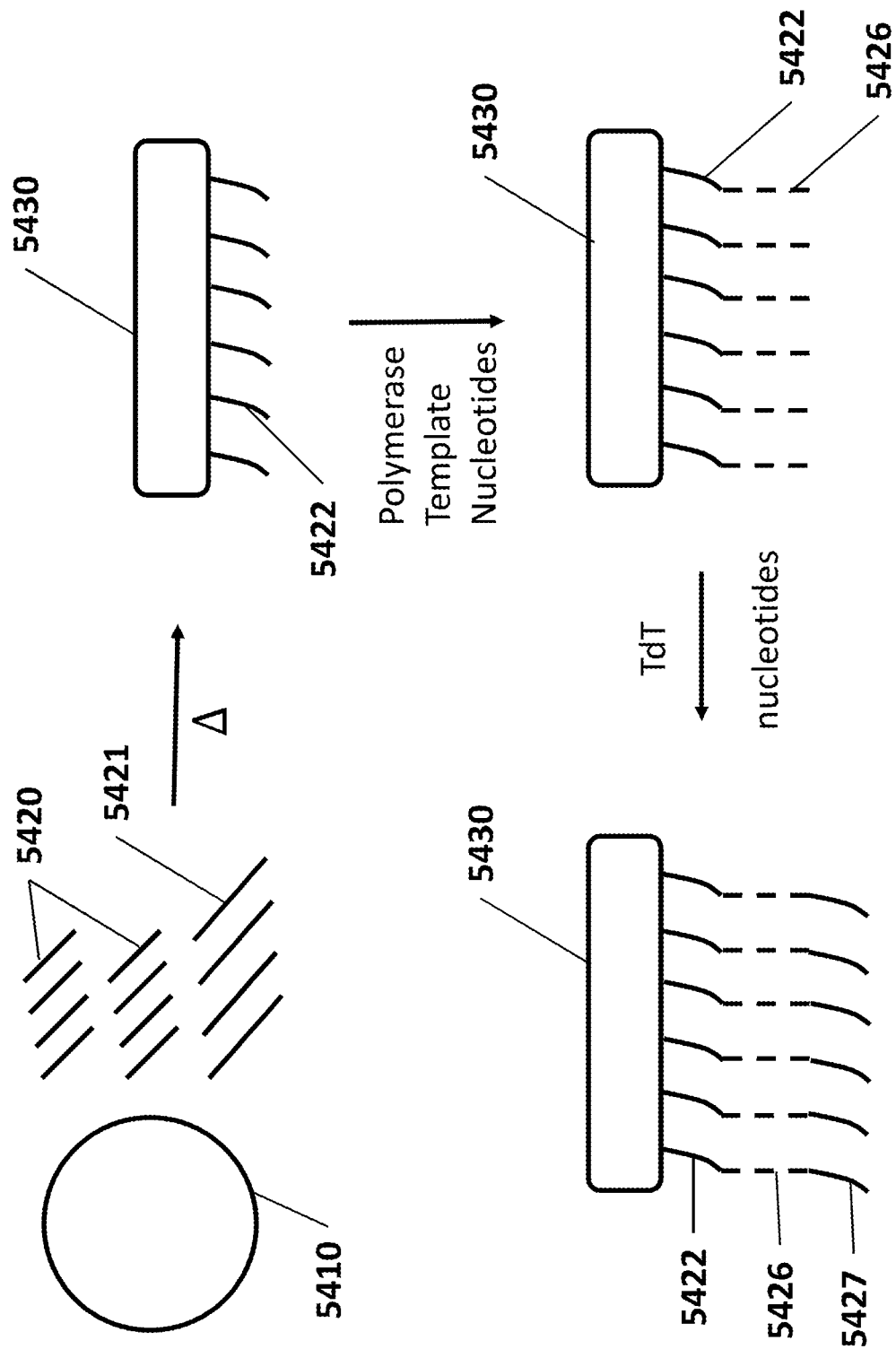

FIGS. 54A-54C illustrate a schematic for methods of producing nucleic acid nanostructures in accordance with some embodiments set forth herein (e.g., nucleic acid nanostructures depicted in FIGS. 53A-53E). FIG. 54A depicts a method of forming a nucleic acid nanostructure comprising a plurality of pendant moieties comprising polynucleotide repeats. In a first step, a scaffold strand 5410 may be combined, optionally at an elevated temperature, with a plurality of staple oligonucleotides 5420 that hybridize to the scaffold strand 5410 to form a compacted structure, and a plurality of oligonucleotides 5421 that comprise pendant nucleotide sequences 5422. After cooling the oligonucleotide mixture, a nucleic acid nanostructure is formed comprising a compacted structure 5430 and a plurality of pendant moieties comprising the pendant nucleotide sequences 5422. In a second step, the nucleic acid nanostructures are subsequently contacted with a nucleic acid extension enzyme (e.g., terminal deoxynucleotide transferase or TdT is shown) in the presence of a homogeneous plurality of nucleotides (e.g. deoxythymidine) to produce a plurality of pendant homopolymeric polynucleotides 5423 (e.g., poly-T repeats). Optionally, the nucleotides provided to the enzyme may comprise small quantities of other nucleotides to generate randomly incorporated nucleotides in the polynucleotide repeats. FIG. 54B depicts a method of forming a nucleic acid nanostructure comprising a plurality of pendant moieties comprising homopolymeric polynucleotides, in which the location of each pendant moieties is controlled. In a first step, a scaffold strand 5410 may be combined, optionally at an elevated temperature, with a plurality of staple oligonucleotides 5420 that hybridize to the scaffold strand 5410 to form a compacted structure, and a plurality of oligonucleotides 5421 that comprise pendant nucleotide sequences 5422, as well as a plurality of oligonucleotides 5424 comprising a capping moiety 5425 (e.g., a dideoxynucleotide, a terminator nucleotide, a phosphorylated nucleotide, a terminal residue to buries within the compacted structure 5430, etc.), in which the capping moiety is configured to inhibit the activity of a nucleic acid extension enzyme. After cooling the oligonucleotide mixture, a nucleic acid nanostructure is formed comprising a compacted structure 5430 and a plurality of pendant moieties comprising the pendant nucleotide sequences 5422 at least some of which include the capping moiety 5425. In a second step, the nucleic acid nanostructures are subsequently contacted with a nucleic acid extension enzyme (e.g., terminal deoxynucleotide transferase or TdT) in the presence of a homogeneous plurality of nucleotides (e.g. deoxythymidine) to produce a plurality of pendant polynucleotide repeats 5423 (e.g., poly-T repeats) at any pendant oligonucleotide that does not comprise a capping moiety 5425. FIG. 54C depicts a method of forming a nucleic acid nanostructure comprising a plurality of pendant moieties comprising homopolymeric sequence, in which the homopolymeric sequence is interrupted by an intermediate nucleotide sequence. Nucleic acid nanostructures are formed according to the first step described in FIG. 54A. Optionally, the second step depicted in FIG. 54A may be performed to add a homopolymeric sequence to each pendant moiety. In a second step, a polymerase extension reaction is performed whereby pendant primers 5422 hybridize to template nucleic acids that contain a complement of an intermediate nucleotide sequence 5426. The polymerase extension reaction will produce pendant oligonucleotides including primer sequence 5422 and intermediate nucleotide sequence 5426. In a third step, the enzymatic extension step of FIG. 54A is performed using TdT and nucleotides to form nucleic acid nanostructures with a plurality of pendant moieties, in which each pendant moiety comprises an intermediate nucleotide sequence 5426 flanked by pendant primer sequence 5422 and homopolymer sequence 5427.

A nucleic acid nanostructure or a component structure thereof, as set forth herein, may comprise regions of internal complementarity. Internal complementarity may refer to the extent of double-stranded nucleic acid within a nucleic acid nanostructure or a component structure thereof. Internal complementarity may be quantified as a percentage of nucleotides with a base pair complement in a formed nucleic acid nanostructure or a component structure thereof (e.g., a compacted structure, a pervious structure). Extent of internal complementarity may be calculated with respect to total nucleotide content. For example, a nucleic acid nanostructure may comprise 10000 total nucleotides amongst at least 200 oligonucleotides that form the nucleic acid nanostructure, in which 8500 nucleotides have a base pair complement in a double stranded region, giving the nucleic acid nanostructure 85% internal complementarity. An extent of internal complementarity may be calculated with respect to a single nucleic acid (e.g., a scaffold strand) or a subset of oligonucleotides comprising a nucleic acid nanostructure or a component structure thereof. For example, a compacted structure of a nucleic acid nanostructure may comprise a scaffold strand of at least 7000 nucleotides, in which at least 90% of the nucleotides of the scaffold strand have a base-pair complement in a double stranded region. In another example, a pervious structure of a nucleic acid nanostructure may comprise a plurality of pendant moieties, in which each pendant moiety comprises a nucleotide sequence with no internal complementarity and no complementarity to any other pendant moiety, thereby giving the pervious structure a substantially 0% internal complementarity.

A nucleic acid nanostructure or a component structure thereof (e.g., a compacted structure, a pervious structure) may comprise an internal complementarity of at least about 1%, 5%, 10%, 15%, 20%, 25%, 30%, 35%, 40%, 45%, 50%, 55%, 60%, 65%, 70%, 75%, 80%, 85%, 90%, 95%, 99%, or more than 99%. Alternatively or additionally, a nucleic acid nanostructure or a component structure thereof may comprise an internal complementarity of no more than about 99%, 95%, 90%, 85%, 80%, 75%, 70%, 65%, 60%, 55%, 50%, 45%, 40%, 35%, 30%, 25%, 20%, 15%, 10%, 5%, 1%, or less than 1%. In some configurations, a nucleic acid nanostructure or a component structure thereof may be considered to have high internal complementarity if the internal complementarity exceeds a percentage, such as at least about 80%, 85%, 90%, 91%, 92%, 93%, 94%, 95%, 96%, 97%, 98%, 99%, or more than 99%. In some configurations, a nucleic acid nanostructure or a component structure thereof may be considered to have low internal complementarity if the internal complementarity falls below a percentage, such as no more than 20%, 15%, 10%, 9%, 8%, 7%, 6%, 5%, 4%, 3%, 2%, 1%, or less than 1%.

A nucleic acid nanostructure or a component structure thereof with a high internal complementarity may comprise some amount of single-stranded nucleic acid. A nucleic acid nanostructure or a component structure thereof with a high internal complementarity may comprise at least about 1%, 2%, 3%, 4%, 5%, 6%, 7%, 8%, 9%, 10%, 15%, 20%, or more than 20% single-stranded nucleic acids. In some configurations, a nucleic acid nanostructure or a component structure thereof with a high internal complementarity may comprise no single-stranded nucleic acids. A nucleic acid nanostructure or a component structure thereof with a low internal complementarity may comprise some amount of double-stranded nucleic acid. A nucleic acid nanostructure or a component structure thereof with a low internal complementarity may comprise no more than about 20%, 15%, 10%, 9%, 8%, 7%, 6%, 5%, 4%, 3%, 2%, 1%, or less than 1% double-stranded nucleic acids. In some configurations, a nucleic acid nanostructure or a component structure thereof with a low internal complementarity may comprise no double-stranded nucleic acids.

A nucleic acid nanostructure may comprise a region comprising low internal complementarity (e.g., a pervious structure), in which the region comprising the low internal complementarity comprises a plurality of pendant moieties. A pendant moiety may comprise a capture moiety, as set forth herein. A pendant moiety need not comprise a capture moiety. A nucleic acid nanostructure may comprise a plurality of oligonucleotides, in which each oligonucleotide comprises a first nucleotide sequence that hybridizes to a complementary nucleic acid to form a portion of a structure with high internal complementarity, and in which each oligonucleotide comprises a pendant moiety that does not hybridize to the region of high internal complementarity. In some cases, a pendant moiety may comprise a single-stranded oligonucleotide or a non-nucleic acid polymer chain (e.g., polyethylene glycol, polyethylene, polypropylene, etc.). A pendant moiety may comprise a polymer chain (e.g., a nucleic acid chain, a non-nucleic acid polymer chain), in which the polymer chain comprises a linear chain, a branched chain, a dendrimeric chain, or a combination thereof. In some configurations, a pendant moiety of a plurality of pendant moieties may comprise an unbound terminal residue. In some configurations, a pendant moiety of a plurality of pendant moieties may comprise no self-complementarity. In some configurations, a pendant moiety of a plurality of pendant moieties may comprise a homopolymer sequence selected from the group consisting of poly-T, a poly-A, a poly-G, and a poly-C. For example, an oligonucleotide may be extended by an enzyme (e.g., terminal deoxynucleotidyl transferase) in the presence of a homogeneous plurality of deoxythymidine nucleotides to form a poly-T sequence on the oligonucleotide. A plurality of pendant moieties may comprise a homogeneous plurality of pendant moieties, in which each pendant moiety comprises a same chemical structure as each other pendant moiety of the plurality of pendant moieties. A plurality of pendant moieties may comprise a heterogeneous plurality of pendant moieties, in which a first pendant moiety comprises a different chemical structure from a second pendant moiety of the plurality of pendant moieties.

A pendant moiety or a component thereof may comprise a nucleotide sequence (e.g., a homopolymer, a polynucleotide repeat, an oligonucleotide without self-complementarity, an oligonucleotide with self-complementarity, etc.). A nucleotide sequence of a pendant moiety or a component thereof may have a sequence length or chemical composition exemplified herein for staple oligonucleotides.

A nucleic acid nanostructure may comprise a region comprising a low internal complementarity (e.g., a pervious structure), in which the region comprising the low internal complementarity comprises a quantity of pendant moieties. A region comprising a low internal complementarity may comprise at least 1, 5, 10, 15, 20, 25, 30, 35, 40, 50, 100, 200, 300, 400, 500, 600, 700, 800, 900, 1000, or more than 1000 pendant moieties. Alternatively or additionally, a region comprising a low internal complementarity may comprise no more than about 1000, 900, 800, 700, 600, 500, 400, 300, 200, 100, 50, 40, 35, 30, 25, 20, 15, 10, 5, or less than 5 pendant moieties. A quantity of pendant moieties of a nucleic acid nanostructure may be determined based upon a quantity of positions available on a face (e.g., a capture face, a utility face) of a nucleic acid nanostructure. A quantity of pendant moieties of a nucleic acid nanostructure may be determined based upon a desired surface density of the pendant moieties on a face of the nucleic acid nanostructure. For example, it may be advantageous to maximize surface density of pendant capture moieties on a capture face of a SNAP, in which the pendant capture moieties have a substantially homogeneous surface density. In such an example, the maximum number of pendant moieties that can be provided to the SNAP may be limited by a quantity of suitable positions that comprise an orientation in the capture face and a distance from a nearest suitable position that is within, for example, about 20%, 15%, 10% 5%, or less than 5% of an average distance between suitable positions. A quantity of pendant moieties provided to a nucleic acid nanostructure may be determined based upon a strength of a desired interaction with another entity (e.g., an analyte, a nucleic acid nanostructure, a solid support, a reagent, etc.). For example, additional pendant capture moieties may be added to a nucleic acid nanostructure to increase a strength of a coupling interaction with a surface of a solid support.

A nucleic acid nanostructure may comprise a compacted structure. A compacted structure may comprise a plurality of tertiary structures (e.g., helical double-stranded nucleic acids). Each tertiary structure may comprise an axis of symmetry (e.g., a helical axis) that defines an angular orientation of the tertiary structure. A distance between adjacent or non-adjacent tertiary structures may be measured as a distance between respective axes of symmetry of the tertiary structures. An average distance between adjacent or non-adjacent non-parallel tertiary structures may be measured as an average distance between respective axes of symmetry of the tertiary structures. A compacted structure may comprise a plurality of tertiary structures, in which a position, orientation, and/or freedom of motion is constrained between a first tertiary structure and a second tertiary structure (e.g., an adjacent tertiary structure, a non-adjacent tertiary structure). A position, orientation, and/or freedom of motion between a first tertiary structure and a second tertiary structure may be constrained by one or more linking strands, as set forth herein.

A compacted structure may comprise a plurality of tertiary structures, in which the plurality of tertiary structures comprises a first tertiary structure comprising a first axis of symmetry and a second tertiary structure comprising a second axis of symmetry, in which the first tertiary structure is adjacent to the second tertiary structure, and in which a constrained position of the first tertiary structure relative to the second tertiary structure comprises an average separation distance between the first axis of symmetry and the second axis of symmetry of less than about 50 nanometers (nm), 40 nm, 30 nm, 20 nm, 10 nm, 9 nm, 8 nm, 7 nm, 6 nm, 5 nm, 4 nm, 3 nm, 2 nm, or less than 2 nm. Alternatively or additionally, a compacted structure may comprise a plurality of tertiary structures, in which the plurality of tertiary structures comprises a first tertiary structure comprising a first axis of symmetry and a second tertiary structure comprising a second axis of symmetry, in which the first tertiary structure is adjacent to the second tertiary structure, and in which a constrained position of the first tertiary structure relative to the second tertiary structure comprises an average separation distance between the first axis of symmetry and the second axis of symmetry of at least about 2 nm, 3 nm, 4 nm, 5 nm, 6 nm, 7 nm, 8 nm, 9 nm, 10 nm, 20 nm, 30 nm, 40 nm, 50 nm, or more than 50 nm.

A compacted structure may comprise a plurality of tertiary structures, in which the plurality of tertiary structures comprises a first tertiary structure comprising a first axis of symmetry and a second tertiary structure comprising a second axis of symmetry, in which the first tertiary structure is adjacent to the second tertiary structure, and in which the constrained position of the first tertiary structure relative to the second tertiary structure comprises an average angular offset of at least about 0°, 10°, 20°, 30°, 40°, 50°, 60°, 70°, 80°, 90°, 100°, 110°, 120°, 130°, 140°, 150°, 160°, 170°, or 180° between the first axis of symmetry and the second axis of symmetry. Alternatively or additionally, a compacted structure may comprise a plurality of tertiary structures, in which the plurality of tertiary structures comprises a first tertiary structure comprising a first axis of symmetry and a second tertiary structure comprising a second axis of symmetry, in which the first tertiary structure is adjacent to the second tertiary structure, and in which the constrained position of the first tertiary structure relative to the second tertiary structure comprises an average angular offset of no more than about 180°, 170°, 160°, 150°, 140°, 130°, 120°, 110°, 100°, 90°, 80°, 70°, 60°, 50°, 40°, 30°, 20°, 10°, or 0° between the first axis of symmetry and the second axis of symmetry.

A nucleic acid nanostructure may comprise a compacted structure, in which the compacted structure comprises a nucleic acid origami, as set forth herein. A nucleic acid origami may comprise one or more faces, in which a face of the one or more faces comprises a moiety (e.g., a display moiety, a capture moiety, a utility moiety, etc.), and in which the nucleic acid origami provides a tunable location and/or orientation for the moiety. In some configurations, a nucleic acid origami may comprise a first face and a second face, in which the first face is offset from the second face by an average angle of at least about 30°, 45°, 60°, 90°, 120°, 135°, 150°, 160°, 170°, or 180°. Alternatively or additionally, a nucleic acid origami may comprise a first face and a second face, in which the first face is offset from the second face by an average angle of no more than about 180°, 170°, 160°, 150°, 135°, 120°, 90°, 60°, 45°, 30°, or less than 30°. A nucleic acid origami may comprise a first face and a second face, in which the first face comprises a display moiety, as set forth herein, and the second face is adjacent to a pervious structure. A nucleic acid origami may comprise a first face and a second face, in which the first face comprises a display moiety, as set forth herein, and the second face is coupled to a pervious structure. For example, a nucleic acid origami with a tile structure may comprise a first face that comprises a click-type reaction group that is configured to couple an analyte, and a second face that comprises a capture moiety comprising a plurality of pendant moieties, in which a pervious structure comprises the plurality of pendant moieties, and in which the first face is substantially opposite in orientation from the second face (e.g., about 180° offset).

A nucleic acid nanostructure may comprise a compacted structure and a pervious structure, in which the pervious structure comprises a spatial distribution with respect to the compacted structure. A spatial distribution may comprise an isotropic distribution or an anisotropic distribution. A spatial distribution may be with respect to two spatial dimensions and/or three spatial dimensions. For example, a pervious structure may comprise an isotropic spatial distribution in two spatial dimensions but an anisotropic spatial distribution with respect to three spatial distributions. For example, FIG. 52A depicts a cross-sectional view of a nucleic acid nanostructure with a compacted structure 5210 that is coupled to a pervious structure comprising a plurality of pendant moieties 5212. With respect to a plane of symmetry 5250 centered at an average midline of the compacted structure 5210, the plurality of pendant moieties 5212 are confined to a volume 5230 that is entirely below the plane of symmetry 5250 (e.g., anisotropic with respect to the plane of symmetry 5250). FIG. 52B depicts a top-down view of the nucleic acid nanostructure depicted in FIG. 52A. From the top-down view, the plurality of pendant moieties have a substantially isotropic spatial distribution with respect to a center point of the compacted structure 5210. In some configurations, a spatial distribution of a pervious structure relative to a compacted structure may be determined with respect to an imaginary volume (e.g., a sphere, a hemisphere, a cube, a cylinder, etc.) that fully encloses a nucleic acid nanostructure containing the compacted structure and the pervious structure. In particular configurations, an imaginary volume may be positioned with respect to an alignment of a compacted structure, such as an axis of symmetry, a plane of symmetry, or a face of the compacted structure. In some configurations, an anisotropic volumetric distribution may comprise a fraction of a hemispherical volume surrounding the compacted structure that does not comprise the pervious structure. In some configurations, an anisotropic volumetric distribution may comprise a fraction of a spherical volume surrounding the compacted structure excluding a volume comprising an analyte of interest coupled to the compacted structure.

A nucleic acid nanostructure may comprise a compacted structure and a pervious structure, in which the compacted structure and the pervious structure each occupy a characteristic volume, in which the characteristic volume comprises a minimum, average, or maximum volume occupied by structure on a spatial and/or temporal basis. A volume of a compacted structure and/or a pervious structure may vary depending upon the configuration of a nucleic acid nanostructure comprising the compacted structure and/or pervious structure (e.g., bound to a solid support, unbound to a solid support, coupled to an analyte, coupled to a reagent, etc.). For example, a nucleic acid nanostructure comprising a compacted structure and a pervious structure may bind to a solid support by a capture moiety comprising a pervious structure, in which the volume of the compacted structure is unchanged by the binding but the volume of pervious structure decreases due to the binding. In some configurations, an average volume of a compacted structure need not vary according to a configuration of a nucleic acid nanostructure comprising the compacted structure. In some configurations, a volume occupied by a compacted structure may be larger than a volume occupied by a pervious structure. In other configurations, a volume occupied by a pervious structure may be larger than a volume occupied by a compacted structure.

A nucleic acid nanostructure may comprise an average effective surface area (e.g., a nucleic acid nanostructure in solution) and/or footprint (e.g., a nucleic acid nanostructure coupled to a solid support). A nucleic acid nanostructure may comprise a compacted structure and/or a pervious structure, in which the compacted and/or the pervious structure comprises an average effective surface area and/or footprint. An average effective surface area and/or footprint of a compacted structure and/or a pervious structure may be modified, for example, to modulate the strength of an interaction with another entity (e.g., an analyte, a nucleic acid nanostructure, a solid support, a reagent, etc.). In some configurations, an effective surface area and/or footprint of a pervious structure may be substantially the same as an effective surface area and/or footprint of a nucleic acid nanostructure. In other configurations, an effective surface area of a pervious structure may be smaller than an effective surface area of a nucleic acid nanostructure. In some configurations, an effective surface area of a pervious structure may be smaller than an effective surface area of a compacted structure. In some configurations, an effective surface area of a pervious structure may be larger than an effective surface area of a compacted structure. In some configurations, a footprint of a nucleic acid nanostructure may be larger than an effective surface area of a nucleic acid nanostructure. In other configurations, a footprint of a nucleic acid nanostructure may be less than or equal to an effective surface area of a nucleic acid nanostructure. In some configurations, a footprint of a compacted structure may be less than or equal to an effective surface area of a compacted structure. In some configurations, a nucleic acid nanostructure may comprise a footprint, in which the footprint of the nucleic acid nanostructure is the greater than, equal to, or less than an effective surface area of the nucleic acid nanostructure.

Nucleic Acids at Solid Supports

A nucleic acid, as set forth herein, may be configured to couple with a solid support or a site thereof, as set forth herein. In some configurations, a plurality of nucleic acids may be coupled to a solid support, in which each nucleic acid is configured to couple an analyte of interest to the solid support, thereby forming an array of analytes of interest on the solid support. A nucleic acid may be configured in tandem with a solid support or a surface thereof to increase a likelihood of one or more outcomes of a nucleic acid/solid support interaction, including: 1) binding a nucleic acid to an address of the solid support that is configured to bind the nucleic acid, 2) inhibiting a binding of a nucleic acid to an address of the solid support that is not configured to bind the nucleic acid, 3) inhibiting binding of a second nucleic acid to an address comprising a first nucleic acid, in which the address is not configured to bind a second nucleic acid; 4)

inhibiting an improper binding orientation of a nucleic acid, and 5) displaying an analyte of interest in an accessible fashion for an array-based process (e.g., a characterization assay, a synthesis process, etc.).

Systems of nucleic acids and solid supports may be configured to produce arrays of analytes with a substantially uniform surface density of analytes of interest. Of particular interest are systems of nucleic acids and solid supports that produce high-density arrays of analytes of interest, for example, in which each analyte of the array of analytes is individually resolvable at single-analyte resolution. An array of analytes of interest may comprise one or more properties of: i) comprising a maximal number, density or pitch of individually resolvable array addresses containing one and only one analyte of interest, ii) comprising a minimal number, density or pitch of individually resolvable array addresses containing two or more analytes of interest, iii) comprising a minimal number, density or pitch of individually resolvable array addresses containing no analytes of interest, and iv) comprising a maximal number, density or pitch of individually resolvable array addresses containing no analytes of interest. A useful array of analytes of interest for a single-analyte process may comprise a spatial distribution (e.g. pitch or density) of single analytes at array addresses, in which the spatial distribution contains a higher amount of sites occupied by one and only one single analyte with reference to a statistical distribution, such as a Poisson distribution or a normal distribution. For example, given a system of a solid support containing N analyte binding sites and a plurality of N nucleic acids coupled to analytes contacted with the solid support, or a method for making such a system, in which neither the solid support nor the nucleic acids bias a likelihood of a nucleic acid binding to any particular analyte binding site, a Poisson distribution would predict ~37% of the N analyte binding sites containing no deposited analytes of interest, ~37% of the N analyte binding sites containing one and only one deposited analyte of interest, and ~26% of the N analyte binding sites containing two or more deposited analytes of interest. Accordingly, it is advantageous to configure systems of nucleic acids and solid supports or methods for making such systems that provide single-analyte occupancy at least 40%, 50%, 60%, 70%, 80%, 85%, 90%, 95%, 99%, or greater than 99% of sites of an array. Alternatively or additionally, it is advantageous to configure systems of nucleic acids and solid supports that provide: 1) a maximized ratio of sites with single analyte occupancy:sites with no analyte occupancy, and/or 2) a maximized ratio of sites with single analyte occupancy:sites with multiple analyte occupancy.

The skilled person will readily recognize innumerable combinations of solid supports, as set forth herein, and nucleic acids as set forth herein, for forming arrays of single analytes. In some configurations, an array-forming system may comprise a nucleic acid comprising one or more capture moieties and a solid support comprising one or more surface-linked moieties, in which the nucleic acid is configured to be bound to the solid support by a coupling interaction of the one or more capture moieties with the one or more surface-linked moieties. A capture moiety may be selected for one or more properties of: 1) forming a specific interaction with a surface-linked moiety of a solid support, optionally in a rapid fashion (high kinetic on-rate), 2) forming a specific interaction with a long-duration to a surface-linked moiety of a solid support (low kinetic off-rate), 3) not forming low specificity binding interactions with other entities in the system (e.g., other nucleic acids, analytes coupled to other nucleic acids, non-binding regions of the array, etc.), and 4) providing a physical and/or chemical property that inhibits binding of other nucleic acids at an array site (e.g., steric occlusion, electrostatic repulsion, magnetic repulsion, etc.). A surface-linked moiety may be selected for one or more properties of: 1) forming a specific interaction with a capture moiety of a nucleic acid, optionally in a rapid fashion (high kinetic on-rate), 2) forming a specific interaction with a long-duration to a capture moiety of a nucleic acid (low kinetic off-rate), 3) inhibiting binding interactions with other entities in the system (e.g., analytes), 4) providing a physical and/or chemical property that inhibits binding of other nucleic acids at an array site (e.g., steric occlusion, electrostatic repulsion, magnetic repulsion, etc.), and 5) facilitating binding of a nucleic acid in a specific location and orientation (e.g., centered symmetrically on a site with an analyte of interest not in contact with a solid support).

Surprisingly, a system of nucleic acids and a solid support, or a method for making such a system, may be configured to obtain spatial control of nucleic acid binding locations on single-analyte arrays through the formation of weak binding interactions between one or more capture moieties of a nucleic acid and one or more surface-linked moieties of the solid support. Commonly, molecules are coupled to surfaces through the formation of strong binding interactions (e.g., click-type covalent bonds, streptavidin-biotin coupling, etc.). Such strong binding interactions are advantageous for permanently coupling a molecule to a surface; however, if the molecule initially binds toward an edge of a binding site, sufficient additional space may exist at the binding site to couple one or more additional molecules. In contrast, a system of nucleic acids and a solid support may be configured to obtain spatial control of nucleic acid binding locations on single-analyte arrays through a multi-valency affect in which a plurality of weak binding interactions between one or more capture moiety and a plurality of surface-linked moieties provide a binding strength comparable to a single strong binding interaction while permitting a nucleic acid to spatially re-arrange on a solid support from an initial binding configuration to a more stable final binding configuration. Without wishing to be bound by theory, a stable binding configuration of a nucleic acid comprising one or more capture moieties may be obtained on a binding site comprising an excess of surface-linked moieties due to: 1) energetic favorability of specific binding interactions between the one or more capture moieties and the excess of surface-linked moieties, and 2) entropic favorability caused by numerous possible configurations of binding between the one or more capture moieties and the excess of surface-linked moieties.

Figure 58C:
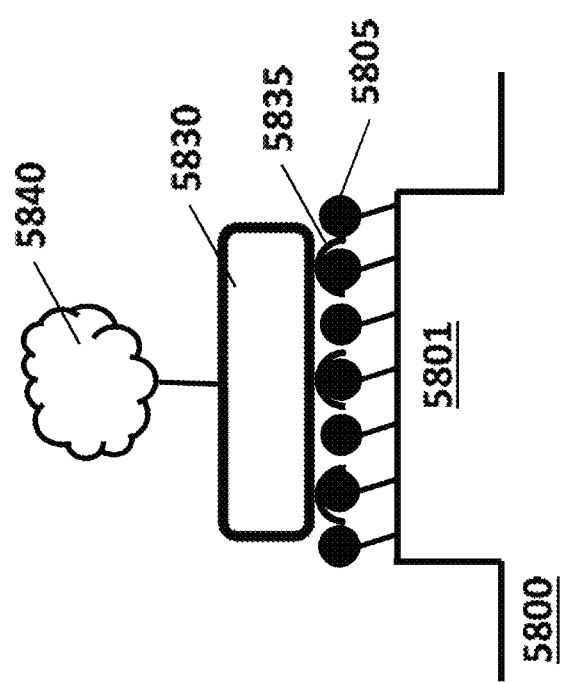

FIGS. 58A-58C illustrate a concept of achieving a stable configuration of a nucleic acid nanostructure on a surface through a multi-valent binding interaction. FIG. 58A illustrates a solid support 5800 comprising a site 5801 with a plurality of surface-linked moieties 5805 that are configured to couple to complementary capture moieties 5835 of a nucleic acid nanostructure 5830. The nucleic acid nanostructure 5830 is optionally coupled to an analyte 5840. FIG. 58B shows an initial configuration of the nucleic acid nanostructure 5830 upon contact of the nucleic acid nanostructure 5830 with the solid support 5800 at a random location of the site 5801. Due to the location of contact, only one coupling interaction has occurred between a surface-linked moiety 5805 and a capture moiety 5835. FIG. 58C depicts a more stable final configuration of the nucleic acid nanostructure 5830 after a spatial rearrangement on the surface of the site 5801. The final configuration may be more stable than the initial configuration due to the increased quantity of coupling interactions between surface-linked moieties 5805 and capture moieties 5835. The final configuration may also be more stable than the initial configuration because it has other possible combinations of couplings between surface-linked moieties 5805 and capture moieties 5835 that the structure can re-arrange into if any coupling between a surface-linked moiety 5805 and a capture moiety 5835 is disrupted.

FIGS. 52A-52H and 53A-53D illustrate configurations of nucleic acid nanostructures that may form multi-valent binding interactions with a solid support or a surface thereof. The nucleic acid nanostructures depicted in FIGS. 53A-53D comprise a plurality of pendant oligonucleotides that are configured to form hybridization binding interactions with complementary oligonucleotides of a solid support. Additional configurations of nucleic acid nanostructures that form multi-valent binding interactions are depicted in FIGS. 55A-55D. FIG. 55A depicts a nucleic acid nanostructure 5530 that is coupled to an analyte 5540. The nucleic acid nanostructure comprises a first internal single-stranded nucleic acid 5532 and a second internal single-stranded nucleic acid 5534 that are configured to couple to a first complementary surface-linked oligonucleotide 5520 and a second surface-linked oligonucleotide 5522, each of which is coupled to a site 5501 of a solid support 5500 in a molar excess relative to available binding sites of the nucleic acid nanostructure 5530. FIG. 55B depicts the nucleic acid nanostructure 5530 in a coupled configuration at the site 5501 of the solid support 5500. The first complementary surface-linked oligonucleotide 5520 and the second surface-linked oligonucleotide 5522 have coupled to the first internal single-stranded nucleic acid 5532 and the second internal single-stranded nucleic acid 5534. Excess surface-linked oligonucleotides 5520 and 5522 remain, thereby facilitating spatial re-arrangement of the nucleic acid nanostructure 5530 by re-arrangement of binding interactions if favorable. FIG. 55C depicts a nucleic acid nanostructure 5530 that is coupled to an analyte 5540. The nucleic acid nanostructure comprises a plurality of capture moieties 5550 (e.g., antibodies, antibody fragments, aptamers, etc.) that are configured to couple to a plurality of surface-linked binding ligands 5555, each of which is coupled to a site 5501 of a solid support 5500 in a molar excess relative to available capture moieties of the nucleic acid nanostructure 5530. The site 5501 may further comprise a plurality of non-coupling moieties 5560 (e.g., passivating moieties that prevent non-specific binding). FIG. 55D depicts the nucleic acid nanostructure 5530 in a coupled configuration at the site 5501 of the solid support 5500. The plurality of capture moieties 5550 have coupled to the plurality of surface-linked binding ligands 5555. Excess surface-linked binding ligands 5555 remain, thereby facilitating spatial re-arrangement of the nucleic acid nanostructure 5530 by re-arrangement of binding interactions if favorable. The configurations depicted in FIGS. 52A-52H and 53A-53D contain various chemical structures and spatial configurations of capture moieties comprising a pervious structure (e.g., a plurality of pendant moieties). An advantageous nucleic acid nanostructure may comprise a pervious structure comprising a plurality of capture moieties, in which each capture moiety is configured to form a binding interaction with a surface-linked moiety of a solid support. An advantageous nucleic acid nanostructure may comprise a pervious structure comprising a capture moiety, in which the capture moiety is configured to form a plurality of binding interactions with a plurality of surface-linked moieties of a solid support.

Figure 56A:
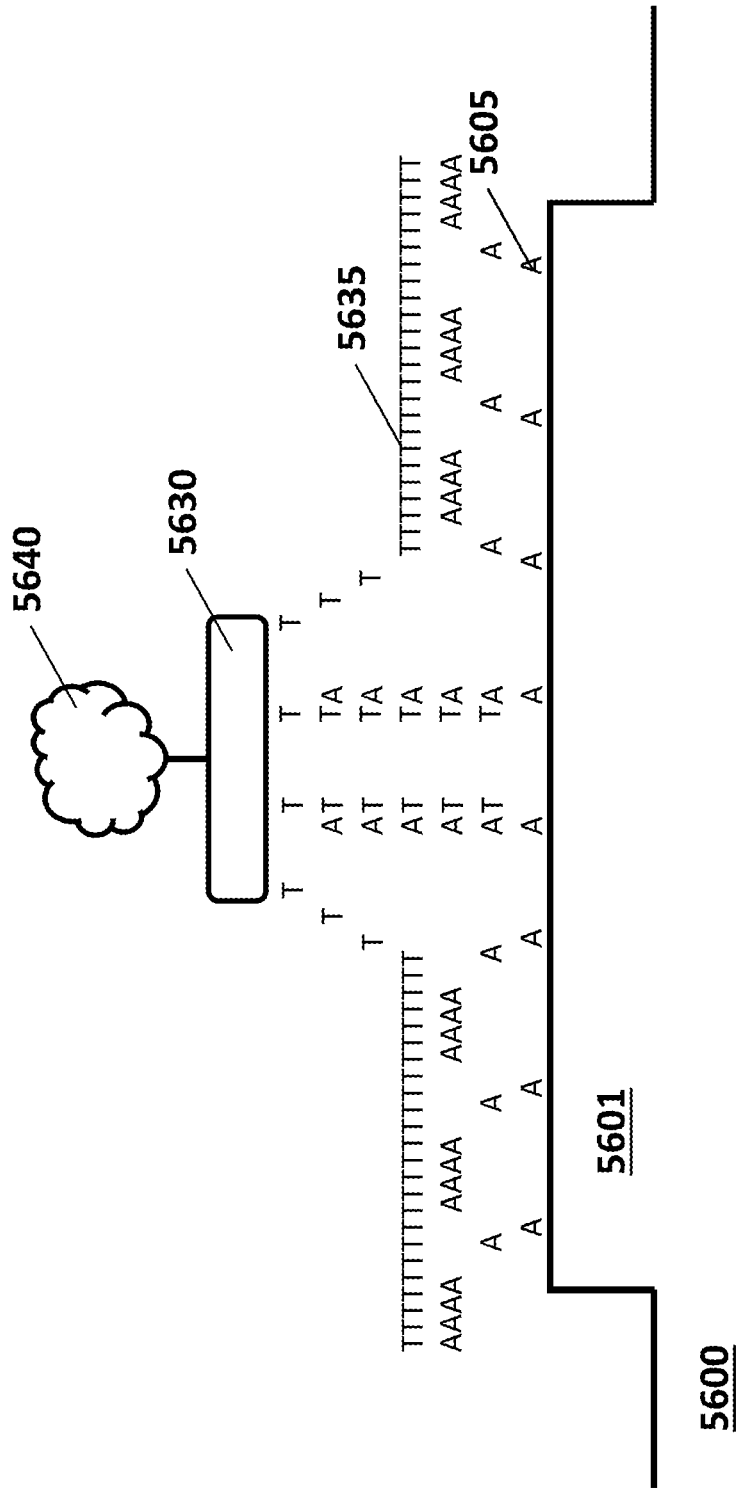
FIGS. 56A, 56B, and 56C depict various configurations of nucleic acid nanostructures comprising pervious structures, in which the pervious structures form multi-valent binding interactions with a solid support, in accordance with some embodiments.
Figure 56B:
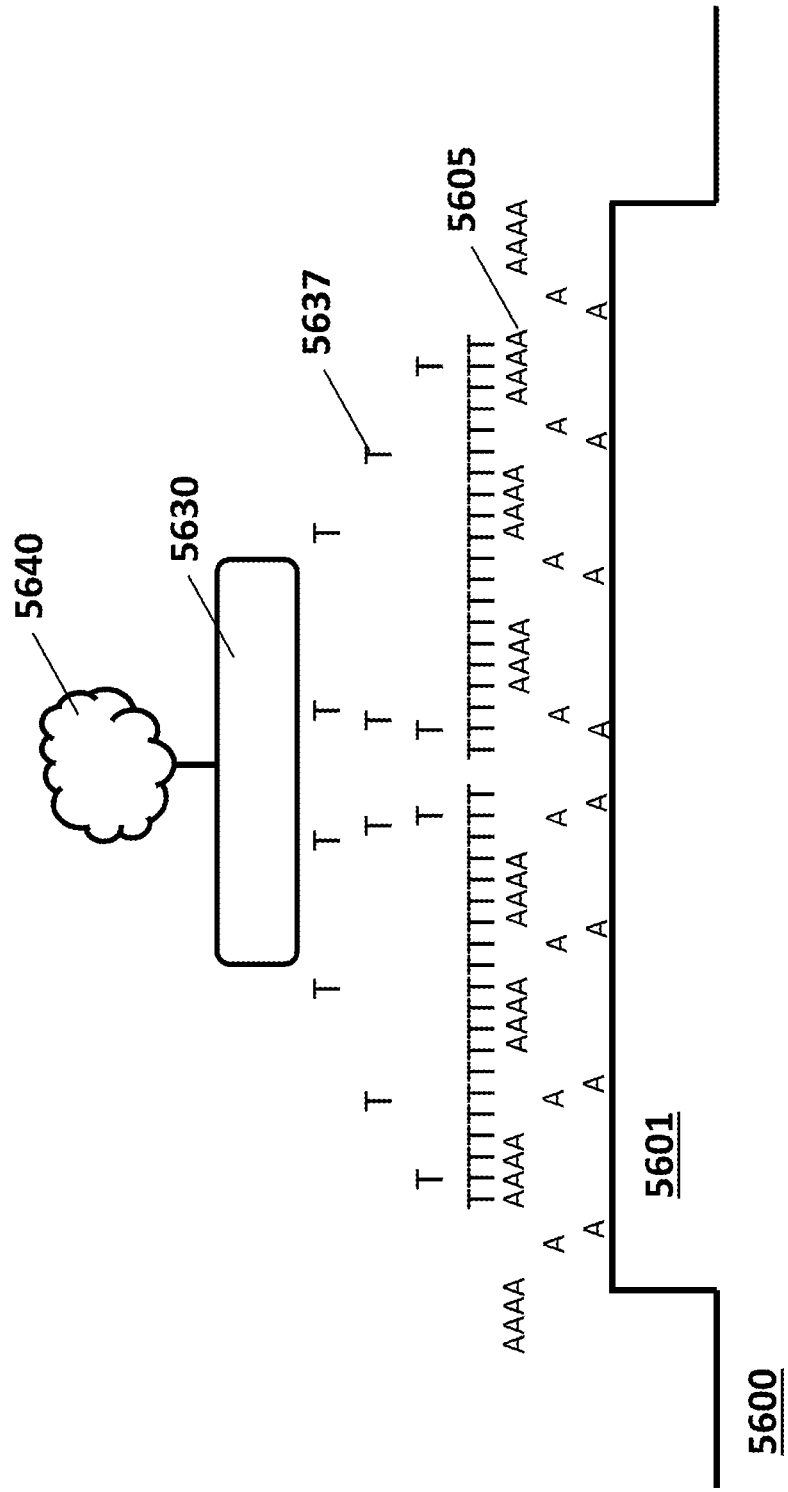
Figure 56C:
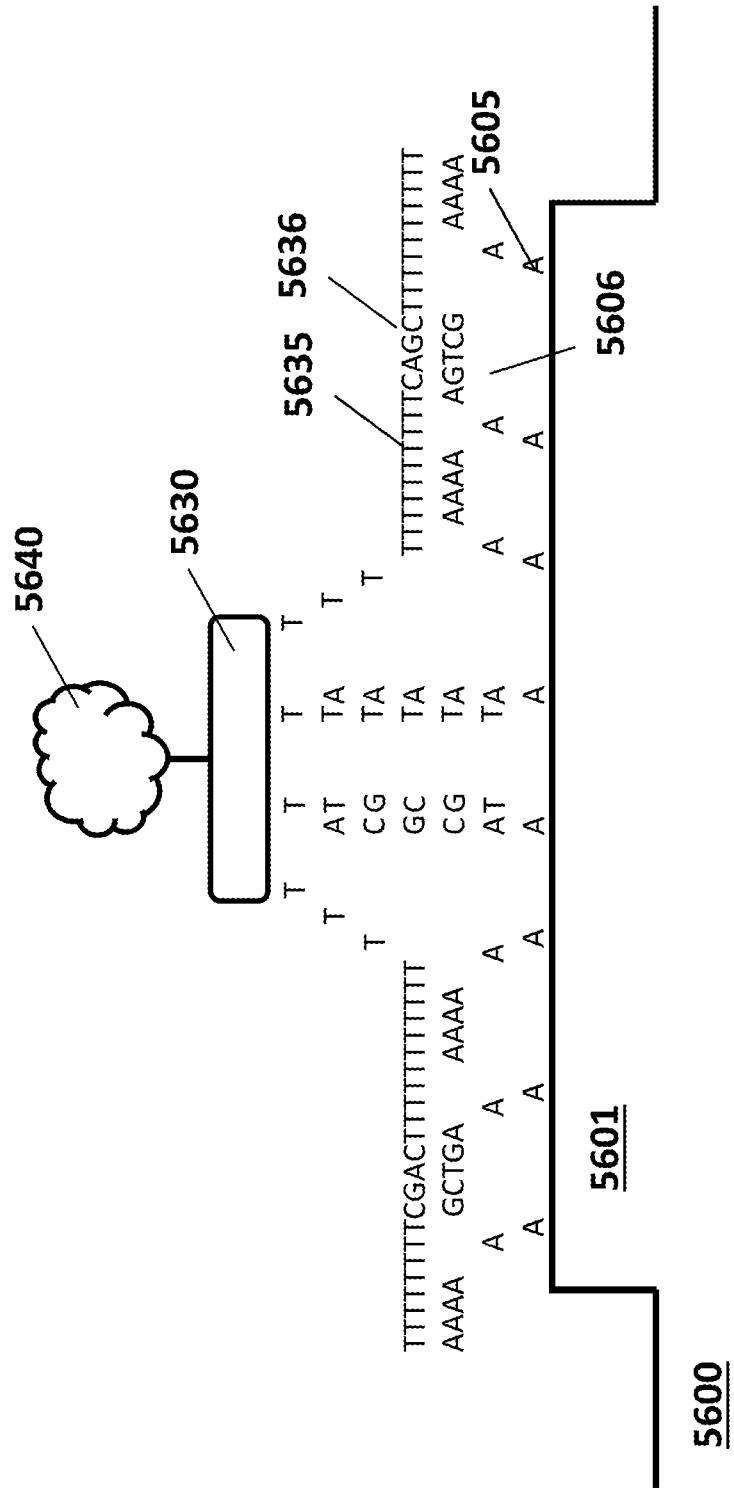

FIGS. 56A-56C depict examples of differing systems of nucleic acid nanostructures coupled to solid supports. FIG. 56A shows a solid support 5600 comprising a site 5601, in which the site comprises a plurality of surface-linked oligonucleotides 5605 comprising poly-A sequences. A nucleic acid nanostructure 5630 is coupled to an analyte 5640, and is further coupled to the site 5601 by a pervious structure comprising a plurality of pendant oligonucleotides 5635 comprising poly-T sequences. Each pendant oligonucleotide 5635 is sufficiently long to couple to multiple surface-linked oligonucleotides 5605, thereby forming a multi-valent binding interaction between the site 5601 and the nucleic acid nanostructure 5630. Optionally, the plurality of pendant oligonucleotides 5635 may comprise oligonucleotides of differing chain lengths. FIG. 56B depicts a similar composition to FIG. 56A, however the nucleic acid nanostructure 5630 instead comprises a pervious structure comprising a plurality of oligonucleotide loops 5637 comprising poly-T sequences. Each pendant oligonucleotide loop 5637 is sufficiently long to couple to multiple surface-linked oligonucleotides 5605, thereby forming a multi-valent binding interaction between the site 5601 and the nucleic acid nanostructure 5630. FIG. 56C shows a solid support 5600 comprising a site 5601, in which the site comprises a first plurality of surface-linked oligonucleotides 5605 comprising poly-A sequences and a second plurality of surface-linked oligonucleotides 5606 comprising complementarity to a heteropolymeric nucleotide sequence 5636. A nucleic acid nanostructure 5630 is coupled to an analyte 5640, and is further coupled to the site 5601 by a pervious structure comprising a plurality of pendant oligonucleotides 5635 comprising poly-T sequences and further containing intermediate nucleotide sequences comprising the non-repeating nucleotide sequence 5636. The number of heteropolymeric nucleotide sequences 5636 or complementary surface-linked oligonucleotides 5606 may be limited to reduce the number of re-arranged configurations available to a nucleic acid nanostructure coupled to a solid support.

Figure 57:
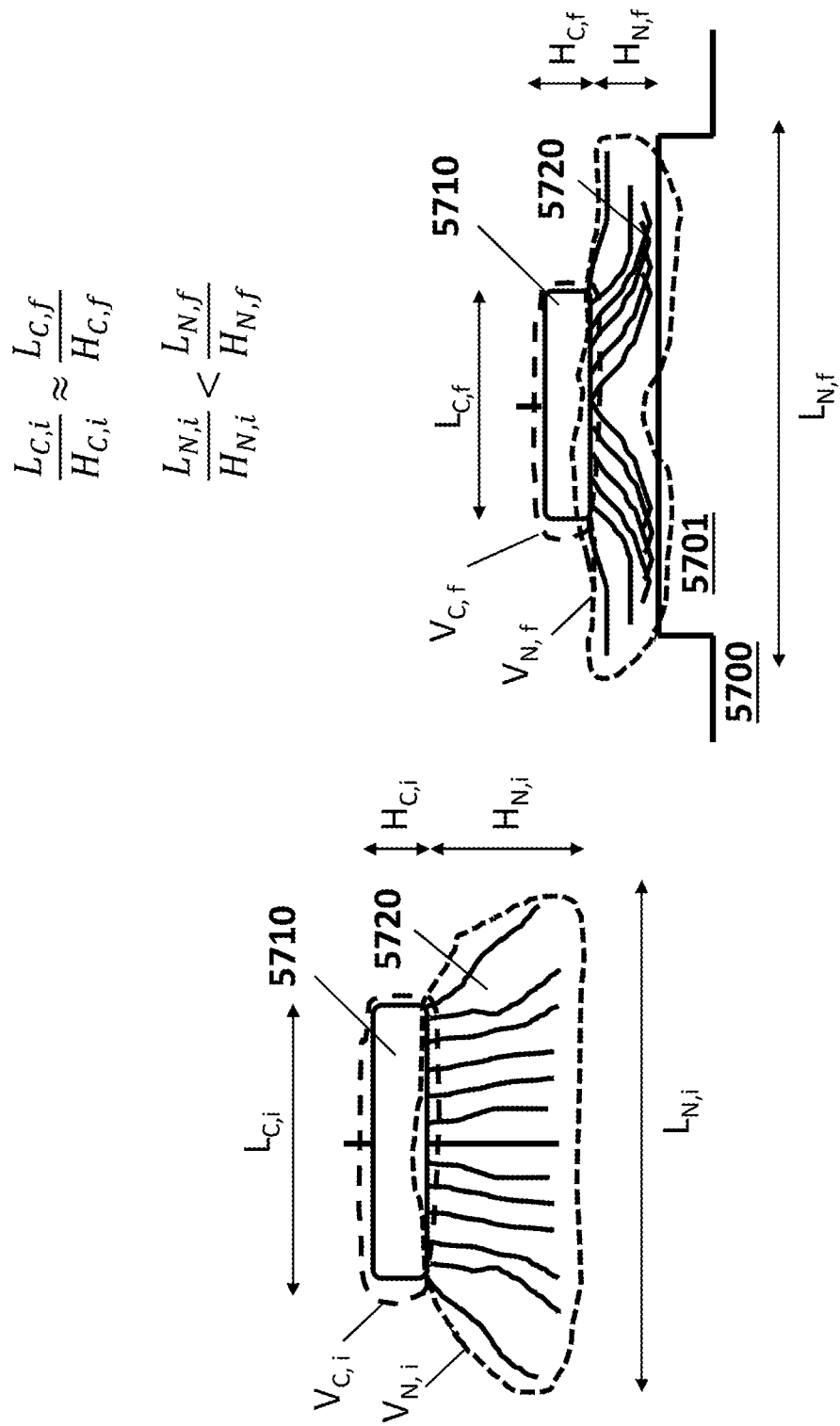
FIG. 57 illustrates a change in conformation for a nucleic acid nanostructure due to a surface-binding interaction, in accordance with some embodiments.

A coupling of a nucleic acid nanostructure to a solid support or a surface thereof may cause a conformational change of the nucleic acid nanostructure. In some configurations, a nucleic acid nanostructure may comprise a compacted structure and a pervious structure, in which coupling of the nucleic acid nanostructure to a solid support or a surface thereof causes no substantial change in conformation (e.g., shape, volume, effective surface area, footprint, etc.) to the compacted structure, and in which coupling of the nucleic acid nanostructure to a solid support or a surface thereof causes a substantial change in conformation (e.g., shape, volume, effective surface area, footprint, etc.) to the pervious structure. FIG. 57 depicts a change in conformation associated with a binding of a nucleic acid nanostructure comprising a compacted structure 5710 and a pervious structure 5720 when the nanostructure binds to a site 5701 of a solid support 5700. In an initial unbound configuration, the compacted structure 5710 comprises a width $L_{C,i}$, a thickness $H_{C,i}$, and a volume $V_{C,i}$ and the pervious structure 5720 comprises a width $L_{N,i}$, a thickness $H_{N,i}$, and a volume $V_{N,i}$. After coupling to the surface, the pervious structure may become compressed and elongated due to the pendant moieties forming a maximal number of binding interactions with a surface of the site 5701. Accordingly, in the final bound configuration, the compacted structure 5710 may comprise a width $L_{C,f}$, a thickness $H_{C,f}$, and a volume $V_{C,f}$ in which the values are substantially unchanged from the initial values. In contrast, the pervious structure 5720 may comprise a width $L_{N,f}$, a thickness $H_{N,f}$, and a volume $V_{N,f}$ in which a final value for the width has increased relative to the initial value, a final value for the height has decreased relative to the initial value, and a final value for the volume may or may not change depending upon the nature of the binding interactions with the site 5701. Nucleic acid nanostructures that have conformational changes may be advantageous for increasing a footprint of the nucleic acid nanostructure on the surface area of the binding site, thereby decreasing available surface area for binding of other nucleic acid nanostructures or other entities.

In an aspect, provided herein is a composition, comprising: a) a solid support comprising a plurality of sites, and b) a plurality of nucleic acid nanostructures (e.g., SNAPs), in which each nucleic acid nanostructure is coupled to, or configured to couple to, an analyte, and in which each nucleic acid nanostructure of the plurality of nucleic acid nanostructures is coupled to a site of the plurality of sites, in which the plurality of sites comprises a first subset comprising a first quantity of sites and a second subset comprising a second quantity of sites, in which each site of the first subset comprises two or more coupled nucleic acid nanostructures, in which each site of the second subset comprises one and only one coupled nucleic acid nanostructure, and in which a ratio of the quantity of sites of the first subset to the quantity of sites of the second subset is less than a ratio predicted by a Poisson distribution.

In another aspect, provided herein is an analyte array, comprising: a) a solid support comprising a plurality of sites; and b) a plurality of nucleic acid nanostructures (e.g., SNAPs), in which each nucleic acid nanostructure is coupled to an analyte of interest, and in which each nucleic acid nanostructure of the plurality of nucleic acid nanostructures is coupled to a site of the plurality of sites, in which at least 40% of sites of the plurality of sites comprise one and only one analyte of interest.

In another aspect, provided herein is a composition, comprising: a) a solid support comprising a site that is configured to couple a nucleic acid nanostructure, and b) the nucleic acid nanostructure, in which the nucleic acid nanostructure is coupled to the site, in which the nucleic acid nanostructure is coupled to an analyte of interest; and in which the nucleic acid nanostructure is configured to prevent contact between the analyte of interest and the solid support.

In another aspect, provided herein is a composition, comprising: a) a solid support comprising a site that is configured to couple a nucleic acid nanostructure, wherein the site comprises a surface area; and b) the nucleic acid nanostructure, in which the nucleic acid nanostructure is coupled to the site, in which the nucleic acid nanostructure is coupled to, or configured to couple to, an analyte of interest; in which the nucleic acid nanostructure comprises a total effective surface area in an unbound configuration, in which the nucleic acid nanostructure comprises a compact structure with an effective surface area in the unbound configuration, in which the effective surface area of the compacted structure is less than 50% of the surface area of the site, and in which the unbound configuration comprises the nucleic acid nanostructure being uncoupled to the site.

An array may comprise a plurality of sites, in which a site has a determinable occupancy. When used in reference to a site of an array, occupancy may refer to a detected or inferred presence of an entity (e.g., a nucleic acid, an analyte, a nucleic acid and an analyte, a nucleic acid coupled to an analyte, a nucleic acid or an analyte, etc.) at the array site. In particular instances, occupancy may further refer to a property (e.g., a chemical property, a physical property, etc.) or characteristic (e.g., a spatial orientation, a temporal orientation, a bound state, an unbound state, etc.) of an entity that is detected or inferred to be present at an array site. For example, when forming an array for a polypeptide assay, a complex comprising a polypeptide coupled to a nucleic acid nanostructure may deposit on an array site by a coupling of the polypeptide to the array site rather than the nucleic acid to the array site, thereby rendering the polypeptide non-interrogable during the polypeptide assay. In such a case, the site may be considered unoccupied by an analyte due to the orientation of the complex on the array site. When used in reference to an array comprising a plurality of sites, an occupancy may refer to a percentage or fraction of sites of the plurality of sites comprising a detected or inferred presence of an entity (e.g., a nucleic acid, an analyte, a nucleic acid and an analyte, a nucleic acid coupled to an analyte, a nucleic acid or an analyte, etc.). In particular instances, occupancy may further refer to a percentage or fraction of sites of the plurality of sites containing a detected or inferred presence of an entity with a property (e.g., a chemical property, a physical property, etc.) or characteristic (e.g., a spatial orientation, a temporal orientation, a bound state, an unbound state, etc.). For example, an array may have a detectable analyte occupancy fraction of 0.9 if 9 sites of every 10 sites contain a detectable analyte. In some configurations, occupancy may refer to a quantity of entities at a site, such as about 0, 1, 2, 3, 4, 5, or more entities at a site. In some configurations, occupancy may refer to a quantity of entities with a particular property or characteristics at a site, such as about 0, 1, 2, 3, 4, 5, or more entities at a site.

Accordingly, an array of analytes may be characterized by a quantitative comparison of two or more measures of occupancy. For example, it may be useful to compare an occupancy of sites of a plurality of sites of an array containing no analytes to an occupancy of sites of the plurality of sites of the array containing at least one analyte. In another example, it may be useful to compare an occupancy of sites of a plurality of sites of an array containing one and only one analyte to an occupancy of sites of the plurality of sites of the array containing two or more analytes. In some configurations, a comparison of two or more measures of occupancy may provide a useful quality control characteristic after forming an array of analytes. For example, an array of analytes may be rejected for further use if a ratio of sites with an occupancy of two or more analytes to sites with an occupancy of one and only one site exceeds a threshold value, such as a ratio predicted by a Poisson distribution. Table I lists pairs of measures of occupancy whose ratios may be useful for characterizing an array, as set forth herein.

TABLE I

| 1st Occupancy Measure | 2nd Occupancy Measure | Critical Ratio of 1st to 2nd |
|---|---|---|
| Sites occupied | Sites unoccupied | >1.72 |
| Sites w/only 1 analyte | Sites w/2+ analytes | >1.40 |
| Sites w/only 1 nucleic acid nanostructure | Sites w/2+ nucleic acid nanostructures | >1.40 |
| Sites w/1+ analyte | Sites w/0 analytes | >1.72 |
| Sites w/1+ nucleic acid nanostructure | Sites w/0 nucleic acid nanostructures | >1.72 |
| Sites w/1+ detectable analyte | Sites w/0 detectable analytes | >1.72 |

In another aspect, provided herein is a method of characterizing an array of analytes, comprising: a) providing an array of analytes, as set forth herein, b) determining a first measure of occupancy for the array of analytes, as set forth herein, c) determining a second measure of occupancy for the array of analytes, as set forth herein, and d) comparing a ratio of the first measure of occupancy to the second measure of occupancy to an array criterium. In some configurations, an array criterium may comprise a ratio of a first measure of occupancy to a second measure of occupancy for a hypothetical array of analytes with an occupancy distribution that fits a statistical or stochastic distribution (e.g., a Poisson distribution, a normal distribution, a binomial distribution, etc.). For example, an array criterium may comprise a critical ratio listed in Table I, or any other conceivable ratio of measures of occupancy. In some configurations, a ratio of a first measure of occupancy to a second measure of occupancy may meet or exceed an array criterium predicted by a statistical or stochastic distribution (e.g., a Poisson distribution). In other configurations, a ratio of a first measure of occupancy to a second measure of occupancy may not meet or exceed an array criterium predicted by a statistical or stochastic distribution (e.g., a Poisson distribution). A method of characterizing an array of analytes may further comprise a step of, based upon comparing a ratio of a first measure of occupancy to a second measure of occupancy to an array criterium, discarding the array of analytes. For example, an array of analytes with a level of analyte occupancy beneath an array criterium may be discarded. A method of characterizing an array of analytes may further comprise a step of, based upon comparing a ratio of a first measure of occupancy to a second measure of occupancy to an array criterium, separating the analytes from the array of analytes. For example, an array of analytes with an analyte occupancy beneath an array criterium may be contacted with a stripping medium (e.g., a denaturant, a chaotrope) to remove coupled analytes and/or nucleic acids before reforming the array of analytes with a new plurality of analytes. A method of characterizing an array of analytes may further comprise a step of, based upon comparing a ratio of a first measure of occupancy to a second measure of occupancy to an array criterium, providing additional analytes to the array of analytes. For example, an array of analytes with a level of analyte occupancy beneath an array criterium may be contacted with additional analytes coupled to nucleic acids to increase the analyte occupancy. A method of characterizing an array of analytes may further comprise a step of, based upon comparing a ratio of a first measure of occupancy to a second measure of occupancy to an array criterium, utilizing the array of analytes in an array-based process (e.g., an assay, a synthesis, etc.).

In some configurations, an array may comprise a plurality of sites, in which the plurality of sites comprise a first subset of sites, in which each site of the first subset comprises a first measure of occupancy (e.g., quantity of entities coupled to the array site, presence of an entity, presence of a detectable entity, etc.), a second subset of sites, in which each site of the second subset comprises a second measure of occupancy, and optionally a third subset of sites, in which each site of the third subset comprises a third measure of occupancy. Occupancy of an array may be determined by a method such as fluorescence microscopy, electron microscopy, atomic force microscopy, etc. An array may comprise a plurality of sites, in which at least about 10%, 20%, 30%, 35%, 37%, 40%, 45%, 50%, 55%, 60%, 65%, 70%, 75%, 80%, 85%, 90%, 95%, 99%, 99.9%, 99.99%, 99.999%, 99.9999%, 99.99999%, or more than 99.99999% of the sites of the plurality of sites comprise an occupancy of at least one analyte. Alternatively or additionally, an array may comprise a plurality of sites, in which no more than about 99.99999%, 99.9999%, 99.999%, 99.99%, 99.9%, 99%, 95%, 90%, 85%, 80%, 75%, 70%, 65%, 60%, 55%, 50%, 45%, 40%, 37%, 35%, 30%, 20%, 10%, or less than 10% of the sites of the plurality of sites comprise an occupancy of at least one analyte. An array may comprise a plurality of sites, in which at least about 10%, 20%, 30%, 35%, 37%, 40%, 45%, 50%, 55%, 60%, 65%, 70%, 75%, 80%, 85%, 90%, 95%, 99%, 99.9%, 99.99%, 99.999%, 99.9999%, 99.99999%, or more than 99.99999% of the sites of the plurality of sites comprise an occupancy of no more than one analyte. Alternatively or additionally, an array may comprise a plurality of sites, in which no more than about 99.99999%, 99.9999%, 99.999%, 99.99%, 99.9%, 99%, 95%, 90%, 85%, 80%, 75%, 70%, 65%, 60%, 55%, 50%, 45%, 40%, 37%, 35%, 30%, 20%, 10%, or less than 10% of the sites of the plurality of sites comprise an occupancy of no more than one analyte.

Continuing with the example of an array comprising a first subset of sites comprising an occupancy of two or more analytes, a second subset of sites comprising an occupancy of one analyte, and a third subset of sites comprising an occupancy of zero analytes, a ratio of a quantity of sites of the first subset to a quantity of sites of the second subset, or a ratio of a quantity of sites of the third subset to a quantity of sites of the second subset may substantially conform to a ratio predicted by a probabilistic or stochastic distribution, such as a Poisson distribution, normal distribution, binomial distribution, etc. A ratio of a quantity of sites of the first subset to a quantity of sites of the second subset, or a ratio of a quantity of sites of the third subset to a quantity of sites of the second subset may deviate from a ratio predicted by a probabilistic or stochastic distribution. A ratio of quantity of sites of the first subset to quantity of sites of the second subset may have a value of no more than about 0.71, 0.7, 0.6, 0.5, 0.4, 0.3, 0.2, 0.1, 0.05, 0.01, 0.005, 0.001, 0.0001, 0.00001, 0.000001, or less than 0.000001. Alternatively or additionally, a ratio of quantity of sites of the first subset to quantity of sites of the second subset may have a value of at least about 0.000001, 0.00001, 0.0001, 0.001, 0.005, 0.01, 0.05, 0.1, 0.2, 0.3, 0.4, 0.5, 0.6, 0.7, 0.71, or more than 0.71. A ratio of quantity of sites of the third subset to quantity of sites of the second subset may have a value of no more than about 0.99, 0.9, 0.8, 0.7, 0.6, 0.5, 0.4, 0.3, 0.2, 0.1, 0.05, 0.01, 0.005, 0.001, 0.0001, 0.00001, 0.000001, or less than 0.000001. Alternatively or additionally, a ratio of quantity of sites of the third subset to quantity of sites of the second subset may have a value of at least about 0.000001, 0.00001, 0.0001, 0.001, 0.005, 0.01, 0.05, 0.1, 0.2, 0.3, 0.4, 0.5, 0.6, 0.7, 0.8, 0.9, 0.99, or more than 0.99.

Nucleic acid nanostructures or nucleic acid nanostructure complexes may be characterized by a spacing or separation between analyte coupling sites on adjacent nucleic acid nanostructures or nucleic acid nanostructure complexes in an array of nucleic acid nanostructures or nucleic acid nanostructure complexes. Nucleic acid nanostructures or nucleic acid nanostructure complexes may have a nearest neighbor separation of at least about 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 120 nm, 140 nm, 160 nm, 180 nm, 200 nm, 250 nm, 300 nm, 350 nm, 400 nm, 450 nm, 500 nm, 600 nm, 700 nm, 800 nm, 900 nm, 1 µm, 2 µm, 3 µm, 4 µm, 5 µm, 10 µm, or more than 10 µm, relative to an adjacent nucleic acid nanostructure or nucleic acid nanostructure complex. Alternatively or additionally, nucleic acid nanostructures or nucleic acid nanostructure complexes may have a nearest neighbor separation of no more than about 10 µm, 5 µm, 4 µm, 3 µm, 2 µm, 1 µm, 900 nm, 800 nm, 700 nm, 600 nm, 500 nm, 450 nm, 400 nm, 350 nm, 300 nm, 250 nm, 200 nm, 180 nm, 160 nm, 140 nm, 120 nm, 100 nm, 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, 10 nm, 5 nm, or less than 5 nm, relative to an adjacent nucleic acid nanostructure or nucleic acid nanostructure complex. Nucleic acid nanostructure or nucleic acid nanostructure complex nearest neighbor separation may be determined by an optical method such as fluorescence microscopy. In some cases, a nucleic acid nanostructure or nucleic acid nanostructure complex nearest neighbor separation may be calculated as an average value based on, for example, a total fluorescence count over a fixed image area, where the total fluorescence count may be correlated to a number of observed nucleic acid nanostructures or nucleic acid nanostructure complexes. In other cases, an optical detection system may have sufficient optical resolution and sensor pixel density to distinguish individual nucleic acid nanostructures or nucleic acid nanostructure complexes and determine separation from all nearest neighbor nucleic acid nanostructures or nucleic acid nanostructure complexes.

A nucleic acid nanostructure, as set forth herein, may be configured to couple with a site of an array and thereby occlude coupling of a second nucleic acid nanostructure to the site. In some configurations, occluding binding may comprise inhibiting transport of a second nucleic acid nanostructure to the site of the array by a first nucleic acid nanostructure. For example, occluding binding may comprise inhibiting deposition of a second nucleic acid nanostructure at an array site during deposition of a first nucleic acid nanostructure at the array site. In some configurations, occluding binding may comprise inhibiting deposition of a second nucleic acid nanostructure at an array site after a first nucleic acid nanostructure has coupled to the array site.

A first nucleic acid nanostructure may occlude binding of a second nucleic acid nanostructure at an array site by occupying a significant portion of a surface area of the array site. In some configurations, a nucleic acid nanostructure complex (e.g., a SNAP complex) may be coupled to an array site, in which the nucleic acid nanostructure complex comprises a coupled plurality of nucleic acid nanostructures, and in which, optionally, the nanostructure complex is coupled to, or configured to couple to, a single analyte of interest. In other configurations, a nucleic acid nanostructure comprising a pervious structure may be coupled to an array site, in which the pervious structure is configured to occlude binding of a second nucleic acid nanostructure to the array site, and in which, optionally, the nanostructure is coupled to, or configured to couple to, a single analyte of interest. In some configurations, a pervious structure may comprise an oligonucleotide that is configured to occlude binding of a second nucleic acid nanostructure to an array site. Exemplary compositions for the pervious structure are set forth elsewhere herein, for example, in the context of capture moieties, pendant moieties and pendant oligonucleotides.

A nucleic acid nanostructure coupled to a solid support may be configured to inhibit or prevent contact between an analyte of interest and a solid support. In some configurations, a nucleic acid nanostructure may be configured to inhibit or prevent contact between an analyte of interest and a solid support during deposition of the nucleic acid nanostructure at an array site on the solid support. For example, a nucleic acid nanostructure may prevent coupling of the analyte directly to the surface by a non-specific binding interaction. In other configurations, a nucleic acid nanostructure may be configured to inhibit or prevent contact between an analyte of interest and a solid support after deposition of the nucleic acid nanostructure at an array site on the solid support. For example, a nucleic acid nanostructure may comprise a linking moiety that couples an analyte to the nucleic acid nanostructure, in which the linking moiety facilitates an increased spatial range of motion for the analyte, and in which the nucleic acid nanostructure further comprises a footprint on an array site that occludes any surface area of the array site that the analyte could access due to its increased range of motion. In some configurations, a nucleic acid nanostructure may comprise a pervious structure, in which the pervious structure comprises a moiety that is configured to prevent contact between an analyte of interest and a solid support. In some configurations, a pervious structure comprises a moiety that is configured to prevent contact between an analyte of interest and a solid support by steric occlusion of the solid support. In particular configurations, a moiety that is configured to prevent contact between an analyte of interest and a solid support comprises a chemical and/or physical property that is configured to prevent contact between the analyte of interest and the solid support. In particular configurations, a moiety that is configured to prevent contact between an analyte of interest and a solid support comprises an electrically-repulsive moiety, a magnetically-repulsive moiety, a hydrophobic moiety, a hydrophilic moiety, an amphipathic moiety, or a combination thereof.

An array site on a solid support may be configured to prevent binding of an analyte to the array site or prevent deposition of more than one nucleic acid nanostructure at the array site. An array site may comprise a moiety that is configured to prevent coupling of an analyte of interest to the site or prevent deposition of more than one nucleic acid nanostructure at the array site. In some configurations, a moiety that is configured to prevent coupling of an analyte of interest to the site or prevent deposition of more than one nucleic acid nanostructure at the array site may comprise (i) an oligonucleotide, (ii) a polymer chain, selected from the group consisting of a linear polymer chain, a branched polymer chain, and a dendrimeric polymer chain, (iii) a moiety that comprises a chemical property that is configured to prevent contact between the analyte of interest and the solid support, or (iv) a moiety that comprises an electrically-repulsive moiety, a magnetically-repulsive moiety, a hydrophobic moiety, a hydrophilic moiety, an amphipathic moiety, or a combination thereof. In some configurations, an array site may comprise a first moiety and a second moiety, in which the first moiety and the second moiety are configured to prevent coupling of an analyte of interest to the site or prevent deposition of more than one nucleic acid nanostructure at the array site, and in which the first moiety and the second moiety comprise a dissimilar chemical structure or a dissimilar property. For example, an array site may comprise a plurality of polymer chains, in which the plurality of chains comprise a mixture of polymer chains with differing structures, such as linear polymer chains (e.g., linear PEG, linear dextrans) and branched polymer chains (e.g., branched PEG, branched dextrans). In another example, an array site may comprise a mixture of polymer chains with differing physical properties, such as a mixture of polar chains (e.g., PEG chains) and non-polar chains (e.g., polyethylene chains).

A nucleic acid nanostructure may comprise a compacted structure (e.g., a nucleic acid origami) that comprises a smaller effective surface area than a surface area of an array site to which the nucleic acid nanostructure is configured to be coupled. For example, a square, tile-shaped DNA origami may have side lengths of approximately 83 nanometers, such that the DNA origami would occupy less than 10% of the surface area of a 300 nanometer-wide, circular array site if the origami was coupled to the array site on one of its square faces. A nucleic acid nanostructure comprising a compacted structure may be configured to occupy a larger surface area of an array site than an effective surface area of the compacted structure. For example, the nucleic acid nanostructure may be coupled to additional nucleic acid nanostructures to form a nucleic acid nanostructure complex with an increased surface area. In another example, a nucleic acid nanostructure may further comprise a pervious structure (e.g., a plurality of pendant oligonucleotides such as shown in FIG. 57) that is configured to increase an effective surface area of the nucleic acid nanostructure. A nucleic acid nanostructure may comprise a compacted structure, in which the compacted structure comprises an effective surface area of no more than about 90%, 80%, 70%, 60%, 50%, 40%, 30%, 25%, 20%, 19%, 18%, 17%, 16%, 15%, 14%, 13%, 12%, 11%, 10%, 9%, 8%, 7%, 6%, 5%, 4%, 3%, 2%, 1%, or less than 1% of a surface area of an array site. Alternatively or additionally, a nucleic acid nanostructure may comprise a compacted structure, in which the compacted structure comprises an effective surface area of at least about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 60%, 70%, 80%, 90%, or more than 90% of a surface area of an array site.

A nucleic acid nanostructure may comprise a pervious region that is configured to increase an effective surface area or a footprint of the nucleic acid nanostructure. In some configurations, a nucleic acid nanostructure may comprise a pervious structure, in which the pervious structure is configured to couple to the site of the solid support (e.g., comprises a capture moiety). In some configurations, a pervious region may comprise an effective surface area or footprint that is larger than an effective surface area or footprint of a compacted region. In other configurations, a pervious region may comprise an effective surface area or footprint that is smaller than an effective surface area or footprint of a compacted region.

In some configurations, a nucleic acid nanostructure, when coupled to a solid support, may comprise a total footprint that is larger than a total effective surface area of the nucleic acid nanostructure when not coupled to a solid support. A nucleic acid nanostructure, when coupled to a solid support, may comprise a total footprint that is at least about 1%, 5%, 10%, 15%, 20%, 25%, 30%, 40%, 50%, 60%, 70%, 80%, 90%, 100%, 110%, 120%, 150%, 200%, or more than 200% of a surface area of an array site. Alternatively or additionally, a nucleic acid nanostructure, when coupled to a solid support, may comprise a total footprint that is no more than about 200%, 150%, 120%, 110%, 100%, 90%, 80%, 70%, 60%, 50%, 30%, 25%, 20%, 15%, 10%, 5%, 1%, or less than 1% of a surface area of an array site. In some configurations, a nucleic acid nanostructure may comprise a footprint that exceeds a surface area of an array site. For example, FIG. 56A depicts a nucleic acid nanostructure 5630 with pendant oligonucleotides 5635 (e.g., polynucleotide repeats obtained from TdT extension) whose length in a coupled configuration extend beyond the array site 5601.

A nucleic acid nanostructure or a component thereof (e.g., a compacted structure) may comprise a face or profile with a particular shape (e.g., square, rectangular, triangular, circular, polygonal, etc.). A shape or profile of a nucleic acid nanostructure or a component thereof may be the same as, or similar to, the shape or profile of an array site, for example as determined by an aspect ratio of the shape or profile. For example, a square-shaped nucleic acid origami may be coupled to a square-shaped array site. In a particular configuration, a nucleic acid nanostructure and an array site may comprise the same, or similar, shape or profile, in which the surface area of the array site is substantially the same as a footprint of the nucleic acid nanostructure. In another particular configuration, a nucleic acid nanostructure and an array site may comprise the same, or similar, shape or profile, in which a surface area of the array site differs from a footprint of the nucleic acid nanostructure (e.g., a larger footprint, a smaller footprint). In other configurations, a shape or profile of a nucleic acid nanostructure or a component thereof may comprise a different shape or profile as an array site, for example as determined by an aspect ratio of the shape or profile. For example, a square-shaped nucleic acid origami may be coupled to a circular array site. In some configurations, a shape or profile of a nucleic acid nanostructure or a component thereof may comprise a different shape or profile as an array site, in which the nucleic acid nanostructure comprises a larger footprint than a surface area of the array site. In other configurations, a shape or profile of a nucleic acid nanostructure or a component thereof may comprise a different shape or profile as an array site, in which the nucleic acid nanostructure comprises a smaller footprint than a surface area of the array site. In other configurations, a shape or profile of a nucleic acid nanostructure or a component thereof may comprise a different shape or profile as an array site, in which the nucleic acid nanostructure comprises a substantially equal footprint as a surface area of the array site.

A plurality of nucleic acid nanostructures or nucleic acid nanostructure complexes, as set forth herein, may be combined to form an array. For example, a plurality of SNAPs can form a random array (e.g., where the plurality of SNAPS occur in a non-repeating pattern on a surface or interface) or an ordered array (e.g. where the plurality of SNAPS are spatially arranged in a regular repeating pattern on a surface or interface). In some configurations, a homogeneous plurality of nucleic acid nanostructures or nucleic acid nanostructure complexes may be combined to form a random or ordered array on a surface or interface. In other configurations, a heterogeneous plurality of nucleic acid nanostructures or nucleic acid nanostructure complexes may be combined to form a random or ordered array on a surface or interface. The homogeneity or heterogeneity of a plurality of nucleic acid nanostructures or nucleic acid nanostructure complexes may be determined based upon the shape, conformation, or structure of the nucleic acid nanostructures or nucleic acid nanostructure complexes. For example, a homogeneous plurality of nucleic acid nanostructure complexes may contain only nucleic acid nanostructure complexes with cross configurations. In another example, a heterogeneous plurality of nucleic acid nanostructure complexes may contain a mixture of nucleic acid nanostructure complexes with cross or square configurations.

Nucleic acid nanostructures or nucleic acid nanostructure complexes may arrange at a surface or interface with a characteristic separation or spacing. The characteristic separation or spacing may be determined by an average or localized distance between adjacent analyte coupling sites on differing nucleic acid nanostructures or nucleic acid nanostructure complexes. The characteristic separation or spacing may be determined by: 1) the sizes of nucleic acid nanostructures or nucleic acid nanostructure complexes; 2) the structure or conformation of nucleic acid nanostructures or nucleic acid nanostructure complexes; 3) the spacing or separation of patterning features on a surface; 4) or a combination thereof. For a structured or patterned array, the characteristic separation or spacing may be determined by the separation or spacing between structured or patterned features. For an unstructured or unpatterned array, the characteristic separation or spacing may be determined by, for example, the size of nucleic acid nanostructure complexes and/or the presence of modifying groups (e.g., steric groups, coupling groups) near the edges of complexes that bind complexes together or generate inter-complex repulsion. FIGS. 17A-17C depict configurations for altering a characteristic separation or spacing of a plurality of nucleic acid nanostructure complexes via the arrangement of the complexes. FIG. 17A depicts an assembled array of homogeneous SNAP complexes with cross configurations 1710 that are arranged by dense packing of the complexes. The assembled array may have a characteristic spacing between nearest adjacent analyte coupling sites of $\Delta g_1$ along diagonal lines between coupling sites. FIG. 17B depicts an assembled array of homogeneous SNAP complexes with cross configurations 1710 that are arranged with a less dense packing structure than the packing shown in FIG. 17A. The assembled array may have a characteristic spacing between nearest adjacent analyte coupling sites of $\Delta g_2$ between any two adjacent analyte coupling sites. FIG. 17C depicts an assembled array of homogeneous SNAP complexes with cross configurations 1710 that are combined with separating SNAPs 1720 (e.g., SNAPs or SNAP complexes with no polypeptide coupling site) to form a separated array. The separating SNAPs 1720 increase the characteristic spacing $\Delta g_3$ between analyte coupling sites on adjacent SNAP complexes. Assuming uniform size of the homogeneous SNAP complexes with cross configurations 1710, a characteristic separation of spacing may increase in the order $\Delta g_3 > \Delta g_2 > \Delta g_1$.

In another aspect, provided herein is a single-analyte array comprising: a) a solid support comprising a plurality of addresses, in which each address of the plurality of addresses is resolvable from each other address at single-analyte resolution, and wherein each address is separated from each adjacent address by one or more interstitial regions; and b) a plurality of analytes, wherein a single analyte of the plurality of analytes is coupled to an address of the plurality of addresses, wherein each address of the plurality of addresses comprises a single analyte of interest (i.e. one and only one analyte of interest), wherein each single analyte is coupled to a coupling surface of the address by a nucleic acid (e.g., a nucleic acid nanostructure, a SNAP, etc.), and wherein the nucleic acid inhibits (e.g. occludes) the single analyte from contacting the coupling surface.

In another aspect, provided herein is a single-analyte array comprising: a) a solid support comprising a plurality of addresses, in which each address of the plurality of addresses is resolvable at single-analyte resolution, in which each address comprises a coupling surface, and in which each coupling surface comprises one or more surface-linked moieties; and b) a plurality of nucleic acid nanostructures, in which each structured nucleic acid particle comprises a coupling moiety, in which the coupling moiety comprises a plurality of oligonucleotides, in which each oligonucleotide of the plurality of oligonucleotides comprises a surface-interacting moiety, in which each structured nucleic acid particle of the plurality of structured nucleic acid particles is coupled to an address of the plurality of addresses by a binding of the surface-interacting moiety of the plurality of oligonucleotides to a surface-linked moiety of the one or more complementary oligonucleotides, and in which a structured nucleic acid particle of the plurality of structured nucleic acid particles comprises a display moiety comprising a coupling site that is coupled to an analyte.

In some configurations, a single-analyte array may comprise an ordered array. In particular configurations, a coupling surface of an ordered array may be formed by a lithographic process. In other particular configurations, an address of a plurality of addresses of an ordered array may be adjacent to one or more interstitial regions, wherein an interstitial region of the one or more interstitial regions does not comprise a coupling surface. An interstitial region of one or more interstitial regions, as set forth herein, may comprise a disrupting moiety, in which the disrupting moiety is configured to reduce, prevent, or inhibit a likelihood of a coupling of a molecule (e.g., an affinity reagent, a fluorophore, etc.) to the interstitial region. In some configurations, an ordered array may comprise a coupling surface, in which the coupling surface comprises a raised surface or a depressed surface relative to an interstitial region of one or more interstitial regions.

In other configurations, a single-analyte array may comprise an unordered array. An unordered array may comprise a solid support that does not comprise coupling surfaces formed by a patterning process (e.g., lithography). An unordered array may comprise, for example, a substantially planar solid support comprising a near-uniform surface layer comprising a plurality of surface-linked moieties. An unordered array may comprise unique, resolvable addresses for nucleic acid nanostructure localization, for example by depositing nucleic acid nanostructures that are configured to prevent co-localization of multiple nucleic acid nanostructures at a single address, or by depositing nucleic acid nanostructures at a concentration that inhibits co-localization.

In particular configurations, an array, whether ordered or unordered, may further comprise a lipid layer (e.g., a monolayer, bilayer, micelle, or colloid) adjacent to the solid support. A nucleic acid nanostructure (e.g., a SNAP) may be anchored to an array via a lipid bilayer, for example if a surface-linked moiety of one or more surface-linked moieties is coupled to a lipid molecule of the lipid layer. In particular configurations, a lipid molecule of a lipid layer may comprise a phospholipid, triglyceride, or a cholesterol.

In some configurations, a plurality of nucleic acid nanostructures or nucleic acid nanostructure complexes, as set forth herein, may be combined to form a self-assembling or self-patterning array. Analyte may be conjugated to nucleic acid nanostructures or nucleic acid nanostructure complexes before, during, or after the formation of a self-assembling or self-patterning array to form an array of analyte. Formation of a self-assembling or self-patterning array may be driven by interactions between nucleic acid nanostructures and a surface or interface, interactions between nucleic acid nanostructure complexes and a surface or interface, interactions between two or more nucleic acid nanostructures, interactions between two or more nucleic acid nanostructure complexes, or a combination thereof. A self-assembling or self-patterned array of nucleic acid nanostructures or nucleic acid nanostructure complexes may be stable, meta-stable or unstable. Stability and/or order of a self-assembled or self-patterning array of nucleic acid nanostructures or nucleic acid nanostructure complexes may be mediated by covalent, non-covalent, electrostatic, or magnetic interactions. For example, a self-assembling array of SNAP complexes may be stabilized by electrostatic interactions between constituent SNAPs and a surface, plus nucleic acid coupling between adjacent SNAPs. Such an array may be destabilized by excess temperature or the presence of a denaturant. In another example, a self-assembling array may be formed by covalent cross-linking between neighboring SNAP complexes that are associated with a multi-phase interface. The covalently cross-linked array may have substantial chemical stability but may be disrupted by excess mechanical stress.

A self-patterning or self-assembling array of nucleic acid nanostructures or nucleic acid nanostructure complexes may form a homogeneous or heterogeneous array at a surface or interface. A self-patterning or self-assembling array of nucleic acid nanostructures or nucleic acid nanostructure complexes may be homogeneous over an entire surface or interface, or homogeneous over a portion of a surface or an interface. FIGS. 18A-18C illustrate array coverage patterns for differing configurations of nucleic acid nanostructures or nucleic acid nanostructure complexes in a self-assembling or self-patterning array. FIG. 18A depicts an array of rectangular SNAPs or SNAP complexes 1820 that completely occupy a region bordered by box 1810. The ordering or patterning of the array is approximately homogeneous across the entire region 1810. FIG. 18B depicts an array of rectangular SNAPs or SNAP complexes 1820 that partially occupy a region bordered by box 1810. The array is heterogeneous in coverage with respect to region 1810, but is approximately homogeneous in the subregion bordered by box 1840. The remaining region 1830 between region 1810 and subregion 1840 may have no SNAPs or SNAP complexes, unorganized or non-arrayed SNAPs or SNAP complexes, or smaller arrays of SNAPs or SNAP complexes. FIG. 18C depicts an array of rectangular SNAPs or SNAP complexes 1820 that are homogeneously distributed within a region bordered by box 1810. The dispersion of SNAPs or SNAP complexes 1820 includes unoccupied subregions with few or no SNAPs or SNAP complexes 1830. A homogeneous dispersion with unoccupied subregions may be formed by, for example, depositing SNAPs or SNAP complexes on a patterned array or combining a plurality of SNAPs or SNAP complexes comprising modifying groups that sterically repel other SNAPs or SNAP complexes.

A plurality of nucleic acid nanostructures or nucleic acid nanostructure complexes, as set forth herein, may assemble into a cohesive and/or continuous structure. For example, a plurality of nucleic acid nanostructures or nucleic acid nanostructure complexes may form a monolayer or membrane. A cohesive and/or continuous structure may form in a solution then deposit on a surface due to sedimentation or other deposition mechanism. A cohesive and/or continuous structure comprising a plurality of assembled nucleic acid nanostructures or nucleic acid nanostructure complexes may form on a surface or at an interface. FIGS. 19A-19B illustrate cohesive or continuous structures formed by the assembly of a plurality of nucleic acid nanostructures or nucleic acid nanostructure complexes. FIG. 19A depicts a plurality of SNAPs 1930 that are configured to associate with an interface 1950 formed between a first denser fluid 1960 and a second less dense fluid 1970. The plurality of SNAPs 1930 are coupled into an analyte array by nucleic acid couplings 1940. The analyte array is further stabilized by couplings 1920 (e.g. streptavidin-biotin, covalent bonds formed by a click reaction, etc.) that secure the analyte array to a vessel 1910 that contains the first denser fluid 1960 and the second less dense fluid 1970. FIG. 19B illustrates a plurality of SNAPs 1930 that are coupled into an analyte array by nucleic acid couplings 1940. The analyte array may form at an interface 1950 or within a fluid 1960 before depositing on a surface of a vessel 1910 that contains the fluid 1960. Without wishing to be bound by theory, the deposition of the assembled analyte array at the surface may be driven by hydrodynamic destabilization caused by array size, density, weight, or other properties.

A self-patterning or self-assembling array of nucleic acid nanostructure complexes may comprise multiple species or configurations of nucleic acid nanostructure complexes, as set forth herein. Species of nucleic acid nanostructure complexes may be distinguished by shape, configuration (e.g., presence or absence of modifying groups, presence of absence of coupling groups, etc.), presence or absence of a particular tag, or coupling specificity. Two or more species of nucleic acid nanostructure complexes may be configured to self-assemble into subregions of a larger array. Two or more species of nucleic acid nanostructure complexes may self-assemble due to complementary coupling groups (e.g., nucleic acids) on each species of a nucleic acid nanostructure complexes.

Figure 20:
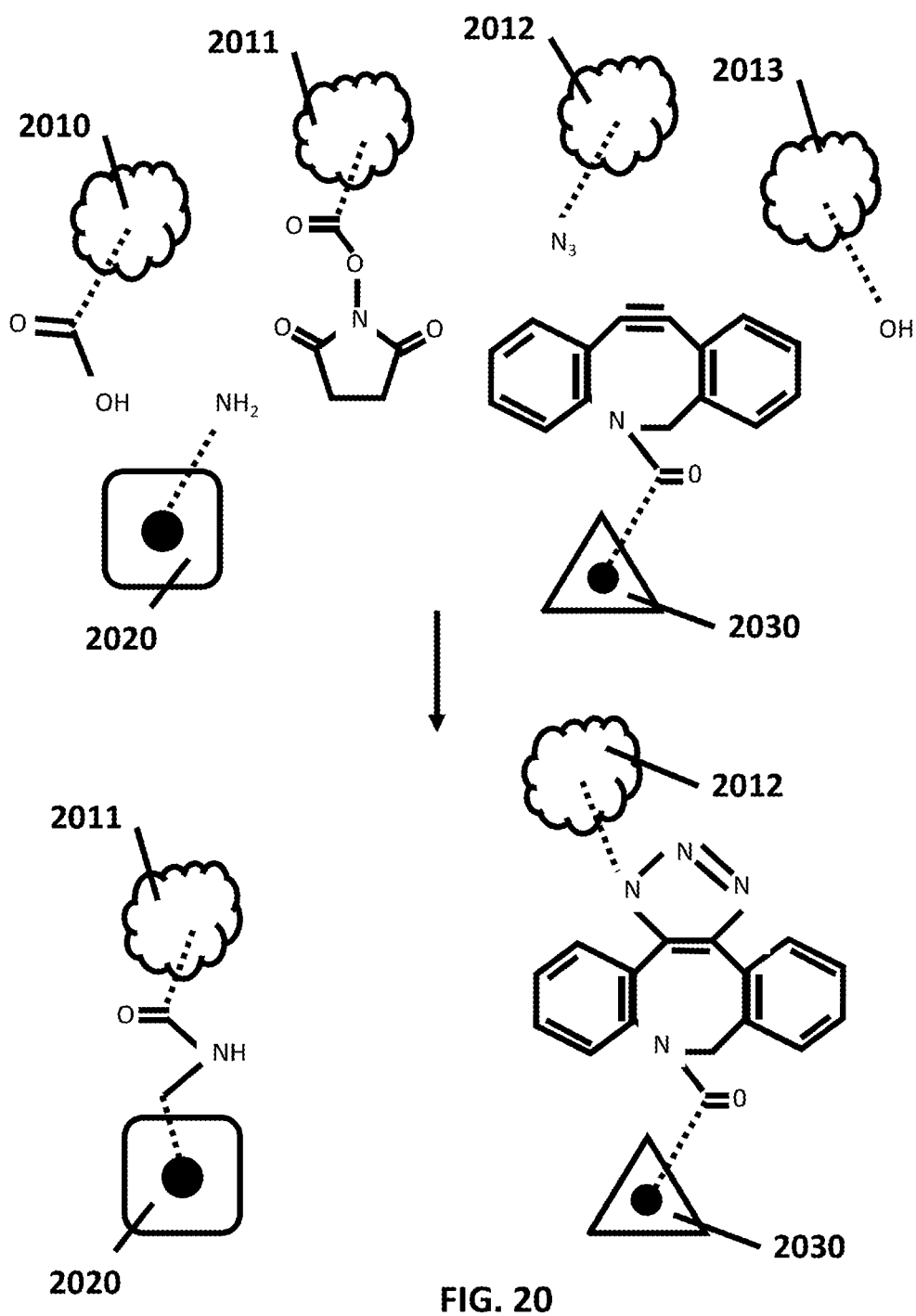
FIG. 20 depicts a method of isolating analyte fractions onto different SNAP species, in accordance with some embodiments.

Differing species of nucleic acid nanostructures or nucleic acid nanostructure complexes, as set forth herein, may be formed for the purpose of distinguishing different types of analytes. In some configurations, an analyte sample may be divided into separate fractions (e.g., by size, by charge, by mass, by polarity, by location in cell, etc.), with each separate fraction being placed on a different species of nucleic acid nanostructure or nucleic acid nanostructure complex. In other configurations, sample analytes may be coupled to one species of nucleic acid nanostructure or nucleic acid nanostructure complex and a standard or control analyte may be coupled to a different species of nucleic acid nanostructure or nucleic acid nanostructure complex. FIG. 20 illustrates a method of forming differing species of SNAPs or SNAP complexes by selectively targeting polypeptides from a polypeptide sample onto differing SNAPs or SNAP complexes. A square species of SNAP or SNAP complex comprising an amine reactive group 2020 and a triangular species of SNAP or SNAP complex comprising a DBCO reactive group 2030 are contacted with a polypeptide sample comprising differentially labeled polypeptides, including carboxylated polypeptides 2010, activated ester-labeled polypeptides 2011, azide-labeled polypeptides 2012, and hydroxyl-labeled polypeptides 2013. Due to the relative reactivities of the SNAP-based reactive groups and the polypeptide-based reactive groups, the square species of SNAP or SNAP complex 2020 covalently conjugates to the activated ester-labeled polypeptide 2011 to form a polypeptide-coupled SNAP or SNAP complex. Likewise, the triangular species of SNAP or SNAP complex 2030 covalently conjugates to the activated ester-labeled polypeptide 2012 to form a polypeptide-coupled SNAP or SNAP complex.

Two differing species of nucleic acid nanostructures or nucleic acid nanostructure complexes in an assembled array may be distinguished by differing types of displayed analytes. Differing analytes may be sorted on the basis of any analyte property, including, but not limited to size, weight, length, cellular location (e.g., extracellular, membrane, cytoplasmic, organelle, nuclear, etc.), organism or system of origin (e.g., cell-free synthesis), isoelectric point, hydrodynamic radius, post-translational modification, or any other measurable or observable polypeptide characteristic. For example, a first species of SNAPs or SNAP complexes in a polypeptide array may comprise polypeptides from a polypeptide-containing sample and a second species of SNAPs or SNAP complexes in a polypeptide array may comprise polypeptides from a standard or control sample (i.e., a quality control marker polypeptide, positive control polypeptide, negative control polypeptide, etc.). In another example, polypeptides from a first organism may be placed on a first species of SNAPs or SNAP complexes and polypeptides from a second organism may be placed on a second species of SNAPs or SNAP complexes.

Figure 22:
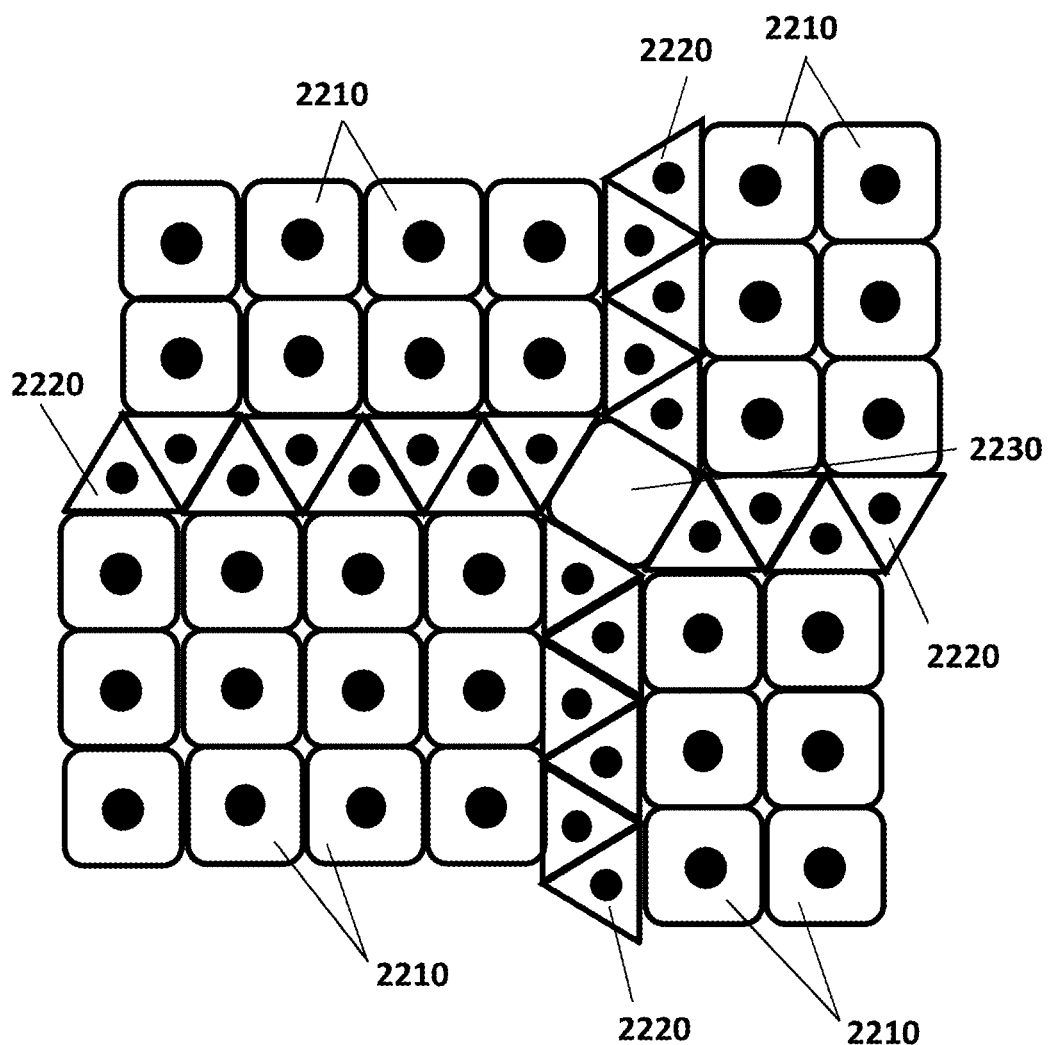
FIG. 22 illustrates an array comprising multiple species of SNAPs, in accordance with some embodiments.
Figure 23B:
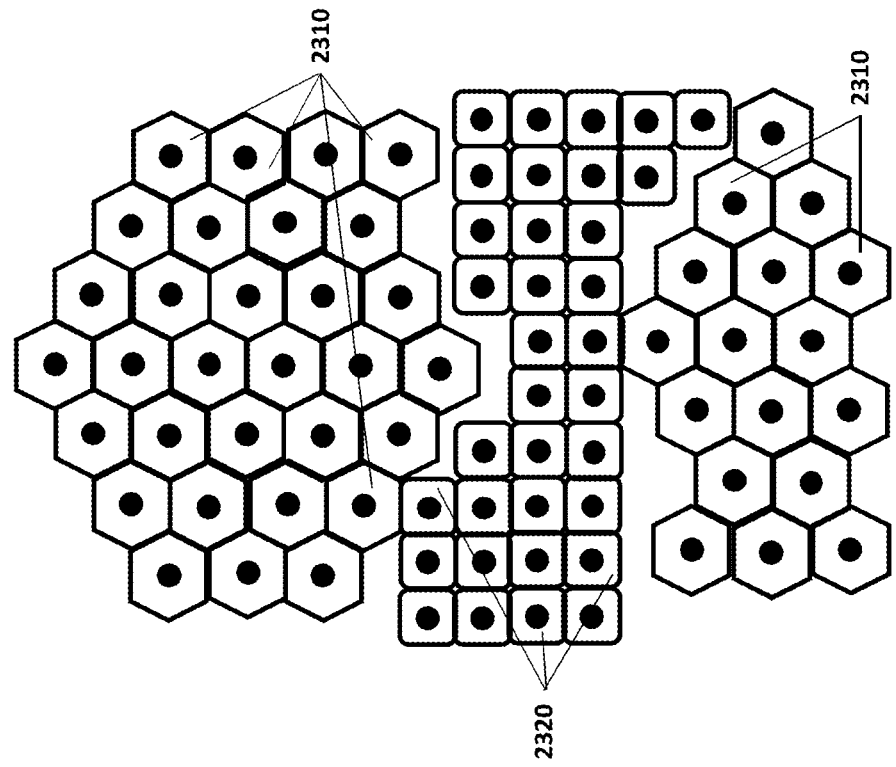
FIGS. 23A and 23B illustrate an array comprising multiple species of SNAPs, in accordance with some embodiments.

Two or more differing species of nucleic acid nanostructures or nucleic acid nanostructure complexes may assemble to form an array with a distinctive, rational, ordered, or segregated arrangement. FIGS. 22-24 depict examples of localized patterning of SNAP complexes to generate different array conformations. Differing species of SNAPs or SNAP complexes may self-assemble into ordered or patterned arrays.

FIG. 22 depicts an array of SNAPs or SNAP complexes formed by combining two differing species of SNAPs or SNAP complexes that are geometrically matched and configured to bind to each other to form a symmetrical array. The square SNAPs or SNAP complexes may self-arrange into regions of homogeneous SNAPs that are divided by arranged complexes of segregating SNAPs or SNAP complexes 2220. The arranged complexes of segregating SNAPs or SNAP complexes 2220 may be readily observable or detectable by some detection methods (e.g., fluorescence microscopy), allowing rapid spatial identification of the locations in an array of the segregated square SNAP or SNAP complexes 2210, or the segregating SNAPs or SNAP complexes 2220. The self-segregation may be promoted by fabricating SNAPs or SNAP complexes with certain utility faces comprising coupling groups that are intended to couple with SNAPs or SNAP complexes of the same species, and other utility faces comprising coupling groups that are intended to couple with SNAPs or SNAP complexes of the differing species. The ordered array may also comprise unoccupied regions of SNAPs or SNAP complexes that are not configured to couple an analyte 2230. The unoccupied regions or SNAPs or SNAP complexes that are not configured to couple an analyte 2230 may be used to maintain array stability and/or facilitate the formation of the array patterning. FIG. 24 depicts a similar array to the array depicted in FIG. 22 utilizing several species of SNAPs or SNAP complexes. The large square SNAPs or SNAP complexes 2410, small square SNAPs or SNAP complexes 2411, large right triangular SNAP complexes 2412, and small right triangular SNAPs or SNAP complexes 2413 may be configured to self-segregate into homogeneous regions of like SNAPs or SNAP complexes. In some configurations, the segregating SNAPs or SNAP complexes 2220 or 2420 may be coupled with standard or control polypeptides (e.g., quality control polypeptides, positive control polypeptides, negative control polypeptides, etc.) to generate patterned fiducial or gridding lines for image registration when detecting SNAP arrays, quality control of processes utilizing SNAP arrays, or the like.

Figure 23A:
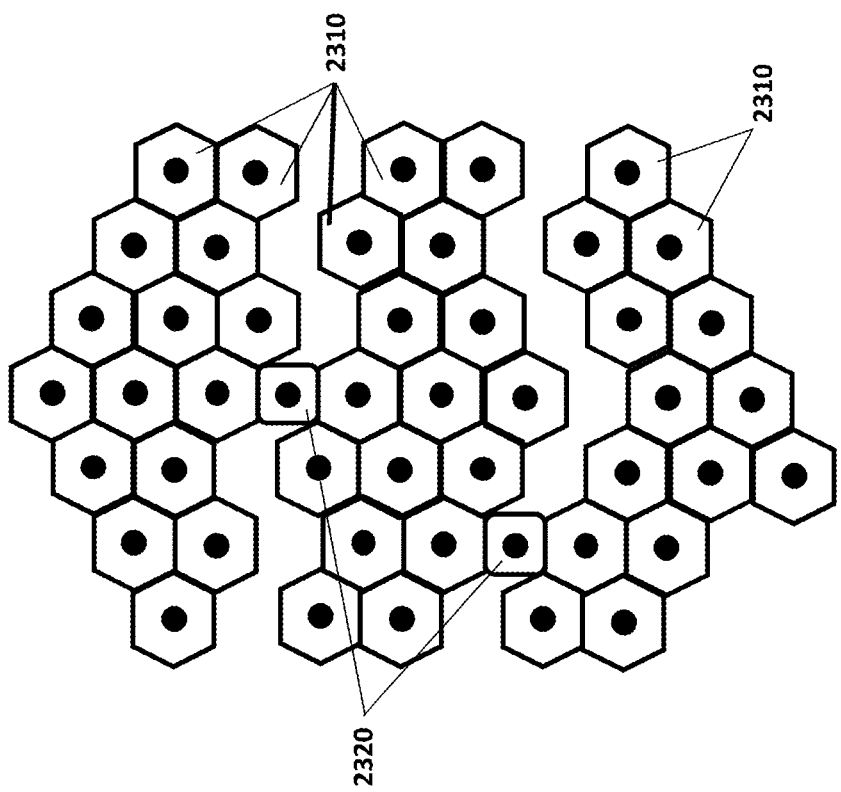
Figure 24:
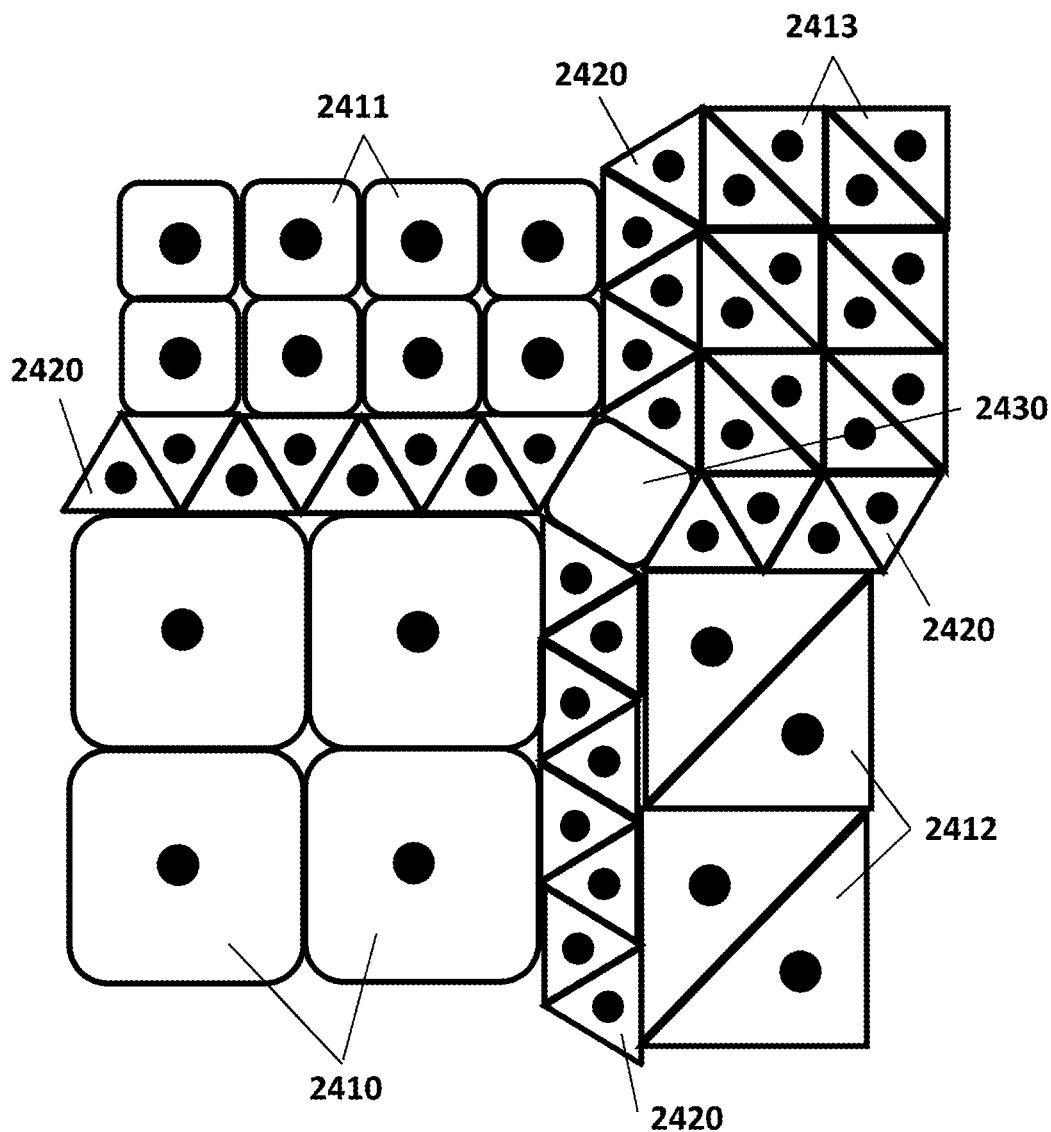
FIG. 24 illustrates an array comprising multiple species of SNAPs, in accordance with some embodiments.

FIG. 23A shows an array of SNAPs or SNAP complexes formed by combining two differing species of SNAPs or SNAP complexes that are geometrically mismatched but configured to bind to each other. The binding of a hexagonal SNAP or SNAP complex 2310 to a square SNAP or SNAP complex 2320 creates mismatches or discontinuities in the arrangement patterns of arrayed SNAPs or SNAP complexes. The mismatches or discontinuities may be readily observable or detectable by some detection methods (e.g., fluorescence microscopy), allowing rapid spatial identification of the locations in an array of the square SNAP or SNAP complexes 2320. This type of array may be useful in situations where one species of SNAP or SNAP complex is fewer in total number relative to a second species of SNAP or SNAP complex. FIG. 23B shows an array of SNAPs or SNAP complexes formed by combining two differing species of SNAPs or SNAP complexes that are geometrically mismatched but configured to bind to each other. The binding of a hexagonal SNAP or SNAP complex 2310 to a square SNAP or SNAP complex 2320 creates mismatches or discontinuities in the arrangement patterns of arrayed SNAPs or SNAP complexes. In some configurations (e.g., approximately equal concentrations of each species), both species may selectively self-segregate, leading to limited regions of binding between the two species. The locations of mismatches or discontinuities may be readily observable or detectable by some detection methods (e.g., fluorescence microscopy), allowing rapid spatial identification of the locations in an array of the segregated square SNAP or SNAP complexes 2320, or the segregated hexagonal SNAPs or SNAP complexes 2310.

An array comprising a plurality of nucleic acid nanostructures or nucleic acid nanostructure complexes, as set forth herein, may remain stable for a particular time period. The stability of an array may be a function of a threshold quantity of nucleic acid nanostructures or nucleic acid nanostructure complexes remaining coupled to or with the array. For example, a stable array may comprise at least about 25%, 30%, 35%, 40%, 45%, 50%, 55%, 60%, 65%, 70%, 75%, 80%, 85%, 90%, 95%, 99%, or more than 99% of nucleic acid nanostructures or nucleic acid nanostructure complexes remaining coupled to the array after a set period of time such as, for example, at least about 1 s, 1 min, 5 min, 10 min, 30 min, 1 hr, 3 hr, 6 hr, 12 hr, 1 day, 2 day, 3 day, 1 week, 1 month, 6 months, 1 year, 5 years, or more than 5 years.

In some configurations, a capture moiety of a nucleic acid nanostructure may be coupled to a coupling surface of a solid support. In other configurations, a capture moiety of a nucleic acid nanostructure need not be coupled to the surface. For example, a SNAP may be uncoupled (e.g., suspended or solvated in a fluidic medium) from a coupling surface before deposition of the SNAP, or after the SNAP has been selectively released from the coupling surface (e.g., via cleavage of a cleavable linker). A solid support may comprise any conceivable material or combinations thereof, including metals, metal oxides, glasses, ceramics, semiconductors, and polymers. A solid support may comprise a gel such as a hydrogel. A solid support may comprise a plurality of surface-displayed functional groups or moieties (e.g., amines, epoxides, carboxylates, polymer chains, oligonucleotides, etc.). Functional groups may be displayed on a solid support, for example, to passivate the surface, provide coupling sites, or block the binding of molecules to the surface. Surface-displayed functional groups may be configured to form covalent interactions or non-covalent interactions with a nucleic acid nanostructure (e.g., a SNAP) or other molecule or particle. A solid support may further comprise an adjacent or coupled layer, e.g., a lipid monolayer, a lipid bilayer, a plurality of colloids or micelles, etc. An adjacent or coupled layer may comprise a plurality of molecules that alter a surface property of the solid support, such as a surface tension, a surface energy, a hydrophobicity, a hydrophilicity, or a tendency or likelihood to non-specifically bind a particular molecule (e.g., a protein). An adjacent or coupled layer may comprise a surfactant or a detergent species. An adjacent or coupled layer may comprise a lipid species, such as a phospholipid, a triglyceride, or a sterol.

A solid support may comprise an address comprising one or more surface-linked moieties, in which the address may be resolvable at single-analyte resolution. In some configurations, an address may comprise one or more surfaces, in which the one or more surfaces may comprise a coupling surface, and in which the coupling surface comprises the one or more surface-linked moieties. In particular configurations, one or more surfaces of an address on a solid support may form a three-dimensional structure on the solid support. For example, a three-dimensional structure may comprise a raised structure (e.g., a pillar, post, column, dome, pyramid, convex region, etc.) or a well structure (e.g., a concave region, channel or well, such as a picowell, nanowell or a microwell).

A coupling surface of a solid support, as set forth herein, may comprise a plurality of surface-linked moieties (e.g., surface-linked oligonucleotides, surface-linked reactive groups, surface-linked coupling groups, etc.). Surface-linked moieties may be covalently or non-covalently linked to a coupling surface of a solid support. In some configurations, a surface-linked moiety distribution or density on a coupling surface may be substantially uniform over the coupling surface. In other configurations, a surface-linked moiety density of a coupling surface need not be substantially uniform over the coupling surface. For example, a fraction of a plurality of surface-linked moieties may be located within a central region of a coupling surface. In another example, a second fraction of the plurality of surface-linked moieties may be located within an outer region of a coupling surface. A plurality of surface-linked moieties may have an average surface density over a region of a coupling surface (e.g. the region can be a site or address of an array) of at least about 0.001 picomoles per square nanometer ($pmol/nm^2$), 0.005 $pmol/nm^2$, 0.01 $\mu mol/nm^2$, 0.05 $\mu mol/nm^2$, 0.1 $\mu mol/nm^2$, 0.5 $\mu mol/nm^2$, 1 $\mu mol/nm^2$, 5 $pmol/nm^2$, 10 $\mu mol/nm^2$, 50 $\mu mol/nm^2$, 100 $\mu mol/nm^2$, or more than 100 $\mu mol/nm^2$. Alternatively or additionally, a plurality of surface-linked moieties may have an average surface density over a region of a coupling surface of no more than about 100 $\mu mol/nm^2$, 50 $\mu mol/nm^2$, 10 $\mu mol/nm^2$, 5 $pmol/nm^2$, 1 $\mu mol/nm^2$, 0.5 $\mu mol/nm^2$, 0.1 $\mu mol/nm^2$, 0.05 $\mu mol/nm^2$, 0.01 $\mu mol/nm^2$, 0.005 $pmol/nm^2$, 0.001 $\mu mol/nm^2$, or less than 0.001 $\mu mol/nm^2$.

A solid support, as set forth herein, may comprise a coupling surface containing a plurality of surface-linked moieties, in which a fraction of the surface-linked moieties are coupled to at least one surface-interacting moiety of a nucleic acid nanostructure (e.g., a SNAP). In some configurations, a fraction of surface-interacting moieties of a nucleic acid nanostructure is coupled to a fraction of surface-linked moieties of a plurality of surface-linked moieties on a solid support. A fraction of surface-interacting moieties coupled to at least one surface-linked moiety may be at least about 0.000001, 0.00001, 0.0001, 0.0005, 0.001, 0.005, 0.01, 0.05, 0.1, 0.2, 0.25, 0.3, 0.35, 0.4, 0.45, 0.5, 0.55, 0.6, 0.65, 0.7, 0.75, 0.8, 0.85, 0.9, 0.95, 0.99, 0.999, 0.9999, 0.99999, or more than 0.99999. Alternatively or additionally, a fraction of surface-interacting moieties coupled to at least one surface-linked moiety may be no more than about 0.99999, 0.9999, 0.999, 0.99, 0.95, 0.9, 0.85, 0.8, 0.75, 0.7, 0.65, 0.6, 0.55, 0.5, 0.45, 0.4, 0.35, 0.3, 0.25, 0.2, 0.1, 0.05, 0.01, 0.005, 0.001, 0.0005, 0.0001, 0.00001, 0.000001, or less than 0.000001.

FIG. 40C illustrates a configuration of a SNAP composition with differing fractions of coupled surface-interacting moieties and surface-linked moieties. The SNAP 4010 is coupled to the coupling surface 4002 by binding interactions for each of its 5 surface-interacting moieties. Accordingly, the overall fraction of surface-interacting moieties coupled to at least one surface-linked moiety is 1. The coupling surface comprises a depicted 15 surface-linked moieties, of which 5 are involved in forming a binding interaction with the SNAP 4010. Accordingly, the fraction of surface-linked moieties coupled to at least one surface-interacting moiety is 0.26. Likewise, fractions can be calculated for each unique type of surface-linked species (e.g., 0.22 for the surface-linked oligonucleotides 4038 and 1 for the surface-linked complementary coupling group 4039).

A solid support, as set forth herein, may comprise a passivating layer. A passivating layer may be configured to reduce, inhibit, or prevent non-specific binding of particular molecules (e.g., affinity agents, uncoupled analytes, etc.) with a solid support. In some configurations, a passivating layer may comprise a plurality of molecules that are configured to prevent non-specific binding of a molecule to the solid support. In particular configurations, a plurality of molecules may comprise a plurality of surface-linked polymers selected from the groups consisting of polyethylene glycol, polyethylene oxide, an alkane, a nucleic acid, or a dextran. In some configurations, a molecule of a plurality of molecules comprising a passivating layer may further comprise a surface-linked moiety. In some configurations, a passivating layer may comprise a molecule of a plurality of molecules that further comprises a linker that couples a surface-linked moiety to the coupling surface. In some configurations, a linking group may comprise a group that forms a covalent or coordination bond with a solid support, such as a silane, a phosphate, or a phosphonate.

A random or ordered array of nucleic acid nanostructures or nucleic acid nanostructure complexes may be formed from a plurality of nucleic acid nanostructures or nucleic acid nanostructure complexes at a surface or interface. A random or ordered array of nucleic acid nanostructures or nucleic acid nanostructure complexes may be formed from a plurality of nucleic acid nanostructures or nucleic acid nanostructure complexes at a structured or patterned surface. A random or ordered array of nucleic acid nanostructures or nucleic acid nanostructure complexes may be formed from a plurality of nucleic acid nanostructures or nucleic acid nanostructure complexes at an unstructured or non-patterned surface such as a surface having a continuous lawn or monolith of attachment points for nucleic acid nanostructures or nucleic acid nanostructure complexes.

A structured or patterned surface may be formed on a solid support by any suitable method, such as photolithography, Dip-Pen nanolithography, nanoimprint lithography, nanosphere lithography, nanoball lithography, nanopillar arrays, nanowire lithography, scanning probe lithography, thermochemical lithography, thermal scanning probe lithography, chemical or plasma etching, local oxidation nanolithography, molecular self-assembly, stencil lithography, or electron-beam lithography. A lithographic method may facilitate formation of a two-dimensional or three-dimensional feature on a surface of a solid support. In some configurations, a substantially planar solid support comprising an original surface may be formed to provide a plurality of sites, in which each site of the plurality of sites comprises a face comprising a region of the original surface, and in which each site of the plurality of sites is adjacent to one or more interstitial regions, in which the one or more interstitial regions comprise a formed surface, in which the formed surface comprises a surface produced by a forming process (e.g., lithography, deposition, etc.). For example, photolithography may be utilized to etch material from a planar solid support, thereby producing a plurality of raised sites surrounded by etched lanes, in which a thickness of the solid support at each raised site is substantially the same as an original thickness of the solid support, and a thickness of the solid support at an interstitial region is less than the original thickness of the solid support. In another example, an array may be formed by patterning a solid material (e.g., a metal, a metal oxide, etc.) onto a surface of a planar solid support to produce a plurality of sites surrounded by raised interstitial regions of deposited solid material, in which a thickness of the array at each site is substantially the same as an original thickness of the solid support, and a thickness of the array at an interstitial region is substantially a sum of the original thickness of the solid support and a thickness of the deposited solid material. A site on a solid support may be formed with a shape or morphology that is substantially the same as a shape of a nucleic acid nanostructure, as set forth herein. For example, a substantially square nucleic acid nanostructure may be coupled to a substantially square array site. A site on a solid support may be formed with a shape or morphology that is not substantially the same as a shape of a nucleic acid nanostructure, as set forth herein. For example, a substantially square nucleic acid nanostructure may be coupled to a substantially circular array site. In some configurations, a solid support, a surface thereof, and/or a site thereof may undergo two or more surface forming processes to form nanoscale or microscale features on the surface (e.g. raised features, indented features). For example, a solid support may be formed by photolithography followed by etching (e.g., in potassium hydroxide) to produce a regularly ordered array of sites, in which each site of the regularly ordered array of sites comprises a three-dimensional well feature (e.g., a pyramidal well, a conical well, a hemispherical well, etc.). See, for example, Hookway, et. al, *Methods*, 101, 2016, which is incorporated by reference in its entirety.

Figure 66A:
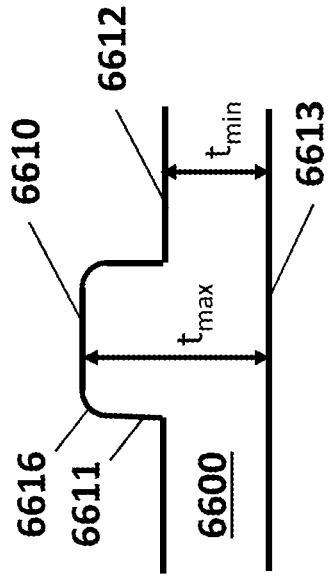
FIGS. 66A, 66B, 66C, and 66D display various shapes and morphologies of formed array features in accordance with some embodiments.
Figure 66B:
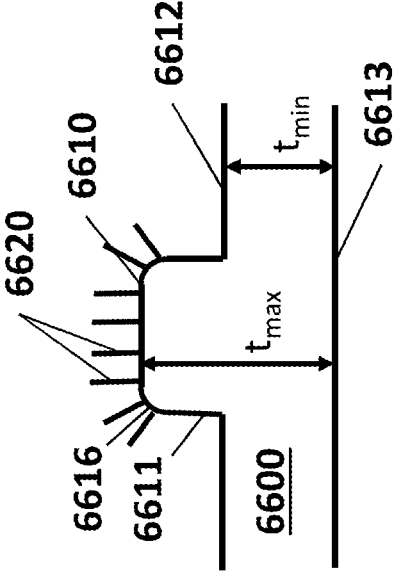
Figure 66C:
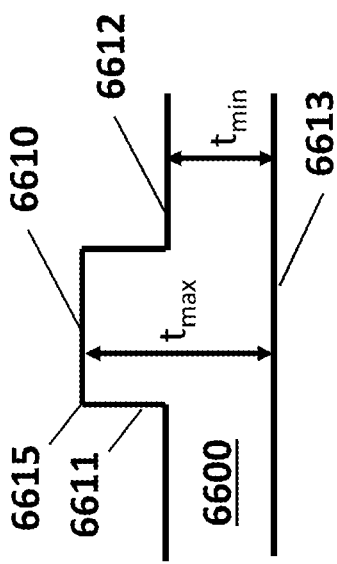
Figure 66D:
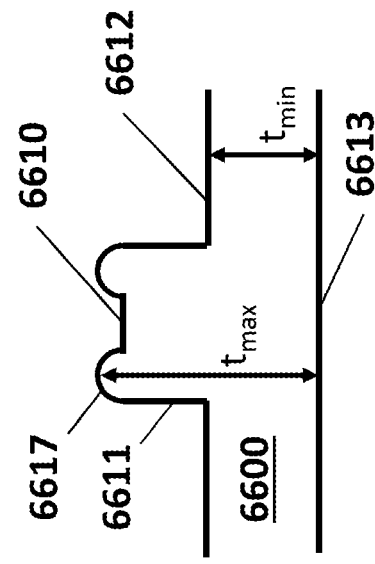

In some configurations, a site of a plurality of sites may comprise a three-dimensional shape or morphology. A forming process (e.g., lithography) may produce a site or a feature thereof (e.g., a raised feature, an indented feature) with a three-dimensional shape or morphology. FIGS. 66A-66D illustrate particular aspects of site morphology for a solid support comprising raised sites, although it will be readily understood that similar considerations can apply to indented features or sites. The raised features depicted in FIGS. 66A-66D can be formed by a process that removes material from a solid support or by a process that deposits a second solid support material onto a first solid support material. FIG. 66A depicts a cross-sectional view of a solid support comprising a raised feature (e.g., a site) comprising a substantially planar top surface 6610 and a lower surface 6612 that surrounds the raised feature, in which both surfaces 6610 and 6612 are substantially parallel to a bottom surface 6613 of the solid support 6613. The raised feature comprises sides surfaces 6611 that are substantially orthogonal to the substantially planar top surface 6610 and the lower surface 6612, thereby forming a sharp transition 6615 at the top of the raised feature. The total thickness of the solid support 6600 may vary from a maximum thickness, $t_{max}$, between the substantially planar top surface 6610 and the bottom surface 6613 to a minimum thickness, $t_{min}$, between the lower surface 6612 and the bottom surface 6613. FIG. 66B depicts a cross-sectional view of a solid support comprising a raised feature (e.g., a site) comprising a substantially planar top surface 6610 and a lower surface 6612 that surrounds the raised feature, in which both surfaces 6610 and 6612 are substantially parallel to a bottom surface 6613 of the solid support 6613. The raised feature comprises side surfaces 6611 that are substantially orthogonal to the substantially planar top surface 6610 and the lower surface 6612, but the transitions 6616 between the side surfaces 6611 and the substantially planar top surface 6610 are diffuse (e.g., rounded, curved, inclined, etc.). The total thickness of the solid support 6600 may vary from a maximum thickness, $t_{max}$, between the substantially planar top surface 6610 and the bottom surface 6613 to a minimum thickness, $t_{min}$, between the lower surface 6612 and the bottom surface 6613. FIG. 66C depicts a cross-sectional view of a solid support comprising a raised feature (e.g., a site) comprising a substantially planar top surface 6610 and a lower surface 6612 that surrounds the raised feature, in which both surfaces 6610 and 6612 are substantially parallel to a bottom surface 6613 of the solid support 6613. The raised feature comprises sides surfaces 6611 that are substantially orthogonal to the substantially planar top surface 6610 and the lower surface 6612. The substantially planar top surface 6610 comprises one or more non-planar surface features 6617. The non-planar surface features 6617 may occur due to a natural roughness of a solid support material or may be an artifact of an array formation process (e.g., anisotropic lithography, anisotropic deposition of a layer on a surface, anisotropic removal of a processing intermediate such as a photoresist, etc.). The total thickness of the solid support 6600 may vary from a maximum thickness, $t_{max}$, between the non-planar surface feature 6617 and the bottom surface 6613 to a minimum thickness, $t_{min}$, between the lower surface 6612 and the bottom surface 6613. FIG. 66D depicts a raised feature such as the feature of FIG. 66B, in which a plurality of moieties 6620 (e.g., surface-linked moieties) have been coupled to the raised feature. Due to the morphology of the surface (e.g., the diffuse transition 6616), orientations of moieties of the plurality of moieties 6620 may vary over the raised feature. In some configurations, varied orientations of surface-coupled moieties, for example near an edge of a site, may facilitate coupling of a nucleic acid nanostructure to a site or a feature thereof. For example, a surface-linked moiety near an edge of an array site may couple to a nucleic acid nanostructure adjacent to the array site (e.g., an interstitial region), thereby permitting re-arrangement of the spatial position of the nucleic acid nanostructure from the adjacent area to the array site. In some configurations, varied orientations of surface-coupled moieties, for example near an edge of a site, may inhibit non-specific coupling of entities to a site or a feature thereof. For example, PEG chains near an edge of a site may inhibit binding of entities (e.g., affinity agents, other nucleic acids) to an array site when a nucleic acid is already coupled to the array site.

Figure 64:
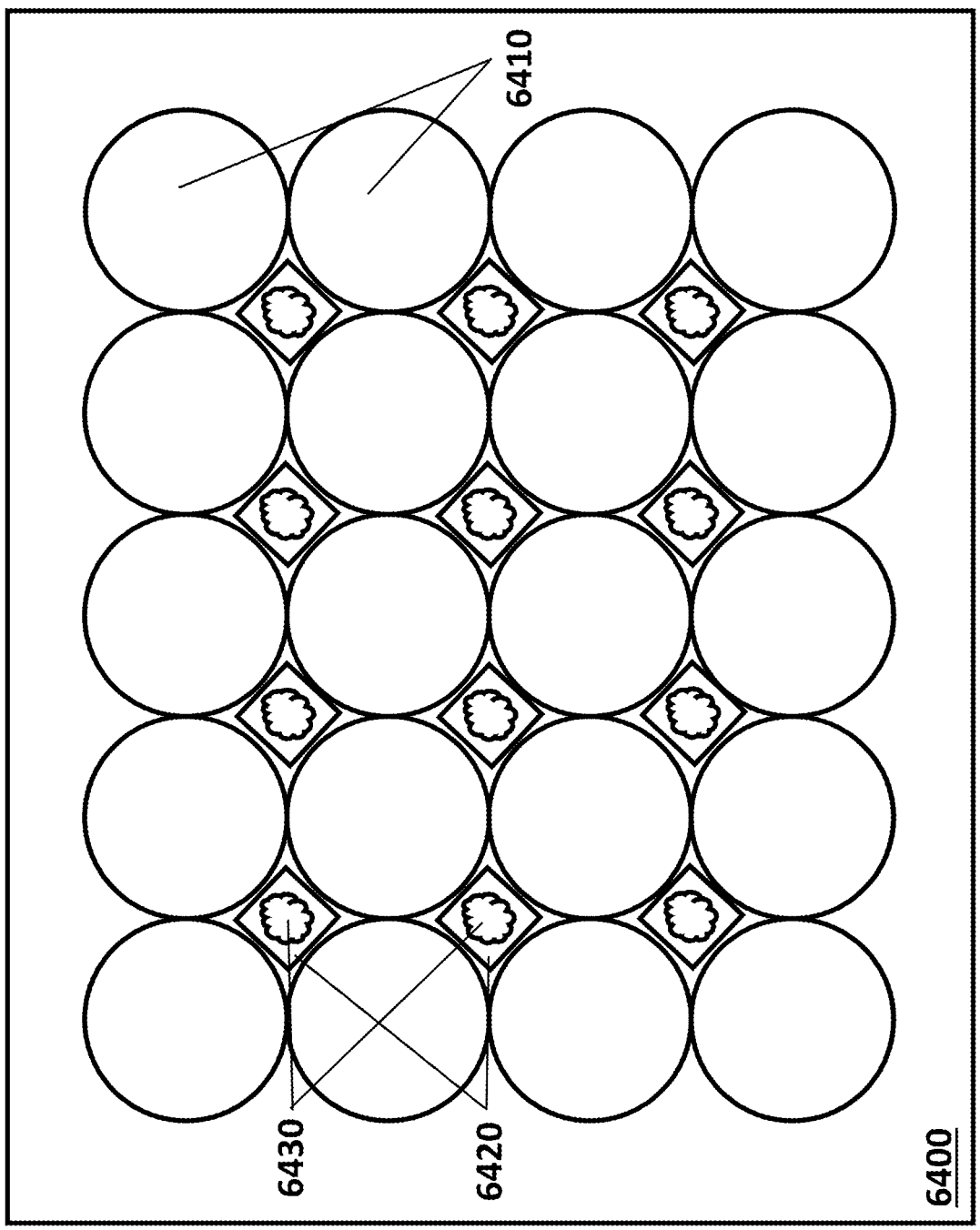
FIG. 64 depicts an array of analytes formed by a non-lithographic method, in accordance with some embodiments.

Optionally, a solid support may be formed into an array that is configured to couple a plurality of analytes, as set forth herein, by a non-lithographic method. In some cases, an array may comprise a solid support comprising a plurality of sites and a separating material, in which the separating material separates each site of the plurality of sites from each other site of the plurality of sites. A separating material may comprise one or more characteristics of: i) being configured to couple (e.g., covalently couple, non-covalently couple) to a solid support or a surface thereof, ii) providing spatial separation between each site of a plurality of sites, iii) facilitating contact of a nucleic acid nanostructure, as set forth herein, with the solid support or the surface thereof, and iv) inhibiting binding of the nucleic acid nanostructure to the separating material. FIG. 64 depicts an array of analytes formed by a non-lithographic method. A solid support 6400 may comprise a plurality of nanoparticles or microparticles 6410 that arrange on a surface of the solid support 6400 to create spatial regions of the surface of the solid support 6400 that are occluded from contact with nucleic acids 6420, and wells between nanoparticles or microparticles 6410 that are sufficiently large enough (e.g., as determined by volume, as determined by area) to facilitate contact of a nucleic acid 6420 with the surface of the solid support 6400. Optionally, the surface of the solid support 6400 may comprise a moiety that facilitates coupling of the nanoparticles or microparticles 6410 and/or the nucleic acids 6420. Optionally, a nucleic acid 6420 may be coupled to an analyte 6430. In some configurations, a separating material (e.g., a nanoparticle or microparticle) may comprise a surface charge (e.g., a carboxylated microparticle, an aminated microparticle) that is configured to form an electrostatic interaction with an electrically-charged surface moiety (e.g., an amine, a carboxylate, etc.). In particular configurations, a separating material may further comprise a passivating moiety that is configured to inhibit binding of an entity to the separating material (e.g., a PEG moiety, a dextran moiety, etc.).

An unstructured or non-patterned surface may be formed by any suitable method, such as atomic layer deposition, chemical vapor deposition, or chemical liquid deposition. A surface may comprise a plurality of functional groups to facilitate an interaction with a nucleic acid nanostructure or a nucleic acid nanostructure complex, as set forth herein, such as forming a covalent, non-covalent, or electrostatic interaction. A surface-bound functional group may include an amine, thiol, carboxylic acid, activate ester, silane, silanol, siloxane, siloxide, silyl halide, silene, silyl hydride, phosphate, phosphonate, epoxide, azide, or sulfhydryl. For example, a silicon-containing surface (e.g., glass, fused silica, silicon wafer, etc.) may comprise a monolayer coating of a silane compound, such as (3-aminopropyl) trimethoxysilane (APTMS), (3-aminopropyl)triethoxysilane (APTES), (3-glycidyloxypropyl) trimethoxysilane (GOPS), Further N-(3-trthoxysilypropyl-4-hydroxybutyraride (HAPS), 11-acetoxyundecyltriethoxysilane, n-decyltriethoxysilane, 3-iodo-propyltrimethoxysilane, perfluorooctyltrichlorosilane, octylchlorosilane, octadecyltrichlorosilane, (tridecafluoro-1,1,2,2-tetrahydrooctyl)trichlorosilane, or tridecafluoro-1,1,2,2-tetrahydrooctyl)trimethoxysilane. In another example, a metal oxide surface (e.g., $ZrO_2$, $TiO_2$) may comprise a monolayer of a phosphate or phosphonate compound.

In some configurations, a functional group may comprise a click-type reaction group. In some cases, a functional group may comprise an oligonucleotide. A surface may comprise a passivating layer, such as a layer of PEG, PEO, dextrans, or nucleic acids. A functionalized or non-functionalized surface may comprise a positive, negative, or neutral electrical charge.

A solid support or a surface thereof, as set forth herein, may be patterned to form a patterned or ordered plurality of sites on the solid support or surface thereof. A plurality of sites on a solid support or a surface thereof may be considered to be patterned or ordered, for example, if it comprises one or more characteristics of: i) comprising a substantially uniform average pitch or average spacing between adjacent sites (e.g., as measured from a center point of a first site to a center point of a second site; as measured from nearest edge of a first site to nearest edge of a second site, etc.), ii) comprising a substantially uniform average site size (e.g., as measured by site diameter, site width, site circumference, site surface area, etc.), iii) comprising a repeating pattern of sites or iv) comprising at least a minimum fraction of sites (e.g., at least about 0.8, 0.85, 0.9, 0.95, 0.99, 0.999, 0.9999, 0.99999, or more than 0.99999, etc.) in a range comprising the average site size between a minimum site size and a maximum site size (e.g., comprising a 0.9 fraction of sites in a diameter range between 300 nm and 400 nm). A patterned or ordered grid may comprise a grid geometry, such as a rectangular grid, a radial grid, or a hexagonal grid. In some configurations, an array may comprise a plurality of sites, in which the sites do not conform to a grid or spatial pattern. In particular configurations, a plurality of sites may not conform to a grid or spatial pattern, but the plurality of sites may comprise an average pitch and/or average site size that is sufficient for single-analyte detection of moieties coupled to a site. A patterned or ordered plurality of sites on a solid support or a surface thereof may comprise one or more sites or addresses that disrupt a pattern, including intentional disruptions (e.g., placement of fiducial elements, placement of separation spaces between subarrays, etc.) and unintentional disruptions (e.g., manufacturing defects, damage, etc.).

Figure 63:
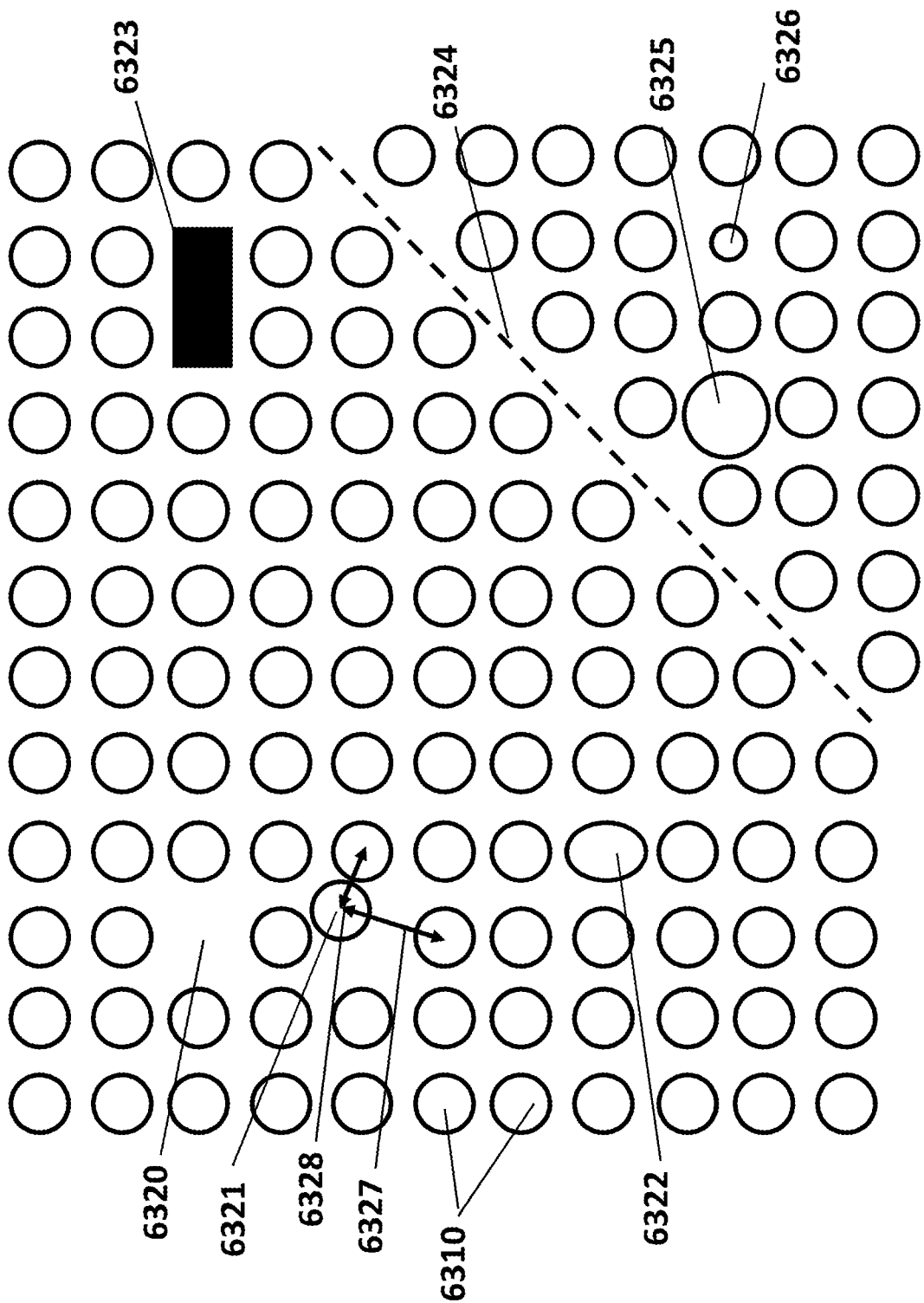
FIG. 63 shows a plurality of sites of an array comprising various defects or disruptions, in accordance with some embodiments.

A plurality of sites may be characterized as having an average disruption rate or an average disruption density. An average disruption rate may refer to a measured or expected quantity of site disruptions per a unit quantity of sites (e.g., 1 per 1000, etc.). An average disruption density may refer to an areal density of disruptions on a solid support of a surface thereof (e.g., 1 per square centimeter, etc.). As shown in FIG. 63, a disruption may refer to a site 6310 that has one or more characteristics of: 1) being misaligned relative to a grid pattern (6321), 2) being a member of a subset of sites that are misaligned relative to a grid pattern (6324), 3) having a pitch that falls below a minimum pitch size (6328), 4) having a pitch that exceeds a maximum pitch size (6327), 5) having a site dimension (e.g., width, length, diameter, area, etc.) that falls below a minimum site dimension (6326), 6) having a site dimension that exceeds a maximum site dimension (6325), 7) comprising an improper morphology (e.g., two-dimensional shape, three-dimensional topography, etc.) (6322), and 8) lacking a structure (6320, 6323) or chemistry that facilitates moiety deposition.

A solid support or a surface thereof may comprise an average, minimum or maximum site pitch of at least about 10 nanometers (nm), 50 nm, 100 nm, 200 nm, 300 nm, 400 nm, 500 nm, 600 nm, 700 nm, 800 nm, 900 nm, 1 micron (µm), 1.1 µm, 1.2 µm, 1.3 µm, 1.4 µm, 1.5 µm, 1.6 µm, 1.7 µm, 1.8 µm, 1.9 µm, 2 µm, 2.1 µm, 2.2 µm, 2.3 µm, 2.4 µm, 2.5 µm, 2.6 µm, 2.7 µm, 2.8 µm, 2.9 µm, 3 µm, 3.1 µm, 3.2 µm, 3.3 µm, 3.4 µm, 3.5 µm, 3.6 µm, 3.7 µm, 3.8 µm, 3.9 µm, 4 µm, 4.5 µm, 5 µm, 10 µm, 20 µm, 30 µm, 40 µm, 50 µm, or more than 50 µm. Alternatively or additionally, a solid support or a surface thereof may comprise an average, minimum or maximum site pitch of no more than about 50 µm, 40 µm, 30 µm, 20 µm, 10 µm, 5 µm, 4.5 µm, 4.0 µm, 3.9 µm, 3.8 µm, 3.7 µm, 3.6 µm, 3.5 µm, 3.4 µm, 3.3 µm, 3.2 µm, 3.1 µm, 3.0 µm, 2.9 µm, 2.8 µm, 2.7 µm, 2.6 µm, 2.5 µm, 2.4 µm, 2.3 µm, 2.2 µm, 2.1 µm, 2 µm, 1.9 µm, 1.8 µm, 1.7 µm, 1.6 µm, 1.5 µm, 1.4 µm, 1.3 µm, 1.2 µm, 1.1 µm, 1 µm, 900 nm, 800 nm, 700 nm, 600 nm, 500 nm, 400 nm, 300 nm, 200 nm, 100 nm, 50 nm, 10 nm, or less than 10 nm. An average pitch may be determined based upon a spatial resolution of a method used to form a solid support (e.g., photolithography), a desired array density, and/or a necessary spatial separation between neighboring sites to obtain single-analyte resolution of moieties bound to each site A solid support or a surface thereof may comprise an average, minimum or maximum site size (e.g., width, length, diameter, etc.) of at least about 10 nanometers (nm), 50 nm, 100 nm, 200 nm, 300 nm, 400 nm, 500 nm, 600 nm, 700 nm, 800 nm, 900 nm, 1 micron (µm), 1.1 µm, 1.2 µm, 1.3 µm, 1.4 µm, 1.5 µm, 1.6 µm, 1.7 µm, 1.8 µm, 1.9 µm, 2 µm, 2.1 µm, 2.2 µm, 2.3 µm, 2.4 µm, 2.5 µm, 2.6 µm, 2.7 µm, 2.8 µm, 2.9 µm, 3 µm, 3.1 µm, 3.2 µm, 3.3 µm, 3.4 µm, 3.5 µm, 3.6 µm, 3.7 µm, 3.8 µm, 3.9 µm, 4 µm, 4.5 µm, 5 µm, 10 µm, 20 µm, 30 µm, 40 µm, 50 µm, or more than 50 µm. Alternatively or additionally, a solid support or a surface thereof may comprise an average, minimum or maximum site size of no more than 50 µm, 40 µm, 30 µm, 20 µm, 10 µm, 5 µm, 4.5 µm, 4.0 µm, 3.9 µm, 3.8 µm, 3.7 µm, 3.6 µm, 3.5 µm, 3.4 µm, 3.3 µm, 3.2 µm, 3.1 µm, 3.0 µm, 2.9 µm, 2.8 µm, 2.7 µm, 2.6 µm, 2.5 µm, 2.4 µm, 2.3 µm, 2.2 µm, 2.1 µm, 2 µm, 1.9 µm, 1.8 µm, 1.7 µm, 1.6 µm, 1.5 µm, 1.4 µm, 1.3 µm, 1.2 µm, 1.1 µm, 1 µm, 900 nm, 800 nm, 700 nm, 600 nm, 500 nm, 400 nm, 300 nm, 200 nm, 100 nm, 50 nm, 10 nm, or less than 10 nm. A site size may be determined based upon a spatial resolution of a method used to form a solid support (e.g., photolithography) and/or a size of an analyte or nucleic acid that is to be deposited on a site.

A binding site or region may have a surface area of at least about 25 nm$^2$, 100 nm$^2$, 500 nm$^2$, 1000 nm$^2$, 2000 nm$^2$, 3000 nm$^2$, 4000 nm$^2$, 5000 nm$^2$, 5500 nm$^2$, 6000 nm$^2$, 6500 nm$^2$, 7000 nm$^2$, 7500 nm$^2$, 8000 nm$^2$, 8500 nm$^2$, 9000 nm$^2$, 10000 nm$^2$, 15000 nm$^2$, 20000 nm$^2$, 25000 nm$^2$, 50000 nm$^2$, 100000 nm$^2$, 250000 nm$^2$, 500000 nm$^2$, or more than 1000000 nm$^2$. Alternatively or additionally, a binding site or region may have a surface area of no more than about 1000000 nm$^2$, 500000 nm$^2$, 250000 nm$^2$, 100000 nm$^2$, 50000 nm$^2$, 25000 nm$^2$, 20000 nm$^2$, 15000 nm$^2$, 10000 nm$^2$, 9000 nm$^2$, 8500 nm$^2$, 8000 nm$^2$, 7500 nm$^2$, 7000 nm$^2$, 6500 nm$^2$, 6000 nm$^2$, 5500 nm$^2$, 5000 nm$^2$, 4000 nm$^2$, 3000 nm$^2$, 2000 nm$^2$, 1000 nm$^2$, 500 nm$^2$, 100 nm$^2$, 25 nm$^2$, or less than 25 nm$^2$.

A solid support or a surface thereof, as set forth herein, may comprise a plurality of sites, in which each site of the plurality of sites is configured to couple an entity (e.g., an analyte, a nucleic acid, etc.). A solid support, a surface thereof, and/or a site thereof may be provided with one or more moieties that facilitate a binding interaction with an entity, such as a nucleic acid. In some configurations, a solid support, a surface thereof, and/or a site thereof may be provided with two or more differing moieties that facilitate a binding interaction with an entity, such as a nucleic acid. In some configurations, the first moiety of the two or more moieties facilitates a first binding interaction and a second moiety of the two or more moieties facilitates a second binding interaction. In a particular configuration, the first binding interaction is the same type of binding interaction as the second binding interaction (e.g., both nucleic acid base-pair hybridization, both covalent bonding, both receptor-ligand binding, etc.). In another particular configuration, the first binding interaction is a different type of binding interaction from the second binding interaction (e.g., a nucleic acid base-pair hybridization and a covalent bonding, a nucleic acid base-pair hybridization and a receptor-ligand binding, etc.). In some configurations, a solid support, a surface thereof, and/or a site thereof may be provided with two or more differing moieties, in which a first moiety of the two or more moieties facilitates a first binding interaction with a first binding affinity for a first binding complement, and a second moiety of the two or more moieties facilitates a second binding interaction with a second binding affinity for a second binding complement. In a particular configuration, a first binding affinity of a first moiety for a first binding complement may be stronger than a second binding affinity of a second moiety for a second binding complement. For example, a surface may comprise a mixture of oligonucleotides and streptavidin, in which the streptavidin has a significantly stronger affinity for biotin than the oligonucleotide has for its complementary oligonucleotide. In other configurations, a first binding affinity of a first moiety for a first binding complement may be substantially equal to a second binding affinity of a second moiety for a second binding complement. For example, a surface may comprise a mixture of a first oligonucleotide and a second oligonucleotide, in which both have substantially similar affinities for their respective complementary oligonucleotides. In other configurations, a first binding affinity of a first moiety for a first binding complement may be stronger than a second binding affinity of a second moiety for the first binding complement. For example, a surface may comprise a mixture of a first oligonucleotide and a second oligonucleotide, in which sequences of the first and second oligonucleotides differ by a single nucleotide, and in which the second nucleotide has a marginally lower affinity for the complementary oligonucleotide of the first oligonucleotide due to the misalignment of the single nucleotide. A binding affinity between a surface moiety and a complement or ligand may be characterized by a quantitative measure, such as a dissociation constant ($K_D$), an on-rate ($k_{on}$), or an off-rate ($k_{off}$). A binding affinity between a surface moiety and a complement or ligand may have a dissociation constant of no more than about 1 milliMolar, 100 micromolar (µM), 10 µM, 1 µM, 100 nanomolar (nM), 10 nM, 1 nM, 100 picoMolar (µM), 10 µM, 1 µM, 0.1 µM, 0.01 µM, or less than 0.01 µM. Alternatively or additionally, a binding affinity between a surface moiety and a complement or ligand may have a dissociation constant of at least about 0.01 µM, 0.1 µM, 1 µM, 10 µM, 100 µM, 1 nM, 10 nM, 100 nM, 1 µM, 10 µM, 100 µM, 1 mM, or more than 1 mM. In some cases, a solid support, a surface thereof, and/or a site thereof may comprise a first moiety and a second moiety, in which a first dissociation constant for a first moiety and its binding complement and a second dissociation constant for a second moiety and its binding complement may differ by at least 1, 2, 3, 4, 5, 6, 7, 8, 9, 10, or more than 10 orders of magnitude. In other cases, a solid support, a surface thereof, and/or a site thereof may comprise a first moiety and a second moiety, in which a first dissociation constant for a first moiety and its binding complement and a second dissociation constant for a second moiety and its binding complement may differ by no more than about 10, 9, 8, 7, 6, 5, 4, 3, 2, 1, or less than 1 order of magnitude.

Figure 60A:
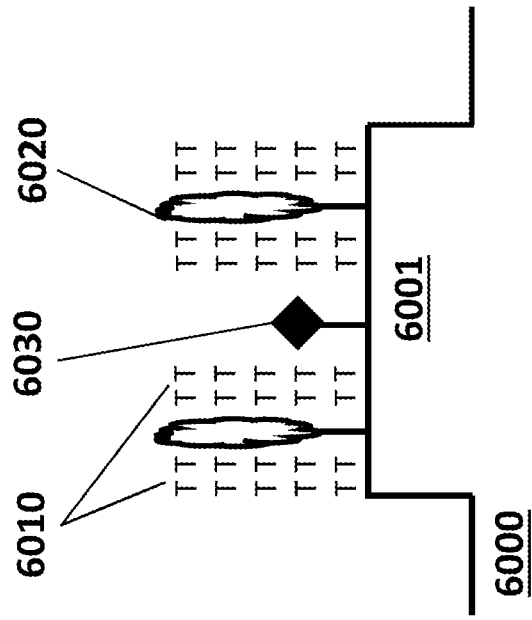
FIGS. 60A, 60B, 60C, and 60D depict various configurations of array sites comprising two or more types of coupled surface moieties, in accordance with some embodiments.
Figure 60B:
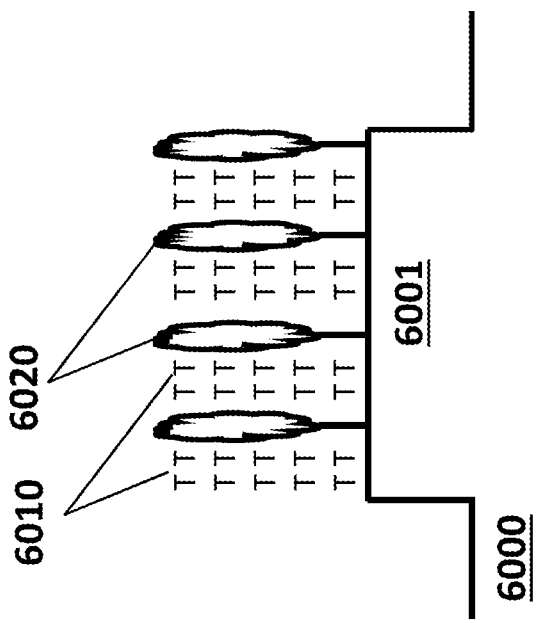

FIGS. 60A and 60B depict surface chemistry configurations of a solid support comprising two or more differing moieties. FIG. 60A depicts a solid support 6000 comprising a site, in which the site 6001 comprises a plurality of oligonucleotides 6010 and a plurality of polymer chains 6020 (e.g., PEG chains). The plurality of oligonucleotides 6010 and the plurality of polymer chains 6020 comprise a substantially homogeneous spatial distribution on the site 6001. Optionally, the plurality of oligonucleotides 6010 and the plurality of polymer chains 6020 may comprise a heterogeneous spatial distribution on the site 6001. The configuration of FIG. 60A may be useful for coupling a nucleic acid nanostructure (e.g., a SNAP) while preventing non-specific binding of a non-nucleic acid entity (e.g., an analyte). FIG. 60B illustrates a solid support 6000 comprising a site, in which the site 6001 comprises a plurality of oligonucleotides 6010, a plurality of polymer chains 6020 (e.g., PEG chains), and an additional coupling moiety 6030 (e.g., a Click-type reagent, a streptavidin, etc.). In some configurations, an oligonucleotide of the plurality of oligonucleotides 6010 may a significantly different binding affinity than the additional coupling moiety 6030. The configuration of FIG. 60B may be useful for weakly coupling a nucleic acid nanostructure to a site 6001, then more strongly coupling the nucleic acid nanostructure once it has found a more stable configuration on the site 6001.

A solid support, a surface thereof, or a site thereof comprising a first plurality of a first surface-coupled moiety (e.g., a coupling moiety, a higher affinity binding moiety, etc.) and a second plurality of a second surface-coupled moiety (e.g., a non-coupling moiety, a lower affinity binding moiety, etc.) may be configured with an advantageous molar ratio of the first plurality to the second plurality. A first plurality of a first surface-coupled moiety and a second plurality of a second surface-coupled moiety may have a molar ratio of at least about 1:1, 1.5:1, 2:1, 3:1, 5:1, 10:1, 20:1, 50:1, 100:1, 1000:1, 10000:1, 100000:1, 1000000:1, or more than 1000000:1. Alternatively or additionally, a first plurality of a first surface-coupled moiety and a second plurality of a second surface-coupled moiety may have a molar ratio of no more than about 1000000:1, 100000:1, 10000:1, 1000:1, 100:1, 50:1, 20:1, 10:1, 5:1, 3:1, 2:1, 1.5:1, or less than 1.5:1.

A solid support, a surface thereof, and/or a site thereof may be provided with two or more differing moieties. In some configurations, a first moiety of the two or more moieties facilitates a first binding interaction and a second moiety of the two or more moieties inhibits a binding interaction. For example, a surface of a site may be functionalized with a first plurality of oligonucleotides that are configured to bind complementary oligonucleotides of a nucleic acid nanostructure, and a second plurality of PEG moieties that are configured to inhibit non-specific binding of non-nucleic acid entities to the surface of the site.

A surface chemistry or functionalization may be provided to a solid support, a surface thereof, and/or a site thereof by an appropriate method, such as chemical vapor deposition or chemical liquid deposition. A surface chemistry deposition method may include one or more steps to form a layer, or a plurality of layers on a solid support, a surface thereof, and/or a site thereof. For example, a method of providing a plurality of surface-linked oligonucleotides to a surface may comprise the steps of: i) coupling a plurality of aminated silane molecules to the surface, and ii) coupling an azide-terminated PEG molecule to each silane molecule, iii) coupling a dibenzocyclooctylene (DBCO)-terminated oligonucleotide to each azide group. In some configurations, an impurity from a surface synthesis may be expected to be present on a solid support, a surface thereof, and/or a site thereof. For example, in the prior example of providing a surface layer of oligonucleotides, some unreacted azide may be present on the surface. In some configurations, a surface impurity may be passivated by contacting a passivating molecule with the surface impurity. A passivating molecule may form a covalent bond with a surface impurity to passivate the impurity. A passivating molecule need not form a covalent bond with a surface impurity to passivate the impurity (e.g., an electrostatic interaction). In some configurations, a surface impurity may facilitate binding of an entity (e.g., a nucleic acid nanostructure) to a solid support, a surface thereof, and/or a site thereof.

Figure 61B:
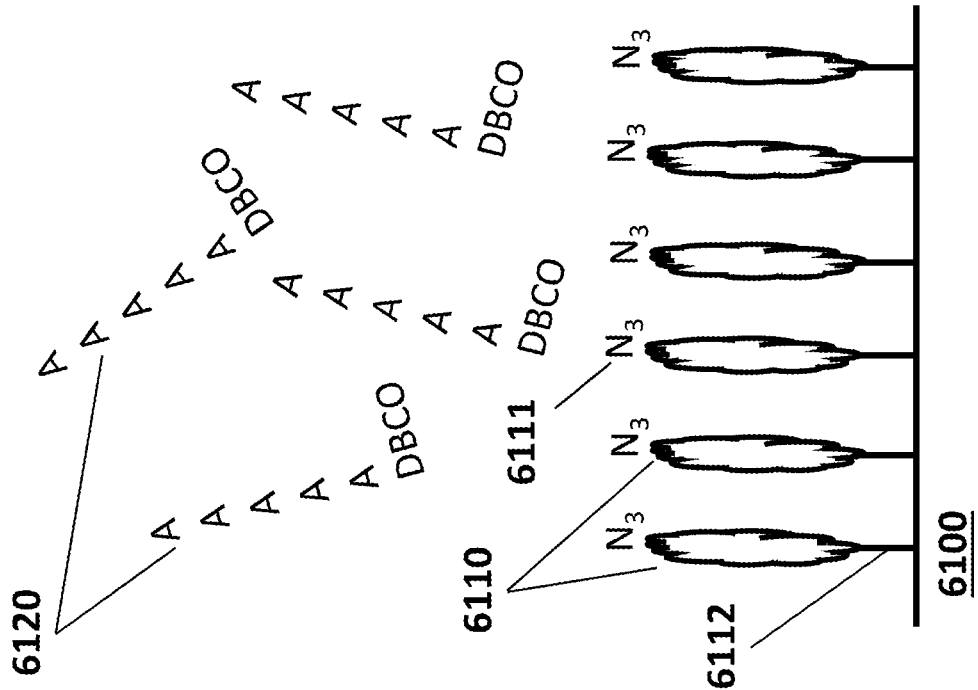
Figure 61A:
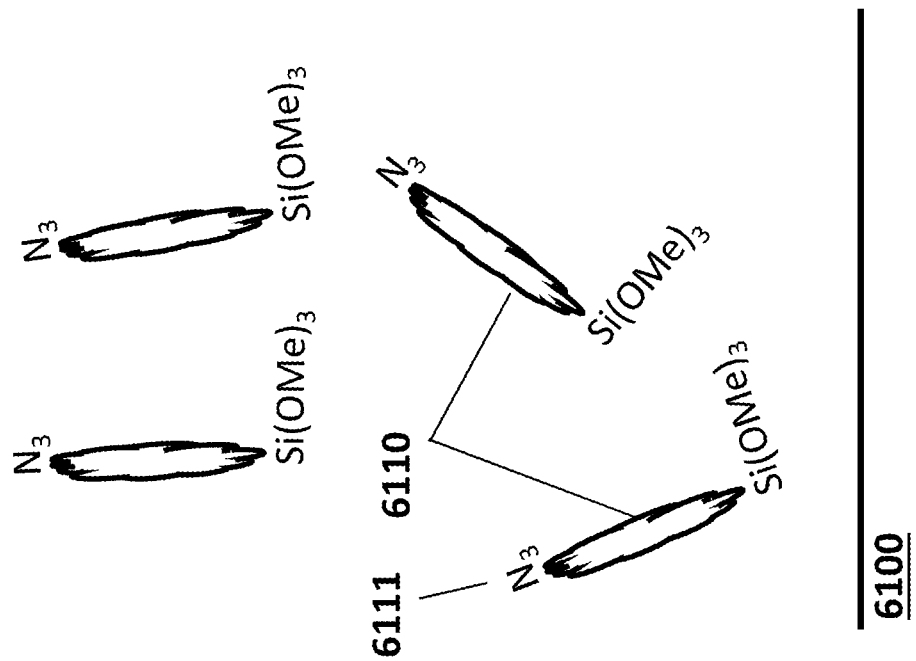
Figure 61E:
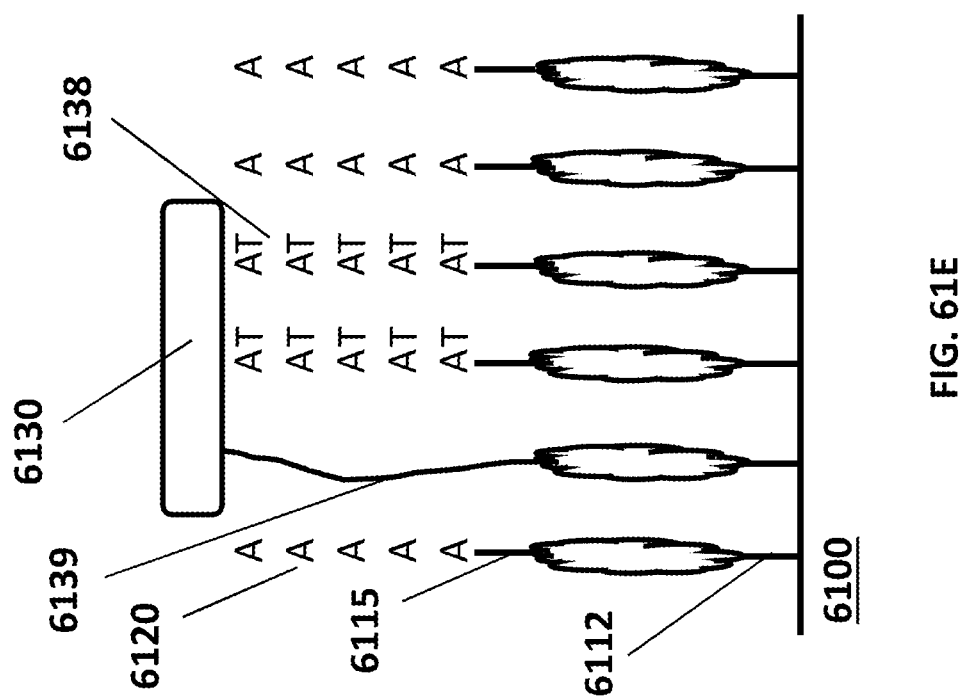

FIGS. 61A-61E illustrate a method of coupling a nucleic acid nanostructure to a surface. FIG. 61A shows contacting of a silicon-containing surface 6100 with a plurality of silanated molecules comprising a PEG chain 6110 and a terminal azide group 6111. FIG. 61B illustrates the surface 6100 coupled by covalent bonds 6112 to the PEG chains 6110 with terminal azide groups 6111. The surface is contacted with a plurality of poly-A oligonucleotides 6120 comprising terminal DBCO moieties that are configured to form a covalent bond with azide groups 6111. FIG. 61C displays the surface 6100 now comprising PEG chains 6110 terminated with poly-A oligonucleotides 6120, excluding at least one unreacted azide group 6111. The surface is contacted by a nucleic acid nanostructure 6130 comprising a plurality of complementary poly-T oligonucleotides 6135 and a DBCO moiety 6132. FIG. 61D shows a coupling of the nucleic acid nanostructure 6130 to the surface 6100 due to the nucleic acid hybridization of the poly-A oligonucleotides 6120 to the poly-T oligonucleotides 6135 of the nucleic acid nanostructure 6130. FIG. 61E depicts a subsequent step of reacting the DBCO moiety 6132 of the nucleic acid nanostructure 6130 to the unreacted azide group 6111 to covalently bind the nucleic acid nanostructure 6130 to the surface 6100.

A solid support, a surface thereof, and/or a site thereof may be configured to form a multiplexed array of analytes. A multiplexed array of analytes may comprise a plurality of sites, in which each site of a first subset of sites of the plurality of sites comprises an analyte of a first plurality of analytes, and in which each site of a second subset of sites of the plurality of sites comprises an analyte of a second plurality of analytes. A multiplexed array may comprise a first plurality of analyte and a second plurality of analytes, in which the first plurality of analytes and the second plurality of analytes differ in at least one aspect (e.g., type, source, preparation method, etc.). A multiplexed array may comprise a first plurality of analyte and a second plurality of analytes, in which the first plurality of analytes and the second plurality of analytes do not differ in at least one aspect (e.g., duplicate or replicate samples, etc.). In some configurations, a solid support that is configured to form a multiplexed array may comprise a substantially uniform surface chemistry (e.g., solid support composition and/or composition of surface-coupled moieties on the solid support or sites thereof). For example, FIGS. 50A-50B depict formation of a multiplexed array of analytes, in which a first plurality of analytes 5020 and a second plurality of analytes 5025 are coupled to nucleic acid nanostructures 5010, in which the nucleic acid nanostructures 5010 for the first plurality of analytes 5020 comprise a first functional nucleic acid 5030, and in which the nucleic acid nanostructures 5010 for the second plurality of analytes 5020 comprise a second functional nucleic acid 5035. In such an example, the type of analyte coupled to a nucleic acid nanostructure 5010 is configured to be identified based upon the component functional nucleic acid, thereby facilitating use of a substantially uniform surface chemistry on each site of the array and a substantially uniform structure of a capture face or capture moiety of each nucleic acid nanostructure 5010.

In other configurations, a multiplexed array may comprise a plurality of sites, in which a first subset of the plurality of sites comprises a first coupling moiety and a second subset of the plurality of sites comprises a second coupling moiety, in which the first coupling moiety is configured to couple a first entity (e.g., a nucleic acid nanostructure, an analyte, etc.), and in which the second coupling moiety is configured to couple a second entity. In a particular configuration, the first subset of the plurality of sites comprises a spatially contiguous or spatially consecutive group of sites (e.g., a cluster of sites), and/or in which the second subset of the plurality of sites comprises a spatially contiguous or spatially consecutive group of sites. In another particular configuration, the first subset of the plurality of sites does not comprise a spatially contiguous or spatially consecutive group of sites (e.g., a cluster of sites), and/or in which the second subset of the plurality of sites does not comprise a spatially contiguous or spatially consecutive group of sites.

FIGS. 62A-62E depict methods of forming an array of sites that is configured for multiplexing of analytes. FIG.

62A depicts a method of printing an array to form two or more regions with differing binding characteristics. In a first step, a solid support 6200 comprising an array of sites 6201 may be provided. In a second step, a barrier material 6210 (e.g., a photoresist) may be provided to portions of the solid support 6200 to divide a first contiguous subset of sites of the plurality of sites 6201 from a second contiguous subset of sites of the plurality of sites 6201. In a third step, a printing device 6220 (e.g., an ink-based printer) may deposit a first fluidic medium 6221 comprising a first species of coupling moiety 6222 in contact with the first contiguous subset of sites of the plurality of sites 6201, and may deposit a second fluidic medium 6225 comprising a second species of coupling moiety 6226 in contact with the second contiguous subset of sites of the plurality of sites 6201. Optionally, after depositing the first species of coupling moiety 6222 on the first contiguous subset of sites of the plurality of sites 6201, and depositing the second species of coupling moiety 6226 on the second contiguous subset of sites of the plurality of sites 6201, the barrier material 6210 may be removed or stripped from the solid support 6200. FIG. 62B depicts a method of lithographically forming an array comprising two or more regions with differing binding characteristics. In a first step, a solid support material 6200 comprising a coupled surface layer 6205 (e.g., a passivating layer), and an optional barrier material 6210 (e.g., a photoresist) may be provided. In a second step, the barrier material 6210 and the coupled surface layer 6205 may be patterned to expose regions of the solid support 6200. In a third step, a printing device 6220 (e.g., an ink-based printer) may deposit a first fluidic medium 6221 comprising a first species of coupling moiety 6222 in contact with a first contiguous subset of sites of the plurality of sites 6201, and may deposit a second fluidic medium 6225 comprising a second species of coupling moiety 6226 in contact with a second contiguous subset of sites of the plurality of sites 6201. Optionally, after depositing the first species of coupling moiety 6222 on the first contiguous subset of sites of the plurality of sites 6201, and depositing the second species of coupling moiety 6226 on the second contiguous subset of sites of the plurality of sites 6201, the barrier material 6210 may be removed or stripped from the solid support 6200. FIG. 62C depicts a method of lithographically forming an array comprising randomly distributed. In a first step, a solid support material 6200 comprising a coupled surface layer 6205 (e.g., a passivating layer), and an optional barrier material 6210 (e.g., a photoresist) may be provided. In a second step, the barrier material 6210 and the coupled surface layer 6205 may be patterned to expose regions of the solid support 6200. In a third step, a printing device 6220 (e.g., an ink-based printer) may deposit a fluidic medium 6223 comprising a first species of coupling moiety 6222 and a second species of coupling moiety 6226 in contact with the plurality of sites 6201. Optionally, after depositing the first species of coupling moiety 6222 and the second species of coupling moiety 6226 on the plurality of sites 6201 in a spatially random distribution, the barrier material 6210 may be removed or stripped from the solid support 6200.

Figure 62A:
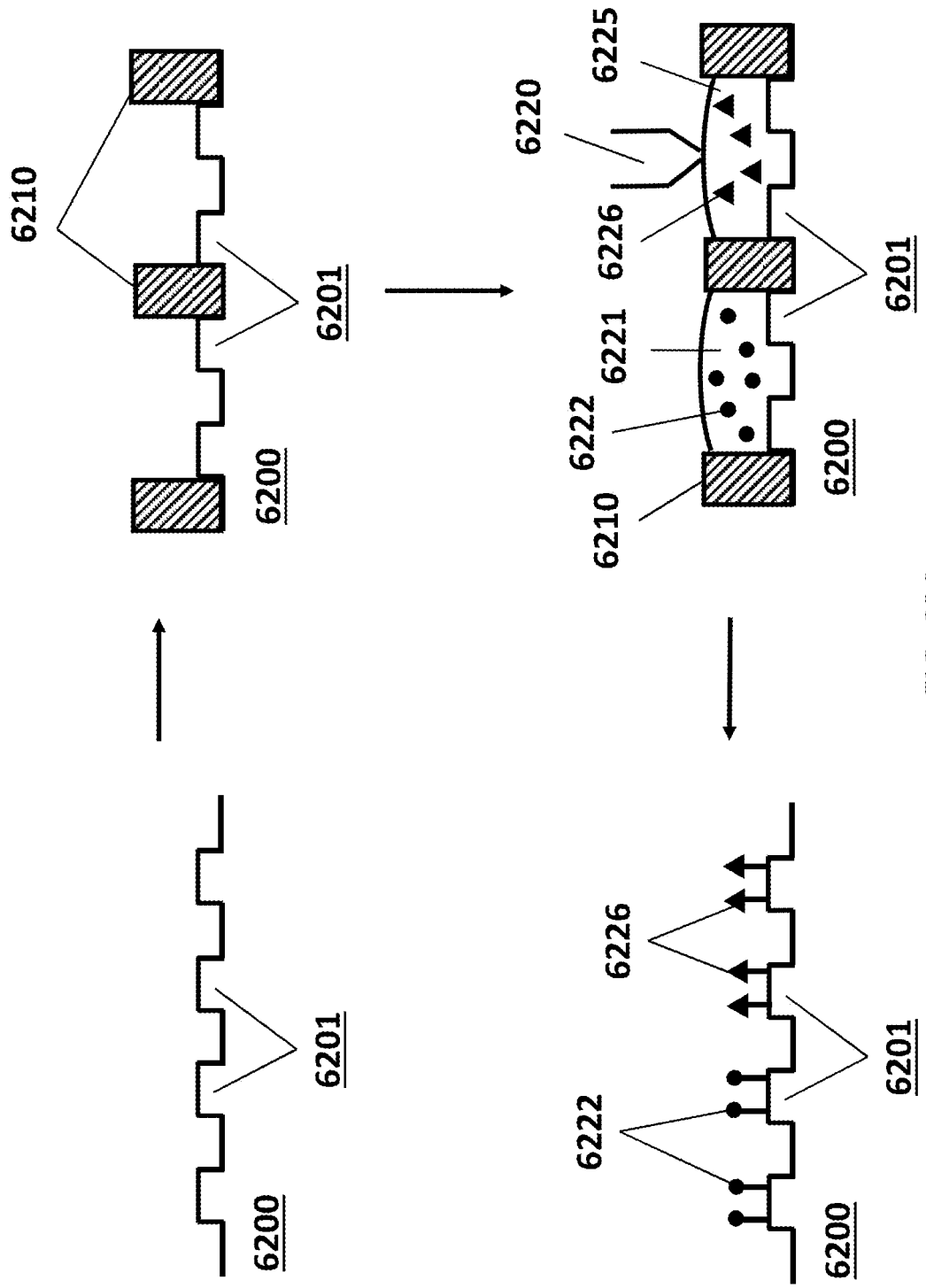
Figure 62B:
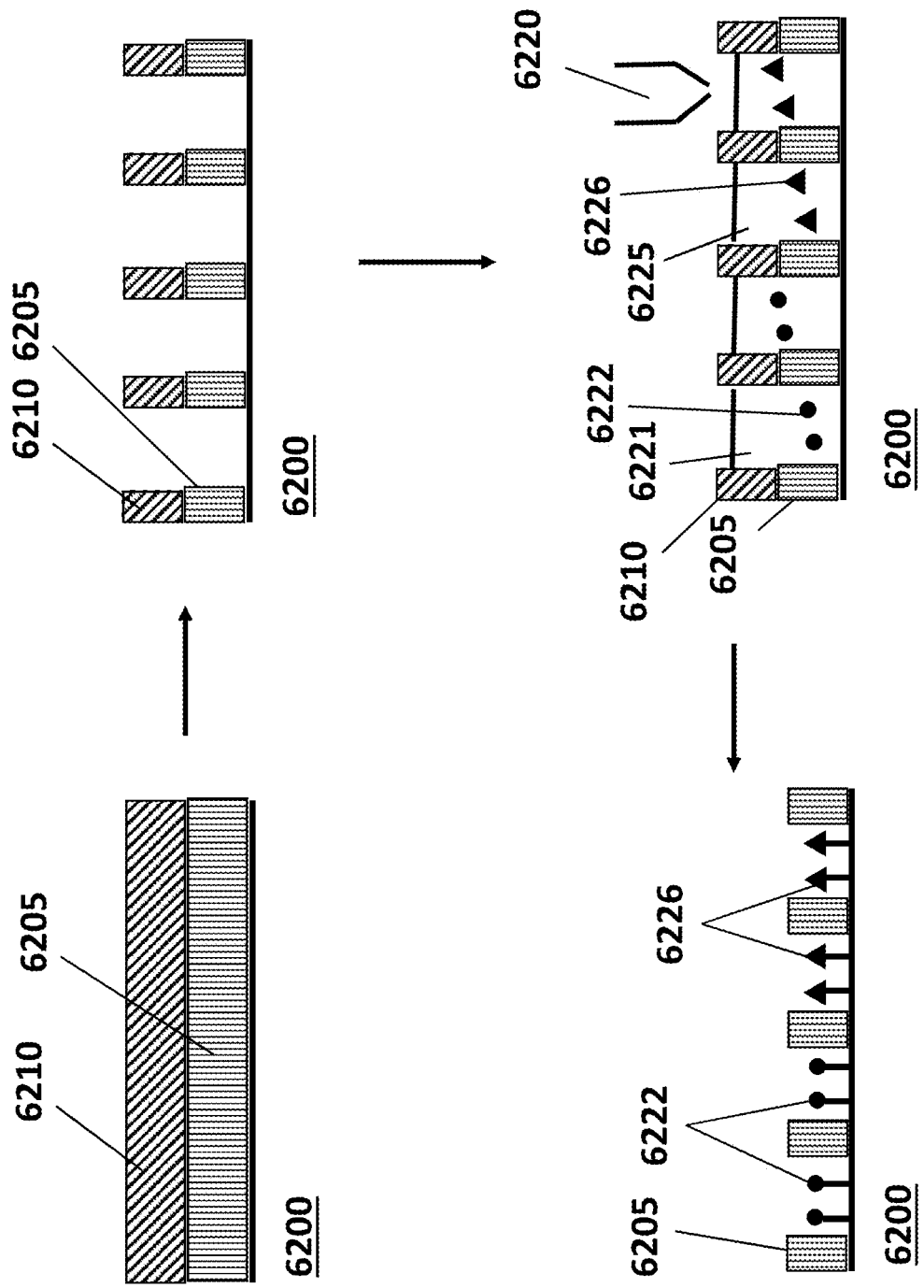
Figure 62C:
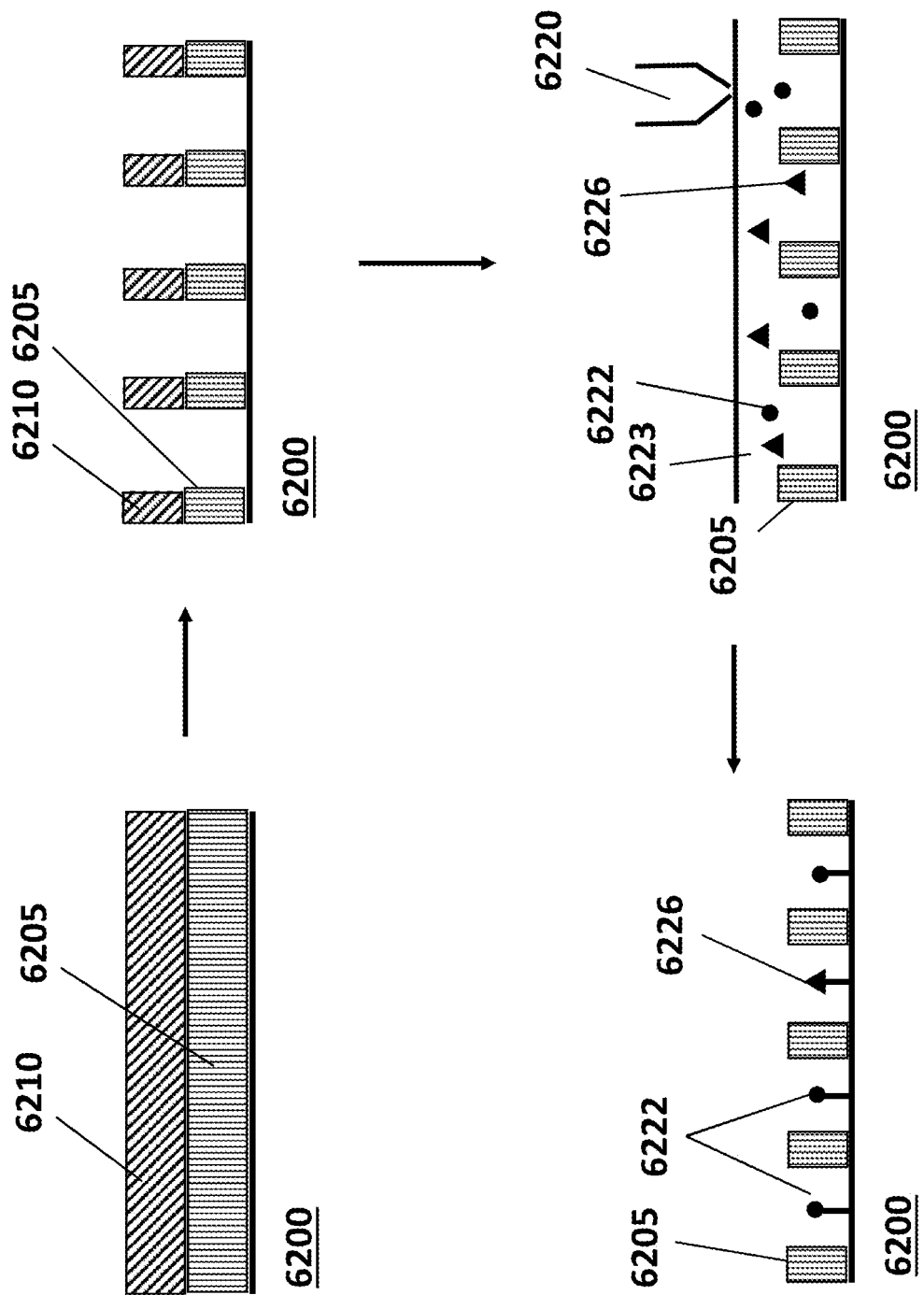

FIGS. 62D-62E depict a method of forming a multiplexed array of analytes utilizing an array such as those depicted in FIG. 62A-62C. In a first step, a solid support comprising a first subset of sites and a second subset of sites may be contacted with a first plurality of nucleic acid nanostructures 6241 and a second plurality of nucleic acid nanostructures 6242, in which the first subset of sites comprises a first coupling moiety 6222 and the second subset of sites comprises a second coupling moiety 6226, in which each nucleic acid nanostructure of the first plurality of nucleic acid nanostructures 6241 is configured to couple to a first coupling moiety 6222, and in which each nucleic acid nanostructure of the second plurality of nucleic acid nanostructures 6242 is configured to couple to a second coupling moiety 6226. Optionally, each nucleic acid nanostructure of the first plurality of nucleic acid nanostructures 6241 may be coupled to an analyte of a first plurality of analytes 6251, and each nucleic acid nanostructure of the second plurality of nucleic acid nanostructures 6242 may be coupled to an analyte of a second plurality of analytes 6252. In a second step, a single nucleic acid nanostructure of the first plurality of nucleic acid nanostructures 6241 may deposit at a site comprising a first coupling moiety 6222, and a single nucleic acid nanostructure of the second plurality of nucleic acid nanostructures 6242 may deposit at a site comprising a second coupling moiety 6226.

A solid support, a surface thereof, and/or a site thereof may be configured to couple a nucleic acid nanostructure by a charge-mediated interaction. A charge-mediated interaction may be a binding interaction in which an electrically-charged intermediate facilitates an entity (e.g., an analyte, a nucleic acid nanostructure, etc.) in forming a binding interaction with a solid support, a surface thereof, and/or a site thereof. In some configurations, a charge-mediated interaction may comprise an ion-mediated interaction, in which an ionic species (e.g., a cation, an anion) facilitates a coupling interaction between an entity and a solid support, a surface thereof, or a site thereof. For example, a cationic species (e.g., $Na^+$, $Mg^{2+}$, $Ca^{2+}$, etc.) may provide an electrostatic bridging interaction that facilitates binding of a nucleic acid to an electrically-charge surface. In particular configurations, an ion-mediated interaction may facilitate a coupling interaction between an electrically-charged capture face or capture moiety of a nucleic acid nanostructure and an electrically-charged surface (e.g., a surface functionalized with an amine or carboxylate, etc.), in which the electrically-charged capture face or capture moiety of the nucleic acid nanostructure and the electrically-charged surface comprise a same polarity of electrical charge (e.g., both positively charged, both negatively charged). For example, magnesium ions may form a bridging interaction between a negatively-charged nucleic acid and a negatively-charged surface. In another particular configuration, an ion-mediated interaction may facilitate a coupling interaction between an electrically-charged capture face or capture moiety of a nucleic acid nanostructure and an electrically-charged surface (e.g., a surface functionalized with an amine or carboxylate, etc.), in which the electrically-charged capture face or capture moiety of the nucleic acid nanostructure and the electrically-charged surface comprise a differing polarity of electrical charge (e.g., one positively charged, one negatively charged). For example, a concentration of a cationic species or anionic species may be varied to modulate a strength of interaction between a positively-charge surface and a negatively-charged nucleic acid.

Figure 65:
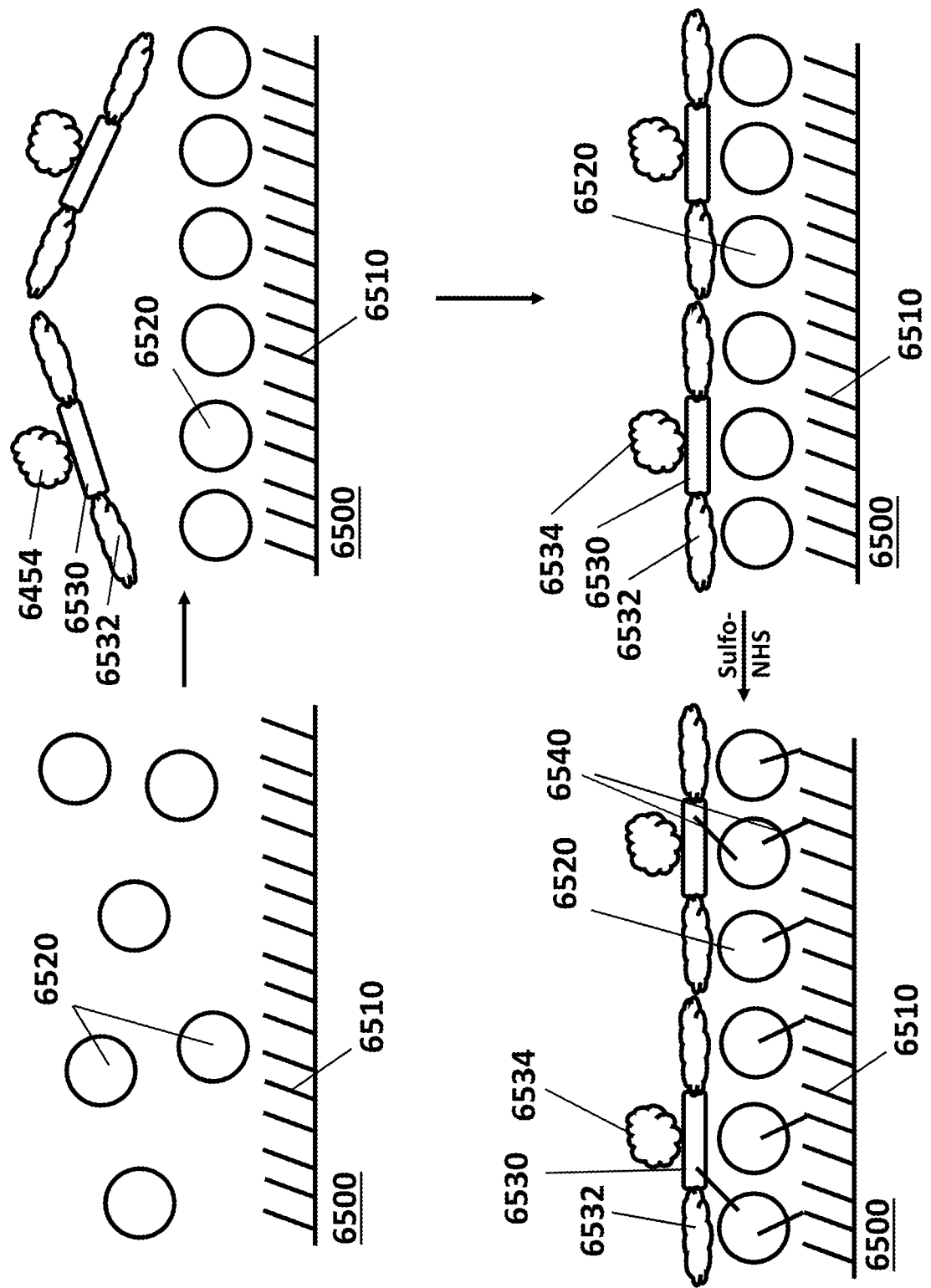
FIG. 65 shows a method of forming an array of analytes via a charge-mediated interaction, in accordance with some embodiments.

In some configurations, a charge-mediated interaction may be utilized to form an array of analytes. FIG. 65 depicts a method of forming an array of analytes on an unpatterned surface comprising an electrically-charged species. In a first step, a solid support 6500 comprising a plurality of surface-coupled, positively-charged species 6510 (e.g., aminated silanes) is provided. The solid support 6500 is contacted with a plurality of negatively-charged nanoparticles or microparticles 6520 (e.g., carboxylated dextran, carboxylated polystyrene, etc.). The plurality of negatively-charged nanoparticles or microparticles 6520 may couple to the surface-coupled, positively-charged species 6510 due to an electrostatic interaction. In a second step, the formed layer comprising the plurality of negatively-charged nanoparticles or microparticles 6520 may be contacted with a plurality of nucleic acid nanostructures 6530, as set forth herein. A nucleic acid nanostructure of the plurality of nucleic acid nanostructures 6530 may be coupled to an analyte 6534. A nucleic acid nanostructure may comprise a capture face or capture moiety (e.g., an amine) comprising a positively-charge moiety that is configured to form an electrostatic interaction with a negatively-charged nanoparticle or microparticle 6520. A nucleic acid nanostructure of the plurality of nucleic acid nanostructures 6530 may further comprise a utility face or utility moiety comprising a moiety 6532 that is configured to inhibit contact between adjacent nucleic acid nanostructures 6350. In a third step, the plurality of nucleic acid nanostructures 6530 may be deposited on the array, in which each nucleic acid nanostructure 6530 is spatially separated from each adjacent nucleic acid nanostructure 6530, optionally by a utility moiety 6532. In an optional final step, the electrostatically-coupled array of nucleic acid nanostructures 6530 and negatively-charged nanoparticles or microparticles 6520 may be covalently coupled by a cross-linking agent, such as sulfo-N-hydroxysuccinimide (sulfo-NHS), thereby permanently confining the spatial location of each nucleic acid and/or analyte of the array.

A solid support, a surface thereof, and/or a site thereof, may be configured to form a weak binding interaction with an entity (e.g., an analyte, a nucleic acid nanostructure, a non-nucleic acid, a reagent). In some configurations, a solid support, a surface thereof, and/or a site thereof, may be configured to form a plurality of weak binding interactions with a nucleic acid nanostructure in an initial configuration, and in which the solid support, the surface thereof, and/or the site thereof, is configured to facilitate a rearrangement of the nucleic acid nanostructure from the initial configuration to a more-stable final configuration. Without wishing to be bound by theory, a weak binding interaction may comprise a coupling of a first moiety (e.g., a surface-coupled moiety) to a second moiety (e.g., a capture moiety), in which the weak binding interaction is weakly biased toward association or dissociation (e.g., an equilibrium constant between about 0.01 and 100, about 0.05 and 50, about 0.1 and 10, about 0.5 and 5, etc.), and/or in which the weak binding interaction is kinetically reversible on a time-scale shorter than a time-scale of an array-based process (e.g., capable of dissociating within a time-scale of a nucleic acid deposition process, capable of dissociating during an array rinsing process, etc.).

A plurality of moieties may be provided to a solid support, a surface thereof, and/or a site thereof, in which a subset of the plurality of moieties is configured to form a plurality of binding interactions with one or more surface-coupling moieties of a nucleic acid nanostructure. In some configurations, a subset of a plurality of moieties may couple to one or more coupling moieties of a nucleic acid nanostructure, thereby coupling the nucleic acid nanostructure to a solid support, a surface thereof, and/or a site thereof. In a particular configuration, a solid support, a surface thereof, and/or a site thereof may be provided a plurality of moieties, in which the plurality of moieties comprises an excess of coupling moieties relative to an available quantity of capture moieties of a nucleic acid nanostructure. For example, a nucleic acid nanostructure may comprise 20 pendant surface-coupling moieties, each comprising 10 segmented poly-T repeats of 20 nucleotides length (e.g., 200 total capture moieties), and a site on a solid support may comprise 1000 surface-linked poly-A oligonucleotides of 20 nucleotide lengths, thereby giving an excess of 5:1 for surface-linked moieties. In some configurations, a solid support, a surface thereof, and/or a site thereof may comprise a plurality of moieties, in which a subset of the plurality of moieties are not configured to couple to an entity. For example, an array site may comprise a first plurality of moieties comprising oligonucleotides that are configured to couple a complementary oligonucleotide of a nucleic acid nanostructure and a second plurality of moieties comprising polymer chains that are configured to inhibit non-specific binding interactions between entities and the solid support, the surface thereof, and/or the site thereof.

Figure 60D:
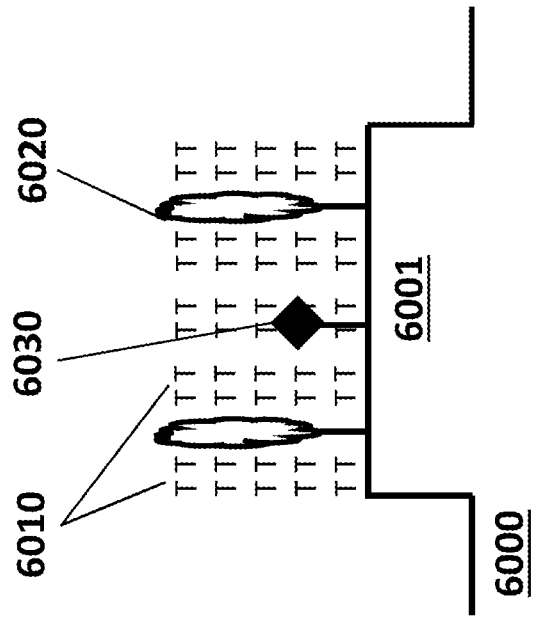
Figure 60C:
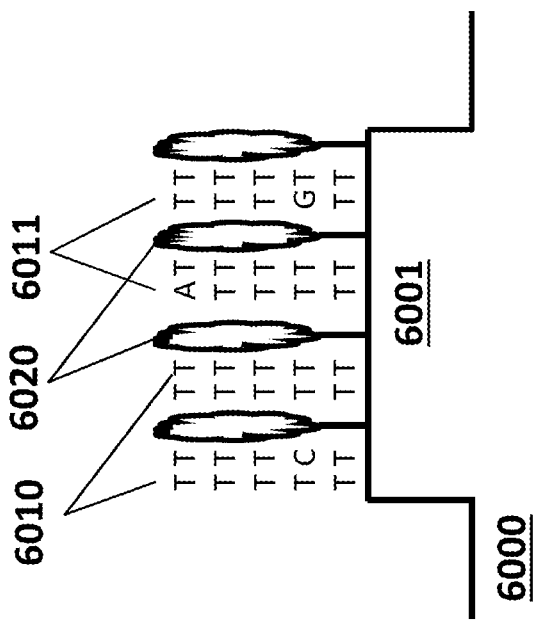

FIGS. 60A-60D present configurations of pluralities of moieties on an array site that facilitate formation of a plurality of weak binding interactions. FIGS. 60A and 60B comprise variations of differing binding and non-binding moieties, as described herein. FIG. 60C illustrates a solid support 6000 comprising a site 6001 that contains a coupled plurality of moieties, including a first plurality of oligonucleotides 6010 that are complementary to a surface-coupling oligonucleotide of a nucleic acid nanostructure, a second plurality of oligonucleotides 6011 that contain random nucleotide substitutions, thereby providing a plurality of nucleotide sequences with lower binding affinities to the complementary surface-coupling oligonucleotides of the nucleic acid nanostructure, and a third plurality of non-binding moieties 6020 (e.g. polymer chains). Such a configuration may be modified to comprise, for example, a component of a receptor-ligand pair and a modified version thereof. For example, a surface may be provided an antibody fragment and one or more mutated versions thereof, in which the mutated versions have a lower binding affinity for a ligand of the antibody fragment that is coupled to a capture face of a nucleic acid nanostructure. FIG. 60D comprises a modification of the array site of FIG. 60B, in which the additional coupling moiety 6030 is effectively buried or screened amongst other moieties, thereby inhibiting its ability to form binding interactions with a complementary coupling moieties of a nucleic acid nanostructure. Such a configuration may be useful for slowing a rate of interaction formation for a high-affinity binding system (e.g., a Click-type reaction, streptavidin-biotin, etc.). It may be advantageous to form high-affinity interactions between nucleic acid nanostructures and solid supports to prevent dissociation of the nucleic acid nanostructure from the solid support, but at a slow enough rate to facilitate rearrangement of nucleic acid nanostructures into more-stable configurations on the solid support and/or facilitate disruption of co-localized pairs of nucleic acid nanostructures from an address of a solid support before both become permanently coupled to the surface by a high-affinity binding interaction. For example, a streptavidin moiety may be buried within a plurality of polymer chains (e.g., PEG, alkanes, dextrans, etc.), thereby necessitating transfer of a complementary biotin moiety coupled to a nucleic acid nanostructure (e.g., via a polymer linking moiety) through the plurality of polymer chains to the streptavidin moiety (e.g., by a diffusional mechanism or reptation, etc.).

A surface or solid support, as set forth herein, may comprise a material with desired characteristics such as hydrophobicity or hydrophilicity, amphipathicity, low adhesion of particular chemical or biological species, and particular chemical, optical, electrical, or mechanical properties. In some cases, a surface or solid support material may be chosen for its compatibility with a detection technique or method (e.g., confocal fluorescent microscopy). For example, a material may be selected due to its low autofluorescence characteristic. A surface or solid support may comprise a solid surface to which molecules can be covalently or non-covalently attached. Non-limiting examples of solid substrates include slides, surfaces of elements of devices, membranes, flow cells, wells, chambers, and microfluidic or microfluidic chambers. Surfaces and/or solid supports used herein may be flat or curved, or can have other shapes, and can be smooth or textured. In some cases, solid support surfaces may contain microwells. In some cases, solid support surfaces may contain nanowells. Such wells can be configured as sites or addresses of an array. In some cases, solid support surfaces may contain one or more microwells in combination with one or more nanowells, for example, each microwell accommodating an array of nanowells.

A surface or solid support may comprise polymers, glasses, semiconductors (e.g., silicon, germanium), ceramics, metals, minerals (e.g., mica), or other materials. In some instances, a surface or solid support may comprise components made of a glass such as borosilicate glass, fused silica, or quartz. In other instances, a surface or solid support may comprise an optical glass or a photochromatic glass. In some cases, a glass with a high sodium or potassium content may be selected as a material for a fluidic device component. A surface or solid support may be fabricated from polymers or plastics such as polycarbonate, polyethylene, polypropylene, polyethylene terephthalate, polyvinyl chloride, polymethyl methacrylate, polydimethylsiloxane, polystyrene acrylics, latex and others. A surface or solid support may comprise metals, metal alloys, metal oxides, metal nitrides, or combinations thereof, such as stainless steel, gold, chromium, titanium, titanium oxide, tin oxide, zirconium oxide or aluminum. A surface or solid support may comprise carbohydrates such as dextrans or cellulose. In some cases, a surface or solid support may comprise two or more components with different (e.g. plastic vs. glass) or differing (e.g. borosilicate vs. quartz glass) material types.

A surface or solid support, as set forth herein, may be characterized by a thickness or depth. The thickness of a surface or solid support may be uniform or may vary over the body of the surface or solid support. The thickness of the surface or solid support may be altered by a fabrication, forming or machining process. In some cases, a surface or solid support may have a thickness of at least about 1 nanometer (nm), 10 nm, 100 nm, 1 micrometer (μm), 10 μm, 50 μm, 100 μm, 250 μm, 500 μm, 750 μm, 1 millimeter (mm), 5 mm, 1 centimeter (cm), 10 cm or more than 10 cm. Alternatively or additionally, a surface or solid support may have a thickness of no more than about 10 cm, 1 cm, 5 mm, 1 mm, 750 μm, 500 μm, 250 μm, 100 μm, 50 μm, 10 μm, 1 μm, 100 nm, 10 nm, 1 nm, or less than 1 nm.

A surface or solid support, as set forth herein, may comprise one or more surface coatings. A surface coating may be organic or inorganic. In some cases, a surface coating may be deposited by a suitable deposition process, e.g., atomic layer deposition, chemical vapor deposition, chemical liquid deposition, spin coating, self-assembling monolayers. In some cases, a surface coating may be patterned by a suitable patterning process, e.g., dry etch, wet etch, lift-off, deep UV lithography or combination thereof. A deposited surface coating may have a uniform thickness or a variable thickness over a surface of a solid support. In some cases, a surface coating may comprise an atomic or molecular monolayer. In some cases, a surface coating may comprise a self-assembled monolayer or sub-monolayer. In some cases, a surface coating may comprise a metal or metal oxide layer. In some cases, a surface coating may comprise a silane layer (e.g., ethoxy-, methoxy- or chloro-silane, silanol, siloxane, etc.), a phosphonate layer, a carboxylate layer (e.g., carboxylate transition metal oxides), a thiol layer (e.g., thiolated gold), or a phosphate layer. In some cases, a surface coating may comprise a polymer, a mineral, a ceramic, or an ink. A surface or solid support may comprise a layer or coating comprising a functional group or moiety that is configured to couple to a complementary functional group or moiety on a SNAP or SNAP complex. A surface or solid support may have a gel coating.

A surface coating on a surface or solid support, as set forth herein, may be characterized by a particular thickness. A surface coating may be at least about 1 Angstrom (Å), 5 Å, 1 nanometer (nm), 5 nm, 10 nm, 20 nm, 30 nm, 40 nm, 50 nm, 100 nm, 250 nm, 500 nm, 1 micrometer (μm), 5 μm, 10 μm, 50 μm, 100 μm or more. Alternatively or additionally, a surface coating may be no more than about 100 μm, 50 μm, 10 μm, 5 μm, 1 μm, 500 nm, 250 nm, 100 nm, 50 nm, 40 nm, 30 nm, 20 nm, 10 nm, 5 nm, 1 nm, 5 Å, 1 Å or less.

A surface or a surface coating of a solid support, as set forth herein, may be characterized by a surface roughness. A surface roughness may be due to an intrinsic character of a material or processing method used to form the material or surface. A surface roughness may be calculated as an average size of roughness features (e.g., depressions, bumps, etc.) or may be provided as a distribution of feature sizes relative to a mean or average surface height or level. A surface may be provided with a coating or layer to alter the average surface roughness or distribution of roughness features on the surface. For example, a surface may be coated to decrease the average surface roughness of a material. In other cases, a surface may be etched, coated, or otherwise treated to increase the surface roughness.

Figure 25A:
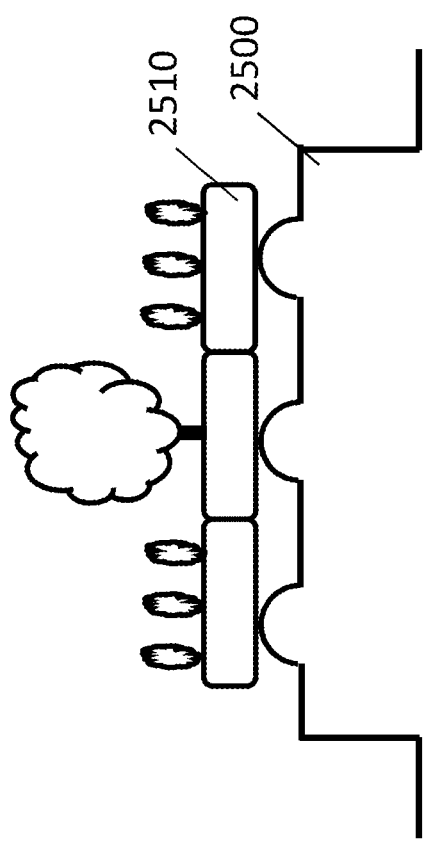
FIGS. 25A, 25B, and 25C depict a SNAP complex on a surface comprising surface roughness, in accordance with some embodiments.
Figure 25B:
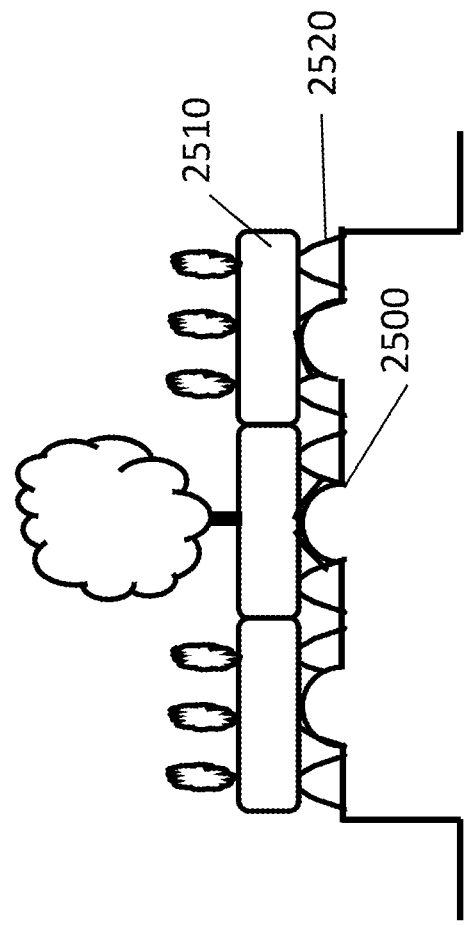
Figure 25C:
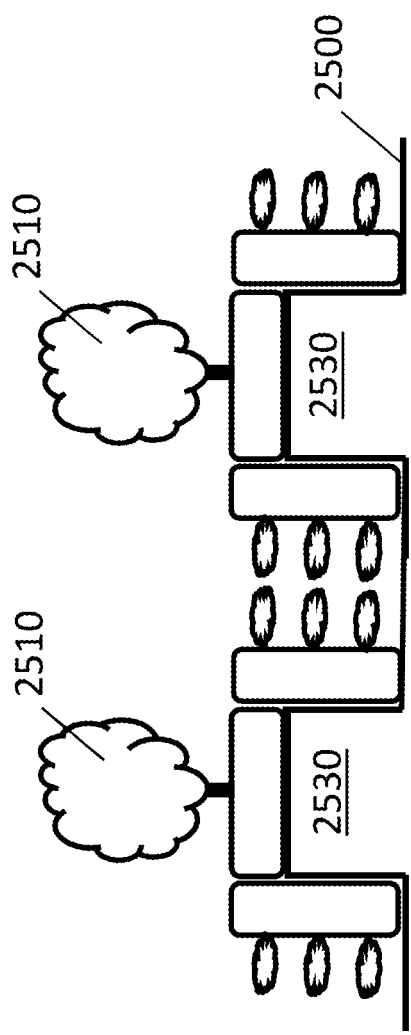

In some configurations, a SNAP or a SNAP complex may comprise a capture face or capture moiety that is structured to facilitate coupling to a surface with surface roughness. For example, a SNAP may comprise a capture face comprising a plurality of single-stranded nucleic acids or other interacting groups (e.g., electrically-charged moieties, magnetic moieties, etc.) that may form an increased interaction area with a surface. FIG. 25A-25C illustrate examples of forming interactions with surfaces comprising a surface roughness. FIG. 25A depicts the contacting of a SNAP complex 2510 with component SNAPs having unmodified capture faces with a surface 2500 comprising surface roughness. The SNAP complex 2510 can only form limited interactions with the surface where the capture faces contact the surface 2500 high points. FIG. 25B depicts the contacting of a SNAP complex 2510 with component SNAPs having capture faces modified with single stranded nucleic acids 2520 (or other interacting groups) with a surface 2500 comprising surface roughness. The SNAP complex 2510 can form increased interactions with the surface where the single-stranded nucleic acids 2520 contact the surface 2500 high points. FIG. 25C illustrates contacting a plurality of SNAP complexes 2510 with a nanostructured surface 2500 comprising a plurality of pillar-type structures 2530. The SNAP complex 2510 may be configured to facilitate the display of an analyte at the top of each nanostructured feature of the surface 2500. For example, utility SNAPs of a SNAP complex 2510 may comprise utility moieties (e.g., hydrophobic moieties) on a utility face that can interact with utility moieties of other SNAP complexes 2510, thereby increasing the likelihood that the utility SNAPs of adjacent SNAP complexes 2510 co-locate in interstitial regions between raised features and display SNAPs of each SNAP complex bind to the top of a pillar-type structure 2530.

A surface such as a solid support may comprise a characterized roughness. Surface roughness may be characterized by a method such as surface profilometry, contact profilometry, atomic force microscopy, optical microscopy, or any other suitable technique. A surface may comprise a characterized average roughness of at least about 0.1 nm, 0.2 nm, 0.3 nm, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, 10 nm, 11 nm, 12 m, 13 nm, 14 nm, 15 nm, 16 nm, 17 nm, 18 nm, 19 nm, 20 nm, or more than 20 nm. A surface may comprise a characterized average roughness of no more than about 20 nm, 19 nm, 18 nm, 17 nm, 16 nm, 15 nm, 14 nm, 13 nm, 12 nm, 11 nm, 10 nm, 9 nm, 8 nm, 7 nm, 6 nm, 5 nm, 4 nm, 3 nm, 2 nm, 1 nm, 0.9 nm, 0.8 nm, 0.7 nm, 0.6 nm, 0.5 nm, 0.4 nm, 0.3 nm, 0.2 nm, 0.1 nm, or less than 0.1 nm.

A surface or solid support may comprise one or more surfaces that are coated with a layer of metal or metal oxide. A metal or metal oxide layer may comprise a particular species depending upon the preferable chemistry. Candidate metals or metal oxides may include zirconium oxide ($ZrO_2$), hafnium (Hf), gold (Au), titanium dioxide ($TiO_2$), aluminum (Al), aluminum oxide ($Al_2O_3$) or a combination thereof.

In some cases, the surface or solid support may be optically opaque. In some cases, all or part of the solid surface or solid support may be optically opaque at one or more wavelengths such as the infrared, visible, red, orange, yellow, green, blue, violet or ultraviolet. In some cases, all or part of the solid surface or solid support may be optically clear, or may be optically clear at one or more wavelengths such as the infrared, visible, red, orange, yellow, green, blue, violet or ultraviolet. For example, a solid surface or solid support may be optically opaque in regions that are not functionalized, and optically clear in regions that are functionalized.

Methods of Coupling Nucleic Acids at Solid Supports

In another aspect, provided herein is a method of coupling a nucleic acid nanostructure to an array site, comprising: a) contacting an array comprising a site with a nucleic acid nanostructure, in which the site comprises a plurality of surface-linked moieties, and in which the nucleic acid nanostructure comprises a plurality of capture moieties, b) coupling the nucleic acid nanostructure to the site in an initial configuration, in which the initial configuration does not comprise a stable configuration, and in which the nucleic acid nanostructure is coupled by a coupling of a capture moiety of the plurality of capture moieties to a surface-linked moiety of the plurality of surface-linked moieties, c) uncoupling the coupling of the capture moiety of the plurality of capture moieties to the surface-linked moiety of the plurality of surface-linked moieties, and d) altering the nucleic acid nanostructure from the initial configuration to the stable configuration, in which each capture moiety of the plurality of capture moieties is coupled to a surface-linked moiety of the plurality of surface-linked moieties. Optionally, the nucleic acid nanostructure can be conjugated to, or configured to conjugate to, an analyte of interest. Other optional compositions for the nucleic acid nanostructure are set forth elsewhere herein.

In some configurations, uncoupling of a capture moiety of a nucleic acid nanostructure from a surface-linked moiety of an array site comprises heating the solid support and/or the nucleic acid nanostructure, and/or contacting the solid support with a fluidic medium that is configured to uncouple the surface-linked moiety from the capture moiety.

In some configurations, a method of coupling a nucleic acid nanostructure to an array site may comprise contacting the array with a fluidic medium, as set forth herein, in which the fluidic medium comprises the nucleic acid nanostructure. Optionally, the fluidic medium can include a plurality of nucleic acid nanostructures, at least a subset of which couple individually to respective sites of the array. In particular configurations, altering a nucleic acid nanostructure from an initial configuration to a stable configuration may further comprise altering a fluidic medium that is contacted with a solid support. In some configurations, altering a fluidic medium in contact with a solid support may comprise introducing a chemical species (e.g., a surfactant, a denaturant, a chaotrope, an ionic species, an acid, a base, etc.). In other configurations, altering a fluidic medium in contact with a solid support may comprise altering a concentration of a chemical species in the fluidic medium (e.g., a surfactant, a denaturant, a chaotrope, an ionic species, an acid, a base, etc.).

A method of coupling a nucleic acid nanostructure to an array site may utilize a nucleic acid nanostructure that comprises one or more capture moieties that are configured to form a multi-valent binding interaction (e.g., coupling to more than one surface-linked moiety). A capture moiety of a nucleic acid nanostructure may comprise a structure that facilitates formation of a multi-valent binding interaction (e.g., a polynucleotide repeat, a first and second polynucleotide repeat separated by an intermediate nucleotide sequence, etc.). A capture moiety may optionally comprise a structure that weakens a binding strength or binding specificity of any individual binding interaction of a multi-valent binding interaction. In some configurations, a nucleic acid nanostructure may comprise a capture moiety comprising a homopolymer sequence or other composition set forth elsewhere herein, for example, in the context of pendant oligonucleotides and staple oligonucleotides. The nucleic acid nanostructure may be coupled to a solid support comprising a first surface-linked moiety that is complementary to or reactive with the surface coupling moiety. In some configurations, a nucleic acid nanostructure may comprise a capture moiety comprising a nucleotide sequence that contains self-complementarity. A method of coupling a nucleic acid nanostructure to a surface may comprise one or more steps of: i) disrupting a self-complementary nucleotide sequence of a capture moiety, and ii) coupling a surface-linked moiety to the self-complementary nucleotide sequence of the capture moiety (e.g., via a toehold-mediated strand displacement reaction, etc.).

A method of coupling a nucleic acid nanostructure to a surface may comprise: i) coupling the nucleic acid nanostructure to the surface in an initial configuration, and ii) altering the nucleic acid nanostructure to a final configuration, in which the final configuration is more stable (temporally, spatially, thermodynamically, kinetically, etc.) than the initial configuration. In some cases, an initial configuration may comprise a spatial positioning of a nucleic acid nanostructure on a site of a solid support, in which the initial configuration comprises a non-maximized or partial quantity of couplings of capture moieties to surface-linked moieties. For example, a nucleic acid nanostructure containing 20 capture moieties may have a non-maximized or partial quantity of coupling if less than 20 of the capture moieties are coupled to surface-linked moieties of an array site. In another example, a nucleic acid nanostructure containing 20 capture moieties may be expected to form coupling interaction with at least 10 surface-linked moieties (e.g., at least 50% of available binding groups utilized) to achieve a maximized quantity of coupling. In other cases, an initial configuration may comprise a non-maximized footprint of a nucleic acid nanostructure on an array site. For example, if only a fraction of a nucleic acid nanostructure is coupled to a surface of an array site (see FIG. 58B), then the nucleic acid nanostructure has not maximized its footprint on the array site and may have a non-maximized quantity of coupling interactions formed. In other cases, an initial configuration may comprise an asymmetric alignment of the nucleic acid nanostructure on the site. For example, a substantially square nucleic acid nanostructure may initially couple to a substantially square array site, in which a center point of the nucleic acid nanostructure is not aligned with a center point of the array site. In some configurations, a more-stable final configuration may comprise a location on an array site in which the nucleic acid nanostructure forms a maximized quantity of couplings of capture moieties to surface-linked moieties. In other configurations, a more-stable final configuration may comprise a maximized footprint of the nucleic acid nanostructure on the site. In other configurations, a more-stable final configuration may comprise a symmetric alignment of the nucleic acid nanostructure on the site.

A nucleic acid nanostructure may be coupled to an array site by a coupling of one or more capture moieties of the nucleic acid nanostructure to a plurality of surface-linked moieties of the array site. An array site may have an excess quantity of surface-linked moieties, in which the excess quantity is determined with respect to a quantity of available binding groups on one or more capture moieties and/or with respect to a spatial density of available binding groups on the one or more capture moieties. For example, a nucleic acid nanostructure may comprise 20 capture moieties comprising poly-T sequences, in which each capture moiety is configured to form about 10 binding interactions with surface-linked poly-A oligonucleotides. In such a case, an array sites containing more than 200 surface-linked poly-A oligonucleotides may be considered to contain an excess quantity of surface-linked moieties. In another example, a nucleic acid nanostructure may comprise a plurality of capture moieties with an average surface density of about 1 capture moiety per 10 square nanometers. In such a case, an array site comprising surface-linked moieties with a surface density exceeding 1 surface-linked moiety per 10 square nanometers may contain excess quantity of surface-linked moieties. An array site may contain a molar excess of surface-linked moieties relative to the quantity of available capture moieties of a nucleic acid nanostructure, on an absolute or spatial density basis, of at least about 1.1-fold, 1.2-fold, 1.5-fold, 2-fold, 3-fold, 4-fold, 5-fold, 10-fold, 25-fold, 50-fold, 100-fold, 250-fold, 500-fold, 1000-fold, 5000-fold, 10000-fold, 100000-fold, 1000000-fold, or more than 1000000-fold. Alternatively or additionally, an array site may contain a molar excess of surface-linked moieties relative to the quantity of available capture moieties of a nucleic acid nanostructure, on an absolute or spatial density basis, of no more than about 1000000-fold, 100000-fold, 10000-fold, 5000-fold, 1000-fold, 500-fold, 250-fold, 100-fold, 50-fold, 25-fold, 10-fold, 5-fold, 4-fold, 3-fold, 2-fold, 1.5-fold, 1.2-fold, 1.1-fold, or less than 1.1 fold. In other configurations, an array site may comprise a molar deficit of surface-linked moieties relative to the quantity of available capture moieties of a nucleic acid nanostructure.

Provided herein is a method of forming an array, comprising providing a plurality of nucleic acid nanostructures or nucleic acid nanostructure complexes, as set forth herein, coupling each nucleic acid nanostructure or nucleic acid nanostructure complex of the plurality of nucleic acid nanostructures or nucleic acid nanostructure complexes to one or more additional nucleic acid nanostructures or nucleic acid nanostructure complexes from the plurality of nucleic acid nanostructures or nucleic acid nanostructure complexes, and coupling each nucleic acid nanostructure or nucleic acid nanostructure complex of the plurality of nucleic acid nanostructures or nucleic acid nanostructure complexes with a surface, where each nucleic acid nanostructure or nucleic acid nanostructure complex comprises a display nucleic acid nanostructure and one or more capture nucleic acid nanostructures or utility nucleic acid nanostructures, and wherein each nucleic acid nanostructure complex comprises a coupling moiety that couples with the surface, thereby forming an array.

In some configurations, each nucleic acid nanostructure complex is assembled prior to being contacted with another nucleic acid nanostructure complex to which it will couple. In other configurations, individual nucleic acid nanostructures are contacted with each other to result in conjugation of nucleic acid nanostructure complexes to other nucleic acid nanostructure complexes. Accordingly, a method of forming an array, can include providing a plurality of nucleic acid nanostructures to produce a plurality of nucleic acid nanostructure complexes, each nucleic acid nanostructure complex comprising at least two nucleic acid nanostructure complexes that are coupled together, and coupling the plurality of nucleic acid nanostructure complexes with a surface, where each nucleic acid nanostructure complex comprises a display nucleic acid nanostructure and one or more utility nucleic acid nanostructures, and where each nucleic acid nanostructure complex comprises a coupling moiety that couples with the surface, thereby forming an array.

A display nucleic acid nanostructure may be coupled to an analyte before or after being incorporated into an array. In some configurations, a method may further comprise a step of coupling an analyte to the display moiety. In some configurations, an analyte may be coupled to a display moiety after a coupling of each nucleic acid nanostructure complex of a plurality of nucleic acid nanostructure complexes with a surface. In some configurations, an analyte may be coupled to a display moiety before a coupling of each nucleic acid nanostructure complex of a plurality of nucleic acid nanostructure complexes with a surface. In some configurations, an analyte may be coupled to a display moiety after a coupling of each nucleic acid nanostructure complex of a plurality of nucleic acid nanostructure complexes to one or more additional nucleic acid nanostructure complexes from a plurality of nucleic acid nanostructure complexes. In some configurations, an analyte may be coupled to a display moiety before a coupling of each nucleic acid nanostructure complex of a plurality of nucleic acid nanostructure complexes to one or more additional nucleic acid nanostructure complexes from a plurality of nucleic acid nanostructure complexes. In some configurations, an analyte may be coupled to a display moiety after a providing of a plurality of nucleic acid nanostructure complexes. In some configurations, an analyte may be coupled to a display moiety before a providing of a plurality of nucleic acid nanostructure complexes.

An array comprising a nucleic acid nanostructure or a nucleic acid nanostructure complex, as set forth herein, may be formed in a particular formation condition. A condition may include a particular solvent or buffering condition. In some configurations, a plurality of nucleic acid nanostructures or nucleic acid nanostructure complexes may be provided in a pH buffer comprising a magnesium salt. In some configurations, coupling of a plurality of nucleic acid nanostructures or nucleic acid nanostructure complexes may occur in a presence of a surfactant. An array may be formed with a display nucleic acid nanostructure that may be coupled to an analyte before or after forming an array. In some configurations, an analyte may be covalently coupled to a display moiety.

An array comprising nucleic acid nanostructures or nucleic acid nanostructure complexes may be formed under a particular temperature configuration. For example, a first SNAP or SNAP complex may be combined with a second SNAP or SNAP complex at a first temperature, then the temperature may be altered (e.g., decreased, increased), thereby coupling the first SNAP or SNAP complex to the second SNAP or SNAP complex to form an array. A step in an array formation process may occur at a temperature of at least about 0° C., 10° C., 25° C., 50° C., 75° C., 90° C., 95° C., or more than 95° C. Alternatively or additionally, a step in an array formation process may occur at a temperature of no more than about 95° C., 90° C., 75° C., 50° C., 25° C., 10° C., 0° C., or less than 0° C. In some configurations, temperature may be utilized to increase the specificity of nucleic acid nanostructure deposition on a surface. For example, it may be advantageous to contact a nucleic acid nanostructure comprising a plurality of surface-interacting oligonucleotides with a coupling surface comprising a plurality of surface-linked complementary oligonucleotides at a higher temperature, then decrease the temperature when the nucleic acid nanostructure has had sufficient time to obtain a most-stable configuration on the coupling surface. Surprisingly, increased temperature of nucleic acid nanostructure or nucleic acid nanostructure complex deposition may increase the likelihood of depositing only one nucleic acid nanostructure on a coupling surface due to the increased energy available for the nucleic acid nanostructure to find a position on a coupling surface where a maximal number of surface-interacting moieties can form a binding interaction, and the increased likelihood that an optimal deposition position for the nucleic acid nanostructure on the coupling surface will obstruct other nucleic acid nanostructures from co-depositing stably on the same coupling surface.

A nucleic acid (e.g., a nucleic acid nanostructure, SNAP, a complex thereof, or a component thereof), or an analyte-coupled version thereof, as set forth herein, may be deposited on a surface or solid support. The methods and compositions set forth below will generally be exemplified with reference to a SNAP or SNAP complex; however, it will be understood that the examples can be extended to any nucleic acid, as set forth herein, including a population having the same species of SNAP or SNAP complex, a population having different species of SNAP or SNAP complex, a population having the same species of analyte-coupled SNAP or SNAP complex, or a population having different species of analyte-coupled SNAP or SNAP complexes.

In an aspect, provided herein is a method comprising: a) contacting a nucleic acid, as set forth herein, with a solid support, as set forth herein; and b) coupling the nucleic acid to the solid support. In some cases, a method may comprise the steps of: a) providing a solid support, as set forth herein, in which the solid support comprises a site and an interstitial region, in which the site is configured to couple a nucleic acid, as set forth herein, and in which the interstitial region is configured to inhibit binding of a nucleic acid, b) contacting the solid support with the nucleic acid, and c) coupling the nucleic acid to the site of the solid support. In some cases, a method may comprise the steps of: a) providing a solid support, as set forth herein, in which the solid support comprises a plurality of sites and one or more interstitial regions, in which a site of the plurality of sites is configured to couple a nucleic acid, as set forth herein, and in which the interstitial region is configured to inhibit binding of a nucleic acid, b) contacting the solid support with a plurality of nucleic acids, in which the plurality of nucleic acids comprises the nucleic acid, and c) coupling the nucleic acid of the plurality of nucleic acids to the site of the plurality of sites.

An analyte may be coupled to a SNAP or SNAP complex before, during, or after deposition of the SNAP or SNAP complex on a surface or solid support. The deposition of a SNAP or SNAP complex on a surface or solid support may be driven by a physical phenomenon such as gravity, centrifugal force, electrostatic interactions, magnetic interactions, covalent binding, or non-covalent binding. In some cases, the deposition of a SNAP or SNAP complex may be due to the electrostatic interaction between a negatively-charged SNAP or SNAP complex and a positively-charged substrate (or other material), or vice versa. In other cases, the deposition of a SNAP or a SNAP complex may be due to coupling interactions between a plurality of surface-interacting moieties on a SNAP with a plurality of surface-linked moieties on a coupling surface.

Before a SNAP, a SNAP complex, or an analyte-coupled version thereof is coupled to a solid support, the SNAP, SNAP complex, or analyte-coupled version thereof may be purified. In some cases, purification may comprise removal of excess or unwanted reagents (e.g., salts, unbound oligonucleotide, unbound analytes, etc.). In some cases, a purification process may comprise removal of SNAPs or SNAP complexes that do not comprise a coupled analyte. In some cases, a purification process may comprise removal of SNAPs or SNAP complexes that comprise more than one coupled analyte. In some cases, a purification process may comprise removal of analytes that are coupled to more than one SNAP or SNAP complex. A SNAP, a SNAP complex, or an analyte-coupled version thereof may be purified by a suitable purification process, such as size exclusion chromatography, high-pressure liquid chromatography, ultrafiltration, tangential flow filtration, reverse osmosis, affinity chromatography, or combinations thereof. A plurality of analytes or SNAP-analyte composites may be characterized based upon a statistical or stochastic measure of purity. In some cases, a plurality of analytes may be provided for preparation of an array of analytes if a measure of purity deviates from an expected measure of purity for a statistical or stochastic distribution (e.g., a Poisson distribution, a normal distribution, a binomial distribution, etc.), in which the statistical or stochastic distribution is calculated for a situation of a single analyte coupled to a single nucleic acid. For example, a plurality of analytes coupled to a plurality of nucleic acid nanostructures may be utilized for a method, as set forth herein, if a purified fraction contains less than 36.8% nucleic acid nanostructures that are not coupled to an analyte (e.g., a lower ratio than predicted by a Poisson distribution). A purified plurality of analytes may be characterized with respect to fraction of unoccupied nucleic acids, fraction of nucleic acids with more than one analyte, fraction of analytes coupled to more than one nucleic acid, or combinations thereof.

SNAPs, SNAP complexes, or analyte-coupled versions thereof may be deposited on a surface or solid support to form a patterned, ordered, or unordered array of SNAPs, SNAP complexes, or analyte-coupled versions thereof. In some cases, the surface or solid support may be structured, engineered, or fabricated to control where the deposition of SNAPs or SNAP complexes may occur. The surface or solid support may contain localized or uniform regions of positive or negative surface charge density that promote electrostatic interactions with a SNAP or SNAP complex. A surface or solid support may be deposited with a coating, layer, or functional group that alters the surface charge density of the surface or material to promote electrostatic interactions with an anchoring group of a protein conjugate. A surface or solid support may be functionalized with a chemical species that permits direct covalent attachment of a SNAP or SNAP complex to the surface or material. Exemplary surfaces and solid supports that can be particularly useful are set forth elsewhere herein.

A deposition of SNAPs, SNAP complexes, or analyte-coupled versions thereof, as set forth herein, on a surface or solid support material may be controlled to ensure sufficient separation between neighboring SNAPs or SNAP complexes. For an analyte assay, SNAPs, SNAP complexes, or analyte-coupled versions thereof may be deposited with sufficient separation to ensure that each SNAP, SNAP complex, or analyte-coupled version thereof is located at a unique, optically observable address or location on a surface or solid support. Separation between neighboring SNAPs, SNAP complexes, or analyte-coupled versions thereof may be controlled by the surface or solid support material; the SNAPs, SNAP complexes, or analyte-coupled versions thereof, or by a combination thereof. For example, features may be present on a surface and each feature may have dimensions or chemical functionalization(s) that accommodate only a single SNAP or SNAP complex. Alternatively or additionally, functional groups may be present on SNAPs or SNAP complexes in an orientation that limits the arrangement of the SNAPs or SNAP complexes on a surface that is reactive to the functional groups. A surface or solid support material may be modified to mediate the deposition of SNAPs, SNAP complexes, or analyte-coupled versions thereof at binding sites. Areas of the surface or solid support between binding sites may be modified to discourage or prevent deposition of SNAPs, SNAP complexes, or analyte-coupled versions thereof. Deposition of SNAPs, SNAP complexes, or analyte-coupled versions thereof may be prevented by surface groups or materials that sterically obstruct a protein conjugate from depositing on the surface, such as tethered dextrans, tethered polyethylene glycol (PEG) macromolecules or sheared salmon sperm DNA. Deposition of SNAPs, SNAP complexes, or analyte-coupled versions thereof to particular regions on a surface, such as interstitial regions which are intended to separate addresses where SNAPs are to reside, may be prevented by surface groups that electrostatically or magnetically repel of SNAPs, SNAP complexes, or analyte-coupled versions thereof. For example, a negatively charged SNAP or SNAP complex may be repelled from areas of a substrate surface that have been functionalized with negatively charged groups such as a carboxylic acids, organophosphates, organosulfates, or combinations thereof. In some cases, solvent configuration may be utilized to facilitate and/or inhibit SNAP deposition at areas of a surface or solid support. For example, salts, surfactants, or emulsions may be utilized to areas of more favorable or less favorable binding conditions.

Covalent bonds may be formed between a SNAP, SNAP complex, or analyte-coupled version thereof, as set forth herein, and a surface or solid support. A covalent bond may be formed directly between a SNAP, SNAP complex, or analyte-coupled version thereof and a surface or solid support. A covalent bond may be formed between a functional group on a SNAP, SNAP complex, or analyte-coupled version thereof and a surface or solid support. For example, a SNAP, SNAP complex, or analyte-coupled version thereof functionalized with an organosilane group may be bonded to a silicon surface or solid support by a coordination bond. A covalent bond may be formed between a functional group on a SNAP, SNAP complex, or analyte-coupled version thereof and a functional group on a surface or solid support. For example, a SNAP, SNAP complex, or analyte-coupled version thereof containing an activated ester functional group may be bonded to a surface or solid support containing an aminated functional group (e.g., 3 amino-propyl triethoxysilane, silanol, etc.). In some cases, a SNAP, SNAP complex, or analyte-coupled version thereof may be coupled to a solid support or surface by a covalent bond formed by a Click-type reaction.

A SNAP or a SNAP complex, as set forth herein, may be deposited on a material, surface, or solid support comprising an ordered or unordered surface. An ordered surface may comprise a surface that is patterned with a plurality of binding sites or regions separated by interstitial regions, where each binding site may be configured to bind a SNAP complex, and where the interstitial regions may be configured to not bind the SNAP complex. In some configurations, a surface or solid support may comprise a patterned array. An ordered surface may facilitate deposition of SNAPs or SNAP complexes by limiting regions where SNAPs or SNAP complexes may deposit, or by providing ordered features that encourage the deposition of SNAPs or SNAP complexes. In other configurations, an unordered surface may comprise a surface with no patterned or structured features. For example, a surface may comprise a uniform coating or layer of functional groups or moieties that are configured to couple SNAPs or SNAP complexes. In some configurations, an unordered surface may comprise a phase boundary between two fluids, such as a gas/liquid interface or a liquid/liquid interface. In other configurations, an unordered surface may comprise a mobile layer (e.g., a lipid monolayer or bilayer, a layer of tethered or adhered micelles or colloids, etc.). SNAPs or SNAP complexes may be configured to self-assemble or self-pattern on an unordered surface. For example, SNAPs or SNAP complexes may comprise utility moieties on one or more faces that sterically block the approach of other SNAPs or SNAP complexes, thereby limiting the ability for two SNAP to co-locate within a region of steric occlusion or obstruction.

A material may comprise a surface or solid support that is patterned or structured with binding sites or regions and interstitial regions to form a patterned array of SNAPs or SNAP complexes. In some configurations, individual binding sites may further comprise structures that facilitate the deposition of SNAPs or SNAP complexes at the binding site or region, and/or limit or prevent the co-deposition of multiple SNAPs or SNAP complexes at the binding site or region. Surface features that may be altered to facilitate SNAP or SNAP complex deposition may include binding site or region size, binding site or region morphology, and binding site or region chemistry. In some configurations, a solid support, a surface thereof, and/or a site thereof may comprise a two-dimensional and/or three-dimensional feature that facilitates binding of a SNAP or SNAP complex to the surface. In particular configurations, a two-dimensional and/or three-dimensional feature may comprise a shape or morphology that substantially matches a shape or morphology of a SNAP and/or SNAP complex. A shape or morphology of a solid support, a surface thereof, and/or a site thereof may match a shape or morphology of a SNAP if the shape or morphology has a substantially similar surface area to an effective surface area or footprint of a SNAP, SNAP complex, or a face thereof. A shape or morphology of a solid support, a surface thereof, and/or a site thereof may match a shape or morphology of a SNAP if the shape or morphology has a surface contour that substantially align with a contour of a SNAP, SNAP complex, or a face thereof. For example, a triangular SNAP may be deposited on a triangular site. In another example, a site may comprise a pyramidal, three-dimensional raised structure that couples to a pyramidal void space of a SNAP structure. In other particular configurations, a two-dimensional and/or three-dimensional feature may comprise a shape or morphology that does not substantially match a shape or morphology of a SNAP and/or SNAP complex.

Figure 26B:
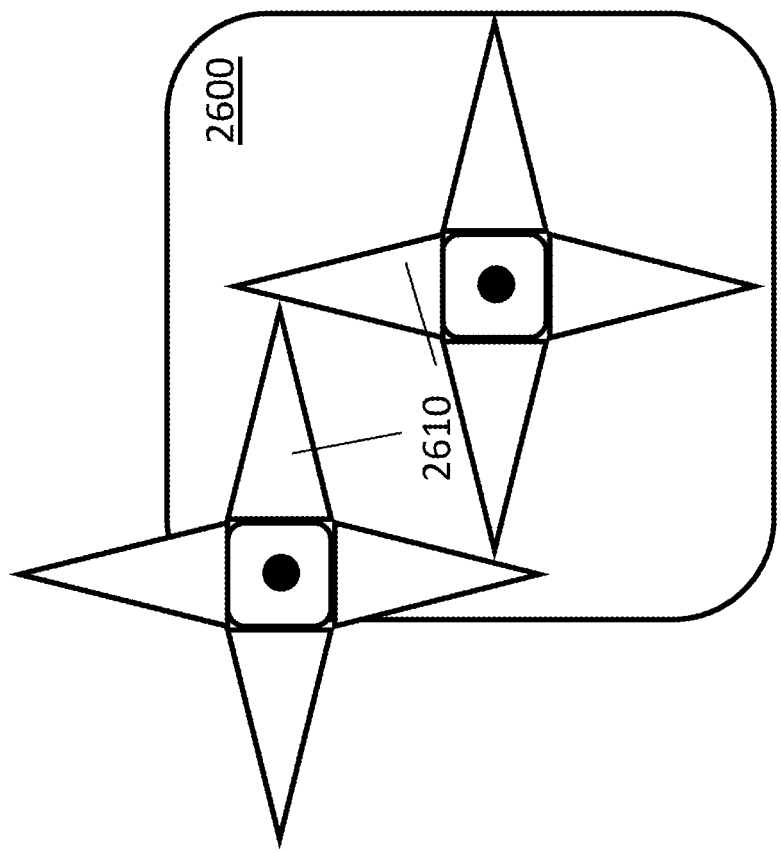
FIGS. 26A, 26B, and 26C depict multiple SNAP complexes on a single binding site, in accordance with some embodiments.
Figure 26A:
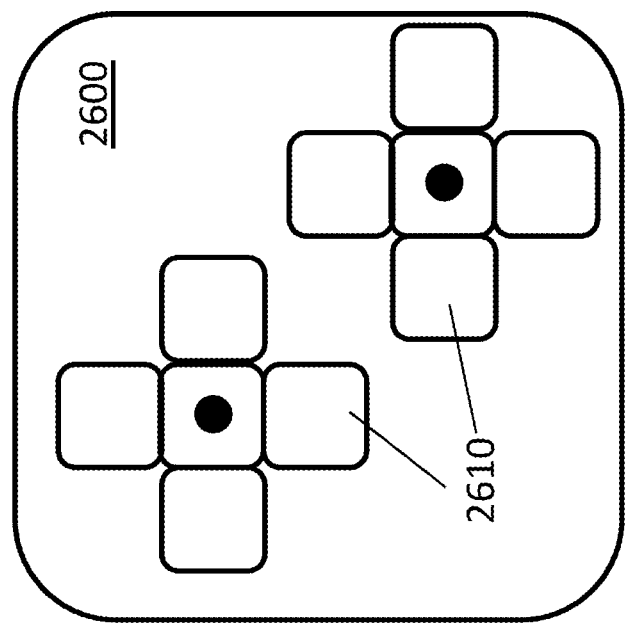
Figure 26C:
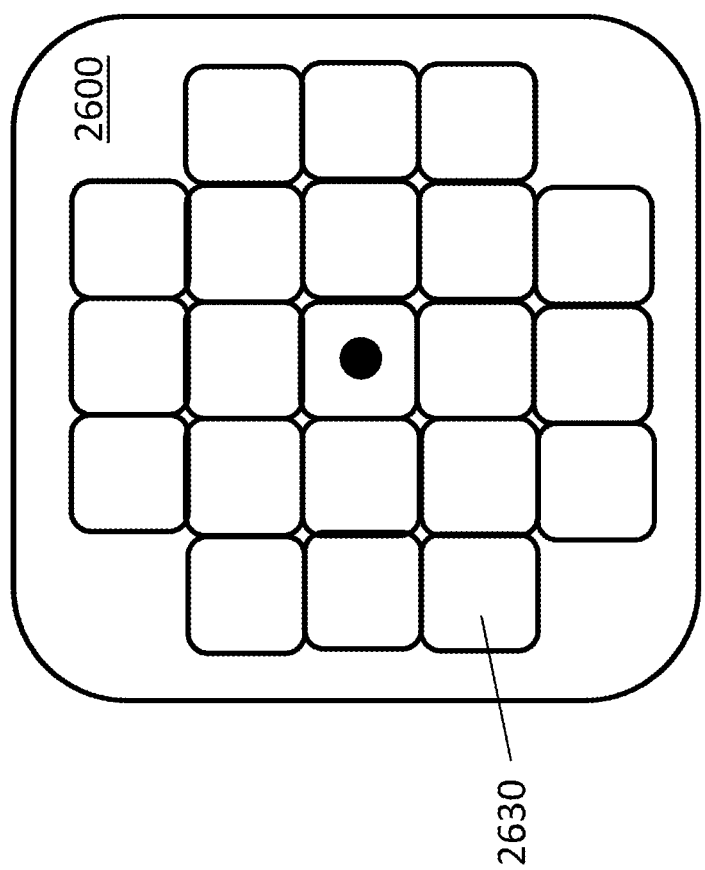

In some configurations, a SNAP or SNAP complex may have a shape or conformation that limits the deposition of SNAPs or SNAP complexes at a binding site or region. FIG. 26A depicts a binding site 2600 comprising 2 electrostatically-bound cross-shaped SNAP complexes 2610. Although both SNAP complexes 2610 each occupy less than 25% of the surface area of the binding site 2600, the cross-shaped conformation limits the ability for more than two SNAP complexes to deposit with sufficient surface contact to form a stable electrostatic binding interaction. FIG. 26B depicts a binding site 2600 comprising 2 electrostatically-bound star-shaped SNAP complexes 2620. Although the combined footprint of the 2 SNAP complexes 2620 is less than the total footprint of the binding site 2600, the conformation of the first complex prevents the second complex from fully occupying the binding site, increasing the likelihood that the second complex may dissociate from the binding site 2600. Thus, the first SNAP complex 2610 to occupy the binding site 2600 will sterically block a second SNAP complex 2610 from co-occupying the binding site 2600. In some configurations, a conformation of a first SNAP or SNAP complex coupled to a binding site or region may prevent a second SNAP or SNAP complex from coupling to the binding site. FIG. 26C depicts a binding site 2600 comprising a SNAP complex 2630 comprising 21 tile-shaped SNAPs that fully occupies the binding site such that no other SNAP complexes may deposit at the binding site 2600.

Figure 27B:
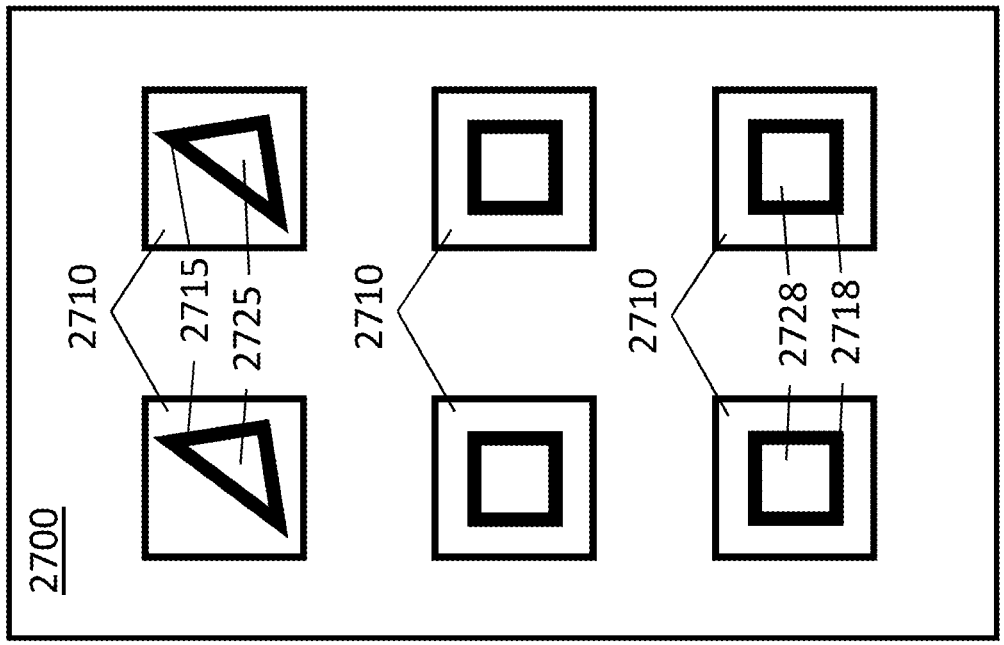
FIGS. 27A and 27B show an array containing patterned binding sites, in accordance with some embodiments.
Figure 27A:
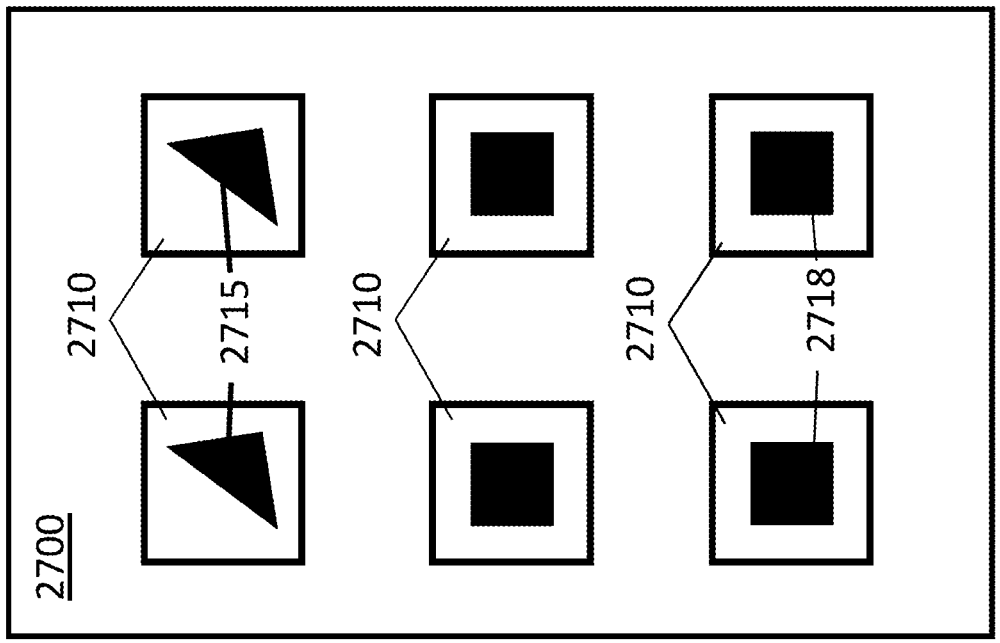

Binding sites or regions may also be configured to facilitate SNAP or SNAP complex deposition due to binding site or region morphology. Binding sites or regions may comprise raised pedestals, wells, or depressions. Surface discontinuities (e.g., edges or boundaries) that form pedestals or wells may limit the deposition of SNAPs due to energetic effects. Without wishing to be bound by theory, SNAPs or SNAP complexes may be less likely to deposit adjacent to edges or discontinuities if portions of the SNAP or SNAP complex may be incompletely in contact with a binding surface. Reducing the size of a binding site or region may also increase the likelihood that only a single SNAP or SNAP complex may favorably bind to a binding site or region. Binding sites or region may further comprise small-scale features that encourage SNAP or SNAP complex deposition within the binding site or region. FIGS. 28A-28B depict raised surface features 2800 that are matched to the conformation of capture faces 2820 on SNAP complexes 2810. Such features may be created by lithographic or depositional techniques to from more specific features to bind SNAPs or SNAP complexes at a binding site. Multiple types of patterned surface features may be utilized to segregate different SNAP or SNAP complex types on a surface. FIG. 27A depicts a surface 2700 comprising 6 binding sites 2710. Two binding sites are patterned with a triangular surface feature 2715 and 4 binding sites are patterned with a square surface feature 2718. As shown in FIG. 27B, after the surface has bee contacted with a mixture of triangular and square SNAP complexes, the triangular SNAP complexes 2725 preferentially bind to the triangular surface features 2715 and the square SNAP complexes 2728 preferentially bind to the square surface features 2718.

The surface chemistry of a binding site or binding region may also be configured to facilitate SNAP or SNAP complex deposition. A binding site or binding region may include localized regions of functional groups or moieties that are configured to couple a SNAP or SNAP complex (e.g., click reactive groups, oligonucleotides, etc.). A binding site or binding region may further comprise regions of blocking or passivating groups that discourage the specific or non-specific binding of SNAPs or SNAP complexes to particular portions of a binding site or region (e.g., edges, boundaries). Localized surface chemistries may be generated by any suitable technique, including deposition and lift-off techniques. Further surface chemistry methods are discussed in PCT/US2020/058416, which is hereby incorporated by reference in its entirety. In some cases, distribution or density of a two or more species of functional groups or moieties (e.g., surface-linked moieties) may be controlled by deposition of mixtures of the two or more species at relative concentrations that produce the desired surface distribution or surface density of each respective species. For example, a coupling surface comprising two surface-linked oligonucleotides with a 1:100 molar ratio may be formed by co-depositing the oligonucleotides from a fluidic medium comprising the two oligonucleotides in an approximately 1:100 molar ratio. In some cases, relative ratios of species may be adjusted due to kinetic differences in deposition.

A plurality of SNAPs, SNAP complexes, or analyte-coupled versions thereof may be deposited on a surface or solid support with a known or characterized efficiency. In certain cases where the available number of binding sites on a surface or substrate exceeds the population size of the plurality of SNAPs, SNAP complexes, or analyte-coupled versions thereof, the efficiency of deposition may be measured based upon the fraction of the plurality of SNAPs, SNAP complexes, or analyte-coupled versions thereof that are deposited on the surface or solid support. In certain cases where the plurality of SNAPs, SNAP complexes, or analyte-coupled versions thereof exceeds the available number of binding sites on a surface or solid support, the efficiency of deposition may be measured based upon the fraction of available binding sites on the surface or solid support that are occupied after deposition.

The binding efficiency of a plurality of SNAPs, SNAP complexes, or analyte-coupled versions thereof to a surface or solid support may be quantified based upon a percentage or fraction of the plurality of SNAPs, SNAP complexes, or analyte-coupled versions thereof that are deposited on the surface or solid support. The binding efficiency of a plurality of SNAPs, SNAP complexes, or analyte-coupled versions thereof may be at least about 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, 99.99%, 99.999%, 99.9999%, 99.99999%, 99.999999%, or more than 99.999999% based upon the available number of SNAPs, SNAP complexes, or analyte-coupled versions thereof in the plurality. Alternatively or additionally, the binding efficiency of a plurality of SNAPs, SNAP complexes, or analyte-coupled versions thereof may be no more than about 99.999999%, 99.99999%, 99.9999%, 99.999%, 99.99%, 99.9%, 99.5%, 99%, 98%, 97%, 96%, 95%, 94%, 93%, 92%, 91%, 90%, 85%, 80%, 75%, 70%, 65%, 60%, 55%, 50%, 45%, 40%, 35%, 30%, 25%, 20%, 15%, 10%, 5%, 1%, or less than about 1% based upon the available number of SNAPs, SNAP complexes, or analyte-coupled versions thereof in the plurality.

The binding efficiency of a plurality of SNAPs, SNAP complexes, or analyte-coupled versions thereof to a surface or solid support may be quantified based upon a percentage or fraction of the available binding sites on the surface or solid support that become occupied with a SNAP, SNAP complex, or analyte-coupled version thereof. The occupancy rate of surface or solid support binding sites may be at least about 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, 99.99%, 99.999%, 99.9999%, 99.99999%, 99.999999%, or more than 99.999999% based upon the total number of available binding sites. Alternatively or additionally, the occupancy rate of surface or solid support binding sites may be no more than about 99.999999%, 99.99999%, 99.9999%, 99.999%, 99.99%, 99.9%, 99.5%, 99%, 98%, 97%, 96%, 95%, 94%, 93%, 92%, 91%, 90%, 85%, 80%, 75%, 70%, 65%, 60%, 55%, 50%, 45%, 40%, 35%, 30%, 25%, 20%, 15%, 10%, 5%, 1%, or less than about 1% based upon the total number of available binding sites.

In particular configurations, more than one SNAP, SNAP complex, or analyte-coupled version thereof, as set forth herein, may deposit on a surface or solid support at a unique location, address, or binding site on the surface or solid support. In some cases, the number of binding sites with more than one SNAP, SNAP complex, or analyte-coupled version thereof may be minimized to accommodate single molecule detection during an analyte assay. In other cases, more than one SNAP, SNAP complex, or analyte-coupled version thereof may be deposited at a plurality, majority, or at all available binding sites, such as during a bulk analyte assay. A surface or solid support comprising a plurality of deposited SNAPs, SNAP complexes, or analyte-coupled versions thereof may be characterized or quantified to determine the number of binding sites with more than one SNAP, SNAP complex, or analyte-coupled version thereof. A surface or solid support binding site may contain more than one SNAP, SNAP complex, or analyte-coupled version thereof, such as, for example, about 2, 3, 4, 5, 6, 7, 8, 9, 10, or more SNAPs, SNAP complexes, or analyte-coupled versions thereof. Binding sites with more than one deposited SNAP, SNAP complex, or analyte-coupled version thereof may exist according to some quantifiable distribution, such as a Poisson distribution, binomial distribution, beta-binomial distribution, hypergeometric distribution, or bimodal distribution.

The percentage of binding sites on a surface or solid support with more than one SNAP, SNAP complex, or analyte-coupled version thereof may be quantified based upon the observed number of molecules detected at each unique location on the surface or solid support. The number of excess molecules at a unique location on a surface or solid support may be quantified by detection of excess fluorescence, luminescence, scintillation, or size (e.g., as characterized by atomic force microscopy). The percentage of binding sites on a surface or solid support with more than one SNAP, SNAP complex, or analyte-coupled version thereof may be no more than about 50%, 40%, 30%, 20%, 10%, 9%, 8%, 7%, 6%, 5%, 4%, 3%, 2%, 1%, 0.5%, 0.10%, 0.05%, 0.01%, 0.005%, 0.001%, 0.0001%, 0.00001%, 0.000001%, 0.0000001%, or less than about 0.0000001% of all available binding sites. Alternatively or additionally, the percentage of binding sites on a surface or solid support with more than one SNAP, SNAP complex, or analyte-coupled version thereof may be at least about 0.0000001%, 0.000001%, 0.00001%, 0.0001%, 0.001%, 0.005%, 0.01%, 0.05%, 0.1%, 0.5%, 1%, 2%, 3%, 4%, 5%, 6%, 7%, 8%, 9%, 10%, 20%, 30%, 40%, 50% or more than about 50% of all available binding sites. In some cases, there may be no observed binding sites on a surface or solid support with more than one deposited SNAP, SNAP complex, or analyte-coupled version thereof.

A SNAP, SNAP complex, or analyte-coupled version thereof may be deposited on a surface or solid support under conditions that encourage the deposition of the SNAP, SNAP complex, or analyte-coupled version thereof at a binding site on the surface or solid support. Deposition may occur under externally applied physical phenomena, such as electric fields, magnetic fields, heating, cooling, or combinations thereof. In some cases, SNAPs, SNAP complexes, or analyte-coupled versions thereof may be deposited on a surface or solid support under a condition that promotes deposition of the SNAP, SNAP complex, or analyte-coupled version thereof. A solvent for deposition may be varied by chemical composition, ionic strength, pH, electrical conductivity, magnetic permeability, heat capacity, thermal conductivity, reactivity, density, viscosity, polarity, and combinations thereof. The chemical composition of a solvent for deposition of SNAPs, SNAP complexes, or analyte-coupled versions thereof may be varied by solvent types and amounts, salt types and amounts, metal types and amounts, surfactant types and amounts, constituent pH, constituent pKa, and constituent reactivity. In some cases, a solvent for the deposition of SNAPs, SNAP complexes, or analyte-coupled versions thereof may be composed to enhance the interactions between SNAPs, SNAP complexes, or analyte-coupled versions thereof and a surface or solid support, for example the electrostatic bonding of a SNAP, SNAP complex, or analyte-coupled version thereof. Without wishing to be bound by theory, a deposition solvent for SNAPs, SNAP complexes, or analyte-coupled versions thereof may minimize the free energy of deposition for the SNAPs, SNAP complexes, or analyte-coupled versions thereof. A deposition solvent may comprise a dispersing agent, such as a surfactant or detergent, that reduces or prevents aggregation of SNAPs, SNAP complexes, or analyte-coupled versions thereof before deposition. In some cases, a SNAP or SNAP complex storage or preparation solvent composition may be utilized as a deposition solvent. A deposition solvent may be configured to increase a likelihood of SNAP and/or SNAP complex deposition at a preferred location of a surface or solid support. A deposition solvent may be configured to decrease a likelihood of SNAP and/or SNAP complex deposition at a non-preferred location of a surface or solid support.

A method of depositing a nucleic acid on a solid support, as set forth herein, may be facilitated by modulating strength of a binding interaction between the nucleic acid and the solid support. For example, a nucleic acid may be deposited on a solid support in an initial configuration, then re-arranged into a more-stable final configuration by disrupting one or more existing binding interactions between the nucleic acid and the solid support at a first address of the solid support, and by forming one or more new binding interactions between the nucleic acid and the solid support at a second address of the solid support. In another example, a nucleic acid that is configured to form a covalent interaction and a non-covalent interaction with a solid support may first be deposited on the solid support in a fluidic medium that inhibits the covalent interaction and facilitates the non-covalent interaction. Then the solid support and/or nucleic acid can be contacted with a second fluidic medium that facilitates the covalent interaction.

A method of depositing a nucleic acid may comprise modulating strength of a binding interaction between the nucleic acid and the solid support by altering a fluidic medium in contact with the nucleic acid and/or the solid support. A fluidic medium, as set forth herein, may be altered by changing a fluidic parameter, in which the fluidic parameter may comprise any conceivable parameter, such as chemical composition (e.g., solvent type, presence and concentration of a species such as a chaotrope or surfactant, etc.), polarity, density, viscosity, boiling point, freezing point, pH, ionic strength, osmotic pressure, and flow rate. Modulating a strength of a binding interaction may comprise one or more steps of a) depositing a nucleic acid, as set forth herein, on a solid support, as set forth herein, in a first fluidic medium comprising a first fluidic parameter, as set forth herein, b) optionally incubating the nucleic acid and/or the solid support in the first fluidic medium, c) contacting the nucleic acid and/or the solid support with a second fluidic medium comprising a second fluidic parameter, in which the first fluidic parameter and the second fluidic parameter differ, d) optionally incubating the nucleic acid and/or the solid support in the second fluidic medium, and e) optionally, displacing the second fluidic medium from the solid support and/or the nucleic acid. In some configurations, a solid support may be contacted with a second fluidic medium before depositing a nucleic acid in a first fluidic medium. For example, a solid support may be incubated in a second fluidic medium that activates a surface of the solid support for forming a binding interaction, then subsequently contacted with a first fluidic medium comprising a nucleic acid, thereby forming the binding interaction between the nucleic acid and the surface. In some configurations, displacing a second fluidic medium from a solid support may comprise displacing the second fluidic medium comprising a second fluidic parameter with a first fluidic medium comprising a first fluidic parameter. For example, a solid support may be incubated in a second fluidic medium that activates a surface of the solid support for forming a binding interaction, then subsequently contacted with a first fluidic medium comprising a nucleic acid, thereby forming the binding interaction between the nucleic acid and the surface. In another example, a solid support comprising a deposited nucleic acid may be contacted with a second fluidic medium, thereby weakening a strength of a binding interaction between the nucleic acid and the solid support, then the second fluidic medium may be displaced by a first fluidic medium, thereby strengthening the strength of the binding interaction between the nucleic acid and the solid support. In some configurations, a displacing a second fluidic medium from a solid support may comprise displacing the second fluidic medium comprising a second fluidic parameter with a third fluidic medium comprising a third fluidic parameter. For example, a second fluidic medium may be displaced by a rinsing buffer that is configured to remove any unbound entities (e.g., nucleic acids, analytes, affinity agents, reagents, etc.) from a solid support or a surface thereof. In another example, a second fluidic medium may be displaced by a medium comprising a cross-linking agent that is configured to couple a nucleic acid to a solid support or a surface thereof.

In some configurations, a method of modulating strength of a binding interaction may comprise displacing a first fluidic medium by a step-wise change to a second fluidic medium. For example, a first fluidic medium may be withdrawn from contact with a solid support, then a second fluidic medium may be contacted with the solid support. In other configurations, a method of modulating a strength of a binding interaction may comprise displacing a first fluidic medium by a gradient change to a second fluidic medium. For example, an ionic strength of a solution in contact with a solid support may be altered from a first ionic strength to a second ionic strength by flowing a fluidic medium past the solid support, in which the fluidic medium undergoes a linear or non-linear gradient in concentration from the first ionic strength to the second ionic strength. In some configurations, a method of modulating a strength of a binding interaction may comprise altering an environmental property of a fluidic medium, a solid support, and/or a nucleic acid, such as a temperature, shear force, electrical field, or a magnetic field. For example, a solid support or a fluidic medium contacted thereto may be heated to weaken a non-covalent binding interaction between a nucleic acid and the solid support (e.g., a nucleic acid base-pair hybridization).

A method, as set forth herein, may comprise forming a multiplexed array. A multiplexed array may comprise a first plurality of analytes and a second plurality of analytes, in which the first plurality of analytes differs from the second plurality of analytes in one or more respects (e.g., sample type, sample source, analyte type, etc.). In some cases, a multiplexed array of analytes may comprise a randomly-ordered array comprising: a) a plurality of sites, in which each sites comprises a fixed address, and b) a first plurality of analytes and a second plurality of analytes, in which each site of the plurality of sites comprises one and only one analyte of the first plurality of analytes or the second plurality of analytes, and in which a spatial distribution of sites comprising an analyte of the first plurality of analytes has a random spatial order. In some cases, a randomly-ordered array may be formed by: a) depositing a first plurality of analytes on a solid support, as set forth herein, and b) after depositing the first plurality of analytes on the solid support, depositing a second plurality of analytes on the solid support. In other cases, a randomly-ordered array may be formed by: a) combining a first plurality of analytes with a second plurality of analytes, and b) depositing the combined first plurality of analytes and the second plurality of analytes on a solid support, as set forth herein. A first plurality of analytes may be distinguishable from a second plurality of analytes by one or more characteristics, such as differing nucleic acid nanostructures, differing detectable labels, differing functional nucleic acids, or combinations thereof. In other cases, a multiplexed array may comprise an ordered array comprising: a plurality of sites, in which each sites comprises a fixed address, and b) a first plurality of analytes and a second plurality of analytes, in which each site of the plurality of sites comprises one and only one analyte of the first plurality of analytes or the second plurality of analytes, and in which a spatial distribution of sites comprising an analyte of the first plurality of analytes has a non-random spatial order. For example, an array may be prepared with a first contiguous plurality of sites and a second contiguous plurality of sites, in which each site of the first contiguous plurality of sites couples to an analyte of a first plurality of analytes, and in which each site of the second contiguous plurality of sites couples to an analyte of a second plurality of analytes. In some cases, an ordered array may be formed by: a) depositing a first plurality of analytes on a solid support, as set forth herein, and b) after depositing the first plurality of analytes on the solid support, depositing a second plurality of analytes on the solid support. For example, a first plurality of analytes may be deposited on a first contiguous region of an array and a second plurality of analytes may be deposited on a second contiguous region of an array by a printing method. In other cases, an ordered array may be formed by: a) combining a first plurality of analytes with a second plurality of analytes, and b) depositing the combined first plurality of analytes and the second plurality of analytes on a solid support, as set forth herein. For example, a first plurality of analytes comprising a first plurality of nucleic acid nanostructures, and a second plurality of analytes comprising a second plurality of nucleic acid nanostructures may be simultaneously deposited on an array comprising a first plurality of sites and a second plurality of sites, in which each site of the first plurality of sites couples a nucleic acid nanostructure of the first plurality of nucleic acid nanostructures, in which each site of the second plurality of sites couples a nucleic acid nanostructure of the second plurality of nucleic acid nanostructures, and in which the first plurality of sites is spatially segregated from the second plurality of sites.

Nucleic Acid Complexes

Described herein are nucleic acid nanostructure (e.g., SNAP) complexes comprising two or more nucleic acid nanostructures, as set forth herein. A nucleic acid nanostructure complex may comprise any structure that comprises a first nucleic acid nanostructure coupled to a second nucleic acid nanostructure. A nucleic acid nanostructure complex may comprise a first nucleic acid nanostructure and a second nucleic acid nanostructure, where the first nucleic acid nanostructure is a display nucleic acid nanostructure or a utility nucleic acid nanostructure, and where the second nucleic acid nanostructure is independently selected from the group consisting of a display nucleic acid nanostructure and a utility nucleic acid nanostructure. Accordingly, nucleic acid nanostructure complex may comprise two or more nucleic acid nanostructures each with a particular function. In some configurations, a nucleic acid nanostructure complex may comprise a utility nucleic acid nanostructure comprising a capture nucleic acid nanostructure, a coupling nucleic acid nanostructure, a structural nucleic acid nanostructure, or a combination thereof. In some configurations, a nucleic acid nanostructure complex may comprise a display nucleic acid nanostructure and one or more additional nucleic acid nanostructures that perform a function for the nucleic acid nanostructure complex, such as: 1) positioning the display nucleic acid nanostructure with respect to a second display nucleic acid nanostructure; 2) positioning the display nucleic acid nanostructure with respect to a non-display nucleic acid nanostructure; 3) altering the display of an analyte that is coupled to the display nucleic acid nanostructure; 4) increasing the strength of coupling of a nucleic acid nanostructure complex to a surface; 5) increasing the size of a surface occupied by a nucleic acid nanostructure complex; 6) adding additional functions to a nucleic acid nanostructure complex (e.g., steric blocking, optical reflection or absorbance, magnetic coupling, barcoding, etc.); 7) increasing the number of analytes displayed on a surface; or 8) a combination thereof. A nucleic acid nanostructure complex may comprise one or more nucleic acid nanostructures comprising a capture face or capture moiety, wherein the capture face or capture moiety comprises one or more surface-interacting moieties that are configured to form a coupling interaction with a coupling surface of a solid support.

A first nucleic acid nanostructure (e.g., a SNAP) and a second nucleic acid nanostructure of a nucleic acid nanostructure complex may be coupled by one or more coupling moieties. A first nucleic acid nanostructure comprising a first coupling face may be configured to couple with a second nucleic acid nanostructure comprising a second coupling face, thereby forming a nucleic acid nanostructure complex. A first nucleic acid nanostructure may comprise a first coupling moiety comprising one or more functional groups or moieties that are configured to couple to a second nucleic acid nanostructure via reaction with a second coupling moiety comprising one or more complementary functional groups or moieties. Two or more nucleic acid nanostructures may be coupled in a nucleic acid nanostructure complex by any suitable coupling interaction, including covalent and non-covalent interactions.

Provided herein is a nucleic acid nanostructure complex (e.g., a SNAP complex), comprising two or more nucleic acid nanostructures, where each nucleic acid nanostructure of the two or more nucleic acid nanostructures may be selected independently from the group consisting of a display nucleic acid nanostructure, a utility nucleic acid nanostructure, or a combination thereof, where the display nucleic acid nanostructure may comprise a display moiety that may be configured to couple to an analyte, where the utility nucleic acid nanostructure may comprise a capture moiety that may be configured to couple with a surface, and where the two or more nucleic acid nanostructures may be coupled to form the nucleic acid nanostructure complex.

Also provided herein is a nucleic acid nanostructure composition (e.g., a SNAP composition), comprising a material comprising a surface and two or more nucleic acid nanostructures, where each nucleic acid nanostructure of the two or more nucleic acid nanostructures may be selected independently from the group consisting of a display nucleic acid nanostructure, a utility nucleic acid nanostructure, or a combination thereof, where the display nucleic acid nanostructure may comprise a display moiety that may be configured to couple to an analyte, where the two or more nucleic acid nanostructures may be coupled to the surface, and where a first nucleic acid nanostructure of the two or more nucleic acid nanostructures may be coupled to a second nucleic acid nanostructure of the two or more nucleic acid nanostructures, thereby forming a nucleic acid nanostructure complex. In particular configurations, the nucleic acid nanostructure composition is an array of nucleic acid nanostructures or nucleic acid nanostructure complexes. The nucleic acid nanostructures or nucleic acid nanostructure complexes can be attached to an analyte or other target molecule of interest, thereby providing an array of the analytes or molecules of interest. Further examples of nucleic acid nanostructure compositions (e.g., SNAP compositions) and nucleic acid nanostructure complexes that can form sites or addresses of an array are set forth in the following paragraphs and elsewhere herein in the context of various array compositions.

Also provided herein is a nucleic acid nanostructure composition (e.g., a SNAP composition), comprising an analyte, a display nucleic acid nanostructure, and one or more utility nucleic acid nanostructures, where the display nucleic acid nanostructure may comprise a display moiety that may be configured to couple to an analyte, where the utility nucleic acid nanostructure may comprise a capture moiety that may be coupled with a surface or configured to couple with a surface, where the display nucleic acid nanostructure may be coupled to the analyte, and where the display nucleic acid nanostructure may be coupled to the one or more nucleic acid nanostructures, thereby forming a nucleic acid nanostructure complex.

Also provided herein is a nucleic acid nanostructure composition (e.g., a SNAP composition), comprising a material comprising a surface, an analyte, a display nucleic acid nanostructure, and one or more utility nucleic acid nanostructures, where the display nucleic acid nanostructure comprises a display moiety that may be configured to couple to an analyte, where the capture nucleic acid nanostructure comprises a capture moiety that may be configured to couple with a surface, where the display nucleic acid nanostructure may be coupled to the analyte, where the display nucleic acid nanostructure may be coupled to the one or more nucleic acid nanostructures, thereby forming a nucleic acid nanostructure complex, and where the nucleic acid nanostructure complex may be coupled to the surface.

A nucleic acid nanostructure complex (e.g., a SNAP complex), as set forth herein, may comprise a display nucleic acid nanostructure and a utility nucleic acid nanostructure. The utility nucleic acid nanostructure may comprise a nucleic acid nanostructure selected from the group consisting of a capture nucleic acid nanostructure, a coupling nucleic acid nanostructure, a structural nucleic acid nanostructure, or a combination thereof. A nucleic acid nanostructure complex may comprise a display nucleic acid nanostructure and one or more capture nucleic acid nanostructures that are configured to couple the nucleic acid nanostructure complex to a surface. A nucleic acid nanostructure complex may comprise a display nucleic acid nanostructure and one or more coupling nucleic acid nanostructures that are configured to bind the nucleic acid nanostructure complex to a second nucleic acid nanostructure or a second nucleic acid nanostructure complex. A nucleic acid nanostructure complex may comprise a display nucleic acid nanostructure and one or more utility nucleic acid nanostructures.

A nucleic acid nanostructure (e.g., a SNAP complex), as set forth herein, may comprise a display nucleic acid nanostructure that is coupled to, or configured to couple to, an analyte. A nucleic acid nanostructure complex may comprise a utility nucleic acid nanostructure that is configured to couple to a surface. In some configurations, a nucleic acid nanostructure may comprise a nucleic acid nanostructure as described by any of the configurations described herein, for example a SNAP comprising a multifunctional moiety.

A nucleic acid nanostructure complex (e.g., a SNAP complex), as set forth herein, may comprise a display nucleic acid nanostructure or a utility nucleic acid nanostructure that comprises a detectable label. In some configurations, a display nucleic acid nanostructure or a utility nucleic acid nanostructure may comprise a utility face, where the utility face comprises a capture moiety, a detectable label, or a sterically blocking moiety. Any of a variety of detectable labels may comprise a fluorescent label, a luminescent label, a nucleic acid barcode, a nanoparticle label, an isotope, or a radiolabel.

A first nucleic acid nanostructure and a second nucleic acid nanostructure may be coupled by one or more coupling moieties. In some configurations, a display nucleic acid nanostructure may comprise a first nucleic acid nanostructure coupling moiety and a utility nucleic acid nanostructure may comprise a second nucleic acid nanostructure coupling moiety, where the display nucleic acid nanostructure may be coupled to the capture nucleic acid nanostructure by a coupling of the first nucleic acid nanostructure coupling moiety to the second nucleic acid nanostructure coupling moiety. In some configurations, a first nucleic acid nanostructure coupling moiety and a second nucleic acid nanostructure coupling moiety may form a covalent bond, for example, between a complementary pair of click-type reaction moieties. In other configurations, a first nucleic acid nanostructure coupling moiety and a second nucleic acid nanostructure coupling moiety can form a non-covalent bond, such as a hydrogen bond, a nucleic acid base pair bond, or a streptavidin-biotin bond.

A nucleic acid nanostructure complex (e.g., a SNAP complex), as set forth herein, may comprise two or more types of nucleic acid nanostructures in specific quantities. In some configurations, a nucleic acid nanostructure complex comprises a plurality of utility nucleic acid nanostructures and a single display nucleic acid nanostructure. In some cases, a nucleic acid nanostructure complex may comprise a particular number of a type of nucleic acid nanostructure (e.g., a display SNAP, a utility SNAP). A nucleic acid nanostructure complex may comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, or more than 100 of a particular number of a type of nucleic acid nanostructure. Alternatively or additionally, a nucleic acid nanostructure complex may comprise no more than about 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or less than 2 of a particular number of a type of nucleic acid nanostructure.

In some cases, a nucleic acid nanostructure complex (e.g., a SNAP complex) may comprise a first type of nucleic acid nanostructure (e.g., a display SNAP) and a second type of SNAP (e.g., a utility SNAP) in a fixed ratio. A nucleic acid nanostructure complex may comprise a first type of nucleic acid nanostructure and a second type of nucleic acid nanostructure in a ratio of at least about 1:1, 1.1:1, 1.25:1, 1.5:1, 1.75:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 55:1, 60:1, 65:1, 70:1, 75:1, 80:1, 85:1, 90:1, 95:1, 100:1, or more than 100:1. Alternatively or additionally, a nucleic acid nanostructure complex may comprise a first type of nucleic acid nanostructure and a second type of nucleic acid nanostructure in a ratio of at most about 100:1, 95:1, 90:1, 85:1, 80:1, 75:1, 70:1, 65:1, 60:1, 55:1, 50:1, 49:1, 48:1, 47:1, 46:1, 45:1, 44:1, 43:1, 42:1, 41:1, 40:1, 39:1, 38:1, 37:1, 36:1, 35:1, 34:1, 33:1, 32:1, 31:1, 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2.5:1, 2:1, 1.75:1, 1.5:1, 1.25:1, 1.1:1, or less than 1.1:1.

A nucleic acid nanostructure complex (e.g., a SNAP complex) may comprise a first type of nucleic acid nanostructure (e.g., a display SNAP) and a second type of nucleic acid nanostructure (e.g., a utility SNAP), where the second type of nucleic acid nanostructure is coupled to a particular face of the first type of nucleic acid nanostructure (e.g., a coupling face). In some configurations, a nucleic acid nanostructure complex may comprise a first type of nucleic acid nanostructure and two or more of a second type of nucleic acid nanostructure coupled to one or more faces of the first type of nucleic acid nanostructure. In some configurations, a nucleic acid nanostructure complex may comprise a display nucleic acid nanostructure and two or more of a utility nucleic acid nanostructure coupled to one or more faces of the display nucleic acid nanostructure. In some configurations, a first utility nucleic acid nanostructure of the two or more utility nucleic acid nanostructures may be coupled to a first face of the display nucleic acid nanostructure, and a second utility nucleic acid nanostructure of the two or more utility nucleic acid nanostructures may be coupled to a second face of the display nucleic acid nanostructure. In some configurations, a face of the first utility nucleic acid nanostructure is coupled to a face of the second utility nucleic acid nanostructure. In some configurations, a first utility nucleic acid nanostructure is not coupled to a second utility nucleic acid nanostructure. In some configurations, a nucleic acid nanostructure complex further comprises a third utility nucleic acid nanostructure. In some configurations, a third utility nucleic acid nanostructure is coupled to a third face of the display nucleic acid nanostructure. In some configurations, a third utility nucleic acid nanostructure is coupled to a face of a first utility nucleic acid nanostructure, a face of the second utility nucleic acid nanostructure, or a combination thereof.

A nucleic acid nanostructure complex (e.g., a SNAP complex), as set forth herein, may comprise two or more nucleic acid nanostructures with differing sizes or shapes, as determined on the basis of a minimum, average, or maximum measure, where the measure is, for example, length, width, depth, circumference, diameter, effective surface area, footprint, effective occupied volume, any measure of structure morphology, or a combination thereof. A nucleic acid nanostructure complex may comprise a first nucleic acid nanostructure (e.g., a display SNAP, or utility SNAP) comprising a first coupling face that is coupled to a second nucleic acid nanostructure (e.g., a display SNAP, or utility SNAP) comprising a second coupling face, where the first coupling face and the second coupling face have differing sizes, dimensions, or morphologies. In various configurations, a coupling face of a first nucleic acid nanostructure is smaller than, larger than, or the same size as a coupling face of a second nucleic acid nanostructure. A nucleic acid nanostructure complex may further comprise a third nucleic acid nanostructure (e.g., a display SNAP, a utility SNAP) comprising a third coupling face that is coupled to the first nucleic acid nanostructure. In some configurations, a coupling face of a third nucleic acid nanostructure is smaller than, larger than or the same size as a coupling face of a first nucleic acid nanostructure.

A nucleic acid nanostructure complex (e.g., a SNAP complex) may comprise a first nucleic acid nanostructure (e.g., a display SNAP, or utility SNAP) comprising a first coupling face and a second nucleic acid nanostructure (e.g., a display SNAP, or utility SNAP) comprising a second coupling face, where the first nucleic acid nanostructure and/or the second nucleic acid nanostructure comprise a display moiety and/or a capture moiety. In some configurations, a first coupling face and a second coupling face do not comprise a capture moiety. In some configurations, a first coupling face and a second coupling face do not comprise a display moiety. In some configurations, a capture moiety may comprise a plurality of surface-interacting moieties.

A nucleic acid nanostructure in a nucleic acid nanostructure complex (e.g., a SNAP complex) may comprise one or more coupling faces that are configured to couple the nucleic acid nanostructure to a second nucleic acid nanostructure. A nucleic acid nanostructure in a nucleic acid nanostructure complex may comprise at least about 1, 2, 3, 4, 5, 6, 7, 8, 9, 10, 11, 12, 13, 14, 15, 16, 17, 18, 19, 20, or more than 20 coupling faces. Alternatively or additionally, a SNAP in a SNAP complex may comprise no more than about 20. 19, 18, 17, 16, 15, 14, 13, 12, 11, 10, 9, 8, 7, 6, 5, 4, 3, 2, or less than 2 coupling faces. In some configurations, each coupling face of a nucleic acid nanostructure in a nucleic acid nanostructure complex may be coupled to a second nucleic acid nanostructure. In some configurations, at least one coupling face of a nucleic acid nanostructure in a nucleic acid nanostructure complex is coupled to a second nucleic acid nanostructure. In some configurations, at least one coupling face of a nucleic acid nanostructure in a nucleic acid nanostructure complex is not coupled to a second nucleic acid nanostructure.

A nucleic acid nanostructure complex (e.g., a SNAP complex) containing two or more nucleic acid nanostructures, as set forth herein, may be configured to comprise a particular symmetry, such as a mirror symmetry or a rotational symmetry. A symmetry of a nucleic acid nanostructure complex may be determined with respect to average dimensions, shapes, or configurations of nucleic acid nanostructures within a nucleic acid nanostructure complex. Variations in positioning of features, for example, due to the helical structure and tertiary structures of a SNAP, may result in small differences between two opposed features of a SNAP complex that is designed to have a symmetrical structure. A symmetric nucleic acid nanostructure may have two symmetric features which lie within about 10% of the expected position with respect to an axis or plane of symmetry.

Symmetry may facilitate one or more functions of nucleic acid nanostructures or nucleic acid nanostructure complexes (e.g., SNAP complexes). Symmetry can be characterized with respect to reference planes that are imaginary constructs for purposes of demonstration. In some aspects, a nucleic acid nanostructure (e.g., a SNAP) may be configured to have symmetry with respect to certain reference planes or axes of rotation and this symmetry can optionally facilitate increased flexibility or molecular motion. A nucleic acid nanostructure complex may be further configured with one or more planes of alignment. A plane of alignment may comprise a reference plane to which one or more coupling faces are aligned. A plane of alignment may encompass a continuous surface in which a first nucleic acid nanostructure has some degree of bending, flexing, or deformation with respect to a second nucleic acid nanostructure. A nucleic acid nanostructure may be designed with symmetry to permit assembly into particular shapes or conformations of nucleic acid nanostructure complexes. A nucleic acid nanostructure complex may possess a particular symmetry that facilitates coupling to a site on a surface that is configured to couple with the complex.

A nucleic acid nanostructure or nucleic acid nanostructure complex, as set forth herein, may be asymmetric generally or with respect to certain reference planes or axes of rotation. For example, a SNAP or SNAP complex may possess asymmetry in a particular orientation, or may possess no planes or axes of symmetry. An asymmetric nucleic acid nanostructure or nucleic acid nanostructure complex may provide the advantage of being more rigid than a symmetric nucleic acid nanostructure or nucleic acid nanostructure complex, for example, due to decreased range of motion for individual nucleic acid nanostructures in the asymmetric complex. Asymmetry in a nucleic acid nanostructure or nucleic acid nanostructure complex may also facilitate the function of the nucleic acid nanostructure or nucleic acid nanostructure complex. For example, asymmetry in the structure of top and bottom SNAP faces may facilitate differential coupling of bottom faces to a surface and top faces to display a SNAP.

FIGS. 12A-12C illustrate aspects of SNAP and SNAP complex configuration relating to symmetry. FIG. 12A shows a SNAP complex formed from a coupling of four utility SNAPs 1210 to a central display SNAP 1220. Each utility SNAP 1210 is coupled to the display SNAP 1220 by coupling of a coupling face on the utility SNAP 1210 to a coupling face on the display SNAP 1220. The coupling faces for both the utility SNAPs 1210 and the display SNAPs 1220 have an effective surface area of about the multiple of the average side length and the average SNAP thickness. The SNAP complex formed by the coupling of the four utility SNAPs 1210 to the display SNAP 1220 has two planes of symmetry indicated by reference planes 1230. FIG. 12B shows a cross-sectional view of the first configuration of the SNAP complex. The utility SNAPs 1210 are coupled to the display SNAP 1220 with sufficient rigidity to create a nearly coplanar alignment between bottom faces of the SNAPs in the SNAP complex. The SNAP complex retains a left-right symmetry around reference plane 1230 but lacks a top-bottom symmetry due to differences in configuration. The SNAP complex also comprises planes of alignment indicated by reference planes 1235 at the coupling faces between the utility SNAPs 1210 and display SNAP 1220. Arrows at the sides of the cross-section depict potential directions of bending or flexing of the utility SNAPs 1210 with respect to the display SNAP 1220. The utility SNAPs 1210 and the display SNAP 1220 may comprise bottom capture faces comprising a plurality of single-stranded nucleic acids 1240 that are configured to facilitate coupling of the SNAP complex to a surface. The utility SNAPs 1210 may further comprise top utility faces comprising a plurality of sterically-blocking groups 1250 that are configured to prevent adhesion of other molecules to the SNAP complex other than the analyte 1260 that is coupled to the display SNAP 1220. FIG. 12C depicts an alternative configuration of the SNAP complex with utility SNAPs 1210 coupled to the display SNAP 1220 at an angle such that the capture faces of the utility SNAPs 1210 and the display SNAP 1220 are not coplanar. In some configurations, the coupling of SNAPs in a SNAP complex may be sufficiently rigid to minimize bending or deformation at interfaces between SNAPs. In other cases, the coupling of SNAPs in a SNAP complex may be sufficiently flexible to permit a SNAP to adopt multiple formations, such as shifting between the formation of FIGS. 12B and 12C.

Figure 13B:
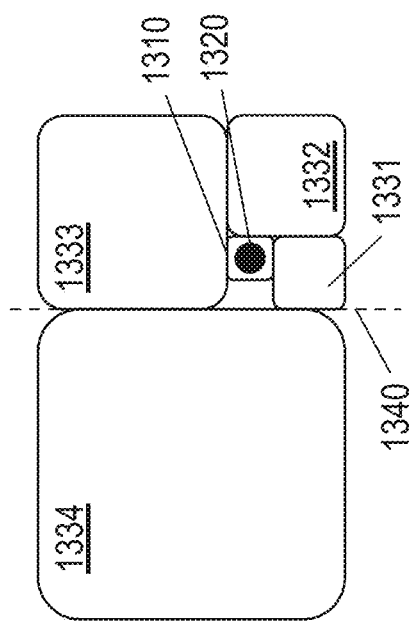
FIGS. 13A, 13B, 13C, and 13D depict differing SNAP symmetries, in accordance with some embodiments.
Figure 13A:
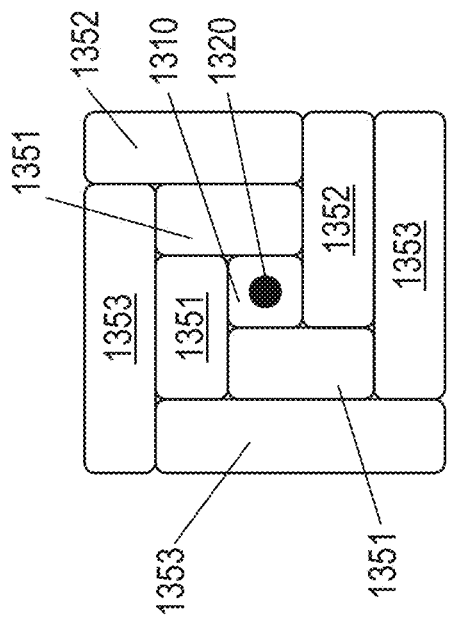

FIGS. 13A-13D show additional aspects of symmetry and asymmetry in relation to the formation of nucleic acid nanostructure complexes. In particular, configurations shown in FIGS. 13A-13D comprise configurations with utility SNAPs that couple to other utility SNAPs in the SNAP complex, thereby decreasing the ability of SNAPs to bend or deform along particular reference planes within the SNAP complex including, for example, reference planes positioned between coupled SNAPs. FIG. 13A depicts a substantially rectangular SNAP complex with an asymmetric configuration. The SNAP complex comprises a central display SNAP 1310 that comprises a display moiety 1320. The SNAP complex further comprises four utility SNAPs (1331, 1332, 1333, 1334). Utility SNAPs 1331, 1332, and 1333 are each coupled via coupling faces to complementary coupling faces of the display SNAP 1310. The fourth utility SNAP 1334 is not coupled directly to the display SNAP but is coupled to the first utility SNAP 1331 and the third utility SNAP 1333. Due to the differing average dimensions of each SNAP in the complex, utility SNAPs 1331, 1332, and 1333 comprise coupling faces with differing dimensions. Utility SNAP 1334 comprises two separate coupling faces that comprise the larger face on the side that couples to utility SNAP 1331 and 1333, thereby forming a plane of alignment that is orthogonal to depicted line 1340. FIG. 13B depicts a substantially square SNAP complex with an asymmetric configuration. The SNAP complex comprises a central display SNAP 1310 that comprises a display moiety 1320. The SNAP complex further comprises eight utility SNAPs, including 3 small utility SNAPs 1351, 2 medium utility SNAPs 1352, and 3 large utility SNAPs 1353. The spiral arrangement of the utility SNAPs and the increasing size of utility SNAPs as the spiral distance increases from the display SNAP 1310. Each utility SNAP in the configuration is coupled to at least 3 other utility SNAPs by at least 2 coupling faces on different sides of the SNAP. The configuration of FIG. 13B lacks any coupling faces between SNAPs that span the full length of the SNAP complex. This configuration beneficially maintains coplanarity of the SNAPS (relative to the plane of the page for the orientation shown in FIG. 13B). because the SNAP complex comprises no uninterrupted planes of alignment along which two adjacent SNAPs can bend or flex relative to each other so as to deviate from coplanarity. Any bending of flexing of a SNAP within the complex would be resisted due to the complex pattern of couplings in the SNAP complex.

Figure 13D:
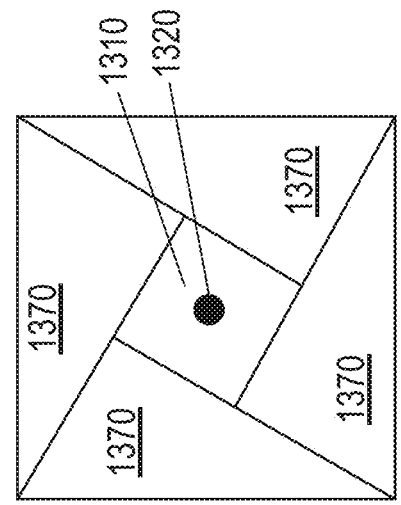
Figure 13C:
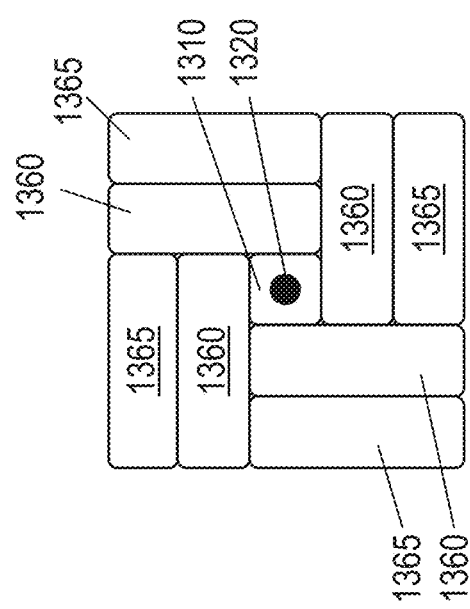
Figure 14B:
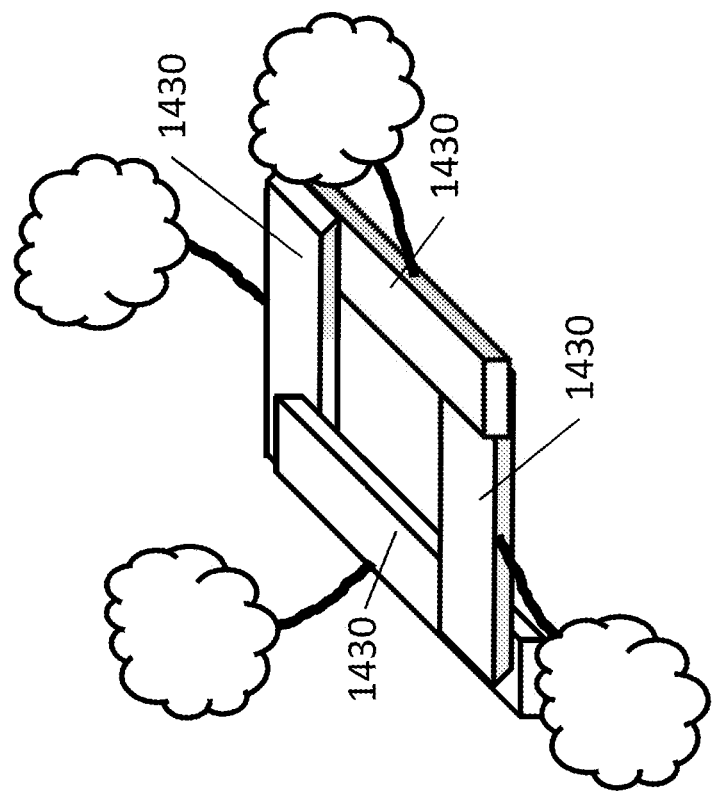
FIGS. 14A and 14B illustrate a three-dimensional SNAP conformation, in accordance with some embodiments.
Figure 14A:
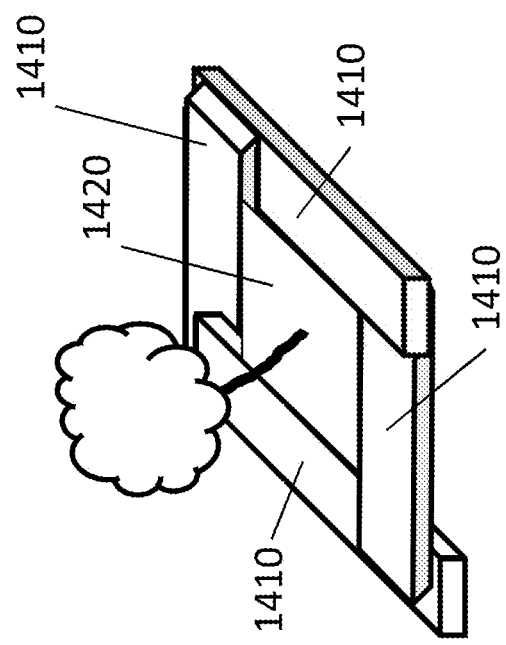

FIG. 13C-13D depict SNAP configurations with rotational symmetry about an axis that is oriented orthogonal to the display moiety 1320 of the central display SNAP 1310. FIG. 13C illustrates a substantially square SNAP complex comprising a display SNAP 1310 and 8 utility SNAPs, including 4 utility SNAPs 1360 that are coupled to coupling faces of the display SNAP 1310, and 4 utility SNAPs 1365 that are coupled only to the display-coupled utility SNAPs 1360. FIG. 13D shows a substantially square SNAP complex comprising a central display SNAP 1310 and 4 triangular utility SNAPs 1370. The display SNAP is coupled to each of the 4 utility SNAPs 1370, and each utility SNAP 1370 is coupled to two other utility SNAPs 1370 in addition to the display SNAP 1310. The configurations depicted in FIGS. 13C-13D have a rotational symmetry such that a 90° rotation about the display moiety produces the same configuration. However, the configurations lack any uninterrupted planes of alignment between SNAPs, thereby increasing the resistance to bending or deformation of the SNAP complex structure (relative to the plane of the page for the orientation shown in FIGS. 13C-13D). Such rigidity may be useful for increasing the stability of larger arrays comprising multiple coupled nucleic acid nanostructure complexes. Maintaining planarity of a nucleic acid nanostructure capture face can be particularly advantageous for facilitating attachment of nucleic acid nanostructure complexes to a planar surface via the capture face and for maintaining the nucleic acid nanostructure complexes in a focal plane for subsequent optical detection. Substantially rigid structures may also have increased binding specificity and strength when contacted with a surface comprising complementary morphologies for the nucleic acid nanostructure complex capture faces. FIGS. 14A-14B depict a SNAP complex structure in three dimensions to demonstrate another example of symmetry. FIG. 14A depicts a SNAP complex comprising a central display SNAP 1420 coupled to four rectangular utility SNAPs 1410 comprising a top coupling face and a bottom coupling face. The SNAP comprises a rotational axis of symmetry through the center of the display SNAP 1420 but the overlapping of the rectangular SNAPs can resist bending or deformation of the SNAPs complex. FIG. 14B depicts a similar SNAP complex comprising four display SNAPs 1430 with a rotational axis of symmetry and overlapped top and bottom coupling faces on each display SNAP 1430.

A nucleic acid nanostructure complex (e.g., a SNAP complex), as set forth herein, may comprise at least one axis of symmetry or one plane of symmetry. A nucleic acid nanostructure complex may further comprise at least one uninterrupted plane of alignment. For example, the uninterrupted plane can be located between adjacent SNAPs and the uninterrupted plane can span the length of the SNAP complex. In some configurations, an axis of symmetry may comprise a rotational axis of symmetry or a reflection axis or plane of symmetry. In some configurations, a nucleic acid nanostructure complex may comprise a rotational axis of symmetry and a reflection axis or plane of symmetry. In other configurations, a nucleic acid nanostructure complex may comprise no axis or plane of symmetry. In some configurations, a nucleic acid nanostructure complex may comprise no uninterrupted planes of alignment. Again, the uninterrupted plane can be located between adjacent nucleic acid nanostructures and the uninterrupted plane can span the length of the nucleic acid nanostructure complex.

Figure 15A:
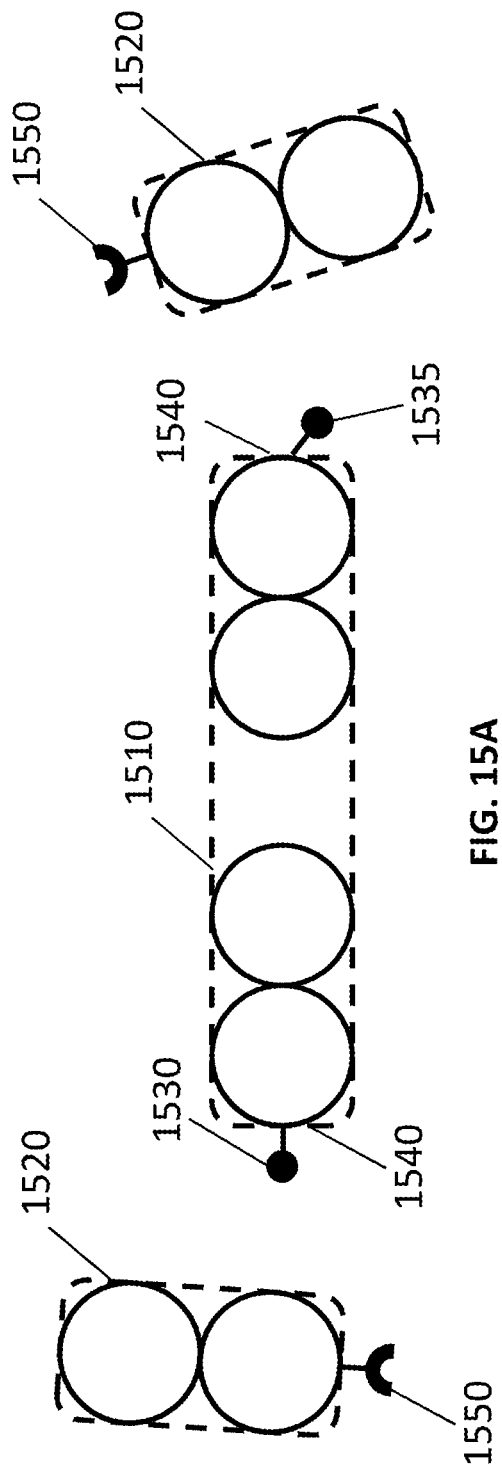
FIGS. 15A and 15B show different orientation of coupled SNAPs, in accordance with some embodiments.
Figure 15B:
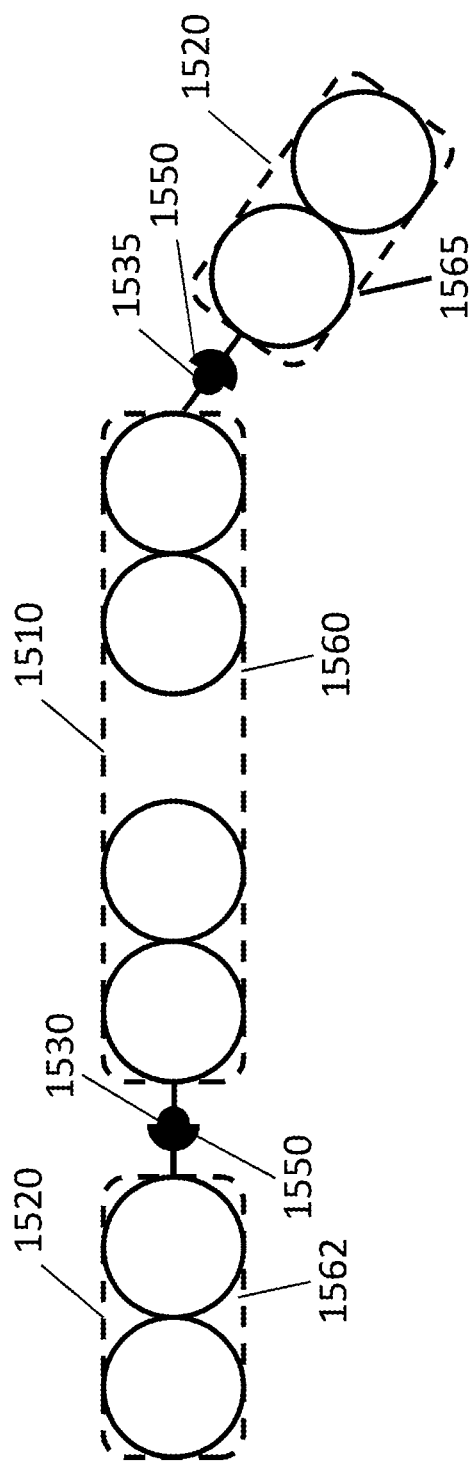

An orientation of a first nucleic acid nanostructure relative to a second nucleic acid nanostructure in a nucleic acid nanostructure complex (e.g., a SNAP complex) may be controlled. In some configurations, a first nucleic acid nanostructure may be oriented relative to a second nucleic acid nanostructure in a nucleic acid nanostructure complex such that a face (e.g., a capture face, a display face, a utility face) of the first nucleic acid nanostructure is substantially parallel or coplanar with a face (e.g., a capture face, a display face, a utility face) of the second nucleic acid nanostructure. In other configurations, a first nucleic acid nanostructure may be oriented relative to a second nucleic acid nanostructure in a nucleic acid nanostructure complex such that a face of the first nucleic acid nanostructure is not parallel or not coplanar with a face of the second nucleic acid nanostructure. The orientation between two nucleic acid nanostructures may be controlled, in part, by the ability to locate coupling moieties at specific nucleotides that comprise one or more tertiary structures of a nucleic acid nanostructure. FIG. 15A-15B depict orientation control utilizing the helical structure of DNA-based SNAPs. FIG. 15A illustrates a cross-sectional view of a first SNAP 1510 that is configured to be coupled to 2 second SNAPs 1520. The first SNAP 1510 comprises a plurality of helical tertiary structures comprising a first coupling group 1530 and a second coupling group 1535. The relative placement of the first coupling group 1530 on the helix orients the first coupling group 1530 nearly orthogonal to a first coupling face 1540. The relative placement of the second coupling group 1535 on the helix orients the second coupling group 1535 at a non-orthogonal angle relative to a second coupling face 1540. The second SNAPs 1520 comprise a plurality of helical tertiary structures comprising a complementary coupling group 1550. FIG. 15B illustrates the conformation of a SNAP complex formed by coupling of the 2 second SNAPs 1520 to the first SNAP 1510. Due to the relative orientation of the first coupling group 1530 and the second coupling group 1535, a bottom face 1560 of one of the second SNAPs 1520 is coplanar with a bottom face 1562 of the first SNAP, while a bottom face 1565 of the other second SNAP 1520 is not coplanar with bottom faces 1560 or 1562.

A nucleic acid nanostructure complex (e.g., a SNAP complex) may comprise a particular shape based upon a two-dimensional projection onto a surface, such as a square, rectangle, triangle, circle, cross, polygon, or an irregular shape. A nucleic acid nanostructure complex may be described in terms of a three-dimensional structure. A nucleic acid nanostructure complex may comprise a first nucleic acid nanostructure comprising a first conformation (e.g., substantially square faces) and a second nucleic acid nanostructure comprising a second conformation (e.g., substantially triangular faces, substantially rectangular faces, etc.). A nucleic acid nanostructure complex may comprise a first nucleic acid nanostructure and a second nucleic acid nanostructure where both nucleic acid nanostructures comprise substantially similar conformations (e.g., substantially square faces, substantially triangular faces, substantially rectangular faces, etc.). A nucleic acid nanostructure complex may comprise one or more conformations of nucleic acid nanostructures. A nucleic acid nanostructure complex may comprise at least about 1, 2, 3, 4, 5, 6, 7, 8, 9, 10, or more than 10 conformations of nucleic acid nanostructures. Alternatively or additionally, a nucleic acid nanostructure complex may comprise no more than about 10, 9, 8, 7, 6, 5, 4, 3, 2, or less than 2 conformations of nucleic acid nanostructures.

A nucleic acid nanostructure complex (e.g., a SNAP complex) may be coupled to, or configured to couple to, one or more analytes. A nucleic acid nanostructure complex may comprise one or more display moieties that are coupled to, or configured to couple to, one or more analytes. A nucleic acid nanostructure complex may comprise one or more display nucleic acid nanostructures that are coupled to, or configured to couple to, one or more analytes. A nucleic acid nanostructure complex may be coupled to a number of analyte molecules that is less than the number of display moieties in the nucleic acid nanostructure complex. For example, a nucleic acid nanostructure complex may only be coupled to a single analyte, or may be coupled to no analytes. In some configurations, a display moiety may be coupled to two or more analytes. In some configurations, two or more display moieties may be coupled to an analyte.

A nucleic acid nanostructure complex (e.g., a SNAP complex) may be configured to occupy a particular amount of surface area on a surface. A surface area occupied by a nucleic acid nanostructure complex may be measured as the effective surface area or footprint created by a two-dimensional projection of the nucleic acid nanostructure complex onto a surface. In some configurations, the effective surface area or footprint may further include surface area of a surface or interface that is excluded from associating with other molecules (nucleic acid nanostructure or non-nucleic acid molecules) due to effects such as steric exclusion or repulsion caused by the nucleic acid nanostructure complex. A nucleic acid nanostructure complex may have an effective surface area or footprint of at least about 25 $nm^2$, 100 $nm^2$, 500 $nm^2$, 1000 $nm^2$, 2000 $nm^2$, 3000 $nm^2$, 4000 $nm^2$, 5000 $nm^2$, 5500 $nm^2$, 6000 $nm^2$, 6500 $nm^2$, 7000 $nm^2$, 7500 $nm^2$, 8000 $nm^2$, 8500 $nm^2$, 9000 $nm^2$, 10000 $nm^2$, 15000 $nm^2$, 20000 $nm^2$, 25000 $nm^2$, 50000 $nm^2$, 100000 $nm^2$, 250000 $nm^2$, 500000 $nm^2$, or more than 1000000 $nm^2$. Alternatively or additionally, a nucleic acid nanostructure complex may have an effective surface area or footprint of no more than about 1000000 $nm^2$, 500000 $nm^2$, 250000 $nm^2$, 100000 $nm^2$, 50000 $nm^2$, 25000 $nm^2$, 20000 $nm^2$, 15000 $nm^2$, 10000 $nm^2$, 9000 $nm^2$, 8500 $nm^2$, 8000 $nm^2$, 7500 $nm^2$, 7000 $nm^2$, 6500 $nm^2$, 6000 $nm^2$, 5500 $nm^2$, 5000 $nm^2$, 4000 $nm^2$, 3000 $nm^2$, 2000 $nm^2$, 1000 $nm^2$, 500 $nm^2$, 100 $nm^2$, 25 $nm^2$, or less than 25 $nm^2$.

Figure 16A:
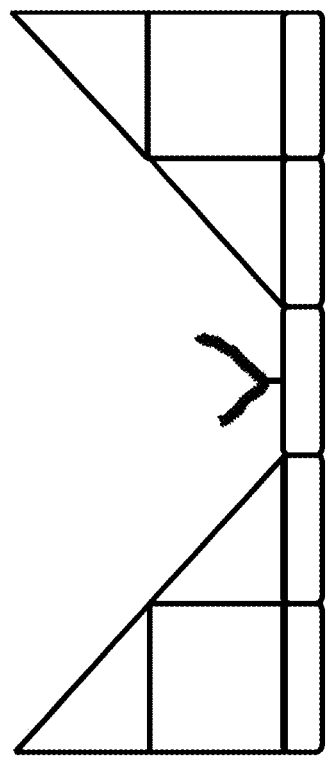
FIGS. 16A and 16B depict a three-dimensional SNAP complex, in accordance with some embodiments.
Figure 16B:
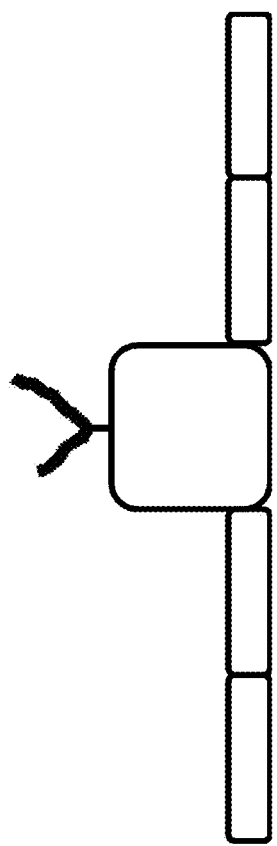

Nucleic acid nanostructure complexes (e.g., SNAP complexes) may comprise three-dimensional structures that improve the display of analytes. Analyte display may be improved by increasing the likelihood of detection and observation of an analyte, increasing the contact of analytes with probes or reagents, and/or decreasing negative interactions between analytes and other molecules. FIGS. 16A-16B depict cross-sectional views of various three-dimensional nucleic acid nanostructure complexes. FIG. 16A depicts a three-dimensional SNAP complex that forms a well-like structure around a central analyte. A well-like structure may be advantageous for affinity-based assay where the reduction in available volume around the analyte may decrease the ability of an affinity reagent to move away from the analyte. Additionally, surrounding utility SNAPs may comprise optical materials that increase the collection of light or decrease background signal, thereby improving the efficiency of optical detection methods. FIG. 16B depicts a three-dimensional SNAP complex that forms a post that elevates an analyte above a surface to which the SNAP complex is associated. An elevated analyte may be less likely to have unwanted interactions, for example with molecules that may non-specifically bind to the nucleic acid nanostructure complex. An elevated analyte may also be more accessible to a receptor that would otherwise experience steric hindrance, charge repulsion or other inhibitory interactions with the surface to which the nucleic acid nanostructure is attached.

Provided herein is a method of forming a nucleic acid nanostructure complex (e.g., a SNAP complex), comprising providing a display nucleic acid nanostructure and one or more capture nucleic acid nanostructures or utility nucleic acid nanostructures, where the display nucleic acid nanostructure comprises one or more coupling moieties, and where the capture nucleic acid nanostructures or utility nucleic acid nanostructures comprise one or more complementary coupling moieties, where the one or more complementary coupling moieties are configured to be coupled with the one or more coupling moieties, and coupling the display nucleic acid nanostructure to the one or more capture nucleic acid nanostructures or utility nucleic acid nanostructures by the coupling of the one or more coupling moieties to the one or more complementary coupling moieties, thereby forming a nucleic acid nanostructure complex, where the nucleic acid nanostructure complex comprises a display moiety that is configured to couple to an analyte, and where the nucleic acid nanostructure complex comprises a capture moiety that is configured to associate with a surface. A nucleic acid nanostructure complex may comprise a display nucleic acid nanostructure and/or a utility nucleic acid nanostructure comprising a capture moiety comprising a plurality of surface-interacting moieties.

A nucleic acid nanostructure complex (e.g., a SNAP complex) formation method may comprise the coupling of one or more coupling moieties to one or more complementary coupling moieties by forming a covalent bond. In some configurations, the covalent bond is formed by performing a click-type reaction. However, other coupling reactions and moieties can be used such as those set forth elsewhere herein. For example, a nucleic acid nanostructure complex formation method may comprise the coupling of the one or more coupling moieties to the one or more complementary coupling moieties by forming a non-covalent bond. In some configurations, forming a non-covalent bond comprises forming a nucleic acid base-pair hybridization. In some configurations, the one or more complementary coupling moieties comprise one or more oligonucleotides with complementary sequences to the set of one or more oligonucleotides. In some configurations, forming a non-covalent bond comprises forming a receptor-ligand complex such as a streptavidin-biotin complex.

A nucleic acid nanostructure complex (e.g., a SNAP complex) may be formed in a particular formation condition. A nucleic acid nanostructure complex may be formed in a fluidic medium. A condition may include a particular solvent, polarity, ionic strength or pH buffering condition. In some configurations, a display nucleic acid nanostructure or a utility nucleic acid nanostructure may be provided in a solution comprising a magnesium salt. In some configurations, coupling a display nucleic acid nanostructure to one or more utility nucleic acid nanostructures may occur in the presence of a surfactant. A nucleic acid nanostructure complex may be formed with a display nucleic acid nanostructure. A display nucleic acid nanostructure may be coupled to an analyte before or after forming a nucleic acid nanostructure complex. In some configurations, an analyte may be covalently coupled to a display moiety.

A nucleic acid nanostructure complex (e.g., a SNAP complex) may be formed under a particular temperature profile. For example, a first nucleic acid nanostructure may be combined with a second nucleic acid nanostructure at a first temperature, then the temperature may be altered (e.g., decreased, increased), thereby coupling the first nucleic acid nanostructure to the second nucleic acid nanostructure to form a nucleic acid nanostructure complex. A step in a nucleic acid nanostructure complex formation process may occur at a temperature of at least about 0° C., 5° C., 10° C., 15° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., or more than 95° C. Alternatively or additionally, a step in a nucleic acid nanostructure complex formation process may occur at a temperature of no more than about 95° C., 94° C., 93° C., 92° C., 91° C., 90° C., 89° C., 88° C., 87° C., 86° C., 85° C., 84° C., 83° C., 82° C., 81° C., 80° C., 79° C., 78° C., 77° C., 76° C., 75° C., 74° C., 73° C., 72° C., 71° C., 70° C., 69° C., 68° C., 67° C., 66° C., 65° C., 64° C., 63° C., 62° C., 61° C., 60° C., 59° C., 58° C., 57° C., 56° C., 55° C., 54° C., 53° C., 52° C., 51° C., 50° C., 49° C., 48° C., 47° C., 46° C., 45° C., 44° C., 43° C., 42° C., 41° C., 40° C., 39° C., 38° C., 37° C., 36° C., 35° C., 34° C., 33° C., 32° C., 31° C., 30° C., 29° C., 28° C., 27° C., 26° C., 25° C., 24° C., 23° C., 22° C., 21° C., 20° C., 15° C., 10° C., 5° C., 0° C., 0° C., or less than 0° C.

A nucleic acid nanostructure complex (e.g., a SNAP complex) may comprise portions that are fully structured and/or portions that are partially structured. A fully structured portion of a nucleic acid nanostructure complex may be defined as a region of a nucleic acid nanostructure complex that maintains each of primary, secondary, and tertiary structure during the course of use. A partially-structured portion of a nucleic acid nanostructure complex may be defined as a region of a nucleic acid nanostructure complex that comprises a primary structure but does not maintain a particular secondary and/or tertiary structure during the course of use. An example of a useful partially-structured portion is a pervious structure or region of a nucleic acid nanostructure. In some configurations, a partially-structured portion of a nucleic acid nanostructure complex may comprise a single-stranded nucleic acid. A single-stranded nucleic acid may be located between regions of double-stranded nucleic acid, or may comprise a pendant or terminal strand of nucleic acid. A single-stranded nucleic acid may comprise a sequence, composition or length exemplified herein for pendant nucleic acids or pendant moieties. In some configurations, a partially-structured portion of a nucleic acid nanostructure complex may comprise an amorphous structure, such as a globular structure (e.g., a nanoball, a dendrimer, etc.). FIG. 37B depicts a SNAP complex comprising a DNA origami SNAP 3710 that is coupled to two DNA nanoball SNAPs 3735 and an analyte 3720. The DNA nanoballs 3735 may be considered partially-structured due to their single-stranded, globular, and/or amorphous structure. Partially-structured regions of the SNAP complex may provide one or more functionalities to the SNAP 3710 such as, for example, increasing binding strength to targeted binding surfaces, decreasing binding strength to non-targeted surfaces, and prevent non-specific binding of other molecules to a SNAP face or a coupled analyte.

Nucleic Acid Compositions

Nucleic acids, such as nucleic acid nanostructures, SNAPs, nucleic acid nanostructure complexes, and/or components thereof (e.g., scaffolds, staples, multifunctional moieties, etc.), as set forth herein, may be stored, prepared, or utilized in a suitable solvent or buffer. The solvent or buffer may provide favorable conditions for promoting the stability of nucleic acids. The solvent or buffer may facilitate a process, such as contacting a nucleic acid (e.g., a nucleic acid nanostructure, SNAP, a complex thereof, or a component thereof) with a surface, or contacting a nucleic acid (e.g., a nucleic acid nanostructure, SNAP, a complex thereof, or a component thereof) with an analyte. In some configurations, a suitable DNA buffer may comprise a magnesium salt and/or EDTA. A nucleic acid may be disposed in a solvent or buffer that is configured to facilitate a wanted interaction (e.g., binding of a nucleic acid to a site of an array, etc.). A nucleic acid may be disposed in a solvent or buffer that is configured to inhibit an unwanted interaction (e.g., aggregation of a first nucleic acid with a second nucleic acid, etc.). An interaction of a nucleic acid (e.g., binding to a solid support, remaining in solution, etc.) may be facilitate by a presence of a chemical species, as set forth herein. For example, binding of a nucleic acid to a solid support surface may be mediated by a cationic species. In another example, a surfactant species may be included in a nucleic acid composition to prevent unwanted aggregation of nucleic acids, for example due to adhesion of a first nucleic acid to an analyte that is coupled to a second nucleic acid. A method, as set forth herein, may utilize a fluidic medium comprising one or more chemical species, as set forth herein. A method, as set forth herein, may comprise a step of altering a fluid medium, as set forth herein, for example by introducing or removing one or more chemical species from the fluidic medium. A method, as set forth herein, may comprise a step of exchanging a first fluidic medium, as set forth herein, for a second fluidic medium.

A solvent or buffer that is contacted with a nucleic acid (e.g., a nucleic acid nanostructure, SNAP, a complex thereof, or a component thereof) may comprise any of a variety of components, such as a solvent species, pH buffering species, a cationic species, an anionic species, a surfactant species, a denaturing species, or a combination thereof. A solvent species may include water, acetic acid, methanol, ethanol, n-propanol, isopropyl alcohol, n-butanol, formic acid, ammonia, propylene carbonate, nitromethane, dimethyl sulfoxide, acetonitrile, dimethylformamide, acetone, ethyl acetate, tetrahydrofuran, dichloromethane, chloroform, carbon tetrachloride, dimethyl ether, diethyl ether, 1-4, dioxane, toluene, benzene, cyclohexane, hexane, cyclopentane, pentane, or combinations thereof. A solvent or solution may include a buffering species including, but not limited to, MES, Tris, Bis-tris, Bis-tris propane, ADA, ACES, PIPES, MOPSO, MOPS, BES, TES, HEPES, HEPBS, HEPPSO, DIPSO, MOBS, TAPSO, TAPS, TABS, POPSO, TEA, EPPS, Tricine, Gly-Gly, Bicine, AMPD, AMPSO, AMP, CHES, CAPSO, CAPS, and CABS. A solvent or solution may include cationic species such as $Na^+$, $K^+$, $Ag^+$, $Cu^+$, $NH_4^+$, $Mg^{2+}$, $Ca^{2+}$, $Cu^{2+}$, $Cd^{2+}$, $Zn^{2+}$, $Fe^{2+}$, $CO^{2+}$, $Ni^{2+}$, $Cr^{2+}$, $Mn^{2+}$, $Ge^{2+}$, $Sn^{2+}$, $Al^{3+}$, $Cr^{3+}$, $Fe^{3+}$, $Co^{3+}$, $Ni^{3+}$, $Ti^{3+}$, $Mn^{3+}$, $Si^{4+}$, $V^{4+}$, $Ti^{4+}$, $Mn^{4+}$, $Ge^{4+}$, $Se^{4+}$, $V^{5+}$, $Mn^{5+}$, $Mn^{6+}$, $Se^{6+}$, and combinations thereof. A solvent or solution may include anionic species such as $F^-$, $Cl^-$, $Br^-$, $ClO_3^-$, $H_2PO_4^-$, $HCO_3^-$, $HSO_4^-$, $OH^-$, $I^-$, $NO_3^-$, $NO_2^-$, $MnO_4^-$, $SCN^-$, $CO_3^{2-}$, $CrO_4^{2-}$, $Cr_2O_7^{2-}$, $HPO_4^{2-}$, $SO_4^{2-}$, $SO_3^{2-}$, $PO_4^{3-}$, and combinations thereof. A solvent or solution may include a surfactant species including, but not limited to, stearic acid, lauric acid, oleic acid, sodium dodecyl sulfate, sodium dodecyl benzene sulfonate, dodecylamine hydrochloride, hexadecyltrimethylammonium bromide, polyethylene oxide, nonylphenyl ethoxylates, Triton X, pentapropylene glycol monododecyl ether, octapropylene glycol monododecyl ether, pentaethylene glycol monododecyl ether, octaethylene glycol monododecyl ether, lauramide monoethylamine, lauramide diethylamine, octyl glucoside, decyl glucoside, lauryl glucoside, Tween 20, Tween 80, n-dodecyl-o-D-maltoside, nonoxynol 9, glycerol monolaurate, polyethoxylated tallow amine, poloxamer, digitonin, zonyl FSO, 2,5-dimethyl-3-hexyne-2,5-diol, Igepal CA630, Aerosol-OT, triethylamine hydrochloride, cetrimonium bromide, benzethonium chloride, octenidine dihydrochloride, cetylpyridinium chloride, adogen, dimethyldioctadecylammonium chloride, CHAPS, CHAPSO, cocamidopropyl betaine, amidosulfobetaine-16, lauryl-N,N-(dimethylammonio)butyrate, lauryl-N,N-(dimethyl)-glycinebetaine, hexadecyl phosphocholine, lauryldimethylamine N-oxide, lauryl-N,N-(dimethyl)-propanesulfonate, 3-(1-pyridinio)-1-propanesulfonate, 3-(4-tert-butyl-1-pyridinio)-1-propanesulfonate, and combinations thereof. A solvent or solution may comprise a denaturing species including, but not limited to, acetic acid, trichloroacetic acid, sulfosalicylic acid, sodium bicarbonate, ethanol, ethylenediamine tetraacetic acid (EDTA), urea, guanidinium chloride, lithium perchlorate, sodium dodecyl sulfate, 2-mercaptoethanol, dithiothreitol, and tris(2-carboxyethyl) phosphine (TCEP).

A pH buffering species, cationic species, anionic species, surfactant species, or denaturing species may be present in a solvent composition at a concentration of at least about 0.0001M, 0.001M, 0.01M, 0.02M, 0.03M, 0.04M, 0.05M, 0.06M, 0.07M, 0.08M, 0.09M, 0.1M, 0.2M, 0.3M, 0.4M, 0.5M, 0.6M, 0.7M, 0.8M, 0.9M, 1M, 1.1M, 1.2M, 1.3M, 1.4M, 1.5M, 1.6M, 1.7M, 1.8M, 1.9M, 2M, 2.1M, 2.2M, 2.3M, 2.4M, 2.5M, 2.6M, 2.7M, 2.8M, 2.9M, 3M, 3.1M, 3.2M, 3.3M, 3.4M, 3.5M, 3.6M, 3.7M, 3.8M, 3.9M, 4M, 4.1M, 4.2M, 4.3M, 4.4M, 4.5M, 4.6M, 4.7M, 4.8M, 4.9M, 5M, 5.1M, 5.2M, 5.3M, 5.4M, 5.5M, 5.6M, 5.7M, 5.8M, 5.9M, 6M, 7M, 8M, 9M or more than 10M. Alternatively or additionally, a pH buffering species, cationic species, anionic species, surfactant species, or denaturing species may be present in a solvent or solution at a concentration of no more than about 10 M, 9M, 8M, 7M, 6M, 5.9M, 5.8M, 5.7M, 5.6M, 5.5M, 5.4M, 5.3M, 5.2M, 5.1M, 5.0M, 4.9M, 4.8M, 4.7M, 4.6M, 4.5M, 4.4M, 4.3M, 4.2M, 4.1M, 4.0M, 3.9M, 3.8M, 3.7M, 3.6M, 3.5M, 3.4M, 3.3M, 3.2M, 3.1M, 3.0M, 2.9M, 2.8M, 2.7M, 2.6M, 2.5M, 2.4M, 2.3M, 2.2M, 2.1M, 2.0M, 1.9M, 1.8M, 1.7M, 1.6M, 1.5M, 1.4M, 1.3M, 1.2M, 1.1M, 1.0M, 0.9M, 0.8M, 0.7M, 0.6M, 0.5M, 0.4M, 0.3M, 0.2M, 0.1M, 0.09M, 0.08M, 0.07M, 0.06M, 0.05M, 0.04M, 0.03M, 0.02M, 0.01M, 0.001M, 0.001M, or less than about 0.001M.

A pH buffering species, cationic species, anionic species, surfactant species, or denaturing species may be present in a solvent composition in a weight percentage of at least about 0.0001 weight percent (wt %), 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.02 wt %, 0.03 wt %, 0.04 wt %, 0.05 wt %, 0.06 wt %, 0.07 wt %, 0.08 wt %, 0.09 wt %, 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, 5 wt %, 6 wt %, 7 wt %, 8 wt %, 9 wt %, 10 wt %, or more than 10 wt %. Alternatively or additionally, a pH buffering species, cationic species, anionic species, surfactant species, or denaturing species may be present in a solvent or solution in a weight percentage of no more than about 10 wt %, 9 wt %, 8 wt %, 7 wt %, 6 wt %, 5 wt %, 4.9 wt %, 4.8 wt %, 4.7 wt %, 4.6 wt %, 4.5 wt %, 4.4 wt %, 4.3 wt %, 4.2 wt %, 4.1 wt %, 4.0 wt %, 3.9 wt %, 3.8 wt %, 3.7 wt %, 3.6 wt %, 3.5 wt %, 3.4 wt %, 3.3 wt %, 3.2 wt %, 3.1 wt %, 3.0 wt %, 2.9 wt %, 2.8 wt %, 2.7 wt %, 2.6 wt %, 2.5 wt %, 2.4 wt %, 2.3 wt %, 2.2 wt %, 2.1 wt %, 2.0 wt %, 1.9 wt %, 1.8 wt %, 1.7 wt %, 1.6 wt %, 1.5 wt %, 1.4 wt %, 1.3 wt %, 1.2 wt %, 1.1 wt %, 1.0 wt %, 0.9 wt %, 0.8 wt %, 0.7 wt %, 0.6 wt %, 0.5 wt %, 0.4 wt %, 0.3 wt %, 0.2 wt %, 0.1 wt %, 0.09 wt %, 0.08 wt %, 0.07 wt %, 0.06 wt %, 0.05 wt %, 0.04 wt %, 0.03 wt %, 0.02 wt %, 0.01 wt %, 0.009 wt %, 0.008 wt %, 0.007 wt %, 0.006 wt %, 0.005 wt %, 0.004 wt %, 0.003 wt %, 0.002 wt %, 0.001 wt %, 0.0001 wt %, or less than 0.0001 wt %.

A solvent or solution, having a nucleic acid (e.g., a nucleic acid nanostructure, SNAP, a complex thereof, or a component thereof), or other composition set forth herein, may be formulated to have a pH at a value or within a range of values. A solvent or solution may have a pH of at least about 0, 0.1, 0.2, 0.3, 0.4, 0.5, 0.6, 0.7, 0.8, 0.9, 1.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0 or more than about 14.0. Alternatively or additionally, a solvent or solution may have a pH of no more than about 14.0, 13.9, 13.8, 13.7, 13.6, 13.5, 13.4, 13.3, 13.2, 13.1, 13.0, 12.9, 12.8, 12.7, 12.6, 12.5, 12.4, 12.3, 12.2, 12.1, 12.0, 11.9, 11.8, 11.7, 11.6, 11.5, 11.4, 11.3, 11.2, 11.1, 11.0, 10.9, 10.8, 10.7, 10.6, 10.5, 10.4, 10.3, 10.2, 10.1, 10.0, 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0, or less than about 0.

A nucleic acid (e.g., a nucleic acid nanostructure, SNAP, a complex thereof, or a component thereof), as set forth herein, may be formed or modified at a particular temperature or temperature range. The temperature at which a nucleic acid is formed or modified may depend upon the components being used. For example, the addition of oligonucleotides to a SNAP structure may be limited by the melting temperature of certain oligonucleotides. In another example, a SNAP component that is conjugated by a click reaction may be added at a benign temperature, such as room temperature. In some configurations, a nucleic acid (e.g., a nucleic acid nanostructure, SNAP, a complex thereof, or a component thereof) may be formed in a single-step reaction (i.e., combining all necessary components) that requires multiple temperature changes (e.g., a melting temperature followed by a nucleic acid annealing temperature followed by a conjugation reaction temperature). In other configurations, a nucleic acid (e.g., a nucleic acid nanostructure, SNAP, a complex thereof, or a component thereof) may be formed in multiple steps, each with a unique temperature profile. A nucleic acid (e.g., a nucleic acid nanostructure, SNAP, a complex thereof, or a component thereof) formation process may occur at a temperature of at least about −100° C., −90° C., −80° C., −70° C., −60° C., −50° C., −40° C., −30° C., −20° C., −10° C., −5° C., 0° C., 4° C., 10° C., 15° C., 20° C., 25° C., 30° C., 35° C., 40° C., 45° C., 50° C., 55° C., 60° C., 65° C., 70° C., 75° C., 80° C., 90° C., or more than 90° C. Alternatively or additionally, a nucleic acid (e.g., a nucleic acid nanostructure, SNAP, a complex thereof, or a component thereof) formation process may occur at a temperature of no more than about 90° C., 80° C., 75° C., 70° C., 65° C., 60° C., 55° C., 50° C., 45° C., 40° C., 35° C., 30° C., 25° C., 20° C., 15° C., 10° C., 4° C., 0° C., −10° C., −20° C., −30° C., −40° C., −50° C., −60° C., −70° C., −80° C., −90° C., 100° C., or less than −100° C.

A nucleic acid (e.g., a nucleic acid nanostructure, SNAP, a complex thereof, or a component thereof), as set forth herein, may be stored in a suitable storage medium (e.g., a storage buffer). A nucleic acid may be stored at a temperature that keeps a storage medium in a liquid state. A nucleic acid may be stored at a temperature that causes a storage medium to freeze into a solid state. A nucleic acid may be stored before or after an analyte (e.g., a polypeptide) has been coupled to the nucleic acid. A nucleic acid may be stored at a temperature in one or more of the ranges set forth above for formation of a nucleic acid nanostructure.

A nucleic acid (e.g., a nucleic acid nanostructure, SNAP, a complex thereof, or a component thereof), as set forth herein, may remain stable during storage. Stability may be indicated by a nucleic acid activity after storage relative to a pre-storage baseline, such as ability to couple an analyte (e.g., a polypeptide), ability to couple with another nucleic acid, or ability to associate with a surface or interface. A nucleic acid may be stabilized against aggregation or sedimentation by the presence of a surfactant or detergent species. A nucleic acid may be stabilized against degradation, such as oxidation, by the presence of anti-oxidants or radical scavengers. A SNAP may be stable when stored for a period of at least about 1 hr, 6 hrs, 12 hrs, 1 day, 2 days, 3 days, 1 wk, 2 wks, 3 wks, 4 wks, 1 mth, 2 mths, 3 mths, 4 mths, 5 mths, 6 mths, 9 mths, 1 yr, 2 yrs, 3 yrs, 4 yrs, 5 yrs, 10 yrs, or more than 10 yrs. Alternatively or additionally, a nucleic acid may be stable when stored for a period of no more than about 10 yrs, 5 yrs, 4 yrs, 3 yrs, 2 yrs, 1 yrs, 9 mths, 6 mths, 5 mths, 4 mths, 3 mths, 2 mths, 1 mth, 4 wks, 3 wks, 2 wks, 1 wk, 3 days, 2 days, 1 day, 12 hrs, 6 hrs, 1 hr, or less than 1 hr.

A nucleic acid, as set forth herein, may be provided as a component of a kit. A kit may comprise a nucleic acid, as set forth herein, that is configured to be coupled to an analyte of interest. A kit may be provided with a nucleic acid, as set forth herein, or a plurality thereof. A collection kit may be specific to a particular assay to be performed on the sample. For example, a collection kit for a polypeptide assay may include polypeptide-specific reagents to protect and/or preserve polypeptides within a sample. A collection kit may include one or more sample vessels, one or more reagents, instructions for use of the sample collection kit and optionally intermediate sample vessels, a sealant for the vessel(s), a label for the vessel(s) such as a barcode or radio frequency identification device (RFID), or packaging for transport and/or storage of the sample vessel(s). A kit may include one or more reagents for any of a variety of purposes, including sample preservation, sample stability, sample quality control, processing and/or purification, and sample storage. A kit may include reagents such as buffers, acids, bases, solvents, denaturants, surfactants, detergents, reactants, labels (e.g., fluorophores, radiolabels), indicator dyes, enzymes, enzyme inhibitors, oxygen scavengers, water scavengers, humectants, affinity reagents (e.g., antibodies), or other capture agents (e.g., biotinylated particles). A kit may include one or more reagents in liquid or solid form. A kit may include one or more separate reagents and/or internal standards that are added to a sample vessel before or after sample preparation. A kit may include one or more reagents and/or internal standards that are provided within a sample collection vessel. For example, reagents and/or internal standards may be provided in a crystallized or coated form on a surface of a collection vessel, or may be in a liquid solution within the collection vessel. In some configurations, a kit may further comprise an array or solid support, as set forth herein. An array or solid support may be provided in a kit with one or more nucleic acids present within or deposited on the array or solid support.

A kit for an assay or other process may be utilized according to a provided set of instructions. The instructions may be directed to use of nucleic acids in accordance with teachings set forth herein. A kit may provide instructions for coupling an analyte of interest to a nucleic acid, for example by a method as set forth herein. A kit may provide instructions for depositing a nucleic acid, as set forth herein, or a nucleic acid coupled to an analyte of interest, to an array or solid support, as set forth herein. A kit may be utilized by a technician or self-collecting subject. A technician utilizing a kit may be specifically trained in the proper utilization of the kit. A kit protocol may employ one or more intermediate steps before preparation of a sample is complete. Intermediate steps during sample preparation may be performed in a vessel or in a separate medium (provided with the kit or provided by the collector). For example, a blood sample may be fractionated by a phlebotomist, with only the red blood cell or plasma fraction saved for preparation. A kit may include indicator dyes, litmus strips, or other methods of confirming successful sample collection and/or preparation. A kit may include a sealant (e.g., an adhesive or sticker) to ensure that a sample has not been tampered with or damaged during storage or transport. A kit may include a label for sample tracking by the collector or the analysis facility. A label for a vessel may include a serial number, RFID, bar code or QR code. A label for a vessel may be pre-printed or pre-applied to a vessel, or may be placed by a collector.

Methods of Nucleic Acid Fabrication

Nucleic acids (e.g., a nucleic acid nanostructure, SNAP, a complex thereof, or a component thereof) as described in the present disclosure may be fabricated by a suitable method. Fabrication of a nucleic acid may comprise one or more of the steps of: 1) providing a scaffold nucleic acid strand that is configured to couple a plurality of oligonucleotides; 2) providing a plurality of oligonucleotides that are configured to couple to the scaffold strand; 3) providing one or more additional oligonucleotides that are configured to couple to the scaffold nucleic acid strand or other oligonucleotides; 4) providing one or more oligonucleotides that are configured to couple to the scaffold nucleic acid strand and are further configured to couple to an analyte; 5) providing one or more oligonucleotides that are configured to couple to the scaffold nucleic acid strand and are coupled to an analyte; 6) providing one or more oligonucleotides that are configured to couple to the scaffold nucleic acid strand and are further configured to couple to a surface; 7) annealing the scaffold nucleic acid strand to a plurality of oligonucleotides to form a SNAP; 8) annealing the scaffold strand to an oligonucleotide that is configured to couple to an analyte; 9) annealing the scaffold strand to an oligonucleotide that is coupled to an analyte; 10) annealing the scaffold strand to an oligonucleotide that is configured to couple to a surface; and 11) forming one or more couplings or cross-links between two or more oligonucleotides of the nucleic acid.

Fabrication of detectable probes comprising nucleic acid retaining components (e.g., DNA origami, DNA nanoballs) may be formed by conventional techniques. DNA nanoballs may be fabricated by a method such as rolling circle amplification to generate a scaffold strand that may be further modified to couple or conjugate a plurality of binding components and/or detectable labels. Exemplary methods for making nucleic acid nanoballs are described, for example, in U.S. Pat. No. 8,445,194, which is incorporated herein by reference. Nucleic acid retaining components comprising sections of double-stranded DNA (e.g., DNA origami) may be fabricated, for example, using techniques described in Rothemund, Nature 440:297-302 (2006) and U.S. Pat. Nos. 8,501,923 and 9,340,416, each of which is incorporated herein by reference. A retaining component may be formed by a scaffold strand that is hybridized with additional oligonucleotides.

Figure 36A:
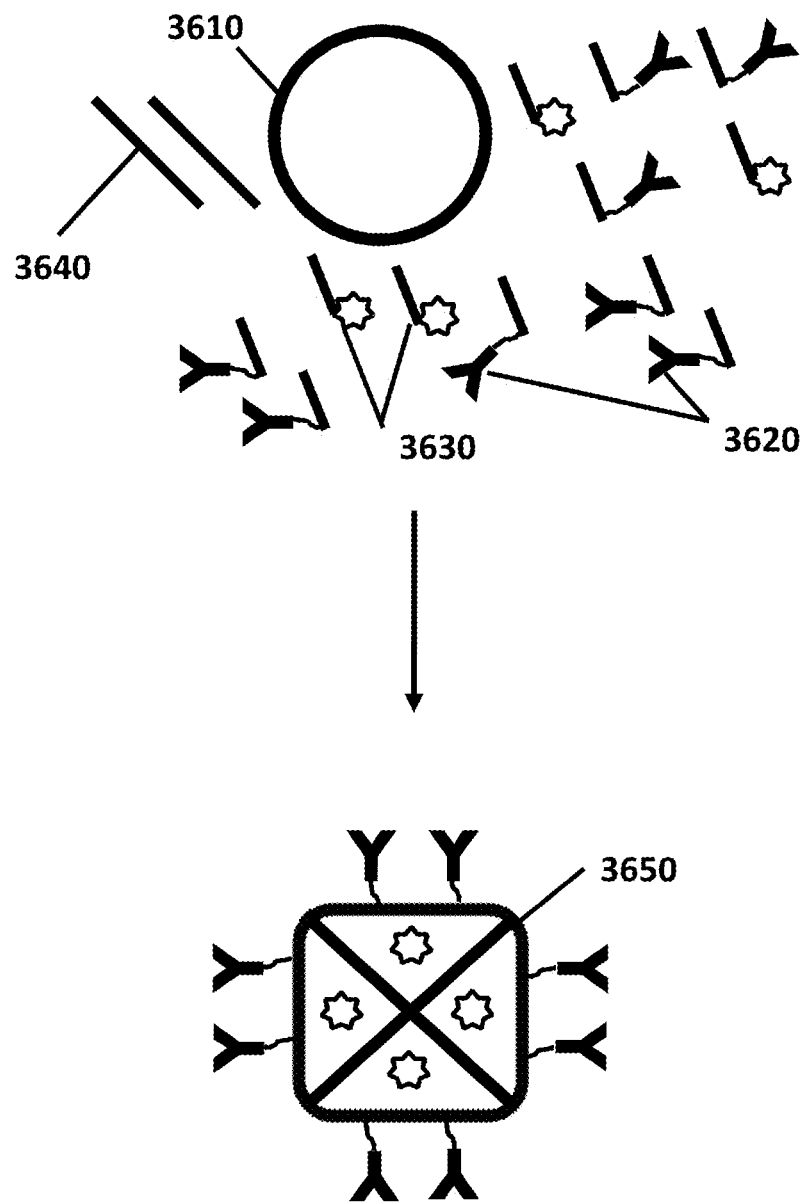
FIGS. 36A and 36B illustrate a scheme for producing SNAPs, in accordance with some embodiments.

FIG. 36A shows a first pathway to forming a SNAP comprising a DNA origami that is coupled to a plurality of analytes and a plurality of detectable labels. Oligonucleotides with coupled or conjugated analytes 3620 and oligonucleotides with conjugated detectable labels 3630 are prepared before the retaining component is assembled. The oligonucleotides with conjugated binding components 3620 and oligonucleotides with coupled or conjugated detectable labels 3630 are contacted with a single-stranded scaffold 3610 (e.g., M13 phage DNA, single-stranded plasmid DNA) and additional structural nucleic acids 3640. The nucleic acids are contacted in a suitable DNA buffer at an elevated temperature (e.g., at least about 50° C., 55° C., 60° C., 65° C., 70° C., 75° C., 80° C., 85° C., 90° C., or about 95° C.), then cooled. Oligonucleotides will hybridize to the scaffold strand 3610 at the appropriate sequence-dependent positions to form a SNAP-analyte conjugate 3650. The number of analytes coupled to a SNAP may be controlled by using fewer or greater numbers of oligonucleotides that are coupled to analytes or are configured to be coupled to analytes, or by altering a sequence of a scaffold strand.

Figure 36B:
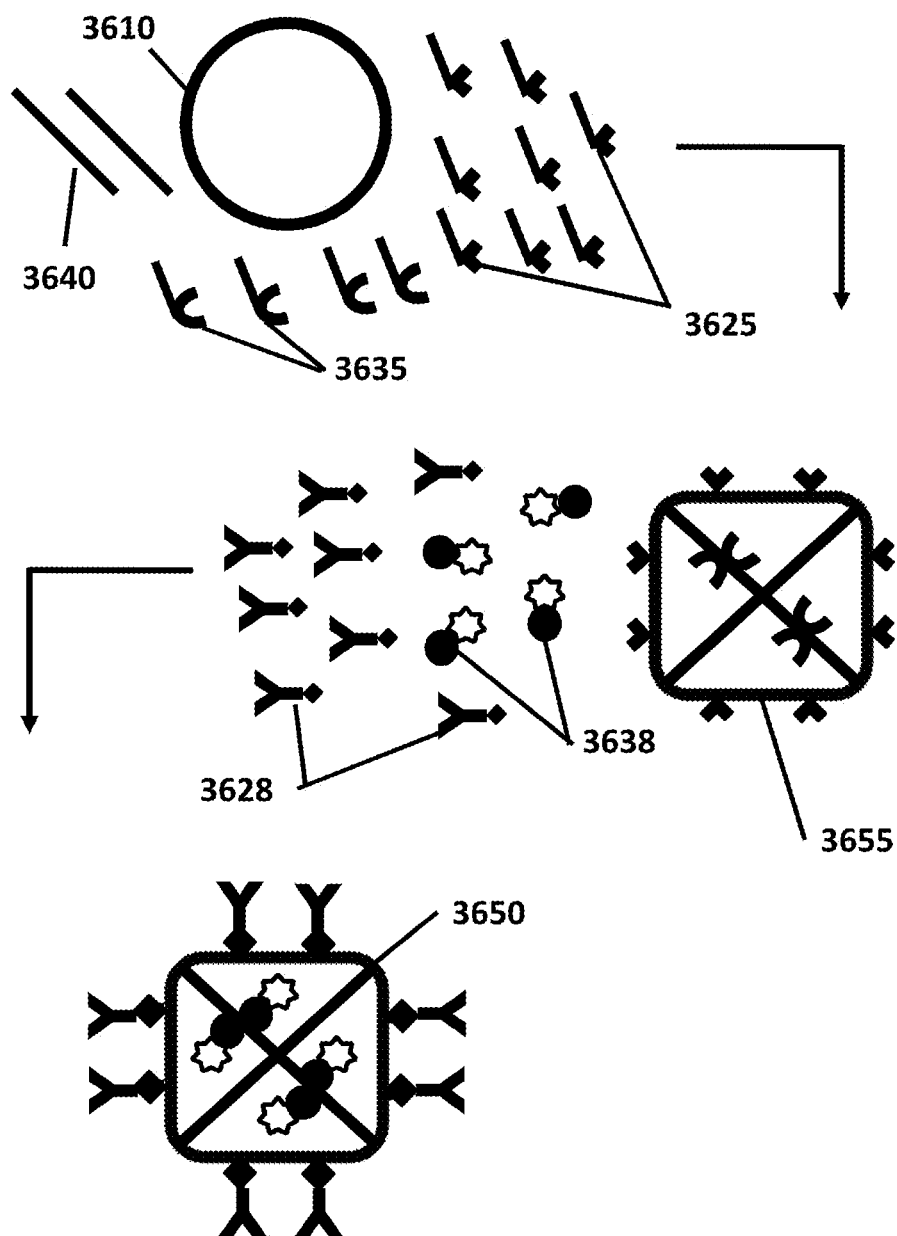

FIG. 36B shows an alternative pathway to forming a SNAP with a plurality of coupled analytes and a plurality of detectable labels. Oligonucleotides with handles that are configured to couple or conjugate analytes 3625 and oligonucleotides with moieties that are configured to couple or conjugate detectable labels 3635 are prepared before the retaining component is assembled. The oligonucleotides with moieties that are configured to conjugate analytes 3625 and oligonucleotides with moieties that are configured to couple or conjugate detectable labels 3635 are contacted with a single-stranded scaffold 3610 (e.g., M13 phage DNA, plasmid DNA) and additional structural nucleic acids 3640. The nucleic acids are contacted in a suitable DNA buffer at an elevated temperature (e.g., at least about 50° C., 55° C., 60° C., 65° C., 70° C., 75° C., 80° C., 85° C., 90° C., or about 95° C.), then cooled. After cooling, a SNAP 3655 that is configured to bind a plurality of analytes and/or label components is formed. The retaining component 3655 is contacted with a plurality of analytes 3628 and/or label components 3638 that have complementary moieties to the moieties on the SNAP 3655 in a suitable conjugation buffer. After coupling or conjugation of the plurality of analytes 3628 and/or the plurality of label components 3638, a SNAP-analyte conjugate 3650 is formed.

In some configurations, a detectable nucleic acid (e.g., a nucleic acid nanostructure, a SNAP), as set forth herein, may be formed by the coupling or conjugation of an analyte and/or a label component by the reaction of a reactive group configured to form a bond with another molecule or group, e.g., a bioorthogonal reaction or click-type chemistry (see, for example, U.S. Pat. Nos. 6,737,236 and 7,427,678, each incorporated herein by reference in its entirety); azide alkyne Huisgen cycloaddition reactions, which use a copper catalyst (see, for example, U.S. Pat. Nos. 7,375,234 and 7,763,736, each incorporated herein by reference in its entirety); Copper-free Huisgen reactions ("metal-free click") using strained alkynes or triazine-hydrazine moieties which can link to aldehyde moieties (see, for example, U.S. Pat. No. 7,259,258, which is incorporated by reference); triazine chloride moieties which can link to amine moieties; carboxylic acid moieties which can link to amine moieties using a coupling reagent, such as EDC; thiol moieties which can link to thiol moieties; alkene moieties which can link to dialkene moieties that are coupled through Diels-Alder reactions; and acetyl bromide moieties which can link to thiophosphate moieties (see, for example, WO 2005/065814, which is incorporated by reference). A reactive handle may comprise a functional group that is configured to react via a click reaction (e.g., metal-catalyzed azide-alkyne cycloaddition, strain-promoted azide-alkyne cycloaddition, strain-promoted azide-nitrone cycloaddition, strained alkene reactions, thiol-ene reaction, Diels-Alder reaction, inverse electron demand Diels-Alder reaction, [3+2] cycloaddition, [4+1] cycloaddition, nucleophilic substitution, dihydroxylation, thiol-yne reaction, photoclick, nitrone dipole cycloaddition, norbornene cycloaddition, oxanobomadiene cycloaddition, tetrazine ligation, tetrazole photoclick reactions). Exemplary silane-derivative CLICK-type reactants may include alkenes, alkynes, azides, epoxides, amines, thiols, nitrones, isonitriles, isocyanides, aziridines, activated esters, and tetrazines (e.g., dibenzocyclooctyne-azide, methyltetrazine—transcyclooctylene, epoxide—thiol, etc.). A click-type reaction may provide an advantageous method of rapidly forming a bond under benign conditions (e.g., room temperature, aqueous solvents). In some configurations, a SNAP may comprise cross-linking molecules that are form bonds that irreversibly couple a first SNAP component to a second SNAP component. Cross-linking molecules may include chemical cross-linking molecules and photo-initiated cross-linking molecules.

In some configurations, a nucleic acid or other component of a nucleic acid may include different species of reactive groups. The use of different reactive groups can provide a level of control over the number and location of different components that will be coupled or conjugated to the nucleic acid. In particular configurations the different reactive groups demonstrate orthogonal reactivity, whereby a first component has a moiety that is reactive for a first reactive handle (i.e. reactive moiety) on the probe but not substantially reactive with a second reactive handle on the probe, and whereby a second component has a moiety that is reactive for the second reactive handle but not the first reactive handle. Accordingly, the number of different analytes and their locations can be adjusted by appropriate use of orthogonal reactive handles on a detectable probe or the number of different label components and their locations can be adjusted by appropriate use of orthogonal reactive handles on a detectable probe. Moreover, analytes can be located differently from label components on a nucleic acid by appropriate use of orthogonal reactive handles, respectively, on the nucleic acid.

Following synthesis of a nucleic acid (e.g., a nucleic acid nanostructure, SNAP, a complex thereof, or a component thereof), as set forth herein, formed structures may be purified by one or more additional processes. A nucleic acid may undergo one or more separation processes to remove unwanted components, such as one or more of: 1) uncoupled oligonucleotides; 2) uncoupled analytes; 3) uncoupled modifying groups; 4) buffer components; 5) partially-formed nucleic acids; 6) misformed nucleic acids; and 7) excess nucleic acids. A nucleic acid may undergo a dilution or concentration process to adjust a concentration of a nucleic acid containing solution. Nucleic acids may be separated from unwanted components by any suitable method, including without limitation, for example high-pressure liquid chromatography (HPLC), size-exclusion chromatography (SEC), affinity chromatography, ultracentrifugation, osmosis, reverse osmosis, and ultrafiltration. In some configurations, a separation may be performed on a separation medium (e.g., a chromatography column) that is not specified for nucleic acids separation. In some configurations, a separation may be performed on a separation medium (e.g., a chromatography column) that is not specified for the expected hydrodynamic size range of the separated nucleic acids.

Polypeptide Assays

The present disclosure provides systems, compositions, and methods for forming particles that are useful for coupling single analytes. The present disclosure further provides systems, compositions, and methods for forming single-analyte arrays that are useful when performing various single-analyte assays, including assays of biological analytes (e.g., genomics, transcriptomics, proteomics, metabolomics, etc.) and non-biological analytes (e.g., carbon nanoparticles, inorganic nanoparticles, etc.). In some configurations, the provided single-analyte arrays may be especially useful for single-polypeptide proteomic assays such as, for example affinity reagent-based characterization assays (e.g., fluorescence-based or barcode-based affinity binding characterizations) or peptide sequencing assays (e.g., Edman-type degradation fluorosequencing or affinity reagent-based assays).

The present disclosure further provides methods for detecting one or more polypeptide (e.g., sample polypeptide, standard polypeptide etc.) or polypeptide product (e.g. sample polypeptide composite, standard polypeptide composite, etc.). A polypeptide can be detected using one or more probes having known binding affinity for the polypeptide. The probe and/or the polypeptide can be bound to form a complex and then formation of the complex can be detected. The complex can be detected directly, for example, due to a label that is present on the probe or polypeptide. In some configurations the complex need not be directly detected, for example, in formats where the complex is formed and then the probe, polypeptide, or a tag or label component that was present in the complex is then detected.

In some detection assays, a protein can be cyclically modified and the modified products from individual cycles can be detected. In some configurations, a protein can be sequenced by a sequential process in which each cycle includes steps of labeling and removing the amino terminal amino acid of a protein and detecting the label. Accordingly, a method of detecting a protein can include steps of (i) exposing a terminal amino acid on the protein; (ii) detecting a change in signal from the protein; and (iii) identifying the type of amino acid that was removed based on the change detected in step (ii). The terminal amino acid can be exposed, for example, by removal of one or more amino acids from the amino terminus or carboxyl terminus of the protein. Steps (i) through (iii) can be repeated to produce a series of signal changes that is indicative of the sequence for the protein.

In a first configuration of the above method, one or more types of amino acids in the protein can be attached to a label that uniquely identifies the type of amino acid. In this configuration, the change in signal that identifies the amino acid can be loss of signal from the respective label. Exemplary compositions and techniques that can be used to remove amino acids from a protein and detect signal changes are those set forth in Swaminathan et al., *Nature Biotech.* 36:1076-1082 (2018); or U.S. Pat. No. 9,625,469 or 10,545,153, each of which is incorporated herein by reference. Methods and apparatus under development by Erisyon, Inc. (Austin, TX) may also be useful for detecting proteins.

In a second configuration of the above method, the terminal amino acid of the protein can be recognized by an affinity agent that is specific for the terminal amino acid or specific for a label moiety that is present on the terminal amino acid. The affinity agent can be detected on the array, for example, due to a label on the affinity agent. Optionally, the label is a nucleic acid barcode sequence that is added to a primer nucleic acid upon formation of a complex. The formation of the complex and identity of the terminal amino acid can be determined by decoding the barcode sequence. Exemplary affinity agents and detection methods are set forth in U.S. Pat. App. Pub. No. 2019/0145982 A1; 2020/0348308 A1; or 2020/0348307 A1, each of which is incorporated herein by reference. Methods and apparatus under development by Encodia, Inc. (San Diego, CA) may also be useful for detecting proteins.

Cyclical removal of terminal amino acids from a protein can be carried out using an Edman-type sequencing reaction in which a phenyl isothiocyanate reacts with a N-terminal amino group under mildly alkaline conditions (e.g., about pH 8) to form a cyclical phenylthiocarbamoyl Edman complex derivative. The phenyl isothiocyanate may be substituted or unsubstituted with one or more functional groups, linker groups, or linker groups containing functional groups. An Edman-type sequencing reaction can include variations to reagents and conditions that yield a detectable removal of amino acids from a protein terminus, thereby facilitating determination of the amino acid sequence for a protein or portion thereof. For example, the phenyl group can be replaced with at least one aromatic, heteroaromatic or aliphatic group which may participate in an Edman-type sequencing reaction, non-limiting examples including: pyridine, pyrimidine, pyrazine, pyridazoline, fused aromatic groups such as naphthalene and quinoline), methyl or other alkyl groups or alkyl group derivatives (e.g., alkenyl, alkynyl, cyclo-alkyl). Under certain conditions, for example, acidic conditions of about pH 2, derivatized terminal amino acids may be cleaved, for example, as a thiazolinone derivative. The thiazolinone amino acid derivative under acidic conditions may form a more stable phenylthiohydantoin (PTH) or similar amino acid derivative which can be detected. This procedure can be repeated iteratively for residual protein to identify the subsequent N-terminal amino acid. Many variations of Edman-type degradation have been described and may be used including, for example, a one-step removal of an N-terminal amino acid using alkaline conditions (Chang, J. Y., *FEBS LETTS.,* 1978, 91 (1), 63-68). In some cases, Edman-type reactions may be thwarted by N-terminal modifications which may be selectively removed, for example, N-terminal acetylation or formylation (e.g., see Gheorghe M. T., Bergman T. (1995) in *Methods in Protein Structure Analysis*, Chapter 8: Deacetylation and internal cleavage of Proteins for N-terminal Sequence Analysis. Springer, Boston, MA.

Non-limiting examples of functional groups for substituted phenyl isothiocyanate may include ligands (e.g. biotin and biotin analogs) for known receptors, labels such as luminophores, or reactive groups such as click functionalities (e.g. compositions having an azide or acetylene moiety). The functional group may be a DNA, RNA, peptide or small molecule barcode or other tag which may be further processed and/or detected.

The removal of an amino terminal amino acid using Edman-type processes utilizes at least two main steps, the first step includes reacting an isothiocyanate or equivalent with protein N-terminal residues to form a relatively stable Edman complex, for example, a phenylthiocarbamoyl complex. The second step includes removing the derivatized N-terminal amino acid, for example, via heating. The protein, now having been shortened by one amino acid, may be detected, for example, by contacting the protein with a labeled affinity agent that is complementary to the amino terminus and examining the protein for binding to the agent, or by detecting loss of a label that was attached to the removed amino acid.

Edman-type processes can be carried out in a multiplex format to detect, characterize or identify a plurality of proteins. A method of detecting a protein can include steps of (i) exposing a terminal amino acid on a protein at an address of an array; (ii) binding an affinity agent to the terminal amino acid, where the affinity agent comprises a nucleic acid tag, and where a primer nucleic acid is present at the address; (iii) extending the primer nucleic acid, thereby producing an extended primer having a copy of the tag; and (iv) detecting the tag of the extended primer. The terminal amino acid can be exposed, for example, by removal of one or more amino acids from the amino terminus or carboxyl terminus of the protein. Steps (i) through (iv) can be repeated to produce a series of tags that is indicative of the sequence for the protein. The method can be applied to a plurality of proteins on the array and in parallel. Whatever the plexity, the extending of the primer can be carried out, for example, by polymerase-based extension of the primer, using the nucleic acid tag as a template. Alternatively, the extending of the primer can be carried out, for example, by ligase- or chemical-based ligation of the primer to a nucleic acid that is hybridized to the nucleic acid tag. The nucleic acid tag can be detected via hybridization to nucleic acid probes (e.g., in an array), amplification-based detections (e.g. PCR-based detection, or rolling circle amplification-based detection) or nuclei acid sequencing (e.g. cyclical reversible terminator methods, nanopore methods, or single molecule, real time detection methods). Exemplary methods that can be used for detecting proteins using nucleic acid tags are set forth in U.S. Pat. App. Pub. No. 2019/0145982 A1; 2020/0348308 A1; or 2020/0348307 A1, each of which is incorporated herein by reference.

Polypeptides can also be detected based on their enzymatic or other biological activity. For example, a polypeptide can be contacted with a reactant that is converted to a detectable product by an enzymatic activity of the polypeptide. In other assay formats, a first polypeptide having a known enzymatic function can be contacted with a second polypeptide to determine if the second polypeptide changes the enzymatic function of the first polypeptide. As such, the first polypeptide serves as a reporter system for detection of the second polypeptide. Exemplary changes that can be observed include, but are not limited to, activation of the enzymatic function, inhibition of the enzymatic function, degradation of the first polypeptide or competition for a reactant or cofactor used by the first polypeptide.

The presence or absence of post-translational modifications (PTM) can be detected using a composition, apparatus or method set forth herein. A PTM can be detected using an affinity agent that recognizes the PTM or based on a chemical property of the PTM. Exemplary PTMs that can be detected, identified or characterized include, but are not limited to, myristoylation, palmitoylation, isoprenylation, prenylation, farnesylation, geranylgeranylation, lipoylation, flavin moiety attachment, Heme C attachment, phosphopantetheinylation, retinylidene Schiff base formation, dipthamide formation, ethanolamine phosphoglycerol attachment, hypusine, beta-Lysine addition, acylation, acetylation, deacetylation, formylation, alkylation, methylation, C-terminal amidation, arginylation, polyglutamylation, polyglyclyation, butyrylation, gamma-carboxylation, glycosylation, glycation, polysialylation, malonylation, hydroxylation, iodination, nucleotide addition, phosphoate ester formation, phosphoramidate formation, phosphorylation, adenylylation, uridylylation, propionylation, pyrolglutamate formation, S-glutathionylation, S-nitrosylation, S-sulfenylation, S-sulfinylation, S-sulfonylation, succinylation, sulfation, glycation, carbamylation, carbonylation, isopeptide bond formation, biotinylation, carbamylation, oxidation, reduction, pegylation, ISGylation, SUMOylation, ubiquitination, neddylation, pupylation, citrullination, deamidation, elminylation, disulfide bridge formation, proteolytic cleavage, isoaspartate formation, racemization, and protein splicing.

PTMs may occur at particular amino acid residues of a protein. For example, the phosphate moiety of a particular proteoform can be present on a serine, threonine, tyrosine, histidine, cysteine, lysine, aspartate or glutamate residue of the protein. In other examples, an acetyl moiety can be present on the N-terminus or on a lysine; a serine or threonine residue can have an O-linked glycosyl moiety; an asparagine residue can have an N-linked glycosyl moiety; a proline, lysine, asparagine, aspartate or histidine amino acid can be hydroxylated; an arginine or lysine residue can be methylated; or the N-terminal methionine or at a lysine amino acid can be ubiquitinated.

Polypeptides can also be detected based on their binding interactions with other molecules such as polypeptides (e.g., with or without post translational modifications), nucleic acids, nucleotides, metabolites, small molecules that participate in biological signal transduction pathways, biological receptors or the like. For example, a polypeptide that participates in a signal transduction pathway can be identified by detecting binding of the polypeptide with a second polypeptide that is known to be its binding partner in the pathway. Generally, a target polypeptide can be conjugated to a SNAP or SNAP complex and then contacted with a probe polypeptide, or other probe molecule, that is known to have affinity for the polypeptide. The target polypeptide can be identified based on observed binding by the probe molecule or lack of binding by the probe molecule. The probe molecule can optionally be labeled using labels set forth herein or known in the art.

In some configurations of the polypeptide detection methods set forth herein, the polypeptides can be detected on a solid support. For example, polypeptides can be attached to a support, the support can be contacted with probes in solution, the probes can interact with the polypeptides, thereby producing a detectable signal, and then the signal can be detected to determine the presence of the polypeptides. In multiplexed versions of this approach, different polypeptides can be attached to different addresses in an array, and the probing and detection steps can occur in parallel. In another example, probes can be attached to a solid support, the support can be contacted with polypeptides in solution, the polypeptides can interact with the probes, thereby producing a detectable signal, and then the signal can be detected to determine the presence of the polypeptides. This approach can also be multiplexed by attaching different probes to different addresses of an array. Polypeptides can be attached to a support via conjugation to SNAPs or SNAP complexes. For example, a plurality of polypeptides can be conjugated to a plurality of SNAPs or SNAP complexes, such that each polypeptide-conjugated SNAP or SNAP complex forms an address in the array. In yet another approach, polypeptides can be detected using mass spectrometry methods. Several exemplary detection methods are set forth below and elsewhere herein. It will be understood that other detection methods can also be used.

Typical polypeptide detection methods, such as enzyme linked immunosorbent assay (ELISA), achieve high-confidence characterization of one or more polypeptide in a sample by exploiting high specificity binding of antibodies, aptamers or other binding reagents to the polypeptide(s) and detecting the binding event while ignoring all other polypeptides in the sample. ELISA is generally carried out at low plex scale (e.g. from one to several hundred different polypeptides detected in parallel or in succession) but can be used at higher plexity. One or more polypeptides can be conjugated to one or more SNAPs or SNAP complexes and the conjugated polypeptide(s) can be detected using ELISA.

ELISA methods can be carried out by detecting immobilized binding reagents and/or polypeptides in multiwell plates, detecting immobilized binding reagents and/or polypeptides on arrays, or detecting immobilized binding reagents and/or polypeptides on particles in microfluidic devices. Exemplary plate-based methods include, for example, the MULTI-ARRAY technology commercialized by MesoScale Diagnostics (Rockville, Maryland) or Simple Plex technology commercialized by Protein Simple (San Jose, CA). Exemplary array-based methods include, but are not limited to those utilizing Simoa® Planar Array Technology or Simoa® Bead Technology, commercialized by Quanterix (Billerica, MA). Further exemplary array-based methods are set forth in U.S. Pat. Nos. 9,678,068; 9,395,359; 8,415,171; 8,236,574; or 8,222,047, each of which is incorporated herein by reference. Exemplary microfluidic detection methods include those commercialized by Luminex (Austin, Texas) under the trade name xMAP® technology or used on platforms identified as MAGPIX®, LUMINEX® 100/200 or FEXMAP 3D®. Plate-based methods of microfluidic detection methods can be modified to use SNAPs or SNAP complexes as set forth herein.

Other detection methods that can also be used, and that are particularly useful at low plex scale include procedures that employ SOMAmer reagents and SOMAscan assays commercialized by Soma Logic (Boulder, CO). In one configuration, a sample is contacted with aptamers that are capable of binding polypeptides with high specificity for the amino acid sequence of the polypeptides. The resulting aptamer-polypeptide complexes can be separated from other sample components, for example, by attaching the complexes to beads, SNAPs or SNAP complexes that are removed from the sample. The aptamers can then be isolated and, because the aptamers are nucleic acids, the aptamers can be detected using any of a variety of methods known in the art for detecting nucleic acids, including for example, hybridization to nucleic acid arrays, PCR-based detection, or nucleic acid sequencing. Exemplary methods and compositions for use in an aptamer-based or other detection method set forth herein are set forth in U.S. Pat. Nos. 8,404,830; 8,975,388; 9,163,056; 9,938,314; 10,239,908; 10,316,321 or 10,221,207. Further examples are set forth in U.S. Pat. Nos. 7,855,054; 7,964,356; 8,975,026; 8,945,830; 9,404,919; 9,926,566; 10,221,421; 10,316,321 or 10,392,621. The above patents are incorporated herein by reference. The aptamers or polypeptides set forth above or in the above references can be attached to SNAPs or SNAP complexes as set forth herein.

Polypeptides can also be detected based on proximity of two or more probes. For example, two probes can each include a receptor component and a nucleic acid component. When the probes bind in proximity to each other, for example, due to ligands for the respective receptors being on a single polypeptide, or due to the ligands being present on two polypeptides that associate with each other, the nucleic acids can interact to cause a modification that is indicative of the proximity. For example, one of the nucleic acids can be extended using the other nucleic acid as a template, one of the nucleic acids can form a template that positions the other nucleic acid for ligation to another nucleic acid, or the like. Exemplary methods are commercialized by Olink Proteomics AB (Uppsala Sweden) or set forth in U.S. Pat. Nos. 7,306,904; 7,351,528; 8,013,134; 8,268,554 or 9,777,315, each of which is incorporated herein by reference. The polypeptides, probes, ligands or receptors set forth above or in the above references can be attached to a nucleic acid (e.g., a nucleic acid nanostructure, SNAP, a complex thereof, or a component thereof) as set forth herein.

A method of detecting a polypeptide, can include a step of detecting a sample polypeptide (e.g. a sample polypeptide conjugate) and/or detecting a standard polypeptide (e.g. a standard polypeptide conjugate). In one configuration, detection can include steps of (i) contacting a first set of binding reagents with a sample polypeptide, and/or a standard polypeptide, and (ii) detecting binding of the sample polypeptide and/or standard polypeptide to a binding reagent in the second set of binding reagents. The method can optionally include one or more of the further steps of (iii) removing the first set of binding reagents, (iv) binding a second set of binding reagents to the sample polypeptide, and/or the standard polypeptide, where binding reagents in the second set are different from binding reagents in the first set, and (v) detecting binding of the sample polypeptide and/or standard polypeptide to a binding reagent in the second set of binding reagents. The method can optionally be carried out for one or more sample polypeptides in an array or standard polypeptides. Methods and apparatus that employ standard polypeptides are set forth in U.S. Pat. App. Ser. No. 63/139,818, which is incorporated herein by reference. The sample polypeptides or standard polypeptides set forth above or in the above reference can be attached to a nucleic acid (e.g., a nucleic acid nanostructure, SNAP, a complex thereof, or a component thereof) as set forth herein.

High specificity binding reagents can be useful in a number of polypeptide detection methods. Alternatively, detection can be based on multiple low specificity detection cycles that are performed on a sample such that the individual cycles may detect multiple polypeptides while not necessarily distinguishing one of the detected polypeptides from another in any one of the cycles. However, using compositions and methods set forth herein, results from multiple cycles can be combined to achieve high-confidence quantification, identification or characterizations of a plurality of individual polypeptides in the sample. In many embodiments, one or more of the individual cycles yield ambiguous results with regard to distinguishing the identity of a subset of polypeptides that produce detectable signal; however, characterizing the signals across the multiple cycles allows individual polypeptides to be individually and unambiguously identified. The resulting set of identified polypeptides can be larger than the number of polypeptides that produce signal from any of the individual cycles.

Some configurations of detection methods that are based on multiple low specificity detection cycles may be understood, to some extent, via analogies to the children's game "20 Questions." An objective of this game is to identify a target answer in as few questions as possible. An effective tactic is to ask questions on characteristics ranging from broad characteristics (e.g., "Is it a person, place, or thing?", "Is the person in this room?") to narrow characteristics (e.g., "Is the person named 'Keith'?"). In general, it is possible to identify a character in the game by asking substantially fewer questions (N) than the possible number of answers (M), i.e. $N \ll M$. By analogy, affinity reagents used in some configurations of the detection methods set forth herein, may have a broad range of interactions with respect to a population of polypeptides. For example, an affinity reagent may be considered to be a 'promiscuous' affinity reagent due to its affinity for a single epitope that is present in a plurality of different polypeptides in a sample, or due to its affinity for a plurality of different epitopes that are present in one or more polypeptides in the sample. By testing for the interaction of an affinity reagent with a polypeptide, information is acquired regardless of whether an interaction is observed. For example, a failure of an affinity reagent to bind a polypeptide is indicative of the polypeptide lacking the epitope for the affinity reagent.

In the above-described analogy of 20 Questions, the outcome is based upon clear articulation of queries and answers, and is also based upon accurate and reliable answers (e.g., type, size, attributes, etc.). By analogy, polypeptide characterization by the measurement of affinity reagent interactions may be more difficult when the measurements are prone to a degree of systematic or random error or uncertainty. For example, measurement accuracy of affinity reagent (e.g., antibody) interactions with binding targets (e.g. epitopes) may be affected by numerous factors such as system detection limits or sensitivity, non-specific interactions between epitopes and affinity reagents (false positives), or stochastic, time-dependent reversal of an interaction (false negatives).

It is not uncommon for polypeptide characterization measurements to contain a degree of uncertainty. High-confidence characterization may be achieved by utilizing multiple low specificity detection cycles in combination with a probabilistic decoding approach. The overlaying or combining of binary polypeptide interaction data (e.g., affinity reagent A1, which interacts with epitope X, was not observed to interact with unknown polypeptide P, therefore, polypeptide P does not contain epitope X) may lead to improper polypeptide characterization due to the inclusion or exclusion of possible candidate states due to measurement error. By contrast, overlaying or combining probabilistic polypeptide interaction data may permit an algorithm to converge to a high-confidence prediction of polypeptide identity without needing to exclude any candidate states. For example, if affinity reagents A1 to A6 are known to interact with a known polypeptide P1 with interaction probabilities, and measurable interactions of affinity reagents A2, A5 and A6 are observed against an unknown polypeptide P, it may be concluded that polypeptide P is likely not polypeptide P1 (2 of 3 likely interactions were not observed; 2 of 3 unlikely interactions were observed). Moreover, a probability-based characterization may be assigned a degree of confidence such that a prediction for each observed polypeptide may be made when the degree of confidence rises above a threshold degree of confidence. For example, in the above observation of polypeptide P, the six described observations need not provide a high enough degree of confidence to eliminate polypeptide P1 as a possible identity, but similar trends over 20 or more affinity reagents may provide sufficient degree of confidence to eliminate P1 as a possible identity. Accordingly, polypeptide P1 can be subjected to binding reactions with a series of promiscuous affinity reagents, and although the observation from each binding reaction taken individually may be ambiguous with regard to identifying the polypeptide, decoding the observations from the series of binding reactions may identify polypeptide P1 with an acceptable level of confidence.

A polypeptide detection assay that is based on multiple low specificity detection cycles may be configured to permit polypeptide characterization at an individual or single-molecule level. Polypeptides to be characterized may be provided on a solid support containing unique, detectably resolvable characterization sites. For example, the polypeptides can be attached to the sites via conjugation to a nucleic acid (e.g., a nucleic acid nanostructure, SNAP, a complex thereof, or a component thereof). Such characterization sites may be spaced, arrayed, or otherwise ordered to allow individual sites to be distinguished one from another when detecting their interactions with affinity reagents. A solid support may comprise a sufficient number of unique, optically resolvable characterization sites to accommodate a plurality, majority, or all polypeptides from a sample, such as at least about $1\times10^4$, $1\times10^5$, $1\times10^6$, $1\times10^7$, $1\times10^8$, $1\times10^9$, $1\times10^{10}$, $1\times10^{11}$, $1\times10^{12}$, or more than $1\times10^{12}$ sites. Each site may contain a known number of polypeptides that are to be characterized. In some cases, a characterization site may contain a single polypeptide molecule to be detected, identified or characterized. In other cases, a site may contain multiple polypeptide molecules, with at least one molecule to be detected. For example, the polypeptide molecule to be detected can be one subunit in a larger protein having multiple different subunits.

In some cases, polypeptide detection assays that are based on multiple low specificity detection cycles may utilize affinity reagents such as antibodies (or functional fragments thereof), aptamers, mini protein binders, or any other suitable binding reagent. Affinity reagents may be promiscuous affinity reagents that possess a likelihood to interact with (e.g., bind to) more than one polypeptide in a sample. In some cases, the affinity reagents may possess a likelihood to interact with two or more unique, structurally dissimilar proteins in a sample. For example, an affinity reagent may bind with near-equal probability to a particular membrane protein and a particular cytoplasmic protein based upon a region of structural similarity. In some cases, a binding affinity reagent may possess a likelihood of binding to a particular amino acid epitope or family of epitopes regardless of the sequence context (e.g., amino acid sequence upchain and/or downchain from the epitope). An affinity reagent can bind to a polypeptide that is conjugated to a nucleic acid (e.g., a nucleic acid nanostructure, SNAP, a complex thereof, or a component thereof).

An affinity reagent that is used for multiple low specificity detection cycles may be characterized such that it has an identified, determined, or assessed probability-based binding profile. An affinity reagent may have the property of binding to a first polypeptide with an identified, determined, or assessed binding probability of greater than about 50% (e.g., at least about 50%, 60%, 70%, 80%, 90%, 95%, 99%, 99.9%, 99.99%, 99.999% or greater than about 99.999%) and binding to a second structurally non-identical polypeptide with an identified, determined, or assessed binding probability of less than about 50% (e.g., no more than about 50%, 40%, 30%, 20%, 10%, 5%, 1%, 0.1%, 0.01%, 0.001% or less than about 0.001%). In a particular case, the difference in observed binding probabilities of the affinity reagent to the first and second polypeptides may be due to the presence, absence, or inaccessibility of a particular epitope or family of epitopes in either the first or second polypeptide. Probabilistic affinity reagent binding profiles may be determined or identified by in vitro measurements or in silico predictions.

Polypeptide detection methods that are based on multiple low specificity detection cycles may further incorporate computational decoding approaches that are optimized for the above-described affinity reagents. The decoding approaches may overlay or combine data from multiple rounds of detecting affinity reagent interaction with individual polypeptides, and can assign a degree of confidence for detection of signal from each polypeptide. For example, affinity reagent interactions can be detected for each site in an array of sites, and a degree of confidence can be assigned to detection of each signal at each site. Similarly, a degree of confidence can be assigned to a series of detection events at each site. A polypeptide may be considered identified or characterized if the degree of confidence for a prediction based upon overlayed or combined affinity reagent interaction data exceeds a threshold degree of confidence. The threshold degree of confidence for a polypeptide characterization prediction may depend upon the nature of the characterization. The threshold degree of confidence may fall in a range from about 50% to about 99.999%, such as about 50%, 60%, 70%, 80%, 90%, 95%, 99%, 99.99%, or about 99.999%. In some cases, the threshold degree of confidence may be outside this range. In some cases, the computational decoding approaches may incorporate machine learning or training algorithms to update or refine the determined or identified probabilistic interaction profile for the affinity reagents or polypeptides with increased information or in ever widening contexts.

Particularly useful methods and algorithms that can be used for detection methods employing multiple low specificity detection cycles are set forth, for example, in U.S. Pat. No. 10,473,654; or PCT Publication No. WO 2019/236749 A2; or U.S. Pat. App. Pub. Nos. 2020/0082914 A1 or 2020/0090785 A1, each of which is incorporated herein by reference. The methods set forth above and in the preceding references can be modified to use SNAPs or SNAP complexes of the present disclosure, for example, to attach polypeptides to a solid support.

A method of detecting a polypeptide, can include a process of detecting a sample polypeptide, the process including steps of (i) binding a first binding reagent to a sample polypeptide at an address of an array, where the binding reagent comprises a nucleic acid tag, and where a primer nucleic acid is present at the address; (ii) extending the primer nucleic acid, thereby producing an extended primer having a copy of the tag; and (iii) detecting the tag of the extended primer. The polypeptide can be attached at the address of the array via conjugation to a nucleic acid (e.g., a nucleic acid nanostructure, SNAP, a complex thereof, or a component thereof). The extending of the primer can be carried out, for example, by polymerase-based extension of the primer, using the nucleic acid tag as a template. Alternatively, the extending of the primer can be carried out, for example, by ligase or chemical based ligation of the primer to a nucleic acid that is hybridized to the nucleic acid tag. The nucleic acid tag can be detected via hybridization to nucleic acid probes (e.g., in a microarray), amplification-based detections (e.g. PCR-based detection, or rolling circle amplification-based detection) or nucleic acid sequencing (e.g. cyclical reversible terminator methods, nanopore methods, or single molecule, real time detection methods). Exemplary methods that can be used for detecting polypeptides using nucleic acid tags are set forth in U.S. Pat. App. Pub. No. 2019/0145982 A1; 2020/0348308 A1; or 2020/0348307 A1, each of which is incorporated herein by reference.

A method of detecting a polypeptide, can include a process of detecting a sample polypeptide, the process including steps of (i) exposing a terminal amino acid on the polypeptide; (ii) detecting a change in signal from the polypeptide; and (iii) identifying the type of amino acid that was removed based on the change detected in step (ii). The terminal amino acid can be exposed, for example, by removal of one or more amino acids from the amino terminus or carboxyl terminus of the polypeptide. Steps (i) through (iii) can be repeated to produce a series of signal changes that is indicative of the sequence for the polypeptide. Optionally, one or more different polypeptides can be attached at respective addresses of a polypeptide array, for example, via conjugation to a nucleic acid (e.g., a nucleic acid nanostructure, SNAP, a complex thereof, or a component thereof) at the addresses. The signal change can optionally be detected at one or more address on an array.

In a first configuration of the above method, one or more types of amino acids in the polypeptide can be attached to a label that uniquely identifies the type of amino acid. In this configuration, the change in signal that identifies the amino acid can be loss of signal from the respective label. Exemplary compositions and techniques that can be used to remove amino acids from a polypeptide and detect signal changes are set forth in Swaminathan et al., *Nature Biotech.* 36:1076-1082 (2018); or U.S. Pat. No. 9,625,469 or 10,545,153, each of which is incorporated herein by reference. The polypeptide can be attached to a solid support via conjugation to a SNAP or SNAP complex.

In a second configuration of the above method, the terminal amino acid of the polypeptide can be recognized by a binding reagent that is specific for the terminal amino acid or specific for a label moiety that is present on the terminal amino acid. The binding reagent can be detected on the array, for example, due to a label on the binding reagent. Exemplary binding reagents and detection methods are set forth in U.S. Pat. App. Pub. No. 2019/0145982 A1; 2020/0348308 A1; or 2020/0348307 A1, each of which is incorporated herein by reference. The polypeptide can be attached to a solid support via conjugation to a nucleic acid (e.g., a nucleic acid nanostructure, SNAP, a complex thereof, or a component thereof).

A method of detecting a polypeptide can include a process of detecting a sample polypeptide of an array of polypeptides, the process including steps of (i) exposing a terminal amino acid on a polypeptide at an address of an array; (ii) binding a binding reagent to the terminal amino acid, where the binding reagent comprises a nucleic acid tag, and where a primer nucleic acid is present at the address; (iii) extending the primer nucleic acid, thereby producing an extended primer having a copy of the tag; and (iv) detecting the tag of the extended primer. The terminal amino acid can be exposed, for example, by removal of one or more amino acids from the amino terminus or carboxyl terminus of the polypeptide. Steps (i) through (iv) can be repeated to produce a series of tags that is indicative of the sequence for the polypeptide. The extending of the primer can be carried out, for example, by polymerase-based extension of the primer, using the nucleic acid tag as a template. Alternatively, the extending of the primer can be carried out, for example, by ligase- or chemical-based ligation of the primer to a nucleic acid that is hybridized to the nucleic acid tag. The nucleic acid tag can be detected via hybridization to nucleic acid probes (e.g., in a microarray), amplification-based detections (e.g. PCR-based detection, or rolling circle amplification-based detection) or nuclei acid sequencing (e.g. cyclical reversible terminator methods, nanopore methods, or single molecule, real time detection methods). Exemplary methods that can be used for detecting polypeptides using nucleic acid tags are set forth in U.S. Pat. App. Pub. No. 2019/0145982 A1; 2020/0348308 A1; or 2020/0348307 A1, each of which is incorporated herein by reference. A polypeptide, primer nucleic acid or template nucleic acid copied by extension of the primer can be attached to a SNAP or SNAP complex.

A method of detecting can include determining a detected property such as a polypeptide sequence, presence of a known epitope, polypeptide size, polypeptide isoelectric point, polypeptide hydrophobicity, polypeptide hydrodynamic radius, polypeptide pKa, the presence of a post-translational modification, the absence of a post-translational modification, polypeptide charge, the presence of a non-natural amino acid or other non-natural amino acid chemical unit, the presence of secondary, tertiary, or quaternary structure, the absence of secondary, tertiary, or quaternary structure, presence of a bound molecule, or absence of a bound molecule. A bound non-polypeptide molecule may comprise a chelated ion, a bound metal cluster, a bound cofactor (e.g., a porphyrin), a bound ligand, a bound substrate, or a bound biomolecule (e.g., polysaccharide, nucleic acid, protein, etc.).

A method or apparatus of the present disclosure can optionally be configured for optical detection (e.g., luminescence detection). Analytes or other entities can be detected, and optionally distinguished from each other, based on measurable characteristics such as the wavelength of radiation that excites a luminophore, the wavelength of radiation emitted by a luminophore, the intensity of radiation emitted by a luminophore (e.g., at particular detection wavelength(s)), luminescence lifetime (e.g. the time that a luminophore remains in an excited state) or luminescence polarity. Other optical characteristics that can be detected, and optionally used to distinguish analytes, include, for example, absorbance of radiation, resonance Raman, radiation scattering, or the like. A luminophore can be an intrinsic moiety of a protein or other analyte to be detected, or the luminophore can be an exogenous moiety that has been synthetically added to a protein or other analyte.

A method or apparatus of the present disclosure can use a light sensing device that is appropriate for detecting a characteristic set forth herein or known in the art. Particularly useful components of a light sensing device can include, but are not limited to, optical sub-systems or components used in nucleic acid sequencing systems. Examples of useful sub systems and components thereof are set forth in U.S. Pat. App. Pub. No. 2010/0111768 A1 or U.S. Pat. Nos. 7,329,860; 8,951,781 or 9,193,996, each of which is incorporated herein by reference. Other useful light sensing devices and components thereof are described in U.S. Pat. Nos. 5,888,737; 6,175,002; 5,695,934; 6,140,489; or 5,863,722; or U.S. Pat. Pub. Nos. 2007/007991 A1, 2009/0247414 A1, or 2010/0111768; or WO2007/123744, each of which is incorporated herein by reference. Light sensing devices and components that can be used to detect luminophores based on luminescence lifetime are described, for example, in U.S. Pat. Nos. 9,678,012; 9,921,157; 10,605,730; 10,712,274; 10,775,305; or 10,895,534, each of which is incorporated herein by reference.

Luminescence lifetime can be detected using an integrated circuit having a photodetection region configured to receive incident photons and produce a plurality of charge carriers in response to the incident photons. The integrated circuit can include at least one charge carrier storage region and a charge carrier segregation structure configured to selectively direct charge carriers of the plurality of charge carriers directly into the charge carrier storage region based upon times at which the charge carriers are produced. See, for example, U.S. Pat. Nos. 9,606,058, 10,775,305, and 10,845,308, each of which is incorporated herein by reference. Optical sources that produce short optical pulses can be used for luminescence lifetime measurements. For example, a light source, such as a semiconductor laser or LED, can be driven with a bipolar waveform to generate optical pulses with FWHM durations as short as approximately 85 picoseconds having suppressed tail emission. See, for example, in U.S. Pat. No. 10,605,730, which is incorporated herein by reference.

For configurations that use optical detection (e.g., luminescent detection), one or more analytes (e.g. proteins) may be immobilized on a surface, and this surface may be scanned with a microscope to detect any signal from the immobilized analytes. The microscope itself may comprise a digital camera or other luminescence detector configured to record, store, and analyze the data collected during the scan. A luminescence detector of the present disclosure can be configured for epiluminescent detection, total internal reflection (TIR) detection, waveguide assisted excitation, or the like.

A light sensing device may be based upon any suitable technology, and may be, for example, a charged coupled device (CCD) sensor that generates pixelated image data based upon photons impacting locations in the device. It will be understood that any of a variety of other light sensing devices may also be used including, but not limited to, a detector array configured for time delay integration (TDI) operation, a complementary metal oxide semiconductor (CMOS) detector, an avalanche photodiode (APD) detector, a Geiger-mode photon counter, a photomultiplier tube (PMT), charge injection device (CID) sensors, JOT image sensor (Quanta), or any other suitable detector. Light sensing devices can optionally be coupled with one or more excitation sources, for example, lasers, light emitting diodes (LEDs), arc lamps or other energy sources known in the art.

An optical detection system can be configured for single molecule detection. For example, waveguides or optical confinements can be used to deliver excitation radiation to locations of a solid support where analytes are located. Zero-mode waveguides can be particularly useful, examples of which are set forth in U.S. Pat. Nos. 7,181,122, 7,302,146, or 7,313,308, each of which is incorporated herein by reference. Analytes can be confined to surface features, for example, to facilitate single molecule resolution. For example, analytes can be distributed into wells having nanometer dimensions such as those set forth in U.S. Pat. No. 7,122,482 or 8,765,359, or U.S. Pat. App. Pub. No 2013/0116153 A1, each of which is incorporated herein by reference. The wells can be configured for selective excitation, for example, as set forth in U.S. Pat. No. 8,798,414 or 9,347,829, each of which is incorporated herein by reference. Analytes can be distributed to nanometer-scale posts, such as high aspect ratio posts which can optionally be dielectric pillars that extend through a metallic layer to improve detection of an analyte attached to the pillar. See, for example, U.S. Pat. Nos. 8,148,264, 9,410,887 or 9,987,609, each of which is incorporated herein by reference. Further examples of nanostructures that can be used to detect analytes are those that change state in response to the concentration of analytes such that the analytes can be quantitated as set forth in WO 2020/176793 A1, which is incorporated herein by reference.

An apparatus or method set forth herein need not be configured for optical detection. For example, an electronic detector can be used for detection of protons or charged labels (see, for example, U.S. Pat. App. Pub. Nos. 2009/0026082 A1; 2009/0127589 A1; 2010/0137143 A1; or 2010/0282617 A1, each of which is incorporated herein by reference in its entirety). A field effect transistor (FET) can be used to detect analytes or other entities, for example, based on proximity of a field disrupting moiety to the FET. The field disrupting moiety can be due to an extrinsic label attached to an analyte or affinity agent, or the moiety can be intrinsic to the analyte or affinity agent being used. Surface plasmon resonance can be used to detect binding of analytes or affinity agents at or near a surface. Exemplary sensors and methods for attaching molecules to sensors are set forth in U.S. Pat. App. Pub. Nos. 2017/0240962 A1; 2018/0051316 A1; 2018/0112265 A1; 2018/0155773 A1 or 2018/0305727 A1; or U.S. Pat. Nos. 9,164,053; 9,829,456; 10,036,064, each of which is incorporated herein by reference.

A composition, apparatus or method of the present disclosure can be used to characterize or identify at least about 0.0000001%, 0.0000010%, 0.000010%, 0.00010%, 0.001%, 0.01%, 0.1%, 1%, 10%, 25%, 50%, 90%, 99%, 99.9%, 99.99%, 99.999%, 99.9999%, 99.99999%, 99.999999%, or more of all protein species in a proteome. Alternatively or additionally, a proteomic characterization method may characterize or no more than about 99.999999%, 99.99999%, 99.9999%, 99.999%, 99.99%, 99.9%, 99%, 90%, 50%, 25%, 10%, 1%, 0.10%, 0.01%, 0.001%, 0.0001%, 0.00001%, 0.000001%, 0.0000001%, or less of all protein species in a proteome.

In some configurations of the compositions, apparatus and methods set forth herein, one or more proteins can be present on a solid support, where the proteins can optionally be detected. For example, a protein can be attached to a solid support, the solid support can be contacted with a detection agent (e.g., affinity agent) in solution, the affinity agent can interact with the protein, thereby producing a detectable signal, and then the signal can be detected to determine the presence, absence, quantity, a characteristic or identity of the protein. In multiplexed versions of this approach, different proteins can be attached to different addresses in an array, and the detection steps can occur in parallel, such that proteins at each address are detected, quantified, characterized, or identified. In another example, detection agents can be attached to a solid support, the support can be contacted with proteins in solution, the proteins can interact with the detection agents, thereby producing a detectable signal, and then the signal can be detected to determine the presence of the proteins. This approach can also be multiplexed by attaching different probes to different addresses of an array.

In multiplexed configurations, different proteins can be attached to different unique identifiers (e.g. addresses in an array), and the proteins can be manipulated and detected in parallel. For example, a fluid containing one or more different affinity agents can be delivered to an array such that the proteins of the array are in simultaneous contact with the affinity agent(s). Moreover, a plurality of addresses can be observed in parallel allowing for rapid detection of binding events. A plurality of different proteins can have a complexity of at least 5, 10, 100, $1 \times 10^3$, $1 \times 10^4$, $1 \times 10^5$ or more different native-length protein primary sequences. Alternatively or additionally, a proteome, proteome subfraction or other protein sample that is analyzed in a method set forth herein can have a complexity that is at most $1 \times 10^5$, $1 \times 10^4$, $1 \times 10^3$, 100, 10, 5 or fewer different native-length protein primary sequences. The total number of proteins of a sample that is detected, characterized, or identified can differ from the number of different primary sequences in the sample, for example, due to the presence of multiple copies of at least some protein species. Moreover, the total number of proteins of a sample that is detected, characterized, or identified can differ from the number of candidate proteins suspected of being in the sample, for example, due to the presence of multiple copies of at least some protein species, absence of some proteins in a source for the sample, or loss of some proteins prior to analysis.

A particularly useful multiplex format uses an array in which proteins and/or affinity agents are attached to unique identifiers such as addresses on a surface. A protein can be attached to a unique identifier using any of a variety of means. The attachment can be covalent or non-covalent. Exemplary covalent attachments include chemical linkers such as those achieved using click chemistry or other linkages known in the art or described in U.S. patent application Ser. No. 17/062,405, which is incorporated herein by reference. Non-covalent attachment can be mediated by receptor-ligand interactions (e.g. (strept)avidin-biotin, antibody-antigen, or complementary nucleic acid strands), for example, wherein the receptor is attached to the unique identifier and the ligand is attached to the protein or vice versa. In particular configurations, a protein is attached to a solid support (e.g., an address in an array) via a structured nucleic acid particle (SNAP). A protein can be attached to a SNAP and the SNAP can interact with a solid support, for example, by non-covalent interactions of the DNA with the support and/or via covalent linkage of the SNAP to the support. Nucleic acid origami or nucleic acid nanoballs are particularly useful. The use of SNAPs and other moieties to attach proteins to unique identifiers such as tags or addresses in an array are set forth in U.S. Pat. App. Ser. Nos. 17/062,405, which is incorporated herein by reference.

The methods, compositions and apparatus of the present disclosure are particularly well suited for use with proteins. Although proteins are exemplified throughout the present disclosure, it will be understood that other analytes can be similarly used. Exemplary analytes include, but are not limited to, biomolecules, polysaccharides, nucleic acids, lipids, metabolites, hormones, vitamins, enzyme cofactors, therapeutic agents, candidate therapeutic agents or combinations thereof. An analyte can be a non-biological atom or molecule, such as a synthetic polymer, metal, metal oxide, ceramic, semiconductor, mineral, or a combination thereof.

One or more proteins that are used in a method, composition or apparatus herein, can be derived from a natural or synthetic source. Exemplary sources include, but are not limited to biological tissues, fluids, cells or subcellular compartments (e.g., organelles). For example, a sample can be derived from a tissue biopsy, biological fluid (e.g., blood, sweat, tears, plasma, extracellular fluid, urine, mucus, saliva, semen, vaginal fluid, synovial fluid, lymph, cerebrospinal fluid, peritoneal fluid, pleural fluid, amniotic fluid, intracellular fluid, extracellular fluid, etc.), fecal sample, hair sample, cultured cell, culture media, fixed tissue sample (e.g., fresh frozen or formalin-fixed paraffin-embedded) or product of a protein synthesis reaction. A protein source may include any sample where a protein is a native or expected constituent. For example, a primary source for a cancer biomarker protein may be a tumor biopsy sample or bodily fluid. Other sources include environmental samples or forensic samples.

Exemplary organisms from which proteins or other analytes can be derived include, for example, a mammal such as a rodent, mouse, rat, rabbit, guinea pig, ungulate, horse, sheep, pig, goat, cow, cat, dog, primate, non-human primate or human; a plant such as *Arabidopsis thaliana*, tobacco, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a dictyostelium discoideum; a fungi such as *Pneumocystis carinii, Takifugu rubripes*, yeast, *Saccharamoyces cerevisiae* or *Schizosaccharomyces pombe*; or a *Plasmodium falciparum*. Proteins can also be derived from a prokaryote such as a bacterium, *Escherichia coli*, staphylococci or *Mycoplasma pneumoniae*; an archae; a virus such as Hepatitis C virus, influenza virus, coronavirus, or human immunodeficiency virus; or a viroid. Proteins can be derived from a homogeneous culture or population of the above organisms or alternatively from a collection of several different organisms, for example, in a community or ecosystem.

In some cases, a protein or other biomolecule can be derived from an organism that is collected from a host organism. For example, a protein may be derived from a parasitic, pathogenic, symbiotic, or latent organism collected from a host organism. A protein can be derived from an organism, tissue, cell or biological fluid that is known or suspected of being linked with a disease state or disorder (e.g., cancer). Alternatively, a protein can be derived from an organism, tissue, cell or biological fluid that is known or suspected of not being linked to a particular disease state or disorder. For example, the proteins isolated from such a source can be used as a control for comparison to results acquired from a source that is known or suspected of being linked to the particular disease state or disorder. A sample may include a microbiome or substantial portion of a microbiome. In some cases, one or more proteins used in a method, composition or apparatus set forth herein may be obtained from a single source and no more than the single source. The single source can be, for example, a single organism (e.g. an individual human), single tissue, single cell, single organelle (e.g. endoplasmic reticulum, Golgi apparatus or nucleus), or single protein-containing particle (e.g., a viral particle or vesicle).

A method, composition or apparatus of the present disclosure can use or include a plurality of proteins having any of a variety of compositions such as a plurality of proteins composed of a proteome or fraction thereof. For example, a plurality of proteins can include solution-phase proteins, such as proteins in a biological sample or fraction thereof, or a plurality of proteins can include proteins that are immobilized, such as proteins attached to a particle or solid support. By way of further example, a plurality of proteins can include proteins that are detected, analyzed, or identified in connection with a method, composition or apparatus of the present disclosure. The content of a plurality of proteins can be understood according to any of a variety of characteristics such as those set forth below or elsewhere herein.

A plurality of proteins can be characterized in terms of total protein mass. The total mass of protein in a liter of plasma has been estimated to be 70 grams and the total mass of protein in a human cell has been estimated to be between 100 picograms (pg) and 500 pg depending upon cells type. See Wisniewski et al. *Molecular & Cellular Proteomics* 13:10.1074/mcp.M113.037309, 3497-3506 (2014), which is incorporated herein by reference. A plurality of proteins used or included in a method, composition or apparatus set forth herein can include at least 1 pg, 10 pg, 100 pg, 1 ng, 10 ng, 100 ng, 1 µg, 10 µg, 100 µg, 1 mg, 10 mg, 100 mg or more protein by mass. Alternatively or additionally, a plurality of proteins may contain at most 100 mg, 10 mg, 1 mg, 100 µg, 10 µg, 1 µg, 100 ng, 10 ng, 1 ng, 100 pg, 10 pg, 1 pg or less protein by mass.

A plurality of proteins can be characterized in terms of percent mass relative to a given source such as a biological source (e.g. cell, tissue, or biological fluid such as blood). For example, a plurality of proteins may contain at least 60%, 75%, 90%, 95%, 99%, 99.9% or more of the total protein mass present in the source from which the plurality of proteins was derived. Alternatively or additionally, a plurality of proteins may contain at most 99.9%, 99%, 95%, 90%, 75%, 60% or less of the total protein mass present in the source from which the plurality of proteins was derived.

A plurality of proteins can be characterized in terms of total number of protein molecules. The total number of protein molecules in a *Saccharomyces cerevisiae* cell has been estimated to be about 42 million protein molecules. See Ho et al., *Cell Systems* (2018), DOI: 10.1016/j.cels.2017.12.004, which is incorporated herein by reference. A plurality of proteins used or included in a method, composition or apparatus set forth herein can include at least 1 protein molecule, 10 protein molecules, 100 protein molecules, $1 \times 10^4$ protein molecules, $1 \times 10^6$ protein molecules, $1 \times 10^8$ protein molecules, $1 \times 10^{10}$ protein molecules, 1 mole ($6.02214076 \times 10^{23}$ molecules) of protein, 10 moles of protein molecules, 100 moles of protein molecules or more. Alternatively or additionally, a plurality of proteins may contain at most 100 moles of protein molecules, 10 moles of protein molecules, 1 mole of protein molecules, $1 \times 10^{10}$ protein molecules, $1 \times 10^8$ protein molecules, $1 \times 10^6$ protein molecules, $1 \times 10^4$ protein molecules, 100 protein molecules, 10 protein molecules, 1 protein molecule or less.

A plurality of proteins can be characterized in terms of the variety of full-length primary protein structures in the plurality. For example, the variety of full-length primary protein structures in a plurality of proteins can be equated with the number of different protein-encoding genes in the source for the plurality of proteins. Whether or not the proteins are derived from a known genome or from any genome at all, the variety of full-length primary protein structures can be counted independent of presence or absence of post translational modifications in the proteins. A human proteome is estimated to have about 20,000 different protein-encoding genes such that a plurality of proteins derived from a human can include up to about 20,000 different primary protein structures. See Aebersold et al., *Nat. Chem. Biol.* 14:206-214 (2018), which is incorporated herein by reference. Other genomes and proteomes in nature are known to be larger or smaller. A plurality of proteins used or included in a method, composition or apparatus set forth herein can have a complexity of at least 2, 5, 10, 100, $1 \times 10^3$, $1 \times 10^4$, $2 \times 10^4$, $3 \times 10^4$ or more different full-length primary protein structures. Alternatively or additionally, a plurality of proteins can have a complexity that is at most $3 \times 10^4$, $2 \times 10^4$, $1 \times 10^4$, $1 \times 10^3$, 100, 10, 5, 2 or fewer different full-length primary protein structures.

In relative terms, a plurality of proteins used or included in a method, composition or apparatus set forth herein may contain at least one representative for at least 60%, 75%, 90%, 95%, 99%, 99.9% or more of the proteins encoded by the genome of a source from which the sample was derived. Alternatively or additionally, a plurality of proteins may contain a representative for at most 99.9%, 99%, 95%, 90%, 75%, 60% or less of the proteins encoded by the genome of a source from which the sample was derived.

A plurality of proteins can be characterized in terms of the variety of primary protein structures in the plurality including transcribed splice variants. The human proteome has been estimated to include about 70,000 different primary protein structures when splice variants ae included. See Aebersold et al., *Nat. Chem. Biol.* 14:206-214 (2018), which is incorporated herein by reference. Moreover, the number of the partial-length primary protein structures can increase due to fragmentation that occurs in a sample. A plurality of proteins used or included in a method, composition or apparatus set forth herein can have a complexity of at least 2, 5, 10, 100, $1 \times 10^3$, $1 \times 10^4$, $7 \times 10^4$, $1 \times 10^5$, $1 \times 10^6$ or more different primary protein structures. Alternatively or additionally, a plurality of proteins can have a complexity that is at most $1 \times 10^6$, $1 \times 10^5$, $7 \times 10^4$, $1 \times 10^4$, $1 \times 10^3$, 100, 10, 5, 2 or fewer different primary protein structures.

A plurality of proteins can be characterized in terms of the variety of protein structures in the plurality including different primary structures and different proteoforms among the primary structures. Different molecular forms of proteins expressed from a given gene are considered to be different proteoforms. Protoforms can differ, for example, due to differences in primary structure (e.g., shorter or longer amino acid sequences), different arrangement of domains (e.g. transcriptional splice variants), or different post translational modifications (e.g. presence or absence of phosphoryl, glycosyl, acetyl, or ubiquitin moieties). The human proteome is estimated to include hundreds of thousands of proteins when counting the different primary structures and proteoforms. See Aebersold et al., *Nat. Chem. Biol.* 14:206-214 (2018), which is incorporated herein by reference. A plurality of proteins used or included in a method, composition or apparatus set forth herein can have a complexity of at least 2, 5, 10, 100, $1 \times 10^3$, $1 \times 10^4$, $1 \times 10^5$, $1 \times 10^6$, $5 \times 10^6$, $1 \times 10^7$ or more different protein structures. Alternatively or additionally, a plurality of proteins can have a complexity that is at most $1 \times 10^7$, $5 \times 10^6$, $1 \times 10^6$, $1 \times 10^5$, $1 \times 10^4$, $1 \times 10^3$, 100, 10, 5, 2 or fewer different protein structures.

A plurality of proteins can be characterized in terms of the dynamic range for the different protein structures in the sample. The dynamic range can be a measure of the range of abundance for all different protein structures in a plurality of proteins, the range of abundance for all different primary protein structures in a plurality of proteins, the range of abundance for all different full-length primary protein structures in a plurality of proteins, the range of abundance for all different full-length gene products in a plurality of proteins, the range of abundance for all different proteoforms expressed from a given gene, or the range of abundance for any other set of different proteins set forth herein. The dynamic range for all proteins in human plasma is estimated to span more than 10 orders of magnitude from albumin, the most abundant protein, to the rarest proteins that have been measured clinically. See Anderson and Anderson *Mol Cell Proteomics* 1:845-67 (2002), which is incorporated herein by reference. The dynamic range for plurality of proteins set forth herein can be a factor of at least 10, 100, $1 \times 10^3$, $1 \times 10^4$, $1 \times 10^6$, $1 \times 10^8$, $1 \times 10^{10}$, or more. Alternatively or additionally, the dynamic range for plurality of proteins set forth herein can be a factor of at most $1 \times 10^{10}$, $1 \times 10^8$, $1 \times 10^6$, $1 \times 10^4$, $1 \times 10^3$, 100, 10 or less.

EXAMPLES

Example 1: Conjugation of Proteins to SNAPs

MTz-functionalized proteins are conjugated to TCO-functionalized DNA origami SNAP complexes comprising one or more TCO functional groups. Each TCO-functionalized DNA origami SNAP complex comprises a tile-shaped display SNAP comprising a TCO-functionalized polypeptide binding group that is coupled to four tile-shaped utility SNAPs. Each display SNAP comprises either 1 or 4 TCO binding groups. The TCO-functionalized DNA origami is provided in a buffer comprising 200 mM NaCl, 5 mM Tris-HCl, 11 mM MgCl$_2$, and 1 mM EDTA at pH 8.0. The amount of mTz-modified protein is calculated based upon the amount of tile to be used in the conjugation reaction. The volume of protein added to the conjugation reaction is calculated according to equation (1):

$$y = (xC_xwz)/C_y \qquad (1)$$

Where y=total volume of mTz-functionalized protein (µl)
x=total volume of DNA origami (µl)
C$_x$=concentration of DNA origami (µM)
C$_y$=concentration of mTz-functionalized protein (µM)
w=molar equivalents of protein to TCO
z=number of TCO moieties per DNA origami molecule Volumes of mTz-functionalized protein and TCO-DNA origami are combined according to the amounts calculated in equation (1). If the volume of mTz-functionalized protein in the reaction mixture exceeds 10% of the total volume (x+y), additional MgCl$_2$ must be added to maintain the magnesium concentration of the reaction mixture. If necessary, 1 µl of MgCl$_2$ should be added to the protein prior to the addition of the DNA origami at a concentration according to equation (2):

$$C_M = 12.4y + 12.4 \qquad (2)$$

Where C$_M$=concentration of MgCl$_2$ (mM)

The reaction mixture is gently mixed, then placed on a thermomixer or thermocycler at 25° C. The reaction tube is jacketed to prevent exposure to light. Reactions with a 10-fold or higher excess of protein are incubated for 5 hours or more. Reactions with less than a 10-fold excess of protein are incubated for 16 hours or more to ensure complete reaction of mTz with TCO.

Protein conjugates are purified on an Agilent 1100 HPLC with an Agilent Bio-SEC5 4.6×300 mm column. The HPLC solvent is filtered 200 mM NaCl, 5 mM Tris-HCl, 11 mM MgCl$_2$, and 1 mM EDTA at pH 8.0. The HPLC is run with isocratic flow at 0.3 ml/min for 25 minutes. Fractions are collected in 30 s intervals between 5 min and 13 mins of the run. Detection of DNA-containing fractions is performed at 260 nm wavelength, with DNA-containing fractions pooled. Pooled DNA-containing fractions are concentrated to a total volume of about 100 µl.

Example 2. Analysis of Protein Conjugates

Protein conjugates of Protein A, maltose-binding protein (MBP), and ubiquitin were formed by a mTz-TCO conjugation chemistry. Protein conjugates were formed with DNA origami containing a single TCO moiety. Single-TCO DNA origami were conjugated to fluorescently-labeled version of the three aforementioned proteins. Protein A was labeled with an Alexa-Fluor 647 fluorescent dye. MBP was labeled with an Alexa-Fluor 488 fluorescent dye. Ubiquitin was labeled with tetramethylrhodamine (~555 nm wavelength). A control reaction was run using mTz-functionalized protein with DNA origami containing no TCO moiety.

Fluorescently-labeled protein conjugates were run on an Agilent 1100 HPLC with an Agilent Bio-SEC5 4.6×300 mm column. The HPLC solvent was filtered 200 mM NaCl, 5 mM Tris-HCl, 11 mM MgCl$_2$, and 1 mM EDTA at pH 8.0. The HPLC was run with isocratic flow at 0.3 ml/min for 25 minutes. The HPLC monitored light absorption across a range of wavelengths between 190 nm and 800 nm. 260 nm wavelength was used to determine the presence of DNA. 488 nm, 553 nm, and 652 nm wavelengths were used to determine the presence of fluorescently-labeled protein as appropriate.

FIG. 30A shows HPLC data for Protein A conjugates. The upper chromatogram depicts 260 nm data, showing the elution of DNA origami around 11 mins. The lower chromatogram depicts 652 nm data, showing elution of protein around 11 mins, with excess unconjugated protein following at around 15 mins. Negative control data shown in FIG. 30B shows no protein eluting with the DNA origami at 11 mins (lower chromatogram) due to available TCO to complete the conjugation.

Figure 30C:
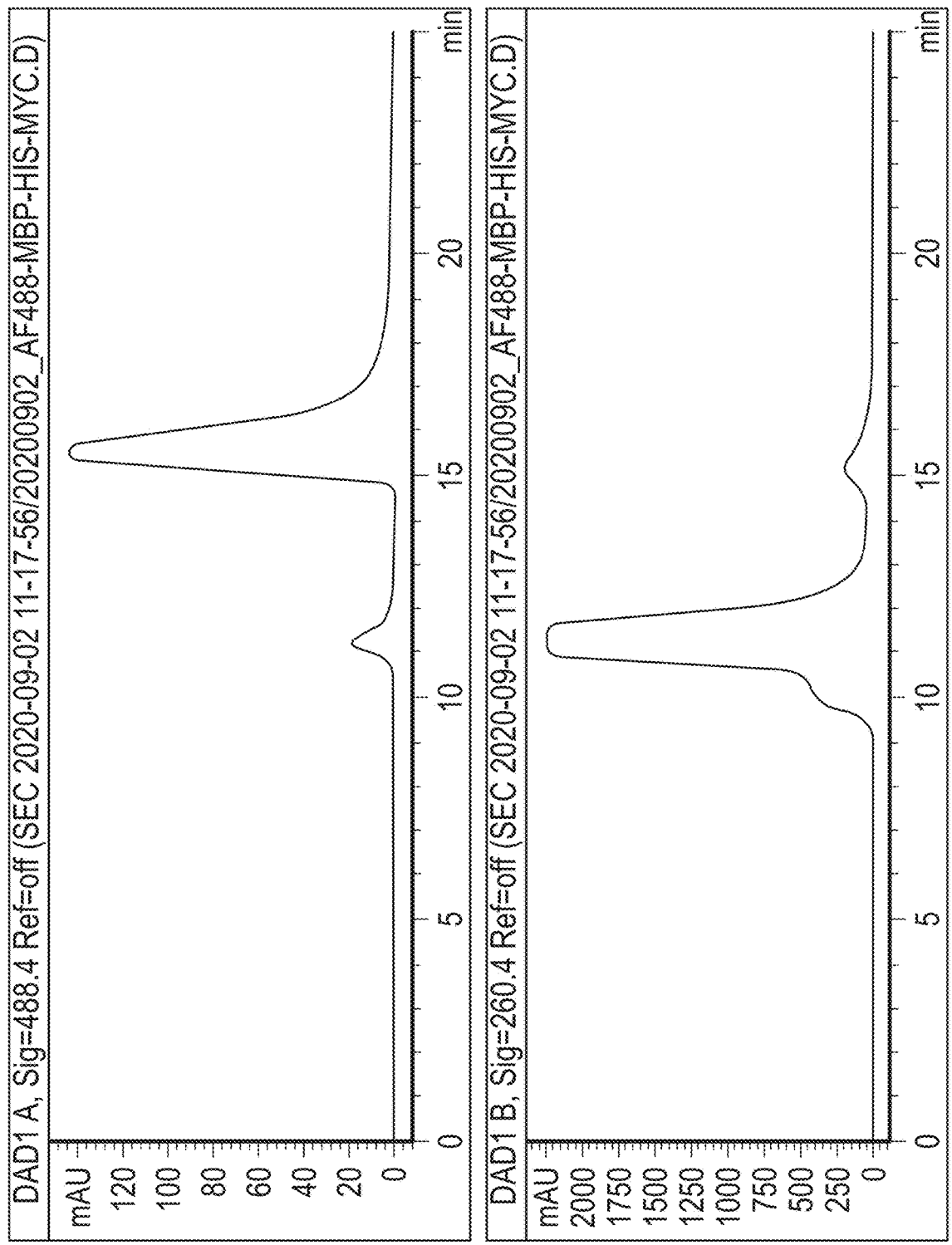
Figure 30D:
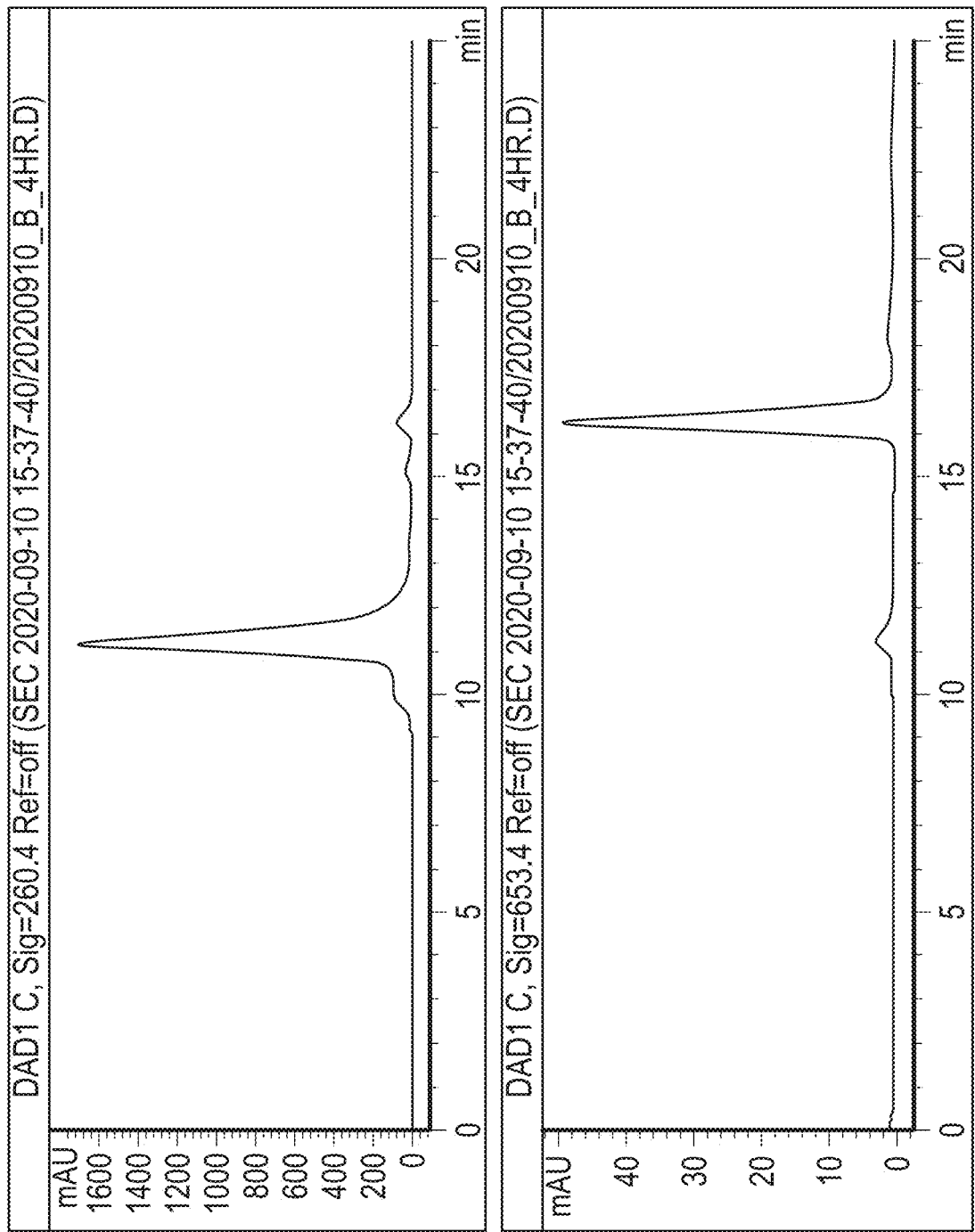

FIG. 30C shows HPLC data for MBP protein conjugates. The lower chromatogram depicts 260 nm data, showing the elution of DNA origami around 11 mins. The upper chromatogram depicts 488 nm data, showing elution of protein around 11 mins, with excess unconjugated protein following at around 15 mins. FIG. 30D shows HPLC data for ubiquitin protein conjugates. The upper chromatogram depicts 260 nm data, showing the elution of DNA origami around 11 mins. The lower chromatogram depicts 553 nm data, showing elution of protein around 11 mins, with excess unconjugated protein following at around 15 mins.

Example 3: Deposition of SNAPs

Figure 31:
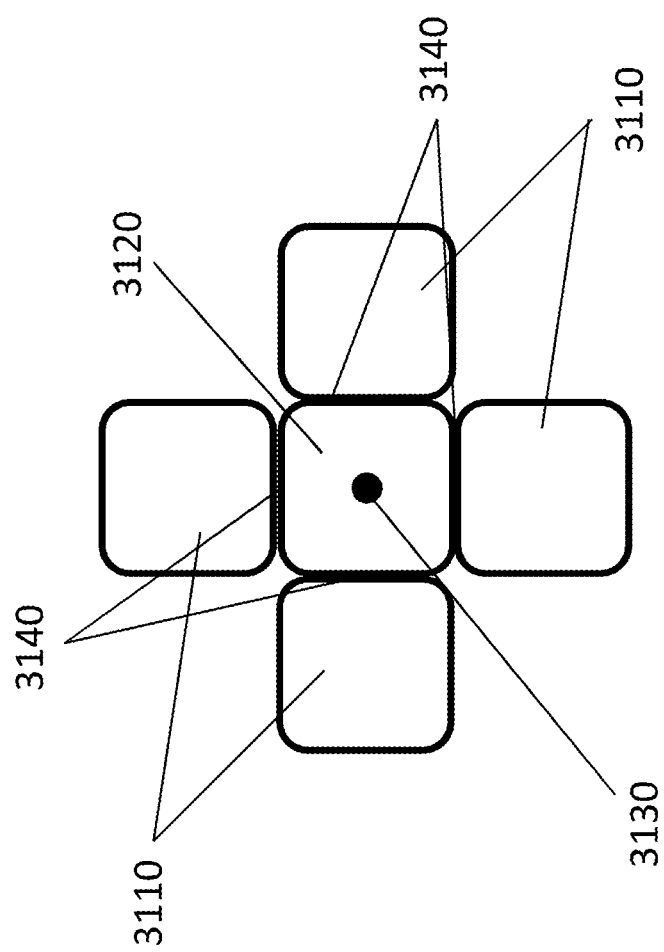
FIG. 31 gives a schematic view of a 5-tile DNA origami SNAP, in accordance with some embodiments.

Anchoring groups comprising 5-tile DNA origami are deposited on a glass substrate. A schematic of the basic structure of 5-tile origami is shown in FIG. 31. The origami complexes comprise four edge tiles 3110 that are joined to a central tile 3120 at a hybridization region 3140. The central tile 3120 comprises a reactive handle 3130 that is configured to conjugate a functionalized protein. DNA origami are labeled with Alexa-Fluor 488 dye to make them optically detectable. The glass substrate is a Nexterion D263 170 µm-thick glass slide that has been coated with a uniform monolayer of (3-aminopropyl)trimethoxysilane (APTMS).

Prior to deposition of the anchoring groups, the glass substrate is incubated in a deposition buffer solution containing 5 mM Tris-HCl—pH 8.0, 205 mM NaCl, 1 mM EDTA, and 12.5 mM $MgCl_2$ for 1 hour. 10 µl of 5-tile DNA origami at 2 ng/µl (91 µM) is applied to the glass substrate in a deposition buffer containing 5 mM Tris-HCl—pH 8.0, 205 mM NaCl, 1 mM EDTA, and 12.5 mM $MgCl_2$. The DNA origami are applied to the glass substrate slowly to prevent shearing. The DNA origami are incubated on the substrate for 10 minutes. After incubation, excess DNA origami are removed from the substrate by a 0.5 ml wash with a buffer containing 1× Neoventures buffer (10 mM HEPES, 120 mM NaCl, 5 mM $MgCl_2$, and 5 mM KCl, pH 7.4), 0.1% Tween-20, and 0.001% Lipidure CM5206. Additional $MgCl_2$ is added to the wash buffer to bring the total $MgCl_2$ concentration to 10 mM. Deposited DNA origami may be imaged by excitation of the labeled DNA origami with 488 nm light.

Example 4. SNAP Deposition Conditions

Anchoring group deposition was studied under differing deposition solvents. 5-tile DNA origami were deposited on a glass substrate. The deposition buffers utilized were: 1) DNA origami buffer (5 mM Tris-HCl—pH 8.0, 205 mM NaCl, 1 mM EDTA, and 12.5 mM $MgCl_2$); 2) DNA origami buffer with an additional 2.5 M NaCl added; and 3) DNA origami buffer with 0.01% Tween-20. DNA origami were deposited on the glass substrate according to the method described in Example 3. Each buffer was utilized for the pre-deposition incubation and the deposition step. Control substrates were prepared by cleaning Nexterion D263 170 µm-thick glass slide with $O_2$ plasma (no APTMS coating), then following the deposition method of Example 3. Each Nexterion D263 glass slide was joined to a second glass slide with an inward-facing PEG 3-6 surface coating to form a 3-lane flow cell with a deposition area on the glass substrate of each lane. Each lane of each flow cell corresponded to one of the three tested deposition buffers. Deposition on APTMS-coated substrate was tested for 3 different flow cells. Deposition on the uncoated substrate was tested for 3 different flow cells.

All glass substrates were imaged at 30 locations by confocal scanning laser microscopy at 488 nm. Pixel intensity counts were performed for each image by an image analysis software. Pixel intensity counts across the series of 30 images for each slide were averaged to provide average fluorescence intensity.

Figure 32C:
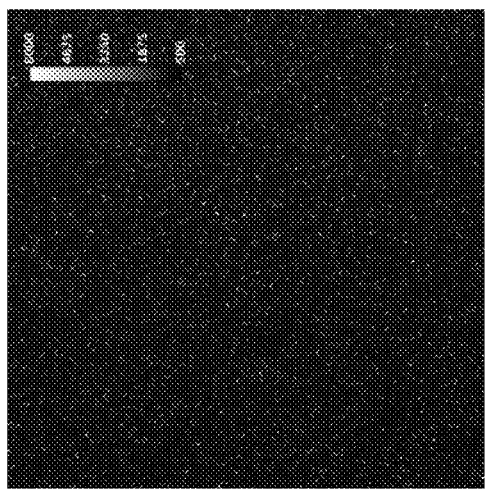
FIGS. 32A, 32B, 32C, 32D, 32E, and 32F show fluorescent confocal scanning microscopy image data for SNAP deposition.
Figure 32F:
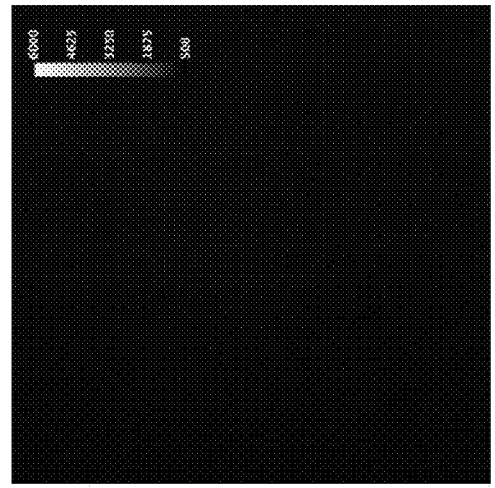
Figure 32B:
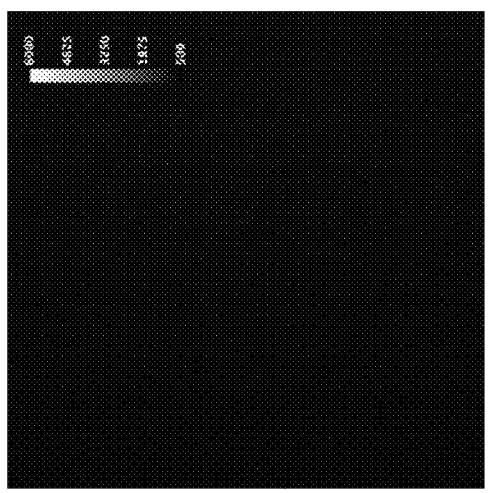
Figure 32E:
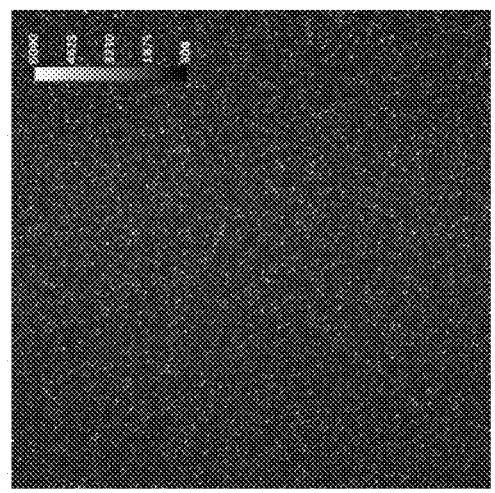
Figure 32A:
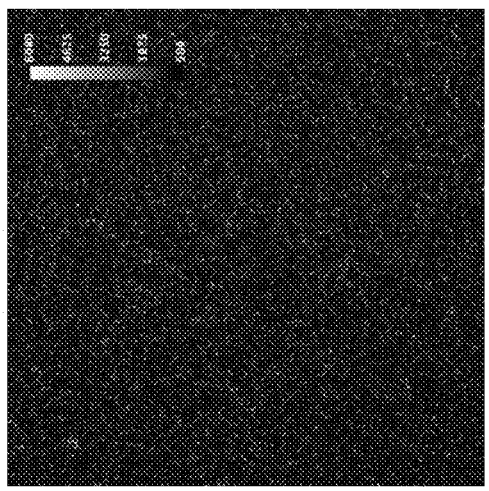
Figure 32D:
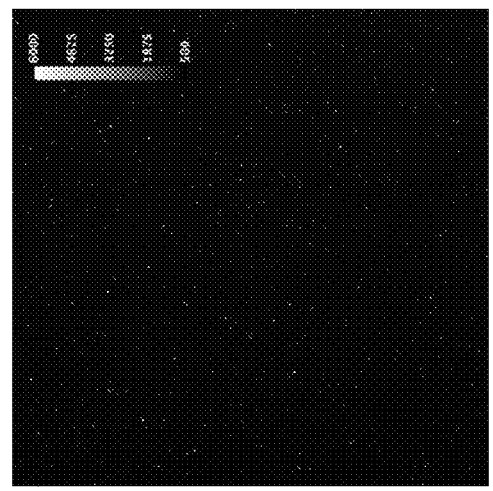
Figure 33:
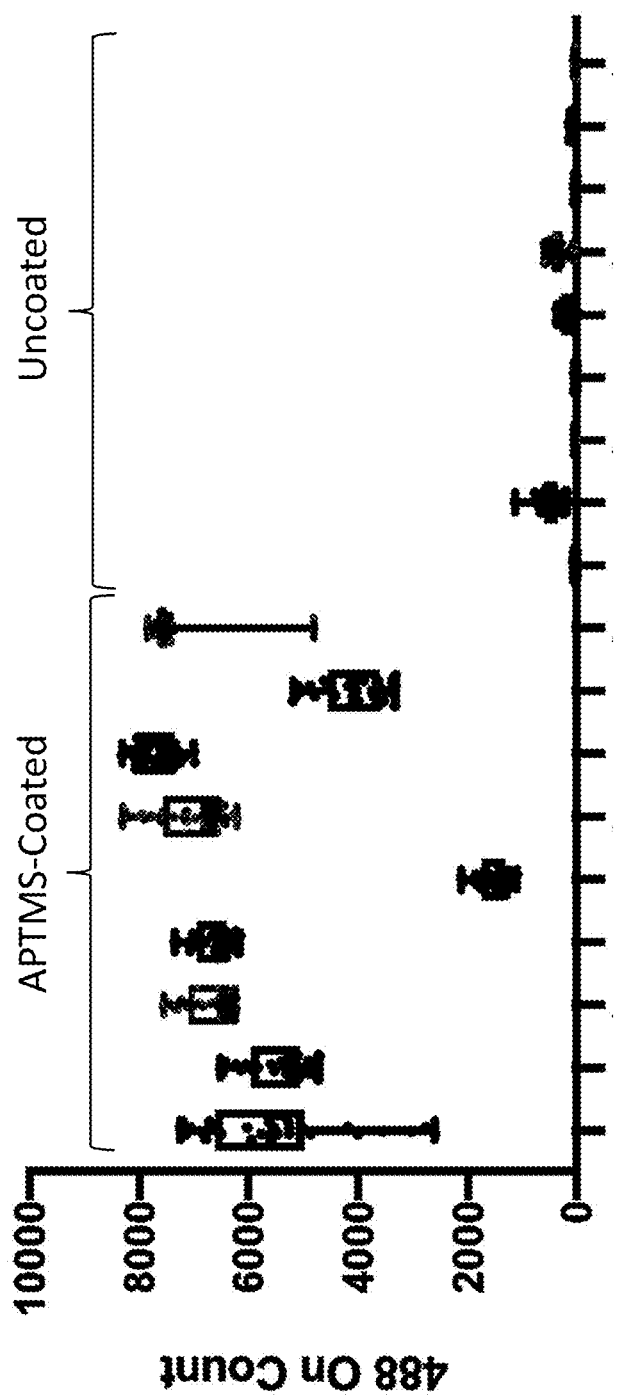
FIG. 33 plots SNAP deposition under differing solvent conditions.

FIGS. 32A and 32B show confocal scanning image results for DNA origami deposition under DNA origami buffer for the APTMS-coated substrate (FIG. 32A) and the uncoated substrate (FIG. 32B). Individual DNA origami can be seen at discrete locations on the surface of the coated substrate. Minimal deposition is apparent on the uncoated substrate. FIGS. 32C and 32D show confocal scanning image results for DNA origami deposition under DNA origami buffer with 2.5 M NaCl for the APTMS-coated substrate (FIG. 32C) and the uncoated substrate (FIG. 32D). Individual DNA origami can be seen at discrete locations on the surface of the coated substrate, although less deposition appears to occur compared to DNA origami buffer without 2.5 M NaCl. Minimal deposition is apparent on the uncoated substrate. FIGS. 32E and 32F show confocal scanning image results for DNA origami deposition under DNA origami buffer with 0.010% Tween-20 for the APTMS-coated substrate (FIG. 32E) and the uncoated substrate (FIG. 32F). Individual DNA origami can be seen at discrete locations on the surface of the coated substrate. No deposition is apparent on the uncoated substrate. FIG. 33 shows average total anchoring group counts for images collected under each buffer for each tested flow cell. The left data series shows results for the APTMS-coated substrate. The right data series shows results for the uncoated substrate. DNA origami are shown to deposit on the coated substrate with standard DNA origami buffer, or in the presence of high salt concentration or surfactants. Minimal deposition of DNA origami is observed on the uncoated substrate. The differences in total deposition on the substrate between different buffer compositions suggests that solvent composition can affect the quantity and density of anchoring groups on the substrate surface.

Example 5. Deposition of Protein Conjugates

Protein conjugates were deposited on glass substrate coated with a layer of APTMS according to the method described in Example 4. The protein conjugates comprised a 5-tile DNA origami conjugated to maltose binding protein (MBP) via a covalent methyltetrazine-transcyclooctene linkage. MBP protein conjugates were labeled with Alexa-Fluor 647 fluorophores to permit detection of protein conjugate deposition. Deposition of each MBP protein conjugate was observed in the same buffering conditions described in Example 4 (DNA origami buffer with or without 2.5 M NaCl or 0.010% Tween-20). Deposition of MBP protein conjugates under DNA origami buffer was tested in two separate flow cells. Deposition of MBP protein conjugates in the presence of 2.5 M NaCl or 0.01% Tween-20 was tested in three separate flow cells. Flows cells incubated with buffers containing no protein conjugates were also observed as negative controls.

Figure 35:
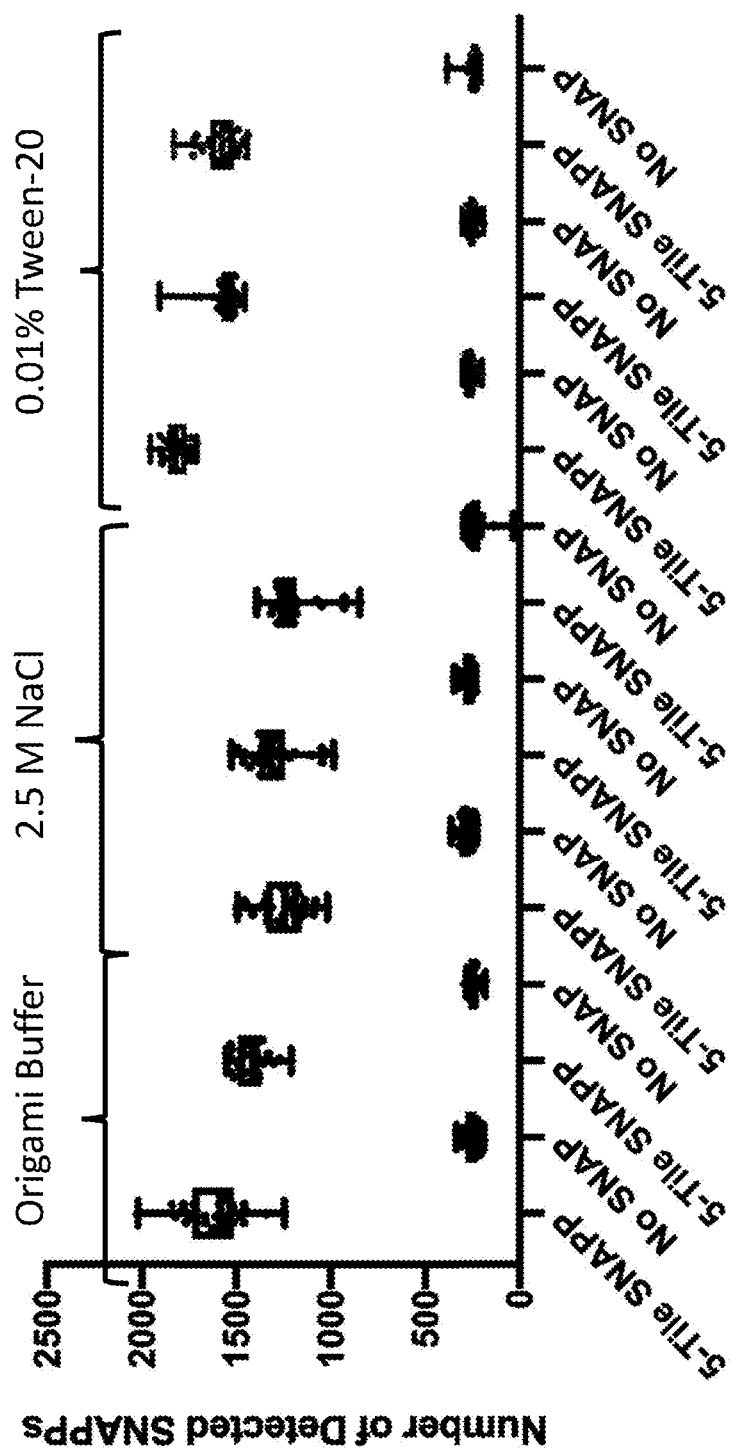
FIG. 35 plots SNAP deposition under differing solvent conditions.

FIGS. 34A-34C show confocal scanning image results for DNA origami deposition under different DNA origami buffer compositions for the APTMS-coated substrate. FIG. 34A shows individual MBP protein conjugates that were deposited in DNA origami buffer. FIG. 34B shows individual MBP protein conjugates that were deposited in DNA origami buffer containing 2.5 M NaCl. FIG. 34C shows individual MBP protein conjugates that were deposited in DNA origami buffer containing 0.01% Tween-20. Individual DNA origami can be seen at discrete locations on the surface of each APTMS coated substrate. FIG. 35 shows average total protein conjugate counts collected under each buffer for each tested flow cell. Data alternates between flow cells tested with protein conjugates and flow cells tested without protein conjugates. The leftmost four counts were for DNA origami buffer only. The middle six counts were for DNA origami buffer containing 2.5 M NaCl. The rightmost six counts were for DNA origami buffer containing 0.01% Tween-20. Deposition of protein conjugates on the APTMS-coated glass substrate was observed for all substrates, with slightly lower counts observed in the presence of 2.5 M NaCl, and slightly higher counts observed in the presence of 0.01% Tween-20. Anchoring groups are observed to efficiently deposit on an APTMS-coated substrate after the formation of protein conjugates.

Example 6. Deposition of Protein Conjugates

Protein conjugates were deposited on a patterned Nexterion D263 glass chip comprising square pattern of binding sites. The patterned region of each glass chip contained a polypeptide binding region having over 190 million binding sites. The polypeptide binding region was patterned with 12544 subgrids, with each subgrid containing 123×123 binding sites in a square configuration (15129 total binding sites per subgrid). Glass chip surfaces were coated with a layer of APTMS. The protein conjugates comprised a 5-tile DNA origami conjugated to his-tagged ubiquitin (Ubi-His) via a covalent methyltetrazine-transcyclooctene linkage. The DNA origami of the Ubi-His protein conjugates were labeled with Alexa-Fluor 488 fluorophores to permit detection of protein conjugate deposition. 15 µl of 0.3 nM protein conjugates were incubated on the chip for 10 minutes in a DNA origami buffer, then rinsed with 40 µl of a rinsing buffer containing 200 mM HEPES, 2.4 M NaCl, 100 mM MgCl$_2$, 100 mM KCl, 0.10% Tween-20, and 0.001% Lipidure CM5206 at pH 7.4. After rinsing, glass chips were imaged by confocal laser scanning microscopy at 488 nm to detect deposited protein conjugates on the patterned glass surface. After the initial imaging, chips were incubated with a blocking buffer containing the same components as the rinsing buffer with 100 mg/ml dextran sulfate. Chips were incubated with 40 µl of blocking buffer for 60 mins, then rinsed again with 40 µl of rinsing buffer. Chips were subsequently incubated with 25 µl of B1 aptamer (his-tag affinity target) labeled with Alexa-Fluor 647 nm fluorescent dye. Chips were imaged at 647 nm to using a Thorlabs confocal laser scanning microscope.

Figure 21B:
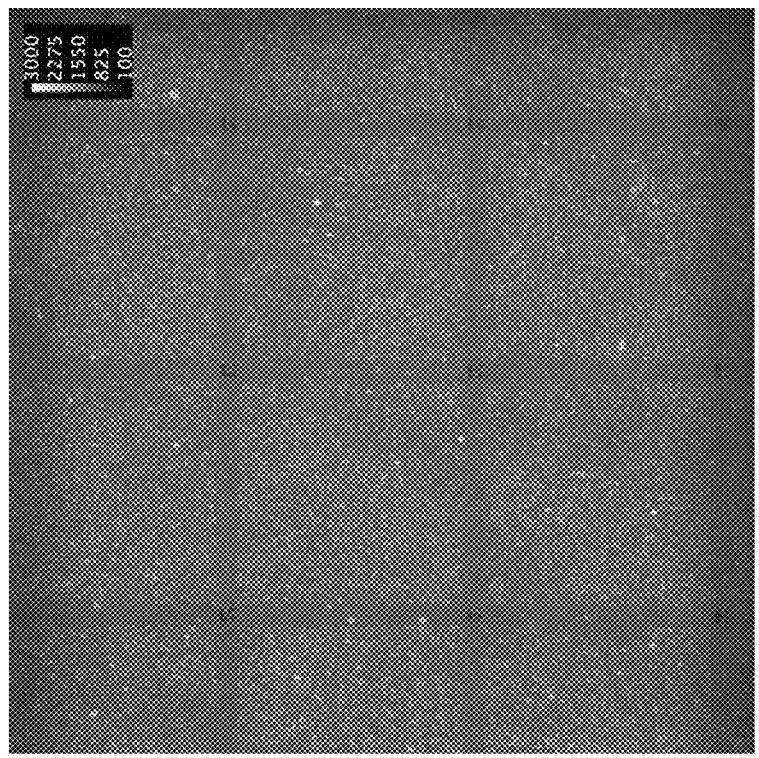
FIGS. 21A and 21B show SNAP-protein conjugate deposition on a patterned array.
Figure 21A:
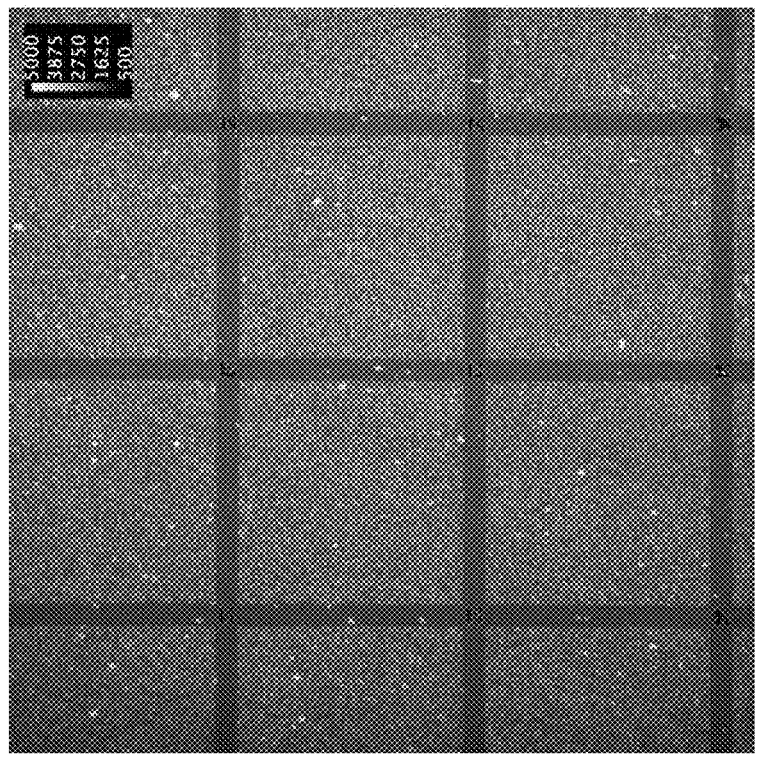

FIG. 21A shows fluorescence microscopy results at 488 nm for DNA origami-Ubi-His conjugates deposited on the patterned glass arrays. DNA origami are observed to have deposited on the array with nearly complete occupancy of binding sites. FIG. 21B shows imaging at 647 nm of the same deposited Ubi-His conjugates imaged with B1 aptamer (positive control). When imaged with the his-tag specific labeled affinity reagents, the grid deposition pattern is again observed, confirming the co-localization of the DNA origami and the conjugated proteins.

Example 7. SNAP Synthesis and Purification

A plurality of tile-shaped SNAPs are formed by combining M13 phage genome scaffold strands with pluralities of 218 differing oligonucleotides, including a plurality of TCO-terminated oligonucleotides that are configured to couple to an analyte. The oligonucleotides are combined in a DNA origami buffer comprising 100 mM MgCl$_2$ and heated to 95° C. After heating, the oligonucleotides are allowed to slowly cool to 20° C. thereby permitting annealing of oligonucleotides into SNAP structures. After SNAP formation, SNAPs are purified from excess oligonucleotides on an HPLC system containing a size-exclusion chromatography column. Surprisingly, it is found that a glycan-specific column effectively purifies formed SNAPs with minimal residual oligonucleotides or other unwanted components.

Example 8. SNAP Synthesis and Purification

SNAPs were synthesized via the method described in Example 7. Synthesized SNAPs were substantially square DNA origami structures with an approximately 83 nanometer (nm) edge length. Each square SNAP contained 65 oligonucleotides with pendant handles for binding of additional components to a SNAP via complementary oligonucleotide conjugation to pendant groups: 1 pendant single-stranded DNA handle for coupling an analyte to an upper display face, 20 pendant single-stranded DNA handles for coupling a SNAP to a surface, and 44 pendant single-stranded DNA handles for coupling detectable fluorescent labels to the 4 edges of the SNAP (11 per side). All oligonucleotide sequences were designed using CAD-NANO2 software.

Table I contains sequence listings for coupling regions of SNAP oligonucleotides. SEQ ID NO: 1 is the sequence listing for the coupling region of an oligonucleotide that is configured to couple to a complementary oligonucleotide that is conjugated to an analyte. SEQ ID NO: 2 is the sequence listing for the coupling region of an oligonucleotide that is configured to couple to a complementary oligonucleotide that is conjugated to the surface of a solid support. SEQ ID NO: 3 is the sequence listing for the coupling region of an oligonucleotide that is configured to couple to a complementary oligonucleotide that is conjugated to a fluorescent Alexa-Fluor™ 488 dye molecule.

Table II contains sequence listings for the 217 staple oligonucleotides utilized to form the SNAPs with 20 pendant surface-linked moieties. Pendant regions of the 65 coupling oligonucleotides are highlighted in bold text. All staple oligonucleotides listed in Table III were combined with M13mp18 single-stranded phage genomic DNA to fold the DNA origami structure.

TABLE II

| SEQ ID | Oligonucleotide Type | 5' - 3' DNA Sequence Listing |
| --- | --- | --- |
| 1 | Analyte Coupling | TTTCACTCACCTCCATCTCCACTCCTACCCA TCCAACTCCCAC |
| 2 | Surface Coupling | TTTTACCATCTTCCTCTCCAC |
| 3 | Label Coupling | TTTAACTACTCCCACTCTCACCCTCACCCTA CTCCAACTCAAC |

TABLE III

| SEQ ID | 5' - 3' DNA Sequence Listing |
|---|---|
| 4 | TCATTTGCTAATAGTAGTAGCATT |
| 5 | CAACTAAAGTACGGTGGGATGGCT |
| 6 | CATTATTAGCAAAAGAAGTTTTGC |
| 7 | ACCCTCATTCAGGGATAGCAAGCC |
| 8 | TTAGGATTAGCGGGGTGGAACCTA |
| 9 | AGGCCGGAACCAGAGCCACCACCG |
| 10 | AGAATATCAGACGACGACAATAAA |
| 11 | TCATATGCGTTATACAAAGGCGTT |
| 12 | CGGGAGAATTTAATGGAAACAGTA |
| 13 | GCGCGTACTTTCCTCGTTAGAATC |
| 14 | AAAGCCGGCGAACGTGTGCCGTAA |
| 15 | AATTCCACGTTTGCGTATTGGGCG |
| 16 | TTAAGAGGGTCCAATACTGCGGATAGCGAG |
| 17 | AGGCTTTTCAGGTAGAAAGATTCAATTACC |
| 18 | TTATGCGATTGACAAGAACCGGAGGTCAAT |
| 19 | CATAAGGGACACTAAAACACTCACATTAAA |
| 20 | CGGGTAAAATTCGGTCGCTGAGGAATGACA |
| 21 | GTCTCTGACACCCTCAGAGCCACATCAAAA |
| 22 | TCACCGGAAACGTCACCAATGAATTATTCA |
| 23 | TTAAAGGTACATATAAAAGAAACAAACGCA |
| 24 | ATAATAACTCAGAGAGATAACCCGAAGCGC |
| 25 | ATTAGACGGAGCGTCTTTCCAGAGCTACAA |
| 26 | TATATAACGTAAATCGTCGCTATATTTGAA |
| 27 | TTACCTTTACAATAACGGATTCGCAAAATT |
| 28 | ATTTGCACCATTTTGCGGAACAAATTTGAG |
| 29 | GATTTAGATTGCTGAACCTCAAAGTATTAA |
| 30 | CACCGCCTGAAAGCGTAAGAATACATTCTG |
| 31 | TGAGTGTTCAGCTGATTGCCCTTGCGCGGG |
| 32 | GAGAGGCGACAACATACGAGCCGCTGCAGG |
| 33 | TCGACTCTGAAGGGCGATCGGTGCGGCCTC |
| 34 | AGGAAGATCATTAAATGTGAGCGTTTTTAA |
| 35 | CCAATAGGAAACTAGCATGTCAAGGAGCAA |
| 36 | TAGAGCTTCAGACCGGAAGCAAACCTATTATA |
| 37 | GTCAGAAGATTGAATCCCCCTCAACCTCGTTT |
| 38 | AAATATTCCAAAGCGGATTGCATCGAGCTTCA |
| 39 | ACCAGACGGAATACCACATTCAACGAGATGGT |
| 40 | AGATTTAGACGATAAAAACCAAAAATCGTCAT |
| 41 | AGTCAGGACATAGGCTGGCTGACCTTTGAAAG |
| 42 | TTAATTTCCAACGTAACAAAGCTGTCCATGTT |

TABLE III-continued

| SEQ ID | 5' - 3' DNA Sequence Listing |
|---|---|
| 43 | GAGTAATCTTTTAAGAACTGGCTCCGGAACAA |
| 44 | ACCCAAATAACTTTAATCATTGTGATCAGTTG |
| 45 | ACTTAGCCATTATACCAAGCGCGAGAGGACTA |
| 46 | AAAAGAATAACCGAACTGACCAACTTCATCAA |
| 47 | AAGACTTTGGCCGCTTTTGCGGGATTAAACAG |
| 48 | GAGTTAAATTCATGAGGAAGTTTCTCTTTGAC |
| 49 | CTTGATACTGAAAATCTCCAAAAAAGCGGAGT |
| 50 | TTTCACGTCGATAGTTGCGCCGACCTTGCAGG |
| 51 | TTATTCTGACTGGTAATAAGTTTTAACAAATA |
| 52 | AATCCTCAACCAGAACCACCACCAGCCCCCTT |
| 53 | GAGCCGCCTTAAAGCCAGAATGGAGATGATAC |
| 54 | ATTAGCGTCCGTAATCAGTAGCGAATTGAGGG |
| 55 | GCCATTTGCAAACGTAGAAAATACCTGGCATG |
| 56 | AGGGAAGGATAAGTTTATTTTGTCAGCCGAAC |
| 57 | AGGTGGCAGAATTATCACCGTCACCATTAGCA |
| 58 | AAAGTTACGCCCAATAATAAGAGCAGCCTTTA |
| 59 | CGCTAATAGGAATACCCAAAAGAAATACATAA |
| 60 | CAGAGAGAACAAAATAAACAGCCATTAAATCA |
| 61 | AGATTAGTATATAGAAGGCTTATCCAAGCCGT |
| 62 | CAAATCAGTGCTATTTTGCACCCAGCCTAATT |
| 63 | AAATAAGAACTTTTTCAAATATATCTGAGAGA |
| 64 | CTACCTTTAGAATCCTTGAAAACAAGAAAACA |
| 65 | TTTCCCTTTTAACCTCCGGCTTAGCAAAGAAC |
| 66 | AAATTAATACCAAGTTACAAAATCCTGAATAA |
| 67 | CTTTGAATTACATTTAACAATTTCTAATTAAT |
| 68 | GTAGATTTGTTATTAATTTTAAAAAACAATTC |
| 69 | TGGAAGGGAGCGGAATTATCATCAACTAATAG |
| 70 | AACATTATGTAAAACAGAAATAAATTTTACAT |
| 71 | CCAGAAGGTTAGAACCTACCATATCCTGATTG |
| 72 | ATTAGAGCAATATCTGGTCAGTTGCAGCAGAA |
| 73 | GCATCACCAGTATTAGACTTTACAGTTTGAGT |
| 74 | CCTCAATCCGTCAATAGATAATACAGAAACCA |
| 75 | GATAAAACTTTTTGAATGGCTATTTTCACCAG |
| 76 | AGACAATAAGAGGTGAGGCGGTCATATCAAAC |
| 77 | TCACACGATGCAACAGGAAAAACGGAAGAACT |
| 78 | CCAGCCATCCAGTAATAAAAGGGACGTGGCAC |
| 79 | AGCACTAAAAAGGGCGAAAAACCGAAATCCCT |
| 80 | TATAAATCGAGAGTTGCAGCAAGCGTCGTGCC |

TABLE III-continued

| SEQ ID | 5' - 3' DNA Sequence Listing |
|---|---|
| 81 | GGCCCTGAAAAAGAATAGCCCGAGCGTGGACT |
| 82 | AGCTGCATAGCCTGGGGTGCCTAAGTAAAACG |
| 83 | AAGTGTAATAATGAATCGGCCAACCACCGCCT |
| 84 | GAATTCGTGCCATTCGCCATTCAGTTCCGGCA |
| 85 | ACGGCCAGTACGCCAGCTGGCGAACATCTGCC |
| 86 | ACTGTTGGAGAGGATCCCCGGGTACCGCTCAC |
| 87 | TTCGCTATTGCCAAGCTTGCATGCGAAGCATA |
| 88 | AGTTTGAGATTCTCCGTGGGAACAATTCGCAT |
| 89 | TTCATCAACGCACTCCAGCCAGCTGCTGCGCA |
| 90 | CCCGTCGGGGACGACGACAGTATCGGGCCTC |
| 91 | TAAATTTTTGATAATCAGAAAAGCACAAAGGC |
| 92 | ACCCCGGTTGTTAAATCAGCTCATAGTAACAA |
| 93 | TATCAGGTAAATCACCATCAATATCAATGCCT |
| 94 | AGACAGTCCATTGCCTGAGAGTCTTCATATGT |
| 95 | GACGGAAAACCATCGATAGCAGCATTGCCATCTTTTCATACACCCTCA |
| 96 | TGCCAGTTATAACATAAAAACAGGACAAGAATTGAGTTAACAGAAGGA |
| 97 | TGCCACTACTTTTTTTGCCACCCTC |
| 98 | AACTGAACATTTTTTTGAATAACC |
| 99 | GCCACGCTGTTTTTTTACCAGTGAG |
| 100 | CAAAAATAATTTTTTTGTTTAGAC |
| 101 | GATACATTTCGCTTTTTTGACCCTGTAAT |
| 102 | ACCGTACTCAGGTTTTTGATCTAAAGTTT |
| 103 | AACATGTAATTTTTTTGAAACCAATCAA |
| 104 | GCGTAACCACCATTTTTGAGTAAAAGAGT |
| 105 | CAGAGGGGTTTTGCCTTCCTGTAGCCAGCT |
| 106 | GAACCGCCTCTTTACCTAAAACGAAAGAGGC |
| 107 | CATAAATCAATTTAGTCAGAGGGTAATTGAG |
| 108 | CCAGGGTGGTTTTGCAAATGAAAAATCTAAA |
| 109 | ACAACCATTTTTTCATACATGGCTTTTAAGCGCA |
| 110 | TTTTATCTTTTTTATCCAATCGCAAGAGTTGGGT |
| 111 | GCCAACATTTTTTCCACTATTAAAGAATAGGGT |
| 112 | ACAAGAGTTTTTTCGCGTTTTAATTCAAAAGA |
| 113 | TGGATAGCAAGCCCGATTTTAATCGTAAACGCCAT |
| 114 | AGAACCGCATTTACCGTTTTACCGATATATACGTAA |
| 115 | TTGCTTCTTATATGTATTTTACGCTAACGGAGAATT |
| 116 | ACGGGCAAGTTCCAGTTTTTTCTGACCTGCAACAGT |
| 117 | GAGAATAGAAAGGAACAACTATTTTCTCAAGAGAAGGA |
| 118 | TTTTATTTTCATCGTAGGAATTTTTAGCCTGTTTAGTA |

TABLE III-continued

| SEQ ID | 5' - 3' DNA Sequence Listing |
|---|---|
| 119 | CAAACTATCGGCCTTGCTGGTTTTTGAGCTTGACGGGG |
| 120 | GAGTAATGTGTAGGTAAAGATTTTTGTTTTAAATATG |
| 121 | AGGACAGATGATTTTTTCACCAGTAGCACCATTACCGACTTGA |
| 122 | ATTAAGACTCCTTTTTAATATACAGTAACAGTACCGAAATTGC |
| 123 | GACAACTCGTATTTTTTCCTGTGTGAAATTGTTATCCGAGCTC |
| 124 | CCGCTTCTGGTTTTTTCGTTAATAAAACGAACTAAATTATACC |
| 125 | TGTCGTCTCAGCCCTCATATTTTTTCGCCACCCTCAGGTGTATC |
| 126 | TAATCGGCCATCCTAATTTTTTTTTTTTCGAGCCAACAACGCC |
| 127 | CTGTCCATTTTTATAATCATTTTTTTCTTAATGCGCCCACGCTGC |
| 128 | ACTTTTGCATCGGTTGTACTTTTTTTAACCTGTTTAGGACCATTA |
| 129 | AAGCGAACAATTGCTGAATATAATGCTGTATTTTTTTGTGAGAAAGGCCGG |
| 130 | AGGAGTGTAAACATGAAAGTATTAAGAGGCTTTTTTTGCGAATAATAATTT |
| 131 | GCGAGAAAATAAACACCGGAATCATAATTATTTTTTTCGCCCAATAGCAAG |
| 132 | CCAACGTCATCGGAACCCTAAAGGGAGCCCTTTTTTTGAACAATATTACCG |
| 133 | GGAATTAGAGCTTTTTTTTCAGACCAGGCGCGTTGGGAAGATTTTTTTTCCAGGCAAAGC |
| 134 | AATCATGGTCATTTTTTTTTTGCCCGAACTCAGGTTTAACTTTTTTTTCAGTATGTTAG |
| 135 | TTTCATTGAGTAGATTTAGTTTCTATATTT |
| 136 | AACAGTTAGGTCTTTACCCTGATCCAACAG |
| 137 | GTGAATATAGTAAATTGGGCTTTAATGCAG |
| 138 | CTCAGCAGGCTACAGAGGCTTTAACAAAGT |
| 139 | GTTAGTAACTTTCAACAGTTTCAAAGGCTC |
| 140 | GTACCAGGTATAGCCCGGAATAGAACCGCC |
| 141 | GCCAGCAGCCTTGATATTCACAAACGGGGT |
| 142 | TAGAAAAGGCGACATTCAACCGCAGAATCA |
| 143 | ATCCCAAAAAAATGAAAATAGCAAGAAACA |
| 144 | CTTATCACTCATCGAGAACAAGCGGTATTC |
| 145 | CCAGTATGAATCGCCATATTTAGTAATAAG |
| 146 | GCTTAGAATCAAAATCATAGGTTTTAGTTA |
| 147 | ATTATCAGTTTGGATTATACTTGCGCAGAG |
| 148 | ATGCGCGTACCGAACGAACCACGCAAATCA |
| 149 | TTAACCGTCACTTGCCTGAGTACTCATGGA |
| 150 | GGAAGGGGGCAAGTGTAGCGGTGCTACAGG |
| 151 | CTGGTTTGTTCCGAAATCGGCATCTATCAG |
| 152 | GTGCTGCCCCAGTCACGACGTTTGAGTGAG |
| 153 | CAGGAAGTAATATTTTGTTAAAAACGGCGG |

TABLE III-continued

| SEQ ID | 5' - 3' DNA Sequence Listing |
|---|---|
| 154 | CCTTTATCATATATTTTAAATGGATATTCA |
| 155 | CCCCAGCGGGAACGAGGCGCAGACTATTCATT |

Analyte-Binding Oligonucleotides

| 156 | AACCGAGGGCAAAGACACCACGGATAAATATTTTTCACTCACCTC CATCTCCACTCCTACCCATCCAACTCCCAC |
|---|---|

Surface-Binding Oligonucleotides

| 157 | GTCAGGAAGAGGTCATTTTTGCTCTGGAAGTTTTACCATCTTCCTC TCCAC |
|---|---|
| 158 | ATACATACAACACTATCATAACATGCTTTATTTTACCATCTTCCTC TCCAC |
| 159 | ACAACGGAAATCCGCGACCTGCCTCATTCATTTTACCATCTTCCTC TCCAC |
| 160 | CAAAAGGTTCGAGGTGAATTTCTCGTCACCTTTTACCATCTTCCTC TCCAC |
| 161 | ATTTCATGACCGTGTGATAAATAATTCTTATTTTACCATCTTCCTC TCCAC |
| 162 | GCGAATTATGAAACAAACATCATAGCGATATTTTACCATCTTCCT CTCCAC |
| 163 | ACAGTTGTTAGGAGCACTAACATATTCCTGTTTTACCATCTTCCTC TCCAC |
| 164 | AATACCTATTTACATTGGCAGAAGTCTTTATTTTACCATCTTCCTC TCCAC |
| 165 | CCATGTACCGTAACACTGTAGCATTCCACAGATTCCAGACTTTTAC CATCTTCCTCTCCAC |
| 166 | CTAAACAGGAGGCCGATAATCCTGAGAAGTGTCACGCAAATTTTA CCATCTTCCTCTCCAC |
| 167 | CAGTGCCCCCCCTGCCTATTTCTTTGCTCATTTTACCATCTTCCTCT CCAC |
| 168 | AGTTTGCGCATTTTCGGTCATAGAGCCGCCTTTTACCATCTTCCTCT CCAC |
| 169 | ATGAAATGAAAAGTAAGCAGATACAATCAATTTTACCATCTTCCT CTCCAC |
| 170 | TAAGAACGGAGGTTTTGAAGCCTATTATTTTTTTACCATCTTCCTC TCCAC |
| 171 | GGCGATGTTTTTGGGGTCGAGGGCGAGAAATTTTACCATCTTCCT CTCCAC |
| 172 | CTAACTCCCAGTCGGGAAACCTGGTCCACGTTTTACCATCTTCCTC TCCAC |
| 173 | ATTGACCCGCATCGTAACCGTGAGGGGGATTTTTACCATCTTCCTC TCCAC |
| 174 | ACCGTTCATTTTTGAGAGATCTCCCAAAAATTTTACCATCTTCCTC TCCAC |
| 175 | AGCTAATGCAGAACGCGAGAAAAATAATATCCTGTCTTTCTTTTAC CATCTTCCTCTCCAC |
| 176 | AATCATACAGGCAAGGCAGAGCATAAAGCTAAGGGAGAAGTTTTA CCATCTTCCTCTCCAC |

Label-Binding Oligonucleotides

| 177 | TTTGGTGGCATCAATTCTAGGGCGCGAGCTGAAAATTTAACTACTC CCACTCTCACCCTCACCCTACTCCAACTCAAC |
|---|---|

TABLE III-continued

| SEQ ID | 5' - 3' DNA Sequence Listing |
|---|---|
| 178 | TTTTCCCAATTCTGCGAACCCATATAACAGTTGATTTTAACTACTC CCACTCTCACCCTCACCCTACTCCAACTCAAC |
| 179 | TTTATTGCTCCTTTTGATATTAGAGAGTACCTTTATTTAACTACTCC CACTCTCACCCTCACCCTACTCCAACTCAAC |
| 180 | TTTCCATAAATCAAAAATCCAGAAAACGAGAATGATTTAACTACT CCCACTCTCACCCTCACCCTACTCCAACTCAAC |
| 181 | TTTCGAGGCATAGTAAGAGACGCCAAAAGGAATTATTTAACTACT CCCACTCTCACCCTCACCCTACTCCAACTCAAC |
| 182 | TTTGAAACACCAGAACGAGAGGCTTGCCCTGACGATTTAACTACTC CCACTCTCACCCTCACCCTACTCCAACTCAAC |
| 183 | TTTCTGATAAATTGTGTCGAGATTTGTATCATCGCTTTAACTACTCC CACTCTCACCCTCACCCTACTCCAACTCAAC |
| 184 | TTTGAACGAGGGTAGCAACGCGAAAGACAGCATCGTTTAACTACT CCCACTCTCACCCTCACCCTACTCCAACTCAAC |
| 185 | TTTGGTTTATCAGCTTGCTAGCCTTTAATTGTATCTTTAACTACTCC CACTCTCACCCTCACCCTACTCCAACTCAAC |
| 186 | TTTGGGATTTTGCTAAACAAATGAATTTTCTGTATTTTAACTACTCC CACTCTCACCCTCACCCTACTCCAACTCAAC |
| 187 | TTTACAAACTACAACGCCTGAGTTTCGTCACCAGTTTTAACTACTC CCACTCTCACCCTCACCCTACTCCAACTCAAC |
| 188 | TTTAGCCACCACCCTCATTGAACCGCCACCCTCAGTTTAACTACTC CCACTCTCACCCTCACCCTACTCCAACTCAAC |
| 189 | TTTGAGAGGGTTGATATAAGCGGATAAGTGCCGTCTTTAACTACTC CCACTCTCACCCTCACCCTACTCCAACTCAAC |
| 190 | TTTGTATAAACAGTTAATGTTGAGTAACAGTGCCCTTTAACTACTC CCACTCTCACCCTCACCCTACTCCAACTCAAC |
| 191 | TTTGCAGGTCAGACGATTGTTGACAGGAGGTTGAGTTTAACTACTC CCACTCTCACCCTCACCCTACTCCAACTCAAC |
| 192 | TTTTAGCGCGTTTTCATCGCTTTAGCGTCAGACTGTTTAACTACTCC CACTCTCACCCTCACCCTACTCCAACTCAAC |
| 193 | TTTGCGCCAAAGACAAAAGTTCATATGGTTTACCATTTAACTACTC CCACTCTCACCCTCACCCTACTCCAACTCAAC |
| 194 | TTTCCGAAGCCCTTTTTAAAGCAATAGCTATCTTATTTAACTACTCC CACTCTCACCCTCACCCTACTCCAACTCAAC |
| 195 | TTTTTTTTTGTTTAACGTCTCCAAATAAGAAACGATTTAACTACTCC CACTCTCACCCTCACCCTACTCCAACTCAAC |
| 196 | TTTAACCTCCCGACTTGCGGCGAGGCGTTTTAGCGTTTAACTACTC CCACTCTCACCCTCACCCTACTCCAACTCAAC |
| 197 | TTTTAAACCAAGTACCGCATTCCAAGAACGGGTATTTTAACTACTC CCACTCTCACCCTCACCCTACTCCAACTCAAC |
| 198 | TTTAGATAAGTCCTGAACACCTGTTTATCAACAATTTTAACTACTC CCACTCTCACCCTCACCCTACTCCAACTCAAC |
| 199 | TTTGTAAAGTAATTCTGTCAAAGTACCGACAAAAGTTTAACTACTC CCACTCTCACCCTCACCCTACTCCAACTCAAC |
| 200 | TTTAGTAGGGCTTAATTGAAAAGCCAACGCTCAACTTTAACTACTC CCACTCTCACCCTCACCCTACTCCAACTCAAC |
| 201 | TTTAATGGTTTGAAATACCCTTCTGACCTAAATTTTTTAACTACTCC CACTCTCACCCTCACCCTACTCCAACTCAAC |
| 202 | TTTAGTCAATAGTGAATTTTAAGACGCTGAGAAGTTTTAACTACTC CCACTCTCACCCTCACCCTACTCCAACTCAAC |
| 203 | TTTTGAGCAAAAGAAGATGATTCATTTCAATTACCTTTAACTACTC CCACTCTCACCCTCACCCTACTCCAACTCAAC |

TABLE III-continued

| SEQ ID | 5' - 3' DNA Sequence Listing |
|---|---|
| 204 | TTTCAATATAATCCTGATTGATGATGGCAATTCATTTTAACTACTCCCACTCTCACCCTCACCCTACTCCAACTCAAC |
| 205 | TTTGTTATCTAAAATATCTAAAGGAATTGAGGAAGTTTAACTACTCCCACTCTCACCCTCACCCTACTCCAACTCAAC |
| 206 | TTTACATCGCCATTAAAAAAACTGATAGCCCTAAATTTAACTACTCCCACTCTCACCCTCACCCTACTCCAACTCAAC |
| 207 | TTTTCGTCTGAAATGGATTACATTTTGACGCTCAATTTAACTACTCCCACTCTCACCCTCACCCTACTCCAACTCAAC |
| 208 | TTTTTGATTAGTAATAACATTGTAGCAATACTTCTTTTAACTACTCCCACTCTCACCCTCACCCTACTCCAACTCAAC |
| 209 | TTTAGGAACGGTACGCCAGTAAAGGGATTTTAGACTTTAACTACTCCCACTCTCACCCTCACCCTACTCCAACTCAAC |
| 210 | TTTGAGCACGTATAACGTGCTATGGTTGCTTTGACTTTAACTACTCCCACTCTCACCCTCACCCTACTCCAACTCAAC |
| 211 | TTTCGGGCGCTAGGGCGCTAAGAAAGCGAAAGGAGTTTAACTACTCCCACTCTCACCCTCACCCTACTCCAACTCAAC |
| 212 | TTTATCACCCAAATCAAGTGCCCACTACGTGAACCTTTAACTACTCCCACTCTCACCCTCACCCTACTCCAACTCAAC |
| 213 | TTTATCCTGTTTGATGGTGGCCCCAGCAGGCGAAATTTAACTACTCCCACTCTCACCCTCACCCTACTCCAACTCAAC |
| 214 | TTTGCTCACTGCCCGCTTTACATTAATTGCGTTGCTTTAACTACTCCCACTCTCACCCTCACCCTACTCCAACTCAAC |
| 215 | TTTGTAACGCCAGGGTTTTAAGGCGATTAAGTTGGTTTAACTACTCCCACTCTCACCCTCACCCTACTCCAACTCAAC |
| 216 | TTTCGTTGGTGTAGATGGGGTAATGGGATAGGTCATTTAACTACTCCCACTCTCACCCTCACCCTACTCCAACTCAAC |
| 217 | TTTTTTAAATTGTAAACGTATTGTATAAGCAAATATTTAACTACTCCCACTCTCACCCTCACCCTACTCCAACTCAAC |
| 218 | TTTGCCGGAGAGGGTAGCTTAGCTGATAAATTAATTTTAACTACTCCCACTCTCACCCTCACCCTACTCCAACTCAAC |
| 219 | TTTAAATTTTTAGAACCCTTTCAACGCAAGGATAATTTAACTACTCCCACTCTCACCCTCACCCTACTCCAACTCAAC |
| 220 | TTTTAAGCAATAAAGCCTCAAAGAATTAGCAAAATTTTAACTACTCCCACTCTCACCCTCACCCTACTCCAACTCAAC |

Example 9. SNAP Synthesis and Purification

SNAPs were synthesized via the method described in Example 7. Synthesized SNAPs were designed to be substantially square DNA origami structures with an approximately 83 nanometer (nm) edge length. Each square SNAP contained 109 oligonucleotides with pendant handles for binding of additional components to a SNAP via complementary oligonucleotide conjugation to pendant groups: 1 pendant single-stranded DNA handle for coupling an analyte to an upper display face, 64 pendant single-stranded DNA handles for coupling a SNAP to a surface, and 44 discrete, pendant single-stranded DNA handles for coupling detectable fluorescent labels to the 4 edges of the SNAP (11 per side). All oligonucleotide sequences were designed using CADNANO2 software.

Table I contains sequence listings for coupling regions of SNAP oligonucleotides. SEQ ID NO:1 is the sequence listing for the coupling region of an oligonucleotide that is configured to couple to a complementary oligonucleotide that is conjugated to an analyte. SEQ ID NO: 2 is the sequence listing for the coupling region of an oligonucleotide that is configured to couple to a complementary oligonucleotide that is conjugated to the surface of a solid support. SEQ ID NO: 3 is the sequence listing for the coupling region of an oligonucleotide that is configured to couple to a complementary oligonucleotide that is conjugated to a fluorescent Alexa-Fluor™ 488 dye molecule. The sequences listed in Table II were each designed to exclude the nucleotide guanosine, thereby avoiding the likelihood of self-complementarity (i.e., the formation of secondary structures). It was expected that pendant single-stranded DNA surface-interacting moieties (e.g., SEQ ID NO: 2) would be more likely to bind to complementary, surface-linked oligonucleotides at ambient temperatures (e.g., about 20° C.) if no secondary structures were present Table III contains sequence listings for the 217 staple oligonucleotides utilized to form the SNAPs with 64 pendant surface-linked moieties. Pendant regions of the 65 coupling oligonucleotides are highlighted in bold text. All staple oligonucleotides listed in Table IV were combined with M13mp18 single-stranded phage genomic DNA to fold the DNA origami structure.

TABLE IV

| SEQ ID | 5' - 3' DNA Sequence Listing |
|---|---|
| 221 | TCATTTGCTAATAGTAGTAGCATT |
| 222 | TTTCATTGAGTAGATTTAGTTTCTATATTT |
| 223 | AACAGTTAGGTCTTTACCCTGATCCAACAG |
| 224 | TAGAGCTTCAGACCGGAAGCAAACCTATTATA |
| 225 | AGATTTAGACGATAAAAACCAAAAATCGTCAT |
| 226 | CATTATTAGCAAAAGAAGTTTTGC |
| 227 | GTGAATATAGTAAATTGGGCTTTAATGCAG |
| 228 | AGGCTTTTCAGGTAGAAAGATTCAATTACC |
| 229 | ACCAGACGGAATACCACATTCAACGAGATGGT |
| 230 | AAAAGAATAACCGAACTGACCAACTTCATCAA |
| 231 | CCCCAGCGGGAACGAGGCGCAGACTATTCATT |
| 232 | CTCAGCAGGCTACAGAGGCTTTAACAAAGT |
| 233 | CATAAGGGACACTAAAACACTCACATTAAA |
| 234 | ACTTAGCCATTATACCAAGCGCGAGAGGACTA |
| 235 | TTTCACGTCGATAGTTGCGCCGACCTTGCAGG |
| 236 | CGGGTAAAATTCGGTCGCTGAGGAATGACA |
| 237 | GTTAGTAACTTTCAACAGTTTCAAAGGCTC |
| 238 | CTTGATACTGAAAATCTCCAAAAAAGCGGAGT |
| 239 | ACCCTCATTCAGGGATAGCAAGCC |
| 240 | GTACCAGGTATAGCCCGGAATAGAACCGCC |
| 241 | GCCAGCAGCCTTGATATTCACAAACGGGGT |
| 242 | TTATTCTGACTGGTAATAAGTTTTAACAAATA |
| 243 | GACGGAAAACCATCGATAGCAGCATTGCCATCTTTTCATACACCCTCA |
| 244 | AGGCCGGAACCAGAGCCACCACCG |
| 245 | TAGAAAAGGCGACATTCAACCGCAGAATCA |
| 246 | TCACCGGAAACGTCACCAATGAATTATTCA |
| 247 | ATTAGCGTCCGTAATCAGTAGCGAATTGAGGG |
| 248 | CGCTAATAGGAATACCCAAAAGAAATACATAA |
| 249 | TGCCAGTTATAACATAAAAACAGGACAAGAATTGAGTTAACAGAAGGA |
| 250 | ATCCCAAAAAAATGAAAATAGCAAGAAACA |
| 251 | ATAATAACTCAGAGAGATAACCCGAAGCGC |
| 252 | AAAGTTACGCCCAATAATAAGAGCAGCCTTTA |
| 253 | ATTAGACGGAGCGTCTTTCCAGAGCTACAA |
| 254 | CTTATCACTCATCGAGAACAAGCGGTATTC |
| 255 | AGATTAGTATATAGAAGGCTTATCCAAGCCGT |

TABLE IV-continued

| SEQ ID | 5' - 3' DNA Sequence Listing |
|---|---|
| 256 | AGAATATCAGACGACGACAATAAA |
| 257 | CCAGTATGAATCGCCATATTTAGTAATAAG |
| 258 | GCTTAGAATCAAAATCATAGGTTTTAGTTA |
| 259 | CTTTGAATTACATTTAACAATTTCTAATTAAT |
| 260 | CGGGAGAATTTAATGGAAACAGTA |
| 261 | CTACCTTTAGAATCCTTGAAAACAAGAAAACA |
| 262 | ATTATCAGTTTGGATTATACTTGCGCAGAG |
| 263 | TTACCTTTACAATAACGGATTCGCAAAATT |
| 264 | GCATCACCAGTATTAGACTTTACAGTTTGAGT |
| 265 | CCTCAATCCGTCAATAGATAATACAGAAACCA |
| 266 | TGGAAGGGAGCGGAATTATCATCAACTAATAG |
| 267 | AGACAATAAGAGGTGAGGCGGTCATATCAAAC |
| 268 | ATGCGCGTACCGAACGAACCACGCAAATCA |
| 269 | GATTTAGATTGCTGAACCTCAAAGTATTAA |
| 270 | CACCGCCTGAAAGCGTAAGAATACATTCTG |
| 271 | GATAAAACTTTTTGAATGGCTATTTTCACCAG |
| 272 | TTAACCGTCACTTGCCTGAGTACTCATGGA |
| 273 | GCGCGTACTTTCCTCGTTAGAATC |
| 274 | GGAAGGGGCAAGTGTAGCGGTGCTACAGG |
| 275 | CTGGTTTGTTCCGAAATCGGCATCTATCAG |
| 276 | AGCACTAAAAAGGGCGAAAAACCGAAATCCCT |
| 277 | AAGTGTAATAATGAATCGGCCAACCACCGCCT |
| 278 | AATTCCACGTTTGCGTATTGGGCG |
| 279 | GTGCTGCCCCAGTCACGACGTTTGAGTGAG |
| 280 | GAGAGGCGACAACATACGAGCCGCTGCAGG |
| 281 | AGCTGCATAGCCTGGGGTGCCTAAGTAAAACG |
| 282 | TTCATCAACGCACTCCAGCCAGCTGCTGCGCA |
| 283 | CCCGTCGGGGACGACGACAGTATCGGGCCTC |
| 284 | CAGGAAGTAATATTTTGTTAAAAACGGCGG |
| 285 | AGGAAGATCATTAAATGTGAGCGTTTTTAA |
| 286 | AGTTTGAGATTCTCCGTGGGAACAATTCGCAT |
| 287 | AGACAGTCCATTGCCTGAGAGTCTTCATATGT |
| 288 | CCAATAGGAAACTAGCATGTCAAGGAGCAA |
| 289 | CCTTTATCATATATTTTAAATGGATATTCA |
| 290 | TATCAGGTAAATCACCATCAATATCAATGCCT |
| 291 | ACTTTTGCATCGGTTGTACTTTTTTAACCTGTTTAGGACCATTA |
| 292 | GAGTAATGTGTAGGTAAAGATTTTTGTTTTAAATATG |
| 293 | ACAAGAGTTTTTTCGCGTTTTAATTCAAAAGA |
| 294 | CAAAAATAATTTTTTTGTTTAGAC |

TABLE IV-continued

| SEQ ID | 5' - 3' DNA Sequence Listing |
|---|---|
| 295 | CCGCTTCTGGTTTTTTCGTTAATAAAACGAACTAAATTATACC |
| 296 | GAACCGCCTCTTTACCTAAAACGAAAGAGGC |
| 297 | AGAACCGCATTTACCGTTTTACCGATATATACGTAA |
| 298 | AGGAGTGTAAACATGAAAGTATTAAGAGGCTTTTTTGCGAATAATAATTT |
| 299 | ACCGTACTCAGGTTTTTGATCTAAAGTTT |
| 300 | TGTCGTCTCAGCCCTCATATTTTTTCGCCACCCTCAGGTGTATC |
| 301 | GAGAATAGAAAGGAACAACTATTTTCTCAAGAGAAGGA |
| 302 | ACAACCATTTTTTCATACATGGCTTTTAAGCGCA |
| 303 | TGCCACTACTTTTTTTGCCACCCTC |
| 304 | AGGACAGATGATTTTTTCACCAGTAGCACCATTACCGACTTGA |
| 305 | AATCATGGTCATTTTTTTTTTGCCCGAACTCAGGTTTAACTTTTTTTCAGTATGTTAG |
| 306 | CATAAATCAATTTAGTCAGAGGGTAATTGAG |
| 307 | TTGCTTCTTATATGTATTTTACGCTAACGGAGAATT |
| 308 | GCGAGAAAATAAACACCGGAATCATAATTATTTTTTCGCCCAATAGCAAG |
| 309 | AACATGTAATTTTTTTGAAACCAATCAA |
| 310 | TAATCGGCCATCCTAATTTTTTTTTTTCGAGCCAACAACGCC |
| 311 | TTTTATTTTCATCGTAGGAATTTTTAGCCTGTTTAGTA |
| 312 | TTTTATCTTTTTTATCCAATCGCAAGAGTTGGGT |
| 313 | AACTGAACATTTTTTTGAATAACC |
| 314 | ATTAAGACTCCTTTTTAATATACAGTAACAGTACCGAAATTGC |
| 315 | CCAGGGTGGTTTTGCAAATGAAAAATCTAAA |
| 316 | ACGGGCAAGTTCCAGTTTTTTCTGACCTGCAACAGT |
| 317 | CCAACGTCATCGGAACCCTAAAGGGAGCCCTTTTTTTGAACAATATTACCG |
| 318 | GCGTAACCACCATTTTTGAGTAAAAGAGT |
| 319 | CTGTCCATTTTTATAATCATTTTTTTCTTAATGCGCCCACGCTGC |
| 320 | CAAACTATCGGCCTTGCTGGTTTTTGAGCTTGACGGGG |
| 321 | GCCAACATTTTTTCCACTATTAAAGAAATAGGGT |
| 322 | GCCACGCTGTTTTTTTACCAGTGAG |
| 323 | GACAACTCGTATTTTTTCCTGTGTGAAATTGTTATCCGAGCTC |
| 324 | GGAATTAGAGCTTTTTTTTCAGACCAGGCGCGTTGGGAAGATTTTTTTTCCAGGCAAAGC |
| 325 | CAGAGGGGGTTTTGCCTTCCTGTAGCCAGCT |
| 326 | TGGATAGCAAGCCCGATTTTAATCGTAAACGCCAT |
| 327 | AAGCGAACAATTGCTGAATATAATGCTGTATTTTTTGTGAGAAAGGCCGG |
| 328 | GATACATTTCGCTTTTTTGACCCTGTAAT |

TABLE IV-continued

| SEQ ID | 5' - 3' DNA Sequence Listing |
|---|---|

Analyte-Binding Oligonucleotides

| 329 | AACCGAGGGCAAAGACACCACGGATAAATATTTTTCACTCACCTCCA TCTCCACTCCTACCCATCCAACTCCCAC |

Surface-Binding Oligonucleotides

| 330 | GTCAGGAAGAGGTCATTTTTGCTCTGGAAGTTTTACCATCTTCCTCTC CAC |
| 331 | CAACTAAAGTACGGTGGGATGGCTTTTTACCATCTTCCTCTCCAC |
| 332 | AAATATTCCAAAGCGGATTGCATCGAGCTTCATTTTACCATCTTCCTC TCCAC |
| 333 | ATACATACAACACTATCATAACATGCTTTATTTTACCATCTTCCTCTC CAC |
| 334 | TTAAGAGGGTCCAATACTGCGGATAGCGAGTTTTACCATCTTCCTCTCC AC |
| 335 | GTCAGAAGATTGAATCCCCCTCAACCTCGTTTTTTACCATCTTCCTC TCCAC |
| 336 | GAGTAATCTTTTAAGAACTGGCTCCGGAACAATTTTACCATCTTCCTC TCCAC |
| 337 | ACCCAAATAACTTTAATCATTGTGATCAGTTGTTTTACCATCTTCCTC TCCAC |
| 338 | ACAACGGAAATCCGCGACCTGCCTCATTCATTTTACCATCTTCCTCTC CAC |
| 339 | AGTCAGGACATAGGCTGGCTGACCTTTGAAAGTTTTACCATCTTCCTC TCCAC |
| 340 | TTATGCGATTGACAAGAACCGGAGGTCAATTTTTACCATCTTCCTCTC CAC |
| 341 | TTAATTTCCAACGTAACAAAGCTGTCCATGTTTTTACCATCTTCCTC TCCAC |
| 342 | GAGTTAAATTCATGAGGAAGTTTCTCTTTGACTTTTACCATCTTCCTC TCCAC |
| 343 | CAAAAGGTTCGAGGTGAATTTCTCGTCACCTTTTACCATCTTCCTCTC CAC |
| 344 | AAGACTTTGGCCGCTTTTGCGGGATTAAACAGTTTTACCATCTTCCTC TCCAC |
| 345 | CCATGTACCGTAACACTGTAGCATTCCACAGATTCCAGACTTTTACCA TCTTCCTCTCCAC |
| 346 | CAGTGCCCCCCCTGCCTATTTCTTTGCTCATTTTACCATCTTCCTCTCC AC |
| 347 | TTAGGATTAGCGGGTGGAACCTATTTTACCATCTTCCTCTCCAC |
| 348 | GAGCCGCCTTAAAGCCAGAATGGAGATGATACTTTTACCATCTTCCT CTCCAC |
| 349 | AGTTTGCGCATTTTCGGTCATAGAGCCGCCTTTTACCATCTTCCTCTC CAC |
| 350 | GTCTCTGACACCCTCAGAGCCACATCAAAATTTTACCATCTTCCTCTC CAC |
| 351 | AATCCTCAACCAGAACCACCACCAGCCCCCTTTTTACCATCTTCCTC TCCAC |
| 352 | AGGTGGCAGAATTATCACCGTCACCATTAGCATTTTACCATCTTCCTC TCCAC |
| 353 | ATGAAATGAAAAGTAAGCAGATACAATCAATTTTACCATCTTCCTCT CCAC |

TABLE IV-continued

| SEQ ID | 5' - 3' DNA Sequence Listing |
|---|---|
| 354 | GCCATTTGCAAACGTAGAAAATACCTGGCATGTTTTACCATCTTCCTCTCCAC |
| 355 | TTAAAGGTACATATAAAAGAAACAAACGCATTTTACCATCTTCCTCTCCAC |
| 356 | AGGGAAGGATAAGTTTATTTTGTCAGCCGAACTTTTACCATCTTCCTCTCCAC |
| 357 | CAAATCAGTGCTATTTTGCACCCAGCCTAATTTTTTACCATCTTCCTCTCCAC |
| 358 | TAAGAACGGAGGTTTTGAAGCCTATTATTTTTTTACCATCTTCCTCTCAC |
| 359 | CAGAGAGAACAAAATAAACAGCCATTAAATCATTTTACCATCTTCCTCTCCAC |
| 360 | AGCTAATGCAGAACGCGAGAAAAATAATATCCTGTCTTTCTTTTACCATCTTCCTCTCCAC |
| 361 | ATTTCATGACCGTGTGATAAATAATTCTTATTTTACCATCTTCCTCTCCAC |
| 362 | TCATATGCGTTATACAAAGGCGTTTTTTACCATCTTCCTCTCCAC |
| 363 | TTTCCCTTTTAACCTCCGGCTTAGCAAAGAACTTTTACCATCTTCCTCTCCAC |
| 364 | AAATAAGAACTTTTTCAAATATATCTGAGAGATTTTACCATCTTCCTCTCCAC |
| 365 | GCGAATTATGAAACAAACATCATAGCGATATTTTACCATCTTCCTCTCCAC |
| 366 | TATATAACGTAAATCGTCGCTATATTTGAATTTTACCATCTTCCTCTCAC |
| 367 | AACATTATGTAAAACAGAAATAAATTTTACATTTTTACCATCTTCCTCTCCAC |
| 368 | CCAGAAGGTTAGAACCTACCATATCCTGATTGTTTTACCATCTTCCTCTCCAC |
| 369 | AAATTAATACCAAGTTACAAAATCCTGAATAATTTTACCATCTTCCTCTCCAC |
| 370 | ACAGTTGTTAGGAGCACTAACATATTCCTGTTTTACCATCTTCCTCTCCAC |
| 371 | GTAGATTTGTTATTAATTTTAAAAAACAATTCTTTTACCATCTTCCTCTCCAC |
| 372 | ATTTGCACCATTTTGCGGAACAAATTTGAGTTTTACCATCTTCCTCTCCAC |
| 373 | ATTAGAGCAATATCTGGTCAGTTGCAGCAGAATTTTACCATCTTCCTCTCCAC |
| 374 | CCAGCCATCCAGTAATAAAAGGGACGTGGCACTTTTACCATCTTCCTCTCCAC |
| 375 | AATACCTATTTACATTGGCAGAAGTCTTTATTTTACCATCTTCCTCTCCAC |
| 376 | TCACACGATGCAACAGGAAAAACGGAAGAACTTTTTACCATCTTCCTCTCCAC |
| 377 | CTAAACAGGAGGCCGATAATCCTGAGAAGTGTCACGCAAATTTTACCATCTTCCTCTCCAC |
| 378 | GGCGATGTTTTTGGGGTCGAGGGCGAGAAATTTTACCATCTTCCTCTCCAC |
| 379 | AAAGCCGGCGAACGTGTGCCGTAATTTTACCATCTTCCTCTCCAC |
| 380 | GGCCCTGAAAAAGAATAGCCCGAGCGTGGACTTTTTACCATCTTCCTCTCCAC |

TABLE IV-continued

| SEQ ID | 5' - 3' DNA Sequence Listing |
|---|---|
| 381 | CTAACTCCCAGTCGGGAAACCTGGTCCACGTTTTACCATCTTCCTCTC CAC |
| 382 | TGAGTGTTCAGCTGATTGCCCTTGCGCGGTTTTACCATCTTCCTCTC CAC |
| 383 | TATAAATCGAGAGTTGCAGCAAGCGTCGTGCCTTTTACCATCTTCCT CCAC |
| 384 | ACTGTTGGAGAGGATCCCCGGGTACCGCTCACTTTTACCATCTTCCT CCAC |
| 385 | TTCGCTATTGCCAAGCTTGCATGCGAAGCATATTTTACCATCTTCCT CCAC |
| 386 | ATTGACCCGCATCGTAACCGTGAGGGGGATTTTTACCATCTTCCTCTC CAC |
| 387 | GAATTCGTGCCATTCGCCATTCAGTTCCGGCATTTTACCATCTTCCTC TCCAC |
| 388 | TCGACTCTGAAGGGCGATCGGTGCGGCCTCTTTTACCATCTTCCTCTC CAC |
| 389 | ACGGCCAGTACGCCAGCTGGCGAACATCTGCCTTTTACCATCTTCCTC TCCAC |
| 390 | ACCCCGGTTGTTAAATCAGCTCATAGTAACAATTTTACCATCTTCCTC TCCAC |
| 391 | ACCGTTCATTTTTGAGAGATCTCCCAAAAATTTTACCATCTTCCTCTC CAC |
| 392 | TAAATTTTTGATAATCAGAAAAGCACAAAGGCTTTTACCATCTTCCTC TCCAC |
| 393 | AATCATACAGGCAAGGCAGAGCATAAAGCTAAGGGAGAAGTTTTACC ATCTTCCTCTCCAC |

Label-Binding Oligonucleotides

| 394 | TTTGGTGGCATCAATTCTAGGGCGCGAGCTGAAAATTTAACTACTCCC ACTCTCACCCTCACCCTACTCCAACTCAAC |
| 395 | TTTTCCCAATTCTGCGAACCCATATAACAGTTGATTTAACTACTCCC ACTCTCACCCTCACCCTACTCCAACTCAAC |
| 396 | TTTATTGCTCCTTTTGATATTAGAGAGTACCTTTATTTAACTACTCCCA CTCTCACCCTCACCCTACTCCAACTCAAC |
| 397 | TTTCCATAAATCAAAAATCCAGAAAACGAGAATGATTTAACTACTCC CACTCTCACCCTCACCCTACTCCAACTCAAC |
| 398 | TTTCGAGGCATAGTAAGAGACGCCAAAAGGAATTATTTAACTACTCC CACTCTCACCCTCACCCTACTCCAACTCAAC |
| 399 | TTTGAAACACCAGAACGAGAGGCTTGCCCTGACGATTTAACTACTCC CACTCTCACCCTCACCCTACTCCAACTCAAC |
| 400 | TTTCTGATAAATTGTGTCGAGATTTGTATCATCGCTTTAACTACTCCC ACTCTCACCCTCACCCTACTCCAACTCAAC |
| 401 | TTTGAACGAGGGTAGCAACGCGAAAGACAGCATCGTTTAACTACTCC CACTCTCACCCTCACCCTACTCCAACTCAAC |
| 402 | TTTGGTTTATCAGCTTGCTAGCCTTTAATTGTATCTTTAACTACTCCCA CTCTCACCCTCACCCTACTCCAACTCAAC |
| 403 | TTTGGGATTTTGCTAAACAAATGAATTTTCTGTATTTTAACTACTCCC ACTCTCACCCTCACCCTACTCCAACTCAAC |
| 404 | TTTACAAACTACAACGCCTGAGTTTCGTCACCAGTTTTAACTACTCCC ACTCTCACCCTCACCCTACTCCAACTCAAC |
| 405 | TTTAGCCACCACCCTCATTGAACCGCCACCCTCAGTTTAACTACTCCC ACTCTCACCCTCACCCTACTCCAACTCAAC |

TABLE IV-continued

| SEQ ID | 5' - 3' DNA Sequence Listing |
|---|---|
| 406 | TTTGAGAGGGTTGATATAAGCGGATAAGTGCCGTCTTTAACTACTCCCACTCTCACCCTCACCCTACTCCAACTCAAC |
| 407 | TTTGTATAAACAGTTAATGTTGAGTAACAGTGCCCTTTAACTACTCCCACTCTCACCCTCACCCTACTCCAACTCAAC |
| 408 | TTTGCAGGTCAGACGATTGTTGACAGGAGGTTGAGTTTAACTACTCCCACTCTCACCCTCACCCTACTCCAACTCAAC |
| 409 | TTTTAGCGCGTTTTCATCGCTTTAGCGTCAGACTGTTTAACTACTCCCACTCTCACCCTCACCCTACTCCAACTCAAC |
| 410 | TTTGCGCCAAAGACAAAAGTTCATATGGTTTACCATTTAACTACTCCCACTCTCACCCTCACCCTACTCCAACTCAAC |
| 411 | TTTCCGAAGCCCTTTTTAAAGCAATAGCTATCTTATTTAACTACTCCCACTCTCACCCTCACCCTACTCCAACTCAAC |
| 412 | TTTTTTTTTGTTTAACGTCTCCAAATAAGAAACGATTTAACTACTCCCACTCTCACCCTCACCCTACTCCAACTCAAC |
| 413 | TTTAACCTCCCGACTTGCGGCGAGGCGTTTTAGCGTTTAACTACTCCCACTCTCACCCTCACCCTACTCCAACTCAAC |
| 414 | TTTTAAACCAAGTACCGCATTCCAAGAACGGGTATTTTAACTACTCCCACTCTCACCCTCACCCTACTCCAACTCAAC |
| 415 | TTTAGATAAGTCCTGAACACCTGTTTATCAACAATTTTAACTACTCCCACTCTCACCCTCACCCTACTCCAACTCAAC |
| 416 | TTTGTAAAGTAATTCTGTCAAAGTACCGACAAAAGTTTAACTACTCCCACTCTCACCCTCACCCTACTCCAACTCAAC |
| 417 | TTTAGTAGGGCTTAATTGAAAAGCCAACGCTCAACTTTAACTACTCCCACTCTCACCCTCACCCTACTCCAACTCAAC |
| 418 | TTTAATGGTTTGAAATACCCTTCTGACCTAAATTTTTTAACTACTCCCACTCTCACCCTCACCCTACTCCAACTCAAC |
| 419 | TTTAGTCAATAGTGAATTTTTAAGACGCTGAGAAGTTTTAACTACTCCCACTCTCACCCTCACCCTACTCCAACTCAAC |
| 420 | TTTTGAGCAAAAGAAGATGATTCATTTCAATTACCTTTAACTACTCCCACTCTCACCCTCACCCTACTCCAACTCAAC |
| 421 | TTTCAATATAATCCTGATTGATGATGGCAATTCATTTTAACTACTCCCACTCTCACCCTCACCCTACTCCAACTCAAC |
| 422 | TTTGTTATCTAAAATATCTAAAGGAATTGAGGAAGTTTAACTACTCCCACTCTCACCCTCACCCTACTCCAACTCAAC |
| 423 | TTTACATCGCCATTAAAAAAACTGATAGCCCTAAATTTAACTACTCCCACTCTCACCCTCACCCTACTCCAACTCAAC |
| 424 | TTTTCGTCTGAAATGGATTACATTTTGACGCTCAATTTAACTACTCCCACTCTCACCCTCACCCTACTCCAACTCAAC |
| 425 | TTTTTGATTAGTAATAACATTGTAGCAATACTTCTTTTAACTACTCCCACTCTCACCCTCACCCTACTCCAACTCAAC |
| 426 | TTTAGGAACGGTACGCCAGTAAAGGGATTTTAGACTTTAACTACTCCCACTCTCACCCTCACCCTACTCCAACTCAAC |
| 427 | TTTGAGCACGTATAACGTGCTATGGTTGCTTTGACTTTAACTACTCCCACTCTCACCCTCACCCTACTCCAACTCAAC |
| 428 | TTTCGGGCGCTAGGGCGCTAAGAAAGCGAAAGGAGTTTAACTACTCCCACTCTCACCCTCACCCTACTCCAACTCAAC |
| 429 | TTTATCACCCAAATCAAGTGCCCACTACGTGAACCTTTAACTACTCCCACTCTCACCCTCACCCTACTCCAACTCAAC |
| 430 | TTTATCCTGTTTGATGGTGGCCCCAGCAGGCGAAATTTAACTACTCCCACTCTCACCCTCACCCTACTCCAACTCAAC |
| 431 | TTTGCTCACTGCCCGCTTTACATTAATTGCGTTGCTTTAACTACTCCCACTCTCACCCTCACCCTACTCCAACTCAAC |

TABLE IV-continued

| SEQ ID | 5' - 3' DNA Sequence Listing |
|---|---|
| 432 | TTTGTAACGCCAGGGTTTTAAGGCGATTAAGTTGGTTTAACTACTCCC ACTCTCACCCTCACCCTACTCCAACTCAAC |
| 433 | TTTCGTTGGTGTAGATGGGGTAATGGGATAGGTCATTTAACTACTCCC ACTCTCACCCTCACCCTACTCCAACTCAAC |
| 434 | TTTTTTAAATTGTAAACGTATTGTATAAGCAAATATTTAACTACTCCC ACTCTCACCCTCACCCTACTCCAACTCAAC |
| 435 | TTTGCCGGAGAGGGTAGCTTAGCTGATAAATTAATTTTAACTACTCCC ACTCTCACCCTCACCCTACTCCAACTCAAC |
| 436 | TTTAAATTTTTAGAACCCTTTCAACGCAAGGATAATTTAACTACTCCC ACTCTCACCCTCACCCTACTCCAACTCAAC |
| 437 | TTTTAAGCAATAAAGCCTCAAAGAATTAGCAAAATTTTAACTACTCCC ACTCTCACCCTCACCCTACTCCAACTCAAC |

Example 10. Deposition of SNAPs on Prepared Surfaces

Figure 42:
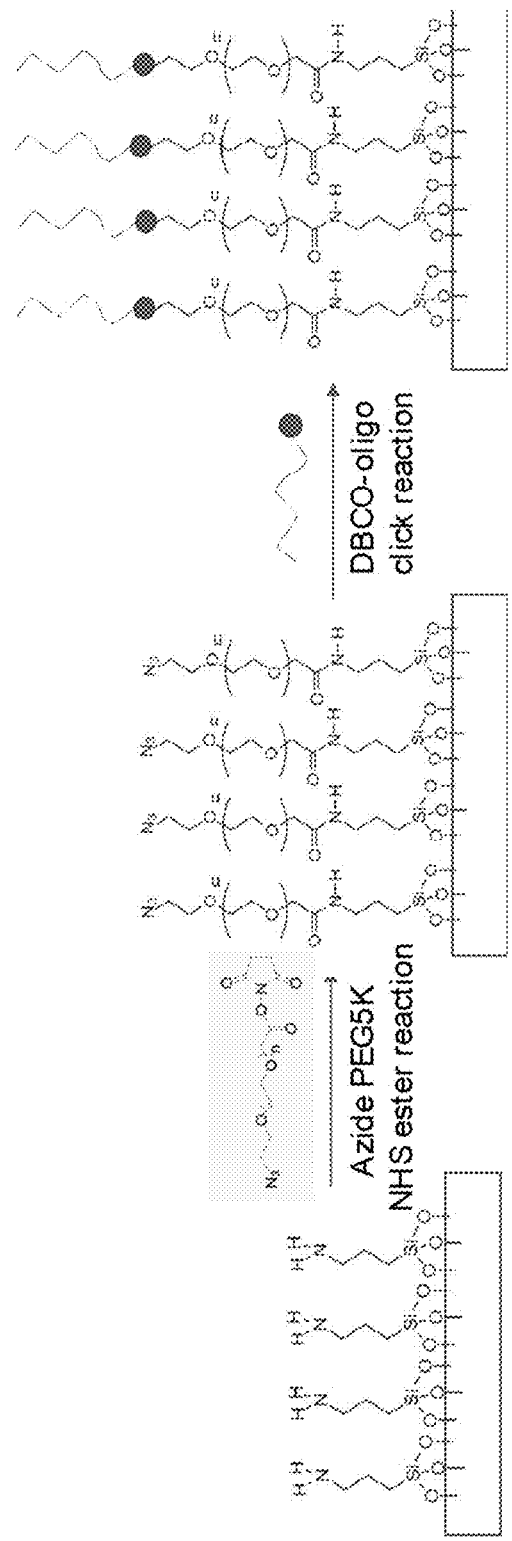
FIG. 42 depicts a scheme for providing a plurality of surface-linked moieties to a solid support for the purpose of facilitating binding interactions with a SNAP, in accordance with some embodiments.

Surfaces were prepared for the formation of unpatterned arrays. A layer of (3-aminopropyl) trimethoxysilane (APTMS) was deposited on the surface of a glass slide. The APTMS-coated surface was subsequently reacted with azide-PEG-NHS ester to covalently form a PEG passivating layer on the surface of the glass slide. After forming the PEG passivating layer, surface-linked azide groups were conjugated to oligonucleotides containing a dibenzylcyclooctyne (DBCO) functional groups. Each oligonucleotide had the sequence 5'-DBCO-TGTGGAGAGGAAGATGGTA-3' (SEQ ID NO: 438). A reactive scheme for the preparation of the glass surface is shown in FIG. 42. Oligonucleotide arrays were formed with varying surface oligonucleotide densities by varying the concentration of oligonucleotide contacted with the azide-containing surface. Oligonucleotide concentrations of 0.01 micromolar (µM), 0.1 µM, and 1 µM were utilized for surface preparation.

Prepared glass surfaces were contacted with DNA origami containing 20 surface-interacting moieties, as described in Example 8. 44 Alexa-Fluor 488 fluorescent dyes were bound to each DNA origami via a complementary oligonucleotide to the pendant region of the label-binding oligonucleotides (see SEQ ID NO: 3). Two polypeptides were bound to each DNA origami via complementary oligonucleotides to the pendant regions of analyte-binding oligonucleotides (see SEQ ID NO: 1, for example). Each polypeptide was a 12-amino acid histidine peptide (SEQ ID NO: 439- HHHHHHHHHHHH), hereafter referred to as His-12.

DNA origami containing the pendant oligonucleotides were deposited on the prepared glass surface by hybridization of pendant surface-interacting oligonucleotides (see SEQ ID NO: 2) to the surface-linked oligonucleotides (see SEQ ID NO: 438). The deposition buffer is described in Example 3. Deposition of His-12 DNA origami was performed for four separate arrays. Two additional arrays were prepared with DNA origami containing the pendant oligonucleotides but no polypeptides (control SNAPs). Arrays were formed using oligonucleotides.

After array formation, SNAP locations on each array were identified by fluorescence microscopy imaging at 488 nm. After determining the position of deposited SNAPs on each array, arrays were contacted with histidine-binding detectable probes. Each detectable probe comprised a DNA origami tile with 20 coupled B1 aptamers and 44 conjugated Alexa-Fluor 647 fluorescent dyes. Probes were contacted with each array at a concentration of 30 nM and were incubated for 30 minutes. Unbound probes were rinsed from each array by a rinse buffer (see Example 3). After rinsing, each array was imaged to identify array addresses where the B1 probes were bound.

Figure 43:
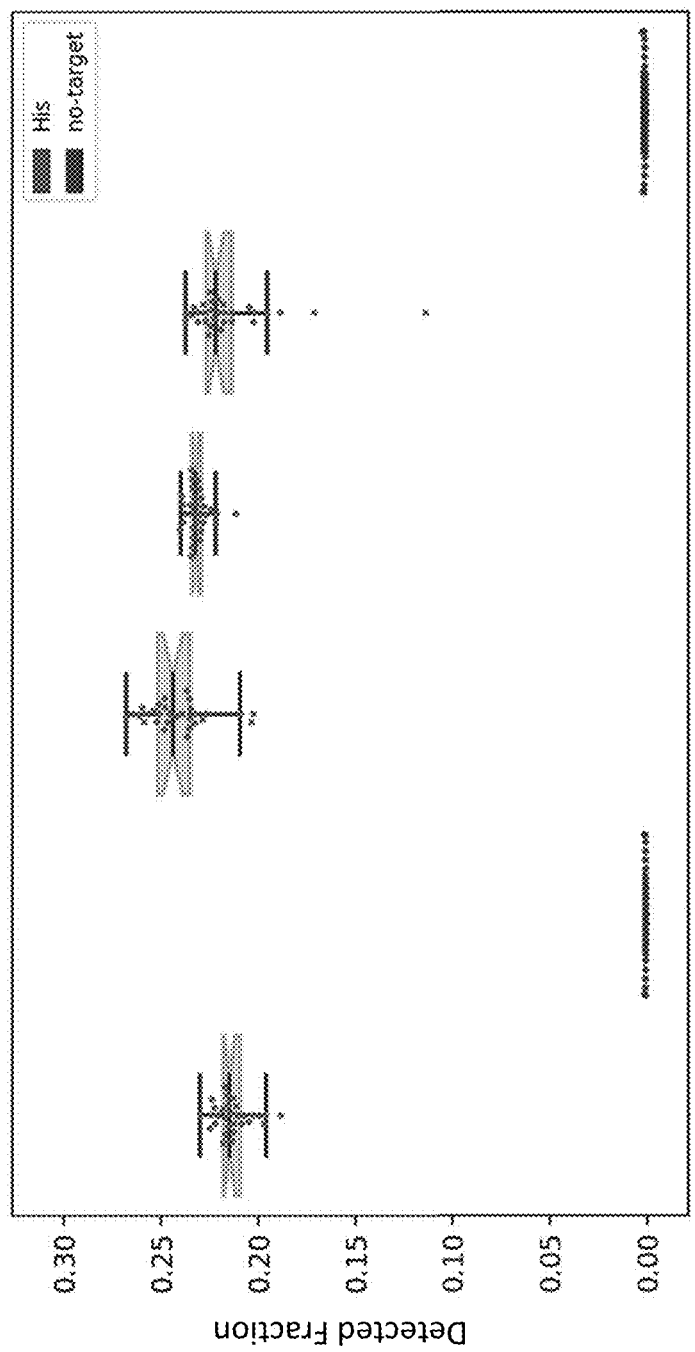
FIG. 43 shows detection of His-12 peptide SNAP arrays by B1 aptamer probes for double His-12 SNAPs on oligonucleotide-coated surfaces.
Figure 46:
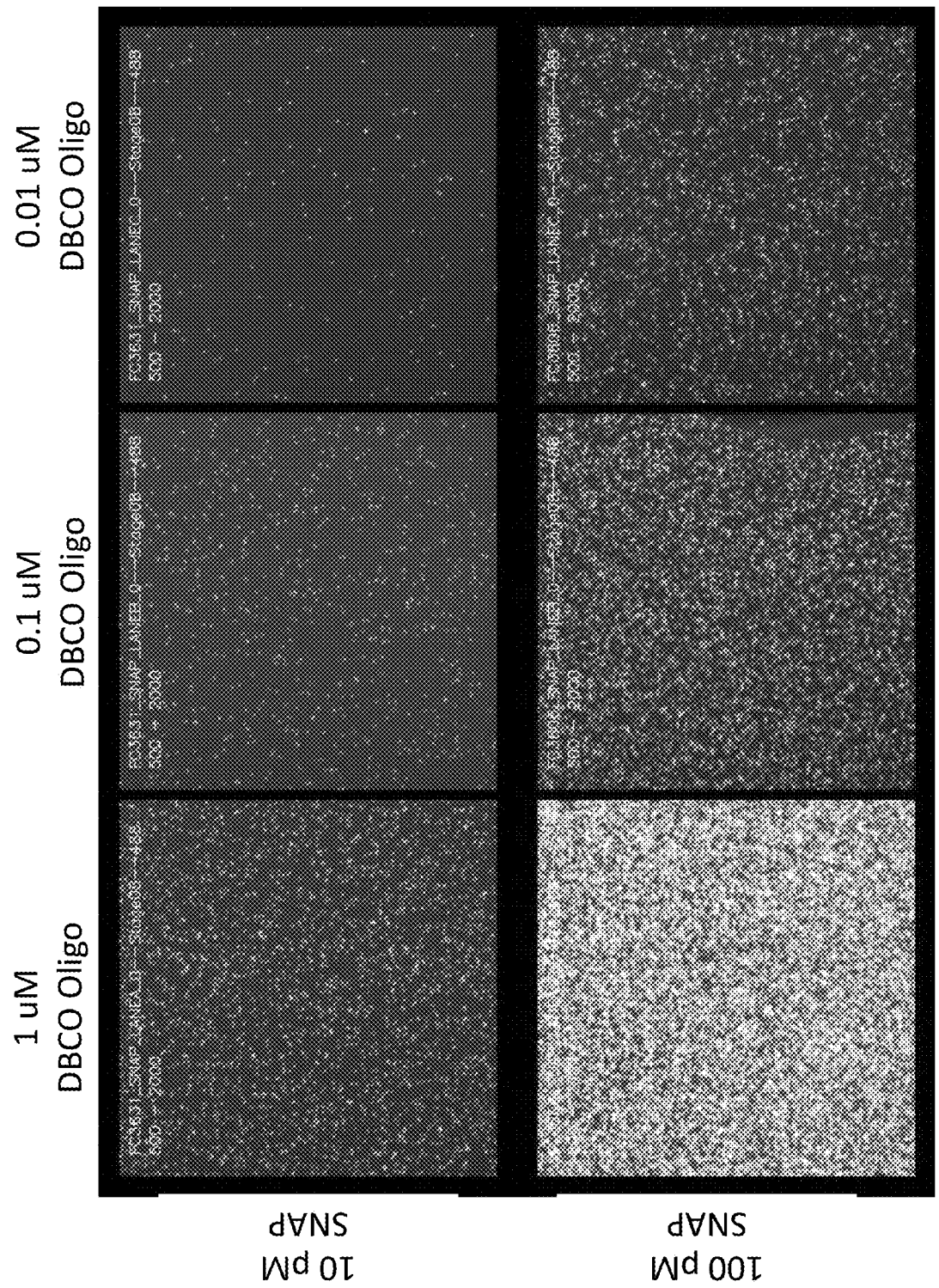
FIG. 46 displays fluorescent imaging data for unpatterned SNAP arrays formed on glass surfaces containing different surface concentrations of oligonucleotides and differing SNAP concentrations.

FIG. 43 shows binding data for the B1 probes against each array of SNAPs. Binding of the B1 probe was observed for at least 20-25% of array addresses. In contrast, near-zero binding of B1 probe to polypeptide-free SNAPs was observed. FIG. 46 shows fluorescent microscopy image data for SNAPs deposited on oligonucleotide-containing surfaces containing differing surface densities of oligonucleotides. SNAPs were contacted with the oligonucleotide-containing surfaces at a concentration of 10 picomolar (pM) or 100 µM. Deposited SNAP densities were observed to increase with increased oligonucleotide surface density and increased SNAP concentration.

Example 11. Detection of Polypeptides on SNAPs

Figure 44:
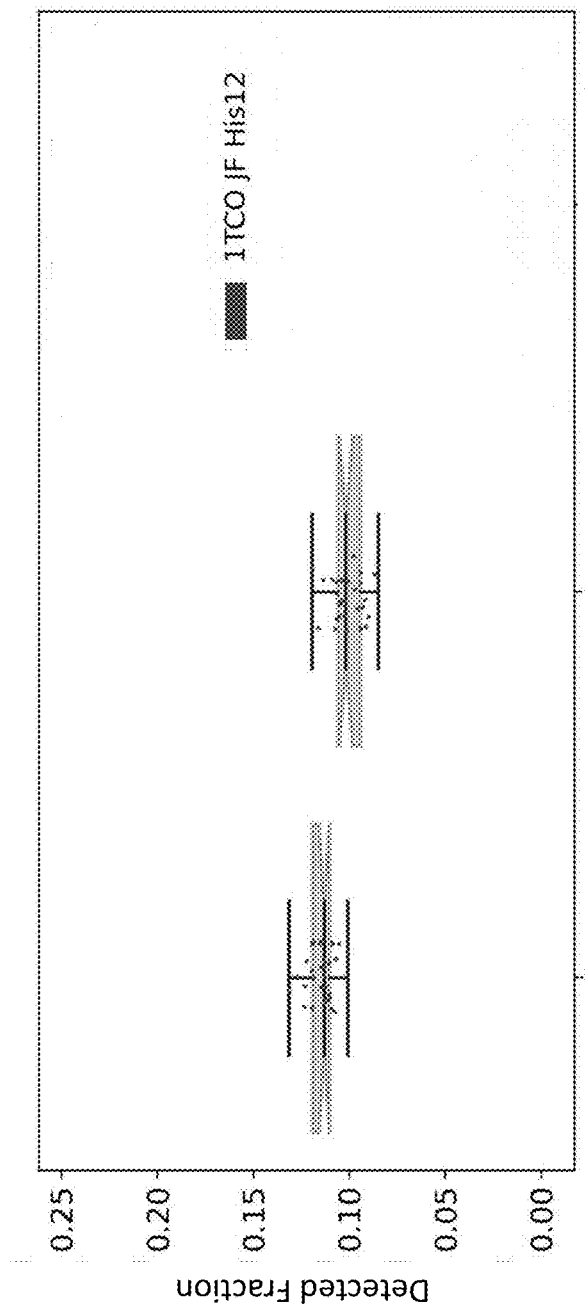
FIG. 44 shows detection of His-12 peptide SNAP arrays by B1 aptamer probes for single His-12 SNAPs on oligonucleotide-coated surfaces.

Two arrays of SNAPs were prepared via the method described in Example 10. Each array was prepared with SNAPs that contained 20 pendant capture oligonucleotides and a single polypeptide coupling oligonucleotide. Each SNAP was coupled to a single His-12 peptide. After array preparation, each array was incubated with B1 probes as described in Example 10. The probes were contacted with each array at a concentration of 10 nM for 20 minutes. Probe binding was detected via fluorescence microscopy at 647 nm. FIG. 44 depicts the fraction of observed array addresses with detected B1 probe binding. About 10% of array addresses were observed to bind B1 probes.

Example 12. Detection of Polypeptides on SNAPs

Oligonucleotide-containing glass surfaces were prepared according to the scheme of FIG. 42. Additional glass surfaces were prepared containing only APTMS surface-linked moieties. SNAPs were prepared with 20 pendant, capture moieties, as described in Example 9. Each SNAP was configured to have two polypeptide binding sites. SNAPs were conjugated to streptavidin polypeptides, with each streptavidin having 2 His-12 tags.

SNAPs were incubated with prepared glass surfaces to form polypeptide arrays. A total of 6 replicates of each type of surface (APTMS-containing and oligo-containing) were tested, with 4 surfaces being incubated with streptavidin-conjugated SNAPs and 2 surfaces being incubated with SNAPs containing no polypeptides.

Figure 45:
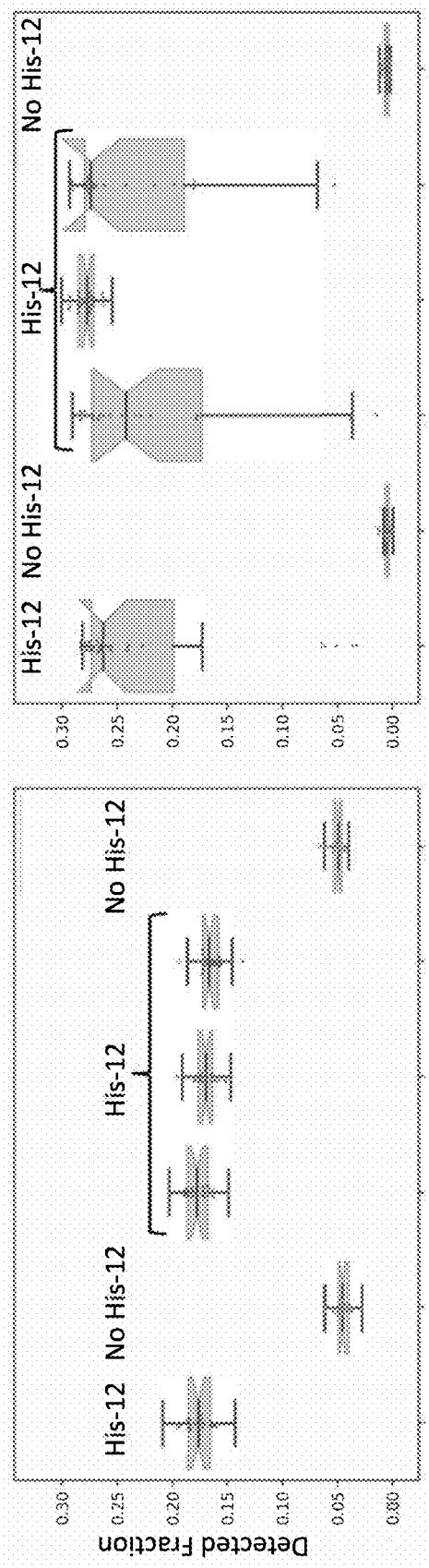
FIG. 45 shows a comparison of His-12 detection by B1 aptamer probes for SNAPs on APTMS-coated and oligonucleotide-containing surfaces.

After SNAP deposition, each glass surface was imaged by confocal fluorescent microscopy to identify arrays addresses for deposited SNAPs. Imaging of SNAP addresses was performed by detection of Alexa-Fluor 488 dyes on each SNAP. After identifying occupied array addresses, SNAPs were contacted with B1 aptamer probes, as described in Examples 10 and 11. Probe binding was detected by confocal fluorescent microscopy by detection of Alexa-Fluor 647 dyes on each probe. 647 nm data was compared to 488 nm data to determine a fraction of occupied array addresses that were observed to bind a B1 probe. FIG. 45 displays binding detection data for SNAPs deposited on APTMS surfaces and oligonucleotide-containing surfaces. APTMS surfaces were observed to have a lower binding detection rate of His-12 containing-polypeptides, and a higher false positive rate (detection of SNAPs containing no polypeptides). Oligonucleotide-containing surfaces were observed to have a higher binding detection rate of His-12 containing polypeptides, and a lower false positive rate. The presence of the PEG passivating layer and the increased specificity of surface interactions between the SNAPs and the oligonucleotide-containing surfaces may have increased the likelihood of true-positive detection and decreased the likelihood of false positive detection.

Example 13. Formation of Unpatterned SNAP Arrays

Figure 47:
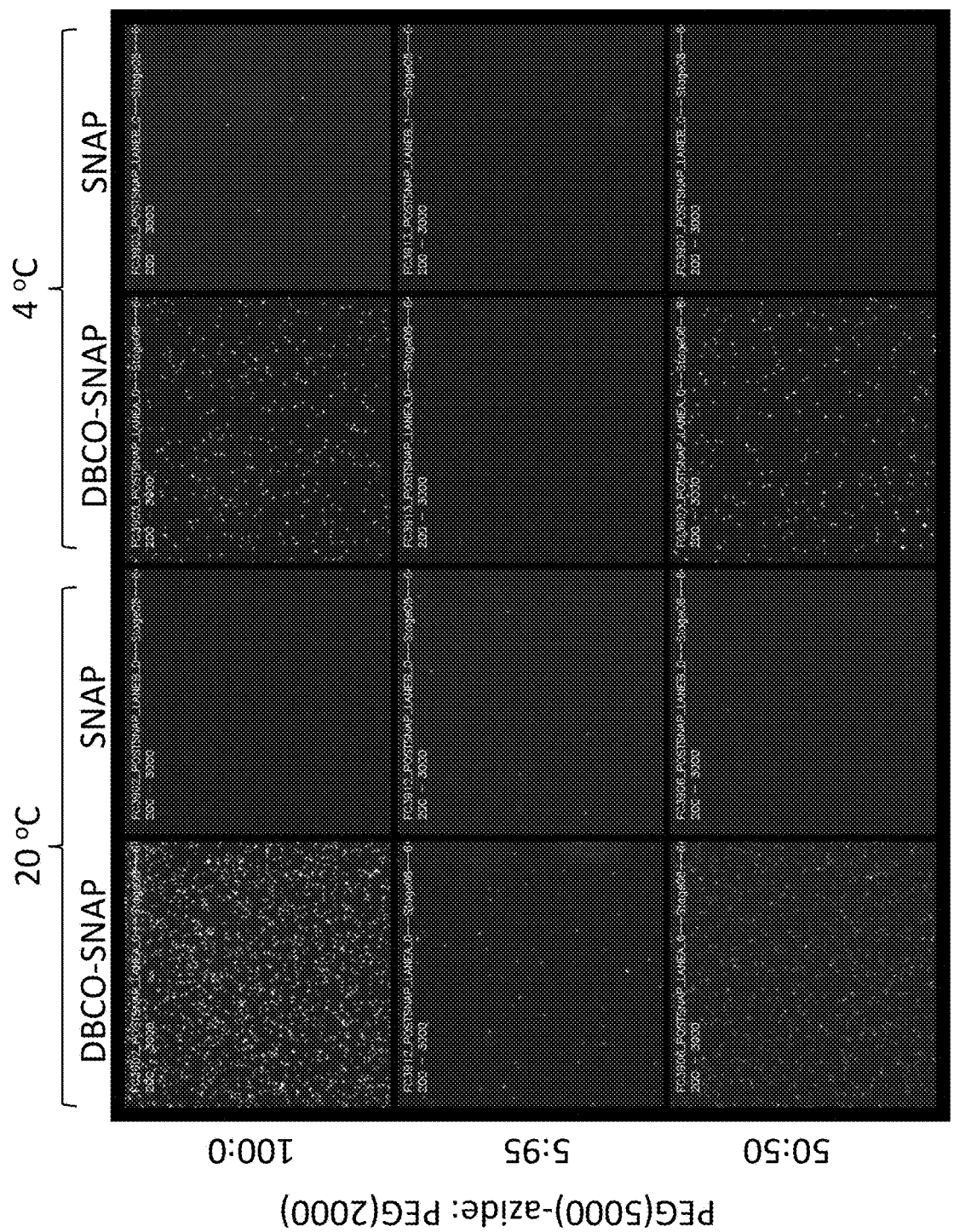
FIG. 47 displays fluorescent imaging data for unpatterned SNAPs arrays formed by direct conjugation of SNAPs to azide-containing surfaces.

SNAPs were deposited on unpatterned glass surfaces containing PEG-azide surface-linked moieties. The glass surfaces were prepared according to the scheme shown in FIG. 42, with the final oligonucleotide conjugation step excluded. The surface concentration of azide groups was varied by mixing NHS-PEG2K-azide molecules and NHS-PEG5K molecules in differing ratios. The ratio of NHS-PEG2K-azide to NHS-PEG5K molecules were varied between 5:95 and 100:0. After forming the azide-containing glass surfaces, SNAPs containing a surface-coupling dibenzocyclooctylene (DBCO) moiety were contacted with the surfaces at a concentration of 1 nanomolar (nM). SNAPs were incubated for at least 12 hours to facilitate formation of Click-type interactions between surface-linked azides and SNAP-coupled DBCO moieties. Incubations were performed at 20° C. and 4° C. to test the affect of temperature on deposition. Negative control arrays were also formed by contacting azide-containing surfaces with SNAPs that did not have a DBCO moiety. FIG. 47 shows fluorescence microscopy images of SNAP arrays as a function of PEG2K-azide:PEG5K ratio and deposition temperature. Deposited SNAP concentrations on the unpatterned arrays were seen to increase with increasing surface densities of azide moieties and increasing temperature. In the absence of a DBCO moiety coupled to a SNAP, minimal deposition of SNAPs was observed on glass surfaces.

Example 14. Synthesis and Characterization of SNAPs with Pervious Structures

Figure 59B:
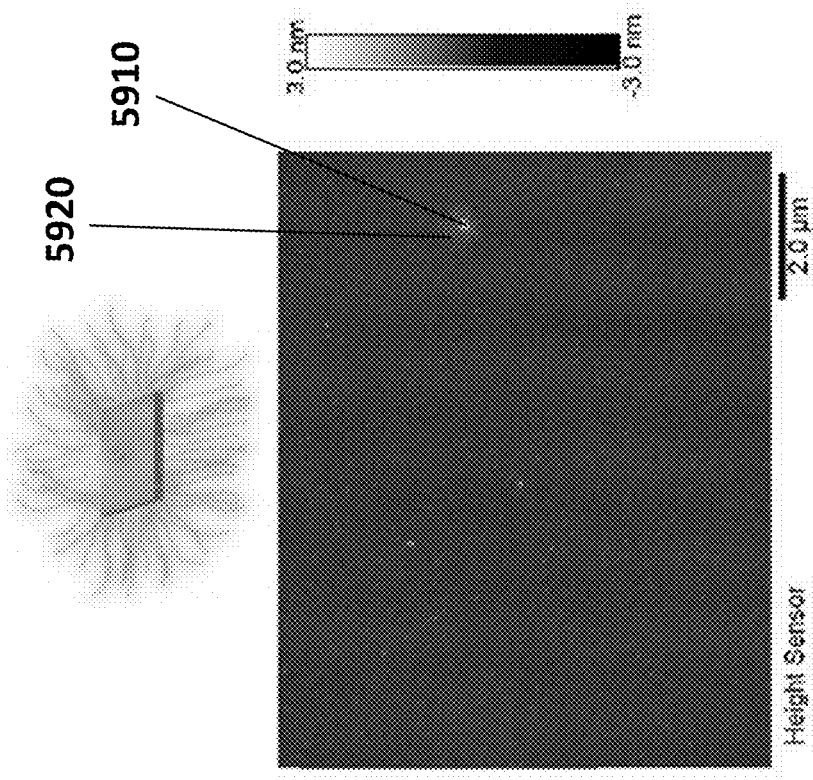
FIGS. 59A-59D show features of nucleic acid nanostructures.
Figure 59A:
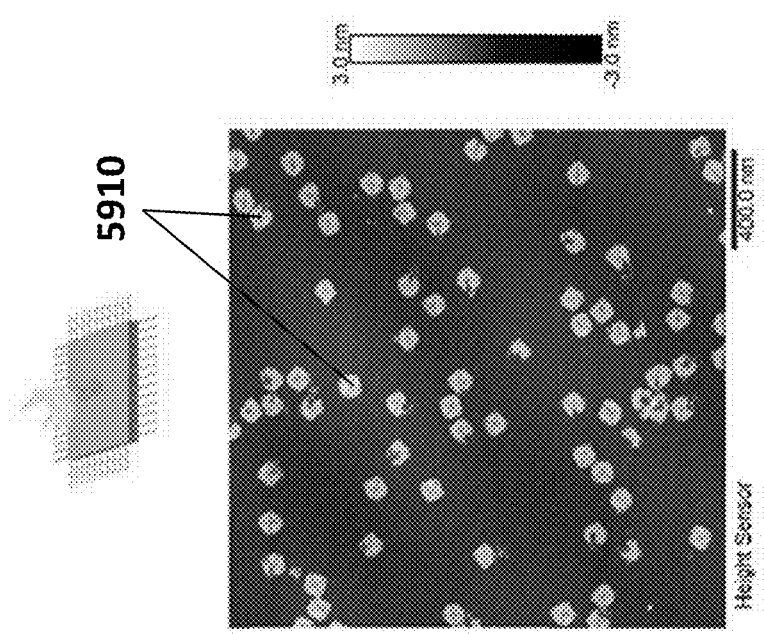

Square, tile-shaped DNA origami comprising single-stranded DNA (ssDNA) were prepared by the method described in Example 7. The DNA origami structure was folded from a mix of ssDNA oligos and the m13mp18 scaffold ssDNA. All the oligos including an oligo with a TCO display moiety were mixed in excess with the scaffold DNA. Purified DNA origami tiles were deposited onto mica for AFM imaging (FIG. 59A). The measured tile dimensions matched the expected tile edge length (80-90 nm) and tile height (2 nm).

After synthesis of the tile origami, a pervious structure was formed on each DNA origami by TdT extension in the presence of an excess of deoxythymidine nucleotides, which extended ssDNA overhangs surrounding the DNA origami tile seed structure. The pervious, poly-T ssDNA extensions are expected to lay substantially flat on a positively charged surface of a solid support. DNA origami tiles with poly-T extensions were imaged on mica with poly-lysine coating or amine (APTMS) covered glass surface (FIG. 59B). The DNA origami tile with poly-T extensions were found to have typical diameters in the range of 600-700 nm; large enough to exclude the deposition of a second brushy tile on a 400 nm size array site on a solid support.

Figure 59C:
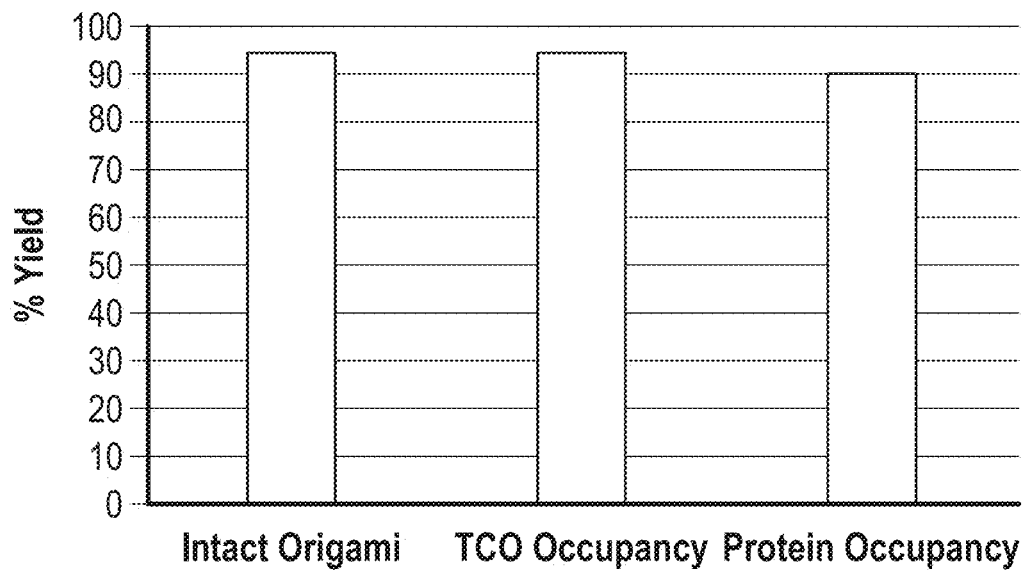
Figure 59D:
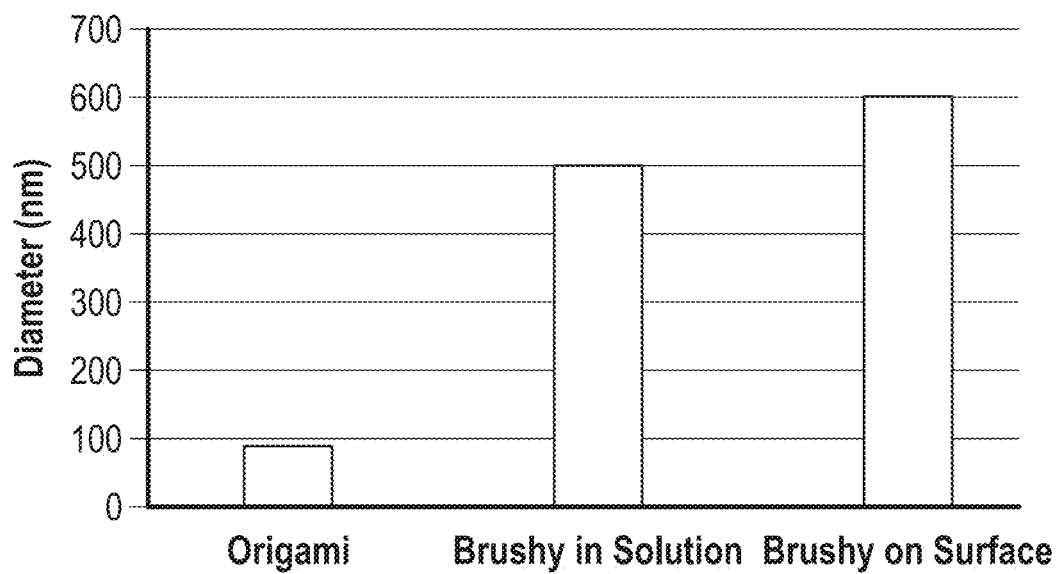

According to AFM data, 95% of the DNA origami tile particles with poly-T extensions were intact (FIG. 59C). DNA origami tiles with poly-T extensions were coupled to an mTz-modified proteins according to the method of Example 1. Analytical HPLC results showed that the fraction of poly-T extended DNA origami tiles with functional TCO groups was 95% and the fraction with conjugated protein was 90% (FIG. 59C). FIG. 59D plots size data for DNA origami in various configurations, including origami-only, with poly-T extensions in solution, and with poly-T extensions on a surface. The mean edge length of the compacted DNA origami tiles was 90 nm. Dynamic light scattering measurements showed that the mean diameter of the poly-T extended DNA origami in solution was 500 nm. Based on the AFM measurements, the mean diameter of poly-T extended DNA origami was 650 nm on the surface. In summary, poly-T extended DNA origami were conjugated to protein with high efficiency, and their large size is configured to prevent deposition of more than one poly-T extended DNA origami at each site on a solid support.

Example 15. Single-Molecule Array Preparation

Figure 67A:
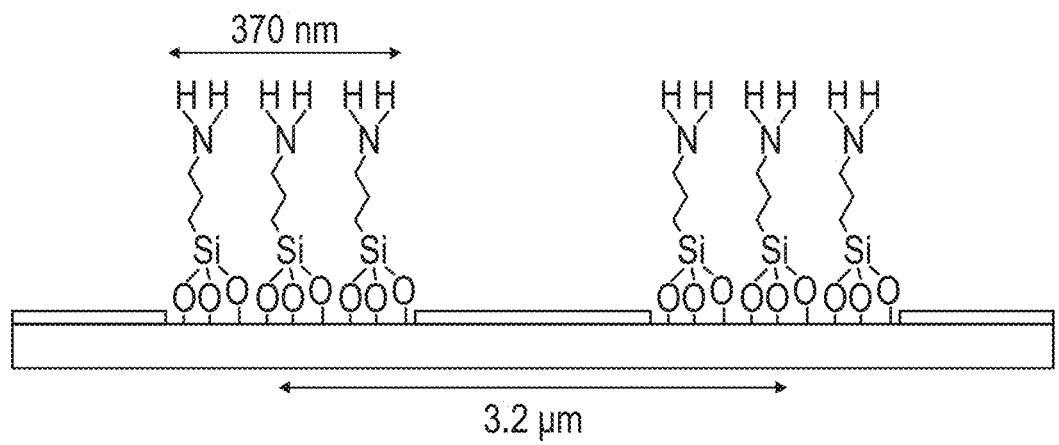
FIGS. 67A-67E show features of array sites formed by lithographic patterning.
Figure 67B:
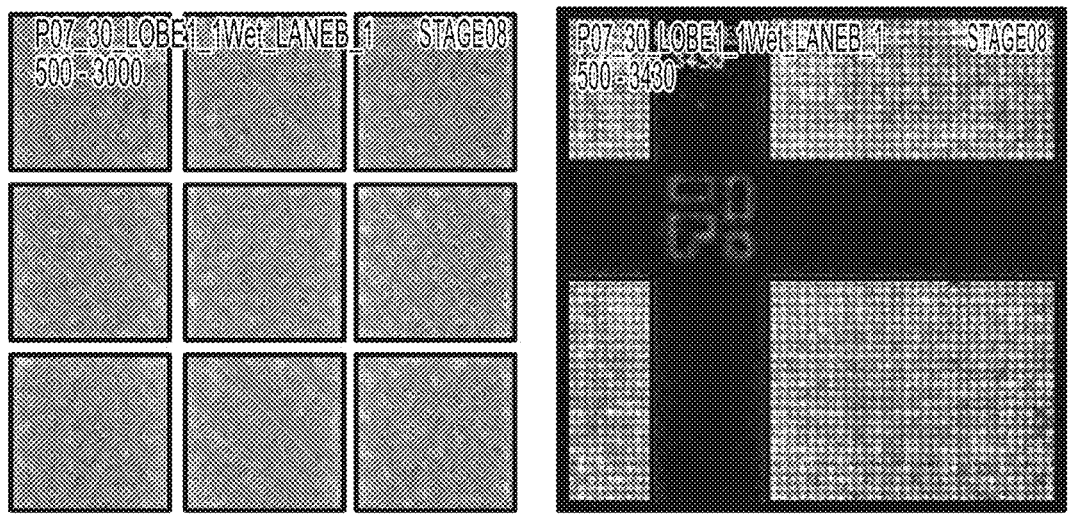
Figure 67C:
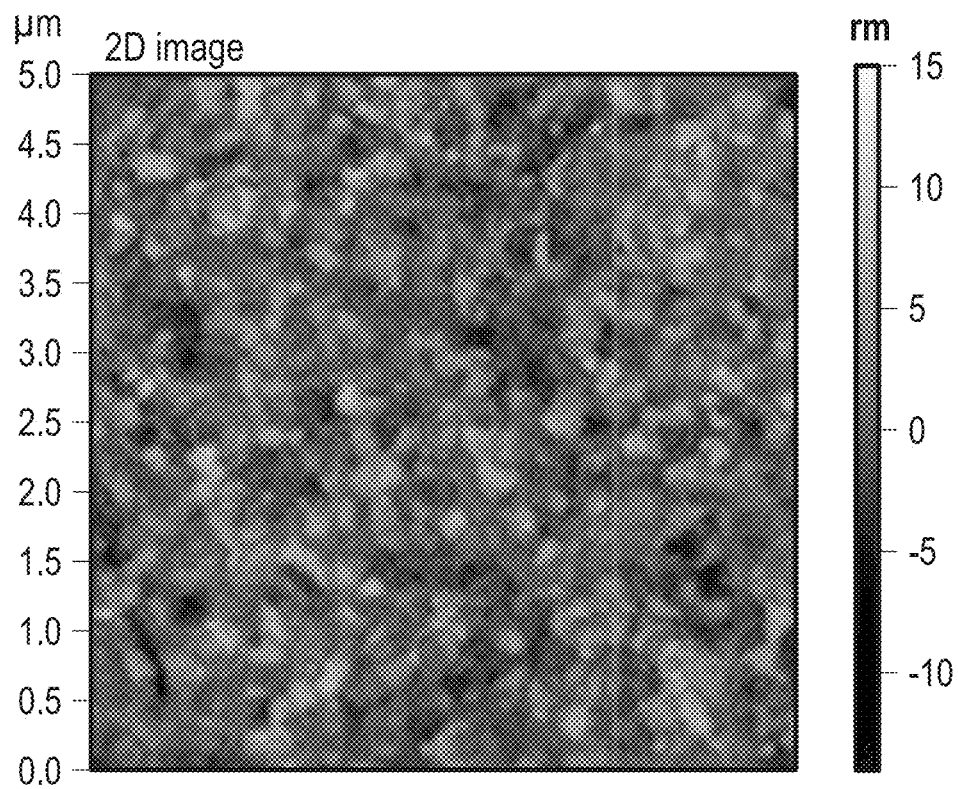
Figure 67D:
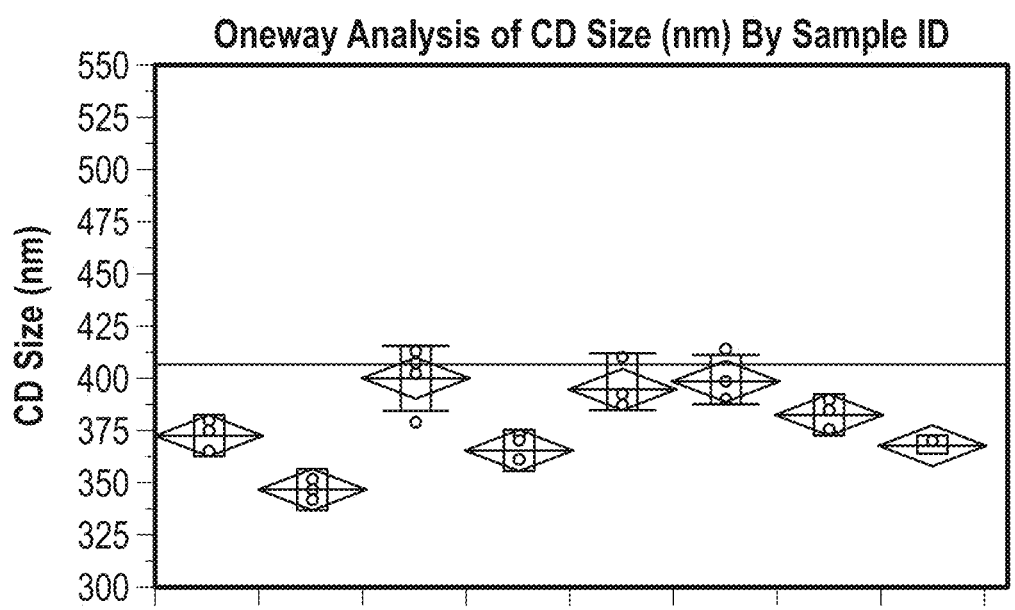
Figure 67E:
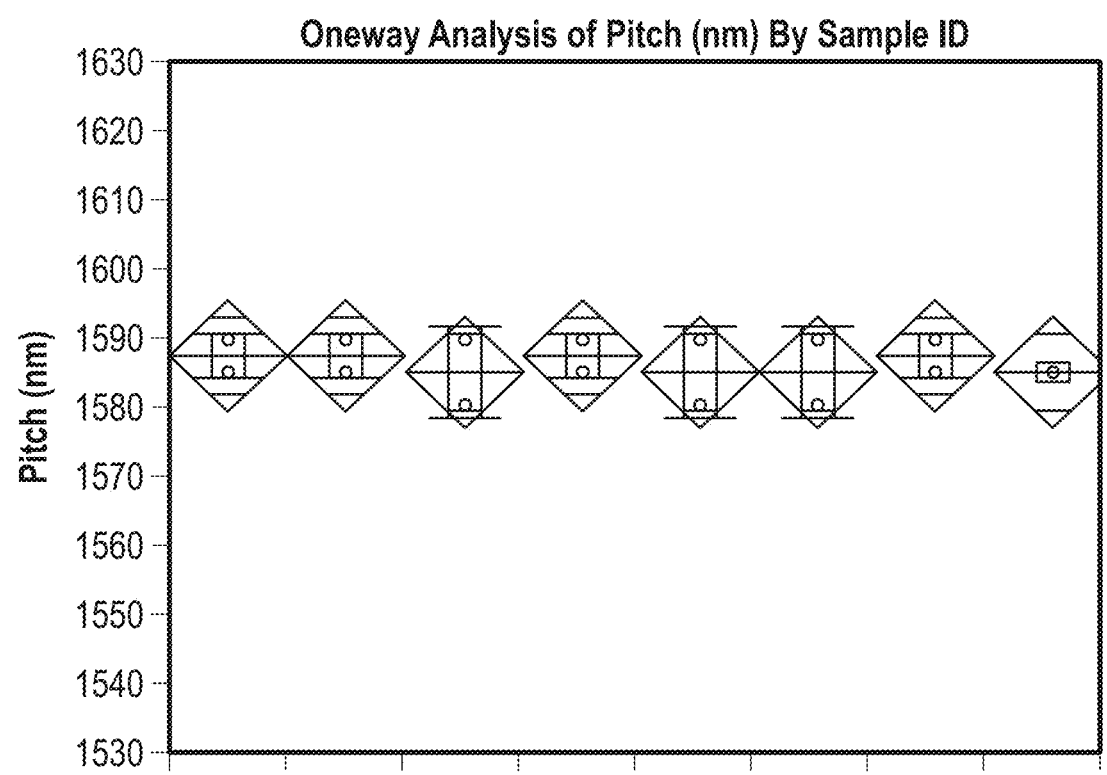

A patterned solid support was formed by photolithographic patterning of a glass substrate. After photolithographic patterning, the solid support was functionalized with APTMS to provide a positively-charge surface coating. After APTMS deposition, the photolithographic photoresist was stripped from the chip to provide a patterned array of binding sites (as shown in FIG. 67A). The patterning of the glass surface matched the expected feature periodicity and spacing, and confirmed that only the patterned features have the positively charged amine coating (FIG. 67B). The uniform intensity of the patterned regions demonstrated that the APTMS coating was consistent within and between the features. High resolution AFM characterization showed that the glass/silicon surface roughness was in the expected and workable range (<2 $nm^2$) (FIG. 67C). The measured feature diameter (FIG. 67D) and pitch (FIG. 67E) matched the expected values of approximately 400 nanometers and 1.4 microns, respectively.

Example 16. Non-Poisson Array Loading with SNAPs Containing Pervious Structures

To assess single molecule occupancy on the chips, two versions of DNA origami tiles with poly-T extensions are produced for mixing experiments. DNA origami tiles with poly-T extensions are produced by the method of Example 14, with a first version being labeled with Alexa-Fluor 488 dyes and a second version being labeled with Alexa-Fluor 647 dyes. An equimolar mixture of the two types of SNAPs is deposited on a patterned glass array, as described in Example 15. By counting the features lit up by a single wavelength (indicating only one deposited tile) and those lit up by both wavelengths (indicating more than one deposited tile), it is possible to estimate single molecule occupancy. Double double-occupancy is observed at 5% of array sites for a 96% occupied array (i.e. 4% of sites containing no observed SNAPs). With no exclusion (Poisson deposition), it would be expected to observe nearly 25% of the spots with double color. Atomic force microscopy (AFM) is also used to demonstrate single molecule occupancy of array sites at high resolution. AFM results suggest that 90% of the spots have a single brushy DNA origami tile.

To estimate a dynamic range afforded by an above-described array utilizing partially-structured SNAPs, dilution experiments and 488/647 mixing experiments are used. At different dilution and 488-to-647 brushy DNA origami tile ratios, a number of observed 488 brushy tiles among $10^5$ spots are determined. By extrapolating the data points, it is demonstrated that a single DNA origami tile can be observed among 107 spots.

Example 17. Functional Nucleic Acids on SNAPs

An array of SNAPs was prepared to determine if a detectable label could be applied and removed from each SNAP on the array over multiple cycles of binding and removal. A chip comprising a glass surface with a blanket layer of (3-aminopropyl) trimethoxysilane (APTMS) was prepared. SNAPs were contacted with the APTMS-coated surface of the chip at a concentration of 4.5 picomolar in a solution containing 1× Neoventures buffer, 0.1% Tween20, 0.001% lipidure, and 10 mM $MgCl_2$. Each SNAP comprised a functional nucleic acid comprising a pendant single-stranded DNA coupled to a tile-shaped DNA origami. The functional nucleic acid had a nucleotide sequence of ATTATACTACATACACC (SEQ ID NO: 440). The SNAP-containing buffer was incubated on the APTMS-coated surface for 10 minutes, then the surface was rinsed with a buffer comprising 1× Neoventures buffer, 0.1% Tween20, 0.0010% lipidure, and 10 mM $MgCl_2$.

After preparing an array of randomly-deposited SNAPs on the APTMS-coated surface, the array underwent 14 detection cycles. Each detection cycle comprised 1) contacting the array with a fluidic medium comprising a fluorescently-labeled oligonucleotide with a nucleotide sequence of TAATATGATGTATGTGG (SEQ ID NO: 441) and 5 Alexa-Fluor dyes, 2) incubating the fluorescently-labeled oligonucleotide with the array for 1 minute, 3) rinsing the array with a solution containing 1× Neoventures buffer, 0.1% Tween20, 0.001% lipidure, and 10 mM $MgCl_2$, 4) fluorescently imaging the array to detect spatial locations of coupled fluorescently-labeled oligonucleotides, 5) applying a stripping buffer containing 6M guanidinium hydrochloride and 10 mM $MgCl_2$, and 6) rinsing the array with a solution containing 1× Neoventures buffer, 0.10% Tween20, 0.001% lipidure, and 10 mM $MgCl_2$. Odd-numbered cycles (e.g., 1, 3, 5, . . . , etc.) utilized a fluorescently-labeled oligonucleotide comprising an Alexa-Fluor 488 fluorophore, and even-numbered cycles (e.g., 2, 4, 6, . . . , etc.) utilized a fluorescently-labeled oligonucleotide comprising an Alexa-Fluor 647 fluorophore.

FIG. 68 displays fluorescent imaging data for each cycle. Odd-numbered cycles are shown to have detection of fluorescence at array addresses in the 488-nm channel of the fluorescent microscope, but virtually no detection in the 647-nm channel of the fluorescent microscope. Even-numbered cycles are shown to have virtually no detection of fluorescence at array addresses in the 488-nm channel of the fluorescent microscope, but have detection of fluorescence in the 647-nm channel of the fluorescent microscope. The results indicate that it is possible to 1) strip an oligonucleotide detectable label from a functional nucleic acid of a SNAP using a chaotropic agent (e.g., guanidinium hydrochloride), and 2) not disrupt an electrostatic interaction between a SNAP and a charge-surface when contacting the SNAP with a chaotropic agent.

Figure 70:
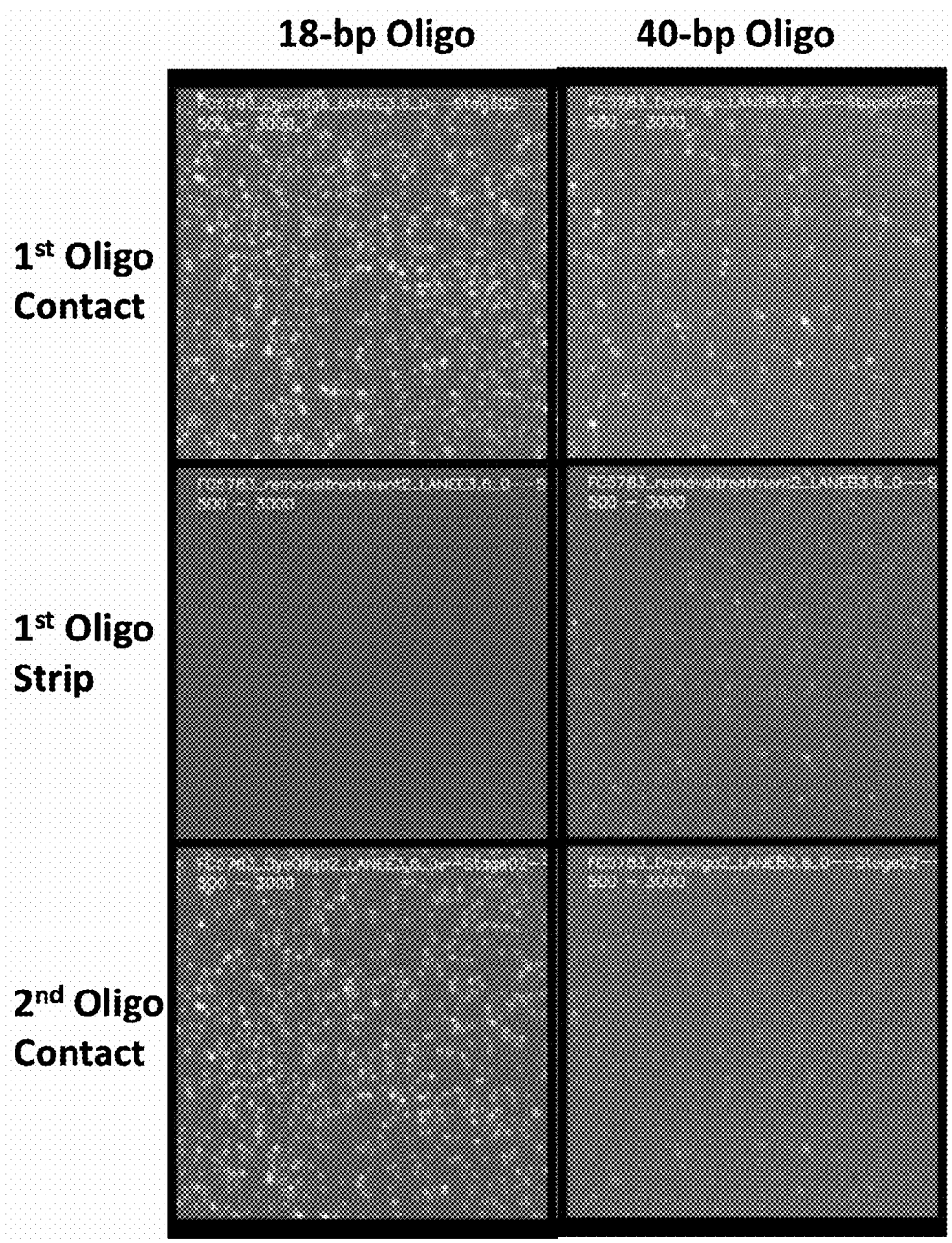
FIG. 70 displays fluorescence microscopy images for arrays comprising functional nucleic acids of differing nucleotide sequence lengths during binding and stripping of fluorescently-labeled oligonucleotides.

An additional experiment was performed to assess the effect of a longer nucleotide sequence on removal of the oligonucleotide under stripping conditions. Two arrays were prepared by the method described above. The first array contained deposited SNAPs with a functional nucleic acid that was configured to couple a fluorescently-labeled oligonucleotide with a nucleotide sequence of ACAACTCAACCTCATCCCACTCCCACTCTCACCCTCATCAA (SEQ ID NO: 442). The second array comprised the SNAPs as described above with the functional nucleic acid with nucleotide sequence TAATATGATGTATGTGG (SEQ ID NO: 441). The arrays were contacted with their respective fluorescently-labeled complementary oligonucleotides (each complementary oligonucleotide containing 5 Alexa-Fluor 488 dyes), fluorescently imaged, incubated with 6M guanidinium chloride, then re-contacted with their respective complementary oligonucleotides. FIG. 70 displays fluorescent imaging data for the two arrays, depicting the fluorescent labeling of the functional nucleic acids, as well as stripping results for each respective array. The longer base-pair oligonucleotide is still detectable in many sites after the guanidinium chloride incubation, suggesting that length of a functional nucleic acid sequence can be modulated to facilitate retention or removal of a complementary oligonucleotide from the functional nucleic acid as necessary.

Example 18. Multiplexed Arrays Utilizing Functional Nucleic Acids

An array of SNAPs was prepared via the method of Example 17. The mixture of deposited SNAP comprises an equimolar mixture of a plurality of first tile-shaped SNAPs with first functional nucleic acids, and a plurality of second tile-shaped SNAPs with second functional nucleic acids. The nucleotide sequence of the first functional nucleic acid was ATTATACTACATACACC (SEQ ID NO: 440), and the nucleotide sequence of the second functional nucleic acid was GTTTGTTGTTTGGGTTG (SEQ ID NO: 443).

Figures 69A, 69B:
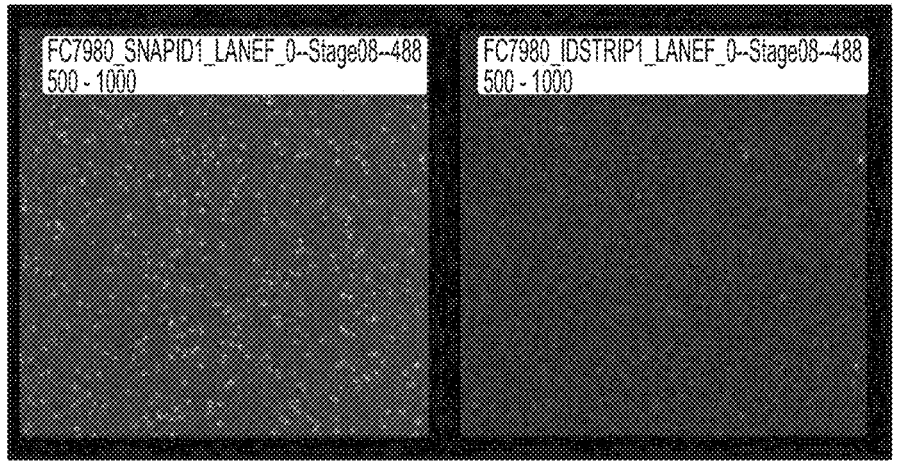
FIGS. 69A, 69B, 69C, and 69D display fluorescence microscopy images for a multiplexed array during binding and stripping of fluorescently-labeled oligonucleotides with functional acids of structured nucleic acid particles.
Figures 69C, 69D:
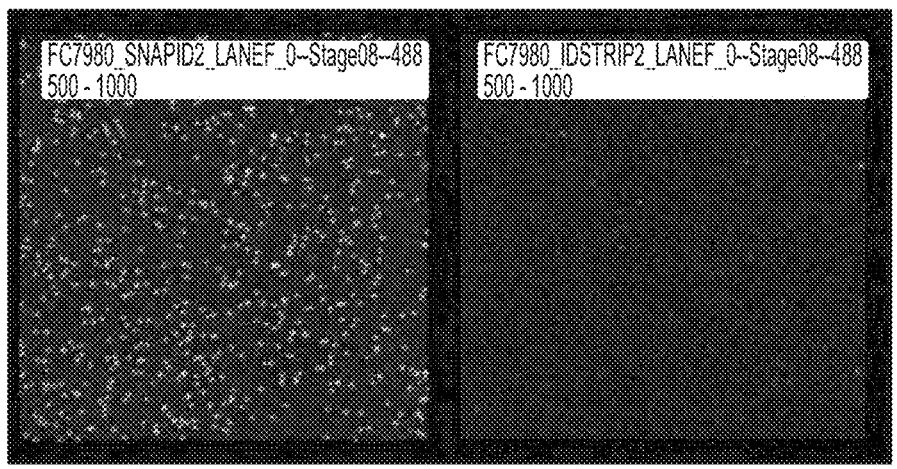

The multiplexed array containing the first tile-shaped SNAPs and the second tile-shaped SNAPs was detected for 2 detection cycles, in which the first cycle utilized an Alexa-Fluor 488-labeled oligonucleotide with a sequence complementary to the first functional nucleic acid, and in which the second cycle utilized an Alexa-Fluor 488-labeled oligonucleotide with a sequence complementary to the second functional nucleic acid. Each complementary oligonucleotide comprised 5 Alexa-Fluor 488 dyes. FIGS. 69A and 69C display fluorescence microscopy images for the binding of the first complementary oligonucleotide and the second complementary oligonucleotide, respectively. FIGS. 69B and 69D display fluorescence microscopy images for the post-application stripping in guanidinium hydrochloride of the first complementary oligonucleotide and the second complementary oligonucleotide, respectively. As shown, the addresses occupied by SNAPs of the first plurality of SNAPs can be distinguished from addresses occupied by the second plurality of SNAPs based upon the detection of binding of complementary oligonucleotides to functional nucleic acids of SNAPs.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention.

Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Notwithstanding the appended claims, the disclosure set forth herein is also defined by the following clauses:

What is claimed is:

1. A method, comprising:
   a) forming a first plurality of nucleic acid nanoparticles, wherein the first plurality of nucleic acid nanoparticles is attached to a first plurality of polypeptides of interest, wherein each nucleic acid nanoparticle of the first plurality of nucleic acid nanoparticles is attached to only one polypeptide of the first plurality of polypeptides of interest, wherein a first unique identifier is attached to each nucleic acid nanoparticle of the first plurality of nucleic acid nanoparticles, and wherein the first plurality of polypeptides of interest comprises at least $10^3$ different native-length protein primary sequences;
   b) forming a second plurality of nucleic acid nanoparticles, wherein the second plurality of nucleic acid nanoparticles is attached to a second plurality of polypeptides of interest, wherein each nucleic acid nanoparticle of the second plurality of nucleic acid nanoparticles is attached to only one polypeptide of the second plurality of polypeptides of interest, wherein a second unique identifier is attached to each nucleic acid nanoparticle of the second plurality of nucleic acid nanoparticles, wherein the first unique identifier and the second unique identifier are different, and wherein the second plurality of polypeptides of interest comprises at least $10^3$ different native-length protein primary sequences;
   c) attaching to each site of a plurality of sites of a solid support only one nucleic acid nanoparticle of the first plurality of nucleic acid nanoparticles or the second plurality of nucleic acid nanoparticles, wherein each site of the plurality of sites is optically resolvable from any other site of the plurality of sites; and
   d) detecting signals from the first unique identifiers at a first set of sites of the plurality of sites, detecting signals from the second unique identifiers at a second set of sites of the plurality of sites.

2. The method of claim 1, further comprising obtaining the first plurality of polypeptides of interest from a first sample.

3. The method of claim 2, further comprising obtaining the second plurality of polypeptides of interest from a second sample.

4. The method of claim 2, further comprising obtaining the second plurality of polypeptides of interest from the first sample.

5. The method of claim 1, wherein attaching to the plurality of sites of the solid support the first plurality of nucleic acid nanoparticles and the second plurality of nucleic acid nanoparticles comprises attaching at a site of the first set of sites a pendant oligonucleotide of a nucleic acid nanoparticle of the first plurality of nanoparticles to a surface-coupled oligonucleotide of the site.

6. The method of claim 1, wherein attaching to the plurality of sites of the solid support the first plurality of nucleic acid nanoparticles and the second plurality of nucleic acid nanoparticles comprises attaching at a site of the second set of sites a pendant oligonucleotide of a nucleic acid nanoparticle of the second plurality of nanoparticles to a surface-coupled oligonucleotide of the site.

7. The method of claim 1, wherein each site of the plurality of sites comprises one or more surface-coupled oligonucleotides, wherein each oligonucleotide of the one or more surface-coupled oligonucleotides comprises an identical nucleotide sequence.

8. The method of claim 7, wherein each nucleic acid nanoparticle of the first plurality of nucleic acid nanoparticles comprises a pendant oligonucleotide, wherein the pendant oligonucleotide comprises a complementary nucleotide sequence to the identical nucleotide sequence.

9. The method of claim 8, wherein each nucleic acid nanoparticle of the second plurality of nucleic acid nanoparticles comprises a pendant oligonucleotide, wherein the pendant oligonucleotide comprises the complementary nucleotide sequence to the identical nucleotide sequence.

10. The method of claim 9, further comprising hybridizing the complementary nucleotide sequence of the pendant oligonucleotide of a nucleic acid nanoparticle of the first plurality of nucleic acid nanoparticles to the identical nucleotide sequence of a site of the first set of sites of the plurality of sites.

11. The method of claim 10, further comprising hybridizing the complementary nucleotide sequence of the pendant oligonucleotide of a nucleic acid nanoparticle of the second plurality of nucleic acid nanoparticles to the identical nucleotide sequence of a site of the second set of sites of the plurality of sites.

12. The method of claim 1, wherein attaching to the plurality of sites of the solid support the first plurality of nucleic acid nanoparticles and the second plurality of nucleic acid nanoparticles comprises:
  i) attaching the first plurality of nucleic acid nanoparticles to the first set of sites; and
  ii) after attaching the first plurality of nucleic acid nanoparticles to the first set of sites, attaching the second plurality of nucleic acid nanoparticles to the second set of sites.

13. The method of claim 12, further comprising, before attaching the second plurality of nucleic acid nanoparticles to the second set of sites, determining the first set of sites containing the first plurality of nucleic acid nanoparticles.

14. The method of claim 13, wherein determining the first set of sites containing the first plurality of nucleic acid nanoparticles comprises detecting signals from nucleic acid nanoparticles at addresses of the first set of sites.

15. The method of claim 12, further comprising, after attaching the second plurality of nucleic acid nanoparticles to the second set of sites, determining the second set of sites containing the second plurality of nucleic acid nanoparticles.

16. The method of claim 15, wherein determining the second set of sites containing the second plurality of nucleic acid nanoparticles comprises detecting signals from nucleic acid nanoparticles at addresses of the second set of sites.

17. The method of claim 1, wherein the first unique identifier comprises a first detectable label and the second unique identifier comprises a second detectable label, wherein the first detectable label differs from the second detectable label.

18. The method of claim 17, wherein the first detectable label and the second detectable label comprise differing fluorophores.

19. The method of claim 17, wherein the first detectable label and the second detectable label comprises differing nucleic acid tags or peptide tags.

20. The method of claim 1, wherein the first set of sites and the second set of sites have random spatial distributions.

21. The method of claim 1, wherein the attaching occurs in the presence of a fluidic medium containing a denaturing species.

22. The method of claim 1, wherein the first plurality of polypeptides of interest or the second plurality of polypeptides of interest comprises at least $10^6$ polypeptide molecules.

23. The method of claim 22, wherein the first plurality of polypeptides of interest comprises at least $10^6$ polypeptide molecules and the second plurality of polypeptides of interest comprises at least $10^6$ polypeptide molecules.

24. The method of claim 22, wherein the first plurality of polypeptides of interest or the second plurality of polypeptides of interest comprises at least $10^8$ polypeptide molecules.

25. The method of claim 1, wherein the plurality of sites comprises at least $10^8$ sites.

26. The method of claim 1, wherein a site of the plurality of sites is separated by at least 500 nm from any other site of the plurality of sites.

27. A method, comprising:
  a) forming a first plurality of nucleic acid nanoparticles, wherein the first plurality of nucleic acid nanoparticles is attached to a first plurality of polypeptides of interest, wherein each nucleic acid nanoparticle of the first plurality of nucleic acid nanoparticles is attached to only one polypeptide of the first plurality of polypeptides of interest, wherein a first unique identifier is attached to each nucleic acid nanoparticle of the first plurality of nucleic acid nanoparticles, and wherein the first plurality of polypeptides comprises at least 25% of polypeptide species of a proteome;
  b) forming a second plurality of nucleic acid nanoparticles, wherein the second plurality of nucleic acid nanoparticles is attached to a second plurality of polypeptides of interest, wherein each nucleic acid nanoparticle of the second plurality of nucleic acid nanoparticles is attached to only one polypeptide of the second plurality of polypeptides of interest, wherein a second unique identifier is attached to each nucleic acid nanoparticle of the second plurality of nucleic acid nanoparticles, wherein the first unique identifier and the second unique identifier are different, and wherein the second plurality of polypeptides comprises at least 25% of polypeptide species of a proteome;
  c) attaching to each site of a plurality of sites of a solid support only one nucleic acid nanoparticle of the first plurality of nucleic acid nanoparticles or the second plurality of nucleic acid nanoparticles, wherein each site of the plurality of sites is optically resolvable from any other site of the plurality of sites; and
  d) detecting signals from the first unique identifiers at a first set of sites of the plurality of sites, and detecting signals from the second unique identifiers at a second set of sites of the plurality of sites.

28. A method, comprising:
  a) forming a first plurality of nucleic acid nanoparticles, wherein the first plurality of nucleic acid nanoparticles is attached to a first plurality of polypeptides of interest, wherein each nucleic acid nanoparticle of the first plurality of nucleic acid nanoparticles is attached to only one polypeptide of the first plurality of polypeptides of interest, wherein a first unique identifier is attached to each nucleic acid nanoparticle of the first plurality of nucleic acid nanoparticles, and wherein the first plurality of polypeptides comprises a complexity of at least $10^5$ different protein structures;
  b) forming a second plurality of nucleic acid nanoparticles, wherein the second plurality of nucleic acid nanoparticles is attached to a second plurality of polypeptides of interest, wherein each nucleic acid nanoparticle of the second plurality of nucleic acid nanoparticles is attached to only one polypeptide of the second plurality of polypeptides of interest, wherein a second unique identifier is attached to each nucleic acid nanoparticle of the second plurality of nucleic acid nanoparticles, wherein the first unique identifier and the second unique identifier are different, and wherein the second plurality of polypeptides comprises a complexity of at least $10^5$ different protein structures;

c) attaching to each site of a plurality of sites of a solid support only one nucleic acid nanoparticle of the first plurality of nucleic acid nanoparticles or the second plurality of nucleic acid nanoparticles, wherein each site of the plurality of sites is optically resolvable from any other site of the plurality of sites; and d) detecting signals from the first unique identifiers at a first set of sites of the plurality of sites, and detecting signals from the second unique identifiers at a second set of sites of the plurality of sites.

29. A method, comprising:

a) forming a first plurality of nucleic acid nanoparticles, wherein the first plurality of nucleic acid nanoparticles is attached to a first plurality of polypeptides of interest, wherein each nucleic acid nanoparticle of the first plurality of nucleic acid nanoparticles is attached to only one polypeptide of the first plurality of polypeptides of interest, wherein a first unique identifier is attached to each nucleic acid nanoparticle of the first plurality of nucleic acid nanoparticles, and wherein the first plurality of polypeptides comprises a dynamic range of at least $10^4$;

b) forming a second plurality of nucleic acid nanoparticles, wherein the second plurality of nucleic acid nanoparticles is attached to a second plurality of polypeptides of interest, wherein each nucleic acid nanoparticle of the second plurality of nucleic acid nanoparticles is attached to only one polypeptide of the second plurality of polypeptides of interest, wherein a second unique identifier is attached to each nucleic acid nanoparticle of the second plurality of nucleic acid nanoparticles, wherein the first unique identifier and the second unique identifier are different, and wherein the second plurality of polypeptides comprises a dynamic range of at least $10^4$;

c) attaching to each site of a plurality of sites of a solid support only one nucleic acid nanoparticle of the first plurality of nucleic acid nanoparticles or the second plurality of nucleic acid nanoparticles, wherein each site of the plurality of sites is optically resolvable from any other site of the plurality of sites; and d) detecting signals from the first unique identifiers at a first set of sites of the plurality of sites, and detecting signals from the second unique identifiers at a second set of sites of the plurality of sites.

* * * * *

```
                              SEQUENCE LISTING

Sequence total quantity: 443
SEQ ID NO: 1            moltype = DNA  length = 43
FEATURE                 Location/Qualifiers
misc_feature            1..43
                        note = synthetic DNA sequence
source                  1..43
                        mol_type = other DNA
                        organism = synthetic construct
SEQUENCE: 1
tttcactcac ctccatctcc actcctaccc atccaactcc cac                    43

SEQ ID NO: 2            moltype = DNA  length = 21
FEATURE                 Location/Qualifiers
misc_feature            1..21
                        note = synthetic DNA sequence
source                  1..21
                        mol_type = other DNA
                        organism = synthetic construct
SEQUENCE: 2
ttttaccatc ttcctctcca c                                            21

SEQ ID NO: 3            moltype = DNA  length = 43
FEATURE                 Location/Qualifiers
misc_feature            1..43
                        note = synthetic DNA sequence
source                  1..43
                        mol_type = other DNA
                        organism = synthetic construct
SEQUENCE: 3
tttaactact cccactctca ccctcaccct actccaactc aac                    43

SEQ ID NO: 4            moltype = DNA  length = 24
FEATURE                 Location/Qualifiers
misc_feature            1..24
                        note = synthetic DNA sequence
source                  1..24
                        mol_type = other DNA
                        organism = synthetic construct
SEQUENCE: 4
tcatttgcta atagtagtag catt                                         24

SEQ ID NO: 5            moltype = DNA  length = 24
FEATURE                 Location/Qualifiers
misc_feature            1..24
                        note = synthetic DNA sequence
source                  1..24
                        mol_type = other DNA
                        organism = synthetic construct
SEQUENCE: 5
caactaaagt acggtgggat ggct                                         24

SEQ ID NO: 6            moltype = DNA  length = 24
FEATURE                 Location/Qualifiers
misc_feature            1..24
                        note = synthetic DNA sequence
source                  1..24
                        mol_type = other DNA
                        organism = synthetic construct
```

```
SEQUENCE: 6
cattattagc aaaagaagtt ttgc                                              24

SEQ ID NO: 7            moltype = DNA  length = 24
FEATURE                 Location/Qualifiers
misc_feature            1..24
                        note = synthetic DNA sequence
source                  1..24
                        mol_type = other DNA
                        organism = synthetic construct
SEQUENCE: 7
accctcattc agggatagca agcc                                              24

SEQ ID NO: 8            moltype = DNA  length = 24
FEATURE                 Location/Qualifiers
misc_feature            1..24
                        note = synthetic DNA sequence
source                  1..24
                        mol_type = other DNA
                        organism = synthetic construct
SEQUENCE: 8
ttaggattag cggggtggaa ccta                                              24

SEQ ID NO: 9            moltype = DNA  length = 24
FEATURE                 Location/Qualifiers
misc_feature            1..24
                        note = synthetic DNA sequence
source                  1..24
                        mol_type = other DNA
                        organism = synthetic construct
SEQUENCE: 9
aggccggaac cagagccacc accg                                              24

SEQ ID NO: 10           moltype = DNA  length = 24
FEATURE                 Location/Qualifiers
misc_feature            1..24
                        note = synthetic DNA sequence
source                  1..24
                        mol_type = other DNA
                        organism = synthetic construct
SEQUENCE: 10
agaatatcag acgacgacaa taaa                                              24

SEQ ID NO: 11           moltype = DNA  length = 24
FEATURE                 Location/Qualifiers
misc_feature            1..24
                        note = synthetic DNA sequence
source                  1..24
                        mol_type = other DNA
                        organism = synthetic construct
SEQUENCE: 11
tcatatgcgt tatacaaagg cgtt                                              24

SEQ ID NO: 12           moltype = DNA  length = 24
FEATURE                 Location/Qualifiers
misc_feature            1..24
                        note = synthetic DNA sequence
source                  1..24
                        mol_type = other DNA
                        organism = synthetic construct
SEQUENCE: 12
cgggagaatt taatggaaac agta                                              24

SEQ ID NO: 13           moltype = DNA  length = 24
FEATURE                 Location/Qualifiers
misc_feature            1..24
                        note = synthetic DNA sequence
source                  1..24
                        mol_type = other DNA
                        organism = synthetic construct
SEQUENCE: 13
gcgcgtactt tcctcgttag aatc                                              24

SEQ ID NO: 14           moltype = DNA  length = 24
FEATURE                 Location/Qualifiers
misc_feature            1..24
                        note = synthetic DNA sequence
```

```
source                  1..24
                        mol_type = other DNA
                        organism = synthetic construct
SEQUENCE: 14
aaagccggcg aacgtgtgcc gtaa                                                24

SEQ ID NO: 15           moltype = DNA   length = 24
FEATURE                 Location/Qualifiers
misc_feature            1..24
                        note = synthetic DNA sequence
source                  1..24
                        mol_type = other DNA
                        organism = synthetic construct
SEQUENCE: 15
aattccacgt ttgcgtattg ggcg                                                24

SEQ ID NO: 16           moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 16
ttaagagggt ccaatactgc ggatagcgag                                          30

SEQ ID NO: 17           moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 17
aggcttttca ggtagaaaga ttcaattacc                                          30

SEQ ID NO: 18           moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 18
ttatgcgatt gacaagaacc ggaggtcaat                                          30

SEQ ID NO: 19           moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 19
cataagggac actaaaacac tcacattaaa                                          30

SEQ ID NO: 20           moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 20
cgggtaaaat tcggtcgctg aggaatgaca                                          30

SEQ ID NO: 21           moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 21
gtctctgaca ccctcagagc cacatcaaaa                                          30
```

```
SEQ ID NO: 22          moltype = DNA   length = 30
FEATURE                Location/Qualifiers
misc_feature           1..30
                       note = synthetic DNA sequence
source                 1..30
                       mol_type = other DNA
                       organism = synthetic construct
SEQUENCE: 22
tcaccggaaa cgtcaccaat gaattattca                                     30

SEQ ID NO: 23          moltype = DNA   length = 30
FEATURE                Location/Qualifiers
misc_feature           1..30
                       note = synthetic DNA sequence
source                 1..30
                       mol_type = other DNA
                       organism = synthetic construct
SEQUENCE: 23
ttaaaggtac atataaaaga aacaaacgca                                     30

SEQ ID NO: 24          moltype = DNA   length = 30
FEATURE                Location/Qualifiers
misc_feature           1..30
                       note = synthetic DNA sequence
source                 1..30
                       mol_type = other DNA
                       organism = synthetic construct
SEQUENCE: 24
ataataactc agagagataa cccgaagcgc                                     30

SEQ ID NO: 25          moltype = DNA   length = 30
FEATURE                Location/Qualifiers
misc_feature           1..30
                       note = synthetic DNA sequence
source                 1..30
                       mol_type = other DNA
                       organism = synthetic construct
SEQUENCE: 25
attagacgga gcgtctttcc agagctacaa                                     30

SEQ ID NO: 26          moltype = DNA   length = 30
FEATURE                Location/Qualifiers
misc_feature           1..30
                       note = synthetic DNA sequence
source                 1..30
                       mol_type = other DNA
                       organism = synthetic construct
SEQUENCE: 26
tatataacgt aaatcgtcgc tatatttgaa                                     30

SEQ ID NO: 27          moltype = DNA   length = 30
FEATURE                Location/Qualifiers
misc_feature           1..30
                       note = synthetic DNA sequence
source                 1..30
                       mol_type = other DNA
                       organism = synthetic construct
SEQUENCE: 27
ttacctttac aataacggat tcgcaaaatt                                     30

SEQ ID NO: 28          moltype = DNA   length = 29
FEATURE                Location/Qualifiers
misc_feature           1..29
                       note = synthetic DNA sequence
source                 1..29
                       mol_type = other DNA
                       organism = synthetic construct
SEQUENCE: 28
tttgcaccat tttgcggaac aaatttgag                                      29

SEQ ID NO: 29          moltype = DNA   length = 30
FEATURE                Location/Qualifiers
misc_feature           1..30
                       note = synthetic DNA sequence
source                 1..30
                       mol_type = other DNA
                       organism = synthetic construct
```

```
SEQUENCE: 29
gatttagatt gctgaacctc aaagtattaa                                          30

SEQ ID NO: 30           moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 30
caccgcctga aagcgtaaga atacattctg                                          30

SEQ ID NO: 31           moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 31
tgagtgttca gctgattgcc cttgcgcggg                                          30

SEQ ID NO: 32           moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 32
gagaggcgac aacatacgag ccgctgcagg                                          30

SEQ ID NO: 33           moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 33
tcgactctga agggcgatcg gtgcggcctc                                          30

SEQ ID NO: 34           moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 34
aggaagatca ttaaatgtga gcgttttttaa                                         30

SEQ ID NO: 35           moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 35
ccaataggaa actagcatgt caaggagcaa                                          30

SEQ ID NO: 36           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 36
tagagcttca gaccggaagc aaacctatta ta                                       32

SEQ ID NO: 37           moltype = DNA  length = 32
FEATURE                 Location/Qualifiers
misc_feature            1..32
                        note = synthetic DNA sequence
```

```
source                  1..32
                        mol_type = other DNA
                        organism = synthetic construct
SEQUENCE: 37
gtcagaagat tgaatccccc tcaacctcgt tt                              32

SEQ ID NO: 38           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 38
aaatattcca aagcggattg catcgagctt ca                              32

SEQ ID NO: 39           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 39
accagacgga ataccacatt caacgagatg gt                              32

SEQ ID NO: 40           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 40
agatttagac gataaaaacc aaaaatcgtc at                              32

SEQ ID NO: 41           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 41
agtcaggaca taggctggct gacctttgaa ag                              32

SEQ ID NO: 42           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 42
ttaatttcca acgtaacaaa gctgtccatg tt                              32

SEQ ID NO: 43           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 43
gagtaatctt ttaagaactg gctccggaac aa                              32

SEQ ID NO: 44           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 44
acccaaataa ctttaatcat tgtgatcagt tg                              32

SEQ ID NO: 45           moltype = DNA  length = 32
FEATURE                 Location/Qualifiers
```

```
misc_feature              1..32
                          note = synthetic DNA sequence
source                    1..32
                          mol_type = other DNA
                          organism = synthetic construct
SEQUENCE: 45
acttagccat taccaagc gcgagaggac ta                                        32

SEQ ID NO: 46             moltype = DNA  length = 32
FEATURE                   Location/Qualifiers
misc_feature              1..32
                          note = synthetic DNA sequence
source                    1..32
                          mol_type = other DNA
                          organism = synthetic construct
SEQUENCE: 46
aaaagaataa ccgaactgac caacttcatc aa                                      32

SEQ ID NO: 47             moltype = DNA  length = 32
FEATURE                   Location/Qualifiers
misc_feature              1..32
                          note = synthetic DNA sequence
source                    1..32
                          mol_type = other DNA
                          organism = synthetic construct
SEQUENCE: 47
aagactttgg ccgcttttgc gggattaaac ag                                      32

SEQ ID NO: 48             moltype = DNA  length = 32
FEATURE                   Location/Qualifiers
misc_feature              1..32
                          note = synthetic DNA sequence
source                    1..32
                          mol_type = other DNA
                          organism = synthetic construct
SEQUENCE: 48
gagttaaatt catgaggaag tttctctttg ac                                      32

SEQ ID NO: 49             moltype = DNA  length = 32
FEATURE                   Location/Qualifiers
misc_feature              1..32
                          note = synthetic DNA sequence
source                    1..32
                          mol_type = other DNA
                          organism = synthetic construct
SEQUENCE: 49
cttgatactg aaaatctcca aaaaagcgga gt                                      32

SEQ ID NO: 50             moltype = DNA  length = 32
FEATURE                   Location/Qualifiers
misc_feature              1..32
                          note = synthetic DNA sequence
source                    1..32
                          mol_type = other DNA
                          organism = synthetic construct
SEQUENCE: 50
tttcacgtcg atagttgcgc cgaccttgca gg                                      32

SEQ ID NO: 51             moltype = DNA  length = 32
FEATURE                   Location/Qualifiers
misc_feature              1..32
                          note = synthetic DNA sequence
source                    1..32
                          mol_type = other DNA
                          organism = synthetic construct
SEQUENCE: 51
ttattctgac tggtaataag ttttaacaaa ta                                      32

SEQ ID NO: 52             moltype = DNA  length = 32
FEATURE                   Location/Qualifiers
misc_feature              1..32
                          note = synthetic DNA sequence
source                    1..32
                          mol_type = other DNA
                          organism = synthetic construct
SEQUENCE: 52
aatcctcaac cagaaccacc accagccccc tt                                      32

SEQ ID NO: 53             moltype = DNA  length = 32
```

```
FEATURE                 Location/Qualifiers
misc_feature            1..32
                        note = synthetic DNA sequence
source                  1..32
                        mol_type = other DNA
                        organism = synthetic construct
SEQUENCE: 53
gagccgcctt aaagccagaa tggagatgat ac                                         32

SEQ ID NO: 54           moltype = DNA   length = 32
FEATURE                 Location/Qualifiers
misc_feature            1..32
                        note = synthetic DNA sequence
source                  1..32
                        mol_type = other DNA
                        organism = synthetic construct
SEQUENCE: 54
attagcgtcc gtaatcagta gcgaattgag gg                                         32

SEQ ID NO: 55           moltype = DNA   length = 32
FEATURE                 Location/Qualifiers
misc_feature            1..32
                        note = synthetic DNA sequence
source                  1..32
                        mol_type = other DNA
                        organism = synthetic construct
SEQUENCE: 55
gccatttgca aacgtagaaa atacctggca tg                                         32

SEQ ID NO: 56           moltype = DNA   length = 32
FEATURE                 Location/Qualifiers
misc_feature            1..32
                        note = synthetic DNA sequence
source                  1..32
                        mol_type = other DNA
                        organism = synthetic construct
SEQUENCE: 56
agggaaggat aagtttattt tgtcagccga ac                                         32

SEQ ID NO: 57           moltype = DNA   length = 32
FEATURE                 Location/Qualifiers
misc_feature            1..32
                        note = synthetic DNA sequence
source                  1..32
                        mol_type = other DNA
                        organism = synthetic construct
SEQUENCE: 57
aggtggcaga attatcaccg tcaccattag ca                                         32

SEQ ID NO: 58           moltype = DNA   length = 32
FEATURE                 Location/Qualifiers
misc_feature            1..32
                        note = synthetic DNA sequence
source                  1..32
                        mol_type = other DNA
                        organism = synthetic construct
SEQUENCE: 58
aaagttacgc ccaataataa gagcagcctt ta                                         32

SEQ ID NO: 59           moltype = DNA   length = 32
FEATURE                 Location/Qualifiers
misc_feature            1..32
                        note = synthetic DNA sequence
source                  1..32
                        mol_type = other DNA
                        organism = synthetic construct
SEQUENCE: 59
cgctaatagg aatacccaaa agaaatacat aa                                         32

SEQ ID NO: 60           moltype = DNA   length = 32
FEATURE                 Location/Qualifiers
misc_feature            1..32
                        note = synthetic DNA sequence
source                  1..32
                        mol_type = other DNA
                        organism = synthetic construct
SEQUENCE: 60
cagagagaac aaaataaaca gccattaaat ca                                         32
```

```
SEQ ID NO: 61            moltype = DNA   length = 32
FEATURE                  Location/Qualifiers
misc_feature             1..32
                         note = synthetic DNA sequence
source                   1..32
                         mol_type = other DNA
                         organism = synthetic construct
SEQUENCE: 61
agattagtat atagaaggct tatccaagcc gt                                     32

SEQ ID NO: 62            moltype = DNA   length = 32
FEATURE                  Location/Qualifiers
misc_feature             1..32
                         note = synthetic DNA sequence
source                   1..32
                         mol_type = other DNA
                         organism = synthetic construct
SEQUENCE: 62
caaatcagtg ctattttgca cccagcctaa tt                                     32

SEQ ID NO: 63            moltype = DNA   length = 32
FEATURE                  Location/Qualifiers
misc_feature             1..32
                         note = synthetic DNA sequence
source                   1..32
                         mol_type = other DNA
                         organism = synthetic construct
SEQUENCE: 63
aaataagaac tttttcaaat atatctgaga ga                                     32

SEQ ID NO: 64            moltype = DNA   length = 32
FEATURE                  Location/Qualifiers
misc_feature             1..32
                         note = synthetic DNA sequence
source                   1..32
                         mol_type = other DNA
                         organism = synthetic construct
SEQUENCE: 64
ctacctttag aatccttgaa aacaagaaaa ca                                     32

SEQ ID NO: 65            moltype = DNA   length = 32
FEATURE                  Location/Qualifiers
misc_feature             1..32
                         note = synthetic DNA sequence
source                   1..32
                         mol_type = other DNA
                         organism = synthetic construct
SEQUENCE: 65
tttcccttt aacctccggc ttagcaaaga ac                                      32

SEQ ID NO: 66            moltype = DNA   length = 32
FEATURE                  Location/Qualifiers
misc_feature             1..32
                         note = synthetic DNA sequence
source                   1..32
                         mol_type = other DNA
                         organism = synthetic construct
SEQUENCE: 66
aaattaatac caagttacaa aatcctgaat aa                                     32

SEQ ID NO: 67            moltype = DNA   length = 32
FEATURE                  Location/Qualifiers
misc_feature             1..32
                         note = synthetic DNA sequence
source                   1..32
                         mol_type = other DNA
                         organism = synthetic construct
SEQUENCE: 67
ctttgaatta catttaacaa tttctaatta at                                     32

SEQ ID NO: 68            moltype = DNA   length = 32
FEATURE                  Location/Qualifiers
misc_feature             1..32
                         note = synthetic DNA sequence
source                   1..32
                         mol_type = other DNA
                         organism = synthetic construct
SEQUENCE: 68
gtagattgt tattaattt aaaaaacaat tc                                       32
```

```
SEQ ID NO: 69          moltype = DNA   length = 32
FEATURE                Location/Qualifiers
misc_feature           1..32
                       note = synthetic DNA sequence
source                 1..32
                       mol_type = other DNA
                       organism = synthetic construct
SEQUENCE: 69
tggaagggag cggaattatc atcaactaat ag                                    32

SEQ ID NO: 70          moltype = DNA   length = 32
FEATURE                Location/Qualifiers
misc_feature           1..32
                       note = synthetic DNA sequence
source                 1..32
                       mol_type = other DNA
                       organism = synthetic construct
SEQUENCE: 70
aacattatgt aaaacagaaa taaattttac at                                    32

SEQ ID NO: 71          moltype = DNA   length = 32
FEATURE                Location/Qualifiers
misc_feature           1..32
                       note = synthetic DNA sequence
source                 1..32
                       mol_type = other DNA
                       organism = synthetic construct
SEQUENCE: 71
ccagaaggtt agaacctacc atatcctgat tg                                    32

SEQ ID NO: 72          moltype = DNA   length = 32
FEATURE                Location/Qualifiers
misc_feature           1..32
                       note = synthetic DNA sequence
source                 1..32
                       mol_type = other DNA
                       organism = synthetic construct
SEQUENCE: 72
attagagcaa tatctggtca gttgcagcag aa                                    32

SEQ ID NO: 73          moltype = DNA   length = 32
FEATURE                Location/Qualifiers
misc_feature           1..32
                       note = synthetic DNA sequence
source                 1..32
                       mol_type = other DNA
                       organism = synthetic construct
SEQUENCE: 73
gcatcaccag tattagactt tacagtttga gt                                    32

SEQ ID NO: 74          moltype = DNA   length = 32
FEATURE                Location/Qualifiers
misc_feature           1..32
                       note = synthetic DNA sequence
source                 1..32
                       mol_type = other DNA
                       organism = synthetic construct
SEQUENCE: 74
cctcaatccg tcaatagata atacagaaac ca                                    32

SEQ ID NO: 75          moltype = DNA   length = 32
FEATURE                Location/Qualifiers
misc_feature           1..32
                       note = synthetic DNA sequence
source                 1..32
                       mol_type = other DNA
                       organism = synthetic construct
SEQUENCE: 75
gataaaactt tttgaatggc tattttcacc ag                                    32

SEQ ID NO: 76          moltype = DNA   length = 32
FEATURE                Location/Qualifiers
misc_feature           1..32
                       note = synthetic DNA sequence
source                 1..32
                       mol_type = other DNA
                       organism = synthetic construct
```

```
SEQUENCE: 76
agacaataag aggtgaggcg gtcatatcaa ac                                      32

SEQ ID NO: 77           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 77
tcacacgatg caacaggaaa aacggaagaa ct                                      32

SEQ ID NO: 78           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 78
ccagccatcc agtaataaaa gggacgtggc ac                                      32

SEQ ID NO: 79           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 79
agcactaaaa agggcgaaaa accgaaatcc ct                                      32

SEQ ID NO: 80           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 80
tataaatcga gagttgcagc aagcgtcgtg cc                                      32

SEQ ID NO: 81           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 81
ggccctgaaa aagaatagcc cgagcgtgga ct                                      32

SEQ ID NO: 82           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 82
agctgcatag cctggggtgc ctaagtaaaa cg                                      32

SEQ ID NO: 83           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 83
aagtgtaata atgaatcggc caaccaccgc ct                                      32

SEQ ID NO: 84           moltype = DNA  length = 32
FEATURE                 Location/Qualifiers
misc_feature            1..32
                        note = synthetic DNA sequence
```

```
source                  1..32
                        mol_type = other DNA
                        organism = synthetic construct
SEQUENCE: 84
gaattcgtgc cattcgccat tcagttccgg ca                              32

SEQ ID NO: 85           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 85
acggccagta cgccagctgg cgaacatctg cc                              32

SEQ ID NO: 86           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 86
actgttggag aggatccccg ggtaccgctc ac                              32

SEQ ID NO: 87           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 87
ttcgctattg ccaagcttgc atgcgaagca ta                              32

SEQ ID NO: 88           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 88
agtttgagat tctccgtggg aacaattcgc at                              32

SEQ ID NO: 89           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 89
ttcatcaacg cactccagcc agctgctgcg ca                              32

SEQ ID NO: 90           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 90
cccgtcgggg gacgacgaca gtatcgggcc tc                              32

SEQ ID NO: 91           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 91
taaattttg ataatcagaa aagcacaaag gc                               32

SEQ ID NO: 92           moltype = DNA  length = 32
FEATURE                 Location/Qualifiers
```

```
misc_feature            1..32
                        note = synthetic DNA sequence
source                  1..32
                        mol_type = other DNA
                        organism = synthetic construct
SEQUENCE: 92
accccggttg ttaaatcagc tcatagtaac aa                                    32

SEQ ID NO: 93           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 93
tatcaggtaa atcaccatca atatcaatgc ct                                    32

SEQ ID NO: 94           moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 94
agacagtcca ttgcctgaga gtcttcatat gt                                    32

SEQ ID NO: 95           moltype = DNA  length = 48
FEATURE                 Location/Qualifiers
misc_feature            1..48
                        note = synthetic DNA sequence
source                  1..48
                        mol_type = other DNA
                        organism = synthetic construct
SEQUENCE: 95
gacggaaaac catcgatagc agcattgcca tcttttcata caccctca                   48

SEQ ID NO: 96           moltype = DNA  length = 48
FEATURE                 Location/Qualifiers
misc_feature            1..48
                        note = synthetic DNA sequence
source                  1..48
                        mol_type = other DNA
                        organism = synthetic construct
SEQUENCE: 96
tgccagttat aacataaaaa caggacaaga attgagttaa cagaagga                   48

SEQ ID NO: 97           moltype = DNA  length = 25
FEATURE                 Location/Qualifiers
misc_feature            1..25
                        note = synthetic DNA sequence
source                  1..25
                        mol_type = other DNA
                        organism = synthetic construct
SEQUENCE: 97
tgccactact tttttgcca ccctc                                             25

SEQ ID NO: 98           moltype = DNA  length = 25
FEATURE                 Location/Qualifiers
misc_feature            1..25
                        note = synthetic DNA sequence
source                  1..25
                        mol_type = other DNA
                        organism = synthetic construct
SEQUENCE: 98
aactgaacat tttttttgaa taacc                                            25

SEQ ID NO: 99           moltype = DNA  length = 25
FEATURE                 Location/Qualifiers
misc_feature            1..25
                        note = synthetic DNA sequence
source                  1..25
                        mol_type = other DNA
                        organism = synthetic construct
SEQUENCE: 99
gccacgctgt tttttacca gtgag                                             25
```

```
SEQ ID NO: 100           moltype = DNA  length = 25
FEATURE                  Location/Qualifiers
misc_feature             1..25
                         note = synthetic DNA sequence
source                   1..25
                         mol_type = other DNA
                         organism = synthetic construct
SEQUENCE: 100
caaaaataat ttttttgtt tagac                                          25

SEQ ID NO: 101           moltype = DNA  length = 29
FEATURE                  Location/Qualifiers
misc_feature             1..29
                         note = synthetic DNA sequence
source                   1..29
                         mol_type = other DNA
                         organism = synthetic construct
SEQUENCE: 101
gatacatttc gctttttga ccctgtaat                                      29

SEQ ID NO: 102           moltype = DNA  length = 29
FEATURE                  Location/Qualifiers
misc_feature             1..29
                         note = synthetic DNA sequence
source                   1..29
                         mol_type = other DNA
                         organism = synthetic construct
SEQUENCE: 102
accgtactca ggttttgat ctaaagttt                                      29

SEQ ID NO: 103           moltype = DNA  length = 29
FEATURE                  Location/Qualifiers
misc_feature             1..29
                         note = synthetic DNA sequence
source                   1..29
                         mol_type = other DNA
                         organism = synthetic construct
SEQUENCE: 103
aacatgtaat ttttttgaa accaatcaa                                      29

SEQ ID NO: 104           moltype = DNA  length = 29
FEATURE                  Location/Qualifiers
misc_feature             1..29
                         note = synthetic DNA sequence
source                   1..29
                         mol_type = other DNA
                         organism = synthetic construct
SEQUENCE: 104
gcgtaaccac cattttgag taaaagagt                                      29

SEQ ID NO: 105           moltype = DNA  length = 31
FEATURE                  Location/Qualifiers
misc_feature             1..31
                         note = synthetic DNA sequence
source                   1..31
                         mol_type = other DNA
                         organism = synthetic construct
SEQUENCE: 105
cagaggggt tttgccttcc tgtagccagc t                                   31

SEQ ID NO: 106           moltype = DNA  length = 31
FEATURE                  Location/Qualifiers
misc_feature             1..31
                         note = synthetic DNA sequence
source                   1..31
                         mol_type = other DNA
                         organism = synthetic construct
SEQUENCE: 106
gaaccgcctc tttacctaaa acgaaagagg c                                  31

SEQ ID NO: 107           moltype = DNA  length = 31
FEATURE                  Location/Qualifiers
misc_feature             1..31
                         note = synthetic DNA sequence
source                   1..31
                         mol_type = other DNA
                         organism = synthetic construct
```

```
SEQUENCE: 107
cataaatcaa tttagtcaga gggtaattga g                                31

SEQ ID NO: 108           moltype = DNA  length = 31
FEATURE                  Location/Qualifiers
misc_feature             1..31
                         note = synthetic DNA sequence
source                   1..31
                         mol_type = other DNA
                         organism = synthetic construct
SEQUENCE: 108
ccagggtggt tttgcaaatg aaaaatctaa a                                31

SEQ ID NO: 109           moltype = DNA  length = 34
FEATURE                  Location/Qualifiers
misc_feature             1..34
                         note = synthetic DNA sequence
source                   1..34
                         mol_type = other DNA
                         organism = synthetic construct
SEQUENCE: 109
acaaccattt tttcatacat ggcttttaag cgca                             34

SEQ ID NO: 110           moltype = DNA  length = 34
FEATURE                  Location/Qualifiers
misc_feature             1..34
                         note = synthetic DNA sequence
source                   1..34
                         mol_type = other DNA
                         organism = synthetic construct
SEQUENCE: 110
ttttatctttt tttatccaat cgcaagagtt gggt                            34

SEQ ID NO: 111           moltype = DNA  length = 34
FEATURE                  Location/Qualifiers
misc_feature             1..34
                         note = synthetic DNA sequence
source                   1..34
                         mol_type = other DNA
                         organism = synthetic construct
SEQUENCE: 111
gccaacatttt tttccactat taaagaaata gggt                            34

SEQ ID NO: 112           moltype = DNA  length = 34
FEATURE                  Location/Qualifiers
misc_feature             1..34
                         note = synthetic DNA sequence
source                   1..34
                         mol_type = other DNA
                         organism = synthetic construct
SEQUENCE: 112
acaagagttt ttttcgcgtt ttaattcaaa aaga                             34

SEQ ID NO: 113           moltype = DNA  length = 36
FEATURE                  Location/Qualifiers
misc_feature             1..36
                         note = synthetic DNA sequence
source                   1..36
                         mol_type = other DNA
                         organism = synthetic construct
SEQUENCE: 113
tggatagcaa gcccgatttt taatcgtaaa cgccat                           36

SEQ ID NO: 114           moltype = DNA  length = 36
FEATURE                  Location/Qualifiers
misc_feature             1..36
                         note = synthetic DNA sequence
source                   1..36
                         mol_type = other DNA
                         organism = synthetic construct
SEQUENCE: 114
agaaccgcat ttaccgttttt accgatatat acgtaa                          36

SEQ ID NO: 115           moltype = DNA  length = 36
FEATURE                  Location/Qualifiers
misc_feature             1..36
                         note = synthetic DNA sequence
```

```
source                  1..36
                        mol_type = other DNA
                        organism = synthetic construct
SEQUENCE: 115
ttgcttctta tatgtatttt acgctaacgg agaatt                              36

SEQ ID NO: 116          moltype = DNA   length = 36
FEATURE                 Location/Qualifiers
misc_feature            1..36
                        note = synthetic DNA sequence
source                  1..36
                        mol_type = other DNA
                        organism = synthetic construct
SEQUENCE: 116
acgggcaagt tccagttttt tctgacctgc aacagt                              36

SEQ ID NO: 117          moltype = DNA   length = 38
FEATURE                 Location/Qualifiers
misc_feature            1..38
                        note = synthetic DNA sequence
source                  1..38
                        mol_type = other DNA
                        organism = synthetic construct
SEQUENCE: 117
gagaatagaa aggaacaact attttctcaa gagaagga                            38

SEQ ID NO: 118          moltype = DNA   length = 38
FEATURE                 Location/Qualifiers
misc_feature            1..38
                        note = synthetic DNA sequence
source                  1..38
                        mol_type = other DNA
                        organism = synthetic construct
SEQUENCE: 118
ttttattttc atcgtaggaa tttttagcct gtttagta                            38

SEQ ID NO: 119          moltype = DNA   length = 38
FEATURE                 Location/Qualifiers
misc_feature            1..38
                        note = synthetic DNA sequence
source                  1..38
                        mol_type = other DNA
                        organism = synthetic construct
SEQUENCE: 119
caaactatcg gccttgctgg tttttgagct tgacgggg                            38

SEQ ID NO: 120          moltype = DNA   length = 38
FEATURE                 Location/Qualifiers
misc_feature            1..38
                        note = synthetic DNA sequence
source                  1..38
                        mol_type = other DNA
                        organism = synthetic construct
SEQUENCE: 120
gagtaatgtg taggtaaaga ttttttgttt taaatatg                            38

SEQ ID NO: 121          moltype = DNA   length = 43
FEATURE                 Location/Qualifiers
misc_feature            1..43
                        note = synthetic DNA sequence
source                  1..43
                        mol_type = other DNA
                        organism = synthetic construct
SEQUENCE: 121
aggacagatg attttttcac cagtagcacc attaccgact tga                      43

SEQ ID NO: 122          moltype = DNA   length = 43
FEATURE                 Location/Qualifiers
misc_feature            1..43
                        note = synthetic DNA sequence
source                  1..43
                        mol_type = other DNA
                        organism = synthetic construct
SEQUENCE: 122
attaagactc cttttttaata tacagtaaca gtaccgaaat tgc                     43

SEQ ID NO: 123          moltype = DNA   length = 43
FEATURE                 Location/Qualifiers
```

```
misc_feature            1..43
                        note = synthetic DNA sequence
source                  1..43
                        mol_type = other DNA
                        organism = synthetic construct
SEQUENCE: 123
gacaactcgt attttttcct gtgtgaaatt gttatccgag ctc                43

SEQ ID NO: 124          moltype = DNA  length = 43
FEATURE                 Location/Qualifiers
misc_feature            1..43
                        note = synthetic DNA sequence
source                  1..43
                        mol_type = other DNA
                        organism = synthetic construct
SEQUENCE: 124
ccgcttctgg tttttcgtt aataaaacga actaaattat acc                 43

SEQ ID NO: 125          moltype = DNA  length = 45
FEATURE                 Location/Qualifiers
misc_feature            1..45
                        note = synthetic DNA sequence
source                  1..45
                        mol_type = other DNA
                        organism = synthetic construct
SEQUENCE: 125
tgtcgtctca gccctcatat tttttcgcc accctcaggt gtatc                45

SEQ ID NO: 126          moltype = DNA  length = 45
FEATURE                 Location/Qualifiers
misc_feature            1..45
                        note = synthetic DNA sequence
source                  1..45
                        mol_type = other DNA
                        organism = synthetic construct
SEQUENCE: 126
taatcggcca tcctaatttt tttttttttt cgagccaaca acgcc               45

SEQ ID NO: 127          moltype = DNA  length = 45
FEATURE                 Location/Qualifiers
misc_feature            1..45
                        note = synthetic DNA sequence
source                  1..45
                        mol_type = other DNA
                        organism = synthetic construct
SEQUENCE: 127
ctgtccattt ttataatcat tttttctta atgcgcccac gctgc                45

SEQ ID NO: 128          moltype = DNA  length = 45
FEATURE                 Location/Qualifiers
misc_feature            1..45
                        note = synthetic DNA sequence
source                  1..45
                        mol_type = other DNA
                        organism = synthetic construct
SEQUENCE: 128
acttttgcat cggttgtact tttttaacc tgtttaggac catta                45

SEQ ID NO: 129          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 129
aagcgaacaa ttgctgaata taatgctgta tttttttgtg agaaaggccg g        51

SEQ ID NO: 130          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 130
aggagtgtaa acatgaaagt attaagaggc tttttttgcg aataataatt t        51
```

```
SEQ ID NO: 131            moltype = DNA   length = 51
FEATURE                   Location/Qualifiers
misc_feature              1..51
                          note = synthetic DNA sequence
source                    1..51
                          mol_type = other DNA
                          organism = synthetic construct
SEQUENCE: 131
gcgagaaaat aaacaccgga atcataatta tttttttcgc ccaatagcaa g              51

SEQ ID NO: 132            moltype = DNA   length = 51
FEATURE                   Location/Qualifiers
misc_feature              1..51
                          note = synthetic DNA sequence
source                    1..51
                          mol_type = other DNA
                          organism = synthetic construct
SEQUENCE: 132
ccaacgtcat cggaaccta aagggagccc ttttttgaa caatattacc g                51

SEQ ID NO: 133            moltype = DNA   length = 60
FEATURE                   Location/Qualifiers
misc_feature              1..60
                          note = synthetic DNA sequence
source                    1..60
                          mol_type = other DNA
                          organism = synthetic construct
SEQUENCE: 133
ggaattagag cttttttttc agaccaggcg cgttgggaag attttttttc caggcaaagc     60

SEQ ID NO: 134            moltype = DNA   length = 60
FEATURE                   Location/Qualifiers
misc_feature              1..60
                          note = synthetic DNA sequence
source                    1..60
                          mol_type = other DNA
                          organism = synthetic construct
SEQUENCE: 134
aatcatggtc atttttttt ttgcccgaac tcaggtttaa cttttttttc agtatgttag      60

SEQ ID NO: 135            moltype = DNA   length = 30
FEATURE                   Location/Qualifiers
misc_feature              1..30
                          note = synthetic DNA sequence
source                    1..30
                          mol_type = other DNA
                          organism = synthetic construct
SEQUENCE: 135
tttcattgag tagatttagt ttctatattt                                      30

SEQ ID NO: 136            moltype = DNA   length = 30
FEATURE                   Location/Qualifiers
misc_feature              1..30
                          note = synthetic DNA sequence
source                    1..30
                          mol_type = other DNA
                          organism = synthetic construct
SEQUENCE: 136
aacagttagg tctttaccct gatccaacag                                      30

SEQ ID NO: 137            moltype = DNA   length = 30
FEATURE                   Location/Qualifiers
misc_feature              1..30
                          note = synthetic DNA sequence
source                    1..30
                          mol_type = other DNA
                          organism = synthetic construct
SEQUENCE: 137
gtgaatatag taaattgggc tttaatgcag                                      30

SEQ ID NO: 138            moltype = DNA   length = 30
FEATURE                   Location/Qualifiers
misc_feature              1..30
                          note = synthetic DNA sequence
source                    1..30
                          mol_type = other DNA
                          organism = synthetic construct
```

```
SEQUENCE: 138
ctcagcaggc tacagaggct ttaacaaagt                                          30

SEQ ID NO: 139          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 139
gttagtaact ttcaacagtt tcaaaggctc                                          30

SEQ ID NO: 140          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 140
gtaccaggta tagcccggaa tagaaccgcc                                          30

SEQ ID NO: 141          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 141
gccagcagcc ttgatattca caaacggggt                                          30

SEQ ID NO: 142          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 142
tagaaaggc gacattcaac cgcagaatca                                           30

SEQ ID NO: 143          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 143
atcccaaaaa aatgaaaata gcaagaaaca                                          30

SEQ ID NO: 144          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 144
cttatcactc atcgagaaca agcggtattc                                          30

SEQ ID NO: 145          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 145
ccagtatgaa tcgccatatt tagtaataag                                          30

SEQ ID NO: 146          moltype = DNA   length = 30
FEATURE                 Location/Qualifiers
misc_feature            1..30
                        note = synthetic DNA sequence
```

```
source                  1..30
                        mol_type = other DNA
                        organism = synthetic construct
SEQUENCE: 146
gcttagaatc aaaatcatag gttttagtta                                            30

SEQ ID NO: 147          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 147
attatcagtt tggattatac ttgcgcagag                                            30

SEQ ID NO: 148          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 148
atgcgcgtac cgaacgaacc acgcaaatca                                            30

SEQ ID NO: 149          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 149
ttaaccgtca cttgcctgag tactcatgga                                            30

SEQ ID NO: 150          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 150
ggaaggggc aagtgtagcg gtgctacagg                                             30

SEQ ID NO: 151          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 151
ctggtttgtt ccgaaatcgg catctatcag                                            30

SEQ ID NO: 152          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 152
gtgctgcccc agtcacgacg tttgagtgag                                            30

SEQ ID NO: 153          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 153
caggaagtaa tattttgtta aaaacggcgg                                            30

SEQ ID NO: 154          moltype = DNA   length = 30
FEATURE                 Location/Qualifiers
```

```
misc_feature            1..30
                        note = synthetic DNA sequence
source                  1..30
                        mol_type = other DNA
                        organism = synthetic construct
SEQUENCE: 154
cctttatcat atattttaaa tggatattca                                          30

SEQ ID NO: 155          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 155
ccccagcggg aacgaggcgc agactattca tt                                       32

SEQ ID NO: 156          moltype = DNA  length = 75
FEATURE                 Location/Qualifiers
misc_feature            1..75
                        note = synthetic DNA sequence
source                  1..75
                        mol_type = other DNA
                        organism = synthetic construct
SEQUENCE: 156
aaccgagggc aaagacacca cggataaata tttttcactc acctccatct ccactcctac         60
ccatccaact cccac                                                          75

SEQ ID NO: 157          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 157
gtcaggaaga ggtcattttt gctctggaag ttttaccatc ttcctctcca c                  51

SEQ ID NO: 158          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 158
atacatacaa cactatcata acatgcttta ttttaccatc ttcctctcca c                  51

SEQ ID NO: 159          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 159
acaacggaaa tccgcgacct gcctcattca ttttaccatc ttcctctcca c                  51

SEQ ID NO: 160          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 160
caaaaggttc gaggtgaatt tctcgtcacc ttttaccatc ttcctctcca c                  51

SEQ ID NO: 161          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 161
atttcatgac cgtgtgataa ataattctta ttttaccatc ttcctctcca c                  51
```

```
SEQ ID NO: 162          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 162
gcgaattatg aaacaaacat catagcgata ttttaccatc ttcctctcca c          51

SEQ ID NO: 163          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 163
acagttgtta ggagcactaa catattcctg ttttaccatc ttcctctcca c          51

SEQ ID NO: 164          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 164
aatacctatt tacattggca gaagtcttta ttttaccatc ttcctctcca c          51

SEQ ID NO: 165          moltype = DNA   length = 61
FEATURE                 Location/Qualifiers
misc_feature            1..61
                        note = synthetic DNA sequence
source                  1..61
                        mol_type = other DNA
                        organism = synthetic construct
SEQUENCE: 165
ccatgtaccg taacactgta gcattccaca gattccagac ttttaccatc ttcctctcca 60
c                                                                 61

SEQ ID NO: 166          moltype = DNA   length = 61
FEATURE                 Location/Qualifiers
misc_feature            1..61
                        note = synthetic DNA sequence
source                  1..61
                        mol_type = other DNA
                        organism = synthetic construct
SEQUENCE: 166
ctaaacagga ggccgataat cctgagaagt gtcacgcaaa ttttaccatc ttcctctcca 60
c                                                                 61

SEQ ID NO: 167          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 167
cagtgccccc cctgcctatt tctttgctca ttttaccatc ttcctctcca c          51

SEQ ID NO: 168          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 168
agtttgcgca ttttcggtca tagagccgcc ttttaccatc ttcctctcca c          51

SEQ ID NO: 169          moltype = DNA   length = 51
FEATURE                 Location/Qualifiers
misc_feature            1..51
                        note = synthetic DNA sequence
source                  1..51
                        mol_type = other DNA
                        organism = synthetic construct
```

```
SEQUENCE: 169
atgaaatgaa aagtaagcag atacaatcaa ttttaccatc ttcctctcca c                    51

SEQ ID NO: 170          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 170
taagaacgga ggttttgaag cctattattt ttttaccatc ttcctctcca c                    51

SEQ ID NO: 171          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 171
ggcgatgttt ttggggtcga gggcgagaaa ttttaccatc ttcctctcca c                    51

SEQ ID NO: 172          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 172
ctaactccca gtcgggaaac ctggtccacg ttttaccatc ttcctctcca c                    51

SEQ ID NO: 173          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 173
attgacccgc atcgtaaccg tgaggggat ttttaccatc ttcctctcca c                     51

SEQ ID NO: 174          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 174
accgttcatt tttgagagat ctcccaaaaa ttttaccatc ttcctctcca c                    51

SEQ ID NO: 175          moltype = DNA  length = 61
FEATURE                 Location/Qualifiers
misc_feature            1..61
                        note = synthetic DNA sequence
source                  1..61
                        mol_type = other DNA
                        organism = synthetic construct
SEQUENCE: 175
agctaatgca gaacgcgaga aaaataatat cctgtctttc ttttaccatc ttcctctcca          60
c                                                                          61

SEQ ID NO: 176          moltype = DNA  length = 61
FEATURE                 Location/Qualifiers
misc_feature            1..61
                        note = synthetic DNA sequence
source                  1..61
                        mol_type = other DNA
                        organism = synthetic construct
SEQUENCE: 176
aatcatacag gcaaggcaga gcataaagct aagggagaag ttttaccatc ttcctctcca          60
c                                                                          61

SEQ ID NO: 177          moltype = DNA  length = 78
FEATURE                 Location/Qualifiers
misc_feature            1..78
                        note = synthetic DNA sequence
```

```
                        source            1..78
                                          mol_type = other DNA
                                          organism = synthetic construct
SEQUENCE: 177
tttggtggca tcaattctag ggcgcgagct gaaaatttaa ctactcccac tctcaccctc    60
accctactcc aactcaac                                                  78

SEQ ID NO: 178          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 178
tttcccaat tctgcgaacc catataacag ttgattttaa ctactcccac tctcaccctc     60
accctactcc aactcaac                                                  78

SEQ ID NO: 179          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 179
tttattgctc cttttgatat tagagagtac ctttatttaa ctactcccac tctcaccctc    60
accctactcc aactcaac                                                  78

SEQ ID NO: 180          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 180
tttccataaa tcaaaaatcc agaaaacgag aatgatttaa ctactcccac tctcaccctc    60
accctactcc aactcaac                                                  78

SEQ ID NO: 181          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 181
tttcgaggca tagtaagaga cgccaaaagg aattatttaa ctactcccac tctcaccctc    60
accctactcc aactcaac                                                  78

SEQ ID NO: 182          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 182
tttgaaacac cagaacgaga ggcttgccct gacgatttaa ctactcccac tctcaccctc    60
accctactcc aactcaac                                                  78

SEQ ID NO: 183          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 183
tttctgataa attgtgtcga gatttgtatc atcgctttaa ctactcccac tctcaccctc    60
accctactcc aactcaac                                                  78

SEQ ID NO: 184          moltype = DNA  length = 78
FEATURE                 Location/Qualifiers
misc_feature            1..78
                        note = synthetic DNA sequence
```

```
source                  1..78
                        mol_type = other DNA
                        organism = synthetic construct
SEQUENCE: 184
tttgaacgag ggtagcaacg cgaaagacag catcgtttaa ctactcccac tctcaccctc   60
accctactcc aactcaac                                                 78

SEQ ID NO: 185          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 185
tttggtttat cagcttgcta gcctttaatt gtatctttaa ctactcccac tctcaccctc   60
accctactcc aactcaac                                                 78

SEQ ID NO: 186          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 186
tttgggattt tgctaaacaa atgaattttc tgtattttaa ctactcccac tctcaccctc   60
accctactcc aactcaac                                                 78

SEQ ID NO: 187          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 187
tttacaaact acaacgcctg agtttcgtca ccagttttaa ctactcccac tctcaccctc   60
accctactcc aactcaac                                                 78

SEQ ID NO: 188          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 188
tttagccacc accctcattg aaccgccacc ctcagtttaa ctactcccac tctcaccctc   60
accctactcc aactcaac                                                 78

SEQ ID NO: 189          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 189
tttgagaggg ttgatataag cggataagtg ccgtctttaa ctactcccac tctcaccctc   60
accctactcc aactcaac                                                 78

SEQ ID NO: 190          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 190
tttgtataaa cagttaatgt tgagtaacag tgccctttaa ctactcccac tctcaccctc   60
accctactcc aactcaac                                                 78

SEQ ID NO: 191          moltype = DNA  length = 78
FEATURE                 Location/Qualifiers
misc_feature            1..78
                        note = synthetic DNA sequence
```

```
source                  1..78
                        mol_type = other DNA
                        organism = synthetic construct
SEQUENCE: 191
tttgcaggtc agacgattgt tgacaggagg ttgagtttaa ctactcccac tctcaccctc   60
accctactcc aactcaac                                                 78

SEQ ID NO: 192          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 192
ttttagcgcg ttttcatcgc tttagcgtca gactgtttaa ctactcccac tctcaccctc   60
accctactcc aactcaac                                                 78

SEQ ID NO: 193          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 193
tttgcgccaa agacaaaagt tcatatggtt taccatttaa ctactcccac tctcaccctc   60
accctactcc aactcaac                                                 78

SEQ ID NO: 194          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 194
tttccgaagc ccttttaaa gcaatagcta tcttatttaa ctactcccac tctcaccctc    60
accctactcc aactcaac                                                 78

SEQ ID NO: 195          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 195
tttttttttg tttaacgtct ccaaataaga aacgatttaa ctactcccac tctcaccctc   60
accctactcc aactcaac                                                 78

SEQ ID NO: 196          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 196
tttaacctcc cgacttgcgg cgaggcgttt tagcgtttaa ctactcccac tctcaccctc   60
accctactcc aactcaac                                                 78

SEQ ID NO: 197          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 197
ttttaaacca agtaccgcat tccaagaacg ggtattttaa ctactcccac tctcaccctc   60
accctactcc aactcaac                                                 78

SEQ ID NO: 198          moltype = DNA  length = 78
FEATURE                 Location/Qualifiers
misc_feature            1..78
                        note = synthetic DNA sequence
```

```
source                   1..78
                         mol_type = other DNA
                         organism = synthetic construct
SEQUENCE: 198
tttagataag tcctgaacac ctgtttatca acaattttaa ctactcccac tctcaccctc    60
accctactcc aactcaac                                                  78

SEQ ID NO: 199           moltype = DNA   length = 78
FEATURE                  Location/Qualifiers
misc_feature             1..78
                         note = synthetic DNA sequence
source                   1..78
                         mol_type = other DNA
                         organism = synthetic construct
SEQUENCE: 199
tttgtaaagt aattctgtca aagtaccgac aaaagtttaa ctactcccac tctcaccctc    60
accctactcc aactcaac                                                  78

SEQ ID NO: 200           moltype = DNA   length = 78
FEATURE                  Location/Qualifiers
misc_feature             1..78
                         note = synthetic DNA sequence
source                   1..78
                         mol_type = other DNA
                         organism = synthetic construct
SEQUENCE: 200
tttagtaggg cttaattgaa aagccaacgc tcaactttaa ctactcccac tctcaccctc    60
accctactcc aactcaac                                                  78

SEQ ID NO: 201           moltype = DNA   length = 78
FEATURE                  Location/Qualifiers
misc_feature             1..78
                         note = synthetic DNA sequence
source                   1..78
                         mol_type = other DNA
                         organism = synthetic construct
SEQUENCE: 201
tttaatggtt tgaaataccc ttctgaccta aattttttaa ctactcccac tctcaccctc    60
accctactcc aactcaac                                                  78

SEQ ID NO: 202           moltype = DNA   length = 78
FEATURE                  Location/Qualifiers
misc_feature             1..78
                         note = synthetic DNA sequence
source                   1..78
                         mol_type = other DNA
                         organism = synthetic construct
SEQUENCE: 202
tttagtcaat agtgaatttt taagacgctg agaagtttaa ctactcccac tctcaccctc    60
accctactcc aactcaac                                                  78

SEQ ID NO: 203           moltype = DNA   length = 78
FEATURE                  Location/Qualifiers
misc_feature             1..78
                         note = synthetic DNA sequence
source                   1..78
                         mol_type = other DNA
                         organism = synthetic construct
SEQUENCE: 203
ttttgagcaa aagaagatga ttcatttcaa ttacctttaa ctactcccac tctcaccctc    60
accctactcc aactcaac                                                  78

SEQ ID NO: 204           moltype = DNA   length = 78
FEATURE                  Location/Qualifiers
misc_feature             1..78
                         note = synthetic DNA sequence
source                   1..78
                         mol_type = other DNA
                         organism = synthetic construct
SEQUENCE: 204
tttcaatata atcctgattg atgatggcaa ttcattttaa ctactcccac tctcaccctc    60
accctactcc aactcaac                                                  78

SEQ ID NO: 205           moltype = DNA   length = 78
FEATURE                  Location/Qualifiers
misc_feature             1..78
                         note = synthetic DNA sequence
```

```
source                  1..78
                        mol_type = other DNA
                        organism = synthetic construct
SEQUENCE: 205
tttgttatct aaaatatcta aaggaattga ggaagtttaa ctactcccac tctcaccctc    60
accctactcc aactcaac                                                  78

SEQ ID NO: 206          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 206
tttacatcgc cattaaaaaa actgatagcc ctaaatttaa ctactcccac tctcaccctc    60
accctactcc aactcaac                                                  78

SEQ ID NO: 207          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 207
ttttcgtctg aaatggatta cattttgacg ctcaatttaa ctactcccac tctcaccctc    60
accctactcc aactcaac                                                  78

SEQ ID NO: 208          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 208
tttttgatta gtaataacat tgtagcaata cttcttttaa ctactcccac tctcaccctc    60
accctactcc aactcaac                                                  78

SEQ ID NO: 209          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 209
tttaggaacg gtacgccagt aaagggattt tagactttaa ctactcccac tctcaccctc    60
accctactcc aactcaac                                                  78

SEQ ID NO: 210          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 210
tttgagcacg tataacgtgc tatggttgct ttgactttaa ctactcccac tctcaccctc    60
accctactcc aactcaac                                                  78

SEQ ID NO: 211          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 211
tttcgggcgc tagggcgcta agaaagcgaa aggagtttaa ctactcccac tctcaccctc    60
accctactcc aactcaac                                                  78

SEQ ID NO: 212          moltype = DNA  length = 78
FEATURE                 Location/Qualifiers
misc_feature            1..78
                        note = synthetic DNA sequence
```

```
source                  1..78
                        mol_type = other DNA
                        organism = synthetic construct
SEQUENCE: 212
tttatcaccc aaatcaagtg cccactacgt gaacctttaa ctactcccac tctcaccctc    60
accctactcc aactcaac                                                  78

SEQ ID NO: 213          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 213
tttatcctgt ttgatggtgg ccccagcagg cgaaatttaa ctactcccac tctcaccctc    60
accctactcc aactcaac                                                  78

SEQ ID NO: 214          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 214
tttgctcact gcccgcttta cattaattgc gttgctttaa ctactcccac tctcaccctc    60
accctactcc aactcaac                                                  78

SEQ ID NO: 215          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 215
tttgtaacgc cagggtttta aggcgattaa gttggtttaa ctactcccac tctcaccctc    60
accctactcc aactcaac                                                  78

SEQ ID NO: 216          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 216
tttcgttggt gtagatgggg taatgggata ggtcatttaa ctactcccac tctcaccctc    60
accctactcc aactcaac                                                  78

SEQ ID NO: 217          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 217
ttttttaaat tgtaaacgta ttgtataagc aaatatttaa ctactcccac tctcaccctc    60
accctactcc aactcaac                                                  78

SEQ ID NO: 218          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 218
tttgccggag agggtagctt agctgataaa ttaattttaa ctactcccac tctcaccctc    60
accctactcc aactcaac                                                  78

SEQ ID NO: 219          moltype = DNA  length = 78
FEATURE                 Location/Qualifiers
misc_feature            1..78
                        note = synthetic DNA sequence
```

```
source                       1..78
                             mol_type = other DNA
                             organism = synthetic construct
SEQUENCE: 219
tttaaatttt tagaacccctt tcaacgcaag gataatttaa ctactcccac tctcaccctc    60
accctactcc aactcaac                                                  78

SEQ ID NO: 220               moltype = DNA  length = 78
FEATURE                      Location/Qualifiers
misc_feature                 1..78
                             note = synthetic DNA sequence
source                       1..78
                             mol_type = other DNA
                             organism = synthetic construct
SEQUENCE: 220
ttttaagcaa taaagcctca aagaattagc aaaattttaa ctactcccac tctcaccctc    60
accctactcc aactcaac                                                  78

SEQ ID NO: 221               moltype = DNA  length = 24
FEATURE                      Location/Qualifiers
misc_feature                 1..24
                             note = synthetic DNA sequence
source                       1..24
                             mol_type = other DNA
                             organism = synthetic construct
SEQUENCE: 221
tcatttgcta atagtagtag catt                                           24

SEQ ID NO: 222               moltype = DNA  length = 30
FEATURE                      Location/Qualifiers
misc_feature                 1..30
                             note = synthetic DNA sequence
source                       1..30
                             mol_type = other DNA
                             organism = synthetic construct
SEQUENCE: 222
tttcattgag tagatttagt ttctatattt                                     30

SEQ ID NO: 223               moltype = DNA  length = 30
FEATURE                      Location/Qualifiers
misc_feature                 1..30
                             note = synthetic DNA sequence
source                       1..30
                             mol_type = other DNA
                             organism = synthetic construct
SEQUENCE: 223
aacagttagg tctttaccct gatccaacag                                     30

SEQ ID NO: 224               moltype = DNA  length = 32
FEATURE                      Location/Qualifiers
misc_feature                 1..32
                             note = synthetic DNA sequence
source                       1..32
                             mol_type = other DNA
                             organism = synthetic construct
SEQUENCE: 224
tagagcttca gaccggaagc aaacctatta ta                                  32

SEQ ID NO: 225               moltype = DNA  length = 32
FEATURE                      Location/Qualifiers
misc_feature                 1..32
                             note = synthetic DNA sequence
source                       1..32
                             mol_type = other DNA
                             organism = synthetic construct
SEQUENCE: 225
agatttagac gataaaaacc aaaaatcgtc at                                  32

SEQ ID NO: 226               moltype = DNA  length = 24
FEATURE                      Location/Qualifiers
misc_feature                 1..24
                             note = synthetic DNA sequence
source                       1..24
                             mol_type = other DNA
                             organism = synthetic construct
SEQUENCE: 226
cattattagc aaaagaagtt ttgc                                           24

SEQ ID NO: 227               moltype = DNA  length = 30
```

```
FEATURE                 Location/Qualifiers
misc_feature            1..30
                        note = synthetic DNA sequence
source                  1..30
                        mol_type = other DNA
                        organism = synthetic construct
SEQUENCE: 227
gtgaatatag taaattgggc tttaatgcag                                    30

SEQ ID NO: 228          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 228
aggcttttca ggtagaaaga ttcaattacc                                    30

SEQ ID NO: 229          moltype = DNA   length = 32
FEATURE                 Location/Qualifiers
misc_feature            1..32
                        note = synthetic DNA sequence
source                  1..32
                        mol_type = other DNA
                        organism = synthetic construct
SEQUENCE: 229
accagacgga ataccacatt caacgagatg gt                                 32

SEQ ID NO: 230          moltype = DNA   length = 32
FEATURE                 Location/Qualifiers
misc_feature            1..32
                        note = synthetic DNA sequence
source                  1..32
                        mol_type = other DNA
                        organism = synthetic construct
SEQUENCE: 230
aaaagaataa ccgaactgac caacttcatc aa                                 32

SEQ ID NO: 231          moltype = DNA   length = 32
FEATURE                 Location/Qualifiers
misc_feature            1..32
                        note = synthetic DNA sequence
source                  1..32
                        mol_type = other DNA
                        organism = synthetic construct
SEQUENCE: 231
ccccagcggg aacgaggcgc agactattca tt                                 32

SEQ ID NO: 232          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 232
ctcagcaggc tacagaggct ttaacaaagt                                    30

SEQ ID NO: 233          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 233
cataaggggac actaaaacac tcacattaaa                                   30

SEQ ID NO: 234          moltype = DNA   length = 32
FEATURE                 Location/Qualifiers
misc_feature            1..32
                        note = synthetic DNA sequence
source                  1..32
                        mol_type = other DNA
                        organism = synthetic construct
SEQUENCE: 234
acttagccat tataccaagc gcgagaggac ta                                 32
```

```
SEQ ID NO: 235          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 235
tttcacgtcg atagttgcgc cgaccttgca gg                                    32

SEQ ID NO: 236          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 236
cgggtaaaat tcggtcgctg aggaatgaca                                       30

SEQ ID NO: 237          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 237
gttagtaact ttcaacagtt tcaaaggctc                                       30

SEQ ID NO: 238          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 238
cttgatactg aaaatctcca aaaaagcgga gt                                    32

SEQ ID NO: 239          moltype = DNA  length = 24
FEATURE                 Location/Qualifiers
misc_feature            1..24
                        note = synthetic DNA sequence
source                  1..24
                        mol_type = other DNA
                        organism = synthetic construct
SEQUENCE: 239
accctcattc agggatagca agcc                                             24

SEQ ID NO: 240          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 240
gtaccaggta tagcccggaa tagaaccgcc                                       30

SEQ ID NO: 241          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 241
gccagcagcc ttgatattca caaacggggt                                       30

SEQ ID NO: 242          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 242
ttattctgac tggtaataag ttttaacaaa ta                                    32
```

```
SEQ ID NO: 243          moltype = DNA   length = 48
FEATURE                 Location/Qualifiers
misc_feature            1..48
                        note = synthetic DNA sequence
source                  1..48
                        mol_type = other DNA
                        organism = synthetic construct
SEQUENCE: 243
gacggaaaac catcgatagc agcattgcca tcttttcata caccctca                  48

SEQ ID NO: 244          moltype = DNA   length = 24
FEATURE                 Location/Qualifiers
misc_feature            1..24
                        note = synthetic DNA sequence
source                  1..24
                        mol_type = other DNA
                        organism = synthetic construct
SEQUENCE: 244
aggccggaac cagagccacc accg                                            24

SEQ ID NO: 245          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 245
tagaaaaggc gacattcaac cgcagaatca                                      30

SEQ ID NO: 246          moltype = DNA   length = 30
FEATURE                 Location/Qualifiers
misc_feature            1..30
                        note = synthetic DNA sequence
source                  1..30
                        mol_type = other DNA
                        organism = synthetic construct
SEQUENCE: 246
tcaccggaaa cgtcaccaat gaattattca                                      30

SEQ ID NO: 247          moltype = DNA   length = 32
FEATURE                 Location/Qualifiers
misc_feature            1..32
                        note = synthetic DNA sequence
source                  1..32
                        mol_type = other DNA
                        organism = synthetic construct
SEQUENCE: 247
attagcgtcc gtaatcagta gcgaattgag gg                                   32

SEQ ID NO: 248          moltype = DNA   length = 32
FEATURE                 Location/Qualifiers
misc_feature            1..32
                        note = synthetic DNA sequence
source                  1..32
                        mol_type = other DNA
                        organism = synthetic construct
SEQUENCE: 248
cgctaatagg aatacccaaa agaaatacat aa                                   32

SEQ ID NO: 249          moltype = DNA   length = 48
FEATURE                 Location/Qualifiers
misc_feature            1..48
                        note = synthetic DNA sequence
source                  1..48
                        mol_type = other DNA
                        organism = synthetic construct
SEQUENCE: 249
tgccagttat aacataaaaa caggacaaga attgagttaa cagaagga                  48

SEQ ID NO: 250          moltype = DNA   length = 30
FEATURE                 Location/Qualifiers
misc_feature            1..30
                        note = synthetic DNA sequence
source                  1..30
                        mol_type = other DNA
                        organism = synthetic construct
```

```
SEQUENCE: 250
atcccaaaaa aatgaaaata gcaagaaaca                                              30

SEQ ID NO: 251          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 251
ataataactc agagagataa cccgaagcgc                                              30

SEQ ID NO: 252          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 252
aaagttacgc ccaataataa gagcagcctt ta                                           32

SEQ ID NO: 253          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 253
attagacgga gcgtctttcc agagctacaa                                              30

SEQ ID NO: 254          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 254
cttatcactc atcgagaaca agcggtattc                                              30

SEQ ID NO: 255          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 255
agattagtat atagaaggct tatccaagcc gt                                           32

SEQ ID NO: 256          moltype = DNA  length = 24
FEATURE                 Location/Qualifiers
misc_feature            1..24
                        note = synthetic DNA sequence
source                  1..24
                        mol_type = other DNA
                        organism = synthetic construct
SEQUENCE: 256
agaatatcag acgacgacaa taaa                                                    24

SEQ ID NO: 257          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 257
ccagtatgaa tcgccatatt tagtaataag                                              30

SEQ ID NO: 258          moltype = DNA  length = 30
FEATURE                 Location/Qualifiers
misc_feature            1..30
                        note = synthetic DNA sequence
```

```
source                  1..30
                        mol_type = other DNA
                        organism = synthetic construct
SEQUENCE: 258
gcttagaatc aaaatcatag gttttagtta                                      30

SEQ ID NO: 259          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 259
ctttgaatta catttaacaa tttctaatta at                                   32

SEQ ID NO: 260          moltype = DNA  length = 24
FEATURE                 Location/Qualifiers
misc_feature            1..24
                        note = synthetic DNA sequence
source                  1..24
                        mol_type = other DNA
                        organism = synthetic construct
SEQUENCE: 260
cgggagaatt taatggaaac agta                                            24

SEQ ID NO: 261          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 261
ctacctttag aatccttgaa aacaagaaaa ca                                   32

SEQ ID NO: 262          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 262
attatcagtt tggattatac ttgcgcagag                                      30

SEQ ID NO: 263          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 263
ttacctttac aataacggat tcgcaaaatt                                      30

SEQ ID NO: 264          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 264
gcatcaccag tattagactt tacagtttga gt                                   32

SEQ ID NO: 265          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 265
cctcaatccg tcaatagata atacagaaac ca                                   32

SEQ ID NO: 266          moltype = DNA  length = 32
FEATURE                 Location/Qualifiers
```

```
misc_feature            1..32
                        note = synthetic DNA sequence
source                  1..32
                        mol_type = other DNA
                        organism = synthetic construct
SEQUENCE: 266
tggaagggag cggaattatc atcaactaat ag                                    32

SEQ ID NO: 267          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 267
agacaataag aggtgaggcg gtcatatcaa ac                                    32

SEQ ID NO: 268          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 268
atgcgcgtac cgaacgaacc acgcaaatca                                       30

SEQ ID NO: 269          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 269
gatttagatt gctgaacctc aaagtattaa                                       30

SEQ ID NO: 270          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 270
caccgcctga aagcgtaaga atacattctg                                       30

SEQ ID NO: 271          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 271
gataaaactt tttgaatggc tattttcacc ag                                    32

SEQ ID NO: 272          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 272
ttaaccgtca cttgcctgag tactcatgga                                       30

SEQ ID NO: 273          moltype = DNA  length = 24
FEATURE                 Location/Qualifiers
misc_feature            1..24
                        note = synthetic DNA sequence
source                  1..24
                        mol_type = other DNA
                        organism = synthetic construct
SEQUENCE: 273
gcgcgtactt tcctcgttag aatc                                             24

SEQ ID NO: 274          moltype = DNA  length = 30
```

```
FEATURE                 Location/Qualifiers
misc_feature            1..30
                        note = synthetic DNA sequence
source                  1..30
                        mol_type = other DNA
                        organism = synthetic construct
SEQUENCE: 274
ggaaggggc aagtgtagcg gtgctacagg                                           30

SEQ ID NO: 275          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 275
ctggtttgtt ccgaaatcgg catctatcag                                          30

SEQ ID NO: 276          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 276
agcactaaaa agggcgaaaa accgaaatcc ct                                       32

SEQ ID NO: 277          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 277
aagtgtaata atgaatcggc caaccaccgc ct                                       32

SEQ ID NO: 278          moltype = DNA  length = 24
FEATURE                 Location/Qualifiers
misc_feature            1..24
                        note = synthetic DNA sequence
source                  1..24
                        mol_type = other DNA
                        organism = synthetic construct
SEQUENCE: 278
aattccacgt ttgcgtattg ggcg                                                24

SEQ ID NO: 279          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 279
gtgctgcccc agtcacgacg tttgagtgag                                          30

SEQ ID NO: 280          moltype = DNA  length = 30
FEATURE                 Location/Qualifiers
misc_feature            1..30
                        note = synthetic DNA sequence
source                  1..30
                        mol_type = other DNA
                        organism = synthetic construct
SEQUENCE: 280
gagaggcgac aacatacgag ccgctgcagg                                          30

SEQ ID NO: 281          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 281
agctgcatag cctggggtgc ctaagtaaaa cg                                       32
```

```
SEQ ID NO: 282           moltype = DNA   length = 32
FEATURE                  Location/Qualifiers
misc_feature             1..32
                         note = synthetic DNA sequence
source                   1..32
                         mol_type = other DNA
                         organism = synthetic construct
SEQUENCE: 282
ttcatcaacg cactccagcc agctgctgcg ca                                 32

SEQ ID NO: 283           moltype = DNA   length = 32
FEATURE                  Location/Qualifiers
misc_feature             1..32
                         note = synthetic DNA sequence
source                   1..32
                         mol_type = other DNA
                         organism = synthetic construct
SEQUENCE: 283
cccgtcgggg gacgacgaca gtatcgggcc tc                                 32

SEQ ID NO: 284           moltype = DNA   length = 30
FEATURE                  Location/Qualifiers
misc_feature             1..30
                         note = synthetic DNA sequence
source                   1..30
                         mol_type = other DNA
                         organism = synthetic construct
SEQUENCE: 284
caggaagtaa tattttgtta aaaacggcgg                                    30

SEQ ID NO: 285           moltype = DNA   length = 30
FEATURE                  Location/Qualifiers
misc_feature             1..30
                         note = synthetic DNA sequence
source                   1..30
                         mol_type = other DNA
                         organism = synthetic construct
SEQUENCE: 285
aggaagatca ttaaatgtga gcgtttttaa                                    30

SEQ ID NO: 286           moltype = DNA   length = 32
FEATURE                  Location/Qualifiers
misc_feature             1..32
                         note = synthetic DNA sequence
source                   1..32
                         mol_type = other DNA
                         organism = synthetic construct
SEQUENCE: 286
agtttgagat tctccgtggg aacaattcgc at                                 32

SEQ ID NO: 287           moltype = DNA   length = 32
FEATURE                  Location/Qualifiers
misc_feature             1..32
                         note = synthetic DNA sequence
source                   1..32
                         mol_type = other DNA
                         organism = synthetic construct
SEQUENCE: 287
agacagtcca ttgcctgaga gtcttcatat gt                                 32

SEQ ID NO: 288           moltype = DNA   length = 30
FEATURE                  Location/Qualifiers
misc_feature             1..30
                         note = synthetic DNA sequence
source                   1..30
                         mol_type = other DNA
                         organism = synthetic construct
SEQUENCE: 288
ccaataggaa actagcatgt caaggagcaa                                    30

SEQ ID NO: 289           moltype = DNA   length = 30
FEATURE                  Location/Qualifiers
misc_feature             1..30
                         note = synthetic DNA sequence
source                   1..30
                         mol_type = other DNA
                         organism = synthetic construct
SEQUENCE: 289
cctttatcat atattttaaa tggatattca                                    30
```

```
SEQ ID NO: 290          moltype = DNA  length = 32
FEATURE                 Location/Qualifiers
misc_feature            1..32
                        note = synthetic DNA sequence
source                  1..32
                        mol_type = other DNA
                        organism = synthetic construct
SEQUENCE: 290
tatcaggtaa atcaccatca atatcaatgc ct                                     32

SEQ ID NO: 291          moltype = DNA  length = 45
FEATURE                 Location/Qualifiers
misc_feature            1..45
                        note = synthetic DNA sequence
source                  1..45
                        mol_type = other DNA
                        organism = synthetic construct
SEQUENCE: 291
acttttgcat cggttgtact tttttttaacc tgtttaggac catta                      45

SEQ ID NO: 292          moltype = DNA  length = 38
FEATURE                 Location/Qualifiers
misc_feature            1..38
                        note = synthetic DNA sequence
source                  1..38
                        mol_type = other DNA
                        organism = synthetic construct
SEQUENCE: 292
gagtaatgtg taggtaaaga tttttttgttt taaatatg                              38

SEQ ID NO: 293          moltype = DNA  length = 34
FEATURE                 Location/Qualifiers
misc_feature            1..34
                        note = synthetic DNA sequence
source                  1..34
                        mol_type = other DNA
                        organism = synthetic construct
SEQUENCE: 293
acaagagttt ttttcgcgtt ttaattcaaa aaga                                   34

SEQ ID NO: 294          moltype = DNA  length = 25
FEATURE                 Location/Qualifiers
misc_feature            1..25
                        note = synthetic DNA sequence
source                  1..25
                        mol_type = other DNA
                        organism = synthetic construct
SEQUENCE: 294
caaaaataat ttttttgtt tagac                                              25

SEQ ID NO: 295          moltype = DNA  length = 43
FEATURE                 Location/Qualifiers
misc_feature            1..43
                        note = synthetic DNA sequence
source                  1..43
                        mol_type = other DNA
                        organism = synthetic construct
SEQUENCE: 295
ccgcttctgg tttttttcgtt aataaaacga actaaattat acc                        43

SEQ ID NO: 296          moltype = DNA  length = 31
FEATURE                 Location/Qualifiers
misc_feature            1..31
                        note = synthetic DNA sequence
source                  1..31
                        mol_type = other DNA
                        organism = synthetic construct
SEQUENCE: 296
gaaccgcctc tttacctaaa acgaaagagg c                                      31

SEQ ID NO: 297          moltype = DNA  length = 36
FEATURE                 Location/Qualifiers
misc_feature            1..36
                        note = synthetic DNA sequence
source                  1..36
                        mol_type = other DNA
                        organism = synthetic construct
```

```
SEQUENCE: 297
agaaccgcat ttaccgtttt accgatatat acgtaa                                      36

SEQ ID NO: 298          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 298
aggagtgtaa acatgaaagt attaagaggc tttttttgcg aataataatt t                     51

SEQ ID NO: 299          moltype = DNA   length = 29
FEATURE                 Location/Qualifiers
misc_feature            1..29
                        note = synthetic DNA sequence
source                  1..29
                        mol_type = other DNA
                        organism = synthetic construct
SEQUENCE: 299
accgtactca ggttttgat ctaaagttt                                               29

SEQ ID NO: 300          moltype = DNA   length = 45
FEATURE                 Location/Qualifiers
misc_feature            1..45
                        note = synthetic DNA sequence
source                  1..45
                        mol_type = other DNA
                        organism = synthetic construct
SEQUENCE: 300
tgtcgtctca gccctcatat ttttttcgcc accctcaggt gtatc                            45

SEQ ID NO: 301          moltype = DNA   length = 38
FEATURE                 Location/Qualifiers
misc_feature            1..38
                        note = synthetic DNA sequence
source                  1..38
                        mol_type = other DNA
                        organism = synthetic construct
SEQUENCE: 301
gagaatagaa aggaacaact attttctcaa gagaagga                                    38

SEQ ID NO: 302          moltype = DNA   length = 34
FEATURE                 Location/Qualifiers
misc_feature            1..34
                        note = synthetic DNA sequence
source                  1..34
                        mol_type = other DNA
                        organism = synthetic construct
SEQUENCE: 302
acaaccattt tttcatacat ggcttttaag cgca                                        34

SEQ ID NO: 303          moltype = DNA   length = 25
FEATURE                 Location/Qualifiers
misc_feature            1..25
                        note = synthetic DNA sequence
source                  1..25
                        mol_type = other DNA
                        organism = synthetic construct
SEQUENCE: 303
tgccactact tttttgcca ccctc                                                   25

SEQ ID NO: 304          moltype = DNA   length = 43
FEATURE                 Location/Qualifiers
misc_feature            1..43
                        note = synthetic DNA sequence
source                  1..43
                        mol_type = other DNA
                        organism = synthetic construct
SEQUENCE: 304
aggacagatg attttttcac cagtagcacc attaccgact tga                              43

SEQ ID NO: 305          moltype = DNA   length = 60
FEATURE                 Location/Qualifiers
misc_feature            1..60
                        note = synthetic DNA sequence
```

```
source                  1..60
                        mol_type = other DNA
                        organism = synthetic construct
SEQUENCE: 305
aatcatggtc attttttttt ttgcccgaac tcaggtttaa cttttttttc agtatgttag    60

SEQ ID NO: 306          moltype = DNA  length = 31
FEATURE                 Location/Qualifiers
misc_feature            1..31
                        note = synthetic DNA sequence
source                  1..31
                        mol_type = other DNA
                        organism = synthetic construct
SEQUENCE: 306
cataaatcaa tttagtcaga gggtaattga g                                   31

SEQ ID NO: 307          moltype = DNA  length = 36
FEATURE                 Location/Qualifiers
misc_feature            1..36
                        note = synthetic DNA sequence
source                  1..36
                        mol_type = other DNA
                        organism = synthetic construct
SEQUENCE: 307
ttgcttctta tatgtattttt acgctaacgg agaatt                             36

SEQ ID NO: 308          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 308
gcgagaaaat aaacaccgga atcataatta ttttttttcgc ccaatagcaa g             51

SEQ ID NO: 309          moltype = DNA  length = 29
FEATURE                 Location/Qualifiers
misc_feature            1..29
                        note = synthetic DNA sequence
source                  1..29
                        mol_type = other DNA
                        organism = synthetic construct
SEQUENCE: 309
aacatgtaat ttttttttgaa accaatcaa                                     29

SEQ ID NO: 310          moltype = DNA  length = 45
FEATURE                 Location/Qualifiers
misc_feature            1..45
                        note = synthetic DNA sequence
source                  1..45
                        mol_type = other DNA
                        organism = synthetic construct
SEQUENCE: 310
taatcggcca tcctaattttt ttttttttttt cgagccaaca acgcc                  45

SEQ ID NO: 311          moltype = DNA  length = 38
FEATURE                 Location/Qualifiers
misc_feature            1..38
                        note = synthetic DNA sequence
source                  1..38
                        mol_type = other DNA
                        organism = synthetic construct
SEQUENCE: 311
ttttattttc atcgtaggaa tttttagcct gtttagta                            38

SEQ ID NO: 312          moltype = DNA  length = 34
FEATURE                 Location/Qualifiers
misc_feature            1..34
                        note = synthetic DNA sequence
source                  1..34
                        mol_type = other DNA
                        organism = synthetic construct
SEQUENCE: 312
ttttatctttt tttatccaat cgcaagagtt gggt                               34

SEQ ID NO: 313          moltype = DNA  length = 25
FEATURE                 Location/Qualifiers
```

```
misc_feature             1..25
                         note = synthetic DNA sequence
source                   1..25
                         mol_type = other DNA
                         organism = synthetic construct
SEQUENCE: 313
aactgaacat ttttttgaa taacc                                                  25

SEQ ID NO: 314           moltype = DNA  length = 43
FEATURE                  Location/Qualifiers
misc_feature             1..43
                         note = synthetic DNA sequence
source                   1..43
                         mol_type = other DNA
                         organism = synthetic construct
SEQUENCE: 314
attaagactc ctttttaata tacagtaaca gtaccgaaat tgc                             43

SEQ ID NO: 315           moltype = DNA  length = 31
FEATURE                  Location/Qualifiers
misc_feature             1..31
                         note = synthetic DNA sequence
source                   1..31
                         mol_type = other DNA
                         organism = synthetic construct
SEQUENCE: 315
ccagggtggt tttgcaaatg aaaaatctaa a                                          31

SEQ ID NO: 316           moltype = DNA  length = 36
FEATURE                  Location/Qualifiers
misc_feature             1..36
                         note = synthetic DNA sequence
source                   1..36
                         mol_type = other DNA
                         organism = synthetic construct
SEQUENCE: 316
acgggcaagt tccagttttt tctgacctgc aacagt                                     36

SEQ ID NO: 317           moltype = DNA  length = 51
FEATURE                  Location/Qualifiers
misc_feature             1..51
                         note = synthetic DNA sequence
source                   1..51
                         mol_type = other DNA
                         organism = synthetic construct
SEQUENCE: 317
ccaacgtcat cggaacccta aagggagccc ttttttgaa caatattacc g                     51

SEQ ID NO: 318           moltype = DNA  length = 29
FEATURE                  Location/Qualifiers
misc_feature             1..29
                         note = synthetic DNA sequence
source                   1..29
                         mol_type = other DNA
                         organism = synthetic construct
SEQUENCE: 318
gcgtaaccac cattttttgag taaaagagt                                            29

SEQ ID NO: 319           moltype = DNA  length = 45
FEATURE                  Location/Qualifiers
misc_feature             1..45
                         note = synthetic DNA sequence
source                   1..45
                         mol_type = other DNA
                         organism = synthetic construct
SEQUENCE: 319
ctgtccattt ttataatcat ttttttctta atgcgcccac gctgc                           45

SEQ ID NO: 320           moltype = DNA  length = 38
FEATURE                  Location/Qualifiers
misc_feature             1..38
                         note = synthetic DNA sequence
source                   1..38
                         mol_type = other DNA
                         organism = synthetic construct
SEQUENCE: 320
caaactatcg gccttgctgg tttttgagct tgacgggg                                   38

SEQ ID NO: 321           moltype = DNA  length = 34
```

```
FEATURE                 Location/Qualifiers
misc_feature            1..34
                        note = synthetic DNA sequence
source                  1..34
                        mol_type = other DNA
                        organism = synthetic construct
SEQUENCE: 321
gccaacattt tttccactat taaagaaata gggt                               34

SEQ ID NO: 322          moltype = DNA  length = 25
FEATURE                 Location/Qualifiers
misc_feature            1..25
                        note = synthetic DNA sequence
source                  1..25
                        mol_type = other DNA
                        organism = synthetic construct
SEQUENCE: 322
gccacgctgt tttttacca gtgag                                          25

SEQ ID NO: 323          moltype = DNA  length = 43
FEATURE                 Location/Qualifiers
misc_feature            1..43
                        note = synthetic DNA sequence
source                  1..43
                        mol_type = other DNA
                        organism = synthetic construct
SEQUENCE: 323
gacaactcgt attttttcct gtgtgaaatt gttatccgag ctc                     43

SEQ ID NO: 324          moltype = DNA  length = 60
FEATURE                 Location/Qualifiers
misc_feature            1..60
                        note = synthetic DNA sequence
source                  1..60
                        mol_type = other DNA
                        organism = synthetic construct
SEQUENCE: 324
ggaattagag cttttttttc agaccaggcg cgttgggaag attttttttc caggcaaagc   60

SEQ ID NO: 325          moltype = DNA  length = 31
FEATURE                 Location/Qualifiers
misc_feature            1..31
                        note = synthetic DNA sequence
source                  1..31
                        mol_type = other DNA
                        organism = synthetic construct
SEQUENCE: 325
cagaggggt tttgccttcc tgtagccagc t                                   31

SEQ ID NO: 326          moltype = DNA  length = 36
FEATURE                 Location/Qualifiers
misc_feature            1..36
                        note = synthetic DNA sequence
source                  1..36
                        mol_type = other DNA
                        organism = synthetic construct
SEQUENCE: 326
tggatagcaa gcccgatttt taatcgtaaa cgccat                             36

SEQ ID NO: 327          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 327
aagcgaacaa ttgctgaata taatgctgta ttttttgtg agaaaggccg g             51

SEQ ID NO: 328          moltype = DNA  length = 29
FEATURE                 Location/Qualifiers
misc_feature            1..29
                        note = synthetic DNA sequence
source                  1..29
                        mol_type = other DNA
                        organism = synthetic construct
SEQUENCE: 328
gatacattc gcttttttga ccctgtaat                                      29
```

```
SEQ ID NO: 329            moltype = DNA   length = 75
FEATURE                   Location/Qualifiers
misc_feature              1..75
                          note = synthetic DNA sequence
source                    1..75
                          mol_type = other DNA
                          organism = synthetic construct
SEQUENCE: 329
aaccgagggc aaagacacca cggataaata tttttcactc acctccatct ccactcctac    60
ccatccaact cccac                                                     75

SEQ ID NO: 330            moltype = DNA   length = 51
FEATURE                   Location/Qualifiers
misc_feature              1..51
                          note = synthetic DNA sequence
source                    1..51
                          mol_type = other DNA
                          organism = synthetic construct
SEQUENCE: 330
gtcaggaaga ggtcattttt gctctggaag ttttaccatc ttcctctcca c              51

SEQ ID NO: 331            moltype = DNA   length = 45
FEATURE                   Location/Qualifiers
misc_feature              1..45
                          note = synthetic DNA sequence
source                    1..45
                          mol_type = other DNA
                          organism = synthetic construct
SEQUENCE: 331
caactaaagt acggtgggat ggcttttac catcttcctc tccac                     45

SEQ ID NO: 332            moltype = DNA   length = 53
FEATURE                   Location/Qualifiers
misc_feature              1..53
                          note = synthetic DNA sequence
source                    1..53
                          mol_type = other DNA
                          organism = synthetic construct
SEQUENCE: 332
aaatattcca aagcggattg catcgagctt cattttacca tcttcctctc cac            53

SEQ ID NO: 333            moltype = DNA   length = 51
FEATURE                   Location/Qualifiers
misc_feature              1..51
                          note = synthetic DNA sequence
source                    1..51
                          mol_type = other DNA
                          organism = synthetic construct
SEQUENCE: 333
atacatacaa cactatcata acatgcttta ttttaccatc ttcctctcca c              51

SEQ ID NO: 334            moltype = DNA   length = 51
FEATURE                   Location/Qualifiers
misc_feature              1..51
                          note = synthetic DNA sequence
source                    1..51
                          mol_type = other DNA
                          organism = synthetic construct
SEQUENCE: 334
ttaagagggt ccaatactgc ggatagcgag ttttaccatc ttcctctcca c              51

SEQ ID NO: 335            moltype = DNA   length = 53
FEATURE                   Location/Qualifiers
misc_feature              1..53
                          note = synthetic DNA sequence
source                    1..53
                          mol_type = other DNA
                          organism = synthetic construct
SEQUENCE: 335
gtcagaagat tgaatccccc tcaacctcgt tttttacca tcttcctctc cac             53

SEQ ID NO: 336            moltype = DNA   length = 53
FEATURE                   Location/Qualifiers
misc_feature              1..53
                          note = synthetic DNA sequence
source                    1..53
                          mol_type = other DNA
                          organism = synthetic construct
```

```
SEQUENCE: 336
gagtaatctt ttaagaactg gctccggaac aattttacca tcttcctctc cac         53

SEQ ID NO: 337         moltype = DNA   length = 53
FEATURE                Location/Qualifiers
misc_feature           1..53
                       note = synthetic DNA sequence
source                 1..53
                       mol_type = other DNA
                       organism = synthetic construct
SEQUENCE: 337
acccaaataa ctttaatcat tgtgatcagt tgttttacca tcttcctctc cac         53

SEQ ID NO: 338         moltype = DNA   length = 51
FEATURE                Location/Qualifiers
misc_feature           1..51
                       note = synthetic DNA sequence
source                 1..51
                       mol_type = other DNA
                       organism = synthetic construct
SEQUENCE: 338
acaacggaaa tccgcgacct gcctcattca ttttaccatc ttcctctcca c           51

SEQ ID NO: 339         moltype = DNA   length = 53
FEATURE                Location/Qualifiers
misc_feature           1..53
                       note = synthetic DNA sequence
source                 1..53
                       mol_type = other DNA
                       organism = synthetic construct
SEQUENCE: 339
agtcaggaca taggctggct gacctttgaa agttttacca tcttcctctc cac         53

SEQ ID NO: 340         moltype = DNA   length = 51
FEATURE                Location/Qualifiers
misc_feature           1..51
                       note = synthetic DNA sequence
source                 1..51
                       mol_type = other DNA
                       organism = synthetic construct
SEQUENCE: 340
ttatgcgatt gacaagaacc ggaggtcaat ttttaccatc ttcctctcca c           51

SEQ ID NO: 341         moltype = DNA   length = 53
FEATURE                Location/Qualifiers
misc_feature           1..53
                       note = synthetic DNA sequence
source                 1..53
                       mol_type = other DNA
                       organism = synthetic construct
SEQUENCE: 341
ttaatttcca acgtaacaaa gctgtccatg ttttttacca tcttcctctc cac         53

SEQ ID NO: 342         moltype = DNA   length = 53
FEATURE                Location/Qualifiers
misc_feature           1..53
                       note = synthetic DNA sequence
source                 1..53
                       mol_type = other DNA
                       organism = synthetic construct
SEQUENCE: 342
gagttaaatt catgaggaag tttctctttg acttttacca tcttcctctc cac         53

SEQ ID NO: 343         moltype = DNA   length = 51
FEATURE                Location/Qualifiers
misc_feature           1..51
                       note = synthetic DNA sequence
source                 1..51
                       mol_type = other DNA
                       organism = synthetic construct
SEQUENCE: 343
caaaaggttc gaggtgaatt tctcgtcacc ttttaccatc ttcctctcca c           51

SEQ ID NO: 344         moltype = DNA   length = 53
FEATURE                Location/Qualifiers
misc_feature           1..53
                       note = synthetic DNA sequence
```

```
source                  1..53
                        mol_type = other DNA
                        organism = synthetic construct
SEQUENCE: 344
aagactttgg ccgcttttgc gggattaaac agttttacca tcttcctctc cac          53

SEQ ID NO: 345          moltype = DNA   length = 61
FEATURE                 Location/Qualifiers
misc_feature            1..61
                        note = synthetic DNA sequence
source                  1..61
                        mol_type = other DNA
                        organism = synthetic construct
SEQUENCE: 345
ccatgtaccg taacactgta gcattccaca gattccagac ttttaccatc ttcctctcca    60
c                                                                    61

SEQ ID NO: 346          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 346
cagtgccccc cctgcctatt tctttgctca ttttaccatc ttcctctcca c             51

SEQ ID NO: 347          moltype = DNA   length = 45
FEATURE                 Location/Qualifiers
misc_feature            1..45
                        note = synthetic DNA sequence
source                  1..45
                        mol_type = other DNA
                        organism = synthetic construct
SEQUENCE: 347
ttaggattag cggggtggaa cctattttac catcttcctc tccac                    45

SEQ ID NO: 348          moltype = DNA   length = 53
FEATURE                 Location/Qualifiers
misc_feature            1..53
                        note = synthetic DNA sequence
source                  1..53
                        mol_type = other DNA
                        organism = synthetic construct
SEQUENCE: 348
gagccgcctt aaagccagaa tggagatgat acttttacca tcttcctctc cac           53

SEQ ID NO: 349          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 349
agtttgcgca ttttcggtca tagagccgcc ttttaccatc ttcctctcca c             51

SEQ ID NO: 350          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 350
gtctctgaca ccctcagagc cacatcaaaa ttttaccatc ttcctctcca c             51

SEQ ID NO: 351          moltype = DNA   length = 53
FEATURE                 Location/Qualifiers
misc_feature            1..53
                        note = synthetic DNA sequence
source                  1..53
                        mol_type = other DNA
                        organism = synthetic construct
SEQUENCE: 351
aatcctcaac cagaaccacc accagccccc tttttaccat cttcctctc cac            53

SEQ ID NO: 352          moltype = DNA   length = 53
FEATURE                 Location/Qualifiers
```

```
misc_feature            1..53
                        note = synthetic DNA sequence
source                  1..53
                        mol_type = other DNA
                        organism = synthetic construct
SEQUENCE: 352
aggtggcaga attatcaccg tcaccattag cattttacca tcttcctctc cac              53

SEQ ID NO: 353          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 353
atgaaatgaa aagtaagcag atacaatcaa ttttaccatc ttcctctcca c                51

SEQ ID NO: 354          moltype = DNA  length = 53
FEATURE                 Location/Qualifiers
misc_feature            1..53
                        note = synthetic DNA sequence
source                  1..53
                        mol_type = other DNA
                        organism = synthetic construct
SEQUENCE: 354
gccatttgca aacgtagaaa atacctggca tgttttacca tcttcctctc cac              53

SEQ ID NO: 355          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 355
ttaaaggtac atataaaaga aacaaacgca ttttaccatc ttcctctcca c                51

SEQ ID NO: 356          moltype = DNA  length = 53
FEATURE                 Location/Qualifiers
misc_feature            1..53
                        note = synthetic DNA sequence
source                  1..53
                        mol_type = other DNA
                        organism = synthetic construct
SEQUENCE: 356
agggaaggat aagtttattt tgtcagccga acttttacca tcttcctctc cac              53

SEQ ID NO: 357          moltype = DNA  length = 53
FEATURE                 Location/Qualifiers
misc_feature            1..53
                        note = synthetic DNA sequence
source                  1..53
                        mol_type = other DNA
                        organism = synthetic construct
SEQUENCE: 357
caaatcagtg ctattttgca cccagcctaa tttttacca tcttcctctc cac               53

SEQ ID NO: 358          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 358
taagaacgga ggttttgaag cctattattt ttttaccatc ttcctctcca c                51

SEQ ID NO: 359          moltype = DNA  length = 53
FEATURE                 Location/Qualifiers
misc_feature            1..53
                        note = synthetic DNA sequence
source                  1..53
                        mol_type = other DNA
                        organism = synthetic construct
SEQUENCE: 359
cagagagaac aaaataaaca gccattaaat cattttacca tcttcctctc cac              53

SEQ ID NO: 360          moltype = DNA  length = 61
```

```
FEATURE                 Location/Qualifiers
misc_feature            1..61
                        note = synthetic DNA sequence
source                  1..61
                        mol_type = other DNA
                        organism = synthetic construct
SEQUENCE: 360
agctaatgca gaacgcgaga aaaataatat cctgtctttc ttttaccatc ttcctctcca    60
c                                                                    61

SEQ ID NO: 361          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 361
atttcatgac cgtgtgataa ataattctta ttttaccatc ttcctctcca c              51

SEQ ID NO: 362          moltype = DNA   length = 45
FEATURE                 Location/Qualifiers
misc_feature            1..45
                        note = synthetic DNA sequence
source                  1..45
                        mol_type = other DNA
                        organism = synthetic construct
SEQUENCE: 362
tcatatgcgt tatacaaagg cgttttttac catcttcctc tccac                    45

SEQ ID NO: 363          moltype = DNA   length = 53
FEATURE                 Location/Qualifiers
misc_feature            1..53
                        note = synthetic DNA sequence
source                  1..53
                        mol_type = other DNA
                        organism = synthetic construct
SEQUENCE: 363
tttccctttt aacctccggc ttagcaaaga acttttacca tcttcctctc cac           53

SEQ ID NO: 364          moltype = DNA   length = 53
FEATURE                 Location/Qualifiers
misc_feature            1..53
                        note = synthetic DNA sequence
source                  1..53
                        mol_type = other DNA
                        organism = synthetic construct
SEQUENCE: 364
aaataagaac tttttcaaat atatctgaga gattttacca tcttcctctc cac           53

SEQ ID NO: 365          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 365
gcgaattatg aaacaaacat catagcgata ttttaccatc ttcctctcca c              51

SEQ ID NO: 366          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 366
tatataacgt aaatcgtcgc tatatttgaa ttttaccatc ttcctctcca c              51

SEQ ID NO: 367          moltype = DNA   length = 53
FEATURE                 Location/Qualifiers
misc_feature            1..53
                        note = synthetic DNA sequence
source                  1..53
                        mol_type = other DNA
                        organism = synthetic construct
SEQUENCE: 367
aacattatgt aaaacagaaa taaatttac attttacca tcttcctctc cac              53
```

```
SEQ ID NO: 368        moltype = DNA  length = 53
FEATURE               Location/Qualifiers
misc_feature          1..53
                      note = synthetic DNA sequence
source                1..53
                      mol_type = other DNA
                      organism = synthetic construct
SEQUENCE: 368
ccagaaggtt agaacctacc atatcctgat tgttttacca tcttcctctc cac            53

SEQ ID NO: 369        moltype = DNA  length = 53
FEATURE               Location/Qualifiers
misc_feature          1..53
                      note = synthetic DNA sequence
source                1..53
                      mol_type = other DNA
                      organism = synthetic construct
SEQUENCE: 369
aaattaatac caagttacaa aatcctgaat aattttacca tcttcctctc cac            53

SEQ ID NO: 370        moltype = DNA  length = 51
FEATURE               Location/Qualifiers
misc_feature          1..51
                      note = synthetic DNA sequence
source                1..51
                      mol_type = other DNA
                      organism = synthetic construct
SEQUENCE: 370
acagttgtta ggagcactaa catattcctg ttttaccatc ttcctctcca c              51

SEQ ID NO: 371        moltype = DNA  length = 53
FEATURE               Location/Qualifiers
misc_feature          1..53
                      note = synthetic DNA sequence
source                1..53
                      mol_type = other DNA
                      organism = synthetic construct
SEQUENCE: 371
gtagatttgt tattaattt aaaaaacaat tcttttacca tcttcctctc cac             53

SEQ ID NO: 372        moltype = DNA  length = 51
FEATURE               Location/Qualifiers
misc_feature          1..51
                      note = synthetic DNA sequence
source                1..51
                      mol_type = other DNA
                      organism = synthetic construct
SEQUENCE: 372
atttgcacca ttttgcggaa caaatttgag ttttaccatc ttcctctcca c              51

SEQ ID NO: 373        moltype = DNA  length = 53
FEATURE               Location/Qualifiers
misc_feature          1..53
                      note = synthetic DNA sequence
source                1..53
                      mol_type = other DNA
                      organism = synthetic construct
SEQUENCE: 373
attagagcaa tatctggtca gttgcagcag aattttacca tcttcctctc cac            53

SEQ ID NO: 374        moltype = DNA  length = 53
FEATURE               Location/Qualifiers
misc_feature          1..53
                      note = synthetic DNA sequence
source                1..53
                      mol_type = other DNA
                      organism = synthetic construct
SEQUENCE: 374
ccagccatcc agtaataaaa gggacgtggc acttttacca tcttcctctc cac            53

SEQ ID NO: 375        moltype = DNA  length = 51
FEATURE               Location/Qualifiers
misc_feature          1..51
                      note = synthetic DNA sequence
source                1..51
                      mol_type = other DNA
                      organism = synthetic construct
```

```
SEQUENCE: 375
aatacctatt tacattggca gaagtcttta ttttaccatc ttcctctcca c          51

SEQ ID NO: 376          moltype = DNA   length = 53
FEATURE                 Location/Qualifiers
misc_feature            1..53
                        note = synthetic DNA sequence
source                  1..53
                        mol_type = other DNA
                        organism = synthetic construct
SEQUENCE: 376
tcacacgatg caacaggaaa aacggaagaa cttttttacca tcttcctctc cac        53

SEQ ID NO: 377          moltype = DNA   length = 61
FEATURE                 Location/Qualifiers
misc_feature            1..61
                        note = synthetic DNA sequence
source                  1..61
                        mol_type = other DNA
                        organism = synthetic construct
SEQUENCE: 377
ctaaacagga ggccgataat cctgagaagt gtcacgcaaa ttttaccatc ttcctctcca  60
c                                                                 61

SEQ ID NO: 378          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 378
ggcgatgttt ttggggtcga gggcgagaaa ttccttccatc ttcctctcca c          51

SEQ ID NO: 379          moltype = DNA   length = 45
FEATURE                 Location/Qualifiers
misc_feature            1..45
                        note = synthetic DNA sequence
source                  1..45
                        mol_type = other DNA
                        organism = synthetic construct
SEQUENCE: 379
aaagccggcg aacgtgtgcc gtaattttac catcttcctc tccac                  45

SEQ ID NO: 380          moltype = DNA   length = 53
FEATURE                 Location/Qualifiers
misc_feature            1..53
                        note = synthetic DNA sequence
source                  1..53
                        mol_type = other DNA
                        organism = synthetic construct
SEQUENCE: 380
ggccctgaaa aagaatagcc cgagcgtgga cttttttacca tcttcctctc cac        53

SEQ ID NO: 381          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 381
ctaactccca gtcgggaaac ctggtccacg ttttaccatc ttcctctcca c          51

SEQ ID NO: 382          moltype = DNA   length = 51
FEATURE                 Location/Qualifiers
misc_feature            1..51
                        note = synthetic DNA sequence
source                  1..51
                        mol_type = other DNA
                        organism = synthetic construct
SEQUENCE: 382
tgagtgttca gctgattgcc cttgcgcggg ttttaccatc ttcctctcca c          51

SEQ ID NO: 383          moltype = DNA   length = 53
FEATURE                 Location/Qualifiers
misc_feature            1..53
                        note = synthetic DNA sequence
```

```
source                  1..53
                        mol_type = other DNA
                        organism = synthetic construct
SEQUENCE: 383
tataaatcga gagttgcagc aagcgtcgtg cctttacca tcttcctctc cac          53

SEQ ID NO: 384          moltype = DNA  length = 53
FEATURE                 Location/Qualifiers
misc_feature            1..53
                        note = synthetic DNA sequence
source                  1..53
                        mol_type = other DNA
                        organism = synthetic construct
SEQUENCE: 384
actgttggag aggatccccg ggtaccgctc acttttacca tcttcctctc cac          53

SEQ ID NO: 385          moltype = DNA  length = 53
FEATURE                 Location/Qualifiers
misc_feature            1..53
                        note = synthetic DNA sequence
source                  1..53
                        mol_type = other DNA
                        organism = synthetic construct
SEQUENCE: 385
ttcgctattg ccaagcttgc atgcgaagca tattttacca tcttcctctc cac          53

SEQ ID NO: 386          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 386
attgacccgc atcgtaaccg tgaggggat ttttaccatc ttcctctcca c             51

SEQ ID NO: 387          moltype = DNA  length = 53
FEATURE                 Location/Qualifiers
misc_feature            1..53
                        note = synthetic DNA sequence
source                  1..53
                        mol_type = other DNA
                        organism = synthetic construct
SEQUENCE: 387
gaattcgtgc cattcgccat tcagttccgg cattttacca tcttcctctc cac          53

SEQ ID NO: 388          moltype = DNA  length = 51
FEATURE                 Location/Qualifiers
misc_feature            1..51
                        note = synthetic DNA sequence
source                  1..51
                        mol_type = other DNA
                        organism = synthetic construct
SEQUENCE: 388
tcgactctga agggcgatcg gtgcggcctc ttttaccatc ttcctctcca c             51

SEQ ID NO: 389          moltype = DNA  length = 53
FEATURE                 Location/Qualifiers
misc_feature            1..53
                        note = synthetic DNA sequence
source                  1..53
                        mol_type = other DNA
                        organism = synthetic construct
SEQUENCE: 389
acggccagta cgccagctgg cgaacatctg cctttacca tcttcctctc cac           53

SEQ ID NO: 390          moltype = DNA  length = 53
FEATURE                 Location/Qualifiers
misc_feature            1..53
                        note = synthetic DNA sequence
source                  1..53
                        mol_type = other DNA
                        organism = synthetic construct
SEQUENCE: 390
accccggttg ttaaatcagc tcatagtaac aattttacca tcttcctctc cac          53

SEQ ID NO: 391          moltype = DNA  length = 51
FEATURE                 Location/Qualifiers
```

```
misc_feature              1..51
                          note = synthetic DNA sequence
source                    1..51
                          mol_type = other DNA
                          organism = synthetic construct
SEQUENCE: 391
accgttcatt tttgagagat ctcccaaaaa ttttaccatc ttcctctcca c          51

SEQ ID NO: 392            moltype = DNA  length = 53
FEATURE                   Location/Qualifiers
misc_feature              1..53
                          note = synthetic DNA sequence
source                    1..53
                          mol_type = other DNA
                          organism = synthetic construct
SEQUENCE: 392
taaattttg ataatcagaa aagcacaaag gcttttacca tcttcctctc cac         53

SEQ ID NO: 393            moltype = DNA  length = 61
FEATURE                   Location/Qualifiers
misc_feature              1..61
                          note = synthetic DNA sequence
source                    1..61
                          mol_type = other DNA
                          organism = synthetic construct
SEQUENCE: 393
aatcatacag gcaaggcaga gcataaagct aagggagaag ttttaccatc ttcctctcca  60
c                                                                 61

SEQ ID NO: 394            moltype = DNA  length = 78
FEATURE                   Location/Qualifiers
misc_feature              1..78
                          note = synthetic DNA sequence
source                    1..78
                          mol_type = other DNA
                          organism = synthetic construct
SEQUENCE: 394
tttggtggca tcaattctag ggcgcgagct gaaaatttaa ctactcccac tctcaccctc  60
accctactcc aactcaac                                               78

SEQ ID NO: 395            moltype = DNA  length = 78
FEATURE                   Location/Qualifiers
misc_feature              1..78
                          note = synthetic DNA sequence
source                    1..78
                          mol_type = other DNA
                          organism = synthetic construct
SEQUENCE: 395
ttttcccaat tctgcgaacc catataacag ttgattttaa ctactcccac tctcaccctc  60
accctactcc aactcaac                                               78

SEQ ID NO: 396            moltype = DNA  length = 78
FEATURE                   Location/Qualifiers
misc_feature              1..78
                          note = synthetic DNA sequence
source                    1..78
                          mol_type = other DNA
                          organism = synthetic construct
SEQUENCE: 396
tttattgctc cttttgatat tagagagtac ctttatttaa ctactcccac tctcaccctc  60
accctactcc aactcaac                                               78

SEQ ID NO: 397            moltype = DNA  length = 78
FEATURE                   Location/Qualifiers
misc_feature              1..78
                          note = synthetic DNA sequence
source                    1..78
                          mol_type = other DNA
                          organism = synthetic construct
SEQUENCE: 397
tttccataaa tcaaaaatcc agaaaacgag aatgatttaa ctactcccac tctcaccctc  60
accctactcc aactcaac                                               78

SEQ ID NO: 398            moltype = DNA  length = 78
FEATURE                   Location/Qualifiers
misc_feature              1..78
                          note = synthetic DNA sequence
```

```
source                  1..78
                        mol_type = other DNA
                        organism = synthetic construct
SEQUENCE: 398
tttcgaggca tagtaagaga cgccaaaagg aattatttaa ctactcccac tctcaccctc    60
accctactcc aactcaac                                                  78

SEQ ID NO: 399          moltype = DNA   length = 78
FEATURE                 Location/Qualifiers
misc_feature            1..78
                        note = synthetic DNA sequence
source                  1..78
                        mol_type = other DNA
                        organism = synthetic construct
SEQUENCE: 399
tttgaaacac cagaacgaga ggcttgccct gacgatttaa ctactcccac tctcaccctc    60
accctactcc aactcaac                                                  78

SEQ ID NO: 400          moltype = DNA   length = 78
FEATURE                 Location/Qualifiers
misc_feature            1..78
                        note = synthetic DNA sequence
source                  1..78
                        mol_type = other DNA
                        organism = synthetic construct
SEQUENCE: 400
tttctgataa attgtgtcga gatttgtatc atcgctttaa ctactcccac tctcaccctc    60
accctactcc aactcaac                                                  78

SEQ ID NO: 401          moltype = DNA   length = 78
FEATURE                 Location/Qualifiers
misc_feature            1..78
                        note = synthetic DNA sequence
source                  1..78
                        mol_type = other DNA
                        organism = synthetic construct
SEQUENCE: 401
tttgaacgag ggtagcaacg cgaaagacag catcgtttaa ctactcccac tctcaccctc    60
accctactcc aactcaac                                                  78

SEQ ID NO: 402          moltype = DNA   length = 78
FEATURE                 Location/Qualifiers
misc_feature            1..78
                        note = synthetic DNA sequence
source                  1..78
                        mol_type = other DNA
                        organism = synthetic construct
SEQUENCE: 402
tttggtttat cagcttgcta gcctttaatt gtatctttaa ctactcccac tctcaccctc    60
accctactcc aactcaac                                                  78

SEQ ID NO: 403          moltype = DNA   length = 78
FEATURE                 Location/Qualifiers
misc_feature            1..78
                        note = synthetic DNA sequence
source                  1..78
                        mol_type = other DNA
                        organism = synthetic construct
SEQUENCE: 403
tttgggattt tgctaaacaa atgaattttc tgtattttaa ctactcccac tctcaccctc    60
accctactcc aactcaac                                                  78

SEQ ID NO: 404          moltype = DNA   length = 78
FEATURE                 Location/Qualifiers
misc_feature            1..78
                        note = synthetic DNA sequence
source                  1..78
                        mol_type = other DNA
                        organism = synthetic construct
SEQUENCE: 404
tttacaaact acaacgcctg agtttcgtca ccagttttaa ctactcccac tctcaccctc    60
accctactcc aactcaac                                                  78

SEQ ID NO: 405          moltype = DNA   length = 78
FEATURE                 Location/Qualifiers
misc_feature            1..78
                        note = synthetic DNA sequence
```

```
source                  1..78
                        mol_type = other DNA
                        organism = synthetic construct
SEQUENCE: 405
tttagccacc accctcattg aaccgccacc ctcagtttaa ctactcccac tctcaccctc   60
accctactcc aactcaac                                                 78

SEQ ID NO: 406          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 406
tttgagaggg ttgatataag cggataagtg ccgtctttaa ctactcccac tctcaccctc   60
accctactcc aactcaac                                                 78

SEQ ID NO: 407          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 407
tttgtataaa cagttaatgt tgagtaacag tgccctttaa ctactcccac tctcaccctc   60
accctactcc aactcaac                                                 78

SEQ ID NO: 408          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 408
tttgcaggtc agacgattgt tgacaggagg ttgagtttaa ctactcccac tctcaccctc   60
accctactcc aactcaac                                                 78

SEQ ID NO: 409          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 409
ttttagcgcg ttttcatcgc tttagcgtca gactgtttaa ctactcccac tctcaccctc   60
accctactcc aactcaac                                                 78

SEQ ID NO: 410          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 410
tttgcgccaa agacaaaagt tcatatggtt taccatttaa ctactcccac tctcaccctc   60
accctactcc aactcaac                                                 78

SEQ ID NO: 411          moltype = DNA  length = 78
FEATURE                 Location/Qualifiers
misc_feature            1..78
                        note = synthetic DNA sequence
source                  1..78
                        mol_type = other DNA
                        organism = synthetic construct
SEQUENCE: 411
tttccgaagc ccttttttaaa gcaatagcta tcttatttaa ctactcccac tctcaccctc   60
accctactcc aactcaac                                                 78

SEQ ID NO: 412          moltype = DNA  length = 78
FEATURE                 Location/Qualifiers
misc_feature            1..78
                        note = synthetic DNA sequence
```

```
source                   1..78
                         mol_type = other DNA
                         organism = synthetic construct
SEQUENCE: 412
ttttttttttg tttaacgtct ccaaataaga aacgatttaa ctactcccac tctcaccctc   60
accctactcc aactcaac                                                  78

SEQ ID NO: 413           moltype = DNA   length = 78
FEATURE                  Location/Qualifiers
misc_feature             1..78
                         note = synthetic DNA sequence
source                   1..78
                         mol_type = other DNA
                         organism = synthetic construct
SEQUENCE: 413
tttaacctcc cgacttgcgg cgaggcgttt tagcgtttaa ctactcccac tctcaccctc   60
accctactcc aactcaac                                                  78

SEQ ID NO: 414           moltype = DNA   length = 78
FEATURE                  Location/Qualifiers
misc_feature             1..78
                         note = synthetic DNA sequence
source                   1..78
                         mol_type = other DNA
                         organism = synthetic construct
SEQUENCE: 414
ttttaaacca agtaccgcat tccaagaacg ggtattttaa ctactcccac tctcaccctc   60
accctactcc aactcaac                                                  78

SEQ ID NO: 415           moltype = DNA   length = 78
FEATURE                  Location/Qualifiers
misc_feature             1..78
                         note = synthetic DNA sequence
source                   1..78
                         mol_type = other DNA
                         organism = synthetic construct
SEQUENCE: 415
tttagataag tcctgaacac ctgtttatca acaattttaa ctactcccac tctcaccctc   60
accctactcc aactcaac                                                  78

SEQ ID NO: 416           moltype = DNA   length = 78
FEATURE                  Location/Qualifiers
misc_feature             1..78
                         note = synthetic DNA sequence
source                   1..78
                         mol_type = other DNA
                         organism = synthetic construct
SEQUENCE: 416
tttgtaaagt aattctgtca aagtaccgac aaaagtttaa ctactcccac tctcaccctc   60
accctactcc aactcaac                                                  78

SEQ ID NO: 417           moltype = DNA   length = 78
FEATURE                  Location/Qualifiers
misc_feature             1..78
                         note = synthetic DNA sequence
source                   1..78
                         mol_type = other DNA
                         organism = synthetic construct
SEQUENCE: 417
tttagtaggg cttaattgaa aagccaacgc tcaactttaa ctactcccac tctcaccctc   60
accctactcc aactcaac                                                  78

SEQ ID NO: 418           moltype = DNA   length = 78
FEATURE                  Location/Qualifiers
misc_feature             1..78
                         note = synthetic DNA sequence
source                   1..78
                         mol_type = other DNA
                         organism = synthetic construct
SEQUENCE: 418
tttaatggtt tgaaataccc ttctgaccta aattttttaa ctactcccac tctcaccctc   60
accctactcc aactcaac                                                  78

SEQ ID NO: 419           moltype = DNA   length = 78
FEATURE                  Location/Qualifiers
misc_feature             1..78
                         note = synthetic DNA sequence
```

```
source                          1..78
                                mol_type = other DNA
                                organism = synthetic construct
SEQUENCE: 419
tttagtcaat agtgaatttt taagacgctg agaagtttaa ctactcccac tctcaccctc    60
accctactcc aactcaac                                                  78

SEQ ID NO: 420                  moltype = DNA   length = 78
FEATURE                         Location/Qualifiers
misc_feature                    1..78
                                note = synthetic DNA sequence
source                          1..78
                                mol_type = other DNA
                                organism = synthetic construct
SEQUENCE: 420
ttttgagcaa aagaagatga ttcatttcaa ttacctttaa ctactcccac tctcaccctc    60
accctactcc aactcaac                                                  78

SEQ ID NO: 421                  moltype = DNA   length = 78
FEATURE                         Location/Qualifiers
misc_feature                    1..78
                                note = synthetic DNA sequence
source                          1..78
                                mol_type = other DNA
                                organism = synthetic construct
SEQUENCE: 421
tttcaatata atcctgattg atgatggcaa ttcattttaa ctactcccac tctcaccctc    60
accctactcc aactcaac                                                  78

SEQ ID NO: 422                  moltype = DNA   length = 78
FEATURE                         Location/Qualifiers
misc_feature                    1..78
                                note = synthetic DNA sequence
source                          1..78
                                mol_type = other DNA
                                organism = synthetic construct
SEQUENCE: 422
tttgttatct aaaatatcta aaggaattga ggaagtttaa ctactcccac tctcaccctc    60
accctactcc aactcaac                                                  78

SEQ ID NO: 423                  moltype = DNA   length = 78
FEATURE                         Location/Qualifiers
misc_feature                    1..78
                                note = synthetic DNA sequence
source                          1..78
                                mol_type = other DNA
                                organism = synthetic construct
SEQUENCE: 423
tttacatcgc cattaaaaaa actgatagcc ctaaatttaa ctactcccac tctcaccctc    60
accctactcc aactcaac                                                  78

SEQ ID NO: 424                  moltype = DNA   length = 78
FEATURE                         Location/Qualifiers
misc_feature                    1..78
                                note = synthetic DNA sequence
source                          1..78
                                mol_type = other DNA
                                organism = synthetic construct
SEQUENCE: 424
ttttcgtctg aaatggatta cattttgacg ctcaatttaa ctactcccac tctcaccctc    60
accctactcc aactcaac                                                  78

SEQ ID NO: 425                  moltype = DNA   length = 78
FEATURE                         Location/Qualifiers
misc_feature                    1..78
                                note = synthetic DNA sequence
source                          1..78
                                mol_type = other DNA
                                organism = synthetic construct
SEQUENCE: 425
tttttgatta gtaataacat tgtagcaata cttcttttaa ctactcccac tctcaccctc    60
accctactcc aactcaac                                                  78

SEQ ID NO: 426                  moltype = DNA   length = 78
FEATURE                         Location/Qualifiers
misc_feature                    1..78
                                note = synthetic DNA sequence
```

| | |
|---|---|
| source | 1..78<br>mol_type = other DNA<br>organism = synthetic construct |

SEQUENCE: 426
tttaggaacg gtacgccagt aaagggattt tagactttaa ctactcccac tctcaccctc  60
accctactcc aactcaac                                                78

| | |
|---|---|
| SEQ ID NO: 427 | moltype = DNA  length = 78 |
| FEATURE | Location/Qualifiers |
| misc_feature | 1..78<br>note = synthetic DNA sequence |
| source | 1..78<br>mol_type = other DNA<br>organism = synthetic construct |

SEQUENCE: 427
tttgagcacg tataacgtgc tatggttgct ttgactttaa ctactcccac tctcaccctc  60
accctactcc aactcaac                                                78

| | |
|---|---|
| SEQ ID NO: 428 | moltype = DNA  length = 78 |
| FEATURE | Location/Qualifiers |
| misc_feature | 1..78<br>note = synthetic DNA sequence |
| source | 1..78<br>mol_type = other DNA<br>organism = synthetic construct |

SEQUENCE: 428
tttcgggcgc tagggcgcta agaaagcgaa aggagtttaa ctactcccac tctcaccctc  60
accctactcc aactcaac                                                78

| | |
|---|---|
| SEQ ID NO: 429 | moltype = DNA  length = 78 |
| FEATURE | Location/Qualifiers |
| misc_feature | 1..78<br>note = synthetic DNA sequence |
| source | 1..78<br>mol_type = other DNA<br>organism = synthetic construct |

SEQUENCE: 429
tttatcaccc aaatcaagtg cccactacgt gaacctttaa ctactcccac tctcaccctc  60
accctactcc aactcaac                                                78

| | |
|---|---|
| SEQ ID NO: 430 | moltype = DNA  length = 78 |
| FEATURE | Location/Qualifiers |
| misc_feature | 1..78<br>note = synthetic DNA sequence |
| source | 1..78<br>mol_type = other DNA<br>organism = synthetic construct |

SEQUENCE: 430
tttatcctgt ttgatggtgg ccccagcagg cgaaatttaa ctactcccac tctcaccctc  60
accctactcc aactcaac                                                78

| | |
|---|---|
| SEQ ID NO: 431 | moltype = DNA  length = 78 |
| FEATURE | Location/Qualifiers |
| misc_feature | 1..78<br>note = synthetic DNA sequence |
| source | 1..78<br>mol_type = other DNA<br>organism = synthetic construct |

SEQUENCE: 431
tttgctcact gcccgcttta cattaattgc gttgctttaa ctactcccac tctcaccctc  60
accctactcc aactcaac                                                78

| | |
|---|---|
| SEQ ID NO: 432 | moltype = DNA  length = 78 |
| FEATURE | Location/Qualifiers |
| misc_feature | 1..78<br>note = synthetic DNA sequence |
| source | 1..78<br>mol_type = other DNA<br>organism = synthetic construct |

SEQUENCE: 432
tttgtaacgc cagggtttta aggcgattaa gttggtttaa ctactcccac tctcaccctc  60
accctactcc aactcaac                                                78

| | |
|---|---|
| SEQ ID NO: 433 | moltype = DNA  length = 78 |
| FEATURE | Location/Qualifiers |
| misc_feature | 1..78<br>note = synthetic DNA sequence |

```
                         source              1..78
                                             mol_type = other DNA
                                             organism = synthetic construct
SEQUENCE: 433
tttcgttggt gtagatgggg taatgggata ggtcatttaa ctactcccac tctcaccctc    60
accctactcc aactcaac                                                   78

SEQ ID NO: 434           moltype = DNA  length = 78
FEATURE                  Location/Qualifiers
misc_feature             1..78
                         note = synthetic DNA sequence
source                   1..78
                         mol_type = other DNA
                         organism = synthetic construct
SEQUENCE: 434
tttttttaaat tgtaaacgta ttgtataagc aaatatttaa ctactcccac tctcaccctc    60
accctactcc aactcaac                                                   78

SEQ ID NO: 435           moltype = DNA  length = 78
FEATURE                  Location/Qualifiers
misc_feature             1..78
                         note = synthetic DNA sequence
source                   1..78
                         mol_type = other DNA
                         organism = synthetic construct
SEQUENCE: 435
tttgccggag agggtagctt agctgataaa ttaattttaa ctactcccac tctcaccctc    60
accctactcc aactcaac                                                   78

SEQ ID NO: 436           moltype = DNA  length = 78
FEATURE                  Location/Qualifiers
misc_feature             1..78
                         note = synthetic DNA sequence
source                   1..78
                         mol_type = other DNA
                         organism = synthetic construct
SEQUENCE: 436
tttaaatttt tagaacccctt tcaacgcaag gataatttaa ctactcccac tctcaccctc    60
accctactcc aactcaac                                                   78

SEQ ID NO: 437           moltype = DNA  length = 78
FEATURE                  Location/Qualifiers
misc_feature             1..78
                         note = synthetic DNA sequence
source                   1..78
                         mol_type = other DNA
                         organism = synthetic construct
SEQUENCE: 437
ttttaagcaa taaagcctca aagaattagc aaaattttaa ctactcccac tctcaccctc    60
accctactcc aactcaac                                                   78

SEQ ID NO: 438           moltype = DNA  length = 19
FEATURE                  Location/Qualifiers
misc_feature             1..19
                         note = synthetic DNA sequence
source                   1..19
                         mol_type = other DNA
                         organism = synthetic construct
SEQUENCE: 438
tgtggagagg aagatggta                                                  19

SEQ ID NO: 439           moltype = AA  length = 12
FEATURE                  Location/Qualifiers
REGION                   1..12
                         note = synthetic amino acid sequence
source                   1..12
                         mol_type = protein
                         organism = synthetic construct
SEQUENCE: 439
HHHHHHHHHH HH                                                         12

SEQ ID NO: 440           moltype = DNA  length = 17
FEATURE                  Location/Qualifiers
misc_feature             1..17
                         note = synthetic DNA sequence
source                   1..17
                         mol_type = other DNA
                         organism = synthetic construct
```

```
SEQUENCE: 440
attatactac atacacc                                                              17

SEQ ID NO: 441          moltype = DNA  length = 17
FEATURE                 Location/Qualifiers
misc_feature            1..17
                        note = synthetic DNA sequence
source                  1..17
                        mol_type = other DNA
                        organism = synthetic construct
SEQUENCE: 441
taatatgatg tatgtgg                                                              17

SEQ ID NO: 442          moltype = DNA  length = 41
FEATURE                 Location/Qualifiers
misc_feature            1..41
                        note = synthetic DNA sequence
source                  1..41
                        mol_type = other DNA
                        organism = synthetic construct
SEQUENCE: 442
acaactcaac ctcatcccac tcccactctc accctcatca a                                   41

SEQ ID NO: 443          moltype = DNA  length = 17
FEATURE                 Location/Qualifiers
misc_feature            1..17
                        note = synthetic DNA sequence
source                  1..17
                        mol_type = other DNA
                        organism = synthetic construct
SEQUENCE: 443
gtttgttgtt tgggttg                                                              17
```